US011744887B2

(12) United States Patent
Sullivan et al.

(10) Patent No.: US 11,744,887 B2
(45) Date of Patent: Sep. 5, 2023

(54) CORONAVIRUS VACCINE COMPOSITIONS AND METHODS

(71) Applicant: Arcturus Therapeutics, Inc., San Diego, CA (US)

(72) Inventors: Sean Michael Sullivan, Escondido, CA (US); Daiki Matsuda, San Diego, CA (US); Kiyoshi Tachikawa, San Diego, CA (US); Padmanabh Chivukula, San Diego, CA (US); Priya Prakash Karmali, San Diego, CA (US); Jared Henry Davis, Poway, CA (US); Yanjie Bao, San Diego, CA (US); Amit Sagi, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 275 days.

(21) Appl. No.: 17/196,889

(22) Filed: Mar. 9, 2021

(65) Prior Publication Data
US 2021/0290756 A1 Sep. 23, 2021

Related U.S. Application Data

(60) Provisional application No. 63/073,900, filed on Sep. 2, 2020, provisional application No. 62/987,191, filed on Mar. 9, 2020.

(51) Int. Cl.
*A61K 39/215* (2006.01)
*C07K 14/005* (2006.01)
*C12N 15/86* (2006.01)
*A61K 47/20* (2006.01)
*A61K 47/26* (2006.01)
*A61K 47/10* (2017.01)
*A61K 9/51* (2006.01)
*A61K 39/12* (2006.01)
*C07K 14/18* (2006.01)
*C12N 7/00* (2006.01)
*A61K 39/00* (2006.01)
*A61K 38/00* (2006.01)

(52) U.S. Cl.
CPC .......... *A61K 39/215* (2013.01); *A61K 9/5123* (2013.01); *A61K 39/12* (2013.01); *A61K 47/10* (2013.01); *A61K 47/20* (2013.01); *A61K 47/26* (2013.01); *C07K 14/005* (2013.01); *C07K 14/1808* (2013.01); *C12N 7/00* (2013.01); *C12N 15/86* (2013.01); *A61K 38/00* (2013.01); *A61K 2039/53* (2013.01); *C12N 2770/20022* (2013.01); *C12N 2770/20034* (2013.01); *C12N 2770/36122* (2013.01); *C12N 2770/36134* (2013.01); *C12N 2830/42* (2013.01); *C12N 2830/50* (2013.01)

(58) Field of Classification Search
CPC .... A61K 39/215; A61K 9/5123; A61K 39/12; A61K 47/10; A61K 47/20; A61K 47/26; A61K 38/00; A61K 2039/53; A61K 39/395; A61K 2039/507; A61K 2039/884; A61K 2039/55555; A61K 2039/572; A61K 2039/575; C07K 14/005; C07K 14/1808; C07K 2317/76; C07K 16/2818; C07K 16/2827; C12N 7/00; C12N 15/86; C12N 2770/20022; C12N 2770/20034; C12N 2770/36122; C12N 2770/36134; C12N 2830/42; C12N 2830/50; C12N 2740/13071; C12N 2760/16134; C12N 2760/16171; C12N 2740/13034; A61P 35/00; A61P 31/14; A61P 31/16; Y02A 50/30

See application file for complete search history.

(56) References Cited

U.S. PATENT DOCUMENTS

| | | | |
|---|---|---|---|
| 7,332,322 B2 | 2/2008 | Frolov et al. |
| 7,425,337 B2 | 9/2008 | Smith et al. |
| 7,442,381 B2 | 10/2008 | Smith et al. |
| 8,093,367 B2 | 1/2012 | Kore et al. |
| 8,158,601 B2 | 4/2012 | Chen et al. |
| 8,304,529 B2 | 11/2012 | Kore et al. |
| 8,961,995 B2 | 2/2015 | Frolov et al. |
| 9,254,265 B2 | 2/2016 | Geall et al. |
| 9,295,646 B2 | 3/2016 | Brito et al. |
| 9,730,997 B2 | 8/2017 | Perri et al. |
| 9,770,463 B2 | 9/2017 | Geall et al. |
| 10,238,733 B2 | 3/2019 | Brito et al. |
| 10,487,105 B2 | 11/2019 | Chivukula et al. |

(Continued)

FOREIGN PATENT DOCUMENTS

| | | |
|---|---|---|
| EP | 2 591 114 B1 | 6/2016 |
| EP | 3 471 778 A2 | 4/2019 |

(Continued)

OTHER PUBLICATIONS

Boles KS, et. al. Synthetic construct H7N9 HA gene, complete cds. GenBank: KY199425.1, Dep. Jul. 18, 2017. (Year: 2017).*

(Continued)

*Primary Examiner* — Rachel B Gill
(74) *Attorney, Agent, or Firm* — Mintz, Levin, Cohn, Ferris Glovsky and Popeo, P.C.

(57) ABSTRACT

Provided herein are nucleic acid molecules encoding viral replication proteins and antigenic coronavirus proteins or fragments thereof. Also provided herein are compositions that include nucleic acid molecules encoding viral replication and antigenic proteins, and lipids. Nucleic acid molecules provided herein are useful for inducing immune responses.

28 Claims, 54 Drawing Sheets

Specification includes a Sequence Listing.

(56) References Cited

U.S. PATENT DOCUMENTS

| | | | |
|---|---|---|---|
| 11,135,283 | B2 | 10/2021 | Berglund et al. |
| 2009/0155301 | A1 | 6/2009 | Mason et al. |
| 2011/0171255 | A1 | 7/2011 | Kiiver et al. |
| 2011/0207223 | A1 | 8/2011 | Tang et al. |
| 2011/0256175 | A1 | 10/2011 | Hope et al. |
| 2012/0027803 | A1 | 2/2012 | Manoharan et al. |
| 2012/0128760 | A1 | 5/2012 | Manoharan et al. |
| 2012/0156251 | A1* | 6/2012 | Brito ................ A61P 31/12 424/193.1 |
| 2013/0171241 | A1 | 7/2013 | Geall |
| 2013/0195968 | A1 | 8/2013 | Geall et al. |
| 2014/0227346 | A1 | 8/2014 | Geall et al. |
| 2014/0242152 | A1 | 8/2014 | Geall et al. |
| 2015/0024002 | A1 | 1/2015 | Perri et al. |
| 2016/0074500 | A1 | 3/2016 | Pushko et al. |
| 2016/0348132 | A1 | 12/2016 | Rayner et al. |
| 2018/0036398 | A1 | 2/2018 | Hagen et al. |
| 2018/0104359 | A1 | 4/2018 | Kamrud |
| 2018/0169268 | A1* | 6/2018 | Payne ............... A61K 48/0025 |
| 2018/0171340 | A1 | 6/2018 | Kamrud et al. |
| 2018/0273576 | A1 | 9/2018 | Hogrefe et al. |
| 2018/0327471 | A1 | 11/2018 | Limphong et al. |
| 2019/0091329 | A1 | 3/2019 | Brito et al. |
| 2019/0224299 | A1 | 7/2019 | Kamrud et al. |
| 2019/0321458 | A1 | 10/2019 | Sahin et al. |
| 2019/0374650 | A1 | 12/2019 | Moon et al. |
| 2020/0010849 | A1 | 1/2020 | Blair et al. |
| 2020/0113830 | A1 | 4/2020 | Geall et al. |
| 2020/0113831 | A1 | 4/2020 | Geall et al. |
| 2020/0222332 | A1 | 7/2020 | Irvine et al. |
| 2020/0230058 | A1 | 7/2020 | Geall et al. |
| 2020/0297634 | A1 | 9/2020 | Karmali et al. |
| 2020/0330585 | A1 | 10/2020 | Mogler et al. |
| 2021/0030859 | A1 | 2/2021 | Bucala et al. |
| 2021/0284974 | A1* | 9/2021 | Chivukula ........... A61K 9/1272 |
| 2021/0290752 | A1 | 9/2021 | Sullivan et al. |
| 2022/0347298 | A1* | 11/2022 | Sullivan ............. A61K 39/3955 |
| 2022/0395570 | A1* | 12/2022 | Rauch .................... A61P 31/14 |

FOREIGN PATENT DOCUMENTS

| | | | |
|---|---|---|---|
| EP | 3433369 | B1 | 3/2020 |
| EP | 2 729 126 | B1 | 12/2020 |
| WO | WO-2009/086558 | A1 | 7/2009 |
| WO | WO-2009/127060 | A1 | 10/2009 |
| WO | WO-2010/048536 | A2 | 4/2010 |
| WO | WO-2010/054406 | A1 | 5/2010 |
| WO | WO-2010/088537 | A2 | 8/2010 |
| WO | WO-2010/129709 | A1 | 11/2010 |
| WO | WO-2011/153493 | A2 | 12/2011 |
| WO | 2014170493 | A2 | 10/2014 |
| WO | WO-2015/051169 | A2 | 4/2015 |
| WO | WO-2015/061491 | A1 | 4/2015 |
| WO | WO-2017/223085 | A2 | 12/2017 |
| WO | WO-2018/078053 | A1 | 5/2018 |
| WO | WO-2018/208856 | A1 | 11/2018 |
| WO | WO-2018/222890 | A1 | 12/2018 |
| WO | WO-2018222926 | A1 * | 12/2018 ......... A61K 31/7115 |
| WO | 2019023566 | A1 | 1/2019 |
| WO | 2020014654 | A1 | 1/2020 |
| WO | WO-2020/035609 | A2 | 2/2020 |
| WO | 2020254535 | A1 | 12/2020 |
| WO | 2020254804 | A1 | 12/2020 |
| WO | WO-2020/255055 | A1 | 12/2020 |
| WO | WO-2021/067181 | A1 | 4/2021 |
| WO | 2021183563 | A1 | 9/2021 |
| WO | 2021183564 | A1 | 9/2021 |
| WO | 2023010128 | A2 | 2/2023 |

OTHER PUBLICATIONS

Altschul et al. (1990) "Basic Local Alignment Search Tool", Journal of Molecular Biology, 215(3):403-410.

Altschul et al. (1997) "Gapped BLAST and PSI-BLAST: A New Generation of Protein Database Search Programs", Nucleic Acids Research, 25(17):3389-3402.

Bochicchio et al. (2014) "Liposomes as siRNA Delivery Vectors", Current Drug Metabolism, 15(9):882-892.

Both et al. (Mar. 1975) "Methylation-Dependent Translation Of Viral Messenger RNAs In Vitro", Proceedings of the National Academy of Sciences, 72(3):1189-1193.

Bouloy et al. (Jul. 1980) "Both the 7-Methyl And the 2'-O-Methyl Groups in the Cap of mRNA Strongly Influence its Ability to Act as Primer for Influenza Virus RNA Transcription", Proceedings of the National Academy of Sciences, 77(7):3952-3956.

Chan, C.Y. et al. (2017) "Early molecular correlates of adverse events following yellow fever vaccination", JCI Insight, 2(19):96031. 12 pages.

Chan, K.R. et al. (2016) "Cross-reactive antibodies enhance live attenuated virus infection for increased immunogenicity", Nat Microbiol, 1: Article No. 16164, 10 pages.

Chan, K.R. et al. (2019) "Metabolic perturbations and cellular stress underpin susceptibility to symptomatic live-attenuated yellow fever infection", Nat Med, 25(8):1218-1224.

Chu et al. (1978) "Paradoxical Observations on the 5' Terminus of Ovalbumin Messenger Ribonucleic Acid", Journal of Biological Chemistry, 253(15):5228-5231.

Cirelli et al. (2019) "Slow Delivery Immunization Enhances HIV Neutralizing Antibody and Germinal Center Responses via Modulation of Immunodominance", Cell, 177(5):1153-1171. e28.

Conticello et al. (2008) "Interaction between Antibody-Diversification Enzyme AID and Spliceosome-Associated Factor CTNNBL1", Mol Cell, 31(4):474-484.

Dabkowska et al. (Mar. 7, 2012) "The Effect of Neutral Helper Lipids on The Structure of Cationic Lipid Monolayer", Journal of the Royal Society Interface, 9(68):548-561.

Dua et al. (Apr.-Jun. 2012) "Liposome: Methods of Preparation and Applications", International Journal of Pharmaceutical Studies and Research, 3:14-20.

Dupuis et al. (Sep. 1, 2000) "Distribution of DNA Vaccines Determines Their Immunogenicity After Intramuscular Injection in Mice", J Immunol, 165 (5) 2850-2858.

Ehrchen et al. (2009) "The endogenous Toll-like receptor 4 agonist S100A8/S100A9 (calprotectin) as innate amplifier of infection, autoimmunity, and cancer", J Leukoc Biol, 86(3): 557-566.

Geall et al. (Sep. 4, 2012) "Nonviral delivery of self-amplifying RNA vaccines", PNAS Sep. 4, 2012 109 (36):14604-14609.

Groom et al. (2011) "CXCR3 in T cell function", Exp Cell Res, 317(5): 620-631.

Gustafsson et al. (Jul. 2004) "Codon Bias and Heterologous Protein Expression", Trends in Biotechnology, 22(7):346-353.

Hashem et al. (2019) "A Highly Immunogenic, Protective, and Safe Adenovirus-Based Vaccine Expressing Middle East Respiratory Syndrome Coronavirus S1-CD40L Fusion Protein in a Transgenic Human Dipeptidyl Peptidase 4 Mouse Model", J Infect Dis, 220(10): 1558-1567.

Hassett et al. (2019) "Optimization of Lipid Nanoparticles for Intramuscular Administration of mRNA Vaccines", Mol Ther Nucleic Acids, 15: 1-11.

Higgins et al. (2019) "Programming Isotype-Specific Plasma Cell Function", Trends Immunol, 40(4): 345-357.

Honda-Okubo et al. (2015, e-published Dec. 17, 2014) "Severe acute respiratory syndrome-associated coronavirus vaccines formulated with delta inulin adjuvants provide enhanced protection while ameliorating lung eosinophilic immunopathology", J Virol, 89(6): p. 2995-3007.

Huang et al. (Aug. 2011) "In Vivo Delivery of RNAi with Lipid-Based Nanoparticles", Annual Review of Biomedical Engineering, 13:507-530.

Hyde et al. (2015, e-published Jan. 25, 2015) "The 5' and 3' ends of alphavirus RNAs—Non-coding is not non-functional", Virus Res. 206:99-107.

Ishikawa et al. (Sep. 27, 2009) "Preparation of Eukaryotic mRNA having Differently Methylated Adenosine at the 5' Terminus and the Effect of the Methyl Group in Translation", Nucleic Acids Symposium, 53(1):129-130.

(56) References Cited

OTHER PUBLICATIONS

Jackson et al. (2020) "The promise of mRNA vaccines: a biotech and industrial perspective", NPJ Vaccines, 5:11: 6 pages.

Jin et al. (2010) "Immunomodulatory Effects of dsRNA and Its Potential as Vaccine Adjuvant", J Biomed Biotechnol, Article ID 690438, 17 pages.

Jokerst et al. (Jun. 2011) "Nanoparticle PEGylation for Imaging and Therapy", Nanomedicine (Lond), 6(4):715-728(27 pages).

Karlin et al. (Mar. 1990) "Methods for Assessing the Statistical Significance of Molecular Sequence Features by Using General Scoring Schemes", Proceedings of the National Academy of Sciences, 87(6):2264-2268.

Karlin et al. (Jun. 1993) "Applications and Statistics for Multiple High-Scoring Segments in Molecular Sequences", Proceedings of the National Academy of Sciences, 90(12):5873-5877.

Kasturi et al. (2011) "Programming the magnitude and persistence of antibody responses with innate immunity", Nature, 470(7335):543-547.

Kawabata et al. (1995) "The Fate of Plasmid DNA After Intravenous Injection in Mice: Involvement of Scavenger Receptors in Its Hepatic Uptake", Pharmaceutical Research, 12:825-830.

Kirchdoerfer et al. (2018, e-published Oct. 24, 2018) "Stabilized coronavirus spikes are resistant to conformational changes induced by receptor recognition or proteolysis", Sci Rep 8, Article No. 15701. 11 pages.

Kowalski et al. (2019, e-published Feb. 19, 2019) "Delivering the Messenger: Advances in Technologies for Therapeutic mRNA Delivery", Mol Ther.; 27(4):710-728.

Kozak, Marilyn (Feb. 1989) "The Scanning Model For Translation: An Update", Journal of Cell Biology, 108(2):229-241.

Kozak, Marilyn (1988) "Leader Length And Secondary Structure Modulate mRNA Function Under Conditions Of Stress", Molecular and Cellular Biology, 8:2737-2744.

Kozak, Marilyn (Nov. 1990) "Downstream Secondary Structure Facilitates Recognition of Initiator Codons by Eukaryotic Ribosomes", Proceedings of the National Academy of Sciences, 87(21):8301-8305.

Kozak, Marilyn (Oct. 25, 1991) "Structural Features In Eukaryotic mRNAs That Modulate the Initiation of Translation", Journal of Biological Chemistry, 266(30):19867-19870.

Kreiter et al. (Jan. 1, 2008) "Increased Antigen Presentation Efficiency by Coupling Antigens to MHC Class I Trafficking Signals", Journal of Immunology, 180(1):309-318.

Kulasegaran-Shylini et al. (2009, e-published Mar. 17, 2009) "The 5'UTR-specific mutation in VEEV TC-83 genome has a strong effect on RNA replication and subgenomic RNA synthesis, but not on translation of the encoded proteins", Virology, 387(1):211-221.

Kulkarni et al. (2018) "Lipid Nanoparticles Enabling Gene Therapies: From Concepts to Clinical Utility", Nucleic Acid Therapeutics, 28(3):146-157.

Lasic, Dan D. (Jul. 1, 1998) "Novel Applications of Liposomes", Trends in Biotechnology, 16(7):307-321.

Li, S-D. et al. (Aug. 3, 2010) "Stealth Nanoparticles: High Density but Sheddable PEG is a Key for Tumor Targeting", Journal of Controlled Release, 145(3):178-181(8 pages).

Li, X. et al. (2011) "Biosynthesis of Nanoparticles by Microorganisms and Their Applications", J. Nanomaterial, Article ID 270974, 16 pages.

Lin et al. (2014) "Lipid-based Nanoparticles in the Systemic Delivery of siRNA", Nanomedicine, 9(1):105-120.

Love et al. (2010) "Lipid-like Materials for Low-dose, In Vivo Gene Silencing", Proceedings of the National Academy of Sciences, 107(5):1864-1869.

Magini et al. (2016) "Self-Amplifying mRNA Vaccines Expressing Multiple Conserved Influenza Antigens Confer Protection against Homologous and Heterosubtypic Viral Challenge", PloS one, 11(8), e0161193. 25 pages.

Maruggi et al. (2019) "mRNA as a Transformative Technology for Vaccine Development to Control Infectious Diseases", Molecular Therapy, vol. 27, No. 427, 757-772.

Maruggi et al. (2013, e-published Oct. 5, 2013) "Engineered alphavirus replicon vaccines based on known attenuated viral mutants show limited effects on immunogenicity", Virology, 447, 254-264.

Muthukrishnan et al. (1975) "5'-Terminal 7-Methylguanosine in Eukaryotic mRNA is Required for Translation", Nature, 255:33-37.

Patil et al. (Jan. 2014, e-published, Nov. 9, 2013) "Novel Methods for Liposome Preparation", Chemistry and Physics of Lipids, 177:8-18.

Pearson et al. (Apr. 1988) "Improved Tools For Biological Sequence Comparison", Proceedings of the National Academy of Sciences, 85:2444-2448.

Pepini et al. (2017, e-published Apr. 17, 2017) "Induction of an IFN-Mediated Antiviral Response by a Self-Amplifying RNA Vaccine: Implications for Vaccine Design", J Immunol, 198(10): p. 4012-4024.

Petkov et al. (2018) "DNA immunization site determines the level of gene expression and the magnitude, but not the type of the induced immune response", PLoS ONE 13(6): e0197902. 22 pages.

Querec, et al. (2009, e-published Nov. 23, 2008) "Systems biology approach predicts immunogenicity of the yellow fever vaccine in humans", Nat Immunol, 10(1):116-125.

Querec, T.D. and Pulendran, B. (2007) "Understanding the Role of Innate Immunity in the Mechanism of Action of the Live Attenuated Yellow Fever Vaccine 17D", In: Katsikis P.D., Schoenberger S.P., Pulendran B. (eds) Crossroads between Innate and Adaptive Immunity. Advances in Experimental Medicine and Biology, vol. 590. pp. 45-53. Springer, Boston, MA.

Ramanathan, A. et al. (2016, e-published Jun. 17, 2016). "mRNA capping: biological functions and applications", Nucleic Acids Research, vol. 44, No. 16, 7511-7526.

Rodriguez-Gascon et al. (2014) "Development of Nucleic Acid Vaccines: Use of Self-Amplifying RNA in Lipid Nanoparticles", International Journal of Nanomedicine, 9:1833-1843.

Salti et al. (2011, e-published Nov. 14, 2011) "Granzyme B Regulates Antiviral CD8$^+$T Cell Responses", J Immunol, 187(12):6301-6309.

Sercombe et al. (Dec. 1, 2015) "Advances and Challenges of Liposome Assisted Drug Delivery", Frontiers in Pharmacology, 6(286):13 Pages.

Slansky et al. (Oct. 2000) "Enhanced Antigen-Specific Antitumor Immunity with Altered Peptide Ligands that Stabilize the MHC-Peptide-TCR Complex", Immunity, 13(4):529-538.

Tam et al. (2016, e-published Oct. 4, 2016) "Sustained antigen availability during germinal center initiation enhances antibody responses to vaccination", Proc Natl Acad Sci, USA, 113(43):E6639-E6648.

Taverniti et al. (Jan. 9, 2015, e-published Nov. 28, 2014) "Elimination of Cap Structures Generated by mRNA Decay Involves the New Scavenger mRNA Decapping Enzyme Aph1/FHIT Together with DcpS", Nucleic Acids Research, 43(1):482-492.

Thompson et al. (2006) "Mucosal and systemic adjuvant activity of alphavirus replicon particles", Proc Natl Acad Sci, USA, 103(10): p. 3722-3727.

Villalobos et al. (2006) "Gene Designer: A Synthetic Biology Tool for Constructing Artificial DNA Segments", BMC Bioinformatics, 7:285. 8 pages.

Von Herrath et al. (2003) "Immune responsiveness, tolerance and dsRNA: implications for traditional paradigms", Trends Immunol. 24(6):289-293.

Wootton et al. (Jun. 1993) "Statistics of Local Complexity in Amino Acid Sequences and Sequence Databases", Computers & Chemistry, 17(2):149-163.

Yu et al. (2000)"APRIL and TALL-I and receptors BCMA and TACI: system for regulating humoral immunity", Nature Immunology, 1(3):252-256.

(Apr. 27, 2019)Cloning Vector pCMV-VEE-GFP, Complete Sequence, GenBank ID: MH891622.1, 7 pages.

International Search Report and Written Opinion for Application No. PCT/US2021/021572, dated Jul. 20, 2021, 11 pages.

International Search Report and Written Opinion for Application No. PCT/US2021/021573, dated Jul. 1, 2021, 12 pages.

International Search Report and Written Opinion for Application No. PCT/US2022/074337, dated Dec. 30, 2022, 16 pages.

(56) References Cited

OTHER PUBLICATIONS (Jul. 18, 2020) Surface Glycoprotein [Severe Acute Respiratory Syndrome Coronavirus 2], GenBank ID: YP_009724390, 3 pages.

Baden et al. (Feb. 4, 2021) "Efficacy and Safety of the mRNA-1273 SARS-CoV-2 Vaccine", The New England Journal of Medicine, 384(5):403-416.

Corbett et al. (Oct. 22, 2020) "SARS-CoV-2 mRNA Vaccine Design Enabled by Prototype Pathogen Preparedness", Nature, 586(7830):567-571.

Corbett et al. (Jun. 11, 2020) "SARS-CoV-2 mRNA Vaccine Development Enabled by Prototype Pathogen Preparedness", bioRxiv, 39 pages.

Hsieh et al. (Sep. 18, 2020) "Structure-based Design of Prefusion-stabilized SARS-CoV-2 Spikes", Science, 369(6510):1501-1505(10 pages).

Kalnin et al. (2021) "Immunogenicity and Efficacy of mRNA COVID-19 vaccine MRT5500 in Preclinical Animal models", NPJ Vaccines, 6(61):12 pages.

Keech et al. (Dec. 10, 2020) "Phase 1-2 Trial of a SARS-CoV-2 Recombinant Spike Protein Nanoparticle Vaccine", The New England Journal of Medicine, 383:2320-2332.

Olmedillas et al. (May 6, 2021) "Structure-based Design of a Highly Stable, Covalently-linked Sars-cov-2 Spike Trimer With Improved Structural Properties and Immunogenicity", bioRxiv, 51 pages.

Polack et al. (Dec. 31, 2020) "Safety and Efficacy of the BNT162b2 mRNA Covid-19 Vaccine", The New England Journal of Medicine, 383:2603-2615.

Sahin et al. (Dec. 11, 2020) "BNT162b2 Induces SARS-CoV-2-Neutralising Antibodies and T cells in Humans", medRxiv, 49 pages.

Sahin et al. (May 27, 2021) "BNT162b2 Vaccine Induces Neutralizing Antibodies and Poly-specific T Cells in Humans", Nature, 595:572-577.

Wrapp et al. (Mar. 13, 2020) "Cryo-EM Structure of the 2019-nCoV Spike in the Prefusion Conformation", Science, 367(6483):1260-1263.

Wu et al. (Mar. 12, 2020) "A New Coronavirus Associated with Human Respiratory Disease in China", Nature, 579 (7798):265-269.

\* cited by examiner

STARR spike (ARCT-021)

VEEV replicase genes — Full length native spike (1273 aa)

5'CAP—|nsP1|nsP2|nsP3|nsP4|—5'UTR—|SARS-CoV-2 spike|—3'UTR—Poly(A)-3' mRNA spike

5'CAP———5'UTR—|SARS-CoV-2 spike|—3'UTR—Poly(A)-3'

FIG. 1A

Lipid nano particle (LNP) formulations

|  | Particle diameter | Polydispersity index (PDI) | RNA trapping efficiency |
|---|---|---|---|
| mRNA | 67 nm | 0.09 | 92% |
| ARCT-021 | 69 nm | 0.09 | 91% |

FIG. 1B

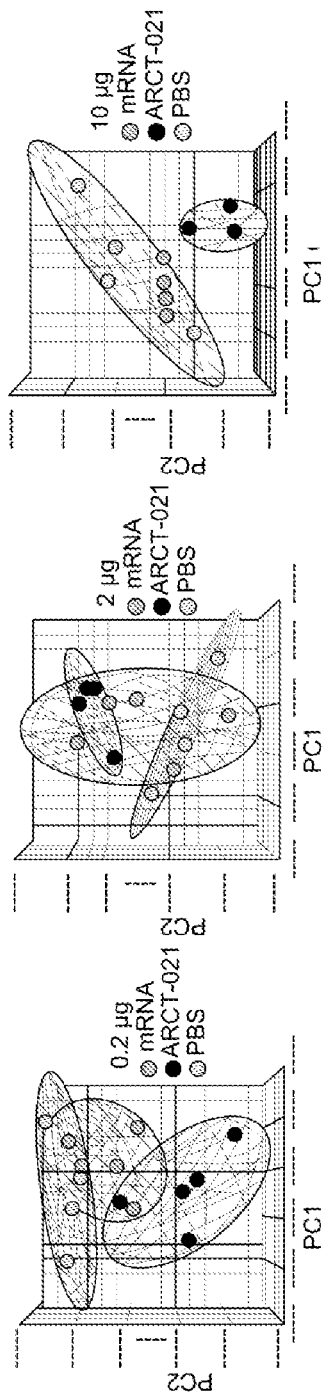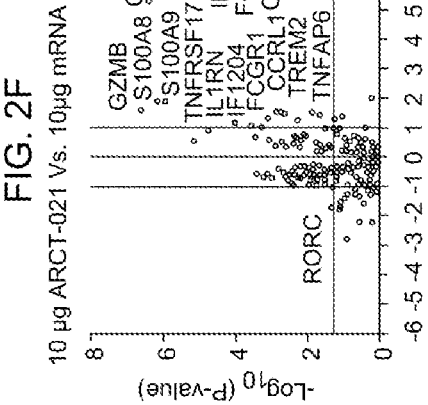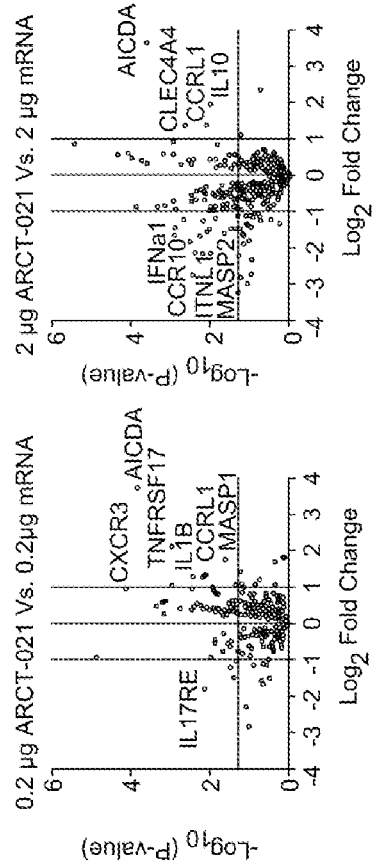

FIG. 18D (continued)

SEQUENCE LISTING

```
<160> NUMBER OF SEQ ID NOS: 129

<210> SEQ ID NO 1
<211> LENGTH: 18
<212> TYPE: DNA
<213> ORGANISM: Artificial sequence
<220> FEATURE:
<223> OTHER INFORMATION: Synthetic polynucleotide

<400> SEQUENCE: 1
gaggaaactt aagauggg                                                 18

<210> SEQ ID NO 2
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 2 ggauggg                                                              7

<210> SEQ ID NO 3
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 3 ggauagg                                                              7

<210> SEQ ID NO 4
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 4 ggagagg                                                              7
```

<210> SEQ ID NO 5
<211> LENGTH: 129
<212> TYPE: RNA
<213> ORGANISM: Artificial sequence
<220> FEATURE:
<223> OTHER INFORMATION: Synthetic polynucleotide

<400> SEQUENCE: 5
ucaacacaac auauacaaaa caaacgaauc ucaagcaauc aagcauucua cuucuauugc     60 agcauuuaa aucauuucuu uuaaagcaaa agcaauuuuc ugaaaauuuu caccauuuac    120
gaacgauag                                                           129

<210> SEQ ID NO 6
<211> LENGTH: 28
<212> TYPE: RNA
<213> ORGANISM: Artificial sequence
<220> FEATURE:
<223> OTHER INFORMATION: Synthetic polynucleotide

<400> SEQUENCE: 6
auuauuacau caaaacaaaa agccgcca                                       28

<210> SEQ ID NO 7
<211> LENGTH: 245
<212> TYPE: RNA
<213> ORGANISM: Artificial sequence
<220> FEATURE:
<223> OTHER INFORMATION: Synthetic polynucleotide

<400> SEQUENCE: 7
cuuaaggggg cgcugccuac ggagguggca gccaucuccu ucucggcauc aagcuuacca     60
uggugcccca ggcccugcuc uuggucccgc ugcuggugu cccccucugc uucggcaagu    120
uccccaucua caccauccc gacaagcugg ggccguggag cccaucgac auccaccacc    180 uguccugccc caacaaccuc guggucgagg acgagggcug caccaaccug agcggguucu    240
ccuac                                                                245

<210> SEQ ID NO 8
<211> LENGTH: 177
<212> TYPE: RNA
<213> ORGANISM: Artificial sequence
<220> FEATURE:
<223> OTHER INFORMATION: Synthetic polynucleotide

<400> SEQUENCE: 8
ugagugucgu acagccucca ggcccccccc ucccgggaga gccauagugg ucugcggaac     60
cggugaguac accggaauug ccgggaagac ugggccuuu cuuggauaaa cccacucuau    120
gcccggccau uugggcgugc ccccgcaaga cugcuagccg aguaguguug gguugcg      177

<210> SEQ ID NO 9
<211> LENGTH: 89
<212> TYPE: RNA
<213> ORGANISM: Artificial sequence
<220> FEATURE:
<223> OTHER INFORMATION: Synthetic polynucleotide

<400> SEQUENCE: 9
aauuauuggu uaaagaagua uauuagugcu aauuccccuc cguuugccu agcuuuucuc     60 uucugucaac cccacacgcc uuuggcaca                                      89

```
<210> SEQ ID NO 10
<211> LENGTH: 569
<212> TYPE: RNA
<213> ORGANISM: Artificial sequence
<220> FEATURE:
<223> OTHER INFORMATION: Synthetic polynucleotide

<400> SEQUENCE: 10
cucccucccc cccccuaac guuacuggcc gaagccgcuu ggaauaaggc cggugugcgu      60
uugucuauau guuauuuucc accauauugc cgucuuuugg caaugugagg gcccggaaac    120
cuggcccugu cuucuugacg agcauuccua ggggucuuuc cccucucgcc aaaggaaugc    180
aaggucuguu gaaugucgug aaggaagcag uuccucugga agcuucuuga agacaaacaa    240
cgucuguagc gacccuuugc aggcagcgga accccccacc uggcgacagg ugccucugcg    300
gccaaaagcc acguguauaa gauacaccug caaaggcggc acaaccccag ugccacguug    360
ugaguuggau aguguggaa agagucaaau ggcucuccuc aagcguauuc aacaaggggc    420
ugaaggaugc ccagaaggua ccccauugua ugggaucuga ucuggggccu cggugcacau    480
gcuuuacgug uguuuagucg agguuaaaaa acgucuaggc ccccgaacc acggggacgu     540 gguuuuccuu ugaaaaacac gaugauaau                                     569

<210> SEQ ID NO 11
<211> LENGTH: 44
<212> TYPE: RNA
<213> ORGANISM: Artificial sequence
<220> FEATURE:
<223> OTHER INFORMATION: Synthetic polynucleotide

<400> SEQUENCE: 11
gucagcuuuc aaacucuuug uuucuuguuu guugauugag aaua                     44

<210> SEQ ID NO 12
<211> LENGTH: 54
<212> TYPE: RNA
<213> ORGANISM: Artificial sequence
<220> FEATURE:
<223> OTHER INFORMATION: Synthetic polynucleotide

<400> SEQUENCE: 12
cucucgccug agaaaaaaaa uccacgaacc aauuucucag caaccagcag cacg           54

<210> SEQ ID NO 13
<211> LENGTH: 52
<212> TYPE: RNA
<213> ORGANISM: Artificial sequence
<220> FEATURE:
<223> OTHER INFORMATION: Synthetic polynucleotide

<400> SEQUENCE: 13
accugugagg guucgaagga aguagcagug uuuuuguuc cuagaggaag ag              52

<210> SEQ ID NO 14
<211> LENGTH: 71
<212> TYPE: RNA
<213> ORGANISM: Artificial sequence
<220> FEATURE:
<223> OTHER INFORMATION: Synthetic polynucleotide

<400> SEQUENCE: 14
acacagaaac auucgcaaaa acaaaauccc aguaucaaaa uucuucucuu uuuuucauau      60
uucgcaaaga c                                                          71
```

<210> SEQ ID NO 15
<211> LENGTH: 52
<212> TYPE: RNA
<213> ORGANISM: Artificial sequence
<220> FEATURE:
<223> OTHER INFORMATION: Synthetic polynucleotide

<400> SEQUENCE: 15
cagaaaaauu ugcuacauug uuucacaaac uucaaauauu auucauuuau uu           52

<210> SEQ ID NO 16
<211> LENGTH: 158
<212> TYPE: RNA
<213> ORGANISM: Artificial sequence
<220> FEATURE:
<223> OTHER INFORMATION: Synthetic polynucleotide

<400> SEQUENCE: 16
cuagugacug acuaggaucu gguuaccacu aaaccagccu caagaacacc cgaauggagu    60
cucuaagcua cauaauacca acuuacacuu acaaaauguu gucccccaaa auguagccau   120
ucguaucugc uccuaauaaa aagaaaguuu cuucacau                          158

<210> SEQ ID NO 17
<211> LENGTH: 166
<212> TYPE: RNA
<213> ORGANISM: Artificial sequence
<220> FEATURE:
<223> OTHER INFORMATION: Synthetic polynucleotide

<400> SEQUENCE: 17
ugcaaggcug gccggaagcc cuugccugaa agcaagauuu cagccuggaa gagggcaaag    60
uggacgggag uggacaggag uggaugcgau aagauguggu uugaagcuga ugggugccag   120
cccugcauug cugagucaau caauaaagag cuuucuuuug acccau                 166

<210> SEQ ID NO 18
<211> LENGTH: 143
<212> TYPE: RNA
<213> ORGANISM: Artificial sequence
<220> FEATURE:
<223> OTHER INFORMATION: Synthetic polynucleotide

<400> SEQUENCE: 18
acgccgaagc cugcagccau gcgaccccac gccaccccgu gccuccugcc uccgcgcagc    60
cugcagcggg agaccccuguc cccgcccag ccguccuccu gggguggacc cuaguuuaau   120
aaagauucac caaguuucac gca                                          143

<210> SEQ ID NO 19
<211> LENGTH: 220
<212> TYPE: RNA
<213> ORGANISM: Artificial sequence
<220> FEATURE:
<223> OTHER INFORMATION: Synthetic polynucleotide

<400> SEQUENCE: 19
uagagcggca aacccuagcu acacuccaua gcuaguuucu uuuuuuuug uuuuuuuuu    60 uuuuuuuuuu uuuuuuuuuu uuuuuuuuuc cuuucuuuuc cuucuuuuuu uccucuuuuc   120 uuggugggcuc caucuuagcc cuaguucacgg cuagcuguga aagguccgug agccgcauga  180
cugcagagag ugccguaacu ggucucucug cagaucaugu                        220

<210> SEQ ID NO 20
<211> LENGTH: 170
<212> TYPE: RNA
<213> ORGANISM: Artificial sequence
<220> FEATURE:
<223> OTHER INFORMATION: Synthetic polynucleotide

<400> SEQUENCE: 20
acacaucaca accacaaccu ucucaggcua cccugagaaa aaaagacaug aagacucagg    60
acucaucuuu ucuguuggug uaaaaucaac acccuaagga acacaaauuu cuuuaaacau   120
uugacuucuu gucucugugc ugcaauuaau aaaaaaugga aagaaucuac              170

<210> SEQ ID NO 21
<211> LENGTH: 110
<212> TYPE: RNA
<213> ORGANISM: Artificial sequence
<220> FEATURE:
<223> OTHER INFORMATION: Synthetic polynucleotide

<400> SEQUENCE: 21
gcuggagccu cgguagccgu uccuccugcc cgcugggccu cccaacgggc ccuccuccccc   60 uccuugcacc ggcccuuccu ggucuuugaa uaaagucuga gugggcagca              110

<210> SEQ ID NO 22
<211> LENGTH: 123
<212> TYPE: RNA
<213> ORGANISM: Artificial sequence
<220> FEATURE:
<223> OTHER INFORMATION: Synthetic polynucleotide

<400> SEQUENCE: 22
uagugcaguc acuggcacaa cgcguugccc gguaagccaa ucggguauac acggucguca    60
uacugcagac agguucuuc uacuuugcaa gauagcuag aguaguaaaa uaaauaguau     120
aag                                                                123

<210> SEQ ID NO 23
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 23 gccacc                                                               6

<210> SEQ ID NO 24
<211> LENGTH: 4
<212> TYPE: RNA
<213> ORGANISM: Artificial sequence
<220> FEATURE:
<223> OTHER INFORMATION: Synthetic polynucleotide

<400> SEQUENCE: 24 gcca                                                                 4

<210> SEQ ID NO 25
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 25
cacaaagagu aaagaagaac a                                          21

<210> SEQ ID NO 26
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 26
aacacuaaaa guagaagaaa a                                          21

<210> SEQ ID NO 27
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 27
cucagaaaga uaagaucagc c                                          21

<210> SEQ ID NO 28
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 28
aaccaaucga aagaaaccaa a                                          21

<210> SEQ ID NO 29
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 29
cucuaaucac caggaguaaa a                                          21

<210> SEQ ID NO 30
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 30
gagagagauc uuaacaaaaa a                                          21

<210> SEQ ID NO 31
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 31
uguguaacaa caacaacaac a                                          21

<210> SEQ ID NO 32
<211> LENGTH: 21
<212> TYPE: RNA

<213> ORGANISM: Artificial sequence
<220> FEATURE:
<223> OTHER INFORMATION: Synthetic polynucleotide

<400> SEQUENCE: 32
ccgcaguagg aagagaaagc c                                              21

<210> SEQ ID NO 33
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 33
aaaaaaaaaa gaaaucauaa a                                              21

<210> SEQ ID NO 34
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 34
gagagaagaa agaagaagac g                                              21

<210> SEQ ID NO 35
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 35
caauuaaaaa uacuuaccaa a                                              21

<210> SEQ ID NO 36
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 36
gcaaacagag uaagcgaaac g                                              21

<210> SEQ ID NO 37
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 37
gcgaagaaga cgaacgcaaa g                                              21

<210> SEQ ID NO 38
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 38
uuaggacugu auugacuggc c                                              21

```
<210> SEQ ID NO 39
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 39
aucaucggaa uucggaaaaa g                                              21

<210> SEQ ID NO 40
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 40
aaaacaaaag uuaaagcaga c                                              21

<210> SEQ ID NO 41
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 41
uuuaucucaa auaagaaggc a                                              21

<210> SEQ ID NO 42
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 42 ggugggagg ugagauuucu u                                               21

<210> SEQ ID NO 43
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 43
ugauuaggaa acuacaaagc c                                              21

<210> SEQ ID NO 44
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 44
cauuuuucaa uuucauaaaa c                                              21

<210> SEQ ID NO 45
<211> LENGTH: 21
<212> TYPE: RNA
<213> ORGANISM: Artificial sequence
<220> FEATURE:
```

<223> OTHER INFORMATION: Synthetic polynucleotide

<400> SEQUENCE: 45
uuacuuuuaa gcccaacaaa a                                              21

<210> SEQ ID NO 46
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 46
ggcgugugug uguuguug a                                                21

<210> SEQ ID NO 47
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 47
guggugaagg ggaagguuua g                                              21

<210> SEQ ID NO 48
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 48 uuguuuuuu uugguuggu u                                                21

<210> SEQ ID NO 49
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 49
atgggcggcg catgagagaa gcccagacca attacctacc caaa                     44

<210> SEQ ID NO 50
<211> LENGTH: 7482
<212> TYPE: DNA
<213> ORGANISM: Artificial sequence
<220> FEATURE:
<223> OTHER INFORMATION: Synthetic polynucleotide

<400> SEQUENCE: 50
atggagaaag ttcacgttga catcgaggaa gacagcccat tcctcagagc tttgcagcgg    60
agcttcccgc agtttgaggt agaagccaag caggtcactg ataatgacca tgctaatgcc   120
agagcgtttt cgcatctggc ttcaaaactg atcgaaacgg aggtggaccc atccgacacg   180
atccttgaca ttggaagtgc gcccgcccgc agaatgtatt ctaagcacaa gtatcattgt   240
atctgtccga tgagatgtgc ggaagatccg gacagattgt ataagtatgc aactaagctg   300
aagaaaaact gtaaggaaat aactgataag gaattggaca agaaaatgaa ggagctggcc   360
gccgtcatga gcgaccctga cctggaaact gagactatgt gcctccacga cgacgagtcg   420
tgtcgctacg aagggcaagt cgctgtttac caggatgtat acgccgtcga cggccccacc   480

```
agcctgtacc accaggccaa caagggcgtg agggtggcct actggatcgg cttcgacacc    540
acacccttca tgttcaagaa cctggccggc gcctacccca gctacagcac caactgggcc    600
gacgagaccg tgctgaccgc caggaacatc ggcctgtgca gcagcgacgt gatggagagg    660
agccggagag gcatgagcat cctgaggaag aaatacctga agcccagcaa caacgtgctg    720
ttcagcgtgg gcagcaccat ctaccacgag aagagggacc tgctcaggag ctggcacctg    780
cccagcgtgt tccacctgag gggcaagcag aactacacct gcaggtgcga gaccatcgtg    840
agctgcgacg gctacgtggt gaagaggatc gccatcagcc ccggcctgta cggcaagccc    900
agcggctacc cgctacaat gcacaggag ggcttcctgt gctgcaaggt gaccgacacc    960
ctgaacggcg agagggtgag cttccccgtg tgcacctacg tgcccgccac cctgtgcgac   1020
cagatgaccg gcatcctggc caccgacgtg agcgccgacg acgcccagaa gctgctcgtg   1080
ggcctgaacc agaggatcgt ggtcaacggc aggacccaga ggaacaccaa cacaatgaag   1140
aactacctgc tgcccgtggt ggcccaggct ttcgccaggt gggccaagga gtacaaggag   1200
gaccaggaag acgagaggcc cctgggcctg agggacaggc agctggtgat gggctgctgc   1260
tgggccttca gcggcacaa gatcaccagc atctacaaga ggcccgacac ccagaccatc   1320
atcaaggtga acagcgactt ccacagcttc gtgctgccca ggatcggcag caacaccctg   1380
gagatcggcc tgaggacccg gatcaggaag atgctggagg aacacaagga gcccagccca   1440
ctgatcaccg ccgaggacgt gcaggaggcc aagtgcgctg ccgacgaggc caaggaggtg   1500
agggaggccg aggaactgag ggccgccctg ccacccctgg ctgccgacgt ggaggaaccc   1560
accctggaag ccgacgtgga cctgatgctg caggaggccg cgccggaag cgtggagaca   1620
cccaggggcc tgatcaaggt gaccagctac gacggcgagg acaagatcgg cagctacgcc   1680
gtgctgagcc cacaggccgt gctgaagtcc gagaagctga gctgcatcca cccactggcc   1740
gagcaggtga tcgtgatcac ccacagcggc aggaagggca ggtacgccgt ggagccctac   1800
cacggcaagg tggtcgtgcc cgagggccac gccatccccg tgcaggactt ccaggccctg   1860
agcgagagcg ccaccatcgt gtacaacgag agggagttcg tgaacaggta cctgcaccat   1920
atcgccaccc acgcggagc cctgaacacc gacgaggaat actacaagac cgtgaagccc   1980
agcgagcacg acggcgagta cctgtacgac atcgacagga gcagtgcgt gaagaaagag   2040
ctggtgaccg gcctgggact gaccggcgag ctggtggacc caccctttcca cgagttcgcc   2100
tacgagagcc tgaggaccag acccgccgct ccctaccagg tgcccaccat cggcgtgtac   2160
ggcgtgcccg cagcggaaa gagcggcatc atcaagagcg ccgtgaccaa gaaagacctg   2220
gtggtcagcg ccaagaaaga gaactgcgcc gagatcatca gggacgtgaa gaagatgaaa   2280
ggcctggacg tgaacgcgcg caccgtggac agcgtgctgc tgaacggctg caagcacccc   2340
gtggagaccc tgtacatcga cgaggccttc gcttgccacg ccggcacccct gagggccctg   2400
atcgccatca tcaggcccaa gaaagccgtg ctgtgcggcg accccaagca gtgcggcttc   2460
ttcaacatga tgtgcctgaa ggtgcacttc aaccacgaga tctgcaccca ggtgttccac   2520
aagagcatca gcaggcggtg caccaagagc gtgaccagcg tcgtgagcac cctgttctac   2580
gacaagaaaa tgaggaccac caaccccaag gagaccaaaa tcgtgatcga caccacaggc   2640
agcaccaagc ccaagcagga cgacctgatc ctgacctgct tcagggggctg ggtgaagcag   2700
ctgcagatcg actacaaggg caacgagatc atgaccgccg ctgccagcca gggcctgacc   2760
aggaagggcg tgtacgccgt gaggtacaag gtgaacgaga acccactgta cgctcccacc   2820
```

```
agcgagcacg tgaacgtgct gctgaccagg accgaggaca ggatcgtgtg gaagaccctg    2880
gccggcgacc cctggatcaa gaccctgacc gccaagtacc ccggcaactt caccgccacc    2940
atcgaagagt ggcaggccga gcacgacgcc atcatgaggc acatcctgga gaggcccgac    3000
cccaccgacg tgttccagaa caaggccaac gtgtgctggg ccaaggccct ggtgcccgtg    3060
ctgaagaccg ccggcatcga catgaccaca gagcagtgga acaccgtgga ctacttcgag    3120
accgacaagg cccacagcgc cgagatcgtg ctgaaccagc tgtgcgtgag gttcttcggc    3180
ctggacctgg acagcggcct gttcagcgcc cccaccgtgc cactgagcat caggaacaac    3240
cactgggaca cagccccag cccaaacatg tacggcctga caaggaggt ggtcaggcag    3300 ctgagcaggc ggtacccaca gctgcccagg gccgtggcca ccggcagggt gtacgacatg    3360
aacaccggca ccctgaggaa ctacgacccc aggatcaacc tggtgcccgt gaacaggcgg    3420
ctgccccacg ccctggtgct gcaccacaac gagcacccac agagcgactt cagctccttc    3480
gtgagcaagc tgaaaggcag gaccgtgctg gtcgtgggcg agaagctgag cgtgcccggc    3540
aagatggtgg actggctgag cgacaggccc gaggccacct tccgggccag gctggacctc    3600
ggcatccccg cgacgtgcc caagtacgac atcatcttcg tgaacgtcag gaccccatac    3660
aagtaccacc attaccagca gtgcgaggac cacgccatca gctgagcat gctgaccaag    3720 aaggcctgcc tgcacctgaa ccccggaggc acctgcgtga gcatcggcta cggctacgcc    3780
gacagggcca gcgagagcat cattggcgcc atcgccaggc tgttcaagtt cagcagggtg    3840
tgcaaaccca gagcagcct ggaggaaacc gaggtgctgt tcgtgttcat cggctacgac    3900
cggaaggcca ggacccacaa cccctacaag ctgagcagca ccctgacaaa catctacacc    3960
ggcagcaggc tgcacgaggc cggctgcgcc cccagctacc acgtggtcag gggcgatatc    4020
gccaccgcca ccgagggcgt gatcatcaac gctgccaaca gcaagggcca gcccggaggc    4080
ggagtgtgcg gcgccctgta caagaagttc cccgagagct tcgacctgca gcccatcgag    4140
gtgggcaagg ccaggctggt gaagggcgcc gctaagcaca tcatccacgc cgtgggcccc    4200
aacttcaaca aggtgagcga ggtggaaggc gacaagcagc tggccgaagc ctacgagagc    4260
atcgccaaga tcgtgaacga caataactac aagagcgtgg ccatcccact gctcagcacc    4320
ggcatcttca gcggcaacaa ggacaggctg acccagagcc tgaaccacct gctcaccgcc    4380
ctggacacca ccgatgccga cgtggccatc tactgcaggg acaagaagtg ggagatgacc    4440
ctgaaggagg ccgtggccag gcgggaggcc gtggaagaga tctgcatcag cgacgactcc    4500
agcgtgaccg agcccgacgc cgagctggtg agggtgcacc ccaagagctc cctggccggc    4560
aggaagggct acagcaccag cgacggcaag accttcagct acctggaggg caccaagttc    4620
caccaggccg ctaaggacat cgccgagatc aacgctatgt ggcccgtggc caccgaggcc    4680
aacgagcagg tgtgcatgta catcctgggc gagagcatgt ccagcatcag gagcaagtgc    4740
cccgtgggag aaagcgaggc cagcacacca cccagcaccc tgccctgcct gtgcatccac    4800
gctatgacac ccgagagggt gcagcggctg aaggccagca ggcccgagca gatcaccgtg    4860
tgcagctcct tcccactgcc caagtacagg atcaccggcg tgcagaagat ccagtgcagc    4920
cagcccatcc tgttcagccc aaaggtgccc gcctacatcc accccaggaa gtacctggtg    4980 gagacccac ccgtggacga gacacccgag ccaagcgccg agaaccagag caccgagggc    5040
acacccgagc agccaccccct gatcaccgag gacgagacaa ggaccggac ccagagcccc    5100 atcattatcg aggaagagga agaggacagc atcagcctgc tgagcgacgg ccccaccccac    5160 caggtgctgc aggtggaggc cgacatccac ggcccaccca gcgtgtccag ctccagctgg    5220
```

-continued

```
agcatcccac acgccagcga cttcgacgtg acagcctga gcatcctgga caccctggag    5280
ggcgccagcg tgacctccgg cgccaccagc gccgagacca acagctactt cgccaagagc    5340
atggagttcc tggccaggcc cgtgccagct cccaggaccg tgttcaggaa cccaccccac    5400
ccagctccca ggaccaggac cccaagcctg gctcccagca gggcctgcag caggaccagc    5460
ctggtgagca ccccacccgg cgtgaacagg gtgatcacca gggaggaact ggaggccctg    5520
acacccagca ggaccccccag caggtccgtg agcaggacta gtctggtgtc caacccaccc    5580
ggcgtgaaca gggtgatcac cagggaggaa ttcgaggcct tcgtgcccca gcaacagaga    5640
cggttcgacg ccggcgccta catcttcagc agcgacaccg gccagggaca cctgcagcaa    5700
aagagcgtga ggcagaccgt gctgagcgag gtggtgctgg agaggaccga gctggaaatc    5760
agctacgccc ccaggctgga ccaggagaag gaggaactgc tcaggaagaa actgcagctg    5820
aaccccaccc cagccaacag gagcaggtac cagagcagga aggtggagaa catgaaggcc    5880
atcaccgcca ggcggatcct gcagggcctg ggacactacc tgaaggccga gggcaaggtg    5940
gagtgctaca ggaccctgca ccccgtgcca ctgtacagct ccagcgtgaa cagggccttc    6000
tccagcccca aggtggccgt ggaggcctgc aacgctatgc tgaaggagaa cttccccacc    6060
gtggccagct actgcatcat ccccgagtac gacgcctacc tggacatggt ggacggcgcc    6120
agctgctgcc tggacaccgc cagcttctgc cccgccaagc tgaggagctt ccccaagaaa    6180
cacagctacc tggagcccac catcaggagc gccgtgccca cgccatcca gaacaccctg    6240 cagaacgtgc tggccgctgc caccaagagg aactgcaacg tgacccagat gagggagctg    6300
cccgtgctgg acagcgctgc cttcaacgtg gagtgcttca gaaatacgc ctgcaacaac    6360 gagtactggg agaccttcaa ggagaacccc atcaggctga ccgaagagaa cgtggtgaac    6420
tacatcacca agctgaaggg ccccaaggcc gctgccctgt cgctaagac ccacaacctg    6480 aacatgctgc aggacatccc aatggacagg ttcgtgatgg acctgaagag ggacgtgaag    6540
gtgacacccg gcaccaagca caccgaggag aggcccaagg tgcaggtgat ccaggccgct    6600
gacccactgg ccaccgccta cctgtgcggc atccacaggg agctggtgag gcggctgaac    6660
gccgtgctgc tgcccaacat ccacaccctg ttcgacatga gcgccgagga cttcgacgcc    6720
atcatcgccg agcacttcca gcccggcgac tgcgtgctgg agaccgacat cgccagcttc    6780
gacaagagcg aggatgacgc tatggccctg accgctctga tgatcctgga ggacctgggc    6840
gtggacgccg agctgctcac cctgatcgag gctgccttcg gcgagatcag ctccatccac    6900
ctgcccacca gaccaagtt caagttcggc gctatgatga aaagcggaat gttcctgacc    6960
ctgttcgtga acaccgtgat caacattgtg atcgccagca gggtgctgcg ggagaggctg    7020
accggcagcc cctgcgctgc cttcatcggc gacgacaaca tcgtgaaggg cgtgaaaagc    7080
gacaagctga tggccgacag gtgcgccacc tggctgaaca tggaggtgaa gatcatcgac    7140
gccgtggtgg cgagaaggc cccctacttc tgccgcggat tcatcctgtg cgacagcgtg    7200
accggcaccg cctgcagggt ggccgacccc ctgaagaggc tgttcaagct gggcaagcca    7260
ctggccgctg acgatgagca cgacgatgac aggcggaggg ccctgcacga ggaaagcacc    7320
aggtggaaca gggtgggcat cctgagcgag ctgtgcaagg ccgtggagag caggtacgag    7380
accgtgggca ccagcatcat cgtgatggct atgaccacac tggccagctc cgtcaagagc    7440
ttctcctacc tgagggggc ccctataact ctctacggct aa                        7482
```

<210> SEQ ID NO 51

```
<211> LENGTH: 2493
<212> TYPE: PRT
<213> ORGANISM: Artificial sequence
<220> FEATURE:
<223> OTHER INFORMATION: Synthetic polypeptide

<400> SEQUENCE: 51

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380
```

-continued

```
Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
            405                 410                 415

Met Gly Cys Cys Trp Ala Phe Arg Arg His Lys Ile Thr Ser Ile Tyr
        420                 425                 430

Lys Arg Pro Asp Thr Gln Thr Ile Ile Lys Val Asn Ser Asp Phe His
            435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
            485                 490                 495

Ala Lys Glu Val Arg Glu Ala Glu Leu Arg Ala Ala Leu Pro Pro
        500                 505                 510

Leu Ala Ala Asp Val Glu Glu Pro Thr Leu Glu Ala Asp Val Asp Leu
    515                 520                 525

Met Leu Gln Glu Ala Gly Ala Gly Ser Val Glu Thr Pro Arg Gly Leu
530                 535                 540

Ile Lys Val Thr Ser Tyr Asp Gly Glu Asp Lys Ile Gly Ser Tyr Ala
545                 550                 555                 560

Val Leu Ser Pro Gln Ala Val Leu Lys Ser Glu Lys Leu Ser Cys Ile
            565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
            645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
            725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
            755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800
```

```
Ile Ala Ile Ile Arg Pro Lys Lys Ala Val Leu Cys Gly Asp Pro Lys
                805             810                 815
Gln Cys Gly Phe Phe Asn Met Met Cys Leu Lys Val His Phe Asn His
        820                 825                 830
Glu Ile Cys Thr Gln Val Phe His Lys Ser Ile Ser Arg Arg Cys Thr
        835                 840                 845
Lys Ser Val Thr Ser Val Val Ser Thr Leu Phe Tyr Asp Lys Lys Met
850                 855                 860
Arg Thr Thr Asn Pro Lys Glu Thr Lys Ile Val Ile Asp Thr Thr Gly
865                 870                 875                 880
Ser Thr Lys Pro Lys Gln Asp Asp Leu Ile Leu Thr Cys Phe Arg Gly
            885                 890                 895
Trp Val Lys Gln Leu Gln Ile Asp Tyr Lys Gly Asn Glu Ile Met Thr
                900                 905                 910
Ala Ala Ala Ser Gln Gly Leu Thr Arg Lys Gly Val Tyr Ala Val Arg
            915                 920                 925
Tyr Lys Val Asn Glu Asn Pro Leu Tyr Ala Pro Thr Ser Glu His Val
        930                 935                 940
Asn Val Leu Leu Thr Arg Thr Glu Asp Arg Ile Val Trp Lys Thr Leu
945                 950                 955                 960
Ala Gly Asp Pro Trp Ile Lys Thr Leu Thr Ala Lys Tyr Pro Gly Asn
                965                 970                 975
Phe Thr Ala Thr Ile Glu Glu Trp Gln Ala Glu His Asp Ala Ile Met
            980                 985                 990
Arg His Ile Leu Glu Arg Pro Asp Pro Thr Asp Val Phe Gln Asn Lys
        995                 1000                1005
Ala Asn Val Cys Trp Ala Lys Ala Leu Val Pro Val Leu Lys Thr
    1010                1015                1020
Ala Gly Ile Asp Met Thr Thr Glu Gln Trp Asn Thr Val Asp Tyr
    1025                1030                1035
Phe Glu Thr Asp Lys Ala His Ser Ala Glu Ile Val Leu Asn Gln
    1040                1045                1050
Leu Cys Val Arg Phe Phe Gly Leu Asp Leu Asp Ser Gly Leu Phe
    1055                1060                1065
Ser Ala Pro Thr Val Pro Leu Ser Ile Arg Asn Asn His Trp Asp
    1070                1075                1080
Asn Ser Pro Ser Pro Asn Met Tyr Gly Leu Asn Lys Glu Val Val
    1085                1090                1095
Arg Gln Leu Ser Arg Arg Tyr Pro Gln Leu Pro Arg Ala Val Ala
    1100                1105                1110
Thr Gly Arg Val Tyr Asp Met Asn Thr Gly Thr Leu Arg Asn Tyr
    1115                1120                1125
Asp Pro Arg Ile Asn Leu Val Pro Val Asn Arg Arg Leu Pro His
    1130                1135                1140
Ala Leu Val Leu His His Asn Glu His Pro Gln Ser Asp Phe Ser
    1145                1150                1155
Ser Phe Val Ser Lys Leu Lys Gly Arg Thr Val Leu Val Val Gly
    1160                1165                1170
Glu Lys Leu Ser Val Pro Gly Lys Met Val Asp Trp Leu Ser Asp
    1175                1180                1185
Arg Pro Glu Ala Thr Phe Arg Ala Arg Leu Asp Leu Gly Ile Pro
    1190                1195                1200
Gly Asp Val Pro Lys Tyr Asp Ile Ile Phe Val Asn Val Arg Thr
```

```
              1205                1210                1215

Pro Tyr Lys Tyr His His Tyr Gln Gln Cys Glu Asp His Ala Ile
    1220                1225                1230

Lys Leu Ser Met Leu Thr Lys Lys Ala Cys Leu His Leu Asn Pro
    1235                1240                1245

Gly Gly Thr Cys Val Ser Ile Gly Tyr Gly Tyr Ala Asp Arg Ala
    1250                1255                1260

Ser Glu Ser Ile Ile Gly Ala Ile Ala Arg Leu Phe Lys Phe Ser
    1265                1270                1275

Arg Val Cys Lys Pro Lys Ser Ser Leu Glu Glu Thr Glu Val Leu
    1280                1285                1290

Phe Val Phe Ile Gly Tyr Asp Arg Lys Ala Arg Thr His Asn Pro
    1295                1300                1305

Tyr Lys Leu Ser Ser Thr Leu Thr Asn Ile Tyr Thr Gly Ser Arg
    1310                1315                1320

Leu His Glu Ala Gly Cys Ala Pro Ser Tyr His Val Val Arg Gly
    1325                1330                1335

Asp Ile Ala Thr Ala Thr Glu Gly Val Ile Ile Asn Ala Ala Asn
    1340                1345                1350

Ser Lys Gly Gln Pro Gly Gly Gly Val Cys Gly Ala Leu Tyr Lys
    1355                1360                1365

Lys Phe Pro Glu Ser Phe Asp Leu Gln Pro Ile Glu Val Gly Lys
    1370                1375                1380

Ala Arg Leu Val Lys Gly Ala Ala Lys His Ile Ile His Ala Val
    1385                1390                1395

Gly Pro Asn Phe Asn Lys Val Ser Glu Val Glu Gly Asp Lys Gln
    1400                1405                1410

Leu Ala Glu Ala Tyr Glu Ser Ile Ala Lys Ile Val Asn Asp Asn
    1415                1420                1425

Asn Tyr Lys Ser Val Ala Ile Pro Leu Leu Ser Thr Gly Ile Phe
    1430                1435                1440

Ser Gly Asn Lys Asp Arg Leu Thr Gln Ser Leu Asn His Leu Leu
    1445                1450                1455

Thr Ala Leu Asp Thr Thr Asp Ala Asp Val Ala Ile Tyr Cys Arg
    1460                1465                1470

Asp Lys Lys Trp Glu Met Thr Leu Lys Glu Ala Val Ala Arg Arg
    1475                1480                1485

Glu Ala Val Glu Glu Ile Cys Ile Ser Asp Asp Ser Ser Val Thr
    1490                1495                1500

Glu Pro Asp Ala Glu Leu Val Arg Val His Pro Lys Ser Ser Leu
    1505                1510                1515

Ala Gly Arg Lys Gly Tyr Ser Thr Ser Asp Gly Lys Thr Phe Ser
    1520                1525                1530

Tyr Leu Glu Gly Thr Lys Phe His Gln Ala Ala Lys Asp Ile Ala
    1535                1540                1545

Glu Ile Asn Ala Met Trp Pro Val Ala Thr Glu Ala Asn Glu Gln
    1550                1555                1560

Val Cys Met Tyr Ile Leu Gly Glu Ser Met Ser Ser Ile Arg Ser
    1565                1570                1575

Lys Cys Pro Val Glu Glu Ser Glu Ala Ser Thr Pro Pro Ser Thr
    1580                1585                1590

Leu Pro Cys Leu Cys Ile His Ala Met Thr Pro Glu Arg Val Gln
    1595                1600                1605
```

```
Arg Leu Lys Ala Ser Arg Pro Glu Gln Ile Thr Val Cys Ser Ser
    1610            1615                1620

Phe Pro Leu Pro Lys Tyr Arg Ile Thr Gly Val Gln Lys Ile Gln
    1625            1630                1635

Cys Ser Gln Pro Ile Leu Phe Ser Pro Lys Val Pro Ala Tyr Ile
    1640            1645                1650

His Pro Arg Lys Tyr Leu Val Glu Thr Pro Val Asp Glu Thr
    1655            1660                1665

Pro Glu Pro Ser Ala Glu Asn Gln Ser Thr Glu Gly Thr Pro Glu
    1670            1675                1680

Gln Pro Pro Leu Ile Thr Glu Asp Glu Thr Arg Thr Arg Thr Pro
    1685            1690                1695

Glu Pro Ile Ile Ile Glu Glu Glu Glu Asp Ser Ile Ser Leu
    1700            1705                1710

Leu Ser Asp Gly Pro Thr His Gln Val Leu Gln Val Glu Ala Asp
    1715            1720                1725

Ile His Gly Pro Pro Ser Val Ser Ser Ser Ser Trp Ser Ile Pro
    1730            1735                1740

His Ala Ser Asp Phe Asp Val Asp Ser Leu Ser Ile Leu Asp Thr
    1745            1750                1755

Leu Glu Gly Ala Ser Val Thr Ser Gly Ala Thr Ser Ala Glu Thr
    1760            1765                1770

Asn Ser Tyr Phe Ala Lys Ser Met Glu Phe Leu Ala Arg Pro Val
    1775            1780                1785

Pro Ala Pro Arg Thr Val Phe Arg Asn Pro Pro His Pro Ala Pro
    1790            1795                1800

Arg Thr Arg Thr Pro Ser Leu Ala Pro Ser Arg Ala Cys Ser Arg
    1805            1810                1815

Thr Ser Leu Val Ser Thr Pro Pro Gly Val Asn Arg Val Ile Thr
    1820            1825                1830

Arg Glu Glu Leu Glu Ala Leu Thr Pro Ser Arg Thr Pro Ser Arg
    1835            1840                1845

Ser Val Ser Arg Thr Ser Leu Val Ser Asn Pro Pro Gly Val Asn
    1850            1855                1860

Arg Val Ile Thr Arg Glu Glu Phe Glu Ala Phe Val Ala Gln Gln
    1865            1870                1875

Gln Arg Arg Phe Asp Ala Gly Ala Tyr Ile Phe Ser Ser Asp Thr
    1880            1885                1890

Gly Gln Gly His Leu Gln Gln Lys Ser Val Arg Gln Thr Val Leu
    1895            1900                1905

Ser Glu Val Val Leu Glu Arg Thr Glu Leu Glu Ile Ser Tyr Ala
    1910            1915                1920

Pro Arg Leu Asp Gln Glu Lys Glu Glu Leu Leu Arg Lys Lys Leu
    1925            1930                1935

Gln Leu Asn Pro Thr Pro Ala Asn Arg Ser Arg Tyr Gln Ser Arg
    1940            1945                1950

Lys Val Glu Asn Met Lys Ala Ile Thr Ala Arg Arg Ile Leu Gln
    1955            1960                1965

Gly Leu Gly His Tyr Leu Lys Ala Glu Gly Lys Val Glu Cys Tyr
    1970            1975                1980

Arg Thr Leu His Pro Val Pro Leu Tyr Ser Ser Ser Val Asn Arg
    1985            1990                1995
```

-continued

```
Ala Phe Ser Ser Pro Lys Val Ala Val Glu Ala Cys Asn Ala Met
    2000            2005               2010
Leu Lys Glu Asn Phe Pro Thr Val Ala Ser Tyr Cys Ile Ile Pro
    2015            2020               2025
Glu Tyr Asp Ala Tyr Leu Asp Met Val Asp Gly Ala Ser Cys Cys
    2030            2035               2040
Leu Asp Thr Ala Ser Phe Cys Pro Ala Lys Leu Arg Ser Phe Pro
    2045            2050               2055
Lys Lys His Ser Tyr Leu Glu Pro Thr Ile Arg Ser Ala Val Pro
    2060            2065               2070
Ser Ala Ile Gln Asn Thr Leu Gln Asn Val Leu Ala Ala Ala Thr
    2075            2080               2085
Lys Arg Asn Cys Asn Val Thr Gln Met Arg Glu Leu Pro Val Leu
    2090            2095               2100
Asp Ser Ala Ala Phe Asn Val Glu Cys Phe Lys Lys Tyr Ala Cys
    2105            2110               2115
Asn Asn Glu Tyr Trp Glu Thr Phe Lys Glu Asn Pro Ile Arg Leu
    2120            2125               2130
Thr Glu Glu Asn Val Val Asn Tyr Ile Thr Lys Leu Lys Gly Pro
    2135            2140               2145
Lys Ala Ala Ala Leu Phe Ala Lys Thr His Asn Leu Asn Met Leu
    2150            2155               2160
Gln Asp Ile Pro Met Asp Arg Phe Val Met Asp Leu Lys Arg Asp
    2165            2170               2175
Val Lys Val Thr Pro Gly Thr Lys His Thr Glu Glu Arg Pro Lys
    2180            2185               2190
Val Gln Val Ile Gln Ala Ala Asp Pro Leu Ala Thr Ala Tyr Leu
    2195            2200               2205
Cys Gly Ile His Arg Glu Leu Val Arg Arg Leu Asn Ala Val Leu
    2210            2215               2220
Leu Pro Asn Ile His Thr Leu Phe Asp Met Ser Ala Glu Asp Phe
    2225            2230               2235
Asp Ala Ile Ile Ala Glu His Phe Gln Pro Gly Asp Cys Val Leu
    2240            2245               2250
Glu Thr Asp Ile Ala Ser Phe Asp Lys Ser Glu Asp Asp Ala Met
    2255            2260               2265
Ala Leu Thr Ala Leu Met Ile Leu Glu Asp Leu Gly Val Asp Ala
    2270            2275               2280
Glu Leu Leu Thr Leu Ile Glu Ala Ala Phe Gly Glu Ile Ser Ser
    2285            2290               2295
Ile His Leu Pro Thr Lys Thr Lys Phe Lys Phe Gly Ala Met Met
    2300            2305               2310
Lys Ser Gly Met Phe Leu Thr Leu Phe Val Asn Thr Val Ile Asn
    2315            2320               2325
Ile Val Ile Ala Ser Arg Val Leu Arg Glu Arg Leu Thr Gly Ser
    2330            2335               2340
Pro Cys Ala Ala Phe Ile Gly Asp Asp Asn Ile Val Lys Gly Val
    2345            2350               2355
Lys Ser Asp Lys Leu Met Ala Asp Arg Cys Ala Thr Trp Leu Asn
    2360            2365               2370
Met Glu Val Lys Ile Ile Asp Ala Val Val Gly Glu Lys Ala Pro
    2375            2380               2385
Tyr Phe Cys Gly Gly Phe Ile Leu Cys Asp Ser Val Thr Gly Thr
```

| | | | | | | | | | |
|---|---|---|---|---|---|---|---|---|---|
| | | 2390 | | | 2395 | | | 2400 | |
| Ala | Cys | Arg | Val | Ala | Asp | Pro | Leu | Lys | Arg | Leu | Phe | Lys | Leu | Gly |

Ala Cys Arg Val Ala Asp Pro Leu Lys Arg Leu Phe Lys Leu Gly
        2405                2410                2415

Lys Pro Leu Ala Ala Asp Asp Glu His Asp Asp Asp Arg Arg Arg
        2420                2425                2430

Ala Leu His Glu Glu Ser Thr Arg Trp Asn Arg Val Gly Ile Leu
        2435                2440                2445

Ser Glu Leu Cys Lys Ala Val Glu Ser Arg Tyr Glu Thr Val Gly
        2450                2455                2460

Thr Ser Ile Ile Val Met Ala Met Thr Thr Leu Ala Ser Ser Val
        2465                2470                2475

Lys Ser Phe Ser Tyr Leu Arg Gly Ala Pro Ile Thr Leu Tyr Gly
        2480                2485                2490

<210> SEQ ID NO 52
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 52
cctgaatgga ctacgacata gtctagtccg ccaaggccgc cacc            44

<210> SEQ ID NO 53
<211> LENGTH: 468
<212> TYPE: DNA
<213> ORGANISM: Artificial sequence
<220> FEATURE:
<223> OTHER INFORMATION: Synthetic polynucleotide

<400> SEQUENCE: 53
actcgagtat gttacgtgca aggtgattg tcacccccg aaagaccata ttgtgacaca      60
ccctcagtat cacgcccaaa catttacagc cgcggtgtca aaaaccgcgt ggacgtggtt    120
aacatccctg ctgggaggat cagccgtaat tattataatt ggcttggtgc tggctactat    180
tgtggccatg tacgtgctga ccaaccagaa acataattga atacagcagc aattggcaag    240
ctgcttacat agaactcgcg gcgattggca tgccgcctta aaatttttat tttatttttt    300 cttttcttt ccgaatcgga ttttgttttt aatatttcaa aaaaaaaaa aaaaaaaa       360 aaatctagaa aaaaaaaaa aaaaaaaa aaaaaaaa aaaaaaaa aaaaaaaa            420 aaaaaaaaa aaaaaaaa aaaaaaaa aaaaaaaa aaaaaaa                         468

<210> SEQ ID NO 54
<211> LENGTH: 7485
<212> TYPE: DNA
<213> ORGANISM: Artificial sequence
<220> FEATURE:
<223> OTHER INFORMATION: Synthetic polynucleotide

<400> SEQUENCE: 54
atgcccgaga aggtgcacgt ggacatcgag aggacagcc ccttcctgag ggccctgcag      60
aggagcttcc cacagttcga agtggaggcc aagcaggtga ccgacaacga ccacgccaac    120
gccagggcct tcagccacct ggccagcaag ctgatcgaga ccgaggtgga ccccagcgac    180
accatcctgg acatcggcag cgccccagcc aggagaatgt acagcaagca agtaccac      240 tgcatctgcc ccatgaggtg cgccgaggac cccgacaggc tgtacaagta cgccaccaaa    300
ctgaagaaga actgcaagga gatcaccgac aaggagctgg acaagaaaat gaaggagctg    360

-continued

```
gccgccgtga tgagcgaccc cgacctggag accgagacaa tgtgcctgca cgacgacgag    420
agctgcaggt acgagggcca ggtggccgtc taccaggacg tgtacgccgt cgacggcccc    480
accagcctgt accaccaggc caacaagggc gtgagggtgg cctactggat cggcttcgac    540
accacaccct tcatgttcaa gaacctggcc ggcgcctacc ccagctacag caccaactgg    600
gccgacgaga ccgtgctgac cgccaggaac atcggctgt gcagcagcga cgtgatggag    660
aggagccgga gaggcatgag catcctgagg aagaaatacc tgaagcccag caacaacgtg    720
ctgttcagcg tgggcagcac catctaccac gagaagaggg acctgctcag gagctggcac    780
ctgcccagcg tgttccacct gaggggcaag cagaactaca cctgcaggtg cgagaccatc    840
gtgagctgcg acggctacgt ggtgaagagg atcgccatca gccccggcct gtacggcaag    900
cccagcggct acgccgctac aatgcacagg gagggcttcc tgtgctgcaa ggtgaccgac    960
accctgaacg gcgagagggt gagcttcccc gtgtgcacct acgtgcccgc caccctgtgc    1020
gaccagatga ccggcatcct ggccaccgac gtgagcgccg acgacgccca gaagctgctc    1080
gtgggcctga ccagaggat cgtggtcaac ggcaggaccc agaggaacac caacacaatg    1140
aagaactacc tgctgcccgt ggtggcccag gctttcgcca ggtgggccaa ggagtacaag    1200
gaggaccagg aagacgagag gcccctgggc ctgagggaca ggcagctggt gatgggctgc    1260
tgctgggcct tcaggcggca caagatcacc agcatctaca gaggcccga cacccagacc    1320 atcatcaagg tgaacagcga cttccacagc ttcgtgctgc ccaggatcgg cagcaacacc    1380
ctggagatcg gcctgaggac ccggatcagg aagatgctgg aggaacacaa ggagcccagc    1440
ccactgatca ccgccgagga cgtgcaggag gccaagtgcg ctgccgacga ggccaaggag    1500
gtgagggagg ccgaggaact gagggccgcc ctgccacccc tggctgccga cgtggaggaa    1560 cccacccctgg aagccgacgt ggacctgatg ctgcaggagg ccggcgccgg aagcgtggag    1620
acacccaggg gcctgatcaa ggtgaccagc tacgacggcg aggacaagat cggcagctac    1680
gccgtgctga gcccacaggc cgtgctgaag tccgagaagc tgagctgcat ccacccactg    1740
gccgagcagg tgatcgtgat cacccacagc ggcaggaagg gcaggtacgc cgtggagccc    1800
taccacggca aggtggtcgt gcccgagggc cacgccatcc ccgtgcagga cttccaggcc    1860
ctgagcgaga cgccaccat cgtgtacaac gagagggagt tcgtgaacag gtacctgcac    1920
catatcgcca cccacggcgg agccctgaac accgacgagg aatactacaa gaccgtgaag    1980
cccagcgagc acgacggcga gtacctgtac gacatcgaca ggaagcagtg cgtgaagaaa    2040
gagctggtga ccggcctggg actgaccggc gagctggtgg acccacccttt ccacgagttc    2100 gcctacgaga gcctgaggac cagacccgcc gctccctacc aggtgcccac catcggcgtg    2160
tacggcgtgc ccgcagcgg aaagagcgga atcatcaaga cgccgtgac caagaaagac    2220 ctggtggtca gcgccaagaa agagaactgc gccgagatca tcaggacgt gaagaagatg    2280 aaaggcctgg acgtgaacgc gcgcaccgtg acagcgtgc tgctgaacgg ctgcaagcac    2340
cccgtggaga ccctgtacat cgacgaggcc ttcgcttgcc acgccggcac cctgagggcc    2400
ctgatcgcca tcatcaggcc caagaaagcc gtgctgtgcg gcgaccccaa gcagtgcggc    2460
ttcttcaaca tgatgtgcct gaaggtgcac ttcaaccacg atctgcac ccaggtgttc    2520 cacaagagca tcagcaggcg gtgcaccaag agcgtgacca gcgtcgtgag caccctgttc    2580
tacgacaaga aaatgaggac caccaacccc aaggagacca aaatcgtgat cgacaccaca    2640
ggcagcacca agcccaagca ggacgacctg atcctgacct gcttcagggg ctgggtgaag    2700
```

```
cagctgcaga tcgactacaa gggcaacgag atcatgaccg ccgctgccag ccagggcctg    2760
accaggaagg gcgtgtacgc cgtgaggtac aaggtgaacg agaacccact gtacgctccc    2820
accagcgagc acgtgaacgt gctgctgacc aggaccgagg acaggatcgt gtggaagacc    2880
ctggccggcg acccctggat caagaccctg accgccaagt accccggcaa cttcaccgcc    2940
accatcgaag agtggcaggc cgagcacgac gccatcatga ggcacatcct ggagaggccc    3000
gaccccaccg acgtgttcca gaacaaggcc aacgtgtgct gggccaaggc cctggtgccc    3060
gtgctgaaga ccgccggcat cgacatgacc acagagcagt ggaacaccgt ggactacttc    3120
gagaccgaca aggcccacag cgccgagatc gtgctgaacc agctgtgcgt gaggttcttc    3180
ggcctggacc tggacagcgg cctgttcagc gcccccaccg tgccactgag catcaggaac    3240
aaccactggg acaacagccc cagcccaaac atgtacggcc tgaacaagga ggtggtcagg    3300
cagctgagca ggcggtaccc acagctgccc agggccgtgg ccaccggcag ggtgtacgac    3360
atgaacaccg gcaccctgag gaactacgac cccaggatca acctggtgcc cgtgaacagg    3420
cggctgcccc acgccctggt gctgcaccac aacgagcacc cacagagcga cttcagctcc    3480
ttcgtgagca agctgaaagg caggaccgtg ctggtcgtgg gcgagaagct gagcgtgccc    3540
ggcaagatgg tggactggct gagcgacagg cccgaggcca ccttccgggc caggctggac    3600
ctcggcatcc ccggcgacgt gcccaagtac gacatcatct tcgtgaacgt caggacccca    3660
tacaagtacc accattacca gcagtgcgag gaccacgcca tcaagctgag catgctgacc    3720
aagaaggcct gcctgcacct gaaccccgga ggcacctgcg tgagcatcgg ctacggctac    3780
gccgacaggg ccagcgagag catcattggc gccatcgcca ggctgttcaa gttcagcagg    3840
gtgtgcaaac ccaagagcag cctggaggaa accgaggtgc tgttcgtgtt catcggctac    3900
gaccggaagg ccaggaccca caaccccatc aagctgagca gcaccctgac aaacatctac    3960
accggcagca ggctgcacga ggccggctgc gcccccagct accacgtggt caggggcgat    4020
atcgccaccg ccaccgaggg cgtgatcatc aacgctgcca acagcaaggg ccagcccgga    4080
ggcggagtgt gcggcgccct gtacaagaag ttccccgaga gcttcgacct gcagcccatc    4140
gaggtgggca aggccaggct ggtgaagggc ccgctaagc acatcatcca cgccgtgggc    4200
cccaacttca caaggtgagc gaggtggaa ggcgacaagc agctggccga agcctacgag    4260
agcatcgcca agatcgtgaa cgacaataac tacaagagcg tggccatccc actgctcagc    4320
accggcatct tcagcggcaa caaggacagg ctgacccaga gcctgaacca cctgctcacc    4380
gccctggaca ccaccgatgc cgacgtggcc atctactgca gggacaagaa gtgggagatg    4440
accctgaagg aggccgtggc caggcgggag gccgtggaag agatctgcat cagcgacgac    4500
tccagcgtga ccgagcccga cgccgagctg tgagggtgc accccaagag ctccctggcc    4560
ggcaggaagg gctacagcac cagcgacggc aagaccttca gctacctgga gggcaccaag    4620
ttccaccagg ccgctaagga catcgccgag atcaacgcta tgtggcccgt ggccaccgag    4680
gccaacgagc aggtgtgcat gtacatcctg ggcgagagca tgtccagcat caggagcaag    4740
tgccccgtgg aggaaagcga ggccagcaca ccacccagca ccctgccctg cctgtgcatc    4800
cacgctatga cacccgagag ggtgcagcgg ctgaaggcca gcaggccgga gcagatcacc    4860
gtgtgcagct ccttcccact gcccaagtac aggatcaccg gcgtgcagaa gatccagtgc    4920
agccagccca tcctgttcag cccaaaggtg cccgcctaca tccacccag gaagtacctg    4980 gtggagaccc cacccgtgga cgagacaccc gagccaagcg ccgagaacca gagcaccgag    5040
ggcacacccg agcagccacc cctgatcacc gaggacgaga caaggacccg gacccagag    5100
```

```
cccatcatta tcgaggaaga ggaagaggac agcatcagcc tgctgagcga cggccccacc      5160
caccaggtgc tgcaggtgga ggccgacatc cacggcccac ccagcgtgtc cagctccagc      5220
tggagcatcc cacacgccag cgacttcgac gtggacagcc tgagcatcct ggacaccctg      5280
gagggcgcca gcgtgacctc cggcgccacc agcgccgaga ccaacagcta cttcgccaag      5340
agcatggagt tcctggccag gcccgtgcca gctcccagga ccgtgttcag gaacccaccc      5400
cacccagctc ccaggaccag gaccccaagc ctggctccca gcagggcctg cagcaggacc      5460
agcctggtga gcaccccacc cggcgtgaac agggtgatca ccaggaggaa ctggaggcc      5520 ctgacaccca gcaggacccc cagcaggtcc gtgagcagga ctagtctggt gtccaaccca      5580
cccggcgtga acagggtgat caccaggag gaattcgagg ccttcgtggc ccagcaacag      5640
agacggttcg acgccggcgc ctacatcttc agcagcgaca ccggccaggg cacctgcag       5700 caaaagagcg tgaggcagac cgtgctgagc gaggtggtgc tggagaggac cgagctggaa      5760
atcagctacg ccccccaggct ggaccaggag aaggaggaac tgctcaggaa gaaactgcag      5820
ctgaacccca ccccagccaa caggagcagg taccagagca ggaaggtgga gaacatgaag      5880
gccatcaccg ccaggcggat cctgcagggc ctgggacact acctgaaggc cgagggcaag      5940
gtggagtgct acaggaccct gcaccccgtg ccactgtaca gctccagcgt gaacagggcc      6000
ttctccagcc ccaaggtggc cgtggaggcc tgcaacgcta tgctgaagga aacttcccc       6060 accgtggcca gctactgcat catccccgag tacgacgcct acctggacat ggtggacggc      6120
gccagctgct gcctggacac cgccagcttc tgccccgcca agctgaggag cttccccaag      6180
aaacacagct acctggagcc caccatcagg agcgccgtgc ccagcgccat ccagaacacc      6240
ctgcagaacg tgctggccgc tgccaccaag aggaactgca acgtgaccca gatgagggag      6300
ctgcccgtgc tggacagcgc tgccttcaac gtggagtgct tcaagaaata cgcctgcaac      6360
aacgagtact gggagacctt caaggagaac cccatcaggc tgaccgaaga gaacgtggtg      6420
aactacatca ccaagctgaa gggccccaag gccgctgccc tgttcgctaa gacccacaac      6480
ctgaacatgc tgcaggacat cccaatggaa ggttcgtga tggacctgaa gagggacgtg       6540
aaggtgacac ccggcaccaa gcacaccgag gagaggccca aggtgcaggt gatccaggcc      6600
gctgacccac tggccaccgc ctacctgtgc ggcatccaca gggagctggt gaggcggctg      6660
aacgccgtgc tgctgcccaa catccacacc ctgttcgaca tgagcgccga ggacttcgac      6720
gccatcatcg ccgagcactt ccagcccggc gactgcgtgc tggagaccga catcgccagc      6780
ttcgacaaga gcgaggatga cgctatggcc ctgaccgctc tgatgatcct ggaggacctg      6840
ggcgtggacg ccgagctgct caccctgatc gaggctgcct tcggcgagat cagctccatc      6900
cacctgccca ccaagaccaa gttcaagttc ggcgctatga tgaaaagcgg aatgttcctg      6960
accctgttcg tgaacaccgt gatcaacatt gtgatcgcca gcagggtgct gcgggagagg       7020
ctgaccggca gcccctgcgc tgccttcatc ggcgacgaca acatcgtgaa gggcgtgaaa      7080
agcgacaagc tgatggccga caggtgcgcc acctggctga acatggaggt gaagatcatc      7140
gacgccgtgg tgggcgagaa ggcccccctac ttctgcggcg gattcatcct gtgcgacagc      7200
gtgaccggca ccgcctgcag ggtggccgac ccctgaaga ggctgttcaa gctgggcaag       7260
ccactggccg ctgacgatga gcacgacgat gacaggcgga gggccctgca cgaggaaagc      7320
accaggtgga acagggtggg catcctgagc gagctgtgca aggccgtgga gagcaggtac      7380
gagaccgtgg gcaccagcat catcgtgatg gctatgacca cactggccag ctccgtcaag      7440
```
agcttctcct acctgagggg ggcccctata actctctacg gctaa    7485

<210> SEQ ID NO 55
<211> LENGTH: 2494
<212> TYPE: PRT
<213> ORGANISM: Artificial sequence
<220> FEATURE:
<223> OTHER INFORMATION: Synthetic polypeptide

<400> SEQUENCE: 55

```
Met Pro Glu Lys Val His Val Asp Ile Glu Glu Asp Ser Pro Phe Leu
1               5                   10                  15

Arg Ala Leu Gln Arg Ser Phe Pro Gln Phe Glu Val Glu Ala Lys Gln
            20                  25                  30

Val Thr Asp Asn Asp His Ala Asn Ala Arg Ala Phe Ser His Leu Ala
        35                  40                  45

Ser Lys Leu Ile Glu Thr Glu Val Asp Pro Ser Asp Thr Ile Leu Asp
    50                  55                  60

Ile Gly Ser Ala Pro Ala Arg Arg Met Tyr Ser Lys His Lys Tyr His
65                  70                  75                  80

Cys Ile Cys Pro Met Arg Cys Ala Glu Asp Pro Asp Arg Leu Tyr Lys
                85                  90                  95

Tyr Ala Thr Lys Leu Lys Lys Asn Cys Lys Glu Ile Thr Asp Lys Glu
            100                 105                 110

Leu Asp Lys Lys Met Lys Glu Leu Ala Ala Val Met Ser Asp Pro Asp
        115                 120                 125

Leu Glu Thr Glu Thr Met Cys Leu His Asp Asp Glu Ser Cys Arg Tyr
130                 135                 140

Glu Gly Gln Val Ala Val Tyr Gln Asp Val Tyr Ala Val Asp Gly Pro
145                 150                 155                 160

Thr Ser Leu Tyr His Gln Ala Asn Lys Gly Val Arg Val Ala Tyr Trp
                165                 170                 175

Ile Gly Phe Asp Thr Thr Pro Phe Met Phe Lys Asn Leu Ala Gly Ala
            180                 185                 190

Tyr Pro Ser Tyr Ser Thr Asn Trp Ala Asp Glu Thr Val Leu Thr Ala
        195                 200                 205

Arg Asn Ile Gly Leu Cys Ser Ser Asp Val Met Glu Arg Ser Arg Arg
    210                 215                 220

Gly Met Ser Ile Leu Arg Lys Lys Tyr Leu Lys Pro Ser Asn Asn Val
225                 230                 235                 240

Leu Phe Ser Val Gly Ser Thr Ile Tyr His Glu Lys Arg Asp Leu Leu
                245                 250                 255

Arg Ser Trp His Leu Pro Ser Val Phe His Leu Arg Gly Lys Gln Asn
            260                 265                 270

Tyr Thr Cys Arg Cys Glu Thr Ile Val Ser Cys Asp Gly Tyr Val Val
        275                 280                 285

Lys Arg Ile Ala Ile Ser Pro Gly Leu Tyr Gly Lys Pro Ser Gly Tyr
    290                 295                 300

Ala Ala Thr Met His Arg Glu Gly Phe Leu Cys Cys Lys Val Thr Asp
305                 310                 315                 320

Thr Leu Asn Gly Glu Arg Val Ser Phe Pro Val Cys Thr Tyr Val Pro
                325                 330                 335

Ala Thr Leu Cys Asp Gln Met Thr Gly Ile Leu Ala Thr Asp Val Ser
            340                 345                 350

Ala Asp Asp Ala Gln Lys Leu Leu Val Gly Leu Asn Gln Arg Ile Val
```

```
              355                 360                 365
Val Asn Gly Arg Thr Gln Arg Asn Thr Asn Thr Met Lys Asn Tyr Leu
370                     375                 380

Leu Pro Val Val Ala Gln Ala Phe Ala Arg Trp Ala Lys Glu Tyr Lys
385                     390                 395                 400

Glu Asp Gln Glu Asp Glu Arg Pro Leu Gly Leu Arg Asp Arg Gln Leu
                    405                 410                 415

Val Met Gly Cys Cys Trp Ala Phe Arg Arg His Lys Ile Thr Ser Ile
                420                 425                 430

Tyr Lys Arg Pro Asp Thr Gln Thr Ile Ile Lys Val Asn Ser Asp Phe
            435                 440                 445

His Ser Phe Val Leu Pro Arg Ile Gly Ser Asn Thr Leu Glu Ile Gly
        450                 455                 460

Leu Arg Thr Arg Ile Arg Lys Met Leu Glu His Lys Glu Pro Ser
465                 470                 475                 480

Pro Leu Ile Thr Ala Glu Asp Val Gln Glu Ala Lys Cys Ala Ala Asp
                485                 490                 495

Glu Ala Lys Glu Val Arg Glu Ala Glu Leu Arg Ala Ala Leu Pro
            500                 505                 510

Pro Leu Ala Ala Asp Val Glu Glu Pro Thr Leu Glu Ala Asp Val Asp
        515                 520                 525

Leu Met Leu Gln Glu Ala Gly Ala Gly Ser Val Glu Thr Pro Arg Gly
530                 535                 540

Leu Ile Lys Val Thr Ser Tyr Asp Gly Glu Asp Lys Ile Gly Ser Tyr
545                 550                 555                 560

Ala Val Leu Ser Pro Gln Ala Val Leu Lys Ser Glu Lys Leu Ser Cys
                565                 570                 575

Ile His Pro Leu Ala Glu Gln Val Ile Val Ile Thr His Ser Gly Arg
                580                 585                 590

Lys Gly Arg Tyr Ala Val Glu Pro Tyr His Gly Lys Val Val Pro
            595                 600                 605

Glu Gly His Ala Ile Pro Val Gln Asp Phe Gln Ala Leu Ser Glu Ser
        610                 615                 620

Ala Thr Ile Val Tyr Asn Glu Arg Glu Phe Val Asn Arg Tyr Leu His
625                 630                 635                 640

His Ile Ala Thr His Gly Gly Ala Leu Asn Thr Asp Glu Glu Tyr Tyr
                645                 650                 655

Lys Thr Val Lys Pro Ser Glu His Asp Gly Glu Tyr Leu Tyr Asp Ile
                660                 665                 670

Asp Arg Lys Gln Cys Val Lys Lys Glu Leu Val Thr Gly Leu Gly Leu
            675                 680                 685

Thr Gly Glu Leu Val Asp Pro Pro Phe His Glu Phe Ala Tyr Glu Ser
        690                 695                 700

Leu Arg Thr Arg Pro Ala Ala Pro Tyr Gln Val Pro Thr Ile Gly Val
705                 710                 715                 720

Tyr Gly Val Pro Gly Ser Gly Lys Ser Gly Ile Ile Lys Ser Ala Val
                725                 730                 735

Thr Lys Lys Asp Leu Val Val Ser Ala Lys Lys Glu Asn Cys Ala Glu
                740                 745                 750

Ile Ile Arg Asp Val Lys Lys Met Lys Gly Leu Asp Val Asn Ala Arg
            755                 760                 765

Thr Val Asp Ser Val Leu Leu Asn Gly Cys Lys His Pro Val Glu Thr
        770                 775                 780
```

-continued

```
Leu Tyr Ile Asp Glu Ala Phe Ala Cys His Ala Gly Thr Leu Arg Ala
785                 790                 795                 800

Leu Ile Ala Ile Ile Arg Pro Lys Lys Ala Val Leu Cys Gly Asp Pro
            805                 810                 815

Lys Gln Cys Gly Phe Phe Asn Met Met Cys Leu Lys Val His Phe Asn
        820                 825                 830

His Glu Ile Cys Thr Gln Val Phe His Lys Ser Ile Ser Arg Arg Cys
    835                 840                 845

Thr Lys Ser Val Thr Ser Val Ser Thr Leu Phe Tyr Asp Lys Lys
850                 855                 860

Met Arg Thr Thr Asn Pro Lys Glu Thr Lys Ile Val Ile Asp Thr Thr
865                 870                 875                 880

Gly Ser Thr Lys Pro Lys Gln Asp Asp Leu Ile Leu Thr Cys Phe Arg
            885                 890                 895

Gly Trp Val Lys Gln Leu Gln Ile Asp Tyr Lys Gly Asn Glu Ile Met
        900                 905                 910

Thr Ala Ala Ala Ser Gln Gly Leu Thr Arg Lys Gly Val Tyr Ala Val
    915                 920                 925

Arg Tyr Lys Val Asn Glu Asn Pro Leu Tyr Ala Pro Thr Ser Glu His
930                 935                 940

Val Asn Val Leu Leu Thr Arg Thr Glu Asp Arg Ile Val Trp Lys Thr
945                 950                 955                 960

Leu Ala Gly Asp Pro Trp Ile Lys Thr Leu Thr Ala Lys Tyr Pro Gly
            965                 970                 975

Asn Phe Thr Ala Thr Ile Glu Glu Trp Gln Ala Glu His Asp Ala Ile
        980                 985                 990

Met Arg His Ile Leu Glu Arg Pro Asp Pro Thr Asp Val Phe Gln Asn
    995                 1000                1005

Lys Ala Asn Val Cys Trp Ala Lys Ala Leu Val Pro Val Leu Lys
    1010                1015                1020

Thr Ala Gly Ile Asp Met Thr Thr Glu Gln Trp Asn Thr Val Asp
    1025                1030                1035

Tyr Phe Glu Thr Asp Lys Ala His Ser Ala Glu Ile Val Leu Asn
    1040                1045                1050

Gln Leu Cys Val Arg Phe Gly Leu Asp Leu Asp Ser Gly Leu
    1055                1060                1065

Phe Ser Ala Pro Thr Val Pro Leu Ser Ile Arg Asn Asn His Trp
    1070                1075                1080

Asp Asn Ser Pro Ser Pro Asn Met Tyr Gly Leu Asn Lys Glu Val
    1085                1090                1095

Val Arg Gln Leu Ser Arg Arg Tyr Pro Gln Leu Pro Arg Ala Val
    1100                1105                1110

Ala Thr Gly Arg Val Tyr Met Asn Thr Gly Thr Leu Arg Asn
    1115                1120                1125

Tyr Asp Pro Arg Ile Asn Leu Val Pro Val Asn Arg Arg Leu Pro
    1130                1135                1140

His Ala Leu Val Leu His His Asn Glu His Pro Gln Ser Asp Phe
    1145                1150                1155

Ser Ser Phe Val Ser Lys Leu Lys Gly Arg Thr Val Leu Val Val
    1160                1165                1170

Gly Glu Lys Leu Ser Val Pro Gly Lys Met Val Asp Trp Leu Ser
    1175                1180                1185
```

```
Asp Arg Pro Glu Ala Thr Phe Arg Ala Arg Leu Asp Leu Gly Ile
1190                1195                1200

Pro Gly Asp Val Pro Lys Tyr Asp Ile Ile Phe Val Asn Val Arg
1205                1210                1215

Thr Pro Tyr Lys Tyr His His Tyr Gln Gln Cys Glu Asp His Ala
1220                1225                1230

Ile Lys Leu Ser Met Leu Thr Lys Lys Ala Cys Leu His Leu Asn
1235                1240                1245

Pro Gly Gly Thr Cys Val Ser Ile Gly Tyr Gly Tyr Ala Asp Arg
1250                1255                1260

Ala Ser Glu Ser Ile Ile Gly Ala Ile Ala Arg Leu Phe Lys Phe
1265                1270                1275

Ser Arg Val Cys Lys Pro Lys Ser Ser Leu Glu Glu Thr Glu Val
1280                1285                1290

Leu Phe Val Phe Ile Gly Tyr Asp Arg Lys Ala Arg Thr His Asn
1295                1300                1305

Pro Tyr Lys Leu Ser Ser Thr Leu Thr Asn Ile Tyr Thr Gly Ser
1310                1315                1320

Arg Leu His Glu Ala Gly Cys Ala Pro Ser Tyr His Val Val Arg
1325                1330                1335

Gly Asp Ile Ala Thr Ala Thr Glu Gly Val Ile Ile Asn Ala Ala
1340                1345                1350

Asn Ser Lys Gly Gln Pro Gly Gly Val Cys Gly Ala Leu Tyr
1355                1360                1365

Lys Lys Phe Pro Glu Ser Phe Asp Leu Gln Pro Ile Glu Val Gly
1370                1375                1380

Lys Ala Arg Leu Val Lys Gly Ala Ala Lys His Ile Ile His Ala
1385                1390                1395

Val Gly Pro Asn Phe Asn Lys Val Ser Glu Val Glu Gly Asp Lys
1400                1405                1410

Gln Leu Ala Glu Ala Tyr Glu Ser Ile Ala Lys Ile Val Asn Asp
1415                1420                1425

Asn Asn Tyr Lys Ser Val Ala Ile Pro Leu Leu Ser Thr Gly Ile
1430                1435                1440

Phe Ser Gly Asn Lys Asp Arg Leu Thr Gln Ser Leu Asn His Leu
1445                1450                1455

Leu Thr Ala Leu Asp Thr Thr Asp Ala Asp Val Ala Ile Tyr Cys
1460                1465                1470

Arg Asp Lys Lys Trp Glu Met Thr Leu Lys Glu Ala Val Ala Arg
1475                1480                1485

Arg Glu Ala Val Glu Glu Ile Cys Ile Ser Asp Asp Ser Ser Val
1490                1495                1500

Thr Glu Pro Asp Ala Glu Leu Val Arg Val His Pro Lys Ser Ser
1505                1510                1515

Leu Ala Gly Arg Lys Gly Tyr Ser Thr Ser Asp Gly Lys Thr Phe
1520                1525                1530

Ser Tyr Leu Glu Gly Thr Lys Phe His Gln Ala Ala Lys Asp Ile
1535                1540                1545

Ala Glu Ile Asn Ala Met Trp Pro Val Ala Thr Glu Ala Asn Glu
1550                1555                1560

Gln Val Cys Met Tyr Ile Leu Gly Glu Ser Met Ser Ser Ile Arg
1565                1570                1575

Ser Lys Cys Pro Val Glu Glu Ser Glu Ala Ser Thr Pro Pro Ser
```

-continued

|  | 1580 |  |  |  | 1585 |  |  |  | 1590 |  |
|---|---|---|---|---|---|---|---|---|---|---|

Thr Leu Pro Cys Leu Cys Ile His Ala Met Thr Pro Glu Arg Val
    1595                1600                1605

Gln Arg Leu Lys Ala Ser Arg Pro Glu Gln Ile Thr Val Cys Ser
    1610                1615                1620

Ser Phe Pro Leu Pro Lys Tyr Arg Ile Thr Gly Val Gln Lys Ile
    1625                1630                1635

Gln Cys Ser Gln Pro Ile Leu Phe Ser Pro Lys Val Pro Ala Tyr
    1640                1645                1650

Ile His Pro Arg Lys Tyr Leu Val Glu Thr Pro Val Asp Glu
    1655                1660                1665

Thr Pro Glu Pro Ser Ala Glu Asn Gln Ser Thr Glu Gly Thr Pro
    1670                1675                1680

Glu Gln Pro Pro Leu Ile Thr Glu Asp Glu Thr Arg Thr Arg Thr
    1685                1690                1695

Pro Glu Pro Ile Ile Glu Glu Glu Glu Asp Ser Ile Ser
    1700                1705                1710

Leu Leu Ser Asp Gly Pro Thr His Gln Val Leu Gln Val Glu Ala
    1715                1720                1725

Asp Ile His Gly Pro Pro Ser Val Ser Ser Ser Trp Ser Ile
    1730                1735                1740

Pro His Ala Ser Asp Phe Asp Val Asp Ser Leu Ser Ile Leu Asp
    1745                1750                1755

Thr Leu Glu Gly Ala Ser Val Thr Ser Gly Ala Thr Ser Ala Glu
    1760                1765                1770

Thr Asn Ser Tyr Phe Ala Lys Ser Met Glu Phe Leu Ala Arg Pro
    1775                1780                1785

Val Pro Ala Pro Arg Thr Val Phe Arg Asn Pro Pro His Pro Ala
    1790                1795                1800

Pro Arg Thr Arg Thr Pro Ser Leu Ala Pro Ser Arg Ala Cys Ser
    1805                1810                1815

Arg Thr Ser Leu Val Ser Thr Pro Pro Gly Val Asn Arg Val Ile
    1820                1825                1830

Thr Arg Glu Glu Leu Glu Ala Leu Thr Pro Ser Arg Thr Pro Ser
    1835                1840                1845

Arg Ser Val Ser Arg Thr Ser Leu Val Ser Asn Pro Pro Gly Val
    1850                1855                1860

Asn Arg Val Ile Thr Arg Glu Glu Phe Glu Ala Phe Val Ala Gln
    1865                1870                1875

Gln Gln Arg Arg Phe Asp Ala Gly Ala Tyr Ile Phe Ser Ser Asp
    1880                1885                1890

Thr Gly Gln Gly His Leu Gln Gln Lys Ser Val Arg Gln Thr Val
    1895                1900                1905

Leu Ser Glu Val Val Leu Glu Arg Thr Glu Leu Glu Ile Ser Tyr
    1910                1915                1920

Ala Pro Arg Leu Asp Gln Glu Lys Glu Leu Leu Arg Lys Lys
    1925                1930                1935

Leu Gln Leu Asn Pro Thr Pro Ala Asn Arg Ser Arg Tyr Gln Ser
    1940                1945                1950

Arg Lys Val Glu Asn Met Lys Ala Ile Thr Ala Arg Arg Ile Leu
    1955                1960                1965

Gln Gly Leu Gly His Tyr Leu Lys Ala Glu Gly Lys Val Glu Cys
    1970                1975                1980

```
Tyr Arg Thr Leu His Pro Val Pro Leu Tyr Ser Ser Ser Val Asn
    1985            1990            1995

Arg Ala Phe Ser Ser Pro Lys Val Ala Val Glu Ala Cys Asn Ala
    2000            2005            2010

Met Leu Lys Glu Asn Phe Pro Thr Val Ala Ser Tyr Cys Ile Ile
    2015            2020            2025

Pro Glu Tyr Asp Ala Tyr Leu Asp Met Val Asp Gly Ala Ser Cys
    2030            2035            2040

Cys Leu Asp Thr Ala Ser Phe Cys Pro Ala Lys Leu Arg Ser Phe
    2045            2050            2055

Pro Lys Lys His Ser Tyr Leu Glu Pro Thr Ile Arg Ser Ala Val
    2060            2065            2070

Pro Ser Ala Ile Gln Asn Thr Leu Gln Asn Val Leu Ala Ala Ala
    2075            2080            2085

Thr Lys Arg Asn Cys Asn Val Thr Gln Met Arg Glu Leu Pro Val
    2090            2095            2100

Leu Asp Ser Ala Ala Phe Asn Val Glu Cys Phe Lys Lys Tyr Ala
    2105            2110            2115

Cys Asn Asn Glu Tyr Trp Glu Thr Phe Lys Glu Asn Pro Ile Arg
    2120            2125            2130

Leu Thr Glu Glu Asn Val Val Asn Tyr Ile Thr Lys Leu Lys Gly
    2135            2140            2145

Pro Lys Ala Ala Ala Leu Phe Ala Lys Thr His Asn Leu Asn Met
    2150            2155            2160

Leu Gln Asp Ile Pro Met Asp Arg Phe Val Met Asp Leu Lys Arg
    2165            2170            2175

Asp Val Lys Val Thr Pro Gly Thr Lys His Thr Glu Glu Arg Pro
    2180            2185            2190

Lys Val Gln Val Ile Gln Ala Ala Asp Pro Leu Ala Thr Ala Tyr
    2195            2200            2205

Leu Cys Gly Ile His Arg Glu Leu Val Arg Arg Leu Asn Ala Val
    2210            2215            2220

Leu Leu Pro Asn Ile His Thr Leu Phe Asp Met Ser Ala Glu Asp
    2225            2230            2235

Phe Asp Ala Ile Ile Ala Glu His Phe Gln Pro Gly Asp Cys Val
    2240            2245            2250

Leu Glu Thr Asp Ile Ala Ser Phe Asp Lys Ser Glu Asp Asp Ala
    2255            2260            2265

Met Ala Leu Thr Ala Leu Met Ile Leu Glu Asp Leu Gly Val Asp
    2270            2275            2280

Ala Glu Leu Leu Thr Leu Ile Glu Ala Ala Phe Gly Glu Ile Ser
    2285            2290            2295

Ser Ile His Leu Pro Thr Lys Thr Lys Phe Lys Phe Gly Ala Met
    2300            2305            2310

Met Lys Ser Gly Met Phe Leu Thr Leu Phe Val Asn Thr Val Ile
    2315            2320            2325

Asn Ile Val Ile Ala Ser Arg Val Leu Arg Glu Arg Leu Thr Gly
    2330            2335            2340

Ser Pro Cys Ala Ala Phe Ile Gly Asp Asp Asn Ile Val Lys Gly
    2345            2350            2355

Val Lys Ser Asp Lys Leu Met Ala Asp Arg Cys Ala Thr Trp Leu
    2360            2365            2370
```

| | | | | | | | | | | |
|---|---|---|---|---|---|---|---|---|---|---|
| Asn | Met | Glu | Val | Lys | Ile | Ile | Asp | Ala | Val | Val | Gly | Glu | Lys | Ala |
| | 2375 | | | | 2380 | | | | | 2385 | | | | |
| Pro | Tyr | Phe | Cys | Gly | Gly | Phe | Ile | Leu | Cys | Asp | Ser | Val | Thr | Gly |
| 2390 | | | | | 2395 | | | | | 2400 | | | | |
| Thr | Ala | Cys | Arg | Val | Ala | Asp | Pro | Leu | Lys | Arg | Leu | Phe | Lys | Leu |
| 2405 | | | | | 2410 | | | | | 2415 | | | | |
| Gly | Lys | Pro | Leu | Ala | Ala | Asp | Asp | Glu | His | Asp | Asp | Arg | Arg |
| 2420 | | | | | 2425 | | | | | 2430 | | | | |
| Arg | Ala | Leu | His | Glu | Glu | Ser | Thr | Arg | Trp | Asn | Arg | Val | Gly | Ile |
| 2435 | | | | | 2440 | | | | | 2445 | | | | |
| Leu | Ser | Glu | Leu | Cys | Lys | Ala | Val | Glu | Ser | Arg | Tyr | Glu | Thr | Val |
| 2450 | | | | | 2455 | | | | | 2460 | | | | |
| Gly | Thr | Ser | Ile | Ile | Val | Met | Ala | Met | Thr | Thr | Leu | Ala | Ser | Ser |
| 2465 | | | | | 2470 | | | | | 2475 | | | | |
| Val | Lys | Ser | Phe | Ser | Tyr | Leu | Arg | Gly | Ala | Pro | Ile | Thr | Leu | Tyr |
| 2480 | | | | | 2485 | | | | | 2490 | | | | |
| Gly |

<210> SEQ ID NO 56
<211> LENGTH: 9739
<212> TYPE: RNA
<213> ORGANISM: Artificial sequence
<220> FEATURE:
<223> OTHER INFORMATION: Synthetic polynucleotide

<400> SEQUENCE: 56

```
augggcggcg caugagagaa gcccagacca auuaccuacc caaaauggag aaaguucacg      60
uugacaucga ggaagacagc ccauuccuca gagcuuugca gcggagcuuc ccgcaguuug     120
agguagaagc caagcagguc acugauaaug accaugcuaa ugccagagcg uuuucgcauc     180
uggcuucaaa acugaucgaa acggaggugg acccauccga cacgauccuu gacauuggaa     240
gugcgcccgc ccgcagaaug uauucuaagc acaaguauca uuguaucugu ccgaugagau     300
gugcggaaga uccggacaga uuguauaagu augcaacuaa gcugaagaaa aacuguaagg     360
aaauaacuga uaaggaauug acaagaaaaa ugaaggagcu ggccgccguc augagcgacc     420
cugaccugga aacugagacu augugccucc acgacgacga gucgucgcgc uacgaagggc     480
aagucgcugu uuaccaggau guauacgccg ucgacggccc caccagccug uaccaccagg     540
ccaacaaggg cgugagggug gccuacugga ucggcuucga caccacaccc uucauguuca     600
agaaccuggc cggcgccuac cccagcuaca gcaccaacug gccgacgag accgugcuga     660
ccgccaggaa caucggccug ugcagcagcg acgugaugga gaggagccgg agaggcauga     720
gcauccugag gaagaaauac cugaagccca gcaacaacgu gcuguucagc gugggcagca     780
ccaucuacca cgagaagagg gaccugcuca ggagcuggca ccugcccagc guguccacc     840
ugaggggcaa gcagaacuac accugcaggu gcgagaccau cgugagcugc gacggcuacg     900
ugguaagag gaucgccauc agccccggcc uguacgcaa gcccagcggc uacgccgcua     960
caaugcacag ggagggcuuc cugugcugca ggugaccga cacccugaac ggcgagaggg    1020
ugagcuuccc cgugugcacc uacgugcccg ccacccugug cgaccagaug accggcaucc    1080
uggccaccga cgugagcgcc gacgacgccc agaagcugcu cgugggccug aaccagagga    1140
ucgugguaa cggcaggacc cagaggaaca ccaacacaau gaagaacuac cugcugcccg    1200
ugguggccca ggcuuucgcc aggugggcca aggaguacaa ggaggaccag aagacgaga    1260
ggccccuggg ccugagggac aggcagcugg ugaugggcug cugcugggcc uucaggcggc    1320
```

```
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga cacccagg ggccugauca    1680 aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aaggugguCg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gccagcgag cacgacggcg    2040 aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccugguggug agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgucugugc ggcgacccca agcagugcgg cuucuucaac augaugugcc    2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gcagggccu gaccaggaag ggcguguacg    2820
ccgugaggua caagguguac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca cuucaccgc caccaucgaa gaguggcagg    3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgccccacc gugccacuga gcaucaggaa caaccacugg gacaacagcc    3300
ccagcccaaa caugacggc cugaacaagg aggugucag gcagcugagc aggcgguacc    3360
cacagcugcc cagggccgug gccaccggca gggugacga caugaacacc ggcacccuga   3420
ggaacuacga ccccaggauc aaccuggugc ccgugaacag gcggcugccc cacgcccugg   3480
ugcugcacca caacgagcac ccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc cccggcgacg   3660
```

-continued

```
ugcccaagua cgacaucauc uucgugaacg ucaggacccc auacaaguac caccauuacc    3720
agcagugcga ggaccacgcc aucaagcuga gcaugcugac caagaaggcc ugccugcacc    3780
ugaaccccgg aggcaccugc gugagcaucg gcuacggcua cgccgacagg gccagcgaga    3840
gcaucauugg cgccaucgcc aggcuguuca aguucagcag ggugugcaaa cccaagagca    3900
gccuggagga aaccgaggug cuguucgugu ucaucggcua cgaccggaag gccaggaccc    3960
acaaccccua caagcugagc agcacccuga caaacaucua caccggcagc aggcugcacg    4020
aggccggcug cgcccccagc uaccacgugg ucagggcga uaucgccacc gccaccgagg    4080
gcgugaucau caacgcugcc aacagcaagg gccagcccgg aggcggagug ugcggcgccc    4140
uguacaagaa guuccccgag agcuucgacc ugcagcccau cgaggugggc aaggccaggc    4200
ugguuaaggg cgccgcuaag cacaucaucc acgccguggg ccccaacuuc aacaagguga    4260
gcgaggugga aggcgacaag cagcuggccg aagccuacga gagcaucgcc aagaucguga    4320
acgacaauaa cuacaagagc guggccaucc cacugcucag caccggcauc uucagcggca    4380
acaaggacag gcugacccag agccugaacc accugcucac cgcccuggac accaccgaug    4440
ccgacguggc caucuacugc agggacaaga guggagau gacccugaag gaggccgugg    4500
ccaggcggga ggccguggaa gagaucugca ucagcgacga cuccagcgug accgagcccg    4560
acgccgagcu ggugagggug cacccccaaga gcucccuggc cggcaggaag ggcuacagca    4620
ccagcgacgg caagaccuuc agcuaccugg agggcaccaa guccaccag gccgcuaagg    4680 acaucgccga gaucaacgcu augggcccg uggccaccga ggccaacgag caggugugca    4740
uguacauccu gggcgagagc augccagca ucaggagcaa gugccccgug gaggaaagcg    4800
aggccagcac accacccagc acccugcccu gccugugcau ccacgcuaug acacccgaga    4860 ggggugcagcg gcugaaggcc agcagggccg agcagaucac cgugugcagc ccuucccac    4920 ugcccaagua caggaucacc ggcgugcaga agauccagug cagccagccc auccuguuca    4980
gcccaaaggu gcccgccuac auccacccca ggaaguaccu ggugggagacc ccacccgugg    5040 acgagacacc cgagccaagc gccgagaacc agagcaccga gggcacaccc gagcagccac    5100
cccugaucac cgaggacgag acaaggaccc ggaccccaga gcccaucauu aucgaggaag    5160
aggaagagga cagcaucagc cugcugagcg acggcccac ccaccaggug cugcagggtgg    5220 aggccgacau ccacgcccca cccagcgugu ccagcucucag cuggagcauc ccacacgcca    5280
gcgacuucga cguggacagc cugagcaucc uggacacccu ggagggcgcc agcgugaccu    5340
ccggcgccac cagcgccgag accaacagcu acuucgccaa gagcauggag uuccuggcca    5400 ggccccguggcc agcucccagg accguguuca ggaacccacc ccacccagcu cccaggacca    5460
ggaccccaag ccuggcuccc agcagggccu gcagcaggac cagccuggug agcaccccac    5520
ccggcgugaa cagggugauc accagggagg aacuggaggc ccugacaccc agcaggaccc    5580
ccagcagguc cgugagcagg acuagucugg uguccaaccc acccgggcug aacagggtga    5640
ucaccaggga ggaauucgag gccuucgugg cccagcaaca gagacggtuuc gacgccgggcg    5700 ccuaccaucuu cagcagcgac accggccagg acaccugca gcaaaagagc gugaggcaga    5760
ccgugcugag cgaggguggut cuggagagga ccgagcggga aacucagcu accc ccaggc    5820 uggaccagga gaaggaggaa cugcucagga gaaacugca gcugaacccc accccagcca    5880
acaggagcag guaccagagc aggaagugtgg agaacauggaa ggccaucacc gccaggcgga    5940
uccugcaggg ccugggacac uaccugaagg ccgagggcaa ggugagagc uacaaggaccc    6000 ugcaccccgu gccacugguac agcuccagcg ugaacagggc cuucucagc cccaaggugg    6060
```

-continued

| | |
|---|---|
| ccguggaggc cugcaacgcu augcugaagg agaacuuccc caccguggcc agcuacugca | 6120 |
| ucaucccga guacgacgcc uaccggaca ugguggacgg cgccagcugc ugccuggaca | 6180 |
| ccgccagcuu cugccccgcc aagcugagga gcuuccccaa gaaacacagc uaccuggagc | 6240 |
| ccaccaucag gagcgccgug cccagcgcca uccagaacac ccugcagaac gugcuggccg | 6300 |
| cugccaccaa gaggaacugc aacgugaccc agaugaggga gcugcccgug cuggacagcg | 6360 |
| cugccuucaa cguggagugc uucaagaaau acgccugcaa caacgaguac ugggagaccu | 6420 |
| ucaaggagaa ccccaucagg cugaccgaag agaacguggu gaacuacauc accaagcuga | 6480 |
| agggccccaa ggccgcugcc cuguucgcua gacccacaa ccugaacaug cugcaggaca | 6540 |
| ucccaaugga cagguucgug auggaccuga agagggacgu gaaggugaca cccggcacca | 6600 |
| agcacaccga ggagaggccc aaggugcagg ugauccaggc cgcugaccca cuggccaccg | 6660 |
| ccuaccugug cggcauccac agggagcugg ugaggcggcu gaacgccgug cugcugccca | 6720 |
| acauccacac ccuguucgac augagcgccg aggacuucga cgccaucauc gccgagcacu | 6780 |
| uccagcccgg cgacugcgug cuggagaccg acaucgccag cuucgacaag agcgaggaug | 6840 |
| acgcuauggc ccugaccgcu cugaugaucc uggaggaccu gggcguggac gccgagcugc | 6900 |
| ucacccugau cgaggcugcc uucggcgaga ucagcccau ccaccugccc accaagacca | 6960 |
| aguucaaguu cggcgcuaug augaaaagcg gaauguuccu gacccuguuc gugaacaccg | 7020 |
| ugaucaacau ugugaucgcc agcagggugc ugcgggagag gcugaccggc agccccugcg | 7080 |
| cugccuucau cggcgacgac aacaucguga agggcgugaa aagcgacaag cugauggccg | 7140 |
| acaggugcgc caccuggcug aacauggagg ugaagaucau cgacgccgug gugggcgaga | 7200 |
| aggcccccua cuucgcggc ggauucaucc ugugcgacag cgugaccggc accgccugca | 7260 |
| ggguggccga cccccugaag aggcuguuca agcugggcaa gccacuggcc gcugacgaug | 7320 |
| agcacgacga ugacaggcgg agggcccugc acgaggaaag caccaggugg aacaggugg | 7380 |
| gcauccugag cgagcugugc aaggccgugg agagcaggua cgagaccgug ggcaccagca | 7440 |
| ucaucgugau ggcuaugacc acacuggcca gcuccgucaa gagcuucccc uaccugaggg | 7500 |
| gggcccuau aacucucuac ggcuaaccug aauggacuac gacauagucu aguccgccaa | 7560 |
| ggccgccacc augaaggcua uccugguggu gcugcucuac accuuugcca gccaaaugc | 7620 |
| ugacacccug uguauuggcu accaugccaa caacagcaca gacacagugg acacaguguu | 7680 |
| ggagaagaau gugacaguga cccacucugu gaaccuguug gaggacaaac acaauggcaa | 7740 |
| acuguuaaa cugagggag uggcuccacu gcaccgggc aaguguaaca uugcuggcug | 7800 |
| gauucugggc aaccugagu gugagucccu gagcacagcc uccuccuggu ccuacauugu | 7860 |
| ggagacacca uccucugaca auggcacuug uuacccugga gacuucauug acuaugagga | 7920 |
| acugagggaa caacuuuccu cugugucccu cuuugagagg uuugagauuu uccaaagac | 7980 |
| cuccuccugg ccaaaccaug acagcaacaa gggagugaca gcagccuguc cacaugcugg | 8040 |
| agccaagucc uucuacaaga accugauuug gcugggugaag aagggcaacu ccuacccaaa | 8100 |
| acugagcaag uccuacauca augacaaggg caaggaggug cugguggugu ggggcauccca | 8160 |
| ccacccaagc accucugcug accaacaguc ccucuaccag aaugcugacg ccuauguguu | 8220 |
| uguggggucc agcagauaca gcaagaaguu caagccugag auugccauca gaccaaaggu | 8280 |
| gagggaucag gagggcagga ugaacuacua cuggacccug guggaaccug agacaagau | 8340 |
| uaccuuugag gcuacaggca accugguggu gccaagauau gccuuugcua uggagaggaa | 8400 | ugcuggcucu ggcaucauca ucucugacac accuguccau gacuguaaca ccacuuguca 8460 gacaccaaag ggagccauca acaccucccu gccauuccag aacauccacc caaucaccau 8520 uggcaagugu ccaaaauaug ucaagagcac caaacugaga cuggcuacag gacugaggaa 8580 caucccaagc auccagagca ggggacuguu uggagccauu gcuggcuuca uugagggagg 8640 cuggacaggg augguggaug gcugguaugg cuaccaccac cagaaugaac agggcucugg 8700 cuaugcugcu gaccugaaaa gcacccagaa ugccauugau gagauuacca acaaggugaa 8760 cucugugauu gagaagauga acacccaguu cacagcagug ggcaaggagu ucaaccacuu 8820 ggagaagagg auugagaacc ugaacaagaa gguggaugau ggcuuccugg acaucuggac 8880 cuacaaugcu gaacugcugg ugcuguugga gaaugagagg acccuggacu accaugacag 8940 caaugugaag aaccucuaug agaaggugag gagccaacuu aaaaacaaug ccaaggagau 9000 uggcaauggc uguuuugagu ucuaccacaa gugugacaac acuuguaugg agucugugaa 9060 gaauggcacc uaugacuacc caaaauacuc ugaggaggcu aaacugaaca gggaggagau 9120 ugauggagug aaauuggaga gcaccaggau uuaccagauc cuggccaucu acagcaccgu 9180 ggccagcagc cuggugcugg uggugagccu gggcgccauc agcuucugga ugugcagcaa 9240 cggcagcuug cagugcagga ucugcaucua aacucgagua uguuacgugc aaaggugauu 9300 gucacccccc gaaagaccau auugugacac acccucagua ucacgcccaa acauuuacag 9360 ccgcggugucc aaaaaccgcg uggacguggu uaacaucccu gcugggagga ucagccguaa 9420 uuauuauaau uggcuuggug cuggcuacua uuguggccau guacgugcug accaaccaga 9480 aacauaauug aauacagcag caauuggcaa gcugcuuaca uagaacucgc ggcgauuggc 9540 augccgccuu aaaauuuuua uuuuauuuuu ucuuuucuuu uccgaaucgg auuuuguuuu 9600 uaauauuuca aaaaaaaaaa aaaaaaaaaa aaaaucuaga aaaaaaaaaa aaaaaaaaaa 9660 aaaaaaaaaa aaaaaaaaaa aaaaaaaaaa aaaaaaaaaa aaaaaaaaaa aaaaaaaaaa 9720 aaaaaaaaaa aaaaaaaaa 9739

<210> SEQ ID NO 57
<211> LENGTH: 448
<212> TYPE: RNA
<213> ORGANISM: Artificial sequence
<220> FEATURE:
<223> OTHER INFORMATION: Synthetic polynucleotide

<400> SEQUENCE: 57
gauaggcggc gcaugagaga agcccagacc aauuaccuac ccaaauagga gaaaguucac 60
guugacaucg aggaagacag cccauuccuc agagcuuugc agcggagcuu cccgcaguuu 120
gagguagaag ccaagcaggu cacugauaau gaccaugcua augccagagc guuuucgcau 180
cuggcuucaa aacugaucga aacggaggug gacccauccg acacgauccu ugacauugga 240
auagucagca uaguacauuu caucugacua auacuacaac accaccacca ugaauagagg 300
auucuuuaac augcucggcc gccgccccuu cccggccccc acugccaugu ggaggccgcg 360
gagaaggagg caggcggccc cgggaagcgg agcuacuaac uucagccugc ugaagcaggc 420
uggagacgug gaggagaacc cuggaccu 448

<210> SEQ ID NO 58
<211> LENGTH: 8
<212> TYPE: RNA
<213> ORGANISM: Artificial sequence
<220> FEATURE:
<223> OTHER INFORMATION: Synthetic polynucleotide

```
<400> SEQUENCE: 58 gggauggg                                                                8

<210> SEQ ID NO 59
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 59 gagagg                                                                  6

<210> SEQ ID NO 60
<211> LENGTH: 5
<212> TYPE: RNA
<213> ORGANISM: Artificial sequence
<220> FEATURE:
<223> OTHER INFORMATION: Synthetic polynucleotide

<400> SEQUENCE: 60 gaggg                                                                   5

<210> SEQ ID NO 61
<211> LENGTH: 8
<212> TYPE: RNA
<213> ORGANISM: Artificial sequence
<220> FEATURE:
<223> OTHER INFORMATION: Synthetic polynucleotide

<400> SEQUENCE: 61 gagauggg                                                                8

<210> SEQ ID NO 62
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 62 gagugg                                                                  6

<210> SEQ ID NO 63
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 63 gagggg                                                                  6

<210> SEQ ID NO 64
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 64 gaguagg                                                                 7

<210> SEQ ID NO 65
```

```
<211> LENGTH: 7
<212> TYPE: RNA
<213> ORGANISM: Artificial sequence
<220> FEATURE:
<223> OTHER INFORMATION: Synthetic polynucleotide

<400> SEQUENCE: 65 gaguggg                                                                    7

<210> SEQ ID NO 66
<211> LENGTH: 6
<212> TYPE: RNA
<213> ORGANISM: Artificial sequence
<220> FEATURE:
<223> OTHER INFORMATION: Synthetic polynucleotide

<400> SEQUENCE: 66 gauggg                                                                     6

<210> SEQ ID NO 67
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 67
atggactacg acatagtcta gtccgccaag                                          30

<210> SEQ ID NO 68
<211> LENGTH: 16
<212> TYPE: DNA
<213> ORGANISM: Artificial sequence
<220> FEATURE:
<223> OTHER INFORMATION: Synthetic polynucleotide

<400> SEQUENCE: 68
atggactacg acatag                                                         16

<210> SEQ ID NO 69
<211> LENGTH: 15
<212> TYPE: DNA
<213> ORGANISM: Artificial sequence
<220> FEATURE:
<223> OTHER INFORMATION: Synthetic polynucleotide

<400> SEQUENCE: 69
atggactacg acata                                                          15

<210> SEQ ID NO 70
<211> LENGTH: 5
<212> TYPE: DNA
<213> ORGANISM: Artificial sequence
<220> FEATURE:
<223> OTHER INFORMATION: Synthetic polynucleotide

<400> SEQUENCE: 70 atgga                                                                      5

<210> SEQ ID NO 71
<211> LENGTH: 3
<212> TYPE: DNA
<213> ORGANISM: Artificial sequence
<220> FEATURE:
<223> OTHER INFORMATION: Synthetic polynucleotide

<400> SEQUENCE: 71
``` atg                                                                              3

<210> SEQ ID NO 72
<211> LENGTH: 7482
<212> TYPE: DNA
<213> ORGANISM: Artificial sequence
<220> FEATURE:
<223> OTHER INFORMATION: Synthetic polynucleotide

<400> SEQUENCE: 72

| | | | | | | |
|---|---|---|---|---|---|---|
| atggagaaag | ttcacgttga | catcgaggaa | gacagcccat | tcctcagagc | tttgcagcgg | 60 |
| agcttcccgc | agtttgaggt | agaagccaag | caggtcactg | ataatgacca | tgctaatgcc | 120 |
| agagcgtttt | cgcatctggc | ttcaaaactg | atcgaaacgg | aggtggaccc | atccgacacg | 180 |
| atccttgaca | ttggaagtgc | gcccgcccgc | agaatgtatt | ctaagcacaa | gtatcattgt | 240 |
| atctgtccga | tgagatgtgc | ggaagatccg | gacagattgt | ataagtatgc | aactaagctg | 300 |
| aagaaaaact | gtaaggaaat | aactgataag | gaattggaca | gaaaatgaa | ggagctggcc | 360 |
| gccgtcatga | gcgaccctga | cctggaaact | gagactatgt | gcctccacga | cgacgagtcg | 420 |
| tgtcgctacg | aagggcaagt | cgctgtttac | caggatgtat | acgccgtcga | cggccccacc | 480 |
| agcctgtacc | accaggccaa | caagggcgtg | agggtggcct | actggatcgg | cttcgacacc | 540 |
| acacccttca | tgttcaagaa | cctggccggc | gcctacccca | gctacagcac | caactgggcc | 600 |
| gacgagaccg | tgctgaccgc | caggaacatc | ggcctgtgca | gcgacgt | gatggagagg | 660 |
| agccggagag | gcatgagcat | cctgaggaag | aaatacctga | gcccagcaa | caacgtgctg | 720 |
| ttcagcgtgg | gcagcaccat | ctaccacgag | aagagggacc | tgctcaggag | ctggcacctg | 780 |
| cccagcgtgt | tccacctgag | gggcaagcag | aactacacct | gcaggtgcga | gaccatcgtg | 840 |
| agctgcgacg | gctacgtggt | gaagaggatc | gccatcagcc | ccggcctgta | cggcaagccc | 900 |
| agcggctacg | ccgctacaat | gcacaggagg | ggcttcctgt | gctgcaaggt | gaccgacacc | 960 |
| ctgaacggcg | agagggtgag | cttccccgtg | tgcacctacg | tgcccgccac | cctgtgcgac | 1020 |
| cagatgaccg | gcatcctggc | caccgacgtg | agcgccgacg | acgcccagaa | gctgctcgtg | 1080 |
| ggcctgaacc | agaggatcgt | ggtcaacggc | aggacccaga | ggaacaccaa | cacaatgaag | 1140 |
| aactacctgc | tgcccgtggt | ggcccaggct | ttcgccaggt | gggccaagga | gtacaaggag | 1200 |
| gaccaggaag | acgagaggcc | cctgggcctg | agggacaggc | agctggtgat | gggctgctgc | 1260 |
| tgggccttca | ggcggcacaa | gatcaccagc | atctacaaga | ggcccgacac | ccagaccatc | 1320 |
| atcaaggtga | cagcgactt | ccacagcttc | gtgctgccca | ggatcggcag | caacaccctg | 1380 |
| gagatcggcc | tgaggacccg | gatcaggaag | atgctggagg | aacacaagga | gcccagccca | 1440 |
| ctgatcaccg | ccgaggacgt | gcaggaggcc | aagtgcgctg | ccgacgaggc | caaggaggtg | 1500 |
| agggaggccg | aggaactgag | ggccgccctg | ccacccctgg | ctgccgacgt | ggaggaaccc | 1560 |
| accctggaag | ccgacgtgga | cctgatgctg | caggaggccg | cgccggaag | cgtggagaca | 1620 |
| cccagggggcc | tgatcaaggt | gaccagctac | gacggcgagg | acaagatcgg | cagctacgcc | 1680 |
| gtgctgagcc | cacaggccgt | gctgaagtcc | gagaagctga | gctgcatcca | cccactggcc | 1740 |
| gagcaggtga | tcgtgatcac | ccacagcggc | aggaagggca | ggtacgccgt | ggagccctac | 1800 |
| cacggcaagg | tggtcgtgcc | cgagggccac | gccatccccg | tgcaggactt | ccaggccctg | 1860 |
| agcgagagcg | ccaccatcgt | gtacaacgag | agggagttcg | tgaacaggta | cctgcaccat | 1920 |
| atcgccaccc | acggcggagc | cctgaacacc | gacgaggaat | actacaagac | cgtgaagccc | 1980 |

```
agcgagcacg acggcgagta cctgtacgac atcgacagga agcagtgcgt gaagaaagag    2040
ctggtgaccg gcctgggact gaccggcgag ctggtggacc cacccttcca cgagttcgcc    2100
tacgagagcc tgaggaccag acccgccgct ccctaccagg tgcccaccat cggcgtgtac    2160
ggcgtgcccg gcagcggaaa gagcggcatc atcaagagcg ccgtgaccaa gaaagacctg    2220
gtggtcagcg ccaagaaaga gaactgcgcc gagatcatca gggacgtgaa gaagatgaaa    2280
ggcctggacg tgaacgcgcg caccgtggac agcgtgctgc tgaacggctg caagcacccc    2340
gtggagaccc tgtacatcga cgaggccttc gcttgccacg ccggcaccct gagggccctg    2400
atcgccatca tcaggcccaa gaaagccgtg ctgtgcggcg accccaagca gtgcggcttc    2460
ttcaacatga tgtgcctgaa ggtgcacttc aaccacgaga tctgcaccca ggtgttccac    2520
aagagcatca gcaggcggtg caccaagagc gtgaccagcg tcgtgagcac cctgttctac    2580
gacaagaaaa tgaggaccac caaccccaag gagaccaaaa tcgtgatcga caccacaggc    2640
agcaccaagc ccaagcagga cgacctgatc ctgacctgct tcaggggctg ggtgaagcag    2700
ctgcagatcg actacaaggg caacgagatc atgaccgccg ctgccagcca gggcctgacc    2760
aggaagggcg tgtacgccgt gaggtacaag gtgaacgaga acccactgta cgctcccacc    2820
agcgagcacg tgaacgtgct gctgaccagg accgaggaca ggatcgtgtg gaagaccctg    2880
gccggcgacc cctggatcaa gaccctgacc gccaagtacc ccggcaactt caccgccacc    2940
atcgaagagt ggcaggccga gcacgacgcc atcatgaggc acatcctgga gaggcccgac    3000
cccaccgacg tgttccagaa caaggccaac gtgtgctggg ccaaggccct ggtgcccgtg    3060
ctgaagaccg ccggcatcga catgaccaca gagcagtgga acaccgtgga ctacttcgag    3120
accgacaagg cccacagcgc cgagatcgtg ctgaaccagc tgtgcgtgag gttcttcggc    3180
ctggacctgg acagcggcct gttcagcgcc cccaccgtgc cactgagcat caggaacaac    3240
cactgggaca cagccccag cccaaacatg tacggcctga caaggaggt ggtcaggcag    3300
ctgagcaggc ggtacccaca gctgcccagg gccgtggcca ccggcagggt gtacgacatg    3360
aacaccggca ccctgaggaa ctacgacccc aggatcaacc tggtgcccgt gaacaggcgg    3420
ctgcccacg ccctggtgct gcaccacaac gagcacccac agagcgactt cagctccttc    3480
gtgagcaagc tgaaaggcag gaccgtgctg gtcgtgggcg agaagctgag cgtgcccggc    3540
aagatggtgg actggctgag cgacaggccc gaggccacct tccgggccag gctggacctc    3600
ggcatccccg gcgacgtgcc caagtacgac atcatcttcg tgaacgtcag gacccccata    3660
aagtaccacc attaccagca gtgcgaggac cacgccatca gctgagcat gctgaccaag    3720
aaggcctgcc tgcacctgaa ccccggaggc acctgcgtga gcatcggcta cggctacgcc    3780
gacagggcca gcgagagcat cattggcgcc atcgccaggc tgttcaagtt cagcagggtg    3840
tgcaaaccca agagcagcct ggaggaaacc gaggtgctgt tcgtgttcat cggctacgac    3900
cggaaggcca ggacccacaa ccctacaag ctgagcagca ccctgacaaa catctacacc    3960
ggcagcaggc tgcacgaggc cggctgcgcc cccagctacc acgtggtcag gggcgatatc    4020
gccaccgcca ccgagggcgt gatcatcaac gctgccaaca gcaagggcca gcccggaggc    4080
ggagtgtgcg gcgccctgta caagaagttc ccccgagagct cgacctgca gcccatcgag    4140
gtgggcaagg ccaggctggt gaagggcgcc gctaagcaca tcatccacgc cgtgggcccc    4200
aacttcaaca aggtgagcga ggtggaaggc gacaagcagc tggccgaagc ctacgagagc    4260
atcgccaaga tcgtgaacga caataactac aagagcgtgg ccatcccact gctcagcacc    4320
ggcatcttca gcggcaacaa ggacaggctg acccagagcc tgaaccacct gctcaccgcc    4380
```

-continued

```
ctggacacca ccgatgccga cgtggccatc tactgcaggg acaagaagtg ggagatgacc      4440
ctgaaggagg ccgtggccag gcgggaggcc gtggaagaga tctgcatcag cgacgactcc      4500
agcgtgaccg agcccgacgc cgagctggtg agggtgcacc ccaagagctc cctggccggc      4560
aggaagggct acagcaccag cgacggcaag accttcagct acctggaggg caccaagttc      4620
caccaggccg ctaaggacat cgccgagatc aacgctatgt ggcccgtggc caccgaggcc      4680
aacgagcagg tgtgcatgta catcctgggc gagagcatgt ccagcatcag gagcaagtgc      4740
cccgtggagg aaagcgaggc cagcacacca cccagcaccc tgccctgcct gtgcatccac      4800
gctatgacac ccgagagggt gcagcggctg aaggccagca ggcccgagca gatcaccgtg      4860
tgcagctcct tcccactgcc caagtacagg atcaccggcg tgcagaagat ccagtgcagc      4920
cagcccatcc tgttcagccc aaaggtgccc gcctacatcc accccaggaa gtacctggtg      4980 gagacccccac ccgtggacga gacccccgag ccaagcgccg agaaccagag caccgagggc      5040
acacccgagc agccaccccct gatcaccgag gacgagacaa ggaccgggac cccagagccc      5100
atcattatcg aggaagagga agaggacagc atcagcctgc tgagcgacgg ccccacccac      5160
caggtgctgc aggtggaggc cgacatccac ggcccaccca gcgtgtccag ctccagctgg      5220
agcatcccac acgccagcga cttcgacgtg gacagcctga gcatcctgga caccctggag      5280
ggcgccagcg tgacctccgg cgccaccagc gccgagacca cagctactt cgccaagagc      5340 atggagttcc tggccaggcc cgtgccagct cccaggaccg tgttcaggaa cccacccac      5400 ccagctccca ggaccaggac cccaagcctg gctcccagca gggcctgcag caggaccagc      5460
ctggtgagca ccccacccgg cgtgaacagg gtgatcacca gggaggaact ggaggccctg      5520
acacccagca ggacccccag caggtccgtg agcaggacta gtctggtgtc aacccaccc      5580 ggcgtgaaca gggtgatcac cagggaggaa ttcgaggcct cgtggcccaa gcaacagaga      5640
cggttcgacg ccggcgccta catcttcagc agcgacaccg gccagggaca cctgcagcaa      5700
aagagcgtga ggcagaccgt gctgagcgag gtggtgctgg agaggaccga gctggaaatc      5760
agctacgccc ccaggctgga ccaggagaag gaggaactgc tcaggaagaa actgcagctg      5820
aaccccaccc cagccaacag gagcaggtac cagagcagga aggtggagaa catgaaggcc      5880
atcaccgcca gcggatcct gcagggcctg ggacactacc tgaaggccga gggcaaggtg      5940
gagtgctaca ggaccctgca ccccgtgcca ctgtacagct ccagcgtgaa cagggccttc      6000
tccagcccca aggtggccgt ggaggcctgc aacgctatgc tgaaggagaa cttcccacc      6060 gtggccagct actgcatcat ccccgagtac gacgcctacc tggacatggt ggacggcgcc      6120
agctgctgcc tggacaccgc cagcttctgc ccgccaagc tgaggagctt ccccaagaaa      6180
cacagctacc tggagcccac catcaggagc gccgtgccca gcgccatcca gaacaccctg      6240
cagaacgtgc tggccgctgc caccaagagg aactgcaacg tgacccagat gagggagctg      6300
cccgtgctgg acagcgctgc cttcaacgtg gagtgcttca gaaatacgc ctgcaacaac      6360 gagtactggg agaccttcaa ggagaacccc atcaggctga ccgaagagaa cgtggtgaac      6420
tacatcacca gctgaagggg ccccaaggcc gctgccctgt cgctaagac ccacaacctg      6480 aacatgctgc aggacatccc aatggacagg ttcgtgatgg acctgaagag ggacgtgaag      6540
gtgacacccg gcaccaagca caccgaggag aggcccaagg tgcaggtgat ccaggccgct      6600
gacccactgg ccaccgccta cctgtgcgg atccacaggg agctggtgag gcggctgaac      6660
gccgtgctgc tgcccaacat ccacaccctg ttcgacatga gcgccgagga cttcgacgcc      6720
```

| | |
|---|---|
| atcatcgccg agcacttcca gcccggcgac tgcgtgctgg agaccgacat cgccagcttc | 6780 |
| gacaagagcg aggatgacgc tatggccctg accgctctga tgatcctgga ggacctgggc | 6840 |
| gtggacgccg agctgctcac cctgatcgag gctgccttcg gcgagatcag ctccatccac | 6900 |
| ctgcccacca agaccaagtt caagttcggc gctatgatga aaagcggaat gttcctgacc | 6960 |
| ctgttcgtga acaccgtgat caacattgtg atcgccagca gggtgctgcg ggagaggctg | 7020 |
| accggcagcc cctgcgctgc cttcatcggc gacgacaaca tcgtgaaggg cgtgaaaagc | 7080 |
| gacaagctga tggccgacag gtgcgccacc tggctgaaca tggaggtgaa gatcatcgac | 7140 |
| gccgtggtgg gcgagaaggc cccctacttc tgcggcggat tcatcctgtg cgacagcgtg | 7200 |
| accggcaccg cctgcagggt ggccgacccc ctgaagaggc tgttcaagct gggcaagcca | 7260 |
| ctggccgctg acgatgagca cgacgatgac aggcggaggg ccctgcacga ggaaagcacc | 7320 |
| aggtggaaca gggtgggcat cctgagcgag ctgtgcaagg ccgtggagag caggtacgag | 7380 |
| accgtgggca ccagcatcat cgtgatggct atgaccacac tggccagctc cgtcaagagc | 7440 |
| ttctcctacc tgagggggc ccctataact ctctacggct aa | 7482 |

<210> SEQ ID NO 73
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 73

| | |
|---|---|
| atgggcggcg catgagagaa gcccagacca attacctacc caaa | 44 |

<210> SEQ ID NO 74
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 74

| | |
|---|---|
| gatgggcggc gcatgagaga agcccagacc aattacctac ccaaa | 45 |

<210> SEQ ID NO 75
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 75

| | |
|---|---|
| gataggcggc gcatgagaga agcccagacc aattacctac ccaaa | 45 |

<210> SEQ ID NO 76
<211> LENGTH: 468
<212> TYPE: DNA
<213> ORGANISM: Artificial sequence
<220> FEATURE:
<223> OTHER INFORMATION: Synthetic polynucleotide

<400> SEQUENCE: 76

| | |
|---|---|
| actcgagtat gttacgtgca aaggtgattg tcacccccg aaagaccata ttgtgacaca | 60 |
| ccctcagtat cacgcccaaa catttacagc cgcggtgtca aaaccgcgt ggacgtggtt | 120 |
| aacatccctg ctgggaggat cagccgtaat tattataatt ggcttggtgc tggctactat | 180 |
| tgtggccatg tacgtgctga ccaaccagaa acataattga atacagcagc aattggcaag | 240 |

```
ctgcttacat agaactcgcg gcgattggca tgccgcctta aaattttat tttatttttt      300 cttttctttt ccgaatcgga ttttgttttt aatatttcaa aaaaaaaaaa aaaaaaaaaa      360
aaatctagaa aaaaaaaaaa aaaaaaaaaa aaaaaaaaaa aaaaaaaaaa aaaaaaaaaa      420
aaaaaaaaaa aaaaaaaaaa aaaaaaaaaa aaaaaaaaaa aaaaaaaa                   468
```

<210> SEQ ID NO 77
<211> LENGTH: 44
<212> TYPE: DNA
<213> ORGANISM: Artificial sequence
<220> FEATURE:
<223> OTHER INFORMATION: Synthetic polynucleotide

<400> SEQUENCE: 77

```
cctgaatgga ctacgacata gtctagtccg ccaaggccgc cacc                       44
```

<210> SEQ ID NO 78
<211> LENGTH: 8038
<212> TYPE: DNA
<213> ORGANISM: Artificial sequence
<220> FEATURE:
<223> OTHER INFORMATION: Synthetic polynucleotide

<400> SEQUENCE: 78

```
atgggcggcg catgagagaa gcccagacca attacctacc caaaatggag aaagttcacg      60
ttgacatcga ggaagacagc ccattcctca gagctttgca gcggagcttc ccgcagtttg      120
aggtagaagc caagcaggtc actgataatg accatgctaa tgccagagcg ttttcgcatc      180
tggcttcaaa actgatcgaa acggaggtgg acccatccga cacgatcctt gacattggaa      240
gtgcgcccgc ccgcagaatg tattctaagc acaagtatca ttgtatctgt ccgatgagat      300
gtgcggaaga tccggacaga ttgtataagt atgcaactaa gctgaagaaa aactgtaagg      360
aaataactga taaggaattg acaagaaaaa tgaaggagct ggccgccgtc atgagcgacc      420
ctgacctgga aactgagact atgtgcctcc acgacgacga gtcgtgtcgc tacgaagggc      480
aagtcgctgt ttaccaggat gtatacgccg tcgacggccc caccagcctg taccaccagg      540
ccaacaaggg cgtgagggtg gcctactgga tcggcttcga caccacaccc ttcatgttca      600
agaacctggc cggcgcctac cccagctaca gcaccaactg ggccgacgag accgtgctga      660
ccgccaggaa catcggcctg tgcagcagcg acgtgatgga ggagccggag agaggcatga      720
gcatcctgag gaagaaatac ctgaagccca gcaacaacgt gctgttcagc gtgggcagca      780
ccatctacca cgagaagagg gacctgctca ggagctggac cctgcccagc gtgttccacc      840
tgaggggcaa gcagaactac acctgcaggt gcgagaccat cgtgagctgc gacggctacg      900
tggtgaagag gatcgccatc agccccggcc tgtacgccaa gccagcggc tacgccgcta      960 caatgcacag ggagggcttc ctgtgctgca aggtgaccga caccctgaac ggcgagaggg      1020
tgagcttccc cgtgtgcacc tacgtgcccg ccaccctgtg cgaccagatg accggcatcc      1080
tggccaccga cgtgagcgcc gacgacgccc agaagctgct cgtgggcctg aaccagagga      1140
tcgtggtcaa cggcaggacc cagaggaaca ccaacacaat gaagaactac ctgctgcccg      1200
tggtggccca ggctttcgcc aggtgggcca aggagtacaa ggaggaccag gaagacgaga      1260 ggccccctggg cctgagggac aggcagctgg tgatgggctg ctgctgggcc ttcaggcggc      1320
acaagatcac cagcatctac aagaggcccg cacccagac catcatcaag gtgaacagcg      1380
acttccacag cttcgtgctg cccagggatcg gcagcaacac cctggagatc ggcctgagga      1440
```

```
cccggatcag gaagatgctg gaggaacaca aggagcccag cccactgatc accgccgagg      1500
acgtgcagga ggccaagtgc gctgccgacg aggccaagga ggtgagggag gccgaggaac      1560
tgagggccgc cctgccaccc ctggctgccg acgtggagga acccaccctg gaagccgacg      1620
tggacctgat gctgcaggag gccggcgccg gaagcgtgga gacacccagg ggcctgatca      1680
aggtgaccag ctacgacggc gaggacaaga tcggcagcta cgccgtgctg agcccacagg      1740
ccgtgctgaa gtccgagaag ctgagctgca tccacccact ggccgagcag gtgatcgtga      1800
tcacccacag cggcaggaag ggcaggtacg ccgtggagcc ctaccacggc aaggtggtcg      1860
tgcccgaggg ccacgccatc cccgtgcagg acttccaggc cctgagcgag agcgccacca      1920
tcgtgtacaa cgagagggag ttcgtgaaca ggtacctgca ccatatcgcc acccacggcg      1980
gagccctgaa caccgacgag gaatactaca agaccgtgaa gcccagcgag cacgacggcg      2040
agtacctgta cgacatcgac aggaagcagt gcgtgaagaa agagctggtg accggcctgg      2100
gactgaccgg cgagctggtg gacccaccct tccacgagtt cgcctacgag agcctgagga      2160
ccagacccgc cgctccctac caggtgccca ccatcggcgt gtacgccgtg cccggcagcg      2220
gaaagagcgg catcatcaag agcgccgtga ccaagaaaga cctggtggtc agcgccaaga      2280
aagagaactg cgccgagatc atcagggacg tgaagaagat gaaaggcctg gacgtgaacg      2340
cgcgcaccgt ggacagcgtg ctgctgaacg gctgcaagca ccccgtggag accctgtaca      2400
tcgacgaggc cttcgcttgc cacgccggca ccctgagggc cctgatcgcc atcatcaggc      2460
ccaagaaagc cgtgctgtgc ggcgaccccca agcagtgcgg cttcttcaac atgatgtgcc      2520
tgaaggtgca cttcaaccac gagatctgca cccaggtgtt ccacaagagc atcagcaggc      2580
ggtgcaccaa gagcgtgacc agcgtcgtga gcaccctgtt ctacgacaag aaaatgagga      2640
ccaccaaccc caaggagacc aaaatcgtga tcgacaccac aggcagcacc aagcccaagc      2700
aggacgacct gatcctgacc tgcttcaggg gctgggtgaa gcagctgcag atcgactaca      2760
agggcaacga gatcatgacc gccgctgcca gccaggcct gaccaggaag ggcgtgtacg      2820
ccgtgaggta caaggtgaac gagaacccac tgtacgctcc caccagcgag cacgtgaacg      2880
tgctgctgac caggaccgag gacaggatcg tgtggaagac cctggccggc gacccctgga      2940
tcaagaccct gaccgccaag taccccggca acttcaccgc caccatcgaa gagtggcagg      3000
ccgagcacga cgccatcatg aggcacatcc tggagaggcc cgaccccacc gacgtgttcc      3060
agaacaaggc caacgtgtgc tgggccaagg ccctggtgcc cgtgctgaag accgccggca      3120
tcgacatgac cacagagcag tggaacaccg tggactactt cgagaccgac aaggcccaca      3180
gcgccgagat cgtgctgaac cagctgtgcg tgaggttctt cggcctggac ctggacagcg      3240
gcctgttcag cgccccccacc gtgccactga gcatcaggaa caaccactgg gacaacagcc      3300
ccagcccaaa catgtacggc ctgaacaagg aggtggtcag gcagctgagc aggcggtacc      3360
cacagctgcc cagggccgtg gccaccggca gggtgtacga catgaacacc ggcacccctga      3420 ggaactacga ccccaggatc aacctggtgc ccgtgaacag gcggctgccc cacgccctgg      3480
tgctgcacca acgagcac ccacagagcg acttcagctc cttcgtgagc aagctgaaag      3540
gcaggaccgt gctggtcgtg ggcgagaagc tgagcgtgcc cggcaagatg gtggactggc      3600
tgagcgacag gccccgaggcc accttccggg ccaggctgga cctcggcatc cccggcgacg      3660
tgcccaagta cgacatcatc ttcgtgaacg tcaggacccc atacaagtac caccattacc      3720
agcagtgcga ggaccacgcc atcaagctga gcatgctgac caagaaggcc tgcctgcacc      3780
tgaaccccgg aggcacctgc gtgagcatcg gctacggcta cgccgacagg gccagcgaga      3840
```

```
gcatcattgg cgccatcgcc aggctgttca agttcagcag ggtgtgcaaa cccaagagca    3900
gcctggagga aaccgaggtg ctgttcgtgt tcatcggcta cgaccggaag gccaggaccc    3960
acaaccccta caagctgagc agcaccctga caaacatcta caccggcagc aggctgcacg    4020
aggccggctg cgccccagc taccacgtgg tcaggggcga tatcgccacc gccaccgagg    4080
gcgtgatcat caacgctgcc aacagcaagg ccagcccgg aggcggagtg tgcggcgccc    4140
tgtacaagaa gttccccgag agcttcgacc tgcagcccat cgaggtgggc aaggccaggc    4200
tggtgaaggg cgccgctaag cacatcatcc acgccgtggg ccccaacttc aacaaggtga    4260
gcgaggtgga aggcgacaag cagctggccg aagcctacga gagcatcgcc aagatcgtga    4320
acgacaataa ctacaagagc gtggccatcc cactgctcag caccggcatc ttcagcggca    4380
acaaggacag gctgacccag agcctgaacc acctgctcac cgccctggac accaccgatg    4440
ccgacgtggc catctactgc agggacaaga agtgggagat gaccctgaag gaggccgtgg    4500
ccaggcggga ggccgtggaa gagatctgca tcagcgacga ctccagcgtg accgagcccg    4560
acgccgagct ggtgagggtg caccccaaga gctccctggc cggcaggaag ggctacagca    4620
ccagcgacgc caagaccttc agctacctgg agggcaccaa gttccaccag gccgctaagg    4680
acatcgccga gatcaacgct atgtggcccg tggccaccga ggccaacgag caggtgtgca    4740
tgtacatcct gggcgagagc atgtccagca tcaggagcaa gtgccccgtg gaggaaagcg    4800
aggccagcac accacccagc accctgccct gcctgtgcat ccacgctatg acacccgaga    4860
gggtgcagcg gctgaaggcc agcaggcccg agcagatcac cgtgtgcagc tccttcccac    4920
tgcccaagta caggatcacc ggcgtgcaga agatccagtg cagccagccc atcctgttca    4980
gcccaaaggt gcccgcctac atccaccccca ggaagtacct ggtggagacc ccacccgtgg    5040
acgagacacc cgagccaagc gccgagaacc agagcaccga gggcacaccc gagcagccac    5100
ccctgatcac cgaggacgag acaaggaccc ggaccccaga gcccatcatt atcgaggaag    5160
aggaagagga cagcatcagc ctgctgagcg acggccccac ccaccaggtg ctgcaggtgg    5220
aggccgacat ccacgcccca cccagcgtgt ccagctccag ctggagcatc ccacacgcca    5280
gcgacttcga cgtggacagc ctgagcatcc tggacacccct ggagggcgcc agcgtgacct    5340
ccggcgccac cagcgccgag accaacagct acttcgccaa gagcatggag ttcctggcca    5400
ggcccgtgcc agctcccagg accgtgttca ggaacccacc ccaccagct cccaggacca    5460 ggaccccaag cctggctccc agcagggcct gcagcaggac cagcctggtg agcaccccac    5520
ccggcgtgaa cagggtgatc accagggagg aactggaggc cctgacaccc agcaggaccc    5580
ccagcaggtc cgtgagcagg actagtctgg tgtccaaccc acccggcgtg aacagggtga    5640
tcaccaggga ggaattcgag gccttcgtgg cccagcaaca gagacggttc gacgccggcg    5700
cctacatctt cagcagcgac accggccagg acacctgca gcaaaagagc gtgaggcaga    5760
ccgtgctgag cgaggtggtg ctggagagga ccgagctgga aatcagctac gcccccaggc    5820
tggaccagga gaaggaggaa ctgctcagga agaaactgca gctgaacccc accccagcca    5880
acaggagcag gtaccagagc aggaaggtgg agaacatgaa ggccatcacc gccaggcgga    5940
tcctgcaggg cctgggacac tacctgaagg ccgagggcaa ggtggagtgc tacaggaccc    6000
tgcaccccgt gccactgtac agctccagcg tgaacagggc cttctccagc cccaaggtgg    6060 ccgtggagc ctgcaacgct atgctgaagg agaacttccc caccgtggcc agctactgca    6120 tcatcccga gtacgacgcc tacctggaca tggtggacgg cgccagctgc tgcctggaca    6180
```

```
ccgccagctt ctgccccgcc aagctgagga gcttccccaa gaaacacagc tacctggagc    6240
ccaccatcag gagcgccgtg cccagcgcca tccagaacac cctgcagaac gtgctggccg    6300
ctgccaccaa gaggaactgc aacgtgaccc agatgaggga gctgcccgtg ctggacagcg    6360
ctgccttcaa cgtggagtgc ttcaagaaat acgcctgcaa caacgagtac tgggagacct    6420
tcaaggagaa ccccatcagg ctgaccgaag agaacgtggt gaactacatc accaagctga    6480
agggccccaa ggccgctgcc ctgttcgcta gacccacaa cctgaacatg ctgcaggaca    6540
tcccaatgga caggttcgtg atggacctga gagggacgt gaaggtgaca cccggcacca    6600
agcacaccga ggagaggccc aaggtgcagg tgatccaggc cgctgaccca ctggccaccg    6660
cctacctgtg cggcatccac agggagctgg tgaggcggct gaacgccgtg ctgctgccca    6720
acatccacac cctgttcgac atgagcgccg aggacttcga cgccatcatc gccgagcact    6780
tccagcccgg cgactgcgtg ctggagaccg acatcgccag cttcgacaag agcgaggatg    6840
acgctatggc cctgaccgct ctgatgatcc tggaggacct gggcgtggac gccgagctgc    6900
tcaccctgat cgaggctgcc ttcggcgaga tcagctccat ccacctgccc accaagacca    6960
agttcaagtt cggcgctatg atgaaaagcg gaatgttcct gaccctgttc gtgaacaccg    7020
tgatcaacat tgtgatcgcc agcagggtgc tgcgggagag gctgaccggc agccctgcg    7080 ctgccttcat cggcgacgac aacatcgtga agggcgtgaa agcgacaag ctgatggccg    7140 acaggtgcgc cacctggctg aacatggagg tgaagatcat cgacgccgtg gtgggcgaga    7200
aggcccccta cttctgcggc ggattcatcc tgtgcgacag cgtgaccggc accgcctgca    7260
gggtggccga cccctgaag aggctgttca gctgggcaa gccactggcc gctgacgatg    7320
agcacgacga tgacaggcgg agggccctgc acgaggaaag caccaggtgg aacagggtgg    7380
gcatcctgag cgagctgtgc aaggccgtgg agagcaggta cgagaccgtg ggcaccagca    7440
tcatcgtgat ggctatgacc acactggcca gctccgtcaa gagcttctcc tacctgaggg    7500
gggcccctat aactctctac ggctaacctg aatggactac gacatagtct agtccgccaa    7560
ggccgccacc actcgagtat gttacgtgca aggtgattg tcaccccccg aaagaccata    7620
ttgtgacaca ccctcagtat cacgcccaaa catttacagc cgcggtgtca aaaaccgcgt    7680
ggacgtggtt aacatccctg ctgggaggat cagccgtaat tattataatt ggcttggtgc    7740
tggctactat tgtggccatg tacgtgctga ccaaccagaa acataattga atacagcagc    7800
aattggcaag ctgcttacat agaactcgcg gcgattggca tgccgcctta aaatttttat    7860 tttattttt cttttctttt ccgaatcgga ttttgttttt aatatttcaa aaaaaaaaa     7920 aaaaaaaaaa aaatctagaa aaaaaaaaa aaaaaaaaa aaaaaaaaa aaaaaaaaa      7980 aaaaaaaaa aaaaaaaaaa aaaaaaaaa aaaaaaaaa aaaaaaaaa aaaaaaa         8038
```

<210> SEQ ID NO 79
<211> LENGTH: 2493
<212> TYPE: PRT
<213> ORGANISM: Artificial sequence
<220> FEATURE:
<223> OTHER INFORMATION: Synthetic polypeptide

<400> SEQUENCE: 79

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser

```
            35                  40                  45
Lys Leu Ile Glu Thr Glu Val Asp Pro Ser Asp Thr Ile Leu Asp Ile
 50                  55                  60

Gly Ser Ala Pro Ala Arg Arg Met Tyr Ser Lys His Lys Tyr His Cys
 65                  70                  75                  80

Ile Cys Pro Met Arg Cys Ala Glu Asp Pro Asp Arg Leu Tyr Lys Tyr
                 85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
450                 455                 460
```

```
Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
            485                 490                 495

Ala Lys Glu Val Arg Glu Ala Glu Glu Leu Arg Ala Ala Leu Pro Pro
        500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
530                 535                 540

Ile Lys Val Thr Ser Tyr Asp Gly Glu Asp Lys Ile Gly Ser Tyr Ala
545                 550                 555                 560

Val Leu Ser Pro Gln Ala Val Leu Lys Ser Glu Lys Leu Ser Cys Ile
            565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Pro Glu
        595                 600                 605

Gly His Ala Ile Pro Val Gln Asp Phe Gln Ala Leu Ser Glu Ser Ala
610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
            645                 650                 655

Thr Val Lys Pro Ser Glu His Asp Gly Glu Tyr Leu Tyr Asp Ile Asp
        660                 665                 670

Arg Lys Gln Cys Val Lys Lys Glu Leu Val Thr Gly Leu Gly Leu Thr
675                 680                 685

Gly Glu Leu Val Asp Pro Pro Phe His Glu Phe Ala Tyr Glu Ser Leu
690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
            725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
            755                 760                 765

Val Asp Ser Val Leu Leu Asn Gly Cys Lys His Pro Val Glu Thr Leu
        770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
            835                 840                 845

Lys Ser Val Thr Ser Val Val Ser Thr Leu Phe Tyr Asp Lys Lys Met
        850                 855                 860

Arg Thr Thr Asn Pro Lys Glu Thr Lys Ile Val Ile Asp Thr Thr Gly
865                 870                 875                 880
```

```
                                        -continued

Ser Thr Lys Pro Lys Gln Asp Asp Leu Ile Leu Thr Cys Phe Arg Gly
            885                 890                 895

Trp Val Lys Gln Leu Gln Ile Asp Tyr Lys Gly Asn Glu Ile Met Thr
        900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
            965                 970                 975

Phe Thr Ala Thr Ile Glu Glu Trp Gln Ala Glu His Asp Ala Ile Met
        980                 985                 990

Arg His Ile Leu Glu Arg Pro Asp Pro Thr Asp Val Phe Gln Asn Lys
        995                 1000                1005

Ala Asn Val Cys Trp Ala Lys Ala Leu Val Pro Val Leu Lys Thr
        1010                1015                1020

Ala Gly Ile Asp Met Thr Thr Glu Gln Trp Asn Thr Val Asp Tyr
        1025                1030                1035

Phe Glu Thr Asp Lys Ala His Ser Ala Glu Ile Val Leu Asn Gln
        1040                1045                1050

Leu Cys Val Arg Phe Phe Gly Leu Asp Leu Asp Ser Gly Leu Phe
        1055                1060                1065

Ser Ala Pro Thr Val Pro Leu Ser Ile Arg Asn Asn His Trp Asp
        1070                1075                1080

Asn Ser Pro Ser Pro Asn Met Tyr Gly Leu Asn Lys Glu Val Val
        1085                1090                1095

Arg Gln Leu Ser Arg Arg Tyr Pro Gln Leu Pro Arg Ala Val Ala
        1100                1105                1110

Thr Gly Arg Val Tyr Asp Met Asn Thr Gly Thr Leu Arg Asn Tyr
        1115                1120                1125

Asp Pro Arg Ile Asn Leu Val Pro Val Asn Arg Arg Leu Pro His
        1130                1135                1140

Ala Leu Val Leu His His Asn Glu His Pro Gln Ser Asp Phe Ser
        1145                1150                1155

Ser Phe Val Ser Lys Leu Lys Gly Arg Thr Val Leu Val Val Gly
        1160                1165                1170

Glu Lys Leu Ser Val Pro Gly Lys Met Val Asp Trp Leu Ser Asp
        1175                1180                1185

Arg Pro Glu Ala Thr Phe Arg Ala Arg Leu Asp Leu Gly Ile Pro
        1190                1195                1200

Gly Asp Val Pro Lys Tyr Asp Ile Ile Phe Val Asn Val Arg Thr
        1205                1210                1215

Pro Tyr Lys Tyr His His Tyr Gln Gln Cys Glu Asp His Ala Ile
        1220                1225                1230

Lys Leu Ser Met Leu Thr Lys Ala Cys Leu His Leu Asn Pro
        1235                1240                1245

Gly Gly Thr Cys Val Ser Ile Gly Tyr Gly Tyr Ala Asp Arg Ala
        1250                1255                1260

Ser Glu Ser Ile Ile Gly Ala Ile Ala Arg Leu Phe Lys Phe Ser
        1265                1270                1275

Arg Val Cys Lys Pro Lys Ser Ser Leu Glu Glu Thr Glu Val Leu
```

-continued

```
            1280                1285                1290
Phe Val Phe Ile Gly Tyr Asp Arg Lys Ala Arg Thr His Asn Pro
            1295                1300                1305
Tyr Lys Leu Ser Ser Thr Leu Thr Asn Ile Tyr Thr Gly Ser Arg
            1310                1315                1320
Leu His Glu Ala Gly Cys Ala Pro Ser Tyr His Val Val Arg Gly
            1325                1330                1335
Asp Ile Ala Thr Ala Thr Glu Gly Val Ile Ile Asn Ala Ala Asn
            1340                1345                1350
Ser Lys Gly Gln Pro Gly Gly Gly Val Cys Gly Ala Leu Tyr Lys
            1355                1360                1365
Lys Phe Pro Glu Ser Phe Asp Leu Gln Pro Ile Glu Val Gly Lys
            1370                1375                1380
Ala Arg Leu Val Lys Gly Ala Ala Lys His Ile Ile His Ala Val
            1385                1390                1395
Gly Pro Asn Phe Asn Lys Val Ser Glu Val Glu Gly Asp Lys Gln
            1400                1405                1410
Leu Ala Glu Ala Tyr Glu Ser Ile Ala Lys Ile Val Asn Asp Asn
            1415                1420                1425
Asn Tyr Lys Ser Val Ala Ile Pro Leu Leu Ser Thr Gly Ile Phe
            1430                1435                1440
Ser Gly Asn Lys Asp Arg Leu Thr Gln Ser Leu Asn His Leu Leu
            1445                1450                1455
Thr Ala Leu Asp Thr Thr Asp Ala Asp Val Ala Ile Tyr Cys Arg
            1460                1465                1470
Asp Lys Lys Trp Glu Met Thr Leu Lys Glu Ala Val Ala Arg Arg
            1475                1480                1485
Glu Ala Val Glu Glu Ile Cys Ile Ser Asp Asp Ser Ser Val Thr
            1490                1495                1500
Glu Pro Asp Ala Glu Leu Val Arg Val His Pro Lys Ser Ser Leu
            1505                1510                1515
Ala Gly Arg Lys Gly Tyr Ser Thr Ser Asp Gly Lys Thr Phe Ser
            1520                1525                1530
Tyr Leu Glu Gly Thr Lys Phe His Gln Ala Ala Lys Asp Ile Ala
            1535                1540                1545
Glu Ile Asn Ala Met Trp Pro Val Ala Thr Glu Ala Asn Glu Gln
            1550                1555                1560
Val Cys Met Tyr Ile Leu Gly Glu Ser Met Ser Ser Ile Arg Ser
            1565                1570                1575
Lys Cys Pro Val Glu Glu Ser Glu Ala Ser Thr Pro Pro Ser Thr
            1580                1585                1590
Leu Pro Cys Leu Cys Ile His Ala Met Thr Pro Glu Arg Val Gln
            1595                1600                1605
Arg Leu Lys Ala Ser Arg Pro Glu Gln Ile Thr Val Cys Ser Ser
            1610                1615                1620
Phe Pro Leu Pro Lys Tyr Arg Ile Thr Gly Val Gln Lys Ile Gln
            1625                1630                1635
Cys Ser Gln Pro Ile Leu Phe Ser Pro Lys Val Pro Ala Tyr Ile
            1640                1645                1650
His Pro Arg Lys Tyr Leu Val Glu Thr Pro Val Asp Glu Thr
            1655                1660                1665
Pro Glu Pro Ser Ala Glu Asn Gln Ser Thr Glu Gly Thr Pro Glu
            1670                1675                1680
```

```
Gln Pro Pro Leu Ile Thr Glu Asp Glu Thr Arg Thr Arg Thr Pro
    1685                1690                1695

Glu Pro Ile Ile Ile Glu Glu Glu Glu Asp Ser Ile Ser Leu
    1700                1705                1710

Leu Ser Asp Gly Pro Thr His Gln Val Leu Gln Val Glu Ala Asp
    1715                1720                1725

Ile His Gly Pro Pro Ser Val Ser Ser Ser Trp Ser Ile Pro
    1730                1735                1740

His Ala Ser Asp Phe Asp Val Asp Ser Leu Ser Ile Leu Asp Thr
    1745                1750                1755

Leu Glu Gly Ala Ser Val Thr Ser Gly Ala Thr Ser Ala Glu Thr
    1760                1765                1770

Asn Ser Tyr Phe Ala Lys Ser Met Glu Phe Leu Ala Arg Pro Val
    1775                1780                1785

Pro Ala Pro Arg Thr Val Phe Arg Asn Pro His Pro Ala Pro
    1790                1795                1800

Arg Thr Arg Thr Pro Ser Leu Ala Pro Ser Arg Ala Cys Ser Arg
    1805                1810                1815

Thr Ser Leu Val Ser Thr Pro Pro Gly Val Asn Arg Val Ile Thr
    1820                1825                1830

Arg Glu Glu Leu Glu Ala Leu Thr Pro Ser Arg Thr Pro Ser Arg
    1835                1840                1845

Ser Val Ser Arg Thr Ser Leu Val Ser Asn Pro Pro Gly Val Asn
    1850                1855                1860

Arg Val Ile Thr Arg Glu Glu Phe Glu Ala Phe Val Ala Gln Gln
    1865                1870                1875

Gln Arg Arg Phe Asp Ala Gly Ala Tyr Ile Phe Ser Ser Asp Thr
    1880                1885                1890

Gly Gln Gly His Leu Gln Gln Lys Ser Val Arg Gln Thr Val Leu
    1895                1900                1905

Ser Glu Val Val Leu Glu Arg Thr Glu Leu Glu Ile Ser Tyr Ala
    1910                1915                1920

Pro Arg Leu Asp Gln Glu Lys Glu Glu Leu Leu Arg Lys Lys Leu
    1925                1930                1935

Gln Leu Asn Pro Thr Pro Ala Asn Arg Ser Arg Tyr Gln Ser Arg
    1940                1945                1950

Lys Val Glu Asn Met Lys Ala Ile Thr Ala Arg Arg Ile Leu Gln
    1955                1960                1965

Gly Leu Gly His Tyr Leu Lys Ala Glu Gly Lys Val Glu Cys Tyr
    1970                1975                1980

Arg Thr Leu His Pro Val Pro Leu Tyr Ser Ser Ser Val Asn Arg
    1985                1990                1995

Ala Phe Ser Ser Pro Lys Val Ala Val Glu Ala Cys Asn Ala Met
    2000                2005                2010

Leu Lys Glu Asn Phe Pro Thr Val Ala Ser Tyr Cys Ile Ile Pro
    2015                2020                2025

Glu Tyr Asp Ala Tyr Leu Asp Met Val Asp Gly Ala Ser Cys Cys
    2030                2035                2040

Leu Asp Thr Ala Ser Phe Cys Pro Ala Lys Leu Arg Ser Phe Pro
    2045                2050                2055

Lys Lys His Ser Tyr Leu Glu Pro Thr Ile Arg Ser Ala Val Pro
    2060                2065                2070
```

```
Ser Ala Ile Gln Asn Thr Leu Gln Asn Val Leu Ala Ala Ala Thr
2075                2080                2085

Lys Arg Asn Cys Asn Val Thr Gln Met Arg Glu Leu Pro Val Leu
2090                2095                2100

Asp Ser Ala Ala Phe Asn Val Glu Cys Phe Lys Lys Tyr Ala Cys
2105                2110                2115

Asn Asn Glu Tyr Trp Glu Thr Phe Lys Glu Asn Pro Ile Arg Leu
2120                2125                2130

Thr Glu Glu Asn Val Val Asn Tyr Ile Thr Lys Leu Lys Gly Pro
2135                2140                2145

Lys Ala Ala Ala Leu Phe Ala Lys Thr His Asn Leu Asn Met Leu
2150                2155                2160

Gln Asp Ile Pro Met Asp Arg Phe Val Met Asp Leu Lys Arg Asp
2165                2170                2175

Val Lys Val Thr Pro Gly Thr Lys His Thr Glu Glu Arg Pro Lys
2180                2185                2190

Val Gln Val Ile Gln Ala Ala Asp Pro Leu Ala Thr Ala Tyr Leu
2195                2200                2205

Cys Gly Ile His Arg Glu Leu Val Arg Arg Leu Asn Ala Val Leu
2210                2215                2220

Leu Pro Asn Ile His Thr Leu Phe Asp Met Ser Ala Glu Asp Phe
2225                2230                2235

Asp Ala Ile Ile Ala Glu His Phe Gln Pro Gly Asp Cys Val Leu
2240                2245                2250

Glu Thr Asp Ile Ala Ser Phe Asp Lys Ser Glu Asp Asp Ala Met
2255                2260                2265

Ala Leu Thr Ala Leu Met Ile Leu Glu Asp Leu Gly Val Asp Ala
2270                2275                2280

Glu Leu Leu Thr Leu Ile Glu Ala Ala Phe Gly Glu Ile Ser Ser
2285                2290                2295

Ile His Leu Pro Thr Lys Thr Lys Phe Lys Phe Gly Ala Met Met
2300                2305                2310

Lys Ser Gly Met Phe Leu Thr Leu Phe Val Asn Thr Val Ile Asn
2315                2320                2325

Ile Val Ile Ala Ser Arg Val Leu Arg Glu Arg Leu Thr Gly Ser
2330                2335                2340

Pro Cys Ala Ala Phe Ile Gly Asp Asp Asn Ile Val Lys Gly Val
2345                2350                2355

Lys Ser Asp Lys Leu Met Ala Asp Arg Cys Ala Thr Trp Leu Asn
2360                2365                2370

Met Glu Val Lys Ile Ile Asp Ala Val Val Gly Glu Lys Ala Pro
2375                2380                2385

Tyr Phe Cys Gly Gly Phe Ile Leu Cys Asp Ser Val Thr Gly Thr
2390                2395                2400

Ala Cys Arg Val Ala Asp Pro Leu Lys Arg Leu Phe Lys Leu Gly
2405                2410                2415

Lys Pro Leu Ala Ala Asp Asp Glu His Asp Asp Asp Arg Arg Arg
2420                2425                2430

Ala Leu His Glu Glu Ser Thr Arg Trp Asn Arg Val Gly Ile Leu
2435                2440                2445

Ser Glu Leu Cys Lys Ala Val Glu Ser Arg Tyr Glu Thr Val Gly
2450                2455                2460

Thr Ser Ile Ile Val Met Ala Met Thr Thr Leu Ala Ser Ser Val
```

```
                    2465                2470                2475
Lys Ser  Phe Ser Tyr Leu Arg  Gly Ala Pro Ile Thr  Leu Tyr Gly
         2480                2485                2490
```

<210> SEQ ID NO 80
<211> LENGTH: 2494
<212> TYPE: PRT
<213> ORGANISM: Artificial sequence
<220> FEATURE:
<223> OTHER INFORMATION: Synthetic polypeptide

<400> SEQUENCE: 80

```
Met Pro Glu Lys Val His Val Asp Ile Glu Glu Asp Ser Pro Phe Leu
1               5                   10                  15

Arg Ala Leu Gln Arg Ser Phe Pro Gln Phe Glu Val Glu Ala Lys Gln
            20                  25                  30

Val Thr Asp Asn Asp His Ala Asn Ala Arg Ala Phe Ser His Leu Ala
        35                  40                  45

Ser Lys Leu Ile Glu Thr Glu Val Asp Pro Ser Asp Thr Ile Leu Asp
    50                  55                  60

Ile Gly Ser Ala Pro Ala Arg Arg Met Tyr Ser Lys His Lys Tyr His
65                  70                  75                  80

Cys Ile Cys Pro Met Arg Cys Ala Glu Asp Pro Asp Arg Leu Tyr Lys
                85                  90                  95

Tyr Ala Thr Lys Leu Lys Lys Asn Cys Lys Glu Ile Thr Asp Lys Glu
            100                 105                 110

Leu Asp Lys Lys Met Lys Glu Leu Ala Ala Val Met Ser Asp Pro Asp
        115                 120                 125

Leu Glu Thr Glu Thr Met Cys Leu His Asp Asp Glu Ser Cys Arg Tyr
    130                 135                 140

Glu Gly Gln Val Ala Val Tyr Gln Asp Val Tyr Ala Val Asp Gly Pro
145                 150                 155                 160

Thr Ser Leu Tyr His Gln Ala Asn Lys Gly Val Arg Val Ala Tyr Trp
                165                 170                 175

Ile Gly Phe Asp Thr Thr Pro Phe Met Phe Lys Asn Leu Ala Gly Ala
            180                 185                 190

Tyr Pro Ser Tyr Ser Thr Asn Trp Ala Asp Glu Thr Val Leu Thr Ala
        195                 200                 205

Arg Asn Ile Gly Leu Cys Ser Ser Asp Val Met Glu Arg Ser Arg Arg
    210                 215                 220

Gly Met Ser Ile Leu Arg Lys Lys Tyr Leu Lys Pro Ser Asn Asn Val
225                 230                 235                 240

Leu Phe Ser Val Gly Ser Thr Ile Tyr His Glu Lys Arg Asp Leu Leu
                245                 250                 255

Arg Ser Trp His Leu Pro Ser Val Phe His Leu Arg Gly Lys Gln Asn
            260                 265                 270

Tyr Thr Cys Arg Cys Glu Thr Ile Val Ser Cys Asp Gly Tyr Val Val
        275                 280                 285

Lys Arg Ile Ala Ile Ser Pro Gly Leu Tyr Gly Lys Pro Ser Gly Tyr
    290                 295                 300

Ala Ala Thr Met His Arg Glu Gly Phe Leu Cys Cys Lys Val Thr Asp
305                 310                 315                 320

Thr Leu Asn Gly Glu Arg Val Ser Phe Pro Val Cys Thr Tyr Val Pro
                325                 330                 335

Ala Thr Leu Cys Asp Gln Met Thr Gly Ile Leu Ala Thr Asp Val Ser
```

-continued

Ala Asp Asp Ala Gln Lys Leu Leu Val Gly Leu Asn Gln Arg Ile Val
             340                 345                 350
        355                 360                 365

Val Asn Gly Arg Thr Gln Arg Asn Thr Asn Thr Met Lys Asn Tyr Leu
        370                 375                 380

Leu Pro Val Val Ala Gln Ala Phe Ala Arg Trp Ala Lys Glu Tyr Lys
385                 390                 395                 400

Glu Asp Gln Glu Asp Glu Arg Pro Leu Gly Leu Arg Asp Arg Gln Leu
                405                 410                 415

Val Met Gly Cys Cys Trp Ala Phe Arg Arg His Lys Ile Thr Ser Ile
                420                 425                 430

Tyr Lys Arg Pro Asp Thr Gln Thr Ile Ile Lys Val Asn Ser Asp Phe
        435                 440                 445

His Ser Phe Val Leu Pro Arg Ile Gly Ser Asn Thr Leu Glu Ile Gly
        450                 455                 460

Leu Arg Thr Arg Ile Arg Lys Met Leu Glu Glu His Lys Glu Pro Ser
465                 470                 475                 480

Pro Leu Ile Thr Ala Glu Asp Val Gln Glu Ala Lys Cys Ala Ala Asp
                485                 490                 495

Glu Ala Lys Glu Val Arg Glu Ala Glu Glu Leu Arg Ala Ala Leu Pro
                500                 505                 510

Pro Leu Ala Ala Asp Val Glu Glu Pro Thr Leu Glu Ala Asp Val Asp
        515                 520                 525

Leu Met Leu Gln Glu Ala Gly Ala Gly Ser Val Glu Thr Pro Arg Gly
        530                 535                 540

Leu Ile Lys Val Thr Ser Tyr Asp Gly Glu Asp Lys Ile Gly Ser Tyr
545                 550                 555                 560

Ala Val Leu Ser Pro Gln Ala Val Leu Lys Ser Glu Lys Leu Ser Cys
                565                 570                 575

Ile His Pro Leu Ala Glu Gln Val Ile Val Ile Thr His Ser Gly Arg
                580                 585                 590

Lys Gly Arg Tyr Ala Val Glu Pro Tyr His Gly Lys Val Val Val Pro
        595                 600                 605

Glu Gly His Ala Ile Pro Val Gln Asp Phe Gln Ala Leu Ser Glu Ser
        610                 615                 620

Ala Thr Ile Val Tyr Asn Glu Arg Glu Phe Val Asn Arg Tyr Leu His
625                 630                 635                 640

His Ile Ala Thr His Gly Gly Ala Leu Asn Thr Asp Glu Glu Tyr Tyr
                645                 650                 655

Lys Thr Val Lys Pro Ser Glu His Asp Gly Glu Tyr Leu Tyr Asp Ile
                660                 665                 670

Asp Arg Lys Gln Cys Val Lys Lys Glu Leu Val Thr Gly Leu Gly Leu
        675                 680                 685

Thr Gly Glu Leu Val Asp Pro Pro Phe His Glu Phe Ala Tyr Glu Ser
        690                 695                 700

Leu Arg Thr Arg Pro Ala Ala Pro Tyr Gln Val Pro Thr Ile Gly Val
705                 710                 715                 720

Tyr Gly Val Pro Gly Ser Gly Lys Ser Gly Ile Ile Lys Ser Ala Val
                725                 730                 735

Thr Lys Lys Asp Leu Val Val Ser Ala Lys Lys Glu Asn Cys Ala Glu
                740                 745                 750

Ile Ile Arg Asp Val Lys Lys Met Lys Gly Leu Asp Val Asn Ala Arg
        755                 760                 765

-continued

```
Thr Val Asp Ser Val Leu Leu Asn Gly Cys Lys His Pro Val Glu Thr
    770             775                 780
Leu Tyr Ile Asp Glu Ala Phe Ala Cys His Ala Gly Thr Leu Arg Ala
785             790                 795                 800
Leu Ile Ala Ile Ile Arg Pro Lys Lys Ala Val Leu Cys Gly Asp Pro
                805                 810                 815
Lys Gln Cys Gly Phe Phe Asn Met Met Cys Leu Lys Val His Phe Asn
            820                 825                 830
His Glu Ile Cys Thr Gln Val Phe His Lys Ser Ile Ser Arg Arg Cys
                835                 840                 845
Thr Lys Ser Val Thr Ser Val Val Ser Thr Leu Phe Tyr Asp Lys Lys
        850                 855                 860
Met Arg Thr Thr Asn Pro Lys Glu Thr Lys Ile Val Ile Asp Thr Thr
865                 870                 875                 880
Gly Ser Thr Lys Pro Lys Gln Asp Asp Leu Ile Leu Thr Cys Phe Arg
                885                 890                 895
Gly Trp Val Lys Gln Leu Gln Ile Asp Tyr Lys Gly Asn Glu Ile Met
            900                 905                 910
Thr Ala Ala Ser Gln Gly Leu Thr Arg Lys Gly Val Tyr Ala Val
                915                 920                 925
Arg Tyr Lys Val Asn Glu Asn Pro Leu Tyr Ala Pro Thr Ser Glu His
        930                 935                 940
Val Asn Val Leu Leu Thr Arg Thr Glu Asp Arg Ile Val Trp Lys Thr
945                 950                 955                 960
Leu Ala Gly Asp Pro Trp Ile Lys Thr Leu Thr Ala Lys Tyr Pro Gly
                965                 970                 975
Asn Phe Thr Ala Thr Ile Glu Glu Trp Gln Ala Glu His Asp Ala Ile
            980                 985                 990
Met Arg His Ile Leu Glu Arg Pro Asp Pro Thr Asp Val Phe Gln Asn
                995                 1000                1005
Lys Ala Asn Val Cys Trp Ala Lys Ala Leu Val Pro Val Leu Lys
        1010                1015                1020
Thr Ala Gly Ile Asp Met Thr Thr Glu Gln Trp Asn Thr Val Asp
    1025                1030                1035
Tyr Phe Glu Thr Asp Lys Ala His Ser Ala Glu Ile Val Leu Asn
    1040                1045                1050
Gln Leu Cys Val Arg Phe Gly Leu Asp Leu Asp Ser Gly Leu
    1055                1060                1065
Phe Ser Ala Pro Thr Val Pro Leu Ser Ile Arg Asn Asn His Trp
    1070                1075                1080
Asp Asn Ser Pro Ser Pro Asn Met Tyr Gly Leu Asn Lys Glu Val
    1085                1090                1095
Val Arg Gln Leu Ser Arg Tyr Pro Gln Leu Pro Arg Ala Val
    1100                1105                1110
Ala Thr Gly Arg Val Tyr Asp Met Asn Thr Gly Thr Leu Arg Asn
    1115                1120                1125
Tyr Asp Pro Arg Ile Asn Leu Val Pro Val Asn Arg Arg Leu Pro
    1130                1135                1140
His Ala Leu Val Leu His His Asn Glu His Pro Gln Ser Asp Phe
    1145                1150                1155
Ser Ser Phe Val Ser Lys Leu Lys Gly Arg Thr Val Leu Val Val
    1160                1165                1170
```

```
Gly Glu Lys Leu Ser Val Pro Gly Lys Met Val Asp Trp Leu Ser
    1175                 1180                1185

Asp Arg Pro Glu Ala Thr Phe Arg Ala Arg Leu Asp Leu Gly Ile
    1190                 1195                1200

Pro Gly Asp Val Pro Lys Tyr Asp Ile Ile Phe Val Asn Val Arg
    1205                 1210                1215

Thr Pro Tyr Lys Tyr His His Tyr Gln Gln Cys Glu Asp His Ala
    1220                 1225                1230

Ile Lys Leu Ser Met Leu Thr Lys Lys Ala Cys Leu His Leu Asn
    1235                 1240                1245

Pro Gly Gly Thr Cys Val Ser Ile Gly Tyr Gly Tyr Ala Asp Arg
    1250                 1255                1260

Ala Ser Glu Ser Ile Ile Gly Ala Ile Ala Arg Leu Phe Lys Phe
    1265                 1270                1275

Ser Arg Val Cys Lys Pro Lys Ser Ser Leu Glu Glu Thr Glu Val
    1280                 1285                1290

Leu Phe Val Phe Ile Gly Tyr Asp Arg Lys Ala Arg Thr His Asn
    1295                 1300                1305

Pro Tyr Lys Leu Ser Ser Thr Leu Thr Asn Ile Tyr Thr Gly Ser
    1310                 1315                1320

Arg Leu His Glu Ala Gly Cys Ala Pro Ser Tyr His Val Val Arg
    1325                 1330                1335

Gly Asp Ile Ala Thr Ala Thr Glu Gly Val Ile Ile Asn Ala Ala
    1340                 1345                1350

Asn Ser Lys Gly Gln Pro Gly Gly Gly Val Cys Gly Ala Leu Tyr
    1355                 1360                1365

Lys Lys Phe Pro Glu Ser Phe Asp Leu Gln Pro Ile Glu Val Gly
    1370                 1375                1380

Lys Ala Arg Leu Val Lys Gly Ala Ala Lys His Ile Ile His Ala
    1385                 1390                1395

Val Gly Pro Asn Phe Asn Lys Val Ser Glu Val Glu Gly Asp Lys
    1400                 1405                1410

Gln Leu Ala Glu Ala Tyr Glu Ser Ile Ala Lys Ile Val Asn Asp
    1415                 1420                1425

Asn Asn Tyr Lys Ser Val Ala Ile Pro Leu Leu Ser Thr Gly Ile
    1430                 1435                1440

Phe Ser Gly Asn Lys Asp Arg Leu Thr Gln Ser Leu Asn His Leu
    1445                 1450                1455

Leu Thr Ala Leu Asp Thr Thr Asp Ala Asp Val Ala Ile Tyr Cys
    1460                 1465                1470

Arg Asp Lys Lys Trp Glu Met Thr Leu Lys Glu Ala Val Ala Arg
    1475                 1480                1485

Arg Glu Ala Val Glu Glu Ile Cys Ile Ser Asp Asp Ser Ser Val
    1490                 1495                1500

Thr Glu Pro Asp Ala Glu Leu Val Arg Val His Pro Lys Ser Ser
    1505                 1510                1515

Leu Ala Gly Arg Lys Gly Tyr Ser Thr Ser Asp Gly Lys Thr Phe
    1520                 1525                1530

Ser Tyr Leu Glu Gly Thr Lys Phe His Gln Ala Ala Lys Asp Ile
    1535                 1540                1545

Ala Glu Ile Asn Ala Met Trp Pro Val Ala Thr Glu Ala Asn Glu
    1550                 1555                1560

Gln Val Cys Met Tyr Ile Leu Gly Glu Ser Met Ser Ser Ile Arg
```

-continued

```
            1565                1570                1575
Ser Lys Cys Pro Val Glu Glu Ser Glu Ala Ser Thr Pro Pro Ser
       1580                1585                1590
Thr Leu Pro Cys Leu Cys Ile His Ala Met Thr Pro Glu Arg Val
       1595                1600                1605
Gln Arg Leu Lys Ala Ser Arg Pro Glu Gln Ile Thr Val Cys Ser
       1610                1615                1620
Ser Phe Pro Leu Pro Lys Tyr Arg Ile Thr Gly Val Gln Lys Ile
       1625                1630                1635
Gln Cys Ser Gln Pro Ile Leu Phe Ser Pro Lys Val Pro Ala Tyr
       1640                1645                1650
Ile His Pro Arg Lys Tyr Leu Val Glu Thr Pro Pro Val Asp Glu
       1655                1660                1665
Thr Pro Glu Pro Ser Ala Glu Asn Gln Ser Thr Glu Gly Thr Pro
       1670                1675                1680
Glu Gln Pro Pro Leu Ile Thr Glu Asp Glu Thr Arg Thr Arg Thr
       1685                1690                1695
Pro Glu Pro Ile Ile Ile Glu Glu Glu Glu Asp Ser Ile Ser
       1700                1705                1710
Leu Leu Ser Asp Gly Pro Thr His Gln Val Leu Gln Val Glu Ala
       1715                1720                1725
Asp Ile His Gly Pro Pro Ser Val Ser Ser Ser Trp Ser Ile
       1730                1735                1740
Pro His Ala Ser Asp Phe Asp Val Asp Ser Leu Ser Ile Leu Asp
       1745                1750                1755
Thr Leu Glu Gly Ala Ser Val Thr Ser Gly Ala Thr Ser Ala Glu
       1760                1765                1770
Thr Asn Ser Tyr Phe Ala Lys Ser Met Glu Phe Leu Ala Arg Pro
       1775                1780                1785
Val Pro Ala Pro Arg Thr Val Phe Arg Asn Pro Pro His Pro Ala
       1790                1795                1800
Pro Arg Thr Arg Thr Pro Ser Leu Ala Pro Ser Arg Ala Cys Ser
       1805                1810                1815
Arg Thr Ser Leu Val Ser Thr Pro Pro Gly Val Asn Arg Val Ile
       1820                1825                1830
Thr Arg Glu Glu Leu Glu Ala Leu Thr Pro Ser Arg Thr Pro Ser
       1835                1840                1845
Arg Ser Val Ser Arg Thr Ser Leu Val Ser Asn Pro Pro Gly Val
       1850                1855                1860
Asn Arg Val Ile Thr Arg Glu Glu Phe Glu Ala Phe Val Ala Gln
       1865                1870                1875
Gln Gln Arg Arg Phe Asp Ala Gly Ala Tyr Ile Phe Ser Ser Asp
       1880                1885                1890
Thr Gly Gln Gly His Leu Gln Gln Lys Ser Val Arg Gln Thr Val
       1895                1900                1905
Leu Ser Glu Val Val Leu Glu Arg Thr Glu Leu Glu Ile Ser Tyr
       1910                1915                1920
Ala Pro Arg Leu Asp Gln Glu Lys Glu Glu Leu Leu Arg Lys Lys
       1925                1930                1935
Leu Gln Leu Asn Pro Thr Pro Ala Asn Arg Ser Arg Tyr Gln Ser
       1940                1945                1950
Arg Lys Val Glu Asn Met Lys Ala Ile Thr Ala Arg Arg Ile Leu
       1955                1960                1965
```

```
Gln Gly Leu Gly His Tyr Leu Lys Ala Glu Gly Lys Val Glu Cys
    1970            1975                1980

Tyr Arg Thr Leu His Pro Val Pro Leu Tyr Ser Ser Ser Val Asn
    1985            1990                1995

Arg Ala Phe Ser Ser Pro Lys Val Ala Val Glu Ala Cys Asn Ala
    2000            2005                2010

Met Leu Lys Glu Asn Phe Pro Thr Val Ala Ser Tyr Cys Ile Ile
    2015            2020                2025

Pro Glu Tyr Asp Ala Tyr Leu Asp Met Val Asp Gly Ala Ser Cys
    2030            2035                2040

Cys Leu Asp Thr Ala Ser Phe Cys Pro Ala Lys Leu Arg Ser Phe
    2045            2050                2055

Pro Lys Lys His Ser Tyr Leu Glu Pro Thr Ile Arg Ser Ala Val
    2060            2065                2070

Pro Ser Ala Ile Gln Asn Thr Leu Gln Asn Val Leu Ala Ala Ala
    2075            2080                2085

Thr Lys Arg Asn Cys Asn Val Thr Gln Met Arg Glu Leu Pro Val
    2090            2095                2100

Leu Asp Ser Ala Ala Phe Asn Val Glu Cys Phe Lys Lys Tyr Ala
    2105            2110                2115

Cys Asn Asn Glu Tyr Trp Glu Thr Phe Lys Glu Asn Pro Ile Arg
    2120            2125                2130

Leu Thr Glu Glu Asn Val Val Asn Tyr Ile Thr Lys Leu Lys Gly
    2135            2140                2145

Pro Lys Ala Ala Ala Leu Phe Ala Lys Thr His Asn Leu Asn Met
    2150            2155                2160

Leu Gln Asp Ile Pro Met Asp Arg Phe Val Met Asp Leu Lys Arg
    2165            2170                2175

Asp Val Lys Val Thr Pro Gly Thr Lys His Thr Glu Glu Arg Pro
    2180            2185                2190

Lys Val Gln Val Ile Gln Ala Ala Asp Pro Leu Ala Thr Ala Tyr
    2195            2200                2205

Leu Cys Gly Ile His Arg Glu Leu Val Arg Arg Leu Asn Ala Val
    2210            2215                2220

Leu Leu Pro Asn Ile His Thr Leu Phe Asp Met Ser Ala Glu Asp
    2225            2230                2235

Phe Asp Ala Ile Ile Ala Glu His Phe Gln Pro Gly Asp Cys Val
    2240            2245                2250

Leu Glu Thr Asp Ile Ala Ser Phe Asp Lys Ser Glu Asp Asp Ala
    2255            2260                2265

Met Ala Leu Thr Ala Leu Met Ile Leu Glu Asp Leu Gly Val Asp
    2270            2275                2280

Ala Glu Leu Leu Thr Leu Ile Glu Ala Ala Phe Gly Glu Ile Ser
    2285            2290                2295

Ser Ile His Leu Pro Thr Lys Thr Lys Phe Lys Phe Gly Ala Met
    2300            2305                2310

Met Lys Ser Gly Met Phe Leu Thr Leu Phe Val Asn Thr Val Ile
    2315            2320                2325

Asn Ile Val Ile Ala Ser Arg Val Leu Arg Glu Arg Leu Thr Gly
    2330            2335                2340

Ser Pro Cys Ala Ala Phe Ile Gly Asp Asp Asn Ile Val Lys Gly
    2345            2350                2355
```

```
Val Lys Ser Asp Lys Leu Met Ala Asp Arg Cys Ala Thr Trp Leu
    2360                2365                2370

Asn Met Glu Val Lys Ile Ile Asp Ala Val Val Gly Glu Lys Ala
    2375                2380                2385

Pro Tyr Phe Cys Gly Gly Phe Ile Leu Cys Asp Ser Val Thr Gly
    2390                2395                2400

Thr Ala Cys Arg Val Ala Asp Pro Leu Lys Arg Leu Phe Lys Leu
    2405                2410                2415

Gly Lys Pro Leu Ala Ala Asp Glu His Asp Asp Arg Arg
    2420                2425                2430

Arg Ala Leu His Glu Glu Ser Thr Arg Trp Asn Arg Val Gly Ile
    2435                2440                2445

Leu Ser Glu Leu Cys Lys Ala Val Glu Ser Arg Tyr Glu Thr Val
    2450                2455                2460

Gly Thr Ser Ile Ile Val Met Ala Met Thr Thr Leu Ala Ser Ser
    2465                2470                2475

Val Lys Ser Phe Ser Tyr Leu Arg Gly Ala Pro Ile Thr Leu Tyr
    2480                2485                2490

Gly

<210> SEQ ID NO 81
<211> LENGTH: 2492
<212> TYPE: PRT
<213> ORGANISM: Artificial sequence
<220> FEATURE:
<223> OTHER INFORMATION: Synthetic polypeptide

<400> SEQUENCE: 81

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
                20                  25                  30

Thr Asp Asn Asp His Ala Asn Ala Arg Ala Phe Ser His Leu Ala Ser
            35                  40                  45

Lys Leu Ile Glu Thr Glu Val Asp Pro Ser Asp Thr Ile Leu Asp Ile
        50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
                100                 105                 110

Asp Lys Lys Met Lys Glu Leu Ala Ala Val Met Ser Asp Pro Asp Leu
            115                 120                 125

Glu Thr Glu Thr Met Cys Leu His Asp Asp Glu Ser Cys Arg Tyr Glu
        130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
                180                 185                 190

Pro Ser Tyr Ser Thr Asn Trp Ala Asp Glu Thr Val Leu Thr Ala Arg
            195                 200                 205

Asn Ile Gly Leu Cys Ser Ser Asp Val Met Glu Arg Ser Arg Arg Gly
```

-continued

```
                210                 215                 220
Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Ile Gln Glu Ala Lys Cys Ala Ala Asp Glu
                485                 490                 495

Ala Lys Glu Val Arg Glu Ala Glu Leu Arg Ala Ala Leu Pro Pro
            500                 505                 510

Leu Ala Ala Asp Phe Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640
```

-continued

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
                660                 665                 670

Arg Lys Gln Cys Val Lys Lys Glu Leu Val Thr Gly Leu Gly Leu Thr
                675                 680                 685

Gly Glu Leu Val Asp Pro Pro Phe His Glu Phe Ala Tyr Glu Ser Leu
            690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
            755                 760                 765

Val Asp Ser Val Leu Leu Asn Gly Cys Lys His Pro Val Glu Thr Leu
        770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
                820                 825                 830

Glu Ile Cys Thr Gln Val Phe His Lys Ser Ile Ser Arg Arg Cys Thr
            835                 840                 845

Lys Ser Val Thr Ser Val Val Ser Thr Leu Phe Tyr Asp Lys Arg Met
850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
                900                 905                 910

Ala Ala Ala Ser Gln Gly Leu Thr Arg Lys Gly Val Tyr Ala Val Arg
            915                 920                 925

Tyr Lys Val Asn Glu Asn Pro Leu Tyr Ala Pro Thr Ser Glu His Val
930                 935                 940

Asn Val Leu Leu Thr Arg Thr Glu Asp Arg Ile Val Trp Lys Thr Leu
945                 950                 955                 960

Ala Gly Asp Pro Trp Ile Lys Ile Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp Pro Thr Asp Val Phe Gln Asn Lys
            995                 1000                1005

Ala Asn Val Cys Trp Ala Lys Ala Leu Val Pro Val Leu Lys Thr
    1010                1015                1020

Ala Gly Ile Asp Met Thr Thr Glu Gln Trp Asn Thr Val Asp Tyr
    1025                1030                1035

Phe Glu Thr Asp Lys Ala His Ser Ala Glu Ile Val Leu Asn Gln
    1040                1045                1050

```
Leu Cys Val Arg Phe Phe Gly Leu Asp Leu Asp Ser Gly Leu Phe
    1055                1060                1065

Ser Ala Pro Thr Val Pro Leu Ser Ile Arg Asn Asn His Trp Asp
    1070                1075                1080

Asn Ser Pro Ser Pro Asn Met Tyr Gly Leu Asn Lys Glu Val Val
    1085                1090                1095

Arg Gln Leu Ser Arg Arg Tyr Pro Gln Leu Pro Arg Ala Val Ala
    1100                1105                1110

Thr Gly Arg Val Tyr Asp Met Asn Thr Gly Thr Leu Arg Asn Tyr
    1115                1120                1125

Asp Pro Arg Ile Asn Leu Val Pro Val Asn Arg Arg Leu Pro His
    1130                1135                1140

Ala Leu Val Leu His His Asn Glu His Pro Gln Ser Asp Phe Ser
    1145                1150                1155

Ser Phe Val Ser Lys Leu Lys Gly Arg Thr Val Leu Val Val Gly
    1160                1165                1170

Glu Lys Leu Ser Val Pro Gly Lys Lys Val Asp Trp Leu Ser Asp
    1175                1180                1185

Gln Pro Glu Ala Thr Phe Arg Ala Arg Leu Asp Leu Gly Ile Pro
    1190                1195                1200

Gly Asp Val Pro Lys Tyr Asp Ile Val Phe Ile Asn Val Arg Thr
    1205                1210                1215

Pro Tyr Lys Tyr His His Tyr Gln Gln Cys Glu Asp His Ala Ile
    1220                1225                1230

Lys Leu Ser Met Leu Thr Lys Lys Ala Cys Leu His Leu Asn Pro
    1235                1240                1245

Gly Gly Thr Cys Val Ser Ile Gly Tyr Gly Tyr Ala Asp Arg Ala
    1250                1255                1260

Ser Glu Ser Ile Ile Gly Ala Ile Ala Arg Gln Phe Lys Phe Ser
    1265                1270                1275

Arg Val Cys Lys Pro Lys Ser Ser His Glu Glu Thr Glu Val Leu
    1280                1285                1290

Phe Val Phe Ile Gly Tyr Asp Arg Lys Ala Arg Thr His Asn Pro
    1295                1300                1305

Tyr Lys Leu Ser Ser Thr Leu Thr Asn Ile Tyr Thr Gly Ser Arg
    1310                1315                1320

Leu His Glu Ala Gly Cys Ala Pro Ser Tyr His Val Val Arg Gly
    1325                1330                1335

Asp Ile Ala Thr Ala Thr Glu Gly Val Ile Ile Asn Ala Ala Asn
    1340                1345                1350

Ser Lys Gly Gln Pro Gly Gly Gly Val Cys Gly Ala Leu Tyr Lys
    1355                1360                1365

Lys Phe Pro Glu Ser Phe Asp Leu Gln Pro Ile Glu Val Gly Lys
    1370                1375                1380

Ala Arg Leu Val Lys Gly Ala Ala Lys His Ile Ile His Ala Val
    1385                1390                1395

Gly Pro Asn Phe Asn Lys Val Ser Glu Val Glu Gly Asp Lys Gln
    1400                1405                1410

Leu Ala Glu Ala Tyr Glu Ser Ile Ala Lys Ile Val Asn Asp Asn
    1415                1420                1425

Asn Tyr Lys Ser Val Ala Ile Pro Leu Leu Ser Thr Gly Ile Phe
    1430                1435                1440

Ser Gly Asn Lys Asp Arg Leu Thr Gln Ser Leu Asn His Leu Leu
```

-continued

```
            1445                1450                1455
Thr Ala Leu Asp Thr Thr Asp Ala Asp Val Ala Ile Tyr Cys Arg
            1460                1465                1470
Asp Lys Lys Trp Glu Met Thr Leu Lys Glu Ala Val Ala Arg Arg
            1475                1480                1485
Glu Ala Val Glu Glu Ile Cys Ile Ser Asp Asp Ser Ser Val Thr
            1490                1495                1500
Glu Pro Asp Ala Glu Leu Val Arg Val His Pro Lys Ser Ser Leu
            1505                1510                1515
Ala Gly Arg Lys Gly Tyr Ser Thr Ser Asp Gly Lys Thr Phe Ser
            1520                1525                1530
Tyr Leu Glu Gly Thr Lys Phe His Gln Ala Ala Lys Asp Ile Ala
            1535                1540                1545
Glu Ile Asn Ala Met Trp Pro Val Ala Thr Glu Ala Asn Glu Gln
            1550                1555                1560
Val Cys Met Tyr Ile Leu Gly Glu Ser Met Ser Ser Ile Arg Ser
            1565                1570                1575
Lys Cys Pro Val Glu Glu Ser Glu Ala Ser Thr Pro Pro Ser Thr
            1580                1585                1590
Leu Pro Cys Leu Cys Ile His Ala Met Thr Pro Glu Arg Val Gln
            1595                1600                1605
Arg Leu Lys Ala Ser Arg Pro Glu Gln Ile Thr Val Cys Ser Ser
            1610                1615                1620
Phe Pro Leu Pro Lys Tyr Arg Ile Thr Gly Val Gln Lys Ile Gln
            1625                1630                1635
Cys Ser Gln Pro Ile Leu Phe Ser Pro Lys Val Pro Ala Tyr Ile
            1640                1645                1650
His Pro Arg Lys Tyr Leu Val Glu Thr Pro Pro Val Glu Glu Thr
            1655                1660                1665
Pro Glu Ser Pro Ala Glu Asn Gln Ser Thr Glu Gly Thr Pro Glu
            1670                1675                1680
Gln Pro Ala Leu Val Asn Val Asp Ala Thr Arg Thr Arg Met Pro
            1685                1690                1695
Glu Pro Ile Ile Ile Glu Glu Glu Glu Asp Ser Ile Ser Leu
            1700                1705                1710
Leu Ser Asp Gly Pro Thr His Gln Val Leu Gln Val Glu Ala Asp
            1715                1720                1725
Ile His Gly Ser Pro Ser Val Ser Ser Ser Ser Trp Ser Ile Pro
            1730                1735                1740
His Ala Ser Asp Phe Asp Val Asp Ser Leu Ser Ile Leu Asp Thr
            1745                1750                1755
Leu Asp Gly Ala Ser Val Thr Ser Gly Ala Val Ser Ala Glu Thr
            1760                1765                1770
Asn Ser Tyr Phe Ala Arg Ser Met Glu Phe Arg Ala Arg Pro Val
            1775                1780                1785
Pro Ala Pro Arg Thr Val Phe Arg Asn Pro His Pro Ala Pro
            1790                1795                1800
Arg Thr Arg Thr Pro Pro Leu Ala His Ser Arg Ala Ser Ser Arg
            1805                1810                1815
Thr Ser Leu Val Ser Thr Pro Pro Gly Val Asn Arg Val Ile Thr
            1820                1825                1830
Arg Glu Glu Leu Glu Ala Leu Thr Pro Ser Arg Ala Pro Ser Arg
            1835                1840                1845
```

Ser Ala Ser Arg Thr Ser Leu Val Ser Asn Pro Pro Gly Val Asn
1850                1855                    1860

Arg Val Ile Thr Arg Glu Glu Phe Glu Ala Phe Val Ala Gln Gln
1865                1870                    1875

Gln Arg Phe Asp Ala Gly Ala Tyr Ile Phe Ser Ser Asp Thr Gly
1880                1885                    1890

Gln Gly His Leu Gln Gln Lys Ser Val Arg Gln Thr Val Leu Ser
1895                1900                    1905

Glu Val Val Leu Glu Arg Thr Glu Leu Glu Ile Ser Tyr Ala Pro
1910                1915                    1920

Arg Leu Asp Gln Glu Lys Glu Leu Leu Arg Lys Lys Leu Gln
1925                1930                    1935

Leu Asn Pro Thr Pro Ala Asn Arg Ser Arg Tyr Gln Ser Arg Arg
1940                1945                    1950

Val Glu Asn Met Lys Ala Ile Thr Ala Arg Arg Ile Leu Gln Gly
1955                1960                    1965

Leu Gly His Tyr Leu Lys Ala Glu Gly Lys Val Glu Cys Tyr Arg
1970                1975                    1980

Thr Leu His Pro Val Pro Leu Tyr Ser Ser Ser Val Asn Arg Ala
1985                1990                    1995

Phe Ser Ser Pro Lys Val Ala Val Glu Ala Cys Asn Ala Met Leu
2000                2005                    2010

Lys Glu Asn Phe Pro Thr Val Ala Ser Tyr Cys Ile Ile Pro Glu
2015                2020                    2025

Tyr Asp Ala Tyr Leu Asp Met Val Asp Gly Ala Ser Cys Cys Leu
2030                2035                    2040

Asp Thr Ala Ser Phe Cys Pro Ala Lys Leu Arg Ser Phe Pro Lys
2045                2050                    2055

Lys His Ser Tyr Leu Glu Pro Thr Ile Arg Ser Ala Val Pro Ser
2060                2065                    2070

Ala Ile Gln Asn Thr Leu Gln Asn Val Leu Ala Ala Ala Thr Lys
2075                2080                    2085

Arg Asn Cys Asn Val Thr Gln Met Arg Glu Leu Pro Val Leu Asp
2090                2095                    2100

Ser Ala Ala Phe Asn Val Glu Cys Phe Lys Lys Tyr Ala Cys Asn
2105                2110                    2115

Asn Glu Tyr Trp Glu Thr Phe Lys Glu Asn Pro Ile Arg Leu Thr
2120                2125                    2130

Glu Glu Asn Val Val Asn Tyr Ile Thr Lys Leu Lys Gly Pro Lys
2135                2140                    2145

Ala Ala Ala Leu Phe Ala Lys Thr His Asn Leu Asn Met Leu Gln
2150                2155                    2160

Asp Ile Pro Met Asp Arg Phe Val Met Asp Leu Lys Arg Asp Val
2165                2170                    2175

Lys Val Thr Pro Gly Thr Lys His Thr Glu Glu Arg Pro Lys Val
2180                2185                    2190

Gln Val Ile Gln Ala Ala Asp Pro Leu Ala Thr Ala Asp Leu Cys
2195                2200                    2205

Gly Ile His Arg Glu Leu Val Arg Arg Leu Asn Ala Val Leu Leu
2210                2215                    2220

Pro Asn Ile His Thr Leu Phe Asp Met Ser Ala Glu Asp Phe Asp
2225                2230                    2235

| | | | | | | | | | | | |
|---|---|---|---|---|---|---|---|---|---|---|---|
| Ala | Ile | Ile | Ala | Glu | His | Phe | Gln | Pro | Gly | Asp | Cys | Val | Leu | Glu |
| | | 2240 | | | 2245 | | | | 2250 | | |
| Thr | Asp | Ile | Ala | Ser | Phe | Asp | Lys | Ser | Glu | Asp | Ala | Met | Ala |
| 2255 | | | | 2260 | | | | 2265 | | | |
| Leu | Thr | Ala | Leu | Met | Ile | Leu | Glu | Asp | Leu | Gly | Val | Asp | Ala | Glu |
| 2270 | | | | | 2275 | | | | 2280 | | |
| Leu | Leu | Thr | Leu | Ile | Glu | Ala | Ala | Phe | Gly | Glu | Ile | Ser | Ser | Ile |
| 2285 | | | | | 2290 | | | | 2295 | | |
| His | Leu | Pro | Thr | Lys | Thr | Lys | Phe | Lys | Phe | Gly | Ala | Met | Met | Lys |
| 2300 | | | | | 2305 | | | | 2310 | | |
| Ser | Gly | Met | Phe | Leu | Thr | Leu | Phe | Val | Asn | Thr | Val | Ile | Asn | Ile |
| 2315 | | | | | 2320 | | | | 2325 | | |
| Val | Ile | Ala | Ser | Arg | Val | Leu | Arg | Glu | Arg | Leu | Thr | Gly | Ser | Pro |
| 2330 | | | | | 2335 | | | | 2340 | | |
| Cys | Ala | Ala | Phe | Ile | Gly | Asp | Asp | Asn | Ile | Val | Lys | Gly | Val | Lys |
| 2345 | | | | | 2350 | | | | 2355 | | |
| Ser | Asp | Lys | Leu | Met | Ala | Asp | Arg | Cys | Ala | Thr | Trp | Leu | Asn | Met |
| 2360 | | | | | 2365 | | | | 2370 | | |
| Glu | Val | Lys | Ile | Ile | Asp | Ala | Val | Val | Gly | Glu | Lys | Ala | Pro | Tyr |
| 2375 | | | | | 2380 | | | | 2385 | | |
| Phe | Cys | Gly | Gly | Phe | Ile | Leu | Cys | Asp | Ser | Val | Thr | Gly | Thr | Ala |
| 2390 | | | | | 2395 | | | | 2400 | | |
| Cys | Arg | Val | Ala | Asp | Pro | Leu | Lys | Arg | Leu | Phe | Lys | Leu | Gly | Lys |
| 2405 | | | | | 2410 | | | | 2415 | | |
| Pro | Leu | Ala | Val | Asp | Asp | Glu | His | Asp | Asp | Asp | Arg | Arg | Arg | Ala |
| 2420 | | | | | 2425 | | | | 2430 | | |
| Leu | His | Glu | Glu | Ser | Thr | Arg | Trp | Asn | Arg | Val | Gly | Ile | Leu | Pro |
| 2435 | | | | | 2440 | | | | 2445 | | |
| Glu | Leu | Cys | Lys | Ala | Val | Glu | Ser | Arg | Tyr | Glu | Thr | Val | Gly | Thr |
| 2450 | | | | | 2455 | | | | 2460 | | |
| Ser | Ile | Ile | Val | Met | Ala | Met | Thr | Thr | Leu | Ala | Ser | Ser | Val | Lys |
| 2465 | | | | | 2470 | | | | 2475 | | |
| Ser | Phe | Ser | Tyr | Leu | Arg | Gly | Ala | Pro | Ile | Thr | Leu | Tyr | Gly |
| 2480 | | | | | 2485 | | | | 2490 | |

<210> SEQ ID NO 82
<211> LENGTH: 146
<212> TYPE: DNA
<213> ORGANISM: Artificial sequence
<220> FEATURE:
<223> OTHER INFORMATION: Synthetic polynucleotide

<400> SEQUENCE: 82
aggaaactta agtcaacaca acatatacaa aacaaacgaa tctcaagcaa tcaagcattc      60
tacttctatt gcagcaattt aaatcatttc ttttaaagca aaagcaattt tctgaaaatt     120
ttcaccattt acgaacgata gccacc                                          146

<210> SEQ ID NO 83
<211> LENGTH: 270
<212> TYPE: DNA
<213> ORGANISM: Artificial sequence
<220> FEATURE:
<223> OTHER INFORMATION: Synthetic polynucleotide

<400> SEQUENCE: 83
actcgagcta gtgactgact aggatctggt taccactaaa ccagcctcaa gaacacccga      60

```
atggagtctc taagctacat aataccaact tacacttaca aaatgttgtc ccccaaaatg    120
tagccattcg tatctgctcc taataaaaag aaagtttctt cacattctag aaaaaaaaaa    180
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa                                    270
```

<210> SEQ ID NO 84
<211> LENGTH: 1653
<212> TYPE: RNA
<213> ORGANISM: Artificial sequence
<220> FEATURE:
<223> OTHER INFORMATION: Synthetic polynucleotide

<400> SEQUENCE: 84

```
auggaagaug ccaaaaacau uaagaagggc ccagcgccau ucucccacu cgaagacggg      60 accgccggcg agcagcugca caaagccaug aagcgcuacg cccuggugcc cggcaccauc    120
gccuuuaccg acgcacauau cgagguggac auuaccuacg ccgaguacuu cgagaugagc    180
guucggcugg cagaagcuau gaagcgcuau gggcugaaua caaaccaucg gaucguggug    240
ugcagcgaga auagcuugca guucuucaug cccguguugg gugcccuguu caucggugug    300
gcuguggccc cagcuaacga caucuacaac gagcgcgagc ugcugaacag caugggcauc    360
agccagccca ccgucguauu cgugagcaag aaagggcugc aaaagauccu caacgugcaa    420
aagaagcuac cgaucauaca aaagaucauc aucauggaua gcaagaccga cuaccagggc    480
uuccaaagca uguacaccuu cgugacuucc cauuugccac ccggcuucaa cgaguacgac    540
uucgugcccg agagcuucga ccgggacaaa accaucgccc ugaucaugaa caguaguggc    600
aguaccggau ugcccaaggg cguagcccua ccgcaccgca ccgcuugugu ccgauucagu    660
caugcccgcg accccaucuu cggcaaccag aucauccccg acaccgcuau ccucagcgug    720
gugccauuuc accacggcuu cggcauguuc accacgcugg gcuacuugau cugcggcuuu    780
cgggucgugc ucauguaccg cuucgaggag agcuauucu ugcgcagcuu gcaagacuau    840
aagauucaau cugcccugcu ggugcccaca cuauuuagcu ucuucgcuaa gagcacucuc    900
aucgacaagu acgaccuaag caacuugcac gagaucgcca cgcgcggggc gccgucagc    960 aaggagguag gugaggccgu ggccaaacgc uuccaccuac caggcauccg acagggcuac   1020
ggccugacag aaacaaccag cgccauucug aucaccccg aagggacga caagccuggc   1080 gcaguaggca aggugugcc cuucuucgag gcuaaggugg uggacuugga caccgguaag   1140
acacuggugg ugaaccagcg cggcgagcug ugcgucgcug gccccaugau caugagcggc   1200 uacgguuaaca accccgaggc uacaaacgcu cucaucgaca aggacggcug gcugcacagc   1260
ggcgacaucg ccuacuggga cgaggacgag cacuucuuca ucguggaccg gcugaagucc   1320
cugaucaaau acaagggcua ccagguagcc ccagccgaac uggagagcau ccugcugcaa   1380
caccccaaca ucuucgacgc cggggucgcc ggccugcccg acgacgaugc cggcgagcug   1440
cccgccgcag ucgucgucgu ggaacacggu aaaaccauga ccgagaagga gaucguggac   1500
uauguggcca gccagguuac aaccgccaag aagcugcgcg gugguguugu guucgugag   1560 gagguagccua aggacugacu gcaaguug acgcccgca agauccgcga gauucucauu   1620
aaggccaaga agggcggcaa gaucgccgug uaa                                 1653
```

<210> SEQ ID NO 85
<211> LENGTH: 1653
<212> TYPE: RNA
<213> ORGANISM: Artificial sequence
<220> FEATURE:
<223> OTHER INFORMATION: Synthetic polynucleotide

<400> SEQUENCE: 85

```
auggaagaug ccaaaaacau uaagaagggc ccagcgccau ucucccacu cgaagacggg      60
accgccggcg agcagcugca caaagccaug aagcgcuacg cccuggugcc cggcaccauc    120
gccuuuaccg acgcacauau cgagguggac auuaccuacg ccgaguacuu cgagaugagc    180
guucggcugg cagaagcuau gaagcgcuau gggcugaaua caaaccaucg gaucguggug    240
ugcagcgaga auagcuugca guucuucaug cccguguugg gugcccuguu caucggugug    300
gcuguggccc cagcuaacga caucuacaac gagcgcgagc ugcugaacag caugggcauc    360
agccagccca ccgucguauu cgugagcaag aaagggcugc aaaagauccu caacgugcaa    420
aagaagcuac cgaucauaca aaagaucauc aucauggaua gcaagaccga cuaccagggc    480
uuccaaagca uguacaccuu cgugacuucc cauuugccac ccggcuucaa cgaguacgac    540
uucgugcccg agagcuucga ccgggacaaa accaucgccc ugaucaugaa caguagugcc    600
aguaccggau ugcccaaggg cguagcccua ccgcaccgca ccgcuugugu ccgauucagu    660
caugcccgcg accccaucuu cggcaaccag aucaucccg acaccgcuau ccucagcgug    720
gugccauuuc accacggcuu cggcauguuc accacgcugg gcuacuugau cugcggcuuu    780
cgggucgugc ucauguaccg cuucgaggag gagcuauucu ugcgcagcuu gcaagacuau    840
aagauucaau cugcccugcu ggugcccaca cuauuuagcu ucuucgcuaa gagcacucuc    900
aucgacaagu acgaccuaag caacuugcac gagaucgcca cgcgcgggc ccgcucagc    960
aaggagguag gugaggccgu ggccaaacgc uuccaccuac caggcauccg acagggcuac   1020
ggccugacag aaacaaccag cgccauucug aucacccccg aaggggacga caagccuggc   1080
gcaguaggca agguggugcc cuucuucgag gcuaagguug uggacuugga caccgguaag   1140
acacugggug ugaaccagcg cggcgagcug ugcguccgug gccccaugau caugagcggc   1200
uacguuaaca ccccgaggc uacaaacgcu cucaucgaca ggacggcug gcugcacagc   1260
ggcgacaucg ccuacuggga cgaggacgag cacuucuuca ucguggaccg gcugaagucc   1320
cugaucaaau acaagggcua ccagguagcc ccagccgaac uggagagcau ccugcugcaa   1380
caccccaaca ucuucgacgc cggggucgcc ggccugcccg acgacgaugc cggcgagcug   1440
cccgccgcag ucgucgugcu ggaacacggu aaaaccauga ccgagaagga gaucguggac   1500
uaugguggcca gccagguuac aaccgccaag aagcugcgcg gguguuugu uucguggac   1560
gaggugccua aggacugac cggcaaguug acgccccgca agauccgcga gauucucauu   1620
aaggccaaga agggcggcaa gaucgccgug uaa                                1653
```

<210> SEQ ID NO 86
<211> LENGTH: 1653
<212> TYPE: RNA
<213> ORGANISM: Artificial sequence
<220> FEATURE:
<223> OTHER INFORMATION: Synthetic polynucleotide

<400> SEQUENCE: 86

```
auggaagaug ccaaaaacau uaagaagggc ccagcgccau ucucccacu cgaagacggg      60
accgccggcg agcagcugca caaagccaug aagcgcuacg cccuggugcc cggcaccauc    120
gccuuuaccg acgcacauau cgagguggac auuaccuacg ccgaguacuu cgagaugagc    180
guucggcugg cagaagcuau gaagcgcuau gggcugaaua caaaccaucg gaucguggug    240
```

```
ugcagcgaga auagcuugca guucuucaug cccguguugg gugcccuguu caucggugug    300
gcuguggccc cagcuaacga caucuacaac gagcgcgagc ugcugaacag caugggcauc    360
agccagccca ccgucguauu cgugagcaag aaagggcugc aaaagauccu caacgugcaa    420
aagaagcuac cgaucauaca aaagaucauc aucauggaua gcaagaccga cuaccagggc    480
uuccaaagca uguacaccuu cgugacuucc cauuugccac ccggcuucaa cgaguacgac    540
uucgugcccg agagcuucga ccgggacaaa accaucgccc ugaucaugaa caguaguggc    600
aguaccggau ugcccaaggg cguagcccua ccgcaccgca ccgcuugugu ccgauucagu    660
caugcccgcg accccaucuu cggcaaccag aucaucccg acaccgcuau ccucagcgug     720
gugccauuuc accacggcuu cggcauguuc accacgcugg cuacuugau cugcggcuuu     780 cgggucgugc ucauguaccg cuucgaggag gagcuauucu ugcgcagcuu gcaagacuau    840
aagauucaau cugcccugcu ggugcccaca cuauuuagcu ucuucgcuaa gagcacucuc    900
aucgacaagu acgaccuaag caacuugcac gagaucgcca cgggcggggc cgcgcucagc    960
aaggagguag gugaggccgu ggccaaacgc uuccaccuac caggcauccg acagggcuac   1020
ggccugacag aaacaaccag cgccauucug aucaccccg aaggggacga caagccuggc    1080
gcaguaggca aggguggugcc cuucuucgag gcuaaggugg uggacuugga caccgguaag   1140
acacuggguu gaaccagcg cggcgagcug ugcguccgug ccccaugau caugagcggc     1200 uacguuaaca ccccgaggc uacaaacgcu cucaucgaca aggacggcug gcugcacagc    1260
ggcgacaucg ccuacuggga cgaggacgag cacuucuuca ucguggaccg gcugaaguc c  1320 cugaucaaau acaagggcua ccagguagcc ccagccgaac uggagagcau ccugcugcaa   1380 cacccccaaca ucuucgacgc cggggucgcc ggccugcccg acgacgaugc cggcgagcug  1440
cccgccgcag ucgucgugcu ggaacacggu aaaaccauga ccgagaagga gaucguggac   1500
uauguggcca gccagguuac aaccgccaag aagcugcgcg guggguguugu guucguggac   1560 gaggugccua aaggacugac cggcaaguug gacgcccgca agauccgcga gauucucauu   1620
aaggccaaga agggcggcaa gaucgccgug uaa                                1653

<210> SEQ ID NO 87
<211> LENGTH: 57
<212> TYPE: RNA
<213> ORGANISM: Artificial sequence
<220> FEATURE:
<223> OTHER INFORMATION: Synthetic polynucleotide

<400> SEQUENCE: 87
augaaguugg ugguuguggg ggccgggggu guuggcaaaa gcgcccuuac aauuuga       57

<210> SEQ ID NO 88
<211> LENGTH: 66
<212> TYPE: RNA
<213> ORGANISM: Artificial sequence
<220> FEATURE:
<223> OTHER INFORMATION: Synthetic polynucleotide

<400> SEQUENCE: 88
auggauccua gacgcuacgc cccaaugauc cgaccagcaa aacucgaugu acuuccgagg    60
aacuga                                                              66

<210> SEQ ID NO 89
<211> LENGTH: 837
<212> TYPE: RNA
<213> ORGANISM: Artificial sequence
```

```
<220> FEATURE:
<223> OTHER INFORMATION: Synthetic polynucleotide

<400> SEQUENCE: 89
augagaguga cagccccuag aaccuuacug cuucugcuuu ggggagcugu ugcucugaca        60
gagacauggg cuggaucucu gagcgaggug accggccagg gccugugcau cggcgccgug       120
cccaagaccc accaggugcu gugcaacacc acccagaaga ccagcgacgg cagcuacuac       180
cuggccgcuc ccaccggcac caccugggcc ugcagcaccg gccugacccc uugcaucagc       240
accaccaucc ugaaccugac caccgacuac ugcgugcugg uggagcugug gcccaggguc       300
accuaccaca gccccagcua cgccuaccac caguucgaga ggagggccaa guacaagagg       360
gagcccguga gccugacccu ggcccugcug cuggcggcc ugacaauggg cggcaucgcc        420
gccggcgugg gcaccggcac caccgcccug guggccaccc agcaguucca gcagcugcag       480
gccgccaugc acgacgaccu gaaggaggug gagaagucca ucaccaaccu ggagaagucc       540
cugaccagcc ugagcgaggu ggugcugcag aacaggaggg ccuggaccu gcuguuccug        600 aaggagggcg ccugugcgc cgcccugaag gaggagugcu gccuguacgc cgaccacacc        660
ggccugguga ucgugggcau ugucgcugge cuggccguce ucgccguggu ggugauugga       720
gcuguggucg cagcuguuau gugcagaaga aagucauccg gcggaaaggg aggcuccuac       780
ucucaggcug cuucgcuac agugccuaga gcucuuaugu guuuaucuca gcuguaa          837

<210> SEQ ID NO 90
<211> LENGTH: 378
<212> TYPE: RNA
<213> ORGANISM: Artificial sequence
<220> FEATURE:
<223> OTHER INFORMATION: Synthetic polynucleotide

<400> SEQUENCE: 90
augagaguga cagccccuag aaccuuacug cuucugcuuu ggggagcugu ugcucugaca        60
gagacauggg cuggaucuua ccacagcccc agcuacgccu accaccaguu cgagaggggg       120
ggaggaggcu ccgggggagg aggcucccug aagaucagcc aggccgugca cgccgcccac       180
gccgagauca acgaggccgg ccgggaggug aucgugggca uugucgcugg ccuggccguc       240
cucgccgugg uggugauugg agcuguggue gcagcuguua ugugcagaag aaagucaucc       300
ggcggaaagg gaggcuccua cucucaggcu gcuucgcua cagugccuag agcucuuaug       360
uguuuaucuc agcuguaa                                                    378

<210> SEQ ID NO 91
<211> LENGTH: 876
<212> TYPE: RNA
<213> ORGANISM: Artificial sequence
<220> FEATURE:
<223> OTHER INFORMATION: Synthetic polynucleotide

<400> SEQUENCE: 91
augagaguga cagccccuag aaccuuacug cuucugcuuu ggggagcugu ugcucugaca        60
gagacauggg cuggaucucu gagcgaggug accggccagg gccugugcau cggcgccgug       120
cccaagaccc accaggugcu gugcaacacc acccagaaga ccagcgacgg cagcuacuac       180
cuggccgcuc ccaccggcac caccugggcc ugcagcaccg gccugacccc uugcaucagc       240
accaccaucc ugaaccugac caccgacuac ugcgugcugg uggagcugug gcccaggguc       300
accuaccaca gccccagcua cgccuaccac caguucgaga ggagggccaa guacaagagg       360
```

-continued

```
gagcccguga gccugacccu ggcccugcug cugggcggcc ugacaauggg cggcaucgcc    420
gccggcgugg gcaccggcac caccgcccug guggccaccc agcaguucca gcagcugcag    480
gccgccaugc acgacgaccu gaaggaggug gagaagucca ucaccaaccu ggagaagucc    540
cugaccagcc ugagcgaggu ggugcugcag aacaggaggg gccuggaccu gcuguuccug    600
aaggagggcg gccugugcgc cgcccugaag gaggagugcu gccuguacgc cgaccacacc    660
ggccugguga ucgugggcau ugucgcuggc cuggccgucc ucgccguggu ggugauugga    720
gcuguggucg cagcuguuau gugcagaaga aagucauccg gcggaaaggg aggcuccuac    780
ucucaggcug cuucugcuac agugccuaga gcucuuaugu guuuaucuca gcugggcggc    840
ggaggcagcg acuacaagga cgacgaugac aaguaa                              876
```

```

<210> SEQ ID NO 92
<211> LENGTH: 417
<212> TYPE: RNA
<213> ORGANISM: Artificial sequence
<220> FEATURE:
<223> OTHER INFORMATION: Synthetic polynucleotide

<400> SEQUENCE: 92
augagaguga cagccccuag aaccuuacug cuucugcuuu ggggagcugu ugcucugaca     60
gagacauggg cuggaucuua ccacagcccc agcuacgccu accaccaguu cgagaggggg    120
ggaggaggcu ccgggggagg aggcucccug aagaucagcc aggccgugca cgccgcccac    180
gccgagauca acgaggccgg ccgggaggug aucgugggca uugucgcugg ccuggccguc    240
cucgccgugg uggugauugg agcugugguc gcagcuguua ugugcagaag aaagucaucc    300
ggcggaaagg gaggcuccua cucucaggcu gcuucugcua cagugccuag agcucuuaug    360
uguuuaucuc agcugggcgg cggaggcagc gacuacaagg acgacgauga caaguaa       417
```

```

<210> SEQ ID NO 93
<211> LENGTH: 550
<212> TYPE: PRT
<213> ORGANISM: Artificial sequence
<220> FEATURE:
<223> OTHER INFORMATION: Synthetic polypeptide

<400> SEQUENCE: 93

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140
```

```
Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
            165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
            290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
            530                 535                 540

Gly Gly Lys Ile Ala Val
545                 550
```

```
<210> SEQ ID NO 94
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 94

Met Lys Leu Val Val Val Gly Ala Gly Gly Val Gly Lys Ser Ala Leu
1               5                   10                  15

Thr Ile

<210> SEQ ID NO 95
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 95

Met Asp Pro Arg Arg Tyr Ala Pro Met Ile Arg Pro Ala Lys Leu Asp
1               5                   10                  15

Val Leu Pro Arg Asn
            20

<210> SEQ ID NO 96
<211> LENGTH: 278
<212> TYPE: PRT
<213> ORGANISM: Artificial sequence
<220> FEATURE:
<223> OTHER INFORMATION: Synthetic polypeptide

<400> SEQUENCE: 96

Met Arg Val Thr Ala Pro Arg Thr Leu Leu Leu Leu Leu Trp Gly Ala
1               5                   10                  15

Val Ala Leu Thr Glu Thr Trp Ala Gly Ser Leu Ser Glu Val Thr Gly
                20                  25                  30

Gln Gly Leu Cys Ile Gly Ala Val Pro Lys Thr His Gln Val Leu Cys
            35                  40                  45

Asn Thr Thr Gln Lys Thr Ser Asp Gly Ser Tyr Tyr Leu Ala Ala Pro
        50                  55                  60

Thr Gly Thr Thr Trp Ala Cys Ser Thr Gly Leu Thr Pro Cys Ile Ser
65                  70                  75                  80

Thr Thr Ile Leu Asn Leu Thr Thr Asp Tyr Cys Val Leu Val Glu Leu
                85                  90                  95

Trp Pro Arg Val Thr Tyr His Ser Pro Ser Tyr Ala Tyr His Gln Phe
                100                 105                 110

Glu Arg Arg Ala Lys Tyr Lys Arg Glu Pro Val Ser Leu Thr Leu Ala
            115                 120                 125

Leu Leu Leu Gly Gly Leu Thr Met Gly Gly Ile Ala Ala Gly Val Gly
        130                 135                 140

Thr Gly Thr Thr Ala Leu Val Ala Thr Gln Gln Phe Gln Gln Leu Gln
145                 150                 155                 160

Ala Ala Met His Asp Asp Leu Lys Glu Val Glu Lys Ser Ile Thr Asn
                165                 170                 175

Leu Glu Lys Ser Leu Thr Ser Leu Ser Glu Val Val Leu Gln Asn Arg
                180                 185                 190

Arg Gly Leu Asp Leu Leu Phe Leu Lys Glu Gly Gly Leu Cys Ala Ala
            195                 200                 205
```

```
Leu Lys Glu Glu Cys Cys Leu Tyr Ala Asp His Thr Gly Leu Val Ile
    210                 215                 220

Val Gly Ile Val Ala Gly Leu Ala Val Leu Ala Val Val Ile Gly
225                 230                 235                 240

Ala Val Val Ala Ala Val Met Cys Arg Arg Lys Ser Ser Gly Gly Lys
                245                 250                 255

Gly Gly Ser Tyr Ser Gln Ala Ala Ser Ala Thr Val Pro Arg Ala Leu
            260                 265                 270

Met Cys Leu Ser Gln Leu
            275

<210> SEQ ID NO 97
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 97

Met Arg Val Thr Ala Pro Arg Thr Leu Leu Leu Leu Leu Trp Gly Ala
1               5                   10                  15

Val Ala Leu Thr Glu Thr Trp Ala Gly Ser Tyr His Ser Pro Ser Tyr
                20                  25                  30

Ala Tyr His Gln Phe Glu Arg Gly Gly Gly Ser Gly Gly Gly Gly
            35                  40                  45

Ser Leu Lys Ile Ser Gln Ala Val His Ala Ala His Ala Glu Ile Asn
50                  55                  60

Glu Ala Gly Arg Glu Val Ile Val Gly Ile Val Ala Gly Leu Ala Val
65                  70                  75                  80

Leu Ala Val Val Val Ile Gly Ala Val Val Ala Ala Val Met Cys Arg
                85                  90                  95

Arg Lys Ser Ser Gly Gly Lys Gly Gly Ser Tyr Ser Gln Ala Ala Ser
                100                 105                 110

Ala Thr Val Pro Arg Ala Leu Met Cys Leu Ser Gln Leu
            115                 120                 125

<210> SEQ ID NO 98
<211> LENGTH: 291
<212> TYPE: PRT
<213> ORGANISM: Artificial sequence
<220> FEATURE:
<223> OTHER INFORMATION: Synthetic polypeptide

<400> SEQUENCE: 98

Met Arg Val Thr Ala Pro Arg Thr Leu Leu Leu Leu Leu Trp Gly Ala
1               5                   10                  15

Val Ala Leu Thr Glu Thr Trp Ala Gly Ser Leu Ser Glu Val Thr Gly
                20                  25                  30

Gln Gly Leu Cys Ile Gly Ala Val Pro Lys Thr His Gln Val Leu Cys
            35                  40                  45

Asn Thr Thr Gln Lys Thr Ser Asp Gly Ser Tyr Tyr Leu Ala Ala Pro
50                  55                  60

Thr Gly Thr Thr Trp Ala Cys Ser Thr Gly Leu Thr Pro Cys Ile Ser
65                  70                  75                  80

Thr Thr Ile Leu Asn Leu Thr Thr Asp Tyr Cys Val Leu Val Glu Leu
                85                  90                  95

Trp Pro Arg Val Thr Tyr His Ser Pro Ser Tyr Ala Tyr His Gln Phe
                100                 105                 110
```

```
Glu Arg Arg Ala Lys Tyr Lys Arg Glu Pro Val Ser Leu Thr Leu Ala
        115                 120                 125

Leu Leu Leu Gly Gly Leu Thr Met Gly Gly Ile Ala Ala Gly Val Gly
130             135                 140

Thr Gly Thr Thr Ala Leu Val Ala Thr Gln Gln Phe Gln Gln Leu Gln
145                 150                 155                 160

Ala Ala Met His Asp Asp Leu Lys Glu Val Glu Lys Ser Ile Thr Asn
                165                 170                 175

Leu Glu Lys Ser Leu Thr Ser Leu Ser Glu Val Val Leu Gln Asn Arg
            180                 185                 190

Arg Gly Leu Asp Leu Leu Phe Leu Lys Glu Gly Gly Leu Cys Ala Ala
        195                 200                 205

Leu Lys Glu Glu Cys Cys Leu Tyr Ala Asp His Thr Gly Leu Val Ile
    210                 215                 220

Val Gly Ile Val Ala Gly Leu Ala Val Leu Ala Val Val Ile Gly
225                 230                 235                 240

Ala Val Val Ala Ala Val Met Cys Arg Arg Lys Ser Ser Gly Gly Lys
                245                 250                 255

Gly Gly Ser Tyr Ser Gln Ala Ala Ser Ala Thr Val Pro Arg Ala Leu
        260                 265                 270

Met Cys Leu Ser Gln Leu Gly Gly Gly Ser Asp Tyr Lys Asp Asp
        275                 280                 285

Asp Asp Lys
    290

<210> SEQ ID NO 99
<211> LENGTH: 138
<212> TYPE: PRT
<213> ORGANISM: Artificial sequence
<220> FEATURE:
<223> OTHER INFORMATION: Synthetic polypeptide

<400> SEQUENCE: 99

Met Arg Val Thr Ala Pro Arg Thr Leu Leu Leu Leu Leu Trp Gly Ala
1               5                   10                  15

Val Ala Leu Thr Glu Thr Trp Ala Gly Ser Tyr His Ser Pro Ser Tyr
                20                  25                  30

Ala Tyr His Gln Phe Glu Arg Gly Gly Gly Ser Gly Gly Gly Gly
            35                  40                  45

Ser Leu Lys Ile Ser Gln Ala Val His Ala Ala His Ala Glu Ile Asn
50                  55                  60

Glu Ala Gly Arg Glu Val Ile Val Gly Ile Val Ala Gly Leu Ala Val
65                  70                  75                  80

Leu Ala Val Val Val Ile Gly Ala Val Val Ala Val Met Cys Arg
                85                  90                  95

Arg Lys Ser Ser Gly Gly Lys Gly Gly Ser Tyr Ser Gln Ala Ala Ser
                100                 105                 110

Ala Thr Val Pro Arg Ala Leu Met Cys Leu Ser Gln Leu Gly Gly Gly
        115                 120                 125

Gly Ser Asp Tyr Lys Asp Asp Asp Asp Lys
        130                 135

<210> SEQ ID NO 100
<211> LENGTH: 9690
<212> TYPE: RNA
<213> ORGANISM: Artificial sequence
```

<220> FEATURE:
<223> OTHER INFORMATION: Synthetic polynucleotide

<400> SEQUENCE: 100

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucgugguca a cggcaggacc cagaggaaca ccaacacaau gaagaacuac cugcugcccg   1200
ugguggccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
```

| | |
|---|---|
| gaaagagcgg caucaucaag agcgccguga ccaagaaaga ccuggugguc agcgccaaga | 2280 |
| aagagaacug cgccgagauc aucaggacg ugaagaagau gaaaggccug gacgugaacg | 2340 |
| cgcgcaccgu ggacagcgug cugcugaacg gcugcaagca ccccguggag acccuguaca | 2400 |
| ucgacgaggc cuucgcuugc cacgccggca cccugagggc ccugaucgcc aucaucaggc | 2460 |
| ccaagaaagc cgugcugugc ggcgacccca agcagugcgg cuucuucaac augaugugcc | 2520 |
| ugaaggugca cuucaaccac gagaucugca cccaggguguu ccacaagagc aucagcaggc | 2580 |
| ggugcaccaa gagcgugacc agcgucguga gcacccuguu cuacgacaag aaaaugagga | 2640 |
| ccaccaaccc caaggagacc aaaaucguga ucgacaccac aggcagcacc aagcccaagc | 2700 |
| aggacgaccu gauccugacc ugcuucaggg gcuggguga gcagcugcag aucgacuaca | 2760 |
| agggcaacga gaucaugacc gccgcugcca gccagggccu gaccaggaag ggcguguacg | 2820 |
| ccgugaggua caaggugaac gagaacccac uguacgcucc caccagcgag cacgugaacg | 2880 |
| ugcugcugac caggaccgag gacaggaucg uguggaagac ccuggccggc gaccccugga | 2940 |
| ucaagacccu gaccgccaag uaccccggca acuucaccgc caccaucgaa gaguggcagg | 3000 |
| ccgagcacga cgccaucaug aggcacaucc uggagaggcc cgaccccacc gacguguucc | 3060 |
| agaacaaggc caacgugugc ugggccaagg cccuggugcc cgugcugaag accgccggca | 3120 |
| ucgacaugac cacagagcag uggaacaccg uggacuacuu cgagaccgac aaggcccaca | 3180 |
| gcgccgagau cgugcugaac cagcugcgcg ugagguucuu cggccuggac cuggacagcg | 3240 |
| gccuguucag cgcccccacc gugccacuga gcaucaggaa caaccacugg acaacagcc | 3300 |
| ccagcccaaa cauguacggc cugaacaagg aggugucag gcagcugagc aggcgguacc | 3360 |
| cacagcugcc cagggccgug gccaccggca ggguguacga caugaacacc ggcacccuga | 3420 |
| ggaacuacga ccccaggauc aaccuggugc cgugaacag cggcugccc cacgcccugg | 3480 |
| ugcugcacca caacgagcac ccacagagcg acuucagcuc cuucgugagc aagcugaaag | 3540 |
| gcaggaccgu gcuggucgug ggcgagaagc ugagcgugcc cggcaagaug guggacuggc | 3600 |
| ugagcgacag gcccgaggcc accuuccggg ccaggcugga ccucggcauc cccggcgacg | 3660 |
| ugcccaagua cgacaucauc uucgugaacg ucaggacccc auacaaguac caccauuacc | 3720 |
| agcagugcga ggaccacgcc aucaagcuga gcaugcugac caagaaggcc ugccugcacc | 3780 |
| ugaaccccgg aggcaccugc gugagcaucg gcuacggcua cgccgacagg ccagcgaga | 3840 |
| gcaucauugg cgccaucgcc aggcuguuca guucagcag gggugugcaaa cccaagagca | 3900 |
| gccuggagga aaccgaggug cuguucgugu ucaucggcua cgaccggaag gccaggaccc | 3960 |
| acaaccccua caagcugagc agcacccuga caaacaucua caccggcagc aggcugcacg | 4020 |
| aggcggcug cgcccccagc uaccacgugg ucagggcga uaucgccacc gccaccgagg | 4080 |
| gcgugaucau caacgcugcc aacagcaagg gccagcccgg aggcggagug ugcggcgccc | 4140 |
| uguacaagaa guuccccgag agcuucgacc ugcagcccau cgagguggc aaggccaggc | 4200 |
| uggugaaggg cgccgcuaag cacaucaucc acgccguggg cccaacuuc aacaagguga | 4260 |
| gcgagguga aggcgacaag cagcuggccg aagccuacga gagcaucgcc aagaucguga | 4320 |
| acgacaauaa cuacaagagc guggccaucc cacugcucag caccggcauc uucagcggca | 4380 |
| acaaggacag gcugacccag agccugaacc accugcucac cgcccuggac accaccgaug | 4440 |
| ccgacguggc caucuacugc agggacaaga guggggagau gacccugaag gaggccgugg | 4500 |
| ccaggcggga ggccguggaa gagaucagca ucagcgacga cuccagcgug accgagcccg | 4560 |
| acgccgagcu ggugagggug cacccccaaga gcucccuggc cggcaggaag ggcuacagca | 4620 |

-continued ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240
ccaccaucag gagcgccgug cccagcgcca uccagaacac ccugcagaac gugcuggccg 6300
cugccaccaa gaggaacugc aacgugaccc agaugaggga gcugcccgug cuggacagcg 6360
cugccuucaa cguggagugc uucaagaaau acgccugcaa caacgaguac ugggagaccu 6420
ucaaggagaa ccccaucagg cugaccgaag agaacguggu gaacuacauc accaagcuga 6480
agggccccaa ggccgcugcc cuguucgcua agacccacaa ccugaacaug cugcaggaca 6540
ucccaaugga cagguucgug auggaccuga agagggacgu gaaggugaca cccggcacca 6600
agcacaccga ggagaggccc aaggugcagg ugauccaggc cgcugaccca cuggccaccg 6660
ccuaccugug cggcauccac agggagcugg ugaggcggcu gaacgccgug cugcugccca 6720
acauccacac ccuguucgac augagcgccg aggacuucga cgccaucauc gccgagcacu 6780
uccagcccgg cgacugcgug cuggagaccg acaucgccag cuucgacaag agcgaggaug 6840
acgcuauggc ccugaccgcu cugaugaucc uggaggaccu gggcguggac gccgagcugc 6900
ucacccugau cgaggcugcc uucggcgaga ucagcuccau ccaccugccc accaagacca 6960


| | |
|---|---|
| aguucaaguu cggcgcuaug augaaaagcg gaauguuccu gacccuguuc gugaacaccg | 7020 |
| ugaucaacau ugugaucgcc agcagggugc ugcgggagag gcugaccggc agccccugcg | 7080 |
| cugccuucau cggcgacgac aacaucguga agggcgugaa aagcgacaag cugauggccg | 7140 |
| acaggugcgc caccuggcug aacauggagg ugaagaucau cgacgccgug gugggcgaga | 7200 |
| aggcccccua cuucugcggc ggauucaucc ugugcgacag cgugaccggc accgccugca | 7260 |
| ggguggccga cccccugaag aggcuguuca agcgggcaa gccacuggcc gcugacgaug | 7320 |
| agcacgacga ugacaggcgg agggcccugc acgaggaaag caccaggugg aacagggugg | 7380 |
| gcauccugag cgagcugugc aaggccgugg agagcaggua cgagaccgug ggcaccagca | 7440 |
| ucaucgugau ggcuaugacc acacuggcca gcuccgucaa gagcuucccc uaccugaggg | 7500 |
| gggcccccuau aacucucuac ggcuaaccug aauggacuac gacauagucu aguccgccaa | 7560 |
| ggccgccacc auggaagaug ccaaaaacau uaagaagggc ccagcgccau cuacccacu | 7620 |
| cgaagacggg accgcggcg agcagcugca caaagccaug aagcgcuacg cccuggugcc | 7680 |
| cggcaccauc gccuuuaccg acgcacauau cgaggugac auuaccuacg ccgaguacuu | 7740 |
| cgagaugagc guucggcugg cagaagcuau gaagcgcuau gggcugaaua caaaccaucg | 7800 |
| gaucguggug ugcagcgaga auagcuugca guucuucaug cccguguugg gugcccuguu | 7860 |
| caucggugug gcuguggccc cagcuaacga caucuacaac gagcgcgagc ugcugaacag | 7920 |
| caugggcauc agccagccca ccgucgauau cgugagcaag aaagggcugc aaaagauccu | 7980 |
| caacgugcaa aagaagcuac cgaucauaca aaagaucauc aucauggaua gcaagaccga | 8040 |
| cuaccagggc uuccaaagca uguacacccu cgugacuucc cauuugccac ccggcuucaa | 8100 |
| cgaguacgac uucgugcccg agagcuucga ccggacaaa accaucgccc ugaucaugaa | 8160 |
| caguaguggc aguaccggau ugccaagggc guagcccua ccgcaccgca ccgcuugugu | 8220 |
| ccgauucagu caugcccgcg accccaucuu cggcaaccag aucaucccg acaccgcuau | 8280 |
| ccucagcgug gugccauuuc accacggcu cggcauguuc accacgcugg cuacuugau | 8340 |
| cugcggcuuu cgggucgugc ucauguaccg cuucgaggag gagcuauucu gcgcagcuu | 8400 |
| gcaagacuau aagauucaau cugcccugcu ggugcccaca cuauuuagcu ucuucgcuaa | 8460 |
| gagcacucuc aucgacaagu acgaccuaag caacuugcac gagaucgcca gcggcgggc | 8520 |
| gccgcucagc aaggagguag gugaggccgu ggccaaacgc uuccaccuac caggcauccg | 8580 |
| acagggcuac ggccugacag aaacaaccag cgccauucug aucacccccg aaggggacga | 8640 |
| caagccuggc gcaguaggca aggugguggcc cuucuucgag gcuaaggugg uggacuugga | 8700 |
| caccgguaag acacugggug ugaaccagcg cggcgagcug ugcguccgug gccccaugau | 8760 |
| caugagcggc uacguuaaca accccgaggc uacaaacgcu ucaucgaca aggacggcug | 8820 |
| gcugcacagc ggcgacaucg ccuacuggga cgaggacgag cacuucuuca ucguggaccg | 8880 |
| gcugaaguc cugaucaaau acaagggcua ccaguagcc ccagccgaac uggagagcau | 8940 |
| ccugcugcaa caccccaaca ucuucgacgc cgggucgcc ggccugcccg acgacgaugc | 9000 |
| cggcgagcug cccgccgcag ucgucugcu ggaacacggu aaaaccauga ccgagaagga | 9060 |
| gaucguggac uaugggcca gccagguac aaccgcaag aagcugcgcg gugguuguu | 9120 |
| guucguggac gaggugccua aggacugac cggcaaguug gacgcccgca agauccgcga | 9180 |
| gauucucauu aaggccaaga agggcggcaa gaucgccgug uaacgagu auguuacgug | 9240 |
| caaaggugau ugucacccc cgaaagacca uauugugaca caccucagu aucacgccca | 9300 |
| aacauuuaca gccgcggugu caaaaaccgc guggacgugg uuaacauccc ugcugggagg | 9360 | aucagccgua auuauuauaa uuggcuuggu gcuggcuacu auuguggcca uguacgugcu 9420 gaccaaccag aaacauaauu gaauacagca gcaauuggca agcugcuuac auagaacucg 9480 cggcgauugg caugccgccu uaaaauuuuu auuuuauuuu uucuuuucuu uuccgaaucg 9540 gauuuuguuu uuaauauuuc aaaaaaaaaa aaaaaaaaaa aaaaaucuag aaaaaaaaaa 9600 aaaaaaaaaa aaaaaaaaaa aaaaaaaaaa aaaaaaaaaa aaaaaaaaaa aaaaaaaaaa 9660 aaaaaaaaaa aaaaaaaaaa aaaaaaaaaa 9690

<210> SEQ ID NO 101
<211> LENGTH: 9773
<212> TYPE: RNA
<213> ORGANISM: Artificial sequence
<220> FEATURE:
<223> OTHER INFORMATION: Synthetic polynucleotide

<400> SEQUENCE: 101
auugacggcg uaguacacac uauugaauca aacagccgac caauugcacu accaucacaa 60
uggagaagcc aguaguaaac guagacguag acccccagag uccguuuguc gugcaacugc 120
aaaaaagcuu cccgcaauuu gagguaguag cacagcaggu cacuccaaau gaccaugcua 180
augccagagc auuuucgcau cuggccagua aacuaaucga gcuggagguu ccuaccacag 240
cgacgaucuu ggacauaggc agcgcaccgg cucguagaau guuuuccgag caccaguauc 300
auugugucug ccccaugcgu aguccagaag acccggaccg caugaugaaa uaugccagua 360
aacuggcgga aaaagcgugc aagauuacaa acaagaacuu gcaugagaag auuaaggauc 420
uccggaccgu acuugauacg ccggaugcug aaacaccauc gcucugcuuu cacaacgaug 480
uuaccugcaa caugcgugcc gaauauuccg ucaugcagga cguguauauc aacgcucccg 540
gaacuaucua ucaucaggcu augaaaggcg ugcggacccu guacuggauu ggcuucgaca 600
ccacccaguu cauguucucg gcuauggcag guucguaccc ugcguacaac accaacuggg 660
ccgacgagaa aguccuugaa gcgcguaaca ucggacuuug cagcacaaag cugagugaag 720
guaggacagg aaaauugucg auaaugagga agaaggaguu gaagcccggg ucgcggguuu 780
auuucuccgu aggaucgaca cuuuauccag aacacagagc cagcuugcag agcuggcauc 840
uuccaucggu guuccacuug aauggaaagc agucguacac uugccgcugu gauacagugg 900
ugaguugcga aggcuacgua gugaagaaaa ucaccaucag ucccgggauc acgggagaaa 960
ccgugggaua cgcgguuaca cacaauagcg agggcuucuu gcuaugcaaa guuacugaca 1020
caguaaaagg agaacgggua ucguucccug ugugcacgua cauccc ggcc accauaugcg 1080 aucagaugac ugguauaaug gccacggaua uaucaccuga cgaugcacaa aaacuucugg 1140
uugggcucaa ccagcgaauu gucauuaacg guaggacuaa caggaacacc aacaccaugc 1200
aaaauuaccu ucugccgauc auagcacaag gguucagcaa augggcuaag gagcgcaagg 1260
augaucuuga uaacgagaaa augcugggua cuagagaacg caagcuuacg uauggcugcu 1320 uguggggcguu ucgcacuaag aaaguacauu cguuuuaucg cccaccugga acgcagaccu 1380
gcguaaaagu cccagccucu uuuagcgcuu uucccauguc guccguaugg acgaccucuu 1440
ugcccauguc gcugaggcag aaauugaaac uggcauugca accaaagaag gaggaaaaac 1500
ugcugcaggu cucggaggaa uuagucaugg aggccaaggc ugcuuuugag gaugcucagg 1560
aggaagccag agcggagaag cuccgagaag cacuuccacc auuaguggca gacaaaggca 1620
ucgaggcagc cgcagaaguu gucugcgaag uggaggggcu ccaggcggac aucggagcag 1680

-continued

```
cauuaguuga aaccccgcgc ggucacguaa ggauaauacc ucaagcaaau gaccguauga    1740
ucggacagua uaucguuguc ucgccaaacu cugugcugaa gaaugccaaa cucgcaccag    1800
cgcacccgcu agcagaucag guuaagauca uaacacacuc cggaagauca ggaagguacg    1860
cggucgaacc auacgacgcu aaaguacuga ugccagcagg aggugccgua ccauggccag    1920
aauuccuagc acugagugag agcgccacgu uaguguacaa cgaaagagag uuugugaacc    1980
gcaaacuaua ccacauugcc augcauggcc cgccaagaa uacagaagag gagcaguaca     2040
agguuacaaa ggcagagcuu gcagaaacag aguacguguu ugacguggac aagaagcguu    2100
gcguuaagaa ggaagaagcc ucaggucugg uccucucggg agaacugacc aacccucccu    2160
aucaugagcu agcucuggag ggacugaaga cccgaccugc ggucccguac aaggucgaaa    2220
caauaggagu gauaggcaca ccggggucgg gcaagucagc uauuaucaag ucaacuguca    2280
cggcacgaga ucuuguuacc agcggaaaga aagaaaauug ucgcgaaauu gaggccgacg    2340
ugcuaagacu gaggggguaug cagauuacgc cgaagacagu agauucgguu augcucaacg    2400
gaugccacaa agccguagaa gugcuguacg uugacgaagc guucgcgugc cacgcaggag    2460
cacuacuugc cuugauugcu aucgucaggc cccgcaagaa gguaguacua ugcggagacc    2520
ccaugcaaug cggauucuuc aacaugaugc aacuaaaggu acauuucaau cacccugaaa    2580
aagacauaug caccaagaca uucuacaagu auaucucccg gcguugcaca cagccaguua    2640
cagcuauugu aucgacacug cauuacgaug gaaagaugaa aaccacgaac ccgugcaaga    2700
agaacauuga aaucgauauu acaggggcca caaagccgaa gccaggggau aucauccuga    2760 cauguuccg cggguggguu aagcaauugc aaaucgacua ucccggacau gaaguaauga    2820
cagccgcggc cucacaaggg cuaaccagaa aaggagugua ugccguccgg caaaaaguca    2880
augaaaaccc acuguacgcg aucacaucag agcaugugaa cguguugcuc acccgcacug    2940
aggacaggcu agugguggaaa accuugcagg gcgacccaug gauuaagcag cucacuaaca    3000
uaccuaaagg aaacuuucag gcuacuauag aggacugga agcugaacac aagggaauaa    3060
uugcugcaau aaaacagccccc acuccccgug ccaauccguu cagcugcaag accaacguuu    3120
gcugggcgaa agcauuggaa ccgauacuag ccacggccgg uaucguacuu accgguugcc    3180
aguggagcga acuguuccca caguuugcgg augacaaacc acauucggcc auuuacgccu    3240
uagacguaau uugcauuaag uuuuucggca uggacuugac aagcgacug uuuucuaaac    3300 agagcauccc acuaacguac caucccgccg auucagcgag gccgguagcu cauugggaca    3360
acagcccagg aaccccgcaag uaugggguacg aucacgccau ugccgccgaa cucuccccgua    3420 gauuuccggu guuccagcua gcugggaagg gcacacaacu ugauugcag acggggagaa    3480 ccagaguuau cucugcacag cauaaccugg uccggugaa ccgcaaucuu ccucacgccu    3540
uaguccccga guacaaggag aagcaacccg gcccggucga aaaauucuug aaccaguuca    3600
aacaccacuc aguacuugug guaucagagg aaaaauuga agcuccccgu aagagaaucg    3660
aauggaucgc cccgauuggc auagccggug cagauaagaa cuacaaccug gcuuucgggu    3720
uuccgccgca ggcacgguac gaccugguu ucaucaacau uggaacuaaa uacagaaacc    3780
accacuuuca gcagugcgaa gaccaugcgg cgaccuuaaa aacccuuucg cguucggccc    3840
ugaauugccu uaacccagga ggcacccucg uggugaaguc cuauggcuac gccgaccgca    3900
acagugagga cguagucacc gcucuugcca gaaaguuugu cagggugucu gcagcgagac    3960
cagauugugu cucaagcaau acagaaaugu accugauuuu ccgacaacua gacaacagcc    4020
guacacggca auucaccccg caccaucuga uugcgugau uucguccgug uaugaggggua    4080
```

```
caagagaugg aguuggagcc gcgccgucau accgcaccaa aagggagaau auugcugacu    4140
gucaagagga agcaguuguc aacgcagcca auccgcuggg uagaccaggc gaaggagucu    4200
gccgugccau cuauaaacgu uggccgacca guuuuaccga uucagccacg gagacaggca    4260
ccgcaagaau gacugugugc cuaggaaaga aagugaucca cgcggucggc ccugauuucc    4320
ggaagcaccc agaagcagaa gccuugaaau ugcuacaaaa cgccuaccau gcaguggcag    4380
acuuaguaaa ugaacauaac aucaagucug ucgccauucc acugcuaucu acaggcauuu    4440
acgcagccgg aaaagaccgc cuugaaguau cacuuaacug cuugacaacc gcgcuagaca    4500
gaacugacgc ggacguaacc aucuauugcc uggauaagaa guggaaggaa agaaucgacg    4560
cggcacucca acuuaaggag ucuguaacag agcugaagga ugaagauaug gagaucgacg    4620
augaguuagu auggauccau ccagacaguu gcuugaaggg aagaaaggga uucaguacua    4680
caaaaggaaa auuguauucg uacuucgaag gcaccaaauu ccaucaagca gcaaaagaca    4740
uggcggagau aaagguccug uucccuaaug accaggaaag uaaugaacaa cugugugccu    4800
acauauuggg ugagaccaug gaagcaaucc gcgaaaagug cccggucgac cauaacccgu    4860
cgucuagccc gcccaaaacg uugccgugcc uuugcaugua ugccaugacg ccagaaaggg    4920
uccacagacu uagaagcaau aacgucaaag aaguuacagu augcuccucc ccccccuuc    4980 cuaagcacaa aauuaagaau guucagaagg uucagugcac gaaaguaguc cuguuuaauc    5040
cgcacacucc cgcauucguu cccgcccgua aguacauaga agugccagaa cagccuaccg    5100
cuccuccugc acaggccgag gaggcccccg aaguuguagc gacaccguca ccaucuacag    5160
cugauaacac cucgcuugau gucacagaca ucucacugga uauggaugac aguagcgaag    5220
gcucacuuuu uucgagcuuu agcggaucgg acaacucuau uacuaguaug gacaguuggu    5280
cgucaggacc uaguucacua gagauaguag accgaaggca gguggugug gcugacguuc    5340 augccgucca agagccugcc ccuauuccac cgccaaggcu aaagaagaug gcccgccugg    5400
cagcggcaag aaaagagccc acuccaccgg caagcaauag cucugagucc cuccaccucu    5460 cuuuggugg gguauccaug ucccucggau caauuuucga cggagagacg gcccgccagg    5520
cagcgguaca accccuggca acaggcccca cggaugugcc uaugucuuuc ggaucguuuu    5580
ccgacggaga gauugaugag cugagccgca gaguaacuga guccgaaccc guccuguuug    5640
gaucauuuga accgggcgaa gugaacucaa uuauaucguc ccgaucagcc guaucuuuuc    5700
cucuacgcaa gcagagacgu agacgcagga gcaggaggac ugaauacuga cuaaccgggg    5760
uaggugggua cauauuuucg acggacacag gcccugggca cuugcaaaag aaguccguuc    5820
ugcagaacca gcuuacagaa ccgaccuugg agcgcaaugu ccuggaaaga auucaugccc    5880
cggugcucga cacgucgaaa gaggaacaac ucaaacucag guaccagaug augcccaccg    5940
aagccaacaa aaguagguac cagucucgua aaguagaaaa ucagaaagcc auaaccacug    6000
agcgacuacu gucaggacua cgacuguaua acucugccac agaucagcca gaaugcuaua    6060
agaucaccua uccgaaacca uuguacucca guagcguacc ggcgaacuac uccgauccac    6120
aguucgcugu agcugucugu aacaacuauc ugcaugagaa cuauccgaca guagcaucuu    6180
aucagauuac ugacgaguac gaugcuuacu uggauauggu agacgggaca gucgccgcc    6240 uggacacugc aaccuucugc cccgcuaagc uuagaaguua cccgaaaaaa caugaguaua    6300 gagcccgaa uauccgcagu gcgguccau cagcgaugca gaacacgcua caaaaugugc    6360
ucauugccgc aacuaaaaga aauugcaacg ucacgcagau gcgugaacug ccaacacugg    6420
```

-continued

```
acucagcgac auucaauguc gaaugcuuuc gaaaauaugc auguaaugac gaguauuggg    6480
aggaguucgc ucggaagcca auuaggauua ccacugaguu ugucaccgca uauguagcua    6540
gacugaaagg cccuaaggcc gccgcacuau uugcaaagac guauaauuug gucccauugc    6600
aagaagugcc uauggauaga uucgucaugg acaugaaaag agacgugaaa guuacaccag    6660
gcacgaaaca cacagaagaa agaccgaaag uacaagugau acaagccgca gaaccccugg    6720
cgacugcuua cuuaugcggg auucaccggg aauuagugcg uaggcuuacg gccgucuugc    6780
uuccaaacau ucacacgcuu uuugacaugu cggcggagga uuuugaugca aucauagcag    6840
aacacuucaa gcaaggcgac ccgguacugg agacggauau cgcaucauuc gacaaaagcc    6900
aagacgacgc uauggcguua accggucuga ugaucuugga ggaccugggu guggaucaac    6960
cacuacucga cuugaucgag ugcgccuuug gagaaauauc auccacccau cuaccuacgg    7020
guacucguuu uaaauucggg gcgaugauga auccggaauu guuccucaca cuuuuuguca    7080
acacaguuuu gaaugucguu aucgccagca gaguacuaga ggagcggcuu aaaacguccá    7140 gaugugcagc guucauuggc gacgacaaca ucauacaugg aguaguaucu gacaaagaaa    7200
uggcugagag gugcgccacc uggcucaaca uggagguuaa gaucaucgac gcagucaucg    7260
gugagagacc accuuacuuc ugcggcgau uuaucuugca agauucgguu acuccacag     7320 cgugccgcgu ggcggauccc cugaaaaggc uguuuaaguu ggguaaaccg cucccagccg    7380
acgacgagca agacgaagac agaagacgcg cucugcuaga ugaaacaaag gcgugguuua    7440
gaguagguau aacaggcacu uuagcagugg ccgugacgac ccgguaugag guagacaaua    7500
uuacaccugu ccuacuggca uugagaacuu ugcccagag caaaagagca uccaagcca     7560 ucagagggga aauaaagcau cucuacggug guccuaaaua gucagcauag uacauuucau    7620
cugacuaaua cuacaacacc accaccaugg aagaugccaa aaacauuaag aagggcccag    7680
cgccauucua cccacucgaa gacgggaccg ccggcgagca gcugcacaaa gccaugaagc    7740
gcuacgcccu ggugcccggc accaucgccu uuaccgacgc acauacgag guggacauua     7800 ccuacgccga guacuucgag augagcguuc ggcuggcaga agcuaugaag cgcuaugggc    7860
ugaauacaaa ccaucggauc guggugugca gcgagaauag cuugcaguuc uucaugcccg    7920 uguuggugc ccuguucauc gguguggcug uggccccagc uaacgacauc uacaacgagc    7980
gcgagcugcu gaacagcaug ggcaucagcc agcccaccgu cguauucgug agcaagaaag    8040
ggcugcaaaa gauccucaac gugcaaaaga agcuaccgau cauacaaaag aucaucauca    8100
uggauagcaa gaccgacuac cagggcuucc aaagcaugua caccuucgug acuucccauu    8160
ugccacccgg cuucaacgag uacgacuucg ugcccgagag cuucgaccgg gacaaaacca    8220
ucgcccugau caugaacagu aguggcagua ccggauugcc caaggcgua gcccuaccgc     8280 accgcaccgc uugugcccga uucagucaug cccgcgaccc caucuucggc aaccagauca    8340
uccccgacac cgcuauccuc agcgugguge cauuucacca cggcuucggc auguucacca    8400
cgcugggcua cuugaucugc ggcuuucggg ucgcucau guaccgcuuc gaggaggagc    8460
uauucuugcg cagcuugcaa gacuauaaga uucaaucugc ccugcugguu cccacacuau    8520
uuagcuucuu cgcuaagagc acucucaucg acaaguacga ccuaagcaac uugcacgaga    8580
ucgccagcgg cggggcgccg cucagcaagg agguagguga ggccgugggcc aaacgcuucc    8640 accuaccagg cauccgacag ggcuacggcc ugacagaaac aaccagcgcc auucugauca    8700
cccccgaagg ggacgacaag ccuggcgcag uaggcaaggu ggcccuuc uucgaggcua    8760 aggugguggá cuuggacacc gguaagacac uggguggaa ccagcgcggc gagcugugcg    8820
```

-continued uccguggccc caugaucaug agcggcuacg uuaacaaccc cgaggcuaca aacgcucuca 8880
ucgacaagga cggcuggcug cacagcggcg acaucgccua cugggacgag gacgagcacu 8940
ucuucaucgu ggaccggcug aagucccuga ucaaauacaa gggcuaccag guagccccag 9000
ccgaacugga gagcauccug cugcaacacc ccaacaucuu cgacgccggg gucgccggcc 9060
ugcccgacga cgaugccggc gagcugcccg ccgcagucgu cgugcuggaa cacgguaaaa 9120
ccaugaccga gaaggagauc guggacuaug uggccagcca gguuacaacc gccaagaagc 9180
ugcgcggugg uguuguguuc guggacgagg ugccuaaagg acugaccggc aaguuggacg 9240
cccgcaagau ccgcgagauu cucauuaagg ccaagaaggg cggcaagauc gccguguaaa 9300
cgcgugcuag accauggauc cuagacgcua cgccccaaug auccgaccag caaaacucga 9360
uguacuuccg aggaacugau gugcauaaug caucaggcug guacauuaga uccccgcuua 9420
ccgcgggcaa uauagcaaca cuaaaaacuc gauguacuuc cgaggaagcg cagugcauaa 9480
ugcugcgcag uguugccaca uaaccacuau auuaaccauu uaucuagcgg acgccaaaaa 9540
cucaauguau uucugaggaa gcguggugca uaaugccacg cagcgucugc auaacuuuua 9600
uuauuucuuu uauuaaucaa caaaauuuug uuuuuaacau uucaaaaaaa aaaaaaaaaa 9660
aaaaaaaauc uagaaaaaaa aaaaaaaaaa aaaaaaaaaa aaaaaaaaaa aaaaaaaaaa 9720
aaaaaaaaaa aaaaaaaaaa aaaaaaaaaa aaaaaaaaaa aaaaaaaaaa aaa 9773

<210> SEQ ID NO 102
<211> LENGTH: 2086
<212> TYPE: RNA
<213> ORGANISM: Artificial sequence
<220> FEATURE:
<223> OTHER INFORMATION: Synthetic polynucleotide

<400> SEQUENCE: 102
aggaaacuua agucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gccauggaag augccaaaaa cauuaagaag ggcccagcgc 180
cauucuaccc acucgaagac gggaccgccg gcgagcagcu gcacaaagcc augaagcgcu 240
acgcccuggu gcccggcacc aucgccuuua ccgacgcaca uaucgaggug gacauuaccu 300
acgccgagua cuucgagaug agcguucggc uggcagaagc uaugaagcgc uaugggcuga 360
auacaaacca ucggaucgug gugugcagcg agaauagcuu gcaguucuuc augcccgugu 420
ugggugcccu guucaucggu guggcugugg ccccagcuaa cgacaucuac aacgagcgcg 480
agcugcugaa cagcaugggc aucagccagc ccaccgucgu auucgugagc aagaaagggc 540
ugcaaaagau ccucaacgug caaaagaagc uaccgaucau acaaaagauc aucaucaugg 600
auagcaagac cgacuaccag ggcuuccaaa gcauguacac cuucgugacu ucccauuugc 660
cacccggcuu caacgaguac gacuucgugc ccgagagcuu cgaccgggac aaaaccaucg 720
cccugaucau gaacaguagu ggcaguaccg gauugcccaa gggcguagcc cuaccgcacc 780
gcaccgcuug uguccgauuc agucaugccc gcgaccccau cuucggcaac cagaucaucc 840
ccgacaccgc uauccucagc gugguccau uucaccacgg cuucggcaug uucaccacgc 900
ugggcuacuu gaucugcggc uuucgggucg ugcucaugua ccgcuucgag gaggagcuau 960
ucuugcgcag cuugcaagac uauaagauuc aaucugcccu gcuggugccc acacuauuua 1020
gcuucuucgc uaagagcacu cucaucgaca aguacgaccu aagcaacuug cacgagaucg 1080

```
ccagcggcgg ggcgccgcuc agcaaggagg uaggugaggc cguggccaaa cgcuuccacc   1140
uaccaggcau ccgacagggc uacggccuga cagaaacaac cagcgccauu cugaucaccc   1200
ccgaagggga cgacaagccu ggcgcaguag gcaagguggu gcccuucuuc gaggcuaagg   1260
ugguggacuu ggacaccggu aagacacugg gugugaacca gcgcggcgag cugugcgucc   1320
guggccccau gaucaugagc ggcuacguua acaaccccga ggcuacaaac gcucucaucg   1380
acaaggacgg cuggcugcac agcggcgaca ucgccuacug ggacgaggac gagcacuucu   1440
ucaucgugga ccggcugaag ucccugauca aauacaaggg cuaccaggua gccccagccg   1500
aacuggagag cauccugcug caacacccca acaucuucga cgccggggguc gccggccugc   1560
ccgacgacga ugccggcgag cugcccgccg cagucgucgu gcuggaacac gguaaaacca   1620
ugaccgagaa ggagaucgug gacuaugugg ccagccaggu uacaaccgcc aagaagcugc   1680
gcgguggugu uguguucgug gacgaggugc cuaaaggacu gaccggcaag uuggacgccc   1740
gcaagauccg cgagauucuc auuaaggcca agaagggcgg caagaucgcc guguaacucg   1800
agcuagugac ugacuaggau cugguuacca cuaaaccagc cucaagaaca cccgaaugga   1860
gucucuaagc uacauaauac caacuuacac uuacaaaaug uuguccccca aaauguagcc   1920
auucguaucu gcuccuaaua aaaagaaagu uucuucacau ucuagaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaa                  2086
```

<210> SEQ ID NO 103
<211> LENGTH: 8095
<212> TYPE: RNA
<213> ORGANISM: Artificial sequence
<220> FEATURE:
<223> OTHER INFORMATION: Synthetic polynucleotide

<400> SEQUENCE: 103

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
```
uggccaccga cgugagcgcc gacgacgccc agaagcugcu cgugggccug aaccagagga 1140
ucguggucaa cggcaggacc cagaggaaca ccaacacaau gaagaacuac cugcugcccg 1200
ugguggccca ggcuuucgcc aggugggcca aggaguacaa ggaggaccag gaagacgaga 1260
ggccccuggg ccugagggac aggcagcugg ugaugggcug cugcugggcc uucaggcggc 1320
acaagaucac cagcaucuac aagaggcccg acacccagac caucaucaag gugaacagcg 1380
acuuccacag cuucgugcug cccaggaucg gcagcaacac ccuggagauc ggccugagga 1440
cccggaucag gaagaugcug gaggaacaca aggagcccag cccacugauc accgccgagg 1500
acgugcagga ggccaagugc gcugccgacg aggccaagga ggugagggag gccgaggaac 1560
ugagggccgc ccugccaccc cuggcugccg acguggagga acccacccug gaagccgacg 1620
uggaccugau gcugcaggag gccggcgccg gaagcgugga gacacccagg ggccugauca 1680
aggugaccag cuacgacggc gaggacaaga ucggcagcua cgccgugcug agcccacagg 1740
ccgugcugaa guccgagaag cugagcugca uccacccacu ggccgagcag gugaucguga 1800
ucacccacag cggcaggaag ggcagguacg ccguggagcc cuaccacggc aagguggucg 1860
ugcccgaggg ccacgccauc cccgugcagg acuuccaggc ccugagcgag agcgccacca 1920
ucguguacaa cgagagggag uucgugaaca gguaccugca ccauaucgcc acccacggcg 1980
gagcccugaa caccgacgag gaauacuaca agaccgugaa gcccagcgag cacgacggcg 2040
aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccugguggcc agcgccaaga 2280
aagagaacug cgccgagauc aucagggacg ugaagaagau gaaaggccug gacgugaacg 2340
cgcgcaccgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccagguguu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420

-continued ggaacuacga ccccaggauc aaccuggugc ccgugaacag gcggcugccc cacgcccugg 3480
ugcugcacca caacgagcac ccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaagguga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820

```
uggaccagga gaaggaggaa cugcucagga agaaacugca gcugaacccc accccagcca    5880
acaggagcag guaccagagc aggaaggugg agaaacaugaa ggccaucacc gccaggcgga    5940
uccugcaggg ccugggacac uaccugaagg ccgagggcaa ggrggagugc uacaggaccc    6000
```

```
uggaccagga gaaggaggaa cugcucagga agaaacugca gcugaacccc accccagcca    5880
acaggagcag guaccagagc aggaaggugg agaaacauga ggccaucacc gccaggcgga    5940
uccugcaggg ccugggacac uaccugaagg ccgagggcaa ggrggagugc uacaggaccc    6000
ugcaccccgu gccacuguac agcuccacgc ugaacagggc cuucuccagc cccaaggugg    6060
ccguggaggc cugcaacgcu augcugaagg agaacucucc caccguggcc agcuacugca    6120
ucaucccga guacgacgcc uaccuggaca ugguggacgg cgccagcugc ugccuggaca    6180
ccgccagcuu cugccccgcc aagcugagga gcuuccccaa gaaacacagc uaccuggagc    6240
ccaccaucag gagcgccgug cccagcgcca uccagaacac ccugcagaac gugcuggccg    6300
cugccaccaa gaggaacugc aacgugaccc agaugaggga gcugcccgug cuggacagcg    6360
cugccuucaa cguggagugc uucaagaaau acgccugcaa caacgaguac ugggagaccu    6420
ucaaggagaa ccccaucagg cugaccgaag agaacguggu gaacuacauc accaagcuga    6480
agggccccaa ggccgcugcc cuguucgcua agacccacaa ccugaacaug cugcaggaca    6540
ucccaaugga cagguucgug auggaccuga gagggacgu gaaggugaca cccggcacca    6600
agcacaccga ggagaggccc aaggugcagg ugauccaggc cgcugaccca cuggccaccg    6660
ccuaccugug cggcauccac agggagcugg ugaggcggcu gaacgccgug cugcugccca    6720
acauccacac ccuguucgac augagcgccg aggacuucga cgccaucauc gccgagcacu    6780
uccagcccgg cgacugcgug cuggagaccg acaucgccag cuucgacaag agcgaggaug    6840
acgcuauggc ccugaccgcu cugaugaucc uggaggaccu gggcgrggac gccgagcugc    6900
ucacccugau cgaggcugcc uucggcgaga ucagcuccau ccaccugccc accaagacca    6960
aguucaaguu cggcgcuaug augaaaagcg gaauguuccu gacccuguuc gugaacaccg    7020
ugaucaacau ugugaucgcc agcagggugc ugcgggagag gcugaccggc agccccugcg    7080
cugccuucau cggcgacgac aacaucguga agggcgugaa aagcgacaag cugauggccg    7140
acagguucgc caccggcugu aacaugagg ugaagaucau cgacgccgug gugggcgaga    7200
aggcccccua cuucgcggcc ggauucaucc ugugcgacag cgugaccggc accgccugca    7260
ggguggccga ccccugaag aggcuguuca agcugggcaa gccacuggcc gcugacgaug    7320
agcacgacga ugacaggcgg agggcccugc acgaggaaag caccagguggg aacagguggg    7380
gcauccugag cgagcugugc aaggccgugg agagcaggua cgagaccgug ggcaccagca    7440
ucaucgugau ggcuaugacc acacuggcca gcuccgucaa gagcuucucc uacccugaggg    7500
gggcccuau aacucucuac ggcuaaaccug aauggacuac gacauagucu agucgcgccaa    7560
ggccgccacc caugaaguug gugguguggg gggccggggg uguuggcaaa agcgcccuua    7620
caauugacuu cgaguaugu acgugcaag gugaugca cccccgaaa gaccauauug    7680
ugacacccc ucguaucac gccaaacau uacagcccgc ggugcaaaa accgcgugga    7740
cgugguaa aucccugcug gaggaucag ccguaauau uaauugge uuggugcugg    7800
cuacuauugu ggccauguac gugcugacca acacagaaaaca uaauugaaua cagcagcaau    7860
uggcaagcug cuuacauaga acucgcggcg auuggcaugc cgccuuaaa uuuauauu    7920
auuuuucuu uucuuuuccg aaucggauu uguuuuaau auucaaaa aaaaaaaaaa    7980
aaaaaaaaa ucuagaaaaa aaaaaaaaa aaaaaaaaaa aaaaaaaaaa aaaaaaaaaa    8040
aaaaaaaaaa aaaaaaaaaa aaaaaaaaaa aaaaaaaaaa aaaaaaaaaa aaaaa        8095
```

<210> SEQ ID NO 104

<211> LENGTH: 8120
<212> TYPE: RNA
<213> ORGANISM: Artificial sequence
<220> FEATURE:
<223> OTHER INFORMATION: Synthetic polynucleotide

<400> SEQUENCE: 104

| | | | | | |
|---|---|---|---|---|---|
| auugacggcg | uaguacacac | uauugaauca | aacagccgac | caauugcacu | accaucacaa | 60 |
| uggagaagcc | aguaguaaac | guagacguag | acccccagag | uccguuuguc | gugcaacugc | 120 |
| aaaaaagcuu | cccgcaauuu | gagguaguag | cacagcaggu | cacuccaaau | gaccaugcua | 180 |
| augccagagc | auuuucgcau | cuggccagua | aacuaaucga | gcuggagguu | ccuaccacag | 240 |
| cgacgaucuu | ggacauaggc | agcgcaccgg | cucguagaau | guuuuccgag | caccaguauc | 300 |
| auugugucug | ccccaugcgu | aguccagaag | acccggaccg | caugaugaaa | uaugccagua | 360 |
| aacuggcgga | aaaagcgugc | aagauuacaa | acaagaacuu | gcaugagaag | auuaaggauc | 420 |
| uccggaccgu | acuugauacg | ccggaugcug | aaacaccauc | gcucugcuuu | cacaacgaug | 480 |
| uuaccugcaa | caugcgugcc | gaauauuccg | ucaugcagga | cguguauauc | aacgcucccg | 540 |
| gaacuaucua | ucaucaggcu | augaaaggcg | ugcggacccu | guacuggauu | ggcuucgaca | 600 |
| ccacccaguu | cauguuucg | gcuauggcag | guucguaccc | ugcguacaac | accaacuggg | 660 |
| ccgacgagaa | aguccuugaa | gcgcguaaca | ucggacuuug | cagcacaaag | cugagugaag | 720 |
| guaggacagg | aaaauugucg | auaaugagga | agaaggaguu | gaagcccggg | ucgcggguuu | 780 |
| auuucuccgu | aggaucgaca | cuuuauccag | aacacagagc | cagcuugcag | agcuggcauc | 840 |
| uuccaucggu | guccacuug | aauggaaagc | agucguacac | uugccgcugu | gaucagugg | 900 |
| ugaguugcga | aggcuacgua | gugaagaaaa | uccaucag | ucccgggauc | acgggagaaa | 960 |
| ccgugggaua | cgcgguuaca | cacaauagcg | agggcuucuu | gcuaugcaaa | guuacugaca | 1020 |
| caguaaaagg | agaacgggua | ucguucccug | ugugcacgua | cauccccggcc | accauaugcg | 1080 |
| aucagaugac | ugguauaaug | gccacggaua | uaucaccuga | cgaugcacaa | aaacuucugg | 1140 |
| uugggcucaa | ccagcgaauu | gucauuaacg | guaggacuaa | caggaacacc | aacaccaugc | 1200 |
| aaaauuaccu | ucugccgauc | auagcacaag | gguucagcaa | augggcuaag | gagcgcaagg | 1260 |
| augaucuuga | uaacgagaaa | augcggguua | cuagagaacg | caagcuuacg | uauggcugcu | 1320 |
| ugugggcguu | ucgcacuaag | aaaguacauu | cguuuuaucg | cccaccugga | acgcagaccu | 1380 |
| gcguaaaagu | cccagccucu | uuuagcgcuu | ucccaugauc | guccguaugg | acgaccucuu | 1440 |
| ugcccauguc | gcugaggcag | aaauugaaac | uggcauugca | accaaagaag | gaggaaaaac | 1500 |
| ugcugcaggu | cucggaggaa | uuagucaugg | aggccaaggc | ugcuuuugag | gaugcucagg | 1560 |
| aggaagccag | agcggagaag | cuccgagaag | cacuuccacc | auuaguggca | gacaaaggca | 1620 |
| ucgaggcagc | cgcagaaguu | gucugcgaag | uggaggggcu | ccaggcggac | aucggagcag | 1680 |
| cauuaguuga | aaccccgcgc | ggucacguaa | ggauaauacc | ucaagcaaau | gaccguauga | 1740 |
| ucggacagua | uaucguuguc | ucgccaaacu | cugugcugaa | gaaugccaaa | cucgcaccag | 1800 |
| cgcacccgcu | agcagaucag | guuaagauca | uaacacacuc | cggaagauca | ggaaggguacg | 1860 |
| cggucgaacc | auacgacgcu | aaaguacuga | ugccagcagg | aggugccgua | ccauggccag | 1920 |
| aauuccuagc | acugagugag | agcgccacgu | uaguguacaa | cgaaagagag | uuugugaacc | 1980 |
| gcaaacuaua | ccacauugcc | augcauggcc | ccgccaagaa | uacagaagag | gagcaguaca | 2040 |
| agguuacaaa | ggcagagcuu | gcagaaacag | aguacguguu | ugacguggac | aagaagcguu | 2100 |
| gcguuaagaa | ggaagaagcc | ucaggucugg | uccucucggg | agaacugacc | aacccucccu | 2160 |

-continued

```
aucaugagcu agcucuggag ggacugaaga cccgaccugc gguccoguac aaggucgaaa    2220
caauaggagu gauaggcaca ccggggucgg gcaagucagc uauuaucaag ucaacuguca    2280
cggcacgaga ucuuguuacc agcggaaaga aagaaaauug ucgcgaaauu gaggccgacg    2340
ugcuaagacu gagggguaug cagauuacgu cgaagacagu agauucgguu augcucaacg    2400
gaugccacaa agccguagaa gugcuguacg uugacgaagc guucgcgugc cacgcaggag    2460
cacuacuugc cuugauugcu aucgucaggc cccgcaagaa gguaguacua ugcggagacc    2520
ccaugcaaug cggauucuuc aacaugaugc aacuaaaggu acauuucaau cacccugaaa    2580
aagacauaug caccaagaca uucuacaagu auaucucccg cguugcaca cagccaguua    2640
cagcuauugu aucgacacug cauuacgaug gaaagaugaa aaccacgaac ccgugcaaga    2700
agaacauuga aaucgauauu acaggggcca caaagccgaa gccaggggau aucauccuga    2760
caugauuccg cgggugggu aagcaauugc aaaucgacua ucccggacau gaaguaauga    2820
cagccgcggc cucacaaggg cuaaccagaa aaggagugua ugccguccgg caaaaaguca    2880
augaaaaccc acuguacgcg aucacaucag agcaugugaa cguguugcuc acccgcacug    2940
aggacaggcu agugaaaa accuugcagg gcgacccaug gauuaagcag cucacuaaca    3000
uaccuaaagg aaacuuucag gcuacuauag aggacuggga agcugaacac aagggaauaa    3060
uugcugcaau aaacagcccc acuccccgug ccaauccguu cagcugcaag accaacguuu    3120
gcugggcgaa agcauuggaa ccgauacuag ccacggccgg uaucguacuu accgguugcc    3180
agugagcga acuguccca caguuugcgg augacaaacc acauucggcc auuuacgccu    3240
uagcgaau uugcauuaag uuuucggca uggacuugac aagcggacug uuucuaaac    3300
agagcauccc acuaacguac caucccgccg auucagcgag gccggagcu cauugggaca    3360
acagcccagg aacccgcaag uaugggguacg aucacgccau ugccgccgaa cucucccgua    3420
gauuccggu guccagcua gcugggaagg gcacacaacu ugauugcag acggggagaa    3480
ccagaguuau cucugcacag cauaaccugg ucccggugaa ccgcaaucuu ccucacgccu    3540
uaguccccga guacaaggag aagcaaaccg gcccggucga aaaauucuug aaccaguuca    3600
aacaccacuc aguacuugug guaucagagg aaaaaauuga agcucccgu aagagaaucg    3660
aauggaucgc cccgauuggc auagccggug cagauaagaa cuacaaccug gcuucgggu    3720
uuccgccgca ggcacgguac gaccuggugu caucaacau uggaacuaaa acagaaaacc    3780
accacuuuca gcagugcgaa gaccaugcgg cgaccuuaaa aacccuuucg cguucggccc    3840
ugaauugccu uaacccagga ggcacccucg uggugaaguc cuauggcuac gccgaccgca    3900
acagugagga cguagucacc gcucuugcca gaagguuugu caggguguc gcagcgagac    3960
cagauugugu cucaagcaau acagaaaaugu accugauuuu ccgacaacua gacaacagcc    4020
guacacggca auucaccccg caccaucuga auugcgugau uucguccgug uaugggua    4080
caagagaugg aguggagcc gcgccgucau accgcaccaa aagggagaau auugcugacu    4140
gucaagagga agcaguuguc aacgcagcca auccgcuggg uagaccaggc aaggagucu    4200
gccgugccau cuauaaacgu uggccgacca guuuaccga ucagccacg gagacaggca    4260
ccgcaagaau gacugugugc cuaggaaaga aagugaucca gcggucggc ccugauuucc    4320
ggaagcaccc agaagcagaa gccuugaaau ugcuacaaaa cgccuaccau gcaguggcag    4380
acuuaguaaa ugaacauaac aucaagucug ucgccauucc acugcuaucu acaggcauuu    4440
acgcagccgg aaaagaccgc cuugaaguau cacuuaacug cuugacaacc gcgcuagaca    4500
```

```
gaacugacgc ggacguaacc aucuauugcc uggauaagaa guggaaggaa agaaucgacg    4560
cggcacucca acuuaaggag ucuguaacag agcugaagga ugaagauaug gagaucgacg    4620
augaguuagu auggauccau ccagacaguu gcuugaaggg aagaaaggga uucaguacua    4680
caaaaggaaa auuguauucg uacuucgaag gcaccaaauu ccaucaagca gcaaaagaca    4740
uggcggagau aaagguccug uucccuaaug accaggaaag uaaugaacaa cugugugccu    4800
acauauuggg ugagaccaug gaagcaaucc gcgaaaagug cccggucgac cauaacccgu    4860
cgucuagccc gcccaaaacg uugccgugcc uuugcaugua ugccaugacg ccagaaaggg    4920
uccacagacu uagaagcaau aacgucaaag aaguuacagu augcuccucc accccccuuc    4980
cuaagcacaa aauuaagaau guucagaagg uucagugcac gaaaguaguc cuguuuaauc    5040
cgcacacucc cgcauucguu cccgcccgua aguacauaga agugccagaa cagccuaccg    5100
cuccuccugc acaggccgag gaggccccccg aaguuguagc gacaccguca ccaucuacag    5160
cugauaacac cucgcuugau gucacagaca ucucacugga uaggaugac aguagcgaag    5220
gcucacuuuu uucgagcuuu agcggaucgg acaacucuau uacuaguaug gacaguuggu    5280
cgucaggacc uaguucacua gagauaguag accgaaggca ggugguggug gcugacguuc    5340
augccgucca agagccugcc ccuauuccac cgccaaggcu aaagaagaug gcccgccugg    5400
cagcggcaag aaaagagccc acuccaccgg caagcaauag cucugaguce cuccaccucu    5460
cuuuggugg gguauccaug ucccucggau caauuuucga cggagagacg gcccgccagg    5520
cagcgguaca accccuggca acaggcccca cggaugugcc uaugucuuuc ggaucguuuu    5580
ccgacggaga gauugaugag cugagccgca gaguaacuga guccgaaccc guccuguuug    5640
gaucauuuga accgggcgaa gugaacucaa uuauaucguc ccgaucagcc guaucuuuuc    5700
cucuacgcaa gcagagacgu agacgcagga gcaggaggac ugaauacuga cuaaccgggg    5760
uagguggggua cauauuuucg acggacacag gcccugggca cuugcaaaag aguccguuc    5820
ugcagaacca gcuuacagaa ccgaccuugg agcgcaaugu ccggaaaga uucaugcccc    5880
cggugcucga cacgucgaaa gaggaacaac ucaaacucag guaccagaug augcccaccg    5940
aagccaacaa aaguagguac cagucucgua aaguagaaaa ucagaaagcc auaaccacug    6000
agcgacuacu gucaggacua cgacuguaua acucugccac agaucagcca gaaugcuaua    6060
agaucaccua uccgaaacca uuguacucca guagcguacc ggcgaacuac uccgauccac    6120
aguucgcugu agcugucugu aacaacuauc ugcaugagaa cuauccgaca guagcaucuu    6180
aucagauuac ugacgaguac gaugcuuacu uggauauggu agacgggaca gucgccugcc    6240
uggacacugc aaccuucugc ccgcuaagc uuagaaguua cccgaaaaaa caugaguaua    6300
gagccccgaa uauccgcagu gcgguccau cagcgaugca gaacacgcua caaaaugugc    6360
ucauugccgc aacuaaaaga aauugcaacg ucacgcagau gcgugaacug ccaacacugg    6420
acucagcgac auucaaugac gaaugcuuuc gaaaauaugc auguaaugac gaguauuggg    6480
aggaguucgc ucgaagcca auuaggauua ccacugaguu ugcaccgca uauuagcua    6540
gacugaaagg cccuaaggcc gccgcacuau uugcaaagac guauaauuug ucccauugc    6600
aagaagugcc uauggauaga uucgucaugg acaugaaaag agacgugaaa guuacaccag    6660
gcacgaaaca cacagaagaa agaccgaaag uacaagugau acaagccgca gaaccccugg    6720
cgacugcuua cuuaugcggg auucaccggg aauuagucg uaggcuuacg gccgucuugc    6780
uuccaaacau ucacacgcuu uuugacaugu cggcggagga uuuugaugca aucauagcag    6840
aacacuucaa gcaaggcgac ccgguacugg agacggauau cgcaucauuc gacaaaagcc    6900
```

| | |
|---|---|
| aagacgacgc uauggcguua accggucuga ugaucuugga ggaccuggu gugaucaac | 6960 |
| cacuacucga cuugaucgag ugcgccuuug gagaaauauc auccacccau cuaccuacgg | 7020 |
| guacucguuu uaaauucggg gcgaugauga aauccggaau guuccucaca cuuuuuguca | 7080 |
| acacaguuuu gaaugucguu aucgccagca gaguacuaga ggagcggcuu aaaacgucca | 7140 |
| gaugugcagc guucauggc gacgacaaca ucauacaugg aguaguaucu gacaaagaaa | 7200 |
| uggcugagag gugcgccacc uggcucaaca uggagguuaa gaucaucgac gcagucaucg | 7260 |
| gugagagacc accuuacuuc ugcggcggau uuaucuugca agauucgguu acuccacag | 7320 |
| cgugccgcgu ggcggauccc cugaaaaggc uguuuaaguu ggguaaaccg cucccagccg | 7380 |
| acgacgagca agacgaagac agaagacgcg cucugcuaga ugaaacaaag gcgugguuua | 7440 |
| gaguagguau aacaggcacu uuagcagugg ccgugacgac ccgguaugag guagacaaua | 7500 |
| uuacaccugu ccuacuggca uugagaacuu ugcccagag caaagagca uccaagcca | 7560 |
| ucagagggga aauaaagcau cucuacggug guccuaaaua gucagcauag uacauuucau | 7620 |
| cugacuaaua cuacaacacc accaccacgc gugcuagacc auggauccua gacgcuacgc | 7680 |
| cccaaugauc cgaccagcaa aacucgaugu acuuccgagg aacugaugug cauaaugcau | 7740 |
| caggcuggua cauuagaucc ccgcuuaccg cgggcaauau agcaacacua aaaacucgau | 7800 |
| guacuuccga ggaagcgcag ugcauaaugc ugcgcagugu ugccacauaa ccacuauauu | 7860 |
| aaccauuuau cuagcggacg ccaaaaacuc aauguauuuc ugaggaagcg uggugcauaa | 7920 |
| ugccacgcag cgucugcaua acuuuuauua uuucuuuuau uaaucaacaa aauuugucuu | 7980 |
| uuaacauuuc aaaaaaaaaa aaaaaaaaaa aaaaucuag aaaaaaaaaa aaaaaaaaaa | 8040 |
| aaaaaaaaaa aaaaaaaaaa aaaaaaaaaa aaaaaaaaaa aaaaaaaaaa aaaaaaaaaa | 8100 |
| aaaaaaaaaa aaaaaaaaaa | 8120 |

<210> SEQ ID NO 105
<211> LENGTH: 8875
<212> TYPE: RNA
<213> ORGANISM: Artificial sequence
<220> FEATURE:
<223> OTHER INFORMATION: Synthetic polynucleotide

<400> SEQUENCE: 105

| | |
|---|---|
| augggcggcg caugagagaa gcccagacca auuaccuacc caaaauggag aaaguucacg | 60 |
| uugacaucga ggaagacagc ccauuccuca gagcuuugca gcggagcuuc ccgcaguuug | 120 |
| agguagaagc caagcagguc acugauaaug accaugcuaa ugccagagcg uuuucgcauc | 180 |
| uggcuucaaa acugaucgaa acggaggugg acccauccga cacgauccuu gacauuggaa | 240 |
| gugcgcccgc ccgcagaaug uauucuaagc acaaguauca uuguaucugu ccaugagau | 300 |
| gugcggaaga uccggacaga uuguauaagu augcaacuaa gcugaagaaa acuguaagg | 360 |
| aaauaacuga uaaggaauug gacaagaaaa ugaaggagcu ggccgccguc augagcgacc | 420 |
| cugaccugga aacugagacu auguccucc acgacgacga gucgugucgc uacgaagggc | 480 |
| aagucgcugu uuaccaggau guauacgccg ucgacggccc caccagccug uaccaccagg | 540 |
| ccaacaaggg cgugagggug gccuacugga ucggcuucga caccacacccc uucauguuca | 600 |
| agaaccuggc cggcgccuac cccagcuaca gcaccaacug ggccgacgag accgugcuga | 660 |
| ccgccaggaa caucgccug ugcagcagcg acgugaugga ggagccggag agaggcauga | 720 |
| gcauccugag gaagaaauac cugaagcca gcaacaacgu gcuguucagc gugggcagca | 780 |

-continued

```
ccaucuacca cgagaagagg gaccugcuca ggagcuggca ccugcccagc uguuccacc      840 ugaggggcaa gcagaacuac accugcaggu gcgagaccau cgugagcugc gacggcuacg     900
uggugaagag gaucgccauc agccccggcc uguacggcaa gcccagcggc uacgccgcua     960
caaugcacag ggagggcuuc cugugcugca aggugaccga cacccugaac ggcgagaggg    1020
ugagcuuccc cgugugcacc uacgugcccg ccacccugug cgaccagaug accggcaucc    1080
uggccaccga cgugagcgcc gacgacgccc agaagcugcu cgugggccug aaccagagga    1140
ucguggucaa cggcaggacc cagaggaaca ccaacacaau gaagaacuac cugcugcccg    1200
ugguggccca ggcuuucgcc aggugggcca aggaguacaa ggaggaccag gaagacgaga    1260
ggcccugggg ccugagggac aggcagcugg ugaugggcug cugcugggcc uucaggcggc    1320
acaagaucac cagcaucuac aagaggcccg cacccagac caucaucaag gugaacagcg     1380
acuuccacag cuucgugcug cccaggaucg gcagcaacac ccuggagauc ggccugagga    1440
cccggaucag gaagaugcug gaggaacaca aggagcccag cccacugauc accgccgagg    1500
acgugcagga ggccaagugc gcugccgacg aggccaagga ggugagggag gccgaggaac    1560
ugagggccgc ccugccaccc cuggcugccg acguggagga acccacccug gaagccgacg    1620
uggaccugau gcugcaggag gccggcgccg gaagcgugga cacccaggg ggccugauca     1680 aggugaccag cuacgacggc gaggacaaga ucggcagcua cgccgugcug agcccacagg    1740
ccgugcugaa guccgagaag cugagcugca uccacccacu ggccgagcag gugaucguga    1800
ucacccacag cggcaggaag ggcagguacg ccguggagcc cuaccacggc aaggugucg     1860 ugcccgaggc ccacgccauc cccgugcagg acuuccaggc ccugagcgag agcgccacca    1920
ucguguacaa cgagagggag uucgugaaca gguaccugca ccauacgcc acccacggcg     1980 gagcccugaa caccgacgag gaauacuaca agaccgugaa gcccagcgag cacgacggcg    2040
aguaccugua cgacaucgac aggaagcagu gcgugaagaa agagcugguug accggccugg    2100 gacugaccgg cgagcuggug gacccacccu uccacgaguu cgccuacgag agccugagga    2160
ccagacccgc cgcucccuac caggugccca ccaucggcgu guacggcgug cccggcagcg    2220
gaaagagcgg caucaucaag agcgccguga ccaagaaaga ccugguggc agcgccaaga     2280 aagagaacug cgccgagauc ucagggacg ugaagaagau gaaaggccug gacgugaacg     2340
cgcgcaccgu ggacagcgug cugcugaacg gcugcaagca ccccguggag acccuguaca    2400
ucgacgaggc cuucgcuugc cacgccggca cccugagggc ccugaucgcc aucaucaggc    2460
ccaagaaagc cgugcugugc ggcgaccca gcagugcgg cuucuucaac augaugugcc     2520
ugaaggugca cuucaaccac gagaucugca cccaggug uu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gccaggccu gaccaggaag ggcgguacg     2820 ccgugaggua caaggugaac gagaacccac guacgcucc caccagcgag cacgugaacg   2880
ugcugcugac caggaccgag gacagguaucg uguggaagac ccuggccggc gaccccugga   2940
ucaagacccu gaccgccaag uacccaggca acuuccaccgc caccaucgaa gagaggcagg    3000
ccgagcacga cgccaucaug aggcacaucc uggagaggcc cgaccccacc gacguguucc    3060
agaacaaggc caacgugugc ugggcaagg cccuggugcc cgugcugaag accgccggca    3120
ucgacaugac cacagagcag uggaacaccg uggacuacuu cgagaccgac aaggcccaca    3180
```

-continued

```
gcgccgagau cgugcugaac cagcugugcg ugagguucuu cggccuggac cuggacagcg    3240
gccuguucag cgcccccacc gugccacuga gcaucaggaa caaccacugg gacaacagcc    3300
ccagcccaaa cauguacggc cugaacaagg aggugucag gcagcugagc aggcgguacc     3360
cacagcugcc cagggccgug gccaccggca ggguguacga caugaacacc ggcacccuga    3420
ggaacuacga ccccaggauc aaccuggugc ccgugaacag gcggcugccc acgcccugg    3480 ugcugcacca caacgagcac ccacagagcg acuucagcuc cuucgugagc aagcugaaag    3540
gcaggaccgu gcuggucgug ggcgagaagc ugagcgugcc cggcaagaug guggacuggc    3600
ugagcgacag gcccgaggcc accuuccggg ccaggcugga ccucggcauc cccggcgacg    3660
ugcccaagua cgacaucauc uucgugaacg ucaggacccc auacaaguac caccauuacc    3720
agcagugcga ggaccacgcc aucaagcuga gcaugcugac caagaaggcc ugccugcacc    3780
ugaaccccgg aggcaccugc gugagcaucg gcuacggcua cgccgacagg gccagcgaga    3840
gcaucauugg cgccaucgcc aggcuguuca guucagcag ggugugcaaa cccaagagca    3900
gccuggagga aaccgaggug cuguucgugu ucaucggcua cgaccggaag gccaggaccc    3960
acaaccccua caagcugagc agcacccuga caaacaucua caccggcagc aggcugcacg    4020
aggccggcug cgcccccagc uaccacgugg ucaggggcga uaucgccacc gccaccgagg    4080
gcgugaucau caacgcugcc aacagcaagg gccagcccgg aggcggagug ugcggcgccc    4140
uguacaagaa guuccccgag agcuucgacc ugcagcccau cgaggucggg aaggccaggc    4200
uggugaaggg cgccgcuaag cacaucaucc acgccgcggg ccccaacuuc aacaagguga    4260
gcgaggugga aggcgacaag cagcuggccg aagccuacga gagcaucgcc aagaucguga    4320
acgacaauaa cuacaagagc guggccaucc cacugcucag caccggcauc uucagcggca    4380
acaaggacag gcugacccag agccugaacc accugcucac cgcccuggac accaccgaug    4440
ccgacguggc caucuacugc agggacaaga gugggagau gacccugaag gaggccgugg    4500
ccaggcggga ggccguggaa gagaucugca ucagcgacga cuccagcgug accgagcccg    4560
acgccgagcu ggugagggug cacccccaaga gcucccuggc cggcaggaag ggcuacagca    4620
ccagcgacgg caagaccuuc agcuaccugg agggcaccaa guuccaccag gccgcuaagg    4680
acaucgccga gaucaacgcu auggccccg uggccaccga ggccaacgag caggugugca    4740
uguacauccu gggcgagagc auguccagca ucaggagcaa gugccccgug gaggaaagcg    4800
aggccagcac accacccagc acccugcccu gccugugcau ccacgcuaug acacccgaga    4860 ggguggcagcg gcugaaggcc agcaggcccg agcagaucac cgugugcagc ccuucccac    4920 ugcccaagua caggaucacc ggcgugcaga agauccagug cagccagccc auccuguuca    4980
gcccaaaggu gcccgccuac auccaccca ggaaguaccu gguggagacc cacccgugg    5040 acgagacacc cgagccaagc gccgagaacc agagcaccga gggcacaccc gagcagccac    5100
cccugaucac cgaggacgag acaaggaccc ggacccaga gcccaucauu aucgaggaag    5160
aggaagagga cagcaucagc cugcugagcg acggccccca ccaccaggug cugcaggugg    5220
aggccgacau ccacggccca cccagcgugu ccagcccag cuggagcauc ccacacgcca    5280
gcgacuucga cguggacagc cugagcaucc uggacaccu ggaggcgcc agcgugaccu    5340 ccggcgccac cagcgccgag accaacagcu acuucgccaa gagcauggag uuccuggcca    5400
ggcccgugcc agccucccagg accguguuca ggaacccacc ccaccagcu cccaggacca    5460 ggaccccaag ccuggcuccc agcagggccu gcagcaggac cagccugguga gcaccccac    5520
```

```
ccggcgugaa cagggugauc accagggagg aacuggaggc ccugacaccc agcaggaccc      5580
ccagcagguc cgugagcagg acuagucugg uguccaaccc acccggcgug aacaggguga      5640
ucaccaggga ggaauucgag gccuucgugg cccagcaaca gagacgguuc gacgccggcg      5700
ccuacaucuu cagcagcgac accggccagg acaccugca gcaaaagagc gugaggcaga       5760
ccgugcugag cgaggugguc cuggagagga ccgagcugga aaucagcuac gccccaggc       5820 uggaccagga gaaggaggaa cugcucagga agaaacugca gcugaacccc accccagcca      5880
acaggagcag guaccagagc aggaaggugg agaacaugaa ggccaucacc gccaggcgga      5940
uccugcaggg ccugggacac uaccugaagg ccgagggcaa gguggagugc uacaggaccc      6000
ugcaccccgu gccacuguac agcuccagcg ugaacagggc cuucuccagc cccaaggugg      6060 ccgugggaggc cugcaacgcu augcugaagg agaacuuccc caccguggcc agcuacugca     6120 ucaucccga guacgacgcc uaccuggaca ugguggacgg cgccagcugc ugccuggaca       6180
ccgccagcuu cugccccgcc aagcugagga gcuuccccaa gaaacacagc uaccuggagc      6240
ccaccaucag gagcgccgug cccagcgcca uccagaacac ccugcagaac gugcuggccg      6300
cugccaccaa gaggaacugc aacgugaccc agaugaggga gcugcccgug cuggacagcg      6360
cugccuucaa cguggagugc uucaagaaau acgccugcaa caacgaguac ugggagaccu      6420
ucaaggagaa ccccaucagg cugaccgaag agaacguggu gaacuacauc accaagcuga      6480
agggccccaa ggccgcugcc cuguucgcua agacccacaa ccugaacaug cugcaggaca      6540
ucccaaugga cagguucgug auggaccuga gagggacgu gaaggugaca cccggcacca      6600
agcacaccga ggagaggccc aaggugcagg ugauccaggc cgcugaccca cuggccaccg      6660
ccuaccugug cggcauccac agggagcugg ugaggcggcu gaacgccgug cugcugccca      6720
acauccacac ccugucgac augagcgccg aggacuucga cgccaucauc gccgagcacu      6780
uccagcccgg cgacugcgug cuggagaccg acaucgccag cuucgacaag agcgaggaug      6840 acgcuaugg ccugaccgcu cugaugauc uggaggaccu gggcguggac gccgagcugc       6900
ucacccugau cgaggcugcc uucggcgaga ucagcccau ccaccugccc accaagacca      6960
aguucaaguu cggcgcuaug augaaaagcg gaauguuccu gacccuguuc gugaacaccg      7020
ugaucaacau ugugaucgcc agcagggugc ucgggagag gcugaccggc agccccugcg      7080
cugccuucau cggcgacgac aacaucguga agggcgugaa aagcgacaag cugauggccg      7140
acaggugcgc caccggcug aacauggagg ugaagaucau cgacgccgug gugggcgaga      7200
aggcccccua cuucugcggc ggauucaucc ugugcgacag cgugaccggc accgccugca      7260
ggguggccga ccccugaag aggcuguuca agcugggcaa gccacuggcc gcugacgaug      7320
agcacgacga ugacaggcgg aggccccugc acgaggaag caccaggugg aacaggggug      7380
gcauccugag cgagcugugc aaggccgugg agagcaggua cgagaccgug ggcaccagca      7440
ucaucgugau ggcuaugacc acacuggcca gcuccgucaa gagcuucccc uaccugaggg      7500
gggccccuau aacucucuac ggcuaaccug aauggacuac gacauagucu aguccgccaa      7560
ggccgccacc augagaguga gcagccccua gaaccuuacug cuucugcuuu ggggagcugu     7620
ugcucugaca gagacauggg cuggaucucu gagcgaggug accggccagg ccugugcau       7680 cggcgccgug cccaagaccc accaggugcu gugcaacacc acccagaaga ccagcgacgg      7740
cagcuacuac cuggccgcuc ccaccggcac caccggggcc ugcagcaccg gccugacccc      7800
uugcaucagc accaccaucc ugaaccugac caccgacuac ugcgugcugg uggagcugug      7860
gcccagggug accuaccaca gccccagcua cgccuaccac cuguucgaga ggagggccaa      7920
```

-continued

```
guacaagagg gagcccguga gccugacccu ggcccugcug cugggcggcc ugacaauggg    7980
cggcaucgcc gccggcgugg gcaccggcac caccgcccug guggccaccc agcaguucca    8040
gcagcugcag ccgccaugc acgacgaccu gaaggaggug gagaagucca ucaccaaccu     8100
ggagaagucc cugaccagcc ugagcgaggu ggugcugcag aacaggaggg gccuggaccu    8160
gcuguuccug aaggagggcg gccugugcgc cgcccugaag gaggagugcu gccuguacgc    8220
cgaccacacc ggccugguga ucgugggcau ugucgcuggc cuggccgucc ucgccgugu     8280 ggugauugga gcugggucg cagcuguuau gucagaaga aagucauccg gcggaaaggg      8340
aggcuccuac ucucaggcug cuucugcuac agugccuaga gcucuuaugu guuuaucuca    8400
gcuguaaacu cgaguauguu acgugcaaag gugauuguca cccccgaaa gaccauauug     8460 ugacacaccc ucaguaucac gcccaaacau uuacagccgc ggucaaaa accgcgguga     8520 cgugguuaac aucccugcug ggaggaucag ccguaauuau uauaauuggc uuggugcugg    8580
cuacuauugu ggccauguac gugcugacca accagaaaca uaauugaaua cagcagcaau    8640
uggcaagcug cuuacauaga acucgcggcg auuggcaugc cgccuuaaaa uuuuuauuuu    8700
auuuuuucuu uucuuuuccg aaucggauuu uguuuuaau auuucaaaaa aaaaaaaaa     8760 aaaaaaaaaa ucuagaaaaa aaaaaaaaa aaaaaaaaa aaaaaaaaa aaaaaaaaa       8820 aaaaaaaaaa aaaaaaaaa aaaaaaaaa aaaaaaaaa aaaaaaaaa aaaaa            8875
```

```
<210> SEQ ID NO 106
<211> LENGTH: 8416
<212> TYPE: RNA
<213> ORGANISM: Artificial sequence
<220> FEATURE:
<223> OTHER INFORMATION: Synthetic polynucleotide

<400> SEQUENCE: 106
```

```
augggcggcg caugagagaa gcccagacca auuaccuacc caaaauggag aaaguucacg      60
uugacaucga ggaagacagc ccauuccuca gagcuuugca gcggagcuuc ccgcaguuug     120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug acaagaaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucgccug ugcagcagcg acgugaugga ggagccggg agaggcauga     720 gcauccugag gaagaaauac cugaagccca gcaacaacgu gcguucagc gugggcagca     780 ccaucuacca cgagaagagg gaccugcuca ggagcuggca ccugcccagc guguccacc     840 ugaggggcaa gcagaacuac accugcaggu gcgagaccau cgagcgc gacggcuacg       900 uggugaagag gaucgccauc agccccggcc uguacggcaa gcccagcggc uacgccgcua    960
caaugcacag ggagggcuuc cugugcugca aggugaccga caccugaac ggcgagaggg    1020 ugagcuuccc cgugugcacc uacgugcccg ccacccugug cgaccagaug accggcaucc    1080
```
uggccaccga cgugagcgcc gacgacgccc agaagcugcu cgugggccug aaccagagga 1140
ucgugguccaa cggcaggacc cagaggaaca ccaacacaau gaagaacuac cugcugcccg 1200
ugguggccca ggcuuucgcc aggugggcca aggaguacaa ggaggaccag gaagacgaga 1260
ggccccuggg ccugagggac aggcagcugg ugaugggcug cugcugggcc uucaggcggc 1320
acaagaucac cagcaucuac aagaggcccg acacccagac caucaucaag gugaacagcg 1380
acuuccacag cuucgugcug cccaggaucg gcagcaacac ccuggagauc ggccugagga 1440
cccggaucag gaagaugcug gaggaacaca aggagcccag cccacugauc accgccgagg 1500
acgugcagga ggccaagugc gcugccgacg aggccaagga ggugagggag gccgaggaac 1560
ugagggccgc ccugccaccc cuggcugccg acguggagga acccacccug gaagccgacg 1620
uggaccugau gcugcaggag gccggcgccg gaagcgugga gacacccagg ggccugauca 1680
aggugaccag cuacgacggc gaggacaaga ucggcagcua cgccgugcug agcccacagg 1740
ccgugcugaa guccgagaag cugagcugca uccacccacu ggccgagcag gugaucguga 1800
ucacccacag cggcaggaag ggcagguacg ccguggagcc cuaccacggc aagguggucg 1860
ugcccgaggg ccacgccauc cccgugcagg acuuccaggc ccugagcgag agcgccacca 1920
ucguguacaa cgagagggag uucgugaaca gguaccugca ccauaucgcc acccacggcg 1980
gagcccugaa caccgacgag gaauacuaca agaccgugaa gcccagcgag cacgacggcg 2040
aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccuggugguc agcgccaaga 2280
aagagaacug cgccgagauc aucagggacg ugaagaagau gaaaggccug gacgugaacg 2340
cgcgcacgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccaggugu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgccccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420
ggaacuacga ccccaggauc aaccuggugc ccgugaacag gcggcugccc cacgcccugg 3480
ugcugcacca caacgagcac ccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaagguga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440
ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820


| | |
|---|---|
| uggaccagga gaaggaggaa cugcucagga agaaacugca gcugaacccc accccagcca | 5880 |
| acaggagcag guaccagagc aggaaggugg agaacaugaa ggccaucacc gccaggcgga | 5940 |
| uccugcaggg ccugggacac uaccugaagg ccgagggcaa gguggagugc uacaggaccc | 6000 |
| ugcaccccgu gccacuguac agcuccagcg ugaacagggc cuucuccagc ccaaggugg | 6060 |
| ccguggaggc cugcaacgcu augcugaagg agaacuuccc caccguggcc agcuacugca | 6120 |
| ucauccccga guacgacgcc uaccuggaca ugguggacgg cgccagcugc ugccuggaca | 6180 |
| ccgccagcuu cugccccgcc aagcugagga gcuuccccaa gaaacacagc uaccuggagc | 6240 |
| ccaccaucag gagcgccgug cccagcgcca uccagaacac ccugcagaac gucuggccg | 6300 |
| cugccaccaa gaggaacugc aacgugaccc agaugaggga gcugcccgug cuggacagcg | 6360 |
| cugccuucaa cguggagugc uucaagaaau acgccugcaa caacgaguac ugggagaccu | 6420 |
| ucaaggagaa ccccaucagg cugaccgaag agaacguggu gaacuacauc accaagcuga | 6480 |
| agggccccaa ggccgcugcc cguucgcua gacccacaa ccugaacaug cugcaggaca | 6540 |
| ucccaaugga cagguucgug auggaccuga gagggacgu gaaggugaca cccggcacca | 6600 |
| agcacaccga ggagaggccc aaggugcagg ugauccaggc cgcugaccca cuggccaccg | 6660 |
| ccuaccugug cggcauccac agggagcugg ugaggcggcu gaacgccgug cugcugccca | 6720 |
| acauccacac ccuguucgac augagcgccg aggacuucga cgccaucauc gccgagcacu | 6780 |
| uccagcccgg cgacugcgug cuggagaccg acaucgccag cuucgacaag agcgaggaug | 6840 |
| acgcuauggc ccugaccgcu cugaugaucc uggaggaccu gggcguggac gccgagcugc | 6900 |
| ucacccugau cgaggcugcc uucggcgaga ucagcuccau ccaccugccc accaagacca | 6960 |
| aguucaaguu cggcgcuaug augaaaagcg gaauguuccu gacccuguuc gugaacaccg | 7020 |
| ugaucaacau ugugaucgcc agcagggugc ugcgggagag gcugaccggc agccccugcg | 7080 |
| cugccuucau cggcgacgac aacaucguga agggcgugaa aagcgacaag cugauggccg | 7140 |
| acaggugcgc caccuggcug aacauggagg ugaagaucau cgacgccgug gugggcgaga | 7200 |
| aggcccccua cuucugcggc ggauucaucc ugugcgacag cgugaccggc accgccugca | 7260 |
| gggugggccga cccccugaag aggcuguuca gcugggcaa gccacuggcc gcugacgaug | 7320 |
| agcacgacga ugacaggcgg agggcccugc acgaggaaag caccaggugg aacaggggugg | 7380 |
| gcauccugag cgagcugugc aaggccgugg agagcaggua cgagaccgug ggcaccagca | 7440 |
| ucaucgugau ggcuaugacc acacuggcca gcuccgucaa gagcuucucc uaccugaggg | 7500 |
| gggccccuau aacucucuac ggcuaaccug aauggacuac gacauagucu agucgccaa | 7560 |
| ggccgccacc augagaguga cagcccccag aaccuuacug cuucugcuuu ggggagcugu | 7620 |
| ugcucugaca gagacauggg cuggaucuua ccacagcccc agcuacgccu accaccaguu | 7680 |
| cgagaggggg ggaggaggcu ccgggggagg aggcucccug aagaucagcc aggccgugca | 7740 |
| cgccgcccac gccgagauca acgaggccgg ccggggaggug aucggggca uugucgcugg | 7800 |
| ccuggccguc cucgccgugg uggauuggag cgugguc gcagcuguua ugugcagaag | 7860 |
| aaagucaucc ggcggaaagg gaggcuccua cucucaggcu gcuucugcua cagugccuag | 7920 |
| agcucuuaug uguuuaucuc agcuguaaac ucaguauggu uacgugcaaa ggugauugauc | 7980 |
| accccccgaa agaccauauu gugacacacc cucaguauca cgcccaaaca uuuacagccg | 8040 |
| cggugucaaa aaccgcgugg acguggguaaa cauccccugcu ggggaggauca gccguaauua | 8100 |
| uuauaauugg cuuggugcug gcuacuauug uggccaugua cgucugacc aaccagaaac | 8160 |
| auaauugaau acagcagcaa uuggcaagcu gcuuacauag aacucgcggc gauuggcaug | 8220 |

```
ccgccuuaaa auuuuuauuu uauuuuuucu uuucuuuucc gaaucggauu uuguuuuuaa 8280
uauuucaaaa aaaaaaaaaa aaaaaaaaaa aucuagaaaa aaaaaaaaaa aaaaaaaaaa 8340
aaaaaaaaaa aaaaaaaaaa aaaaaaaaaa aaaaaaaaaa aaaaaaaaaa aaaaaaaaaa 8400
aaaaaaaaaa aaaaaa 8416

<210> SEQ ID NO 107
<211> LENGTH: 8914
<212> TYPE: RNA
<213> ORGANISM: Artificial sequence
<220> FEATURE:
<223> OTHER INFORMATION: Synthetic polynucleotide
<400> SEQUENCE: 107
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu ggccgccguc augagcgacc 420
cugaccugga aacugagacu augugccucc acgacgacga gucgugucgc uacgaagggc 480
aagucgcugu uuaccaggau guauacgccg ucgacggccc caccagccug uaccaccagg 540
ccaacaaggg cgugagggug gccuacugga ucggcuucga caccacaccc uucauguuca 600
agaaccuggc cggcgccuac cccagcuaca gcaccaacug ggccgacgag accgugcuga 660
ccgccaggaa caucggccug ugcagcagcg acgugaugga gaggagccgg agaggcauga 720
gcauccugag gaagaaauac cugaagccca gcaacaacgu gcuguucagc gugggcagca 780
ccaucuacca cgagaagagg gaccugcuca ggagcuggca ccugcccagc guguuccacc 840
ugaggggcaa gcagaacuac accugcaggu gcgagaccau cgugagcugc gacggcuacg 900
uggugaagag gaucgccauc agccccggcc uguacggcaa gcccagcggc uacgccgcua 960
caaugcacag ggagggcuuc cugugcugca aggugaccga cacccugaac ggcgagaggg 1020
ugagcuuccc cgugugcacc uacgugcccg ccacccugug cgaccagaug accggcaucc 1080
uggccaccga cgugagcgcc gacgacgccc agaagcugcu cgugggccug aaccagagga 1140
ucguggucaa cggcaggacc cagaggaaca ccaacacaau gaagaacuac cugcugcccg 1200
ugguggccca ggcuuucgcc aggugggcca aggaguacaa ggaggaccag gaagacgaga 1260
ggccccuggg ccugagggac aggcagcugg ugaugggcug cugcugggcc uucaggcggc 1320
acaagaucac cagcaucuac aagaggcccg acacccagac caucaucaag gugaacagcg 1380
acuuccacag cuucgugcug cccaggaucg gcagcaacac ccuggagauc ggccugagga 1440
cccggaucag gaagaugcug gaggaacaca aggagcccag cccacugauc accgccgagg 1500
acgugcagga ggccaagugc gcugccgacg aggccaagga ggugagggag gccgaggaac 1560
ugagggccgc ccugccaccc cuggcugccg acguggagga acccacccug gaagccgacg 1620
uggaccugau gcugcaggag gccggcgccg gaagcgugga gacacccagg ggccugauca 1680
aggugaccag cuacgacggc gaggacaaga ucggcagcua cgccgugcug agcccacagg 1740
ccgugcugaa guccgagaag cugagcugca uccacccacu ggccgagcag gugaucguga 1800
```

-continued ucacccacag cggcaggaag ggcagguacg ccguggagcc cuaccacggc aagguggucg 1860
ugcccgaggg ccacgccauc cccgugcagg acuuccaggc ccugagcgag agcgccacca 1920
ucguguacaa cgagagggag uucgugaaca gguaccugca ccauaucgcc acccacggcg 1980
gagcccugaa caccgacgag gaauacuaca agaccgugaa gcccagcgag cacgacggcg 2040
aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccuggugguc agcgccaaga 2280
aagagaacug cgccgagauc aucagggacg ugaagaagau gaaaggccug gacgugaacg 2340
cgcgcaccgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccagguguu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420
ggaacuacga ccccaggauc aaccuggugc ccgugaacag gcggcugccc cacgcccugg 3480
ugcugcacca caacgagcac ccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200

-continued

```
uggugaaggg cgccgcuaag cacaucaucc acgccguggg ccccaacuuc aacaaggu ga   4260
gcgaggugga aggcgacaag cagcuggccg aagccuacga gagcaucgcc aagaucguga   4320
acgacaauaa cuacaagagc guggccaucc cacugcucag caccggcauc uucagcggca   4380
acaaggacag gcugacccag agccugaacc accugcucac cgcccuggac accaccgaug   4440
ccgacguggc caucuacugc agggacaaga agugggagau gacccugaag gaggccgugg   4500
ccaggcggga ggccguggaa gagaucugca ucagcgacga cuccagcgug accgagcccg   4560
acgccgagcu ggugagggug caccccaaga gcucccuggc cggcaggaag ggcuacagca   4620
ccagcgacgg caagaccuuc agcuaccugg agggcaccaa guuccaccag gccgcuaagg   4680
acaucgccga gaucaacgcu auguggcccg uggccaccga ggccaacgag caggugugca   4740
uguacauccu gggcgagagc auguccagca ucaggagcaa gugccccgug gaggaaagcg   4800
aggccagcac accacccagc acccugcccu gccugugcau ccacgcuaug acacccgaga   4860
gggugcagcg gcugaaggcc agcaggcccg agcagaucac cgugugcagc uccuucccac   4920
ugcccaagua caggaucacc ggcgugcaga agauccagug cagccagccc auccuguuca   4980
gcccaaaggu gcccgccuac auccacccca ggaaguaccu gguggagacc ccacccgugg   5040
acgagacacc cgagccaagc gccgagaacc agagcaccga gggcacaccc gagcagccac   5100
cccugaucac cgaggacgag acaaggaccc ggaccccaga gcccaucauu aucgaggaag   5160
aggaagagga cagcaucagc cugcugagcg acggccccac ccaccaggug cugcaggugg   5220
aggccgacau ccacggccca cccagcgugu ccagcuccag cuggagcauc ccacacgcca   5280
gcgacuucga cguggacagc cugagcaucc uggacacccu ggagggcgcc agcgugaccu   5340
ccggcgccac cagcgccgag accaacagcu acuucgccaa gagcauggag uuccuggcca   5400
ggcccgugcc agcucccagg accguguuca ggaacccacc ccacccagcu cccaggacca   5460
ggaccccaag ccuggcuccc agcagggccu gcagcaggac cagccuggug agcaccccac   5520
ccggcgugaa cagggugauc accagggagg aacuggaggc ccugacaccc agcaggaccc   5580
ccagcagguc cgugagcagg acuagucugg uguccaaccc acccggcgug aacaggguga   5640
ucaccaggga ggaauucgag gccuucgugg cccagcaaca gagacgguuc gacgccggcg   5700
ccuacaucuu cagcagcgac accggccagg gacaccugca gcaaaagagc gugaggcaga   5760
ccgugcugag cgaggugg ug cuggagagga ccgagcugga aaucagcuac gcccccaggc   5820
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccugggacac uaccugaagg ccgagggcaa ggguggagugc uacaggaccc   6000
ugcaccccgu gccacuguac agcuccagcg ugaacagggc cuucuccagc cccaaggugg   6060
ccguggaggc cugcaacgcu augcugaagg agaacuuccc caccguggcc agcuacugca   6120
ucauccccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cuguucgcua agacccacaa ccugaacaug cugcaggaca   6540
```

-continued

```
ucccaaugga cagguucgug auggaccuga agagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
ggguggccga cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggccccuau aacucucuac ggcuaaccug aauggacuac gacauagucu aguccgccaa   7560
ggccgccacc augagaguga cagccccuag aaccuuacug cuucugcuuu ggggagcugu   7620
ugcucugaca gagacauggg cuggaucucu gagcgaggug accggccagg gccugugcau   7680
cggcgccgug cccaagaccc accaggugcu gugcaacacc acccagaaga ccagcgacgg   7740
cagcuacuac cuggccgcuc ccaccggcac caccugggcc ugcagcaccg gccugacccc   7800
uugcaucagc accaccaucc ugaaccugac caccgacuac ugcgugcugg uggagcugug   7860
gcccagggug accuaccaca gccccagcua cgccuaccac caguucgaga ggagggccaa   7920
guacaagagg gagcccguga gccugacccu ggcccugcug cugggcggcc ugacaauggg   7980
cggcaucgcc gccggcgugg gcaccggcac caccgcccug guggccaccc agcaguucca   8040
gcagcugcag gccgccaugc acgacgaccu gaaggaggug gagaagucca ucaccaaccu   8100
ggagaagucc cugaccagcc ugagcgaggu ggugcugcag aacaggaggg gccuggaccu   8160
gcuguuccug aaggagggcg gccugugcgc cgcccugaag gaggagugcu gccuguacgc   8220
cgaccacacc ggccugguga ucgugggcau ugucgcuggc cuggccgucc ucgccguggu   8280
ggugauugga gcuguggucg cagcuguuau gugcagaaga aagucauccg gcggaaaggg   8340
aggcuccuac ucucaggcug cuucugcuac agugccuaga gcucuuaugu guuuaucuca   8400
gcugggcggc ggaggcagcg acuacaagga cgacgaugac aaguaaacuc gaguauguua   8460
cgugcaaagg ugauugucac cccccgaaag accauauugu gacacacccu caguaucacg   8520
cccaaacauu uacagccgcg gugucaaaaa ccgcguggac gugguuaaca ucccugcugg   8580
gaggaucagc cguaauuauu auaauuggcu uggugcuggc uacuauugug gccauguacg   8640
ugcugaccaa ccagaaacau aauugaauac agcagcaauu ggcaagcugc uuacauagaa   8700
cucgcggcga uuggcaugcc gccuuaaaau uuuuauuuua uuuuuucuuu ucuuuuccga   8760
aucggauuuu guuuuuaaua uuucaaaaaa aaaaaaaaaa aaaaaaaaau cuagaaaaaa   8820
aaaaaaaaaa aaaaaaaaaa aaaaaaaaaa aaaaaaaaaa aaaaaaaaaa aaaaaaaaaa   8880
aaaaaaaaaa aaaaaaaaaa aaaaaaaaaa aaaa                               8914
```

<210> SEQ ID NO 108
<211> LENGTH: 8455
<212> TYPE: RNA
<213> ORGANISM: Artificial sequence
<220> FEATURE:
<223> OTHER INFORMATION: Synthetic polynucleotide

<400> SEQUENCE: 108

| | | | | | |
|---|---|---|---|---|---|
| augggcggcg | caugagagaa | gcccagacca | auuaccuacc | caaaauggag | aaaguucacg | 60 |
| uugacaucga | ggaagacagc | ccauuccuca | gagcuuugca | gcggagcuuc | ccgcaguuug | 120 |
| agguagaagc | caagcagguc | acugauaaug | accaugcuaa | ugccagagcg | uuuucgcauc | 180 |
| uggcuucaaa | acugaucgaa | acggaggugg | acccauccga | cacgauccuu | gacauuggaa | 240 |
| gugcgcccgc | ccgcagaaug | uauucuaagc | acaaguauca | uuguaucugu | ccgaugagau | 300 |
| gugcggaaga | uccggacaga | uuguauaagu | augcaacuaa | gcugaagaaa | aacuguaagg | 360 |
| aaauaacuga | uaaggaauug | gacaagaaaa | ugaaggagcu | ggccgccguc | augagcgacc | 420 |
| cugaccugga | aacugagacu | augugccucc | acgacgacga | gucgugucgc | uacgaagggc | 480 |
| aagucgcugu | uuaccaggau | guauacgccg | ucgacgccc | caccagccug | uaccaccagg | 540 |
| ccaacaaggg | cgugagggug | gccuacugga | ucggcuucga | caccacaccc | uucauguuca | 600 |
| agaaccuggc | cggcgccuac | ccagcuaca | gcaccaacug | ggccgacgag | accgugcuga | 660 |
| ccgccaggaa | caucggccug | ugcagcagcg | acgugaugga | gaggagccgg | agaggcauga | 720 |
| gcauccugag | gaagaaauac | cugaagccca | gcaacaacgu | gcuguucagc | gugggcagca | 780 |
| ccaucuacca | cgagaagagg | gaccugcuca | ggagcuggca | ccugcccagc | guguuccacc | 840 |
| ugaggggcaa | gcagaacuac | accugcaggu | gcgagaccau | cgugagcugc | gacggcuacg | 900 |
| uggugaagag | gaucgccauc | agccccggcc | uguacggcaa | gccagcggc | uacgccgcua | 960 |
| caaugcacag | ggagggcuuc | cugcugcuca | aggugaccga | cacccugaac | ggcgagaggg | 1020 |
| ugagcuuccc | cgugugcacc | uacgugcccg | ccacccugug | cgaccagaug | accggcaucc | 1080 |
| uggccaccga | cgugagcgcc | gacgacgccc | agaagcugcu | cgugggccug | aaccagagga | 1140 |
| ucguggucaa | cggcaggacc | cagaggaaca | ccaacacaau | gaagaacuac | cugcugcccg | 1200 |
| ugguggccca | ggcuuucgcc | agguggccca | aggaguacaa | ggaggaccag | gaagacgaga | 1260 |
| ggccccuggg | ccugagggac | aggcagcugg | ugaugggcug | cugcugggcc | uucaggcggc | 1320 |
| acaagaucac | cagcaucuac | aagaggcccg | acacccagac | caucaucaag | gugaacagcg | 1380 |
| acuuccacag | cuucgugcug | cccaggaucg | gcagcaacac | ccuggagauc | ggccugagga | 1440 |
| cccggaucag | gaagaugcug | gaggaacaca | aggagcccag | cccacugauc | accgccgagg | 1500 |
| acgugcagga | ggccaagugc | gcugccgacg | aggccaagga | ggugagggag | gccgaggaac | 1560 |
| ugagggccgc | ccugccaccc | cuggcugccg | acguggagga | acccacccug | gaagccgacg | 1620 |
| uggaccugau | gcugcaggag | gccggcgccg | aagcgugga | gacacccagg | ggccugauca | 1680 |
| aggugaccag | cuacgacggc | gaggacaaga | ucggcagcua | cgccgugcug | agcccacagg | 1740 |
| ccgugcugaa | guccgagaag | cugagcugca | uccaccccac | uggccgagcag | gugaucguga | 1800 |
| ucacccacag | cggcaggaag | ggcagguacg | ccguggagcc | cuaccacggc | aagguggucg | 1860 |
| ugcccgaggg | ccacgccauc | ccgugcagg | acuuccaggc | ccugagcgag | agcgccacca | 1920 |
| ucguguacaa | cgagggggag | uucgugaaca | gguaccugca | ccauaucgcc | acccacggcg | 1980 |
| gagcccugaa | caccgacgag | gaauacucaca | agaccgugaa | gcccagcgag | cacgacggcg | 2040 |

-continued aguaccugua cgacaucgac aggaagcagu gcgugaagaa agagcuggug accggccugg 2100
gacugaccgg cgagcuggug gacccacccu uccacgaguu cgccuacgag agccugagga 2160
ccagacccgc cgcucccuac caggugccca ccaucggcgu guacggcgug cccggcagcg 2220
gaaagagcgg caucaucaag agcgccguga ccaagaaaga ccugguggauc agcgccaaga 2280
aagagaacug cgccgagauc aucagggacg ugaagaagau gaaaggccug gacgugaacg 2340
cgcgcaccgu ggacagcgug cugcugaacg gcugcaagca ccccguggag acccuguaca 2400
ucgacgaggc cuucgcuugc cacgccggca cccugagggc ccugaucgcc aucaucaggc 2460
ccaagaaagc cgugcugugc ggcgacccca agcagugcgg cuucuucaac augaugugcc 2520
ugaaggugca cuucaaccac gagaucugca cccagguguu ccacaagagc aucagcaggc 2580
ggugcaccaa gagcgugacc agcgucguga gcacccuguu cuacgacaag aaaaugagga 2640
ccaccaaccc caaggagacc aaaaucguga ucgacaccac aggcagcacc aagcccaagc 2700
aggacgaccu gauccugacc ugcuucaggg gcugggugaa gcagcugcag aucgacuaca 2760
agggcaacga gaucaugacc gccgcugcca gccagggccu gaccaggaag ggcguguacg 2820
ccgugaggua caaggugaac gagaacccac uguacgcucc caccagcgag cacgugaacg 2880
ugcugcugac caggaccgag gacaggaucg uguggaagac ccuggccggc gaccccugga 2940
ucaagacccu gaccgccaag uaccccggca acuucaccgc caccaucgaa gaguggcagg 3000
ccgagcacga cgccaucaug aggcacaucc uggagaggcc cgaccccacc gacguguucc 3060
agaacaaggc caacgugugc ugggccaagg cccuggugcc cgugcugaag accgccggca 3120
ucgacaugac cacagagcag uggaacaccg uggacuacuu cgagaccgac aaggcccaca 3180
gcgccgagau cgugcugaac cagcugugcg ugagguucuu cggccuggac cuggacagcg 3240
gccuguucag cgcccccacc gugccacuga gcaucaggaa caaccacugg gacaacagcc 3300
ccagcccaaa cauguacggc cugaacaagg agguggucag gcagcugagc aggcgguacc 3360
cacagcugcc cagggccgug gccaccggca ggguguacga caugaacacc ggcacccuga 3420
ggaacuacga ccccaggauc aaccuggugc ccgugaacag gcggcugccc cacgcccugg 3480
ugcugcacca caacgagcac cccacagagcg acuucagcuc cuucgugagc aagcugaaag 3540
gcaggaccgu gcuggucgug ggcgagaagc ugagcgugcc cggcaagaug guggacuggc 3600
ugagcgacag gcccgaggcc accuuccggg ccaggcugga ccucggcauc cccggcgacg 3660
ugcccaagua cgacaucauc uucgugaacg ucaggacccc auacaaguac caccauuacc 3720
agcagugcga ggaccacgcc aucaagcuga gcaugcugac caagaaggcc ugccugcacc 3780
ugaaccccgg aggcaccugc gugagcaucg gcuacggcua cgccgacagg gccagcgaga 3840
gcaucauugg cgccaucgcc aggcuguuca aguucagcag ggugugcaaa cccaagagca 3900
gccuggagga aaccgaggug cuguucgugu ucaucggcua cgaccggaag gccaggaccc 3960
acaaccccua caagcugagc agcacccuga caaacaucua caccggcagc aggcugcacg 4020
aggccggcug cgcccccagc uaccacgugg ucaggggcga uaucgccacc gccaccgagg 4080
gcgugaucau caacgcugcc aacagcaagg gccagcccgg aggcggagug ugcggcgccc 4140
uguacaagaa guuccccgag agcuucgacc ugcagcccau cgaggugggc aaggccaggc 4200
uggugaaggg cgccgcuaag cacaucaucc acgccguggg ccccaacuuc aacaagguga 4260
gcgaggugga aggcgacaag cagcuggccg aagccuacga gagcaucgcc aagaucguga 4320
acgacaauaa cuacaagagc guggccaucc cacugcucag caccggcauc uucagcggca 4380
acaaggacag gcugacccag agccugaacc accugcucac cgcccuggac accaccgaug 4440

-continued ccgacguggc caucuacugc agggacaaga agugggagau gacccugaag gaggccgugg 4500
ccaggcggga ggccguggaa gagaucugca ucagcgacga cuccagcgug accgagcccg 4560
acgccgagcu ggugagggug caccccaaga gcucccuggc cggcaggaag ggcuacagca 4620
ccagcgacgg caagaccuuc agcuaccugg agggcaccaa guuccaccag gccgcuaagg 4680
acaucgccga gaucaacgcu auguggcccg uggccaccga ggccaacgag caggugugca 4740
uguacauccu gggcgagagc auguccagca ucaggagcaa gugccccgug gaggaaagcg 4800
aggccagcac accacccagc acccugcccu gccugugcau ccacgcuaug acacccgaga 4860
gggugcagcg gcugaaggcc agcaggcccg agcagaucac cgugugcagc uccuucccac 4920
ugcccaagua caggaucacc ggcgugcaga agauccagug cagccagccc auccuguuca 4980
gcccaaaggu gcccgccuac auccacccca ggaaguaccu gguggagacc ccacccgugg 5040
acgagacacc cgagccaagc gccgagaacc agagcaccga gggcacaccc gagcagccac 5100
cccugaucac cgaggacgag acaaggaccc ggaccccaga gcccaucauu aucgaggaag 5160
aggaagagga cagcaucagc cugcugagcg acggccccac ccaccaggug cugcaggugg 5220
aggccgacau ccacggccca cccagcgugu ccagcuccag cuggagcauc ccacacgcca 5280
gcgacuucga cguggacagc cugagcaucc uggacacccu ggagggcgcc agcgugaccu 5340
ccggcgccac cagcgccgag accaacagcu acuucgccaa gagcauggag uuccuggcca 5400
ggcccgugcc agcucccagg accguguuca ggaacccacc ccacccagcu cccaggacca 5460
ggaccccaag ccuggcuccc agcagggccu gcagcaggac cagccuggug agcaccccac 5520
ccggcgugaa cagggugauc accagggagg aacuggaggc ccugacaccc agcaggaccc 5580
ccagcagguc cgugagcagg acuagucugg uguccaaccc acccggcgug aacaggguga 5640
ucaccaggga ggaauucgag gccuucgugg cccagcaaca gagacgguuc gacgccggcg 5700
ccuacaucuu cagcagcgac accggccagg gacaccugca gcaaaagagc gugaggcaga 5760
ccgugcugag cgagguggug cuggagagga ccgagcugga aaucagcuac gcccccaggc 5820
uggaccagga gaaggaggaa cugcucagga agaaacugca gcugaacccc accccagcca 5880
acaggagcag guaccagagc aggaaggugg agaacaugaa ggccaucacc gccaggcgga 5940
uccugcaggg ccugggacac uaccugaagg ccgagggcaa gguggagugc uacaggaccc 6000
ugcaccccgu gccacuguac agcuccagcg ugaacagggc cuucuccagc cccaaggugg 6060
ccguggaggc cugcaacgcu augcugaagg agaacuuccc caccguggcc agcuacugca 6120
ucauccccga guacgacgcc uaccuggaca ugguggacgg cgccagcugc ugccuggaca 6180
ccgccagcuu cugccccgcc aagcugagga gcuuccccaa gaaacacagc uaccuggagc 6240
ccaccaucag gagcgccgug cccagcgcca uccagaacac ccugcagaac gugcuggccg 6300
cugccaccaa gaggaacugc aacgugaccc agaugaggga gcugcccgug cuggacagcg 6360
cugccuucaa cguggagugc uucaagaaau acgccugcaa caacgaguac ugggagaccu 6420
ucaaggagaa ccccaucagg cugaccgaag agaacguggu gaacuacauc accaagcuga 6480
agggccccaa ggccgcugcc cuguucgcua agacccacaa ccugaacaug cugcaggaca 6540
ucccaaugga cagguucgug auggaccuga agagggacgu gaaggugaca cccggcacca 6600
agcacaccga ggagaggccc aaggugcagg ugauccaggc cgcugaccca cuggccaccg 6660
ccuaccugug cggcauccac agggagcugg ugaggcggcu gaacgccgug cugcugccca 6720
acauccacac ccuguucgac augagcgccg aggacuucga cgccaucauc gccgagcacu 6780

```
uccagcccgg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaauguuccu gacccuguuc gugaacaccg   7020
ugaucaacau ugugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
ggguggccga cccccugaag aggcuguuca agcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucucc uaccugaggg   7500
gggccccuau aacucucuac ggcuaaccug aauggacuac gacauagucu aguccgccaa   7560
ggccgccacc augagaguga cagccccuag aaccuuacug cuucugcuuu ggggagcugu   7620
ugcucugaca gagacauggg cuggaucuua ccacagcccc agcuacgccu accaccaguu   7680
cgagaggggg ggaggaggcu ccgggggagg aggcucccug aagaucagcc aggccgugca   7740
cgccgcccac gccgagauca acgaggccgg ccgggaggug aucgugggca uugucgcugg   7800
ccuggccguc cucgccgugg uggugauugg agcuguggue gcagcuguua ugugcagaag   7860
aaagucaucc ggcggaaagg gaggcuccua cucucaggcu gcuucugcua cagugccuag   7920
agcucuuaug uguuuaucuc agcugggcgg cggaggcagc gacuacaagg acgacgauga   7980
caaguaaacu cgaguauguu acgugcaaag gugauuguca ccccccgaaa gaccauauug   8040
ugacacaccc ucaguaucac gcccaaacau uuacagccgc ggugucaaaa accgcgugga   8100
cgugguuaac aucccugcug ggaggaucag ccguaauuau uauaauuggc uuggugcugg   8160
cuacuauugu ggccauguac gugcugacca accagaaaca uaauugaaua cagcagcaau   8220
uggcaagcug cuuacauaga acucgcggcg auuggcaugc cgccuuaaaa uuuuuauuuu   8280
auuuuuucuu uucuuuuccg aaucggauuu uguuuuuaau auuucaaaaa aaaaaaaaaa   8340
aaaaaaaaaa ucuagaaaaa aaaaaaaaaa aaaaaaaaaa aaaaaaaaaa aaaaaaaaaa   8400
aaaaaaaaaa aaaaaaaaaa aaaaaaaaaa aaaaaaaaaa aaaaaaaaaa aaaaa        8455
```

<210> SEQ ID NO 109
<211> LENGTH: 2512
<212> TYPE: PRT
<213> ORGANISM: Artificial sequence
<220> FEATURE:
<223> OTHER INFORMATION: Synthetic polypeptide

<400> SEQUENCE: 109

```
Met Glu Lys Pro Val Val Asn Val Asp Val Asp Pro Gln Ser Pro Phe
1               5                   10                  15

Val Val Gln Leu Gln Lys Ser Phe Pro Gln Phe Glu Val Val Ala Gln
            20                  25                  30

Gln Val Thr Pro Asn Asp His Ala Asn Ala Arg Ala Phe Ser His Leu
        35                  40                  45

Ala Ser Lys Leu Ile Glu Leu Glu Val Pro Thr Thr Ala Thr Ile Leu
    50                  55                  60

Asp Ile Gly Ser Ala Pro Ala Arg Arg Met Phe Ser Glu His Gln Tyr
```

-continued

His Cys Val Cys Pro Met Arg Ser Pro Glu Asp Pro Asp Arg Met Met
65                  70                  75                  80

Lys Tyr Ala Ser Lys Leu Ala Glu Lys Ala Cys Lys Ile Thr Asn Lys
            85                  90                  95

Asn Leu His Glu Lys Ile Lys Asp Leu Arg Thr Val Leu Asp Thr Pro
        100                 105                 110

Asp Ala Glu Thr Pro Ser Leu Cys Phe His Asn Asp Val Thr Cys Asn
    115                 120                 125

Met Arg Ala Glu Tyr Ser Val Met Gln Asp Val Tyr Ile Asn Ala Pro
130                 135                 140

Gly Thr Ile Tyr His Gln Ala Met Lys Gly Val Arg Thr Leu Tyr Trp
145                 150                 155                 160

Ile Gly Phe Asp Thr Thr Gln Phe Met Phe Ser Ala Met Ala Gly Ser
                165                 170                 175

Tyr Pro Ala Tyr Asn Thr Asn Trp Ala Asp Glu Lys Val Leu Glu Ala
            180                 185                 190

Arg Asn Ile Gly Leu Cys Ser Thr Lys Leu Ser Glu Gly Arg Thr Gly
        195                 200                 205

Lys Leu Ser Ile Met Arg Lys Lys Glu Leu Lys Pro Gly Ser Arg Val
    210                 215                 220

Tyr Phe Ser Val Gly Ser Thr Leu Tyr Pro Glu His Arg Ala Ser Leu
225                 230                 235                 240

Gln Ser Trp His Leu Pro Ser Val Phe His Leu Asn Gly Lys Gln Ser
                245                 250                 255

Tyr Thr Cys Arg Cys Asp Thr Val Val Ser Cys Glu Gly Tyr Val Val
            260                 265                 270

Lys Lys Ile Thr Ile Ser Pro Gly Ile Thr Gly Glu Thr Val Gly Tyr
        275                 280                 285

Ala Val Thr His Asn Ser Glu Gly Phe Leu Leu Cys Lys Val Thr Asp
    290                 295                 300

Thr Val Lys Gly Glu Arg Val Ser Phe Pro Val Cys Thr Tyr Ile Pro
305                 310                 315                 320

Ala Thr Ile Cys Asp Gln Met Thr Gly Ile Met Ala Thr Asp Ile Ser
                325                 330                 335

Pro Asp Asp Ala Gln Lys Leu Leu Val Gly Leu Asn Gln Arg Ile Val
            340                 345                 350

Ile Asn Gly Arg Thr Asn Arg Asn Thr Asn Thr Met Gln Asn Tyr Leu
        355                 360                 365

Leu Pro Ile Ile Ala Gln Gly Phe Ser Lys Trp Ala Lys Glu Arg Lys
    370                 375                 380

Asp Asp Leu Asp Asn Glu Lys Met Leu Gly Thr Arg Glu Arg Lys Leu
385                 390                 395                 400

Thr Tyr Gly Cys Leu Trp Ala Phe Arg Thr Lys Lys Val His Ser Phe
                405                 410                 415

Tyr Arg Pro Pro Gly Thr Gln Thr Cys Val Lys Val Pro Ala Ser Phe
            420                 425                 430

Ser Ala Phe Pro Met Ser Ser Val Trp Thr Thr Ser Leu Pro Met Ser
        435                 440                 445

Leu Arg Gln Lys Leu Lys Leu Ala Leu Gln Pro Lys Lys Glu Glu Lys
    450                 455                 460

Leu Leu Gln Val Ser Glu Glu Leu Val Met Glu Ala Lys Ala Ala Phe
465                 470                 475                 480
                485                 490                 495

```
Glu Asp Ala Gln Glu Glu Ala Arg Ala Glu Lys Leu Arg Glu Ala Leu
            500                 505                 510

Pro Pro Leu Val Ala Asp Lys Gly Ile Glu Ala Ala Glu Val Val
            515                 520                 525

Cys Glu Val Glu Gly Leu Gln Ala Asp Ile Gly Ala Ala Leu Val Glu
530                 535                 540

Thr Pro Arg Gly His Val Arg Ile Ile Pro Gln Ala Asn Asp Arg Met
545                 550                 555                 560

Ile Gly Gln Tyr Ile Val Val Ser Pro Asn Ser Val Leu Lys Asn Ala
                565                 570                 575

Lys Leu Ala Pro Ala His Pro Leu Ala Asp Gln Val Lys Ile Ile Thr
            580                 585                 590

His Ser Gly Arg Ser Gly Arg Tyr Ala Val Glu Pro Tyr Asp Ala Lys
            595                 600                 605

Val Leu Met Pro Ala Gly Gly Ala Val Pro Trp Pro Glu Phe Leu Ala
            610                 615                 620

Leu Ser Glu Ser Ala Thr Leu Val Tyr Asn Glu Arg Glu Phe Val Asn
625                 630                 635                 640

Arg Lys Leu Tyr His Ile Ala Met His Gly Pro Ala Lys Asn Thr Glu
                645                 650                 655

Glu Glu Gln Tyr Lys Val Thr Lys Ala Glu Leu Ala Glu Thr Glu Tyr
            660                 665                 670

Val Phe Asp Val Asp Lys Lys Arg Cys Val Lys Lys Glu Ala Ser
            675                 680                 685

Gly Leu Val Leu Ser Gly Glu Leu Thr Asn Pro Pro Tyr His Glu Leu
            690                 695                 700

Ala Leu Glu Gly Leu Lys Thr Arg Pro Ala Val Pro Tyr Lys Val Glu
705                 710                 715                 720

Thr Ile Gly Val Ile Gly Thr Pro Gly Ser Gly Lys Ser Ala Ile Ile
                725                 730                 735

Lys Ser Thr Val Thr Ala Arg Asp Leu Val Thr Ser Gly Lys Lys Glu
            740                 745                 750

Asn Cys Arg Glu Ile Glu Ala Asp Val Leu Arg Leu Arg Gly Met Gln
            755                 760                 765

Ile Thr Ser Lys Thr Val Asp Ser Val Met Leu Asn Gly Cys His Lys
770                 775                 780

Ala Val Glu Val Leu Tyr Val Asp Glu Ala Phe Ala Cys His Ala Gly
785                 790                 795                 800

Ala Leu Leu Ala Leu Ile Ala Ile Val Arg Pro Arg Lys Lys Val Val
                805                 810                 815

Leu Cys Gly Asp Pro Met Gln Cys Gly Phe Phe Asn Met Met Gln Leu
            820                 825                 830

Lys Val His Phe Asn His Pro Glu Lys Asp Ile Cys Thr Lys Thr Phe
            835                 840                 845

Tyr Lys Tyr Ile Ser Arg Arg Cys Thr Gln Pro Val Thr Ala Ile Val
            850                 855                 860

Ser Thr Leu His Tyr Asp Gly Lys Met Lys Thr Thr Asn Pro Cys Lys
865                 870                 875                 880

Lys Asn Ile Glu Ile Asp Ile Thr Gly Ala Thr Lys Pro Lys Pro Gly
                885                 890                 895

Asp Ile Ile Leu Thr Cys Phe Arg Gly Trp Val Lys Gln Leu Gln Ile
            900                 905                 910
```

```
Asp Tyr Pro Gly His Glu Val Met Thr Ala Ala Ala Ser Gln Gly Leu
            915                 920                 925

Thr Arg Lys Gly Val Tyr Ala Val Arg Gln Lys Val Asn Glu Asn Pro
    930                 935                 940

Leu Tyr Ala Ile Thr Ser Glu His Val Asn Val Leu Leu Thr Arg Thr
945                 950                 955                 960

Glu Asp Arg Leu Val Trp Lys Thr Leu Gln Gly Asp Pro Trp Ile Lys
                965                 970                 975

Gln Leu Thr Asn Ile Pro Lys Gly Asn Phe Gln Ala Thr Ile Glu Asp
            980                 985                 990

Trp Glu Ala Glu His Lys Gly Ile Ile Ala Ala Ile Asn Ser Pro Thr
        995                 1000                1005

Pro Arg Ala Asn Pro Phe Ser Cys Lys Thr Asn Val Cys Trp Ala
    1010                1015                1020

Lys Ala Leu Glu Pro Ile Leu Ala Thr Ala Gly Ile Val Leu Thr
    1025                1030                1035

Gly Cys Gln Trp Ser Glu Leu Phe Pro Gln Phe Ala Asp Asp Lys
    1040                1045                1050

Pro His Ser Ala Ile Tyr Ala Leu Asp Val Ile Cys Ile Lys Phe
    1055                1060                1065

Phe Gly Met Asp Leu Thr Ser Gly Leu Phe Ser Lys Gln Ser Ile
    1070                1075                1080

Pro Leu Thr Tyr His Pro Ala Asp Ser Ala Arg Pro Val Ala His
    1085                1090                1095

Trp Asp Asn Ser Pro Gly Thr Arg Lys Tyr Gly Tyr Asp His Ala
    1100                1105                1110

Ile Ala Ala Glu Leu Ser Arg Arg Phe Pro Val Phe Gln Leu Ala
    1115                1120                1125

Gly Lys Gly Thr Gln Leu Asp Leu Gln Thr Gly Arg Thr Arg Val
    1130                1135                1140

Ile Ser Ala Gln His Asn Leu Val Pro Val Asn Arg Asn Leu Pro
    1145                1150                1155

His Ala Leu Val Pro Glu Tyr Lys Glu Lys Gln Pro Gly Pro Val
    1160                1165                1170

Glu Lys Phe Leu Asn Gln Phe Lys His His Ser Val Leu Val Val
    1175                1180                1185

Ser Glu Glu Lys Ile Glu Ala Pro Arg Lys Arg Ile Glu Trp Ile
    1190                1195                1200

Ala Pro Ile Gly Ile Ala Gly Ala Asp Lys Asn Tyr Asn Leu Ala
    1205                1210                1215

Phe Gly Phe Pro Pro Gln Ala Arg Tyr Asp Leu Val Phe Ile Asn
    1220                1225                1230

Ile Gly Thr Lys Tyr Arg Asn His His Phe Gln Gln Cys Glu Asp
    1235                1240                1245

His Ala Ala Thr Leu Lys Thr Leu Ser Arg Ser Ala Leu Asn Cys
    1250                1255                1260

Leu Asn Pro Gly Gly Thr Leu Val Val Lys Ser Tyr Gly Tyr Ala
    1265                1270                1275

Asp Arg Asn Ser Glu Asp Val Val Thr Ala Leu Ala Arg Lys Phe
    1280                1285                1290

Val Arg Val Ser Ala Ala Arg Pro Asp Cys Val Ser Ser Asn Thr
    1295                1300                1305

Glu Met Tyr Leu Ile Phe Arg Gln Leu Asp Asn Ser Arg Thr Arg
```

```
                  1310              1315              1320

Gln Phe Thr Pro His His Leu Asn Cys Val Ile Ser Ser Val Tyr
    1325              1330              1335

Glu Gly Thr Arg Asp Gly Val Gly Ala Ala Pro Ser Tyr Arg Thr
    1340              1345              1350

Lys Arg Glu Asn Ile Ala Asp Cys Gln Glu Glu Ala Val Val Asn
    1355              1360              1365

Ala Ala Asn Pro Leu Gly Arg Pro Gly Glu Gly Val Cys Arg Ala
    1370              1375              1380

Ile Tyr Lys Arg Trp Pro Thr Ser Phe Thr Asp Ser Ala Thr Glu
    1385              1390              1395

Thr Gly Thr Ala Arg Met Thr Val Cys Leu Gly Lys Lys Val Ile
    1400              1405              1410

His Ala Val Gly Pro Asp Phe Arg Lys His Pro Glu Ala Glu Ala
    1415              1420              1425

Leu Lys Leu Leu Gln Asn Ala Tyr His Ala Val Ala Asp Leu Val
    1430              1435              1440

Asn Glu His Asn Ile Lys Ser Val Ala Ile Pro Leu Leu Ser Thr
    1445              1450              1455

Gly Ile Tyr Ala Ala Gly Lys Asp Arg Leu Glu Val Ser Leu Asn
    1460              1465              1470

Cys Leu Thr Thr Ala Leu Asp Arg Thr Asp Ala Asp Val Thr Ile
    1475              1480              1485

Tyr Cys Leu Asp Lys Lys Trp Lys Glu Arg Ile Asp Ala Ala Leu
    1490              1495              1500

Gln Leu Lys Glu Ser Val Thr Glu Leu Lys Asp Glu Asp Met Glu
    1505              1510              1515

Ile Asp Asp Glu Leu Val Trp Ile His Pro Asp Ser Cys Leu Lys
    1520              1525              1530

Gly Arg Lys Gly Phe Ser Thr Thr Lys Gly Lys Leu Tyr Ser Tyr
    1535              1540              1545

Phe Glu Gly Thr Lys Phe His Gln Ala Ala Lys Asp Met Ala Glu
    1550              1555              1560

Ile Lys Val Leu Phe Pro Asn Asp Gln Glu Ser Asn Glu Gln Leu
    1565              1570              1575

Cys Ala Tyr Ile Leu Gly Glu Thr Met Glu Ala Ile Arg Glu Lys
    1580              1585              1590

Cys Pro Val Asp His Asn Pro Ser Ser Ser Pro Lys Thr Leu
    1595              1600              1605

Pro Cys Leu Cys Met Tyr Ala Met Thr Pro Glu Arg Val His Arg
    1610              1615              1620

Leu Arg Ser Asn Asn Val Lys Glu Val Thr Val Cys Ser Ser Thr
    1625              1630              1635

Pro Leu Pro Lys His Lys Ile Lys Asn Val Gln Lys Val Gln Cys
    1640              1645              1650

Thr Lys Val Val Leu Phe Asn Pro His Thr Pro Ala Phe Val Pro
    1655              1660              1665

Ala Arg Lys Tyr Ile Glu Val Pro Glu Gln Pro Thr Ala Pro Pro
    1670              1675              1680

Ala Gln Ala Glu Glu Ala Pro Glu Val Val Ala Thr Pro Ser Pro
    1685              1690              1695

Ser Thr Ala Asp Asn Thr Ser Leu Asp Val Thr Asp Ile Ser Leu
    1700              1705              1710
```

-continued

```
Asp Met Asp Asp Ser Ser Glu Gly Ser Leu Phe Ser Ser Phe Ser
    1715                1720                1725

Gly Ser Asp Asn Ser Ile Thr Ser Met Asp Ser Trp Ser Ser Gly
    1730                1735                1740

Pro Ser Ser Leu Glu Ile Val Asp Arg Arg Gln Val Val Val Ala
    1745                1750                1755

Asp Val His Ala Val Gln Glu Pro Ala Pro Ile Pro Pro Pro Arg
    1760                1765                1770

Leu Lys Lys Met Ala Arg Leu Ala Ala Arg Lys Glu Pro Thr
    1775                1780                1785

Pro Pro Ala Ser Asn Ser Ser Glu Ser Leu His Leu Ser Phe Gly
    1790                1795                1800

Gly Val Ser Met Ser Leu Gly Ser Ile Phe Asp Gly Glu Thr Ala
    1805                1810                1815

Arg Gln Ala Ala Val Gln Pro Leu Ala Thr Gly Pro Thr Asp Val
    1820                1825                1830

Pro Met Ser Phe Gly Ser Phe Ser Asp Gly Glu Ile Asp Glu Leu
    1835                1840                1845

Ser Arg Arg Val Thr Glu Ser Glu Pro Val Leu Phe Gly Ser Phe
    1850                1855                1860

Glu Pro Gly Glu Val Asn Ser Ile Ile Ser Ser Arg Ser Ala Val
    1865                1870                1875

Ser Phe Pro Leu Arg Lys Gln Arg Arg Arg Arg Ser Arg Arg
    1880                1885                1890

Thr Glu Tyr Leu Thr Gly Val Gly Gly Tyr Ile Phe Ser Thr Asp
    1895                1900                1905

Thr Gly Pro Gly His Leu Gln Lys Lys Ser Val Leu Gln Asn Gln
    1910                1915                1920

Leu Thr Glu Pro Thr Leu Glu Arg Asn Val Leu Glu Arg Ile His
    1925                1930                1935

Ala Pro Val Leu Asp Thr Ser Lys Glu Glu Gln Leu Lys Leu Arg
    1940                1945                1950

Tyr Gln Met Met Pro Thr Glu Ala Asn Lys Ser Arg Tyr Gln Ser
    1955                1960                1965

Arg Lys Val Glu Asn Gln Lys Ala Ile Thr Thr Glu Arg Leu Leu
    1970                1975                1980

Ser Gly Leu Arg Leu Tyr Asn Ser Ala Thr Asp Gln Pro Glu Cys
    1985                1990                1995

Tyr Lys Ile Thr Tyr Pro Lys Pro Leu Tyr Ser Ser Ser Val Pro
    2000                2005                2010

Ala Asn Tyr Ser Asp Pro Gln Phe Ala Val Ala Val Cys Asn Asn
    2015                2020                2025

Tyr Leu His Glu Asn Tyr Pro Thr Val Ala Ser Tyr Gln Ile Thr
    2030                2035                2040

Asp Glu Tyr Asp Ala Tyr Leu Asp Met Val Asp Gly Thr Val Ala
    2045                2050                2055

Cys Leu Asp Thr Ala Thr Phe Cys Pro Ala Lys Leu Arg Ser Tyr
    2060                2065                2070

Pro Lys Lys His Glu Tyr Arg Ala Pro Asn Ile Arg Ser Ala Val
    2075                2080                2085

Pro Ser Ala Met Gln Asn Thr Leu Gln Asn Val Leu Ile Ala Ala
    2090                2095                2100
```

```
Thr Lys Arg Asn Cys Asn Val Thr Gln Met Arg Glu Leu Pro Thr
2105                2110                2115

Leu Asp Ser Ala Thr Phe Asn Val Glu Cys Phe Arg Lys Tyr Ala
2120                2125                2130

Cys Asn Asp Glu Tyr Trp Glu Glu Phe Ala Arg Lys Pro Ile Arg
2135                2140                2145

Ile Thr Thr Glu Phe Val Thr Ala Tyr Val Ala Arg Leu Lys Gly
2150                2155                2160

Pro Lys Ala Ala Ala Leu Phe Ala Lys Thr Tyr Asn Leu Val Pro
2165                2170                2175

Leu Gln Glu Val Pro Met Asp Arg Phe Val Met Asp Met Lys Arg
2180                2185                2190

Asp Val Lys Val Thr Pro Gly Thr Lys His Thr Glu Glu Arg Pro
2195                2200                2205

Lys Val Gln Val Ile Gln Ala Ala Glu Pro Leu Ala Thr Ala Tyr
2210                2215                2220

Leu Cys Gly Ile His Arg Glu Leu Val Arg Arg Leu Thr Ala Val
2225                2230                2235

Leu Leu Pro Asn Ile His Thr Leu Phe Asp Met Ser Ala Glu Asp
2240                2245                2250

Phe Asp Ala Ile Ile Ala Glu His Phe Lys Gln Gly Asp Pro Val
2255                2260                2265

Leu Glu Thr Asp Ile Ala Ser Phe Asp Lys Ser Gln Asp Asp Ala
2270                2275                2280

Met Ala Leu Thr Gly Leu Met Ile Leu Glu Asp Leu Gly Val Asp
2285                2290                2295

Gln Pro Leu Leu Asp Leu Ile Glu Cys Ala Phe Gly Glu Ile Ser
2300                2305                2310

Ser Thr His Leu Pro Thr Gly Thr Arg Phe Lys Phe Gly Ala Met
2315                2320                2325

Met Lys Ser Gly Met Phe Leu Thr Leu Phe Val Asn Thr Val Leu
2330                2335                2340

Asn Val Val Ile Ala Ser Arg Val Leu Glu Glu Arg Leu Lys Thr
2345                2350                2355

Ser Arg Cys Ala Ala Phe Ile Gly Asp Asp Asn Ile Ile His Gly
2360                2365                2370

Val Val Ser Asp Lys Glu Met Ala Glu Arg Cys Ala Thr Trp Leu
2375                2380                2385

Asn Met Glu Val Lys Ile Ile Asp Ala Val Ile Gly Glu Arg Pro
2390                2395                2400

Pro Tyr Phe Cys Gly Gly Phe Ile Leu Gln Asp Ser Val Thr Ser
2405                2410                2415

Thr Ala Cys Arg Val Ala Asp Pro Leu Lys Arg Leu Phe Lys Leu
2420                2425                2430

Gly Lys Pro Leu Pro Ala Asp Asp Glu Gln Asp Glu Asp Arg Arg
2435                2440                2445

Arg Ala Leu Leu Asp Glu Thr Lys Ala Trp Phe Arg Val Gly Ile
2450                2455                2460

Thr Gly Thr Leu Ala Val Ala Val Thr Thr Arg Tyr Glu Val Asp
2465                2470                2475

Asn Ile Thr Pro Val Leu Leu Ala Leu Arg Thr Phe Ala Gln Ser
2480                2485                2490

Lys Arg Ala Phe Gln Ala Ile Arg Gly Glu Ile Lys His Leu Tyr
```

Gly Gly Pro Lys
    2510

<210> SEQ ID NO 110
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 110

Ser Pro Ser Tyr Val Tyr His Gln Phe
1               5

<210> SEQ ID NO 111
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 111

Ser Pro Ser Tyr Ala Tyr His Gln Phe
1               5

<210> SEQ ID NO 112
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 112

Thr Pro His Pro Ala Arg Ile Gly Leu
1               5

<210> SEQ ID NO 113
<211> LENGTH: 1701
<212> TYPE: RNA
<213> ORGANISM: Artificial sequence
<220> FEATURE:
<223> OTHER INFORMATION: Synthetic polynucleotide

<400> SEQUENCE: 113

| | | | | |
|---|---|---|---|---|
| augaaggcua | uccuggluggu | gcugcucuac | accuuugcca | cagccaaugc ugacacccug | 60 |
| uguauuggcu | accaugccaa | caacagcaca | gacacagugg | acacaguguu ggagaagaau | 120 |
| gugacaguga | cccacucugu | gaaccuguug | gaggacaaac | acaauggcaa acugcuaaaa | 180 |
| cugaggggag | uggcuccacu | gcaccugggc | aaguguaaca | uugcuggcug gauucugggc | 240 |
| aacccugagu | gugagucccu | gagcacagcc | uccuccuggu | ccuacauugu ggagacacca | 300 |
| uccucugaca | auggcacuug | uuacccugga | gacuucauug | acuaugagga acugagggaa | 360 |
| caacuuuccu | cuguguccuc | cuuugagagg | uuugagauuu | uccaaagac cuccuccugg | 420 |
| ccaaaccaug | acagcaacaa | gggagugaca | gcagccuguc | cacaugcugg agccaagucc | 480 |
| uucuacaaga | accugauuug | gcuggugaag | aagggcaacu | ccuacccaaa acugagcaag | 540 |
| uccuacauca | ugacaagggg | caaggaggug | cuggugcugu | ggggcauccc accccaagc | 600 |
| accucugcug | accaacaguc | ccucuaccag | aaugcugacg | ccuaugcuu uggggcucc | 660 |
| agcagauaca | gcaagaaguu | caagcccgag | auugccauca | gaccaaaggu gagggaucag | 720 |
| gagggcagga | ugaacuacua | cuggacccug | guggaaccug | gagacaagau uaccuuugag | 780 |

-continued

```
gcuacaggca  accugguggu  gccaagauau  gccuuugcua  uggagaggaa  ugcuggcucu    840
ggcaucauca  ucucugacac  accuguccau  gacuguaaca  ccacuuguca  gacaccaaag    900
ggagccauca  acaccucccu  gccauuccag  aacauccacc  caaucaccau  uggcaagugu    960
ccaaaauaug  ucaagagcac  caaacugaga  cuggcuacag  gacugaggaa  caucccaagc   1020
auccagagca  ggggacuguu  uggagccauu  gcuggcuuca  uugagggagg  cuggacaggg   1080
augguggaug  gcugguaugg  cuaccaccac  cagaaugaac  agggcucugg  cuaugcugcu   1140
gaccugaaaa  gcacccagaa  ugccauugau  gagauuacca  acaaggugaa  cucugugauu   1200
gagaagauga  cacccaguu  cacagcagug  ggcaaggagu  caaccacuu  ggagaagagg    1260 auugagaacc  ugaacaagaa  gguggaugau  ggcuuccugg  acaucuggac  cuacaaugcu   1320
gaacugcugg  ugcuguugga  gaaugagagg  acccuggacu  accaugacag  caaugugaag   1380
aaccucuaug  agaaggugag  gagccaacuu  aaaaacaaug  ccaaggagau  uggcaauggc   1440
uguuuugagu  cuaccacaa  gugugacaac  acuuguaugg  agucugugaa  gaauggcacc   1500
uaugacuacc  caaauacuc  ugaggaggcu  aaacugaaca  gggaggagau  ugauggagug   1560
aaauuggaga  gcaccaggau  uuaccagauc  cuggccaucu  acagcaccgu  ggccagcagc   1620
cuggugcugg  uggugagccu  gggcgccauc  agcuucugga  ugcagcaa  cggcagcuug    1680 cagugcagga  ucugcaucua  a                                                1701
```

<210> SEQ ID NO 114
<211> LENGTH: 566
<212> TYPE: PRT
<213> ORGANISM: Artificial sequence
<220> FEATURE:
<223> OTHER INFORMATION: Synthetic polypeptide

<400> SEQUENCE: 114

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
    65                  70                  75                  80

Asn Pro Glu Cys Glu Ser Leu Ser Thr Ala Ser Ser Trp Ser Tyr Ile
                    85                  90                  95

Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
        130                 135                 140

Ser Asn Lys Gly Val Thr Ala Ala Cys Pro His Ala Gly Ala Lys Ser
    145                 150                 155                 160

Phe Tyr Lys Asn Leu Ile Trp Leu Val Lys Lys Gly Asn Ser Tyr Pro
                    165                 170                 175

Lys Leu Ser Lys Ser Tyr Ile Asn Asp Lys Gly Lys Glu Val Leu Val
                180                 185                 190
```

-continued

Leu Trp Gly Ile His His Pro Ser Thr Ser Ala Asp Gln Gln Ser Leu
    195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 115
<211> LENGTH: 9911
<212> TYPE: RNA
<213> ORGANISM: Artificial sequence
<220> FEATURE:
<223> OTHER INFORMATION: Synthetic polynucleotide

<400> SEQUENCE: 115

```
gauaggcggc gcaugagaga agcccagacc aauuaccuac ccaaauagga gaaaguucac    60
guugacaucg aggaagacag cccauuccuc agagcuuugc agcggagcuu cccgcaguuu   120
gagguagaag ccaagcaggu cacugauaau gaccaugcua augccagagc guuucgcau    180
cuggcuucaa aacugaucga aacggaggug gacccauccg acacgauccu ugacauugga   240
auagucagca uaguacauuu caucugacua auacuacaac accaccacca ugaauagagg   300
auucuuuaac augcucggcc gccgccccuu cccggccccc acugccaugu ggaggccgcg   360
gagaaggagg caggcggccc cgggaagcgg agcuacuaac uucagccugc ugaagcaggc   420
uggagacgug gaggagaacc cuggaccuga aaaguucac guugacaucg aggaagacag    480
cccauuccuc agagcuuugc agcggagcuu cccgcaguuu gagguagaag ccaagcaggu   540
cacugauaau gaccaugcua augccagagc guuucgcau cuggcuucaa aacugaucga    600
aacggaggug gacccauccg acacgauccu ugacauugga agugcgcccg cccgcagaau   660
guauucuaag cacaaguauc auuguaucug uccgaugaga ugugcggaag auccggacag   720
auuguauaag uaugcaacua agcugaagaa aaacuguaag gaaauaacug auaaggaauu   780
ggacaagaaa augaaggagc ucgccgccgu caugagcgac ccugaccugg aaacugagac   840
uaugugccuc cacgacgacg agucgucgcg cuacgaaggg caagucgcug uuuaccagga   900
uguauacgcg guugacggac cgacaagucu cuaucaccaa gccaauaagg gaguuagagu   960
cgccuacugg auaggcuuug acaccacccc uuuuauguuu aagaacuugg cuggagcaua  1020
uccaucauac ucuaccaacu gggccgacga aaccguguua acggcucgua acauaggccu  1080
augcagcucu gacguuaugg agcggucacg uagagggaug uccauucuua gaagaaguau  1140
uuugaaacca uccaacaaug uucuauucuc uguuggcucg accaucuacc acgagaagag  1200
ggacuuacug aggagcuggc accugccguc uguauuucac uuacguggca agcaaaauua  1260
cacaugucgg ugugagacua uaguuaguug cgacgggua gucguuaaaa gaauagcuau  1320
caguccaggc cuguauggga agccuucagg cuaugcugcu acgaugcacc gcagggauu   1380
cuugugcugc aaagugacag acacauugaa cggggagagg gucucuuuuc ccgugugcac  1440
guaugugcca gcuacauugu gugaccaaau gacuggcaua cuggcaacag augucagugc  1500
ggacgacgcg caaaaacugc ugguugggcu caaccagcgu auagucguca acggucgcac  1560
ccagagaaac accaauacca ugaaaaauua ccuuuugccc guaguggccc aggcauuugc  1620
uaggugggca aaggaauaua aggaagauca agaagaugaa aggccacuag gacuacgaga  1680
uagacaguua gucaugggu guuguugggc uuuuagaagg cacaagauaa caucuauuua  1740
uaagcgcccg gauacccaaa ccaucaucaa agugaacagc gauuuccacu cauucgugcu  1800
gcccaggaua ggcaguaaca cauuggagau cgggcugaga acaagaauca ggaaaauguu  1860
agaggagcac aaggagccgu caccucucau uaccgccgag gacuacaag aagcuaagug   1920
cgcagccgau gaggcuaagg aggugcguga agccgaggag uugcgcgcag cucuaccacc  1980
uuuggcagcu gauguugagg agcccacucu ggaagccgau gucgacuuga uguuacaaga  2040
ggcugggggcc ggcucagugg agacaccucg uggcuugaua aagguuacca gcuacgaugg  2100
cgaggacaag aucggcucuu acgcugugcu uucuccgcag gcuguacuca agagugaaaa  2160
auuaucuugc auccacccuc ucgcugaaca agcauagug auaacacacu cuggccgaaa  2220
agggcguuau gccguggaac cauaccaugg uaaaguagug gugccagagg gacaugcaau  2280
```

-continued

```
acccguccag gacuuucaag cucugaguga aagugccacc auuguguaca acgaacguga    2340
guucguaaac agguaccugc accauauugc cacacaugga ggagcgcuga acacugauga    2400
agaauauuac aaaacuguca agcccagcga gcacgacggc gaauaccugu acgacaucga    2460
caggaaacag ugcgucaaga aagaacuagu cacugggcua gggcucacag gcgagcuggu    2520
ggauccuccc uuccaugaau cgccuacga gagucugaga acacgaccag ccgcuccuua     2580
ccaaguacca accauagggg uguauggcgu gccaggauca ggcaagucug gcaucauuaa    2640
aagcgcaguc accaaaaaag aucuaguggu gagcgccaag aaagaaaacu gugcagaaau    2700
uauaagggac gucaagaaaa ugaaagggcu ggacgucaau gccagaacug ggacucagu     2760 gcucuugaau ggaugcaaac accccguaga gacccuguau auugacgaag cuuuugcuug    2820
ucaugcaggu acucucagag cgcucauagc cauuauaaga ccuaaaaagg cagugcucug    2880
cggggauccc aaacagugcg guuuuuuaa caugaugugc cugaaagugc auuuuaacca     2940
cgagauuugc acacaagucu uccacaaaag caucucucgc cguucacua aaucugugac     3000 uucggucguc ucaaccuugu uuuacgacaa aaaaaugaga acgacgaauc cgaaagagac    3060
uaagauugug auugacacua ccggcaguac caaaccuaag caggacgauc ucauucucac    3120
uuguuucaga gggguggugga agcaguugca aauagauuac aaaggcaacg aaauaaugac    3180
ggcagcugcc ucucaagggc ugacccguaa aggugugau gccguucggu acaaggugaa     3240
ugaaaauccu cuguacgcac ccaccucuga acaugugaac guccacugua cccgcacgga    3300
ggaccgcauc gugugaaaaaa cacuagccgg cgacccaugg auaaaaacac ugacugccaa    3360
guacccuggg aauuucacug ccacgauaga ggaguggcaa gcagagcaug augccaucau    3420
gaggcacauc uuggagagac cggacccuac cgacgucuuc cagaauaagg caaacgugug    3480
uugggccaag gcuuuagugc cggugcugaa gaccgcuggc auagacauga ccacugaaca    3540
auggaacacu guggauuauu ugaaacgga caaagcucac ucagcagaga uaguauugaa      3600
ccaacuaugc gugagguucu uuggacucga ucuggacucc ggucuauuuu cugcaccac     3660 uguuccguua uccauuagga auaaucacug ggauaacucc ccgucgccua acauguacgg    3720
gcugaauaaa gaaguggucc gucagcucuc ucgcagguac ccacaacugc cucgggcagu    3780
ugccacugga agagucuaug acaugaacac ugguacacug cgcaauuaug auccgcgcau    3840
aaaccuagua ccuguaaaca gaagacgcc ucaugcuuua guccuccacc auaaugaaca     3900
cccacagagu gacuuucuu cauucgucag caaaaugaag ggcagaacug uccugguggu     3960
cggggaaaag uuguccgucc caggcaaaau gguugacugg uugucagacc ggccugaggc    4020
uaccuucaga gcucggcugg auuuaggcau cccaggugau gugcccaaau augacauaau    4080
auuuguuaau gugaggaccc cauauaaaua ccaucacuau cagcagugug aagaccaugc    4140
cauuaagcuu agcauguuga ccaagaaagc uugucugcau cugaaucccg gcggaaccug    4200
ugucagcaua gguuaugguu acgcugacag ggccagcgaa agcaucauug ugcauagc     4260 gcggcaguuc aaguuucc gggaugcaa accgaaauc uucacuugaag agacggaaguu    4320 ucuguuugua uucauggguu acgaucgcaa ggcccguacg cacaauccuu acaagcuuuc    4380
aucaaccuug accaacauuu auacagguuc cagacuccac gaagccggau gugcacccuc    4440
auaucaugug gugcgagggg auauugccac ggccaccgaa ggagugauua uaaaugcugc    4500
uaacagcaaa ggacaaccug gcgggggu gucggagcg cuguauaaga aauucccgga      4560
aagcuucgau uuacagccga ucgaaguagg aaaagcgcga cuggucaaag gugcagcuaa    4620
acauaucauu caugccguag gaccaaacuu caacaaaguu ucggagguug aaggugacaa    4680
```

-continued

```
acaguuggca gaggcuuaug aguccaucgc uaagauuguc aacgauaaca auuacaaguc    4740
aguagcgauu ccacuguugu ccaccggcau cuuuuccggg aacaaagauc gacuaaccca    4800
aucauugaac cauuugcuga cagcuuuaga caccacugau gcagauguag ccauauacug    4860
cagggacaag aaaugggaaa ugacucucaa ggaagcagug gcuaggagag aagcagugga    4920
ggagauaugc auauccgacg acucuucagu gacagaaccu gaugcagagc uggugagggu    4980
gcauccgaag aguucuuggc uggaaggaa gggcuacagc acaagcgaug gcaaaacuuu    5040
cucauauuug aagggacca aguuucacca ggcggccaag gauauagcag aaauuaaugc    5100 caugguggccc guugcaacgg aggccaauga gcagguaugc auguauaucc ucggagaaag    5160
caugagcagu auuaggucga aaugccccgu cgaagagucg gaagccucca caccaccuag    5220
cacgcugccu ugcuugugca uccaugccau gacuccagaa agaguacagc gccuaaaagc    5280
cucacgucca gaacaaauua cugugugcuc auccuuccca uugccgaagu auagaaucac    5340
uggugugcag aagauccaau gcucccagcc uauauuguuc ucaccgaaag ugccugcgua    5400
uauucaucca aggaaguauc ucguggaaac accaccggua gacgagacuc cggagccauc    5460
ggcagagaac caauccacag aggggacacc ugaacaacca ccacuuauaa ccgaggauga    5520
gaccaggacu agaacgccug agccgaucau caucgaagag gaagaagagg auagcauaag    5580
uuugcuguca gauggcccga cccaccaggu gcugcaaguc gaggcagaca uuacgggcc    5640 gcccucugua ucuagcucau ccugguccau uccucaugca uccgacuuug auguggacag    5700
uuuauccaua cuugacaccc uggagggagc uagcgugacc agcggggcaa cgucagccga    5760
gacuaacucu uacuucgcaa agaguaugga guuucuggcg cgaccggugc cugcgccucg    5820
aacaguauuc aggaacccuc cacauccgc uccgcgcaca agaacaccgu cacuugcacc    5880
cagcagggcc ugcucgagaa ccagccuagu uccaccccg ccaggcguga auagggugau    5940
cacuagagag gagcucgagg cgcuuaccc gucacgcacu ccuagcaggu cggucucgag    6000
aaccagccug gucuccaacc cgccaggcgu aaauagggug auuacaagag aggaguuuga    6060
ggcguucgua gcacaacaac aaugacgguu ugaugcgggu gcauacaucu uuucccucga    6120
caccggucaa gggcauuuac aacaaaaauc aguaaggcaa acggugcuau ccgaaguggu    6180
guuggagagg accgaauugg agauuucgua ugcccgcgc cucgaccaag aaaaagaaga    6240
auuacuacgc aagaaauuac aguuaaaucc cacaccugcu aacagaagca gauaccaguc    6300
caggaaggug gagaacauga agccauaac agcuagacgu auucugcaag gccuagggca    6360
uuauuugaag gcagaaggaa aaguggagug cuaccgaacc cugcauccug uuccuuugua    6420
uucaucuagu gugaaccgug ccuuuucaag ccccaagguc gcaguggaag ccuguaacgc    6480 caguugaaa gagaacuuuc cgacuguggc ucuuacugu auuauccag aguacgaugc    6540 cuauuuggac auggugacg gagcuucaug cugcuuagac acugccaguu uugcccugc    6600 aaagcugcgc agcuuccaa agaaacacuc uauuuggaa cccacaauac gaucggcagu    6660
gccuucagcg auccagaaca cgcuccagaa cguccuggca gcugccacaa aagaaauug    6720 caaugucacg caaaugagag aauugcccgu auuggauucg gcggccuuua augugggaaug    6780 cuucaagaaa uaugcgugua auaaugaaua ugggaaacg uuuaaagaaa accccaucag    6840
gcuuacugaa gaaaacgugg uaaauuacau uaccaaauua aaaggaccaa agcugcugc    6900 ucuuuuugcg aagacacaua uuuugauau guugcaggac auaccaaugg acagguuugu    6960
aauggacuua aagagagacg ugaaagugac uccaggaaca aaacauacug aagacggcc    7020
```

-continued

| | |
|---|---|
| caagguacag gugauccagg cugccgaucc gcuagcaaca gcguaucugu gcggaaucca | 7080 |
| ccgagagcug guuaggagau uaaaugcggu ccugcuuccg aacauucaua cacuguuuga | 7140 |
| uaugucggcu gaagacuuug acgcuauuau agccgagcac uuccagccug gggauugugu | 7200 |
| ucuggaaacu gacaucgcgu cguuugauaa aagugaggac gacgccaugg cucugaccgc | 7260 |
| guuaaugauu cuggaagacu aggugugga cgcagagcug uugacgcuga uugaggcggc | 7320 |
| uuucggcgaa auucaucaa uacauuugcu cacuaaaacu aaauuuaaau ucggagccau | 7380 |
| gaugaaaucu ggaauguucc ucacacuguu ugugaacaca gucauuaaca uuguaaucgc | 7440 |
| aagcagagug uugagagaac ggcuaaccgg aucaccaugu gcagcauuca uuggagauga | 7500 |
| caauucgug aaaggaguca aaucggacaa auuaauggca gacaggugcg ccaccugguu | 7560 |
| gaauauggaa gucaagauua uagaugcugu gguggggcgag aaagcgccuu auuucugugg | 7620 |
| aggguuuauu uugugugacu ccgugaccgg cacagcgugc cguguggcag accccccuaaa | 7680 |
| aaggcuguuu aagcuuggca aaccucuggc agcagacgau gaacaugaug augacaggag | 7740 |
| aagggcauug caugaagagu caacacgcug gaaccgagug gguauucuuu cagagcugug | 7800 |
| caaggcagua gaaucaaggu augaaaccgu aggaacuucc aucauaguua uggccaugac | 7860 |
| uacucuagcu agcaguguua aaucauucag cuaccgagda ggggcccua uaacucucua | 7920 |
| cggcuaaccu gaauggacua cgacauaguc uagccgcca agauaucgca ccauggaaga | 7980 |
| ugccaaaaac auuaagaagg gcccagcgcc auucuaccca cucgaagacg ggaccgccgg | 8040 |
| cgagcagcug cacaaagcca ugaagcgcua cgcccuggug cccggcacca ucgccuuuac | 8100 |
| cgacgcacau aucgagguug acauuaccua cgccgaguac uucgagauga gcguucggcu | 8160 |
| ggcagaagcu augaagcgcu augggcugaa uacaaaccau cggaucgugg ugugcagcga | 8220 |
| gaauagcuug caguucuuca ugcccguguu gggugcccug uucaucgguu ggcuguggc | 8280 |
| cccagcuaac gacaucuaca cgagcgcga gcugcugaac agcaugggca ucagccagcc | 8340 |
| caccgucgua uucgugagca gaaaagggcu gcaaaagauc ucaacgugc aaaagaagcu | 8400 |
| accgaucaua caaaagauca ucaucaugga uagcaagacc gacuaccagg gcuuccaaag | 8460 |
| cauguacacc uucgugacuu cccauuugcc accggcuuc aacgaguacg acuucgugcc | 8520 |
| cgagagcuuc gaccgggaca aaaccaucgc ccugaucaug aacagauagu gcaguaccgg | 8580 |
| auugccaag ggcguagccc uaccgcaccg caccgcuugu guccgauuca gucaugcccg | 8640 |
| cgaccccauc uucggcaacc agaucauccc cgacaccgcu auccucagcg uggugccauu | 8700 |
| ucaccacggc uucggcaugu ucaccacgcu gggcuacuug aucugcggcu ucggggucgu | 8760 |
| gcucauguac cgcuucgagg aggagcuauu cuugcgcagc uugcaagacu auaagauuca | 8820 |
| aucugcccug cuggugccca cacuauuuag cuucuucgcu aagagcacuc ucaucgacaa | 8880 |
| guacgaccua agcaacuugc acgagaucgc cagcggcggg gcgccgcuca gcaaggaggu | 8940 |
| aggugaggcc guggccaaac gcuuccaccu accaggcauc cgacagggcu acggccugac | 9000 |
| agaaacaacc agcgccauuc ugaucacccc cgaagggac gacaagccug gcgcaguagg | 9060 |
| caagguggug cccuucuucg aggcuaaggu gguggacuug gacaccggua agacacuggg | 9120 |
| ugugaaccag cgcggcgagc ugugcgucgg uggcccaugu aucaugagcg gcuacguuaa | 9180 |
| caacccugag gcuacaaacg cucucaucga caaggacggc uggcugcaca gcggcgacau | 9240 |
| cgccuacugg gacgaggacg agcacuucuc caucgggac cggcugaagu cccugaucaa | 9300 |
| auacaagggc uaccagguag ccccagccga acugagagc auccgcugc aacccccaa | 9360 |
| caucuucgac gccgggguucg ccggccugcc cgacgacgau gccggcgagc ugcccgccgc | 9420 |

```
agucgucgug cuggaacacg guaaaaccau gaccgagaag gagaucgugg acuauguggc 9480
cagccagguu acaaccgcca agaagcugcg cgguggguguu guguucgugg acgaggugcc 9540
uaaaggacug accggcaagu uggacgcccg caagauccgc gagauucuca uuaaggccaa 9600
gaagggcggc aagaucgccg uguaaggcgc gccguuuaaa cggccggccu uaauuaagua 9660
acgauacagc agcaauuggc aagcugcuua cauagaacuc gcggcgauug gcaugccgcc 9720
uuaaaauuuu uauuuuauuu uuucuuuucu uuuccgaauc ggauuuuguu uuuaauauuu 9780
caaaaaaaaa aaaaaaaaaa aaaaaaucua gaaaaaaaaa aaaaaaaaaa aaaaaaaaaa 9840
aaaaaaaaaa aaaaaaaaaa aaaaaaaaaa aaaaaaaaaa aaaaaaaaaa aaaaaaaaaa 9900
aaaaaaaaaa a 9911

<210> SEQ ID NO 116
<211> LENGTH: 2117
<212> TYPE: RNA
<213> ORGANISM: Artificial sequence
<220> FEATURE:
<223> OTHER INFORMATION: Synthetic polynucleotide
<400> SEQUENCE: 116
aggaaacuua agucaacaca acauauacaa aacaaacgaa ucucaagcaa ucaagcauuc 60
uacuucuauu gcagcaauuu aaaucauuuc uuuuaaagca aaagcaauuu ucugaaaauu 120
uucaccauuu acgaacgaua gccaccauga aggcuauccu gguggugcug cucuacaccu 180
uugccacagc caaugcugac acccugugua uuggcuacca ugccaacaac agcacagaca 240
caguggacac aguguuggag aagaauguga cagugaccca cucugugaac cuguuggagg 300
acaaacacaa uggcaaacug uguaaacuga ggggaguggc uccacugcac cugggcaagu 360
guaacauugc uggcuggauu cugggcaacc cugaguguga gucccugagc acagccuccu 420
ccugguccua cauuguggag acaccauccu cugacaaugg cacuuguuac ccuggagacu 480
ucauugacua ugaggaacug agggaacaac uuuccucugu guccuccuuu gagagguuug 540
agauuuuucc aaagaccucc uccuggccaa accaugacag caacaaggga gugacagcag 600
ccuguccaca ugcuggagcc aaguccuucu acaagaaccu gauuuggcug gugaagaagg 660
gcaacuccua cccaaaacug agcaaguccu acaucaauga caagggcaag gaggugcugg 720
ugcuguggg cauccaccac ccaagcaccu cugcugacca acagucccuc uaccagaaug 780
cugacgccua uguguuugug ggcuccagca gauacagcaa gaaguucaag ccugagauug 840
ccaucagacc aaaggugagg gaucaggagg gcaggaugaa cuacuacugg acccuggugg 900
aaccuggaga caagauuacc uuugaggcua caggcaaccu gguggugcca agauaugccu 960
uugcuaugga gaggaaugcu ggcucuggca ucaucaucuc ugacacaccu guccaugacu 1020
guaacaccac uugucagaca ccaaagggag ccaucaacac cucccugcca uuccagaaca 1080
uccacccaau caccauuggc aaguguccaa aauaugucaa gagcaccaaa cugagacugg 1140
cuacaggacu gaggaacauc ccaagcaucc agagcagggg acuguuugga gccauugcug 1200
gcuucauuga gggaggcugg acagggaugg uggauggcug guauggcuac caccaccaga 1260
augaacaggg cucuggcuau gcugcugacc ugaaaagcac ccagaaugcc auugaugaga 1320
uuaccaacaa ggugaacucu gugauugaga agaugaacac ccaguucaca gcagugggca 1380
aggaguucaa ccacuuggag aagaggauug agaaccugaa caagaaggug gaugauggcu 1440
uccuggacau cuggaccuac aaugcugaac ugcuggugcu guuggagaau gagaggaccc 1500
```
uggacuacca ugacagcaau gugaagaacc ucuaugagaa ggugaggagc caacuuaaaa 1560
acaaugccaa ggagauuggc aauggcuguu uugaguucua ccacaagugu gacaacacuu 1620
guauggaguc ugugaagaau ggcaccuaug acuacccaaa auacucugag gaggcuaaac 1680
ugaacaggga ggagauugau ggagugaaau uggagagcac caggauuuac cagauccugg 1740
ccaucuacag caccguggcc agcagccugg ugcugguggu gagccugggc gccaucagcu 1800
ucuggaugug cagcaacggc agcuugcagu gcaggaucug caucuaaacu cgagcuagug 1860
acugacuagg aucugguuac cacuaaacca gccucaagaa cacccgaaug gagucucuaa 1920
gcuacauaau accaacuuac acuuacaaaa uguuguccccc caaaauguag ccauucguau 1980
cugcuccuaa uaaaaagaaa guuucuucac auucuagaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaa 2117

<210> SEQ ID NO 117
<211> LENGTH: 3822
<212> TYPE: DNA
<213> ORGANISM: Artificial sequence
<220> FEATURE:
<223> OTHER INFORMATION: Synthetic polynucleotide

<400> SEQUENCE: 117
atgtttgttt ttcttgtttt attgccacta gtctctagtc agtgtgttaa tcttacaacc 60
agaactcaat tacccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440

-continued

```
aatggtgttg aaggtttaa ttgttacttt cctttacaat catatggttt ccaacccact    1500
aatggtgttg gttaccaacc atacagagta gtagtacttt cttttgaact tctacatgca    1560
ccagcaactg tttgtggacc taaaaagtct actaatttgg ttaaaaacaa atgtgtcaat    1620
ttcaacttca atggtttaac aggcacaggt gttcttactg agtctaacaa aaagtttctg    1680
cctttccaac aatttggcag agacattgct gacactactg atgctgtccg tgatccacag    1740
acacttgaga ttcttgacat tacaccatgt tcttttggtg gtgtcagtgt tataacacca    1800
ggaacaaata cttctaacca ggttgctgtt ctttatcagg atgttaactg cacagaagtc    1860
cctgttgcta ttcatgcaga tcaacttact cctacttggc gtgtttattc tacaggttct    1920
aatgtttttc aaacacgtgc aggctgttta ataggggctg aacatgtcaa caactcatat    1980
gagtgtgaca tacccattgg tgcaggtata tgcgctagtt atcagactca gactaattct    2040
cctcggcggg cacgtagtgt agctagtcaa tccatcattg cctacactat gtcacttggt    2100
gcagaaaatt cagttgctta ctctaataac tctattgcca tacccacaaa ttttactatt    2160
agtgttacca cagaaattct accagtgtct atgaccaaga catcagtaga ttgtacaatg    2220
tacatttgtg gtgattcaac tgaatgcagc aatcttttgt tgcaatatgg cagttttgt    2280 acacaattaa accgtgcttt aactggaata gctgttgaac aagacaaaaa cacccaagaa    2340 gttttttgcac aagtcaaaca aatttacaaa acaccaccaa ttaaagattt tggtggtttt    2400
aatttttcac aaatattacc agatccatca aaaccaagca gaggtcatt tattgaagat    2460 ctacttttca caaagtgac acttgcagat gctggcttca tcaaacaata tggtgattgc    2520
cttggtgata ttgctgctag agacctcatt tgtgcacaaa agtttaacgg ccttactgtt    2580 ttgccaccctt tgctcacaga tgaaatgatt gctcaataca cttctgcact gttagcgggt    2640
acaatcactt ctggttggac ctttggtgca ggtgctgcat tacaaatacc atttgctatg    2700
caaatggctt ataggtttaa tggtattgga gttacacaga atgttctcta tgagaaccaa    2760
aaattgattg ccaaccaatt taatagtgct attggcaaaa ttcaagactc actttcttcc    2820
acagcaagtg cacttggaaa acttcaagat gtggtcaacc aaaatgcaca agcttttaaac    2880 acgcttgtta acaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga atcagagct    3060 tctgctaatc ttgctgctac taaaatgtca gagtgtgtac ttggacaatc aaaaagagtt    3120 gattttttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaatttttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatattttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg ctaggtttt    3660 atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
```
tctgagccag tgctcaaagg agtcaaatta cattacacat aa           3822

<210> SEQ ID NO 118
<211> LENGTH: 1273
<212> TYPE: PRT
<213> ORGANISM: Artificial sequence
<220> FEATURE:
<223> OTHER INFORMATION: Synthetic polypeptide

<400> SEQUENCE: 118

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu

```
                355                 360                 365
Tyr Asn Ser Ala Ser Phe Ser Thr Phe Lys Cys Tyr Gly Val Ser Pro
    370                 375                 380
Thr Lys Leu Asn Asp Leu Cys Phe Thr Asn Val Tyr Ala Asp Ser Phe
385                 390                 395                 400
Val Ile Arg Gly Asp Glu Val Arg Gln Ile Ala Pro Gly Gln Thr Gly
                405                 410                 415
Lys Ile Ala Asp Tyr Asn Tyr Lys Leu Pro Asp Asp Phe Thr Gly Cys
            420                 425                 430
Val Ile Ala Trp Asn Ser Asn Asn Leu Asp Ser Lys Val Gly Gly Asn
            435                 440                 445
Tyr Asn Tyr Leu Tyr Arg Leu Phe Arg Lys Ser Asn Leu Lys Pro Phe
    450                 455                 460
Glu Arg Asp Ile Ser Thr Glu Ile Tyr Gln Ala Gly Ser Thr Pro Cys
465                 470                 475                 480
Asn Gly Val Glu Gly Phe Asn Cys Tyr Phe Pro Leu Gln Ser Tyr Gly
                485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
            515                 520                 525
Lys Ser Thr Asn Leu Val Lys Asn Lys Cys Val Asn Phe Asn Phe Asn
    530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
                565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
    610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
                645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
            675                 680                 685
Ser Gln Ser Ile Ile Ala Tyr Thr Met Ser Leu Gly Ala Glu Asn Ser
    690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
                725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
    755                 760                 765
Gly Ile Ala Val Glu Gln Asp Lys Asn Thr Gln Glu Val Phe Ala Gln
770                 775                 780
```

-continued

```
Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
        820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185
```

| | | | | | | | | | | |
|---|---|---|---|---|---|---|---|---|---|---|
| Val | Ala | Lys | Asn | Leu | Asn | Glu | Ser | Leu | Ile | Asp | Leu | Gln | Glu | Leu |
| 1190 | | | | | 1195 | | | | | 1200 | | | | |
| Gly | Lys | Tyr | Glu | Gln | Tyr | Ile | Lys | Trp | Pro | Trp | Tyr | Ile | Trp | Leu |
| 1205 | | | | | 1210 | | | | | 1215 | | | | |
| Gly | Phe | Ile | Ala | Gly | Leu | Ile | Ala | Ile | Val | Met | Val | Thr | Ile | Met |
| 1220 | | | | | 1225 | | | | | 1230 | | | | |
| Leu | Cys | Cys | Met | Thr | Ser | Cys | Cys | Ser | Cys | Leu | Lys | Gly | Cys | Cys |
| 1235 | | | | | 1240 | | | | | 1245 | | | | |
| Ser | Cys | Gly | Ser | Cys | Cys | Lys | Phe | Asp | Glu | Asp | Asp | Ser | Glu | Pro |
| 1250 | | | | | 1255 | | | | | 1260 | | | | |
| Val | Leu | Lys | Gly | Val | Lys | Leu | His | Tyr | Thr | | | | | |
| 1265 | | | | | 1270 | | | | | | | | | |

<210> SEQ ID NO 119
<211> LENGTH: 3822
<212> TYPE: DNA
<213> ORGANISM: Artificial sequence
<220> FEATURE:
<223> OTHER INFORMATION: Synthetic polynucleotide

<400> SEQUENCE: 119

| | |
|---|---|
| atgttcgtct tcctggtcct gctgcctctg gtctcctcac agtgcgtcaa tctgacaact | 60 |
| cggactcagc tgccacctgc ttatactaat agcttcacca gaggcgtgta ctatcctgac | 120 |
| aaggtgttta gaagctccgt gctgcactct acacaggatc tgtttctgcc attctttagc | 180 |
| aacgtgacct ggttccacgc catccacgtg agcggcacca tggcacaaa gcggttcgac | 240 |
| aatcccgtgc tgccttttaa cgatggcgtg tacttcgcct ctaccgagaa gagcaacatc | 300 |
| atcagaggct ggatctttgg caccacactg gactccaaga cacagtctct gctgatcgtg | 360 |
| aacaatgcca ccaacgtggt catcaaggtg tgcgagttcc agttttgtaa tgatcccttc | 420 |
| ctgggcgtgt actatcacaa gaacaataag agctggatgg agtccgagtt tagagtgtat | 480 |
| tctagcgcca caactgcac atttgagtac gtgagccagc cttttctgat ggacctggag | 540 |
| ggcaagcagg gcaatttcaa gaacctgagg gagttcgtgt ttaagaatat cgacggctac | 600 |
| ttcaaaatct actctaagca cacccccatc aacctggtgc gcgacctgcc tcagggcttc | 660 |
| agcgccctgg agcccctggt ggatctgcct atcggcatca acatcacccg gtttcagaca | 720 |
| ctgctggccc tgcacagaag ctacctgaca cccggcgact cctctagcgg atggaccgcc | 780 |
| ggcgctgccg cctactatgt gggctacctc cagccccgga ccttcctgct gaagtacaac | 840 |
| gagaatggca ccatcacaga cgcagtggat gcgccctgg accccctgag cgagacaaag | 900 |
| tgtacactga agtcctttac cgtggagaag ggcatctatc agacatccaa tttcagggtg | 960 |
| cagccaaccg agtctatcgt gcgctttcct aatatcacaa acctgtgccc atttggcgag | 1020 |
| gtgttcaacg caacccgctt cgccagcgtg tacgcctgga taggaagcg atcagcaac | 1080 |
| tgcgtggccg actatagcgt gctgtacaac tccgcctctt tcagcacctt taagtgctat | 1140 |
| ggcgtgtccc ccacaaagct gaatgacctg tgctttacca cgtctacgc cgattctttc | 1200 |
| gtgatcaggg gcgacgaggt gcgccagatc gcccccggcc agacaggcaa gatcgcagac | 1260 |
| tacaattata agctgccaga cgatttcacc ggctgcgtga tcgcctggaa cagcaacaat | 1320 |
| ctggattcca agtgggcgg caactacaat tatctgtacc ggctgtttag aaagagcaat | 1380 |
| ctgaagccct tcgagaggga catctctaca gaaatctacc aggccggcag caccccttgc | 1440 |
| aatggcgtgg agggctttaa ctgttattc ccactccagt cctacggctt ccagcccaca | 1500 |
| aacggcgtgg gctatcagcc ttaccgcgtg gtggtgctga gctttgagct gctgcacgcc | 1560 |

```
ccagcaacag tgtgcggccc caagaagtcc accaatctgg tgaagaacaa gtgcgtgaac    1620
ttcaacttca acggcctgac cggcacaggc gtgctgaccg agtccaacaa gaagttcctg    1680
ccatttcagc agttcggcag ggacatcgca gataccacag acgccgtgcg cgacccacag    1740
accctggaga tcctggacat cacacccgtgc tctttcggcg gcgtgagcgt gatcacaccc    1800
ggcaccaata caagcaacca ggtggccgtg ctgtatcagg acgtgaattg taccgaggtg    1860
cccgtggcta tccacgccga tcagctgacc caacatggc gggtgtacag caccggctcc    1920
aacgtcttcc agacaagagc cggatgcctg atcggagcag agcacgtgaa caattcctat    1980
gagtgcgaca tcccaatcgg cgccggcatc tgtgcctctt accagaccca gacaaactct    2040
cccagaagag cccggagcgt ggcctcccag tctatcatcg cctataccat gtccctgggc    2100
gccgagaaca gcgtggccta ctctaacaat agcatcgcca tcccaaccaa cttcacaatc    2160
tctgtgacca cagagatcct gcccgtgtcc atgaccaaga catctgtgga ctgcacaatg    2220
tatatctgtg gcgattctac cgagtgcagc aacctgctgc tccagtacgg cagcttttgt    2280
acccagctga atagagccct gacaggcatc gccgtggagc aggataagaa cacacaggag    2340
gtgttcgccc aggtgaagca aatctacaag acccccccta tcaaggactt tggcggcttc    2400
aattttttccc agatcctgcc tgatccatcc aagccttcta gcggagctt tatcgaggac    2460
ctgctgttca caaggtgac cctggccgat gccggcttca tcaagcagta tggcgattgc    2520
ctgggcgaca tcgcagccag ggacctgatc tgcgcccaga gtttaatgg cctgaccgtg    2580
ctgccacccc tgctgacaga tgagatgatc gcacagtaca caagcgccct gctggccggc    2640
accatcacat ccggatggac cttcggcgca ggagccgccc tccagatccc ctttgccatg    2700
cagatggcct ataggttcaa cggcatcggc gtgacccaga atgtgctgta cgagaaccag    2760
aagctgatcg ccaatcagtt taactccgcc atcggcaaga tccaggacag cctgtcctct    2820
acagccagcg ccctgggcaa gctccaggat gtggtgaatc agaacgccca ggccctgaat    2880
accctggtga agcagctgag cagcaacttc ggcgccatct ctagcgtgct gaatgacatc    2940
ctgagccggc tggacaaggt ggaggcagag gtgcagatcg accggctgat caccggccgg    3000
ctccagagcc tccagaccta tgtgacacag cagctgatca gggccgccga tcagggcc    3060
agcgccaatc tggcagcaac caagatgtcc gagtgcgtgc tgggccagtc taagagagtg    3120
gactttgtg gcaagggcta tcacctgatg tccttccctc agtctgcccc acacggcgtg    3180
gtgtttctgc acgtgaccta cgtgcccgcc caggagaaga acttcaccac agcccctgcc    3240
atctgccacg atggcaaggc ccactttcca agggagggcg tgttcgtgtc caacggcacc    3300
cactggtttg tgacacagcg caatttctac gagccccaga tcatcaccac agacaacacc    3360
ttcgtgagcg gcaactgtga cgtggtcatc ggcatcgtga acaataccgt gtatgatcca    3420
ctccagcccg agctggacag ctttaaggag gagctggata gtatttcaa gaatcacacc    3480
tcccctgacg tggatctggg cgacatcagc ggcatcaatg cctccgtggt gaacatccag    3540
aaggagatcg accgcctgaa cgaggtggct aagaatctga acgagagcct gatcgacctc    3600
caggagctgg gcaagtatga gcagtacatc aagtggcccet ggtacatctg gctgggcttc    3660
atcgccggcc tgatcgccat cgtgatggtg accatcatgc tgtgctgtat gacatcctgc    3720
tgttcttgcc tgaagggctg ctgtagctgt ggctcctgct gtaagtttga cgaggatgac    3780
tctgaacctg tgctgaaggg cgtgaagctg cattacacct aa                       3822
```

<210> SEQ ID NO 120

```
<211> LENGTH: 1273
<212> TYPE: PRT
<213> ORGANISM: Artificial sequence
<220> FEATURE:
<223> OTHER INFORMATION: Synthetic polypeptide

<400> SEQUENCE: 120

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800
```

```
Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
```

1205                1210                1215

Gly Phe Ile Ala Gly Leu Ile Ala Ile Val Met Val Thr Ile Met
        1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 121
<211> LENGTH: 3822
<212> TYPE: DNA
<213> ORGANISM: Artificial sequence
<220> FEATURE:
<223> OTHER INFORMATION: Synthetic polynucleotide

<400> SEQUENCE: 121
atgtttgttt tcttgttttt attgccacta gtctctagtc agtgtgttaa tcttacaacc      60
agaactcaat taccccctgc atacactaat tctttcacac gtggtgttta ttaccctgac     120
aaagttttca gatcctcagt tttacattca actcaggact tgttcttacc tttcttttcc     180
aatgttactt ggttccatgc tatacatgtc tctgggacca atggtactaa gaggtttgat     240
aaccctgtcc taccatttaa tgatggtgtt tattttgctt ccactgagaa gtctaacata     300
ataagaggct ggatttttgg tactacttta gattcgaaga cccagtccct acttattgtt     360
aataacgcta ctaatgttgt tattaaagtc tgtgaatttc aattttgtaa tgatccattt     420
ttgggtgttt attaccacaa aaacaacaaa agttggatgg aaagtgagtt cagagtttat     480
tctagtgcga ataattgcac ttttgaatat gtctctcagc cttttcttat ggaccttgaa     540
ggaaaacagg gtaatttcaa aaatcttagg gaatttgtgt ttaagaatat tgatggttat     600
tttaaaatat attctaagca cacgcctatt aatttagtgc gtgatctccc tcagggtttt     660
tcggctttag aaccattggt agatttgcca ataggtatta acatcactag gtttcaaact     720
ttacttgctt tacatagaag ttatttgact cctggtgatt cttcttcagg ttggacagct     780
ggtgctgcag cttattatgt gggttatctt caacctagga cttttctatt aaaatataat     840
gaaaatggaa ccattacaga tgctgtagac tgtgcacttg accctctctc agaaacaaag     900
tgtacgttga atccttcac tgtagaaaaa ggaatctatc aaacttctaa ctttagagtc     960
caaccaacag aatctattgt tagatttcct aatattacaa acttgtgccc ttttggtgaa    1020
gtttttaacg ccaccagatt tgcatctgtt tatgcttgga acaggaagag aatcagcaac    1080
tgtgttgctg attattctgt cctatataat tccgcatcat tttccacttt taagtgttat    1140
ggagtgtctc ctactaaatt aaatgatctc tgctttacta atgtctatgc agattcattt    1200
gtaattagag gtgatgaagt cagacaaatc gctccagggc aaactggaaa gattgctgat    1260
tataattata aattaccaga tgattttaca ggctgcgtta gcttggaa ttctaacaat    1320 cttgattcta aggttggtgg taattataat tacctgtata gattgtttag aagtctaat    1380 ctcaaacctt ttgagagaga tatttcaact gaaatctatc aggccggtag cacaccttgt    1440
aatggtgttg aaggttttaa ttgttacttt cctttacaat catatggttt ccaacccact    1500
aatggtgttg gttaccaacc atacagagta gtagtacttt cttttgaact tctacatgca    1560
ccagcaactg tttgtggacc taaaaagtct actaatttgg ttaaaaacaa atgtgtcaat    1620
ttcaacttca atggtttaac aggcacaggt gttcttactg agtctaacaa aaagtttctg    1680

```
cctttccaac aatttggcag agacattgct gacactactg atgctgtccg tgatccacag    1740
acacttgaga ttcttgacat acaccatgt tcttttggtg gtgtcagtgt tataacacca    1800
ggaacaaata cttctaacca ggttgctgtt ctttatcagg atgttaactg cacagaagtc    1860
cctgttgcta ttcatgcaga tcaacttact cctacttggc gtgtttattc tacaggttct    1920
aatgttttc aaacacgtgc aggctgttta atagggctg aacatgtcaa caactcatat    1980
gagtgtgaca tacccattgg tgcaggtata tgcgctagtt atcagactca gactaattct    2040
cctcggcggg cacgtagtgt agctagtcaa tccatcattg cctacactat gtcacttggt    2100
gcagaaaatt cagttgctta ctctaataac tctattgcca tacccacaaa ttttactatt    2160
agtgttacca cagaaattct accagtgtct atgaccaaga catcagtaga ttgtacaatg    2220
tacatttgtg gtgattcaac tgaatgcagc aatcttttgt tgcaatatgg cagttttgt    2280
acacaattaa accgtgcttt aactggaata gctgttgaac aagacaaaaa caccaagaa    2340
gtttttgcac aagtcaaaca aatttacaaa acaccaccaa ttaaagattt tggtggtttt    2400
aatttttcac aaatattacc agatccatca aaaccaagca gaggtcatt tattgaagat    2460
ctactttca acaaagtgac acttgcagat gctggcttca tcaaacaata tggtgattgc    2520
cttggtgata ttgctgctag agacctcatt tgtgcacaaa agtttaacgg ccttactgtt    2580
ttgccaccttt tgctcacaga tgaaatgatt gctcaataca cttctgcact gttagcgggt    2640
acaatcactt ctggttggac ctttggtgca ggtgctgcat tacaaatacc atttgctatg    2700
caaatggctt ataggtttaa tggtattgga gttacacaga atgttctcta tgagaaccaa    2760
aaattgattg ccaaccaatt taatagtgct attggcaaaa ttcaagactc actttcttcc    2820
acagcaagtg cacttggaaa acttcaagat gtggtcaacc aaaatgcaca agctttaaac    2880
acgcttgtta acaacttag ctccaatttt ggtgcaattt caagtgtttt aaatgatatc    2940
ctttcacgtc ttgacaaagt tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120
gattttgtg gaaagggcta tcatcttatg tccttccctc agtcagcacc tcatggtgta    3180
gtcttcttgc atgtgactta tgtccctgca caagaaaaga acttcacaac tgctcctgcc    3240
atttgtcatg atggaaaagc acactttcct cgtgaaggtg tctttgtttc aaatggcaca    3300
cactggtttg taacacaaag gaattttat gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata atatttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcagtatata aaatggccat ggtacatttg gctaggtttt    3660
atagctggct tgattgccat agtaatggtg acaattatgc tttgctgtat gaccagttgc    3720
tgtagttgtc tcaagggctg ttgttcttgt ggatcctgct gcaaatttga tgaagacgac    3780
tctgagccag tgctcaaagg agtcaaatta cattacacat aa                      3822
```

<210> SEQ ID NO 122
<211> LENGTH: 3822
<212> TYPE: DNA
<213> ORGANISM: Artificial sequence
<220> FEATURE:

<223> OTHER INFORMATION: Synthetic polynucleotide

<400> SEQUENCE: 122

```
atgttcgtct tcctggtcct gctgcctctg gtctcctcac agtgcgtcaa tctgacaact      60
cggactcagc tgccacctgc ttatactaat agcttcacca gaggcgtgta ctatcctgac     120
aaggtgttta gaagctccgt gctgcactct acacaggatc tgtttctgcc attctttagc     180
aacgtgacct ggttccacgc catccacgtg agcggcacca atggcacaaa gcggttcgac     240
aatcccgtgc tgccttttaa cgatggcgtg tacttcgcct ctaccgagaa gtccaacatc     300
atcagaggct ggatctttgg caccacactg gactccaaga cacagtctct gctgatcgtg     360
aacaatgcca ccaacgtggt catcaaggtg tgcgagttcc agttttgtaa tgatcccttc     420
ctgggcgtgt actatcacaa gaacaataag agctggatgg agtccgagtt tagagtgtat     480
tctagcgcca caactgcac atttgagtac gtgagccagc ctttcctgat ggacctggag     540
ggcaagcagg gcaatttcaa gaacctgagg gagttcgtgt taagaatat cgacggctac     600
ttcaaaatct actctaagca cacccccatc aacctggtgc gcgacctgcc tcagggcttc     660
agcgccctgg agcccctggt ggatctgcct atcggcatca acatcacccg gtttcagaca     720
ctgctggccc tgcacagaag ctacctgaca cccggcgact cctctagcgg atggaccgcc     780
ggcgctgccg cctactatgt gggctacctc cagccccgga ccttcctgct gaagtacaac     840
gagaatggca ccatcacaga cgcagtggat tgcgccctgg accccctgag cgagacaaag     900
tgtacactga agtcctttac cgtggagaag ggcatctatc agacatccaa tttcagggtg     960
cagccaaccg agtctatcgt gcgctttcct aatatcacaa acctgtgccc atttggcgag    1020
gtgttcaacg caacccgctt cgccagcgtg tacgcctgga taggaagcg atcagcaac    1080
tgcgtggccg actatagcgt gctgtacaac tccgcctctt tcagcacctt taagtgctat    1140
ggcgtgtccc ccacaaagct gaatgacctg tgctttacca cgtctacgc cgattctttc    1200
gtgatcaggg gcgacgaggt gcgccagatc gcccccggcc agacaggcaa gatcgcagac    1260
tacaattata gctgccaga cgatttcacc ggctgcgtga tcgcctggaa cagcaacaat    1320
ctggattcca agtgggcgg caactacaat tatctgtacc ggctgtttag aaagagcaat    1380
ctgaagccct cgagaggga catctctaca gaaatctacc aggccggcag caccccttgc    1440
aatggcgtgg agggctttaa ctgttatttc ccactccagt cctacggctt ccagcccaca    1500
aacggcgtgg gctatcagcc ttaccgcgtg gtggtgctga gctttgagct gctgcacgcc    1560
ccagcaacag tgtgcggccc caagaagtcc accaatctgg tgaagaacaa gtgcgtgaac    1620
ttcaacttca cggcctgac cggcacaggc gtgctgaccg agtccaacaa gaagttcctg    1680
ccatttcagc agttcggcag ggacatcgca gataccacag acgccgtgcg cgacccacag    1740
accctggaga tcctggacat cacaccctgc tctttcggcg gcgtgagcgt gatcacaccc    1800
ggcaccaata caagcaacca ggtggccgtg ctgtatcagg acgtgaattg taccgaggtg    1860
cccgtggcta tccacgccga tcagctgacc ccaacatggc gggtgtacag caccggctcc    1920
aacgtcttcc agacaagagc cggatgcctg atcggagcag agcacgtgaa caattcctat    1980
gagtgcgaca tccaatcgg cgccggcatc tgtgcctctt accagaccca gacaaactct    2040
cccagacggg cccggagcgt ggcctcccag tctatcatcg cctataccat gtccctgggc    2100
gccgagaaca gcgtggccta ctctaacaat agcatcgcca tcccaaccaa cttcacaatc    2160
tctgtgacca cagagatcct gcccgtgtcc atgaccaaga catctgtgga ctgcacaatg    2220
tatatctgtg gcgattctac cgagtgcagc aacctgctgc tccagtacgg cagcttttgt    2280
```

```
acccagctga atagagccct gacaggcatc gccgtggagc aggataagaa cacacaggag   2340
gtgttcgccc aggtgaagca aatctacaag accccccctc tcaaggactt tggcggcttc   2400 aattttccc  agatcctgcc tgatccatcc aagccttcta agcggagctt tatcgaggac   2460
ctgctgttca acaaggtgac cctggccgat gccggcttca tcaagcagta tggcgattgc   2520
ctgggcgaca tcgcagccag ggacctgatc tgcgcccaga gtttaatgg  cctgaccgtg   2580 ctgccacccc tgctgacaga tgagatgatc gcacagtaca caagcgccct gctggccggc   2640
accatcacat ccggatggac cttcggcgca ggagccgccc tccagatccc ctttgccatg   2700
cagatggcct ataggttcaa cggcatcggc gtgacccaga atgtgctgta cgagaaccag   2760
aagctgatcg ccaatcagtt taactccgcc atcggcaaga tccaggacag cctgtcctct   2820
acagccagcg ccctgggcaa gctccaggat gtggtgaatc agaacgccca ggccctgaat   2880
accctggtga agcagctgag cagcaacttc ggcgccatct ctagcgtgct gaatgacatc   2940
ctgagccggc tggacaaggt ggaggcagag gtgcagatcg accggctgat caccggccgg   3000
ctccagagcc tccagaccta tgtgacacag cagctgatca gggccgccga tcagggcc    3060 agcgccaatc tggcagcaac caagatgtcc gagtgcgtgc tgggccagtc taagagagtg   3120
gacttttgtg gcaagggcta tcacctgatg tccttccctc agtctgcccc acacggcgtg   3180
gtgtttctgc acgtgaccta cgtgcccgcc aggagaaga  acttcaccac agcccctgcc   3240
atctgccacg atggcaaggc ccactttcca agggagggcg tgttcgtgtc caacggcacc   3300
cactggtttg tgacacagcg caatttctac gagccccaga tcatcaccac agacaacacc   3360
ttcgtgagcg gcaactgtga cgtggtcatc ggcatcgtga caataccgt  gtatgatcca   3420 ctccagcccg agctggacag ctttaaggag gagctggata gtatttcaa  gaatcacacc   3480 tcccctgacg tggatctggg cgacatcagc ggcatcaatg cctccgtggt gaacatccag   3540
aaggagatcg accgcctgaa cgaggtggct aagaatctga acgagagcct gatcgacctc   3600
caggagctgg gcaagtatga gcagtacatc aagtggccct ggtacatctg gctgggcttc   3660
atcgccggcc tgatcgccat cgtgatggtg accatcatgc tgtgctgtat gacatcctgc   3720
tgttcttgcc tgaagggctg ctgtagctgt ggctcctgct gtaagtttga cgaggatgac   3780
tctgaacctg tgctgaaggg cgtgaagctg cattacacct aa               3822
```

<210> SEQ ID NO 123
<211> LENGTH: 1273
<212> TYPE: PRT
<213> ORGANISM: Artificial sequence
<220> FEATURE:
<223> OTHER INFORMATION: Synthetic polypeptide

<400> SEQUENCE: 123

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
```

-continued

```
                85                  90                  95
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
            130                 135                 140

Tyr His Lys Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
            210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
            290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510
```

```
Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925
```

-continued

Ser Ala Ile Gly Lys Ile Gln Asp Ser Leu Ser Ser Thr Ala Ser Ala
930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 124
<211> LENGTH: 11860
<212> TYPE: DNA
<213> ORGANISM: Artificial sequence
<220> FEATURE:
<223> OTHER INFORMATION: Synthetic polynucleotide

<400> SEQUENCE: 124

-continued

```
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtatacgccg tcgacggccc caccagcctg taccaccagg     540
ccaacaaggg cgtgagggtg gcctactgga tcggcttcga caccacaccc ttcatgttca     600
agaacctggc cggcgcctac cccagctaca gcaccaactg ggccgacgag accgtgctga     660
ccgccaggaa catcggcctg tgcagcagcg acgtgatgga gaggagccgg agaggcatga     720
gcatcctgag gaagaaatac ctgaagccca gcaacaacgt gctgttcagc gtgggcagca     780
ccatctacca cgagaagagg gacctgctca ggagctggca cctgcccagc gtgttccacc     840
tgagggggcaa gcagaactac acctgcaggt gcgagaccat cgtgagctgc gacggctacg     900
tggtgaagag gatcgccatc agccccggcc tgtacggcaa gcccagcggc tacgccgcta     960
caatgcacag ggagggcttc ctgtgctgca aggtgaccga cacctgaac ggcgagaggg    1020
tgagcttccc cgtgtgcacc tacgtgcccg ccaccctgtg cgaccagatg accggcatcc    1080
tggccaccga cgtgagcgcc gacgacgccc agaagctgct cgtgggcctg aaccaggaga    1140
tcgtggtcaa cggcaggacc cagaggaaca ccaacacaat gaagaactac ctgctgcccg    1200
tggtggccca ggctttcgcc aggtgggcca aggagtacaa ggaggaccag gaagacgaga    1260
ggccccctggg cctgagggac aggcagctgg tgatgggctg ctgctgggcc ttcaggcggc    1320
acaagatcac cagcatctac aagaggcccg acacccagac catcatcaag gtgaacagcg    1380
acttccacag cttcgtgctg cccaggatcg gcagcaacac cctggagatc ggcctgagga    1440
cccggatcag gaagatgctg gaggaacaca aggagcccag cccactgatc accgccgagg    1500
acgtgcagga ggccaagtgc gctgccgacg aggccaagga ggtgagggag gccgaggaac    1560
tgagggccgc cctgccaccc ctggctgccg acgtggagga acccaccctg aagccgacg    1620
tggacctgat gctgcaggag gccggcgccg gaagcgtgga gacacccagg ggcctgatca    1680
aggtgaccag ctacgacggc gaggacaaga tcggcagcta cgccgtgctg agcccacagg    1740
ccgtgctgaa gtccgagaag ctgagctgca tccacccact ggccgagcag gtgatcgtga    1800
tcacccacag cggcaggaag ggcaggtacg ccgtggagcc ctaccacggc aaggtggtcg    1860
tgcccgaggg ccacgccatc cccgtgcagg acttccaggc cctgagcgag agcgccacca    1920
tcgtgtacaa cgagagggag ttcgtgaaca ggtacctgca ccatatcgcc acccacggcg    1980
gagccctgaa caccgacgag gaatactaca agaccgtgaa gcccagcgag cacgacggcg    2040
agtacctgta cgacatcgac aggaagcagt gcgtgaagaa agagctggtg accggcctgg    2100
gactgaccgg cgagctggtg gacccaccct tccacgagtt cgcctacgag agcctgagga    2160
ccagacccgc cgctccctac caggtgccca ccatcggcgt gtacggcgtg cccggcagcg    2220
gaaagagcgg catcatcaag agccgccgtga ccaagaaaga cctggtggtc agcgccaaga    2280
aagagaactg cgccgagatc atcagggacg tgaagaagat gaaggccctg gacgtgaacg    2340
cgcgcaccgt ggacagcgtg ctgctgaacg gctgcaagca ccccgtggag accctgtaca    2400
```

```
tcgacgaggc cttcgcttgc cacgccggca ccctgagggc cctgatcgcc atcatcaggc    2460
ccaagaaagc cgtgctgtgc ggcgacccca agcagtgcgg cttcttcaac atgatgtgcc    2520
tgaaggtgca cttcaaccac gagatctgca cccaggtgtt ccacaagagc atcagcaggc    2580
ggtgcaccaa gagcgtgacc agcgtcgtga gcaccctgtt ctacgacaag aaaatgagga    2640
ccaccaaccc caaggagacc aaaatcgtga tcgacaccac aggcagcacc aagcccaagc    2700
aggacgacct gatcctgacc tgcttcaggg gctgggtgaa gcagctgcag atcgactaca    2760
agggcaacga gatcatgacc gccgctgcca gccagggcct gaccaggaag ggcgtgtacg    2820
ccgtgaggta caaggtgaac gagaacccac tgtacgctcc caccagcgag cacgtgaacg    2880
tgctgctgac caggaccgag gacaggatcg tgtggaagac cctggccggc gacccctgga    2940
tcaagaccct gaccgccaag taccccggca acttcaccgc caccatcgaa gagtggcagg    3000
ccgagcacga cgccatcatg aggcacatcc tggagaggcc cgaccccacc gacgtgttcc    3060
agaacaaggc caacgtgtgc tgggccaagg ccctggtgcc cgtgctgaag accgccggca    3120
tcgacatgac cacagagcag tggaacaccg tggactactt cgagaccgac aaggcccaca    3180
gcgccgagat cgtgctgaac cagctgtgcg tgaggttctt cggcctggac ctggacagcg    3240
gcctgttcag cgcccccacc gtgccactga gcatcaggaa caaccactgg gacaacagcc    3300
ccagcccaaa catgtacggc ctgaacaagg aggtggtcag gcagctgagc aggcggtacc    3360
cacagctgcc cagggccgtg gccaccggca gggtgtacga catgaacacc ggcaccctga    3420
ggaactacga ccccaggatc aacctggtgc ccgtgaacag gcggctgccc cacgccctgg    3480
tgctgcacca caacgagcac ccacagagcg acttcagctc cttcgtgagc aagctgaaag    3540
gcaggaccgt gctggtcgtg ggcgagaagc tgagcgtgcc cggcaagatg gtggactggc    3600
tgagcgacag gcccgaggcc accttccggg ccaggctgga cctcggcatc cccggcgacg    3660
tgcccaagta cgacatcatc ttcgtgaacg tcaggacccc atacaagtac caccattacc    3720
agcagtgcga ggaccacgcc atcaagctga gcatgctgac caagaaggcc tgcctgcacc    3780
tgaaccccgg aggcacctgc gtgagcatcg gctacggcta cgccgacagg gccagcgaga    3840
gcatcattgg cgccatcgcc aggctgttca agttcagcag ggtgtgcaaa cccaagagca    3900
gcctggagga aaccgaggtg ctgttcgtgt tcatcggcta cgaccggaag gccaggaccc    3960 acaacccccta caagctgagc agcaccctga caaacatcta caccggcagc aggctgcacg    4020
aggccggctg cgcccccagc taccacgtgg tcaggggcga tatcgccacc gccaccgagg    4080
gcgtgatcat caacgctgcc aacagcaagg ccagcccggg aggcggagtg tgcggcgccc    4140
tgtacaagaa gttccccgag agcttcgacc tgcagcccat cgaggtgggc aaggccaggc    4200
tggtgaaggg cgccgctaag cacatcatcc acgccgtggg ccccaacttc aacaaggtga    4260
gcgaggtgga aggcgacaag cagctggccg aagcctacga gagcatcgcc aagatcgtga    4320
acgacaataa ctacaagagc gtggccatcc cactgctcag caccggcatc ttcagcggca    4380
acaaggacag gctgacccag agcctgaacc acctgctcac cgccctggac accaccgatg    4440
ccgacgtggc catctactgc agggacaaga agtgggagat gaccctgaag gaggccgtgg    4500
ccaggcggga ggccgtggaa gagatctgca tcagcgacga ctccagcgtg accgagcccg    4560
acgccgagct ggtgagggtg cacccccaaga gctccctggc cggcaggaag ggctacagca    4620
ccagcgacgc caagaccttc agctacctgg agggcaccaa gttccaccag gccgctaagg    4680
acatcgccga gatcaacgct atgtggcccg tggccaccga ggccaacgag caggtgtgca    4740
```

```
tgtacatcct gggcgagagc atgtccagca tcaggagcaa gtgccccgtg gaggaaagcg      4800
aggccagcac accacccagc accctgccct gcctgtgcat ccacgctatg acacccgaga      4860
gggtgcagcg gctgaaggcc agcaggcccg agcagatcac cgtgtgcagc tccttcccac      4920
tgcccaagta caggatcacc ggcgtgcaga agatccagtg cagccagccc atcctgttca      4980
gcccaaaggt gcccgcctac atccacccca ggaagtacct ggtggagacc ccacccgtgg      5040
acgagacacc cgagccaagc gccgagaacc agagcaccga gggcacaccc gagcagccac      5100
ccctgatcac cgaggacgag acaaggaccc ggaccccaga gcccatcatt atcgaggaag      5160
aggaagagga cagcatcagc ctgctgagcg acggccccac ccaccaggtg ctgcaggtgg      5220
aggccgacat ccacggccca cccagcgtgt ccagctccag ctggagcatc ccacacgcca      5280
gcgacttcga cgtggacagc ctgagcatcc tggacaccct ggagggcgcc agcgtgacct      5340
ccggcgccac cagcgccgag accaacagct acttcgccaa gagcatggag ttcctggcca      5400
ggcccgtgcc agctcccagg accgtgttca ggaacccacc ccaccagct cccaggacca      5460 ggaccccaag cctggctccc agcagggcct gcagcaggac cagcctggtg agcaccccac      5520
ccggcgtgaa cagggtgatc accagggagg aactggaggc cctgacaccc agcaggaccc      5580
ccagcaggtc cgtgagcagg actagtctgg tgtccaaccc accggcgtg aacagggtga      5640 tcaccaggga ggaattcgag gccttcgtgg cccagcaaca gagacggttc gacgccggcg      5700
cctacatctt cagcagcgac accggccagg acacctgca gcaaagagc gtgaggcaga      5760 ccgtgctgag cgaggtggtg ctggagagga ccgagctgga aatcagctac gcccccaggc      5820
tggaccagga gaaggaggaa ctgctcagga agaaactgca gctgaacccc accccagcca      5880
acaggagcag gtaccagagc aggaaggtgg agaacatgaa ggccatcacc gccaggcgga      5940
tcctgcaggg cctgggacac tacctgaagg ccgaggcaa ggtggagtgc tacaggaccc      6000 tgcacccgt gccactgtac agctccagcg tgaacagggc cttctccagc cccaaggtgg      6060
ccgtggaggc ctgcaacgct atgctgaagg agaacttccc caccgtggcc agctactgca      6120
tcatccccga gtacgacgcc tacctggaca tggtggacgg cgccagctgc tgcctggaca      6180
ccgccagctt ctgccccgcc aagctgagga gcttccccaa gaaacacagc tacctggagc      6240
ccaccatcag gagcgccgtg cccagcgcca tccagaacac cctgcagaac gtgctggccg      6300
ctgccaccaa gaggaactgc aacgtgaccc agatgaggga gctgcccgtg ctggacagcg      6360
ctgccttcaa cgtggagtgc ttcaagaaat acgcctgcaa caacgagtac tgggagacct      6420
tcaaggagaa cccatcagg ctgaccgaag agaacgtggt gaactacatc accaagctga      6480
agggccccaa ggccgctgcc ctgttcgcta agacccacaa cctgaacatg ctgcaggaca      6540
tcccaatgga caggttcgtg atggacctga gagggacgt gaaggtgaca cccggcacca      6600
agcacaccga ggagaggccc aaggtgcagg tgatccaggc cgctgaccca ctggccaccg      6660
cctacctgtg cggcatccac agggagctgg tgaggcggct gaacgccgtg ctgctgccca      6720
acatccacac cctgttcgac atgagcgccg aggacttcga cgccatcatc gccgagcact      6780
tccagcccgg cgactgcgtg ctggagaccg acatcgccag cttcgacaag agcgaggatg      6840
acgctatggc cctgaccgct ctgatgatcc tggaggacct gggcgtggac gccgagctgc      6900
tcaccctgat cgaggctgcc ttcggcgaga tcagctccat ccacctgccc accaagacca      6960
agttcaagtt cggcgctatg atgaaaagcg gaatgttcct gacactgttc gtgaacaccg      7020
tgatcaacat tgtgatcgcc agcagggtgc tgcgggagag gctgaccggc agcccctgcg      7080
ctgccttcat cggcgacgac aacatcgtga agggcgtgaa aagcgacaag ctgatggccg      7140
```

```
acaggtgcgc cacctggctg aacatggagg tgaagatcat cgacgccgtg gtgggcgaga      7200 aggccccta cttctgcggc ggattcatcc tgtgcgacag cgtgaccggc accgcctgca       7260
gggtggccga ccccctgaag aggctgttca agctgggcaa gccactggcc gctgacgatg     7320
agcacgacga tgacaggcgg agggccctgc acgaggaaag caccaggtgg aacagggtgg     7380
gcatcctgag cgagctgtgc aaggccgtgg agagcaggta cgagaccgtg ggcaccagca     7440
tcatcgtgat ggctatgacc acactggcca gctccgtcaa gagcttctcc tacctgaggg     7500
gggcccctat aactctctac ggctaacctg aatggactac gacatagtct agtccgccaa     7560
ggccgccacc atgtttgttt ttcttgtttt attgccacta gtctctagtc agtgtgttaa     7620
tcttacaacc agaactcaat taccccctgc atacactaat tctttcacac gtggtgttta     7680
ttaccctgac aaagttttca gatcctcagt tttacattca actcaggact tgttcttacc     7740 tttctttcc aatgttactt ggttccatgc tatacatgtc tctgggacca atggtactaa      7800
gaggtttgat aaccctgtcc taccatttaa tgatggtgtt tattttgctt ccactgagaa     7860
gtctaacata ataagaggct ggattttggg tactacttta gattcgaaga cccagtccct     7920
acttattgtt aataacgcta ctaatgttgt tattaaagtc tgtgaatttc aattttgtaa     7980
tgatccattt ttgggtgttt attaccacaa aaacaacaaa agttggatgg aaagtgagtt     8040
cagagtttat tctagtgcga ataattgcac ttttgaatat gtctctcagc cttttcttat     8100
ggaccttgaa ggaaaacagg gtaatttcaa aaatcttagg gaatttgtgt ttaagaatat     8160
tgatggttat tttaaaatat attctaagca cacgcctatt aatttagtgc gtgatctccc     8220
tcagggtttt tcggctttag aaccattggt agatttgcca ataggtatta acatcactag     8280
gtttcaaact ttacttgctt tacatagaag ttatttgact cctggtgatt cttcttcagg     8340
ttggacagct ggtgctgcag cttattatgt gggttatctt caacctagga cttttctatt     8400
aaaatataat gaaaatggaa ccattacaga tgctgtagac tgtgcacttg accctctctc     8460
agaaacaaag tgtacgttga atccttcac tgtagaaaaa ggaatctatc aaacttctaa    8520
ctttagagtc caaccaacag aatctattgt tagatttcct aatattacaa acttgtgccc     8580
ttttggtgaa gtttttaacg ccaccagatt tgcatctgtt tatgcttgga acaggaagag     8640
aatcagcaac tgtgttgctg attattctgt cctatataat tccgcatcat tttccacttt     8700
taagtgttat ggagtgtctc ctactaaatt aaatgatctc tgctttacta atgtctatgc     8760
agattcattt gtaattagag gtgatgaagt cagacaaatc gctccagggc aaactggaaa     8820
gattgctgat tataattata aattaccaga tgattttaca ggctgcgtta tagcttggaa     8880
ttctaacaat cttgattcta aggttggtgg taattataat tacctgtata gattgtttag     8940
gaagtctaat ctcaaacctt ttgagagaga tatttcaact gaaatctatc aggccggtag     9000
cacaccttgt aatggtgttg aaggttttaa ttgttacttt cctttacaat catatggttt     9060
ccaacccact aatggtgttg gttaccaacc atacagagta gtagtacttt cttttgaact     9120
tctacatgca ccagcaactg tttgtggacc taaaaagtct actaatttgg ttaaaaacaa     9180
atgtgtcaat ttcaacttca atggtttaac aggcacaggt gttcttactg agtctaacaa     9240
aaagtttctg cctttccaac aatttggcag agacattgct gacactactg atgctgtccg     9300
tgatccacag acacttgaga ttcttgacat tacaccatgt tcttttggtg gtgtcagtgt     9360
tataacacca ggaacaaata cttctaacca ggttgctgtt ctttatcagg atgttaactg     9420
cacagaagtc cctgttgcta ttcatgcaga tcaacttact cctacttggc gtgtttattc     9480
```

-continued

```
tacaggttct aatgtttttc aaacacgtgc aggctgttta ataggggctg aacatgtcaa   9540
caactcatat gagtgtgaca tacccattgg tgcaggtata tgcgctagtt atcagactca   9600
gactaattct cctcggcggg cacgtagtgt agctagtcaa tccatcattg cctacactat   9660
gtcacttggt gcagaaaatt cagttgctta ctctaataac tctattgcca tacccacaaa   9720
ttttactatt agtgttacca cagaaattct accagtgtct atgaccaaga catcagtaga   9780
ttgtacaatg tacatttgtg gtgattcaac tgaatgcagc aatcttttgt tgcaatatgg   9840
cagtttttgt acacaattaa accgtgcttt aactggaata gctgttgaac aagacaaaaa   9900
cacccaagaa gtttttgcac aagtcaaaca aatttacaaa acaccaccaa ttaaagattt   9960
tggtggtttt aatttttcac aaatattacc agatccatca aaaccaagca agaggtcatt  10020
tattgaagat ctacttttca acaaagtgac acttgcagat gctggcttca tcaaacaata  10080
tggtgattgc cttggtgata ttgctgctag agacctcatt tgtgcacaaa agtttaacgg  10140
ccttactgtt ttgccacctt tgctcacaga tgaaatgatt gctcaataca cttctgcact  10200
gttagcgggt acaatcactt ctggttggac ctttggtgca ggtgctgcat tacaaatacc  10260
atttgctatg caaatggctt ataggtttaa tggtattgga gttacacaga atgttctcta  10320
tgagaaccaa aaattgattg ccaaccaatt taatagtgct attggcaaaa ttcaagactc  10380
actttcttcc acagcaagtg cacttggaaa acttcaagat gtggtcaacc aaaatgcaca  10440
agctttaaac acgcttgtta aacaacttag ctccaatttt ggtgcaattt caagtgtttt  10500
aaatgatatc ctttcacgtc ttgacaaagt tgaggctgaa gtgcaaattg ataggttgat  10560
cacaggcaga cttcaaagtt tgcagacata tgtgactcaa caattaatta gagctgcaga  10620
aatcagagct tctgctaatc ttgctgctac taaaatgtca gagtgtgtac ttggacaatc  10680
aaaaagagtt gatttttgtg gaaagggcta tcatcttatg tccttccctc agtcagcacc  10740
tcatggtgta gtcttcttgc atgtgactta tgtccctgca caagaaaaga acttcacaac  10800
tgctcctgcc atttgtcatg atggaaaagc acactttcct cgtgaaggtg tctttgtttc  10860
aaatggcaca cactggtttg taacacaaag gaatttttat gaaccacaaa tcattactac  10920
agacaacaca tttgtgtctg gtaactgtga tgttgtaata ggaattgtca acaacacagt  10980
ttatgatcct ttgcaacctg aattagactc attcaaggag gagttagata aatattttaa  11040
gaatcataca tcaccagatg ttgatttagg tgacatctct ggcattaatg cttcagttgt  11100
aaacattcaa aaagaaattg accgcctcaa tgaggttgcc aagaatttaa atgaatctct  11160
catcgatctc caagaacttg gaaagtatga gcagtatata aaatggccat ggtacatttg  11220
gctaggtttt atagctggct tgattgccat agtaatggtg acaattatgc tttgctgtat  11280
gaccagttgc tgtagttgtc tcaagggctg ttgttcttgt ggatcctgct gcaaatttga  11340
tgaagacgac tctgagccag tgctcaaagg agtcaaatta cattacacat aaactcgagt  11400
atgttacgtg caaaggtgat tgtcaccccc cgaaagacca tattgtgaca caccctcagt  11460
atcacgccca aacatttaca gccgcggtgt caaaaaccgc gtggacgtgg ttaacatccc  11520
tgctgggagg atcagccgta attattataa ttggcttggt gctggctact attgtggcca  11580
tgtacgtgct gaccaaccag aaacataatt gaatacagca gcaattggca agctgcttac  11640
atagaactcg cggcgattgg catgccgcct taaaattttt attttatttt ttcttttctt  11700
ttccgaatcg gattttgttt ttaatatttc aaaaaaaaaa aaaaaaaaaa aaaaatctag  11760
aaaaaaaaaa aaaaaaaaaa aaaaaaaaaa aaaaaaaaaa aaaaaaaaaa aaaaaaaaaa  11820
aaaaaaaaaa aaaaaaaaaa aaaaaaaaaa aaaaaaaaaa                        11860
```

<210> SEQ ID NO 125
<211> LENGTH: 11860
<212> TYPE: DNA
<213> ORGANISM: Artificial sequence
<220> FEATURE:
<223> OTHER INFORMATION: Synthetic polynucleotide

<400> SEQUENCE: 125

| | | | | | |
|---|---|---|---|---|---|
| atgggcggcg | catgagagaa | gcccagacca | attacctacc | caaaatggag | aaagttcacg | 60 |
| ttgacatcga | ggaagacagc | ccattcctca | gagctttgca | gcggagcttc | ccgcagtttg | 120 |
| aggtagaagc | caagcaggtc | actgataatg | accatgctaa | tgccagagcg | ttttcgcatc | 180 |
| tggcttcaaa | actgatcgaa | acggaggtgg | acccatccga | cacgatcctt | gacattggaa | 240 |
| gtgcgcccgc | ccgcagaatg | tattctaagc | acaagtatca | ttgtatctgt | ccgatgagat | 300 |
| gtgcggaaga | tccggacaga | ttgtataagt | atgcaactaa | gctgaagaaa | aactgtaagg | 360 |
| aaataactga | taaggaattg | gacaagaaaa | tgaaggagct | ggccgccgtc | atgagcgacc | 420 |
| ctgacctgga | aactgagact | atgtgcctcc | acgacgacga | gtcgtgtcgc | tacgaagggc | 480 |
| aagtcgctgt | ttaccaggat | gtatacgccg | tcgacgcccc | caccagcctg | taccaccagg | 540 |
| ccaacaaggg | cgtgagggtg | gcctactgga | tcggcttcga | caccacaccc | ttcatgttca | 600 |
| agaacctggc | cggcgcctac | cccagctaca | gcaccaactg | gccgacgag | accgtgctga | 660 |
| ccgccaggaa | catcggcctg | tgcagcagcg | acgtgatgga | gaggagccgg | agaggcatga | 720 |
| gcatcctgag | gaagaaatac | ctgaagccca | gcaacaacgt | gctgttcagc | gtgggcagca | 780 |
| ccatctacca | cgagaagagg | gacctgctca | ggagctggca | cctgcccagc | gtgttccacc | 840 |
| tgaggggcaa | gcagaactac | acctgcaggt | gcgagaccat | cgtgagctgc | gacggctacg | 900 |
| tggtgaagag | gatcgccatc | agccccggcc | tgtacgcaa | gccagcggc | tacgccgcta | 960 |
| caatgcacag | ggagggcttc | ctgtgctgca | aggtgaccga | caccctgaac | ggcgagaggg | 1020 |
| tgagcttccc | cgtgtgcacc | tacgtgcccg | ccaccctgtg | cgaccagatg | accggcatcc | 1080 |
| tggccaccga | cgtgagcgcc | gacgacgccc | agaagctgct | cgtgggcctg | aaccagagga | 1140 |
| tcgtggtcaa | cggcaggacc | cagaggaaca | ccaacacaat | gaagaactac | ctgctgcccg | 1200 |
| tggtggccca | ggctttcgcc | aggtgggcca | aggagtacaa | ggaggaccag | gaagacgaga | 1260 |
| ggcccctggg | cctgagggac | aggcagctgg | tgatgggctg | ctgctgggcc | ttcaggcggc | 1320 |
| acaagatcac | cagcatctac | aagaggcccg | acacccagac | catcatcaag | gtgaacagcg | 1380 |
| acttccacag | cttcgtgctg | cccaggatcg | gcagcaacac | cctggagatc | ggcctgagga | 1440 |
| cccggatcag | gaagatgctg | gaggaacaca | aggagcccag | cccactgatc | accgccgagg | 1500 |
| acgtgcagga | ggccaagtgc | gctgccgacg | aggccaagga | ggtgagggag | gccgaggaac | 1560 |
| tgagggccgc | cctgccaccc | ctggctgccg | acgtggagga | acccaccctg | gaagccgacg | 1620 |
| tggacctgat | gctgcaggag | gccggcgcc | gaagcgtgga | gacacccagg | ggcctgatca | 1680 |
| aggtgaccag | ctacgacggc | gaggacaaga | tcggcagcta | cgccgtgctg | agcccacagg | 1740 |
| ccgtgctgaa | gtccgagaag | ctgagctgca | tccaccccact | ggccgagcag | gtgatcgtga | 1800 |
| tcacccacag | cggcaggaag | ggcaggtacg | ccgtggagcc | ctaccacggc | aaggtggtcg | 1860 |
| tgcccgaggg | ccacgccatc | cccgtgcagg | acttccaggc | cctgagcgag | agcgccacca | 1920 |
| tcgtgtacaa | cgagagggag | ttcgtgaaca | ggtacctgca | ccatatcgcc | acccacggcg | 1980 |
| gagccctgaa | caccgacgag | gaatactaca | agaccgtgaa | gcccagcgag | cacgacggcg | 2040 |

```
agtacctgta cgacatcgac aggaagcagt gcgtgaagaa agagctggtg accggcctgg      2100
gactgaccgg cgagctggtg gacccaccct tccacgagtt cgcctacgag agcctgagga      2160
ccagacccgc cgctccctac caggtgccca ccatcggcgt gtacggcgtg cccggcagcg      2220
gaaagagcgg catcatcaag agcgccgtga ccaagaaaga cctggtggtc agcgccaaga      2280
aagagaactg cgccgagatc atcagggacg tgaagaagat gaaaggcctg gacgtgaacg      2340
cgcgcaccgt ggacagcgtg ctgctgaacg gctgcaagca ccccgtggag acctgtaca      2400 tcgacgaggc cttcgcttgc cacgccggca ccctgagggc cctgatcgcc atcatcaggc      2460
ccaagaaagc cgtgctgtgc ggcgacccca gcagtgcgg cttcttcaac atgatgtgcc      2520
tgaaggtgca cttcaaccac gagatctgca cccaggtgtt ccacaagagc atcagcaggc      2580
ggtgcaccaa gagcgtgacc agcgtcgtga gcaccctgtt ctacgacaag aaaatgagga      2640
ccaccaaccc caaggagacc aaaatcgtga tcgacaccac aggcagcacc aagcccaagc      2700
aggacgacct gatcctgacc tgcttcaggg gctgggtgaa gcagctgcag atcgactaca      2760
agggcaacga gatcatgacc gccgctgcca gccaggcct gaccaggaag ggcgtgtacg      2820
ccgtgaggta caaggtgaac gagaacccac tgtacgctcc caccagcgag cacgtgaacg      2880
tgctgctgac caggaccgag gacaggatcg tgtggaagac cctggccggc gacccctgga      2940
tcaagaccct gaccgccaag taccccggca acttcaccgc caccatcgaa gagtggcagg      3000
ccgagcacga cgccatcatg aggcacatcc tggagaggcc cgaccccacc gacgtgttcc      3060
agaacaaggc caacgtgtgc tgggccaagg ccctggtgcc cgtgctgaag accgccggca      3120
tcgacatgac cacagagcag tggaacaccg tggactactt cgagaccgac aaggcccaca      3180
gcgccgagat cgtgctgaac cagctgtgcg tgaggttctt cggcctggac ctggacagcg      3240
gcctgttcag cgcccccacc gtgccactga gcatcaggaa caaccactgg acaacagcc      3300 ccagcccaaa catgtacggc ctgaacaagg aggtggtcag gcagctgagc aggcggtacc      3360
cacagctgcc cagggccgtg gccaccggca gggtgtacga catgaacacc ggcacccctga      3420 ggaactacga ccccaggatc aacctggtgc ccgtgaacag gcggctgccc cacgccctgg      3480
tgctgcacca caacgagcac ccacagagcg acttcagctc cttcgtgagc aagctgaaag      3540
gcaggaccgt gctggtcgtg ggcgagaagc tgagcgtgcc cggcaagatg gtggactggc      3600
tgagcgacag gcccgaggcc accttccggg ccaggctgga cctcggcatc cccgcgacg      3660 tgcccaagta cgacatcatc ttcgtgaacg tcaggacccc atacaagtac caccattacc      3720
agcagtgcga ggaccacgcc atcaagctga gcatgctgac caagaaggcc tgcctgcacc      3780
tgaaccccgg aggcacctgc gtgagcatcg gctacggcta cgccgacagg gccagcgaga      3840
gcatcattgg cgccatcgcc aggctgttca agttcagcag ggtgtgcaaa cccaagagca      3900
gcctggagga aaccgaggtg ctgttcgtgt tcatcggcta cgaccggaag gccaggaccc      3960 acaacccctta caagctgagc agcacctga caaacatcta caccggcagc aggctgcacg      4020
aggccggctg cgcccccagc taccacgtgg tcagggcga tatcgccacc gccaccgagg      4080
gcgtgatcat caacgctgcc aacagcaagg gccagcccgg aggcggagtg tgcggcgccc      4140
tgtacaagaa gttccccgag agcttcgacc tgcagcccat cgaggtgggc aaggccaggc      4200
tggtgaaggg cgccgctaag cacatcatcc acgccgtggg ccccaacttc aacaaggtga      4260
gcgaggtgga aggcgacaag cagctggccg aagcctacga gagcatcgcc aagatcgtga      4320
acgacaataa ctacaagagc gtggccatcc cactgctcag caccggcatc ttcagcggca      4380
acaaggacag gctgacccag agcctgaacc acctgctcac cgccctggac accaccgatg      4440
```

-continued

```
ccgacgtggc catctactgc agggacaaga agtgggagat gaccctgaag gaggccgtgg    4500
ccaggcggga ggccgtggaa gagatctgca tcagcgacga ctccagcgtg accgagcccg    4560
acgccgagct ggtgagggtg caccccaaga gctccctggc cggcaggaag ggctacagca    4620
ccagcgacgg caagaccttc agctacctgg agggcaccaa gttccaccag ccgctaagg     4680
acatcgccga gatcaacgct atgtggcccg tggccaccga ggccaacgag caggtgtgca    4740
tgtacatcct gggcgagagc atgtccagca tcaggagcaa gtgccccgtg gagaaagcg     4800
aggccagcac accacccagc accctgccct gcctgtgcat ccacgctatg cacccgaga     4860
gggtgcagcg gctgaaggcc agcaggcccg agcagatcac cgtgtgcagc tccttcccac    4920
tgcccaagta caggatcacc ggcgtgcaga agatccagtg cagccagccc atcctgttca    4980
gcccaaaggt gcccgcctac atccacccca ggaagtacct ggtggagacc ccacccgtgg    5040
acgagacacc cgagccaagc gccgagaacc agagcaccga gggcacaccc gagcagccac    5100
ccctgatcac cgaggacgag acaaggaccc ggaccccaga gcccatcatt atcgaggaag    5160
aggaagagga cagcatcagc ctgctgagcg acggcccac ccaccaggtg ctgcaggtgg     5220
aggccgacat ccacggccca cccagcgtgt ccagctccag ctggagcatc ccacacgcca    5280
gcgacttcga cgtggacagc ctgagcatcc tggacaccct ggagggcgcc agcgtgacct    5340
ccggcgccac cagcgccgag accaacagct acttcgccaa gagcatggag ttcctggcca    5400
ggcccgtgcc agctcccagg accgtgttca ggaacccacc ccacccagct cccaggacca    5460
ggaccccaag cctggctccc agcagggcct gcagcaggac cagcctggtg agcacccac     5520
ccggcgtgaa cagggtgatc accagggagg aactggaggc cctgacaccc agcaggaccc    5580
ccagcaggtc cgtgagcagg actagtctgg tgtccaaccc accggcgtg aacagggtga     5640
tcaccaggga ggaattcgag gccttcgtgg cccagcaaca gagacggttc gacgccggcg    5700
cctacatctt cagcagcgac accggccagg gacacctgca gcaaaagagc gtgaggcaga    5760
ccgtgctgag cgaggtggtg ctggagagga ccgagctgga aatcagctac gcccccaggc    5820
tggaccagga gaaggaggaa ctgctcagga gaaactgca gctgaacccc accccagcca    5880
acaggagcag gtaccagagc aggaaggtgg agaacatgaa ggccatcacc gccaggcgga    5940
tcctgcaggg cctggacac tacctgaagg ccgagggcaa ggtggagtgc tacaggaccc     6000
tgcaccccgt gccactgtac agctccagcg tgaacaggcc cttctccagc ccaaggtgg     6060
ccgtggaggc ctgcaacgct atgctgaagg agaacttccc caccgtggcc agctactgca    6120
tcatccccga gtacgacgcc tacctggaca tggtggacgg cgccagctgc tgcctggaca    6180
ccgccagctt ctgccccgcc aagctgagga gcttccccaa gaacacagc tacctggagc     6240
ccaccatcag gagcgccgtg cccagcgcca tccagaacac cctgcagaac gtgctggcg     6300
ctgccaccaa gaggaactgc aacgtgaccc agatgaggga gctgcccgtg ctggacagcg    6360
ctgccttcaa cgtggagtgc ttcaagaaat acgcctgcaa caacgagtac tgggagacct    6420
tcaaggagaa ccccatcagg ctgaccgaag agaacgtggt gaactacatc accaagctga    6480
agggccccaa ggccgctgcc ctgttcgcta gacccacaa cctgaacatg ctgcaggaca    6540
tcccaatgga caggttcgtg atggacctga gagggacgt gaaggtgaca cccggcacca    6600
agcacaccga ggagaggccc aaggtgcagg tgatccaggc cgctgaccca ctggccaccg    6660
cctacctgtg cggcatccac agggagctgg tgaggcggct gaacgccgtg ctgctgccca    6720
acatccacac cctgttcgac atgagcgccg aggacttcga cgccatcatc gccgagcact    6780
```

```
tccagcccgg cgactgcgtg ctggagaccg acatcgccag cttcgacaag agcgaggatg    6840
acgctatggc cctgaccgct ctgatgatcc tggaggacct gggcgtggac gccgagctgc    6900
tcaccctgat cgaggctgcc ttcggcgaga tcagctccat ccacctgccc accaagacca    6960
agttcaagtt cggcgctatg atgaaaagcg gaatgttcct gaccctgttc gtgaacaccg    7020
tgatcaacat tgtgatcgcc agcagggtgc tgcgggagag gctgaccggc agccctgcg    7080
ctgccttcat cggcgacgac aacatcgtga agggcgtgaa aagcgacaag ctgatggccg    7140
acaggtgcgc cacctggctg aacatggagg tgaagatcat cgacgccgtg gtgggcgaga    7200
aggcccccta cttctgcggc ggattcatcc tgtgcgacag cgtgaccggc accgcctgca    7260
gggtggccga ccccctgaag aggctgttca agctgggcaa gccactggcc gctgacgatg    7320
agcacgacga tgacaggcgg agggccctgc acgaggaaag caccaggtgg aacagggtgg    7380
gcatcctgag cgagctgtgc aaggccgtgg agagcaggta cgagaccgtg ggcaccagca    7440
tcatcgtgat ggctatgacc acactggcca gctccgtcaa gagcttctcc tacctgaggg    7500
gggcccctat aactctctac ggctaacctg aatggactac gacatagtct agtccgccaa    7560
ggccgccacc atgttcgtct tcctggtcct gctgcctctg gtctcctcac agtgcgtcaa    7620
tctgacaact cggactcagc tgccacctgc ttatactaat agcttcacca gaggcgtgta    7680
ctatcctgac aaggtgttta aagctccgt gctgcactct acacaggatc tgtttctgcc    7740
attctttagc aacgtgacct ggttccacgc catccacgtg agcggcacca atggcacaaa    7800
gcggttcgac aatcccgtgc tgccttttaa cgatggcgtg tacttcgcct ctaccgagaa    7860
gtccaacatc atcagaggct ggatctttgg caccacactg gactccaaga cacagtctct    7920
gctgatcgtg aacaatgcca ccaacgtggt catcaaggtg tgcgagttcc agtttgtaa    7980
tgatccctcc ctgggcgtgt actatcacaa gaacaataag agctggatgg agtccgagtt    8040
tagagtgtat tctagcgcca caactgcac atttgagtac gtgagccagc ctttcctgat    8100
ggacctggag ggcaagcagg gcaatttcaa gaacctgagg gagttcgtgt ttaagaatat    8160
cgacggctac ttcaaaatct actctaagca cacccccatc aacctggtgc gcgacctgcc    8220
tcagggcttc agcgccctgg agcccctggt ggatctgcct atcggcatca acatcacccg    8280
gtttcagaca ctgctggccc tgcacagaag ctacctgaca cccggcgact cctctagcgg    8340
atggaccgcc ggcgctgccg cctactatgt gggctacctc cagcccgga ccttcctgct    8400
gaagtacaac gagaatggca ccatcacaga cgcagtggat tgcgccctgg acccctgag    8460
cgagacaaag tgtacactga agtcctttac cgtggagaag gcatctatc agacatccaa    8520
tttcagggtg cagccaaccg agtctatcgt gcgctttcct aatatcacaa acctgtgccc    8580
atttggcgag gtgttcaacg caacccgctt cgccagcgtg tacgcctgga ataggaagcg    8640
gatcagcaac tgcgtggccg actatagcgt gctgtacaac tccgcctctt tcagcacctt    8700
taagtgctat ggcgtgtccc ccacaaagct gaatgacctg tgctttacca acgtctacgc    8760
cgattctttc gtgatcaggg gcgacgaggt gcgccagatc gcccccggcc agacaggcaa    8820
gatcgcagac tacaattata agctgccaga cgatttcacc ggctgcgtga tcgcctggaa    8880
cagcaacaat ctggattcca agtgggcgg caactacat tatctgtacc ggctgtttag    8940
aaagagcaat ctgaagccct tcgagaggga catctctaca gaaatctacc aggccggcag    9000
caccccttgc aatggcgtgg agggctttaa ctgttatttc ccactccagt cctacggctt    9060
ccagcccaca aacggcgtgg gctatcagcc ttaccgcgtg gtggtgctga gctttgagct    9120
gctgcacgcc ccagcaacag tgtgcggccc caagaagtcc accaatctgg tgaagaacaa    9180
```

-continued

```
gtgcgtgaac ttcaacttca acggcctgac cggcacaggc gtgctgaccg agtccaacaa    9240
gaagttcctg ccatttcagc agttcggcag ggacatcgca gataccacag acgccgtgcg    9300
cgacccacag accctggaga tcctggacat cacaccctgc tctttcggcg gcgtgagcgt    9360
gatcacaccc ggcaccaata caagcaacca ggtggccgtg ctgtatcagg acgtgaattg    9420
taccgaggtg cccgtggcta tccacgccga tcagctgacc ccaacatggc gggtgtacag    9480
caccggctcc aacgtcttcc agacaagagc cggatgcctg atcggagcag agcacgtgaa    9540
caattcctat gagtgcgaca tcccaatcgg cgccggcatc tgtgcctctt accagaccca    9600
gacaaactct cccagacggg cccggagcgt ggcctcccag tctatcatcg cctataccat    9660
gtccctgggc gccgagaaca gcgtggccta ctctaacaat agcatcgcca tcccaaccaa    9720
cttcacaatc tctgtgacca cagagatcct gcccgtgtcc atgaccaaga catctgtgga    9780
ctgcacaatg tatatctgtg gcgattctac cgagtgcagc aacctgctgc tccagtacgg    9840
cagcttttgt acccagctga atagagccct gacaggcatc gccgtggagc aggataagaa    9900
cacacaggag gtgttcgccc aggtgaagca aatctacaag accccccta tcaaggactt    9960 tggcggcttc aatttttccc agatcctgcc tgatccatcc aagccttcta gcggagcttt   10020
tatcgaggac ctgctgttca caaggtgac cctggccgat gccggcttca tcaagcagta    10080
tggcgattgc ctgggcgaca tcgcagccag ggacctgatc tgcgcccaga gtttaatgg    10140 cctgaccgtg ctgccacccc tgctgacaga tgagatgatc gcacagtaca agcgccct    10200 gctggccggc accatcacat ccggatggac cttcggcgca ggagccgccc tccagatccc   10260
ctttgccatg cagatggcct ataggttcaa cggcatcggc gtgacccaga atgtgctgta   10320
cgagaaccag aagctgatcg ccaatcagtt taactccgcc atcggcaaga tccaggacag   10380
cctgtcctct acagccagcg ccctgggcaa gctccaggat gtggtgaatc agaacgccca   10440
ggccctgaat accctggtga agcagctgag cagcaacttc ggcgccatct ctagcgtgct   10500
gaatgacatc ctgagccggc tggacaaggt ggaggcagag gtgcagatcg accggctgat   10560
caccggccgg ctccagagcc tccagaccta tgtgacacag cagctgatca gggccgccga   10620
gatcagggcc agcgccaatc tggcagcaac caagatgtcc gagtgcgtgc tgggccagtc   10680
taagagagtg gacttttgtg gcaagggcta tcacctgatg tccttccctc agtctgcccc   10740
acacggcgtg gtgtttctgc acgtgaccta cgtgccgcc caggagaaga acttcaccac   10800
agcccctgcc atctgccacg atggcaaggc ccactttcca agggagggcg tgttcgtgtc   10860
caacggcacc cactggtttg tgacacagcg caatttctac gagccccaga tcatcaccac   10920
agacaacacc ttcgtgagcg gcaactgtga cgtggtcatc ggcatcgtga acaataccgt   10980
gtatgatcca ctccagcccg agctggacag ctttaaggag gagctggata gtatttcaa    11040 gaatcacacc tcccctgacg tggatctggg cgacatcagc ggcatcaatg cctccgtggt   11100
gaacatccag aaggagatcg accgcctgaa cgaggtggct aagaatctga acgagagcct   11160
gatcgacctc caggagctgg gcaagtatga gcagtacatc aagtggccct ggtacatctg   11220
gctgggcttc atcgccggcc tgatcgccat cgtgatggtg accatcatgc tgtgctgtat   11280
gacatcctgc tgttcttgcc tgaagggctg ctgtagctgt ggctcctgct gtaagtttga    11340
cgaggatgac tctgaacctg tgctgaaggg cgtgaagctg cattacacct aaactcgagt   11400
atgttacgtg caaaggtgat tgtcacccc cgaaagacca tattgtgaca caccctcagt    11460
atcacgccca acatttaca gccgcggtgt caaaaaccgc gtggacgtgg ttaacatccc    11520
```
tgctgggagg atcagccgta attattataa ttggcttggt gctggctact attgtggcca 11580
tgtacgtgct gaccaaccag aaacataatt gaatacagca gcaattggca agctgcttac 11640
atagaactcg cggcgattgg catgccgcct taaaattttt attttatttt ttcttttctt 11700
ttccgaatcg gattttgttt ttaatatttc aaaaaaaaaa aaaaaaaaaa aaaaatctag 11760
aaaaaaaaaa aaaaaaaaaa aaaaaaaaaa aaaaaaaaaa aaaaaaaaaa aaaaaaaaaa 11820
aaaaaaaaaa aaaaaaaaaa aaaaaaaaaa aaaaaaaaaa 11860

<210> SEQ ID NO 126
<211> LENGTH: 4238
<212> TYPE: DNA
<213> ORGANISM: Artificial sequence
<220> FEATURE:
<223> OTHER INFORMATION: Synthetic polynucleotide

<400> SEQUENCE: 126
aggaaactta agtcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gccaccatgt tcgtcttcct ggtcctgctg cctctggtct 180
cctcacagtg cgtcaatctg acaactcgga ctcagctgcc acctgcttat actaatagct 240
tcaccagagg cgtgtactat cctgacaagg tgtttagaag ctccgtgctg cactctacac 300
aggatctgtt tctgccattc tttagcaacg tgacctggtt ccacgccatc cacgtgagcg 360
gcaccaatgg cacaaagcgg ttcgacaatc ccgtgctgcc ttttaacgat ggcgtgtact 420
tcgcctctac cgagaagtcc aacatcatca gaggctggat ctttggcacc acactggact 480
ccaagacaca gtctctgctg atcgtgaaca atgccaccaa cgtggtcatc aaggtgtgcg 540
agttccagtt ttgtaatgat cccttcctgg gcgtgtacta tcacaagaac aataagagct 600
ggatggagtc cgagtttaga gtgtattcta gcgccaacaa ctgcacattt gagtacgtga 660
gccagccttt cctgatggac ctggagggca agcagggcaa tttcaagaac ctgagggagt 720
tcgtgtttaa gaatatcgac ggctacttca aaatctactc taagcacacc cccatcaacc 780
tggtgcgcga cctgcctcag ggcttcagcg ccctggagcc cctggtggat ctgcctatcg 840
gcatcaacat cacccggttt cagacactgc tggccctgca cagaagctac ctgacacccg 900
gcgactcctc tagcggatgg accgccggcg ctgccgccta ctatgtgggc tacctccagc 960
cccggacctt cctgctgaag tacaacgaga atggcaccat cacagacgca gtggattgcg 1020
ccctggaccc cctgagcgag acaaagtgta cactgaagtc ctttaccgtg gagaagggca 1080
tctatcagac atccaatttc agggtgcagc caaccgagtc tatcgtgcgc tttcctaata 1140
tcacaaacct gtgcccattt ggcgaggtgt tcaacgcaac ccgcttcgcc agcgtgtacg 1200
cctggaatag gaagcggatc agcaactgcg tggccgacta tagcgtgctg tacaactccg 1260
cctctttcag cacctttaag tgctatggcg tgtcccccac aaagctgaat gacctgtgct 1320
ttaccaacgt ctacgccgat tctttcgtga tcaggggcga cgaggtgcgc cagatcgccc 1380
ccggccagac aggcaagatc gcagactaca attataagct gccagacgat ttcaccggct 1440
gcgtgatcgc ctggaacagc aacaatctgg attccaaagt gggcggcaac tacaattatc 1500
tgtaccggct gtttagaaag agcaatctga agcccttcga gagggacatc tctacagaaa 1560
tctaccaggc cggcagcacc ccttgcaatg gcgtggaggg ctttaactgt tatttcccac 1620
tccagtccta cggcttccag cccacaaacg gcgtgggcta tcagccttac cgcgtggtgg 1680
tgctgagctt tgagctgctg cacgccccag caacagtgtg cggccccaag aagtccacca 1740

```
atctggtgaa gaacaagtgc gtgaacttca acttcaacgg cctgaccggc acaggcgtgc      1800
tgaccgagtc caacaagaag ttcctgccat ttcagcagtt cggcagggac atcgcagata      1860
ccacagacgc cgtgcgcgac ccacagaccc tggagatcct ggacatcaca ccctgctctt      1920
tcggcggcgt gagcgtgatc acacccggca ccaatacaag caaccaggtg gccgtgctgt      1980
atcaggacgt gaattgtacc gaggtgcccg tggctatcca cgccgatcag ctgaccccaa      2040
catggcgggt gtacagcacc ggctccaacg tcttccagac aagagccgga tgcctgatcg      2100
gagcagagca cgtgaacaat tcctatgagt gcgacatccc aatcggcgcc ggcatctgtg      2160
cctcttacca gacccagaca aactctccca gacgggcccg gagcgtggcc tcccagtcta      2220
tcatcgccta taccatgtcc ctgggcgccg agaacagcgt ggcctactct aacaatagca      2280
tcgccatccc aaccaacttc acaatctctg tgaccacaga gatcctgccc gtgtccatga      2340
ccaagacatc tgtggactgc acaatgtata tctgtggcga ttctaccgag tgcagcaacc      2400
tgctgctcca gtacggcagc ttttgtaccc agctgaatag agccctgaca ggcatcgccg      2460
tggagcagga taagaacaca caggaggtgt tcgcccaggt gaagcaaatc tacaagaccc      2520
cccctatcaa ggactttggc ggcttcaatt ttccccagat cctgcctgat ccatccaagc      2580
cttctaagcg gagctttatc gaggacctgc tgttcaacaa ggtgaccctg ccgatgccg      2640 gcttcatcaa gcagtatggc gattgcctgg gcgacatcgc agccagggac ctgatctgcg      2700
cccagaagtt taatggcctg accgtgctgc cacccctgct gacagatgag atgatcgcac      2760
agtacacaag cgccctgctg gccggcacca tcacatccgg atggaccttc ggcgcaggag      2820 ccgcccctcca gatccccttt gccatgcaga tggcctatag gttcaacggc atcggcgtga      2880
cccagaatgt gctgtacgag aaccagaagc tgatcgccaa tcagtttaac tccgccatcg      2940
gcaagatcca ggacagcctg tcctctacag ccagcgccct gggcaagctc caggatgtgg      3000
tgaatcagaa cgcccaggcc ctgaataccc tggtgaagca gctgagcagc aacttcggcg      3060
ccatctctag cgtgctgaat gacatcctga gccggctgga caaggtggag gcagaggtgc      3120
agatcgaccg gctgatcacc ggccggctcc agagcctcca gacctatgtg acacagcagc      3180
tgatcagggc cgccgagatc agggccagcg ccaatctggc agcaaccaag atgtccgagt      3240
gcgtgctggg ccagtctaag agagtggact tttgtggcaa gggctatcac ctgatgtcct      3300
tccctcagtc tgccccacac ggcgtggtgt ttctgcacgt gacctacgtg cccgcccagg      3360
agaagaactt caccacagcc cctgccatct gccacgatgg caaggcccac tttccaaggg      3420
agggcgtgtt cgtgtccaac ggcacccact ggtttgtgac acagcgcaat ttctacgagc      3480
cccagatcat caccacagac aacaccttcg tgagcggcaa ctgtgacgtg gtcatcggca      3540
tcgtgaacaa taccgtgtat gatccactcc agcccgagct ggacagcttt aaggaggagc      3600
tggataagta tttcaagaat cacacctccc ctgacgtgga tctgggcgac atcagcggca      3660
tcaatgcctc cgtggtgaac atccagaagg agatcgaccg cctgaacgag gtggctaaga      3720
atctgaacga gagcctgatc gacctccagg agctgggcaa gtatgagcag tacatcaagt      3780
ggccctggta catctggctg ggcttcatcg ccggcctgat cgccatcgtg atggtgacca      3840
tcatgctgtg ctgtatgaca tcctgctgtt cttgcctgaa gggctgctgt agctgtggct      3900
cctgctgtaa gtttgacgag gatgactctg aacctgtgct gaagggcgtg aagctgcatt      3960
acacctaaac tcgagctagt gactgactag gatctggtta ccactaaacc agcctcaaga      4020
acacccgaat ggagtctcta agctacataa taccaactta cacttacaaa atgttgtccc      4080
```

```
ccaaaatgta gccattcgta tctgctccta ataaaagaa agtttcttca cattctagaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaa                           4238
```

<210> SEQ ID NO 127
<211> LENGTH: 10508
<212> TYPE: DNA
<213> ORGANISM: Artificial sequence
<220> FEATURE:
<223> OTHER INFORMATION: Synthetic polynucleotide

<400> SEQUENCE: 127

```
atgggcggcg catgagagaa gcccagacca attacctacc caaaatggag aaagttcacg      60
ttgacatcga ggaagacagc ccattcctca gagctttgca gcggagcttc ccgcagtttg     120
aggtagaagc caagcaggtc actgataatg accatgctaa tgccagagcg ttttcgcatc     180
tggcttcaaa actgatcgaa acggaggtgg acccatccga cacgatcctt gacattggaa     240
gtgcgcccgc ccgcagaatg tattctaagc acaagtatca ttgtatctgt ccgatgagat     300
gtgcggaaga tccggacaga ttgtataagt atgcaactaa gctgaagaaa aactgtaagg     360
aaataactga taaggaattg acaagaaaa tgaaggagct ggccgccgtc atgagcgacc     420
ctgacctgga aactgagact atgtgcctcc acgacgacga gtcgtgtcgc tacgaagggc     480
aagtcgctgt ttaccaggat gtatacgccg tcgacgccc caccagcctg taccaccagg     540
ccaacaaggg cgtgagggtg gcctactgga tcggcttcga caccacaccc ttcatgttca     600
agaacctggc cggcgcctac cccagctaca gcaccaactg ggccgacgag accgtgctga     660
ccgccaggaa catcggcctg tgcagcagcg acgtgatgga ggagccgg agaggcatga     720 gcatcctgag gaagaaatac ctgaagccca gcaacaacgt gctgttcagc gtgggcagca     780
ccatctacca cgagaagagg gacctgctca ggagctggca cctgcccagc gtgttccacc     840
tgaggggcaa gcagaactac acctgcaggt gcgagaccat cgtgagctgc gacggctacg     900
tggtgaagag gatcgccatc agccccggcc tgtacggcaa gccagcggc tacgccgcta     960 caatgcacag ggagggcttc ctgtgctgca aggtgaccga caccctgaac ggcgagaggg    1020
tgagcttccc cgtgtgcacc tacgtgcccg ccaccctgtg cgaccagatg accggcatcc    1080
tggccaccga cgtgagcgcc gacgacgccc agaagctgct cgtgggcctg aaccagagga    1140
tcgtggtcaa cggcaggacc cagaggaaca ccaacacaat gaagaactac ctgctgccg    1200 tggtggccca ggctttcgcc aggtgggcca aggagtacaa ggaggaccag gaagacgaga    1260 ggccctgg cctgagggac aggcagctgg tgatgggctg ctgctgggcc ttcaggcggc    1320
acaagatcac cagcatctac aagaggcccg cacccagac catcatcaag gtgaacagcg    1380
acttccacag cttcgtgctg cccaggatcg gcagcaacac cctggagatc ggcctgagga    1440
cccggatcag gaagatgctg gaggaacaca aggagcccag cccactgatc accgccgagg    1500
acgtgcagga ggccaagtgc gctgccgacg aggccaagga ggtgagggag gccgaggaac    1560
tgagggccgc cctgccaccc ctggctgccg acgtggagga acccaccctg aagccgacg    1620 tggacctgat gctgcaggag gccggcgcc gaagcgtgga cacccagg gcctgatca    1680 aggtgaccag ctacgacggc gaggacaaga tcggcagcta cgccgtgctg agcccacagg    1740
ccgtgctgaa gtccgagaag ctgagctgca tccaccccact ggccgagcag gtgatcgtga    1800 tcacccacg cggcaggaag ggcaggtacg ccgtggagcc ctaccacggc aaggtggtcg    1860
tgcccgaggg ccacgccatc cccgtgcagg acttccaggc cctgagcgag agcgccacca    1920
```

```
tcgtgtacaa cgagagggag ttcgtgaaca ggtacctgca ccatatcgcc acccacggcg    1980
gagccctgaa caccgacgag gaatactaca agaccgtgaa gcccagcgag cacgacggcg    2040
agtacctgta cgacatcgac aggaagcagt gcgtgaagaa agagctggtg accggcctgg    2100
gactgaccgg cgagctggtg gacccaccct tccacgagtt cgcctacgag agcctgagga    2160
ccagacccgc cgctccctac caggtgccca ccatcggcgt gtacggcgtg cccggcagcg    2220
gaaagagcgc catcatcaag agcgccgtga ccaagaaaga cctggtggtc agcgccaaga    2280
aagagaactg cgccgagatc atcagggacg tgaagaagat gaaaggcctg acgtgaacg    2340 cgcgcaccgt ggacagcgtg ctgctgaacg gctgcaagca ccccgtggag accctgtaca    2400
tcgacgaggc cttcgcttgc cacgccggca ccctgagggc cctgatcgcc atcatcaggc    2460
ccaagaaagc cgtgctgtgc ggcgacccca agcagtgcgg cttcttcaac atgatgtgcc    2520
tgaaggtgca cttcaaccac gagatctgca cccaggtgtt ccacaagagc atcagcaggc    2580
ggtgcaccaa gagcgtgacc agcgtcgtga gcaccctgtt ctacgacaag aaaatgagga    2640
ccaccaaccc caaggagacc aaaatcgtga tcgacaccac aggcagcacc aagcccaagc    2700
aggacgacct gatcctgacc tgcttcaggg gctgggtgaa gcagctgcag atcgactaca    2760
agggcaacga gatcatgacc gccgctgcca gccagggcct gaccaggaag ggcgtgtacg    2820
ccgtgaggta caaggtgaac gagaacccac tgtacgctcc caccagcgag cacgtgaacg    2880
tgctgctgac caggaccgag gacaggatcg tgtggaagac cctggccggc gacccctgga    2940
tcaagaccct gaccgccaag taccccggca cttcaccgc caccatcgaa gagtggcagg    3000
ccgagcacga cgccatcatg aggcacatcc tggagaggcc cgaccccacc gacgtgttcc    3060
agaacaaggc caacgtgtgc tgggccaagg ccctggtgcc cgtgctgaag accgccggca    3120
tcgacatgac cacagagcag tggaacaccg tggactactt cgagaccgac aaggcccaca    3180
gcgccgagat cgtgctgaac cagctgtgcg tgaggttctt cggcctggac ctggacagcg    3240
gcctgttcag cgccccacc gtgccactga gcatcaggaa caaccactgg gacaacagcc    3300
ccagcccaaa catgtacggc ctgaacaagg aggtggtcag gcagctgagc aggcggtacc    3360
cacagctgcc cagggccgtg gccaccggca gggtgtacga catgaacacc ggcacccctga    3420 ggaactacga ccccaggatc aacctggtgc ccgtgaacag gcggctgccc cacgccctgg    3480
tgctgcacca caacgagcac ccacagagcg acttcagctc cttcgtgagc aagctgaaag    3540
gcaggaccgt gctggtcgtg ggcgagaagc tgagcgtgcc cggcaagatg gtggactggc    3600
tgagcgacag gcccgaggcc accttccggg ccaggctgga cctcggcatc cccggcgacg    3660
tgcccaagta cgacatcatc ttcgtgaacg tcaggacccc atacaagtac caccattacc    3720
agcagtgcga ggaccacgcc atcaagctga gcatgctgac caagaaggcc tgcctgcacc    3780
tgaaccccgg aggcacctgc gtgagcatcg gctacggcta cgccgacagg gccagcgaga    3840
gcatcattgg cgccatcgcc aggctgttca agttcagcag ggtgtgcaaa cccaagcaga    3900
gcctggagga aaccgaggtg ctgttcgtgt tcatcggcta cgaccggaag gccaggaccc    3960 acaacccta caagctgagc agcacccctga caaacatcta caccggcagc aggctgcacg    4020
aggccggctg cgcccccagc taccacgtgg tcaggggcga tatcgccacc gccaccgagg    4080
gcgtgatcat caacgctgcc aacagcaagg gccagcccgg aggcggagtg tgcggcgccc    4140
tgtacaagaa gttccccgag agcttcgacc tgcagcccat cgaggtgggc aaggccaggc    4200
tggtgaaggg cgccgctaag cacatcatcc acgccgtggg ccccaacttc aacaaggtga    4260
```

-continued

```
gcgaggtgga aggcgacaag cagctggccg aagcctacga gagcatcgcc aagatcgtga    4320
acgacaataa ctacaagagc gtggccatcc cactgctcag caccggcatc ttcagcggca    4380
acaaggacag gctgacccag agcctgaacc acctgctcac cgccctggac accaccgatg    4440
ccgacgtggc catctactgc agggacaaga agtgggagat gaccctgaag gaggccgtgg    4500
ccaggcggga ggccgtggaa gagatctgca tcagcgacga ctccagcgtg accgagcccg    4560
acgccgagct ggtgagggtg caccccaaga gctccctggc cggcaggaag ggctacagca    4620
ccagcgacgg caagaccttc agctacctgg agggcaccaa gttccaccag gccgctaagg    4680
acatcgccga gatcaacgct atgtggcccg tggccaccga ggccaacgag caggtgtgca    4740
tgtacatcct gggcgagagc atgtccagca tcaggagcaa gtgccccgtg gaggaaagcg    4800
aggccagcac accacccagc accctgccct gcctgtgcat ccacgctatg cacccgaga    4860 gggtgcagcg gctgaaggcc agcaggcccg agcagatcac cgtgtgcagc tccttcccac    4920
tgcccaagta caggatcacc ggcgtgcaga agatccagtg cagccagccc atcctgttca    4980
gcccaaaggt gcccgcctac atccacccca ggaagtacct ggtggagacc ccaccgtgg    5040 acgagacacc cgagccaagc gccgagaacc agagcaccga gggcacaccc gagcagccac    5100
ccctgatcac cgaggacgag acaaggaccc ggaccccaga gcccatcatt atcgaggaag    5160
aggaagagga cagcatcagc ctgctgagcg acggccccac ccaccaggtg ctgcaggtgg    5220
aggccgacat ccacggccca cccagcgtgt ccagctccag ctggagcatc ccacacgcca    5280
gcgacttcga cgtggacagc ctgagcatcc tggacaccct ggagggcgcc agcgtgacct    5340
ccggcgccac cagcgccgag accaacagct acttcgccaa gagcatggag ttcctggcca    5400
ggcccgtgcc agctcccagg accgtgttca ggaacccacc ccacccagct cccaggacca    5460
ggaccccaag cctggctccc agcagggcct gcagcaggac cagcctggtg agcacccac    5520 ccggcgtgaa cagggtgatc accagggagg aactggaggc cctgacaccc agcaggaccc    5580
ccagcaggtc cgtgagcagg actagtctgg tgtccaaccc accggcgtg aacagggtga    5640 tcaccaggga ggaattcgag gccttcgtgg cccagcaaca gagacggttc gacgccggcg    5700
cctacatctt cagcagcgac accggccagg acacctgca gcaaaagagc gtgaggcaga    5760
ccgtgctgag cgaggtggtg ctggagagga ccgagctgga aatcagctac gccccccaggc    5820 tggaccagga gaaggaggaa ctgctcagga agaaactgca gctgaacccc accccagcca    5880
acaggagcag gtaccagagc aggaaggtgg agaacatgaa ggccatcacc gccaggcgga    5940
tcctgcaggg cctgggacac tacctgaagg ccgaggcaa ggtggagtgc tacaggaccc    6000
tgcaccccgt gccactgtac agctccagcg tgaacagggc cttctccagc ccaaggtgg    6060 ccgtggaggc ctgcaacgct atgctgaagg agaacttccc caccgtggcc agctactgca    6120
tcatccccga gtacgacgcc tacctggaca tggtggacgg cgccagctgc tgcctggaca    6180 ccgcagctt ctgccccgcc aagctgagga gcttccccaa gaacacagc tacctggagc    6240 ccaccatcag gagcgccgtg cccagcgcca tccagaacac cctgcagaac gtgctggcg    6300 ctgccaccaa gaggaactgc aacgtgaccc agatgaggga gctgcccgtg ctggacagcg    6360
ctgccttcaa cgtggagtgc ttcaagaaat acgcctgcaa caacgagtac tgggagacct    6420
tcaaggagaa ccccatcagg ctgaccgaag agaacgtggt gaactacatc accaagctga    6480
agggccccaa ggccgctgcc ctgttcgcta agacccacaa cctgaacatg ctgcaggaca    6540
tcccaatgga caggttcgtg atggacctga gagggacgt gaaggtgaca cccggccacca    6600 agcacaccga ggagaggccc aaggtgcagg tgatccaggc cgctgaccca ctggccaccg    6660
```

```
cctacctgtg cggcatccac agggagctgg tgaggcggct gaacgccgtg ctgctgccca    6720
acatccacac cctgttcgac atgagcgccg aggacttcga cgccatcatc gccgagcact    6780
tccagcccgg cgactgcgtg ctggagaccg acatcgccag cttcgacaag agcgaggatg    6840
acgctatggc cctgaccgct ctgatgatcc tggaggacct gggcgtggac gccgagctgc    6900
tcaccctgat cgaggctgcc ttcggcgaga tcagctccat ccacctgccc accaagacca    6960
agttcaagtt cggcgctatg atgaaaagcg gaatgttcct gaccctgttc gtgaacaccg    7020
tgatcaacat tgtgatcgcc agcagggtgc tgcgggagag gctgaccggc agccctgcg    7080 ctgccttcat cggcgacgac aacatcgtga agggcgtgaa aagcgacaag ctgatggccg    7140
acaggtgcgc cacctggctg aacatggagg tgaagatcat cgacgccgtg gtgggcgaga    7200
aggcccccta cttctgcggc ggattcatcc tgtgcgacag cgtgaccggc accgcctgca    7260
gggtggccga cccctgaag aggctgttca agctgggcaa gccactggcc gctgacgatg    7320
agcacgacga tgacaggcgg aggggccctgc acgaggaaag caccaggtgg aacagggtgg    7380
gcatcctgag cgagctgtgc aaggccgtgg agagcaggta cgagaccgtg ggcaccagca    7440
tcatcgtgat ggctatgacc acactggcca gctccgtcaa gagcttctcc tacctgaggg    7500
gggcccctat aactctctac ggctaacctg aatggactac gacatagtct agccaccatg    7560
agcaagatct acatcgacga gcggagcaac gccgagatcg tgtgcgaggc catcaagacc    7620
atcggcatcg agggcgccac cgccgcccag ctgaccaggc agctgaacat ggagaagcgg    7680
gaggtgaaca aggccctgta cgacctgcag aggagcgcta tggtgtactc cagcgacgac    7740
atccctcccc ggtggttcat gaccaccgag gccgacaagc ccgacgccga cgctatggcc    7800
gacgtgatca tcgacgacgt gagcagggag aagtccatga gggaggacca caagagcttc    7860
gacgacgtga tccccgccaa gaagatcatc gactggaagg gcgccaaccc cgtgaccgtg    7920
atcaacgagt actgccagat caccaggagg gactggagct tccggatcga gagcgtgggc    7980
cccagcaaca gccccacctt ctacgcctgc gtggacatcg acggcagggt gttcgacaag    8040
gccgacggca gagcaagcg ggacgccaag aacaacgccg ccaagctggc cgtggacaag    8100
ctgctgggct acgtgatcat ccggttctaa actcgagcta gtgactgact aggatctggt    8160
taccactaaa ccagcctcaa gaacacccga atggagtctc taagctacat aataccaact    8220
tacacttaca aaatgttgtc ccccaaaatg tagccattcg tatctgctcc taataaaaag    8280
aaagtttctt cacattctag agctccgtca agagcttctc ctacctgagg ggggcccta    8340 taactctcta cggctaacct gaatggacta cgacatagtc tagccaccat ggaagatgcc    8400
aaaaacatta agaagggccc agcgccattc tacccactcg aagacgggac cgccggcgag    8460
cagctgcaca aagccatgaa gcgctacgcc ctggtgcccg gcaccatcgc ctttaccgac    8520
gcacatatcg aggtggacat tacctacgcc gagtacttcg agatgagcgt tcggctggca    8580
gaagctatga gcgctatgg gctgaataca accatcgga tcgtggtgtg cagcgagaat    8640
agcttgcagt tcttcatgcc cgtgttgggt gccctgttca tcggtgtggc tgtggcccca    8700
gctaacgaca tctacaacga gcgcgagctg ctgaacagca tgggcatcag ccagcccacc    8760
gtcgtattcg tgagcaagaa agggctgcaa aagatcctca acgtgcaaaa gaagctaccg    8820
atcatacaaa agatcatcat catggatagc aagaccgact accagggctt ccaaagcatg    8880
tacaccttcg tgacttccca tttgccaccc ggcttcaacg agtacgactt cgtgcccgag    8940
agcttcgacc gggacaaaac catcgccctg atcatgaaca gtagtggcag taccggattg    9000
```

```
cccaagggcg tagccctacc gcaccgcacc gcttgtgtcc gattcagtca tgcccgcgac    9060
cccatcttcg gcaaccagat catccccgac accgctatcc tcagcgtggt gccatttcac    9120
cacggcttcg gcatgttcac cacgctgggc tacttgatct gcggctttcg ggtcgtgctc    9180
atgtaccgct tcgaggagga gctattcttg cgcagcttgc aagactataa gattcaatct    9240
gccctgctgg tgcccacact atttagcttc ttcgctaaga gcactctcat cgacaagtac    9300
gacctaagca acttgcacga gatcgccagc ggcggggcgc cgctcagcaa ggaggtaggt    9360
gaggccgtgg ccaaacgctt ccacctacca ggcatccgac agggctacgg cctgacagaa    9420
acaaccagcg ccattctgat caccccgaa ggggacgaca gcctggcgc agtaggcaag     9480 gtggtgccct tcttcgaggc taaggtggtg gacttggaca ccggtaagac actgggtgtg    9540
aaccagcgcg cgcagctgtg cgtccgtggc cccatgatca tgagcggcta cgttaacaac    9600
cccgaggcta caaacgctct catcgacaag gacggctggc tgcacagcgg cgacatcgcc    9660
tactgggacg aggacgagca cttcttcatc gtggaccggc tgaagtccct gatcaaatac    9720
aagggctacc aggtagcccc agccgaactg gagagcatcc tgctgcaaca ccccaacatc    9780
ttcgacgccg gggtcgccgg cctgcccgac gacgatgccg cgagctgcc cgccgcagtc     9840 gtcgtgctga acacggtaa aaccatgacc gagaaggaga tcgtggacta tgtggccagc    9900
caggttacaa ccgccaagaa gctgcgcggt ggtgttgtgt tcgtggacga ggtgcctaaa    9960
ggactgaccg gcaagttgga cgcccgcaag atccgcgaga ttctcattaa ggccaagaag   10020
ggcggcaaga tcgccgtgta actcgagtat gttacgtgca aggtgattg tcaccccccg    10080 aaagaccata ttgtgacaca ccctcagtat cacgcccaaa catttacagc cgcggtgtca   10140 aaaccgcgt ggacgtggtt aacatccctg ctgggaggat cagccgtaat tattataatt     10200
ggcttggtgc tggctactat tgtggccatg tacgtgctga ccaaccagaa acataattga   10260
atacagcagc aattggcaag ctgcttacat agaactcgcg gcgattggca tgccgcctta   10320 aaattttat tttatttttt cttttctttt ccgaatcgga ttttgttttt aatatttcaa    10380 aaaaaaaaa aaaaaaaaa aaatctagaa aaaaaaaaa aaaaaaaaa aaaaaaaaaa        10440 aaaaaaaaaa aaaaaaaaaa aaaaaaaaaa aaaaaaaaaa aaaaaaaaaa aaaaaaaaaa   10500
aaaaaaaa                                                            10508

<210> SEQ ID NO 128
<211> LENGTH: 11075
<212> TYPE: RNA
<213> ORGANISM: Artificial sequence
<220> FEATURE:
<223> OTHER INFORMATION: Synthetic polynucleotide

<400> SEQUENCE: 128
augggcggcg caugagagaa gcccagacca auuaccuacc caaaauggag aaaguucacg      60
uugacaucga ggaagacagc ccauuccuca gagcuuugca gcggagcuuc ccgcaguuug     120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgucgcgc uacgaagggc    480
aagucgcugu uuaccaggau guauacgccg ucgacggccc caccagccug uaccaccagg    540
```

```
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840 ugagggcaa gcagaacuac accugcaggu gcgagaccau cgugagcugc gacggcuacg    900
uggugaagag gaucgccauc agccccggcc uguacggcaa gcccagcggc uacgccgcua    960
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccaggaga   1140
ucguggucaa cggcaggacc cagaggaaca ccaacacaau gaagaacuac cugcugcccg   1200
ugguggccca ggcuuucgcc aggugggcca aggaguacaa ggaggaccag gaagacgaga   1260
ggcccugggg ccugagggac aggcagcugg ugaugggcug cugcugggcc uucaggcggc   1320
acaagaucac cagcaucuac aagaggcccg cacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccgguggagcc cuaccacggc aaggugguca   1860
ugcccgaggg ccacgccauc cccgugcagg acuuccaggc ccugagcgag agcgccacca   1920
ucguguacaa cgagagggag uucgugaaca gguaccugca ccauucgcc acccacggcg   1980 gagcccugaa caccgacgag gaauacuaca agaccgugaa gcccagcgag cacgacggcg   2040
aguaccugua cgacaucgac aggaagcagu gcgugaagaa agagcugguga ccggccugg   2100 gacugaccgg cgagcuggug gacccacccu uccacgaguu cgccuacgag agccugagga   2160
ccagacccgc cgcucccuac caggugccca ccauggcgu uacggcgug cccggcagcg   2220 gaaagagcgg caucaucaag agcgccguga ccaagaaaga ccuggugguc agcgccaaga   2280
aagagaacug cgccgagauc aucagggacg ugaagaagau gaaggccug gacgugaacg   2340 cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca gcagugcgg cuucuucaac augaugugcc   2520
ugaaggugca cuucaaccac gagaucgca cccaggguguu ccacaagagc aucagcaggc   2580
ggugcaccaa gagcgugacc agcgucguga gcaccugguu cuacgacaag aaaaugagga   2640
ccaccaaccc caaggagacc aaaaucguga ucgacaccac aggcagcacc aagcccaagc   2700
aggacgaccu gaauccgacc ugcuucaggg gcugggugaa gcagcugcag aucgacuaca   2760
agggcaacga gaucaugacc gccgcugcca gcaggccu gaccaggaag ggcguguacg   2820 ccgugagguua caaggugaac gagaacccac ugaucgcucc accagcgag cacgugaacg   2880
```

```
ugcugcugac caggaccgag gacaggaucg uguggaagac ccuggccggc gaccccugga    2940
ucaagacccu gaccgccaag uaccccggca acuucaccgc caccaucgaa gaguggcagg    3000
ccgagcacga cgccaucaug aggcacaucc uggagaggcc cgaccccacc gacguguucc    3060
agaacaaggc caacgugugc ugggccaagg cccugguggc cgugcugaag accgccggca    3120
ucgacaugac cacagagcag uggaacaccg uggacuacuu cgagaccgac aaggcccaca    3180
gcgccgagau cgugcugaac cagcugugcg ugagguucuu cggccuggac cuggacagcg    3240
gccuguucag cgcccccacc gugccacuga gcaucaggaa caaccacugg gacaacagcc    3300
ccagcccaaa cauguacggc cugaacaagg aggugucag gcagcugagc aggcgguacc    3360
cacagcugcc cagggccgug gccaccggca ggguguacga caugaacacc ggcacccuga    3420
ggaacuacga ccccaggauc aaccuggugc ccgugaacag gcggcugccc acgcccuggg    3480
ugcugcacca caacgagcac ccacagagcg acuucagcuc cuucgugagc aagcugaaag    3540
gcaggaccgu gcuggucgug ggcgagaagc ugagcgugcc cggcaagaug guggacuggc    3600
ugagcgacag gccgaggcc accuccgggg ccaggcugga ccucggcauc cccggcgacg    3660
ugcccaagua cgacaucauc uucgugaacg ucaggacccc auacaaguac caccauuacc    3720
agcagugcga ggaccacgcc aucaagcuga gcaugcugac caagaaggcc ugccugcacc    3780
ugaaccccgg aggcaccugc gugagcaucg cuacggcua cgccgacagg gccagcgaga    3840
gcaucauugg cgccaucgcc aggcuguuca aguucagcag gguguggcaaa cccaagagca    3900 gccuggagga aaccgaggug cuguucgugu caucggcua cgaccggaag gccaggaccc    3960
acaaccccua caagcugagc agcacccuga caaacaucua caccggcagc aggcugcacg    4020
aggccggcug cgcccccagc uaccacgugg ucagggggcga uaucgccacc gccaccgagg    4080
gcgugaucau caacgcugcc aacagcaagg gccagcccgg aggcggagug ugcggcgccc    4140
uguacaagaa guuccccgag agcuucgacc ugcagcccau cgaggugggc aaggccaggc    4200
uggugaaggg cgccgcuaag cacaucaucc acgccguggg ccccaacuuc aacaagguga    4260
gcgaggugga aggcgacaag cagcuggccg aagccuacga gagcaucgcc aagaucguga    4320
acgacaauaa cuacaagagc guggccaucc cacugcucag caccggcauc uucagcggca    4380
acaaggacag gcugacccag agccugaacc accugcucac cgcccuggac accaccgaug    4440
ccgacguggc caucuacugc agggacaaga guggggagau gacccugaag gaggccgugg    4500
ccaggcggga ggccguggaa gagaucugca ucagcgacga cuccagcgug accgagcccg    4560
acgccgagcu ggugagggug cacccccaaga gcucccuggc cggcaggaag ggcuacagca    4620
ccagcgacgg caagaccuuc agcuaccugg agggcaccaa guccaccagg ccgcuaagg    4680 acaucgccga gaucaacgcu auggccccg uggccaccga ggcaacgag cagguguggca   4740 uguacauccu gggcgagagc augccagca ucaggagcaa gugcccgug gaggaaagcg   4800 aggccagcac accacccagc acccugcccu gccugugcau ccacgcuaug acacccgaga    4860
ggggucagcg gcugaaggcc agcaggcccg agcagaucac cgugugcagc uccuucccac    4920
ugcccaagua caggaucacc ggcgugcaga agauccagug cagccagccc auccuguuca    4980
gcccaaaggu gcccgccuac auccaccccca ggaaguaccu gguggagacc caccccgugg    5040
acgagacacc cgagccaagc gccgagaacc agagcaccga gggcacaccc gagcagccac    5100
cccuganuac cgaggacgag acaaggacccc ggaccccaga gcccaucauu aucgaggaag    5160
aggaagagga cagcaucagc cugcgagcg acggccccac ccaccaggug cugcaggugg    5220
aggccgacau ccacggccca cccagcgugu ccagcuccag cuggagcauc ccacacgcca    5280
```

```
gcgacuucga cguggacagc cugagcaucc uggacacccu ggagggcgcc agcgugaccu   5340
ccggcgccac cagcgccgag accaacagcu acuucgccaa gagcauggag uuccuggcca   5400
ggcccgugcc agcucccagg accguguuca ggaacccacc ccacccagcu cccaggacca   5460
ggaccccaag ccuggcuccc agcagggccu gcagcaggac cagccggugu agcaccccac   5520
ccggcgugaa cagggugauc accagggagg aacuggaggc ccugacaccc agcaggaccc   5580
ccagcagguc cugagcagg acuagucugg uguccaaccc acccggcgug aacaggguga   5640
ucaccaggga ggaauucgag gccuucgugg cccagcaaca gagacgguuc gacgccggcg   5700
ccuacaucuu cagcagcgac accggccagg acaccugcca gcaaaagagc gugaggcaga   5760
ccgugcugag cgaggugug cuggagagga ccgagcugga aaucagcuac gccccaggc   5820
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccuggacac uaccugaagg ccgagggcaa gguggagugc uacaggaccc   6000
ugcaccccgu gccacuguac agcuccagcg ugaacagggc cuucuccagc ccaagguggg   6060
ccguggaggc cugcaacgcu augcugaagg agaacuuccc caccguggcc agcuacugca   6120
ucaucccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacugggu gaacuacauc accaagcuga   6480
agggccccaa ggccgcugcc cuguucgcua agacccacaa ccugaacaug cugcaggaca   6540
ucccaaugga cagguucgug auggaccuga gagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccguuucgac augagcgccg aggacuucga cgccaucauc gccgagcacu   6780
uccagcccgg cgacgcgug cuggagaccg acaucgccag cuucgacaag agcgaggaug   6840
acgcuauggc ccugaccgcu cugaugaucc uggaggaccu gggcgugggac gccgagcugc   6900
ucacccugau cgaggcugcc uucggcgaga ucagcccau ccaccugccc accaagacca   6960
aguucaaguu cggcgcuaug augaaaagcg gaauguccu gacccuguuc gugaacaccg   7020
ugaucaacau gugaucgcc agcagggugc ugcgggagag gcugaccggc agccccugcg   7080
cugccuucau cggcgacgac aacaucguga agggcgugaa aagcgacaag cugauggccg   7140
acaggugcgc caccuggcug aacauggagg ugaagaucau cgacgccgug gugggcgaga   7200
aggcccccua cuucucggc ggauucaucc ugugcgacag cgugaccggc accgccugca   7260
gggguggccga cccccugaag aggcuguuca gcugggcaa gcacacggcc gcugacgaug   7320
agcacgacga ugacaggcgg aggggccugc acgaggaaag caccagugug acagggugg   7380
gcauccugag cgagcugugc aaggccgugg agagcaggua cgagaccgug ggcaccagca   7440
ucaucgugau ggcuaugacc acacuggcca gcuccgucaa gagcuucccc uaccugaggg   7500
gggcccuau aacucucuac ggcuaaccug aauggacuac gacauagucu aguccgccaa   7560
ggccgccacc auggaagaug ccaaaaacau uaagaagggc ccagcgccau ucuacccacu   7620
```

```
cgaagacggg accgccggcg agcagcugca caaagccaug aagcgcuacg cccuggugcc    7680
cggcaccauc gccuuuaccg acgcacauau cgagguggac auuaccuacg ccgaguacuu    7740
cgagaugagc guucggcugg cagaagcuau gaagcgcuau gggcugaaua caaaccaucg    7800
gaucguggug ugcagcgaga auagcuugca guucuucaug cccguguugg ugcccuguu     7860 caucggugug gcuguggccc cagcuaacga caucuacaac gagcgcgagc ugcugaacag    7920
caugggcauc agccagccca ccgucguauu cgugagcaag aaagggcugc aaaagauccu    7980
caacgugcaa agaagcuac cgaucauaca aaagaucauc aucauggaua gcaagaccga     8040
cuaccagggc uuccaaagca uguacaccuu cgugacuucc cauuugccac ccggcuucaa    8100
cgaguacgac uucgugcccg agagcuucga ccgggacaaa accaucgccc ugaucaugaa    8160
caguaguggc aguaccggau ugcccaaggg cguagcccua ccgcaccgca ccgcuugugu    8220
ccgauucagu caugcccgcg accccaucuu cggcaaccag aucaucccg acaccgcuau     8280 ccucagcgug gugccauuuc accacggcu cggcauguuc accacgcugg gcuacuugau    8340
cugcggcuuu cgggucgugc ucauguaccg cuucgaggag gagcuauucu ugcgcagcuu    8400
gcaagacuau aagauucaau cugcccugcu ggugcccaca cuauuuagcu ucuucgcuaa    8460
gagcacucuc aucgacaagu acgaccuaag caacuugcac gagaucgcca gcggcggggc    8520
gccgcucagc aaggagguag gugaggccgu ggccaaacgc uuccaccuac caggcauccg    8580
acagggcuac ggccugacag aaacaaccag cgccauucug aucaccccg aaggggacga     8640 caagccuggc gcaguaggca aggugguucc cuucuucgag gcuaaggug uggacuugga     8700 caccgguaag acacggguug ugaaccacg cggcgagcug ugcguccgug gcccccaugau    8760 caugagcggc uacguuaaca ccccgaggc uacaaacgcu cucaucgaca aggacggcug    8820
gcugcacagc ggcgacaucg ccuacuggga cgaggacgag cacuucuuca ucguggaccg    8880 gcugaaguccc ugaucaaau acaagggcua ccagguagcc ccagccgaac uggagagcau    8940
ccugcugcaa caccccaaca ucuucgacgc cgggggucgcc ggccugcccg acgacgaugc   9000
cggcgagcug cccgccgcag ucgucgugcu ggaacacggu aaaaccauga ccgagaagga    9060
gaucguggac uauguggcca gccagguuac aaccgccaag aagcugcgcg guuuguugu    9120 guucguggac gaggugccua aggacugac cggcaaguug gacgcccgca gauccgcga     9180 gauucucauu aaggccaaga agggcggcaa gaucgccgug uaacgagcgc ggaaacgca    9240 auagccgaaa acaaaaaaac aaaaaaaaca aaaaaaaaac caaaaaaaca aaacacauua    9300
aaacagccug ugggguugauc ccacccacag gcccauggg cgcuagcacu cuggauaucac    9360 gguaccuuug ugcgccuguu uuauaccccc ucccccaacu guaacuuaga aguaacacac    9420
accgaucaac agcagcgug gcacaccagc cacguuuuga ucaagcacuu cuguuacccc     9480
ggacugagua ucaauagacu gcucacgcgg uugaaggaga aagcguucgu uauccggcca    9540
acuacuucga aaaccuagu aacaccgugg aaguugcaga guguuucgcu cagcacuacc     9600
ccaguguaga ucaggucgau gagucaccgc auucccacg ggcgaccgug gcgguggcug     9660
cguuggcggc cugcccaugg ggaaacccau gggacgcucu aauacagaca uggugcgaag    9720
agucuauuga gcuaguuguu aguccuccgg cccugaaug cggcuaaucc uaacugcgga    9780
gcacacaccc ucaagccaga gggcagugug ucguaacggg caacucugca gcggaaccga    9840 cuacuuggggu guccuguu ucauuuuauu ccuauacugg cugcuuaugg ugacaauuga    9900
gagaucguua ccauauagcu auuggauggc ccaccggug acuaauagag cuauuauaua    9960
ucccuuuguu ggguuauac cacuuuagcu ugaaagaggu uaaaaacauu uaa auucauugu 10020
```

```
uaaguugaau acagcaaaau gagcaagauc uacaucgacg agcggagcaa cgccgagauc  10080
gugugcgagg ccaucaagac caucggcauc gagggcgcca ccgccgccca gcugaccagg  10140
cagcugaaca uggagaagcg ggaggugaac aaggcccugu acgaccugca gaggagcgcu  10200
augguguacu ccagcgacga caucccuccc cgguggguuca ugaccaccga ggccgacaag  10260
cccgacgccg acgcuauggc cgacgugauc aucgacgacg ugagcaggga gaaguccaug  10320
agggaggacc acaagagcuu cgacgacgug auccccgcca agaagaucau cgacuggaag  10380
ggcgccaacc ccgugaccgu gaucaacgag uacugccaga ucaccaggag ggacuggagc  10440
uuccggaucg agagcguggg ccccagcaac agccccaccu ucuacgccug cguggacauc  10500
gacggcaggg uguucgacaa ggccgacggc aagagcaagc gggacgccaa gaacaacgcc  10560
gccaagcugg ccguggacaa gcugcugggc uacgugauca uccgguucua aacguauguu  10620
acgugcaaag gugauuguca ccccccgaaa gaccauauug ugacacaccc ucaguaucac  10680
gcccaaacau uuacagccgc ggugucaaaa accgcgugga cgugguuaac aucccugcug  10740
ggaggaucag ccguaauuau uauaauuggc uuggugcugg cuacuauugu ggccauguac  10800
gugcugacca accagaaaca uaauugaaua cagcagcaau uggcaagcug cuuacauaga  10860
acucgcggcg auuggcaugc cgccuuaaaa uuuuuauuuu auuuuuucuu uucuuuuccg  10920
aaucggauuu uguuuuuaau auuucaaaaa aaaaaaaaaa aaaaaaaaaa ucuagaaaaa  10980
aaaaaaaaaa aaaaaaaaaa aaaaaaaaaa aaaaaaaaaa aaaaaaaaaa aaaaaaaaaa  11040
aaaaaaaaaa aaaaaaaaaa aaaaaaaaaa aaaaa                              11075
```

<210> SEQ ID NO 129
<211> LENGTH: 10851
<212> TYPE: RNA
<213> ORGANISM: Artificial sequence
<220> FEATURE:
<223> OTHER INFORMATION: Synthetic polynucleotide

<400> SEQUENCE: 129

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu ggccgccguc augagcgacc    420
cugaccugga aacugagacu augugccucc acgacgacga gucgugucgc uacgaagggc    480
aagucgcugu uuaccaggau guauacgccg ucgacggccc caccagccug uaccaccagg    540
ccaacaaggg cgugagggug gccuacugga ucggcuucga caccacaccc uucauguuca    600
agaaccuggc cggcgccuac cccagcuaca gcaccaacug ggccgacgag accgugcuga    660
ccgccaggaa caucggccug ugcagcagcg acgugaugga gaggagccgg agaggcauga    720
gcauccugag gaagaaauac cugaagccca gcaacaacgu gcuguucagc gugggcagca    780
ccaucuacca cgagaagagg gaccugcuca ggagcuggca ccugcccagc guguuccacc    840
ugaggggcaa gcagaacuac accugcaggu gcgagaccau cgugagcugc gacggcuacg    900
uggugaagag gaucgccauc agccccggcc uguacggcaa gcccagcggc uacgccgcua    960
```

-continued

```
caaugcacag ggagggcuuc cugugcugca aggugaccga cacccugaac ggcgagaggg   1020
ugagcuuccc cgugugcacc uacgugcccg ccacccugug cgaccagaug accggcaucc   1080
uggccaccga cgugagcgcc gacgacgccc agaagcugcu cgugggccug aaccagagga   1140
ucguggucaa cggcaggacc cagaggaaca ccaacacaau gaagaacuac cugcugcccg   1200
uggugcccca ggcuuucgcc aggugggcca aggaguacaa ggaggaccag gaagacgaga   1260
ggccccuggg ccugagggac aggcagcugg ugaugggcug cugcugggcc uucaggcggc   1320
acaagaucac cagcaucuac aagaggcccg acacccagac caucaucaag gugaacagcg   1380
acuuccacag cuucgugcug cccaggaucg gcagcaacac ccuggagauc ggccugagga   1440
cccggaucag gaagaugcug gaggaacaca aggagcccag cccacugauc accgccgagg   1500
acgugcagga ggccaagugc gcugccgacg aggccaagga ggugagggag gccgaggaac   1560
ugagggccgc ccugccaccc cuggcugccg acguggagga acccacccug gaagccgacg   1620
uggaccugau gcugcaggag gccggcgccg gaagcgugga gacacccagg ggccugauca   1680
aggugaccag cuacgacggc gaggacaaga ucggcagcua cgccgugcug agcccacagg   1740
ccgugcugaa guccgagaag cugagcugca uccacccacu ggccgagcag gugaucguga   1800
ucacccacag cggcaggaag ggcagguacg ccguggagcc cuaccacggc aagguggucg   1860
ugcccgaggg ccacgccauc cccgugcagg acuuccaggc ccugagcgag agcgccacca   1920
ucguguacaa cgagagggag uucgugaaca gguaccugca ccauaucgcc acccacggcg   1980
gagcccugaa caccgacgag gaauacuaca agaccgugaa gcccagcgag cacgacggcg   2040
aguaccugua cgacaucgac aggaagcagu gcgugaagaa agagcuggug accggccugg   2100
gacugaccgg cgagcuggug gacccacccu uccacgaguu cgccuacgag agccugagga   2160
ccagacccgc cgcucccuac caggugccca ccaucggcgu guacggcgug cccggcagcg   2220
gaaagagcgg caucaucaag agcgccguga ccaagaaaga ccuggugguc agcgccaaga   2280
aagagaacug cgccgagauc aucagggacg ugaagaagau gaaaggccug gacgugaacg   2340
cgcgcaccgu ggacagcgug cugcugaacg gcugcaagca ccccguggag acccuguaca   2400
ucgacgaggc cuucgcuugc cacgccggca cccugagggc ccugaucgcc aucaucaggc   2460
ccaagaaagc cgugcugugc ggcgacccca agcagugcgg cuucuucaac augaugugcc   2520
ugaaggugca cuucaaccac gagaucugca cccagguguu ccacaagagc aucagcaggc   2580
ggugcaccaa gagcgugacc agcgucguga gcacccuguu cuacgacaag aaaaugagga   2640
ccaccaaccc caaggagacc aaaaucguga ucgacaccac aggcagcacc aagcccaagc   2700
aggacgaccu gauccugacc ugcuucaggg gcugggugaa gcagcugcag aucgacuaca   2760
agggcaacga gaucaugacc gccgcugcca gccagggccu gaccaggaag ggcguguacg   2820
ccgugaggua caaggugaac gagaacccac uguacgcucc caccagcgag cacgugaacg   2880
ugcugcugac caggaccgag gacaggaucg uguggaagac ccuggccggc gaccccugga   2940
ucaagacccu gaccgccaag uaccccggca acuucaccgc caccaucgaa gaguggcagg   3000
ccgagcacga cgccaucaug aggcacaucc uggagaggcc cgaccccacc gacguguucc   3060
agaacaaggc caacgugugc ugggccaagg cccuggugcc cgugcugaag accgccggca   3120
ucgacaugac cacagagcag uggaacaccg uggacuacuu cgagaccgac aaggcccaca   3180
gcgccgagau cgugcugaac cagcugugcg ugagguucuu cggccuggac cuggacagcg   3240
gccuguucag cgcccccacc gugccacuga gcaucaggaa caaccacugg gacaacagcc   3300
ccagcccaaa cauguacggc cugaacaagg agguggucag gcagcugagc aggcgguacc   3360
```

```
cacagcugcc cagggccgug gccaccggca ggguguacga caugaacacc ggcacccuga   3420
ggaacuacga ccccaggauc aaccuggugc ccgugaacag gcggcugccc cacgcccugg   3480
ugcugcacca caacgagcac ccacagagcg acuucagcuc cuucgugagc aagcugaaag   3540
gcaggaccgu gcuggucgug ggcgagaagc ugagcgugcc cggcaagaug guggacuggc   3600
ugagcgacag gcccgaggcc accuuccggg ccaggcugga ccucggcauc cccggcgacg   3660
ugcccaagua cgacaucauc uucgugaacg ucaggacccc auacaaguac caccauuacc   3720
agcagugcga ggaccacgcc aucaagcuga gcaugcugac caagaaggcc ugccugcacc   3780
ugaaccccgg aggcaccugc gugagcaucg gcuacggcua cgccgacagg gccagcgaga   3840
gcaucauugg cgccaucgcc aggcuguuca aguucagcag ggugugcaaa cccaagagca   3900
gccuggagga aaccgaggug cuguucgugu ucaucggcua cgaccggaag gccaggaccc   3960
acaaccccua caagcugagc agcacccuga caaacaucua caccggcagc aggcugcacg   4020
aggccggcug cgcccccagc uaccacgugg ucaggggcga uaucgccacc gccaccgagg   4080
gcgugaucau caacgcugcc aacagcaagg gccagcccgg aggcggagug ugcggcgccc   4140
uguacaagaa guuccccgag agcuucgacc ugcagcccau cgaggugggc aaggccaggc   4200
uggugaaggg cgccgcuaag cacaucaucc acgccguggg ccccaacuuc aacaagguga   4260
gcgaggugga aggcgacaag cagcuggccg aagccuacga gagcaucgcc aagaucguga   4320
acgacaauaa cuacaagagc guggccaucc cacugcucag caccggcauc uucagcggca   4380
acaaggacag gcugacccag agccugaacc accugcucac cgcccuggac accaccgaug   4440
ccgacguggc caucuacugc agggacaaga agugggagau gacccugaag gaggccgugg   4500
ccaggcggga ggccguggaa gagaucugca ucagcgacga cuccagcgug accgagcccg   4560
acgccgagcu ggugagggug caccccaaga gcucccuggc cggcaggaag ggcuacagca   4620
ccagcgacgg caagaccuuc agcuaccugg agggcaccaa guuccaccag gccgcuaagg   4680
acaucgccga gaucaacgcu auguggcccg uggccaccga ggccaacgag cagguguca   4740
uguacauccu gggcgagagc auguccagca ucaggagcaa gugccccgug gaggaaagcg   4800
aggccagcac accacccagc acccugcccu gccugugcau ccacgcuaug acacccgaga   4860
gggugcagcg gcugaaggcc agcaggcccg agcagaucac cgugugcagc uccuucccac   4920
ugcccaagua caggaucacc ggcgugcaga agauccagug cagccagccc auccuguuca   4980
gcccaaaggu gcccgccuac auccacccca ggaaguaccu gguggagacc ccacccgugg   5040
acgagacacc cgagccaagc gccgagaacc agagcaccga gggcacaccc gagcagccac   5100
cccugaucac cgaggacgag acaaggaccc ggaccccaga gcccaucauu aucgaggaag   5160
aggaagagga cagcaucagc cugcugagcg acggccccac ccaccaggug cugcaggugg   5220
aggccgacau ccacggccca cccagcgugu ccagcuccag cuggagcauc ccacacgcca   5280
gcgacuucga cguggacagc cugagcaucc uggacacccu ggagggcgcc agcgugaccu   5340
ccggcgccac cagcgccgag accaacagcu acuucgccaa gagcauggag uuccuggcca   5400
ggcccgugcc agcucccagg accguguuca ggaacccacc ccacccagcu cccaggacca   5460
ggaccccaag ccuggcuccc agcagggccu gcagcaggac cagccuggug agcaccccac   5520
ccggcgugaa cagggugauc accagggagg aacuggaggc ccugacaccc agcaggaccc   5580
ccagcagguc cgugagcagg acuagucugg uguccaaccc acccggcgug aacaggguga   5640
ucaccaggga ggaauucgag gccuucgugg cccagcaaca gagacgguuc gacgccggcg   5700
```

```
ccuacaucuu cagcagcgac accggccagg gacaccugca gcaaaagagc gugaggcaga   5760
ccgugcugag cgaggugguc cuggagagga ccgagcugga aaucagcuac gcccccaggc   5820
uggaccagga gaaggaggaa cugcucagga agaaacugca gcugaacccc accccagcca   5880
acaggagcag guaccagagc aggaaggugg agaacaugaa ggccaucacc gccaggcgga   5940
uccugcaggg ccugggacac uaccugaagg ccgagggcaa gguggagugc uacaggaccc   6000
ugcaccccgu gccacuguac agcuccagcg ugaacagggc cuucuccagc cccaaggugg   6060
ccguggaggc cugcaacgcu augcugaagg agaacuuccc caccguggcc agcuacugca   6120
ucauccccga guacgacgcc uaccuggaca ugguggacgg cgccagcugc ugccuggaca   6180
ccgccagcuu cugccccgcc aagcugagga gcuuccccaa gaaacacagc uaccuggagc   6240
ccaccaucag gagcgccgug cccagcgcca uccagaacac ccugcagaac gugcuggccg   6300
cugccaccaa gaggaacugc aacgugaccc agaugaggga gcugcccgug cuggacagcg   6360
cugccuucaa cguggagugc uucaagaaau acgccugcaa caacgaguac ugggagaccu   6420
ucaaggagaa ccccaucagg cugaccgaag agaacguggu gaacuacauc accaagcuga   6480
agggccccaa ggccgcugcc cguucgcua agacccacaa ccugaacaug cugcaggaca   6540
ucccaaugga cagguucgug auggaccuga gagggacgu gaaggugaca cccggcacca   6600
agcacaccga ggagaggccc aaggugcagg ugauccaggc cgcugaccca cuggccaccg   6660
ccuaccugug cggcauccac agggagcugg ugaggcggcu gaacgccgug cugcugccca   6720
acauccacac ccuguucgac augagcgccg aggacuucga cgccaucauc gccgagcacu   6780
uccagccggg cgacugcgug cuggagaccg acaucgccag cuucgacaag agcgaggaug   6840
acgcuauggc ccugaccgcu cugaugaucc uggaggaccu gggcguggac gccgagcugc   6900
ucacccugau cgaggcugcc uucggcgaga ucagcuccau ccaccugccc accaagacca   6960
aguucaaguu cggcgcuaug augaaaagcg gaaugucccu gacccuguuc gugaacaccg   7020
ugaucaacau ugugaucgcc agcagggugc ugcgggagag cugaccggc agccccugcg   7080
cugccuucau cggcgacgac aacaucguga agggcgugaa aagcgacaag cugaugcgg   7140
acaggugcgc caccuggcug aacauggagg ugaagaucau cgacgccgug gugggcgaga   7200
aggcccccua cuucugcggc ggauucaucc ugugcgacag cgugaccggc accgccugca   7260
ggguggccga cccccugaag aggcuguuca gcugggcaa gccacuggcc gcugacgaug   7320
agcacgacga ugacaggcgg agggcccugc acgaggaaag caccaggugg aacagggugg   7380
gcauccugag cgagcugugc aaggccgugg agagcaggua cgagaccgug ggcaccagca   7440
ucaucgugau ggcuaugacc acacuggcca gcuccgucaa gagcuucuc uaccugaggg   7500
gggcccuau aacucucuac ggcuaaccug aauggacuac gacauagucu agucgccaa   7560
ggccgccacc auggaagaug ccaaaaaacau uaagaagggc ccagcgccau ucuacccacu   7620
cgaagacggg accgccggcg agcagccuca caaagccaug aagcgcuacg cccuggugcc   7680
cggcaccauc gccuuaccg acgcacauau cgagguggac auuaccuacg ccgaguacuu   7740
cgagaugagc guucggcugg cagaagcuau gaagcgcuau gggcugaaua caaccaucg   7800
gaucguggu ugcagcgaga auagcuucaa guucuucaug cccguguugg gugcccuguu   7860
caucggugug gcuguggccc cagcuaacga caucacaaac gagcgcgagc ugcugaacag   7920
caugggcauc agccagccca ccgucguauu cgugagcaag aaggggcugc aaaagauccu   7980
caacgugcaa aagaagcuac cgaucauaca aaagaucauc aucaugauga gcaagaccga   8040
cuaccagggc uuccaaagca uguacaccuu cgugacuucc cauuugccac ccggcuucaa   8100
```

```
cgaguacgac uucgugcccg agagcuucga ccgggacaaa accaucgccc ugaucaugaa    8160
caguaguggc aguaccggau ugcccaaggg cguagcccua ccgcaccgca ccgcuugugu    8220
ccgauucagu caugcccgcg accccaucuu cggcaaccag aucaucccog acaccgcuau    8280 ccucagcgug gugccauuuc accacggcuu cggcauguuc accacgcugg gcuacuugau    8340
cugcggcuuu cggucgugc ucauguaccg cuucgaggag gagcuauucu ugcgcagcuu    8400
gcaagacuau aagauucaau cugcccugcu ggugcccaca cuauuuagcu ucuucgcuaa    8460
gagcacucuc aucgacaagu acgaccuaag caacuugcac gagaucgcca gcggcggggc    8520
gccgcucagc aaggaggugg gugaggccgu ggccaaacgc uuccaccuac caggcauccg    8580
acagggcuac ggccugacag aaacaaccag cgccauucug aucaccccog aaggggacga    8640 caagccuggc gcaguaggca aggugggcc cuucuucgag gcuaaggugg uggacuugga    8700
caccgguaag acacuggggu ugaaccagcg cggcgagcug ugcguccgug gccccaugau    8760
caugagcggc uacguuaaca accccgaggc uacaaacgcu cucaucgaca aggacggcug    8820
gcugcacagc ggcgacaucg ccuacuggga cgaggacgag cacuucuuca ucguggaccg    8880 gcugaaguco cugaucaaau acaagggcua ccagguagcc ccagccgaac uggagagcau    8940
ccugcugcaa caccccaaca ucuucgacgc cggggucgcc ggccugcccg acgacgaugc    9000
cggcgagcug cccgccgcag ucgucgugcu ggaacacggu aaaaccauga ccgagaagga    9060
gaucguggac uauguggcca gccagguuac aaccgccaag aagcugcgcg guguguugu    9120 guucguggac gagggugccua aaggacugac cggcaaguug gacgcccgca agauccgcga    9180
gauucucauu aaggccaaga agggcggcaa gaucgccgug uaacucgagc cggaaacgca    9240
auagccgaaa aacaaaaaac aaaaaaaaca aaaaaaaaac caaaaaaaca aaacacauua    9300
aaacagccug uggguugauc ccacccacag gccccauggg cgcuagcacu cugguaucac    9360
gguaccuuug ugcgccuguu uuauacccce uccccaacu guaacuuaga aguaacacac    9420
accgaucaac agucagcgug gcacaccagc cacguuuuga ucaagcacuu cuguuacccc    9480
ggacugagua ucaauagacu gcucacgcgg uugaaggaga aagcguucgu uauccggcca    9540
acuacuucga aaaaccuagu aacaccgugg aaguugcaga guguuucgcu cagcacuacc    9600
ccaguguaga ucaggucgau gaguccaccgc auuccccacg ggcgaccgug gcgguggcug    9660
cguuggcggc cugcccaugg ggaaacccau gggacgcucu aauacagaca uggugcgaag    9720
agucuauuga gcuaguuggu aguccuccgg ccccugaaug cggcuaaucc uaacugcgga    9780
gcacacaccc ucaagccaga gggcagugug ucguaacggg caacucugca gcggaaccga    9840
cuacuugggu ugccguguu ucauuuauu ccuauacugg cugcuuaugg ugacaauuga    9900
gagaucguua ccauauagcu auggauugg ccauccggug acuaauagag cuauuauaua    9960
ucccuuuguu ggguuuauac cacuuagcuu gaaagagguu aaaacauuac aauucauugu    10020
uaaguugaau acagcaaaau gagcaagauc uacaucgacg agcggagcaa cgccgagauc    10080
gugugcgagg ccaucaagac caucggcauc gagggcgcca ccgccgccca gcugaccagg    10140
cagcugaaca uggagaagcg ggaggugaac aaggcccgu acgaccugca gaggagcgcu    10200 auggugacu ccagcgacga caucccucccc cgguggcuua ugaccaccga ggcgacaag    10260 cccgacgccg acgcuauggc cgacgugauc aucgacacg ugagcaggga gaaguccaug    10320
agggaggacc acaagagcuu cgacgacgug auccccgcca gaagaucau cgacuggaag    10380 ggcgccaacc ccgugaccgu gaucaacgag uacugccaga ucaccaggag ggacuggagc    10440
```

-continued

```
uuccggaucg agagcguggg ccccagcaac agccccaccu ucuacgccug cguggacauc    10500
gacggcaggg uguucgacaa ggccgacggc aagagcaagc gggacgccaa gaacaacgcc    10560
gccaagcugg ccguggacaa gcugcugggc uacgugauca uccgguucua aacaauuggc    10620
aagcugcuua cauagaacuc gcggcgauug gcaugccgcc uuuaaaauuuu uauuuuauuu    10680 uuucuuuucu uuuccgaauc ggauuuuguu uuuaauauuu caaaaaaaaa aaaaaaaaaa    10740
aaaaaaucua gaaaaaaaaa aaaaaaaaaa aaaaaaaaaa aaaaaaaaaa aaaaaaaaaa    10800
aaaaaaaaaa aaaaaaaaaa aaaaaaaaaa aaaaaaaaaa aaaaaaaaaa a             10851
```

CORONAVIRUS VACCINE COMPOSITIONS AND METHODS

CROSS-REFERENCES TO RELATED APPLICATIONS

This application claims the benefit of U.S. Provisional Application No. 62/987,191, filed Mar. 9, 2020 and U.S. Provisional Application No. 63/073,900, filed Sep. 2, 2020.

REFERENCE TO A SEQUENCE LISTING

The instant application contains a Sequence Listing which has been submitted electronically in ASCII format and is hereby incorporated by reference in its entirety. Said ASCII copy, created on Mar. 8, 2021 is named 049386-538001US_SequenceListing_ST25.txt and is 481,150 bytes in size.

TECHNICAL FIELD

The present disclosure relates generally to inducing immune responses against infectious agents and tumor antigens and more specifically to self-transcribing and replicating RNA for antigen expression.

BACKGROUND

Infectious diseases and cancer represent significant burdens on health worldwide. According to the World Health Organization (WHO), lower respiratory tract infection was the deadliest infectious disease worldwide in 2016, causing approximately 3 million deaths. The impact of infectious diseases is illustrated by the coronavirus disease 2019 (COVID-19) pandemic caused by severe acute respiratory syndrome-coronavirus-2 (SARS-CoV-2). SARS-CoV-2 is a novel coronavirus that was first identified in December 2019 in Wuhan, China and that has caused more than 20 million confirmed infections with more than 700,000 deaths worldwide as of August 2020. Current control measures to curb the rapid worldwide spread of SARS-CoV-2, such as national lockdowns, closure of work places and schools, and reduction of international travel are threatening to result in a global economic recession to an extent not seen since the Great Depression.

Cancer is the second leading cause of death globally, accounting for approximately 9.6 million deaths worldwide in 2018. Cancer is a large group of diseases that can affect almost any organ or tissue in the body. Cancer burden continues to grow globally, exerting physical, emotional, and financial strains on patients and health care providers.

Self-replicating ribonucleic acids (RNAs), e.g., derived from viral replicons, are useful for expression of proteins, such as heterologous proteins, for a variety of purposes, such as expression of therapeutic proteins and expression of antigens for vaccines. A desirable property of such replicons is the ability for sustained expression of the protein.

Few treatments for infections caused by viruses and eukaryotic organisms are available, and resistance to antibiotics for the treatment of bacterial infections is increasing. In addition, rapid responses, including rapid vaccine development, are required to effectively control emerging infectious diseases and pandemics. Moreover, many cancer treatments include costly and painful surgeries and chemotherapies that are often unsuccessful or only modestly prolong life despite serious side effects. Thus, there exists a need for the prevention and/or treatment of infectious diseases and cancer.

SUMMARY

In one aspect, the present disclosure provides a nucleic acid molecule comprising (i) a first polynucleotide encoding one or more viral replication proteins, wherein the first polynucleotide is codon-optimized as compared to a wild-type polynucleotide encoding the one or more viral replication proteins; and (ii) a second polynucleotide comprising a first transgene encoding a first antigenic protein or a fragment thereof, wherein the first antigenic protein is a coronavirus protein.

In some embodiments, the one or more viral replication proteins are alphavirus proteins or rubivirus proteins.

In some embodiments, the alphavirus proteins are from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof.

In some embodiments, the first polynucleotide encodes a polyprotein comprising an alphavirus nsP1 protein, an alphavirus nsP2 protein, an alphavirus nsP3 protein, an alphavirus nsP4 protein, or any combination thereof.

In some embodiments, the first polynucleotide encodes a polyprotein comprising an alphavirus nsP1 protein, an alphavirus nsP2 protein, an alphavirus nsP3 protein, or any combination thereof, and an alphavirus nsP4 protein.

In some embodiments, the nucleic acid molecule further comprises a first intergenic region between a sequence encoding the polyprotein comprising an alphavirus nsP1 protein, an alphavirus nsP2 protein, an alphavirus nsP3 protein, or any combination thereof, and a sequence encoding an alphavirus nsP4 protein.

In some embodiments, the first intergenic region comprises an alphavirus sequence.

In some embodiments, the first polynucleotide comprises a sequence having at least 80% identity to a sequence of SEQ ID NO:72.

In some embodiments, the nucleic acid molecule further comprises a 5' untranslated region (UTR).

In some embodiments, the 5' UTR comprises a viral 5' UTR, a non-viral 5' UTR, or a combination of viral and non-viral 5' UTR sequences.

In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR).

In some embodiments, the 3' UTR comprises a viral 3' UTR, a non-viral 3' UTR, or a combination of viral and non-viral 3' UTR sequences. In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence.

In some embodiments, the 3' UTR comprises a sequence of SEQ ID NO:76.

In some embodiments, the antigenic protein is a SARS-CoV-2 protein.

In some embodiments, the antigenic protein is a SARS-CoV-2 spike glycoprotein.

In some embodiments, the SARS-CoV-2 spike glycoprotein is a wild-type SARS-CoV-2 spike glycoprotein having an amino acid sequence of SEQ ID NO:123.

In some embodiments, the second polynucleotide comprises a sequence having at least 85% identity to a sequence of SEQ ID NO:121 or SEQ ID NO:122.

In some embodiments, the second polynucleotide comprises at least two transgenes.

In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the second transgene encodes a second coronavirus protein.

In some embodiments, the first polynucleotide is located 5' of the second polynucleotide.

In some embodiments, the nucleic acid molecule further comprises a second intergenic region located between the first polynucleotide and the second polynucleotide.

In some embodiments, the second intergenic region comprises a sequence having at least 85% identity to a sequence of SEQ ID NO:77.

In some embodiments, the nucleic acid molecule is
(a) a DNA molecule; or
(b) an RNA molecule, wherein T is substituted with U.

In some embodiments, the DNA molecule further comprises a promoter.

In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap.

In some embodiments, the 5' cap has a Cap 1 structure, a Cap 1 ($^{m6}$A) structure, a Cap 2 structure, a Cap 0 structure, or any combination thereof.

In another aspect, the disclosure provides a nucleic acid molecule comprising
(a) a sequence of SEQ ID NO:124;
(b) a sequence of SEQ ID NO:124, wherein T is substituted with U;
(c) a sequence of SEQ ID NO:125; or
(d) a sequence of SEQ ID NO:125, wherein T is substituted with U.

In some embodiments, the nucleic acid molecule is an RNA molecule.

In some embodiments, the nucleic acid molecule further comprises a 5' cap having a Cap 1 structure.

In yet another aspect the disclosure provides a nucleic acid molecule comprising:
(i) a first polynucleotide comprising a sequence having at least 80% identity to a sequence of SEQ ID NO:72; and
(ii) a second polynucleotide comprising a first transgene encoding a first antigenic protein or a fragment thereof, wherein the first antigenic protein is a coronavirus protein.

In some embodiments, the nucleic acid molecule further comprises a 5' untranslated region (UTR).

In some embodiments, the 5' UTR comprises a viral 5' UTR, a non-viral 5' UTR, or a combination of viral and non-viral 5' UTR sequences.

In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR).

In some embodiments, the 3' UTR comprises a viral 3' UTR, a non-viral 3' UTR, or a combination of viral and non-viral 3' UTR sequences.

In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence.

In some embodiments, the 3' UTR comprises a sequence of SEQ ID NO:76.

In some embodiments, the antigenic protein is a SARS-CoV-2 protein.

In some embodiments, the antigenic protein is a SARS-CoV-2 spike glycoprotein.

In some embodiments, the SARS-CoV-2 spike glycoprotein is a wild-type SARS-CoV-2 spike glycoprotein having an amino acid sequence of SEQ ID NO:123.

In some embodiments, the second polynucleotide comprises a sequence having at least 85% identity to a sequence of SEQ ID NO:121 or SEQ ID NO:122.

In some embodiments, the second polynucleotide comprises at least two transgenes.

In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the second transgene encodes a second coronavirus protein.

In some embodiments, the first polynucleotide is located 5' of the second polynucleotide.

In some embodiments, the nucleic acid molecule further comprises a second intergenic region located between the first polynucleotide and the second polynucleotide.

In some embodiments, the second intergenic region comprises a sequence having at least 85% identity to a sequence of SEQ ID NO:77.

In some embodiments, the nucleic acid molecule is
(a) a DNA molecule; or
(b) an RNA molecule, wherein T is substituted with U.

In some embodiments, the DNA molecule further comprises a promoter.

In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap.

In some embodiments, the 5' cap has a Cap 1 structure, a Cap 1 ($^{m6}$A) structure, a Cap 2 structure, a Cap 0 structure, or any combination thereof.

In yet another aspect, the disclosure provides a composition comprising any of the nucleic acid molecules provided herein. In some embodiments, the composition further comprises a lipid.

In some embodiments, the lipid comprises an ionizable cationic lipid.

In some embodiments, the ionizable cationic lipid has a structure of or a pharmaceutically acceptable salt thereof.

In yet another aspect, the disclosure provides a composition comprising any of the nucleic acid molecules described herein and a lipid formulation.

In some embodiments, the lipid formulation comprises an ionizable cationic lipid.

In some embodiments, the ionizable cationic lipid has a structure of

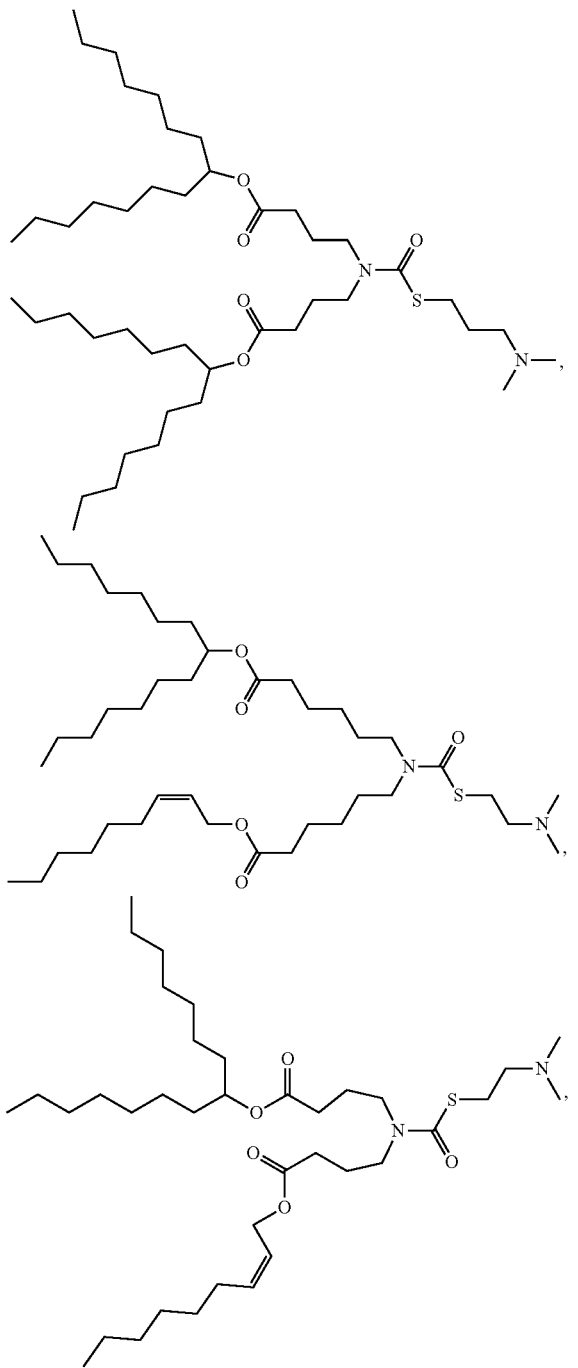

or a pharmaceutically acceptable salt thereof.

In some embodiments, the lipid formulation is selected from a lipoplex, a liposome, a lipid nanoparticle, a polymer-based carrier, an exosome, a lamellar body, a micelle, and an emulsion.

In some embodiments, the lipid formulation is a liposome selected from a cationic liposome, a nanoliposome, a proteoliposome, a unilamellar liposome, a multilamellar liposome, a ceramide-containing nanoliposome, and a multivesicular liposome.

In some embodiments, the lipid formulation is a lipid nanoparticle.

In some embodiments, the lipid nanoparticle has a size of less than about 200 nm. In some embodiments, the lipid nanoparticle has a size of less than about 150 nm. In some embodiments, the lipid nanoparticle has a size of less than about 100 nm. In some embodiments, the lipid nanoparticle has a size of about 55 nm to about 90 nm.

In some embodiments, the lipid formulation comprises one or more cationic lipids.

In some embodiments, the one or more cationic lipids is selected from 5-carboxyspermylglycinedioctadecylamide (DOGS), 2,3-dioleyloxy-N-[2(spermine-carboxamido) ethyl]-N,N-dimethyl-1-propanaminium (DOSPA), 1,2-Dioleoyl-3-Dimethylammonium-Propane (DODAP), 1,2-Dioleoyl-3-Trimethylammonium-Propane (DOTAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), and 2,2-dilinoleyl-4-dimethylaminoethyl-[1,3]-dioxolane or (DLin-K-XTC2-DMA).

In some embodiments, the lipid formulation comprises an ionizable cationic lipid.

In some embodiments, the ionizable cationic lipid has a structure of Formula I:

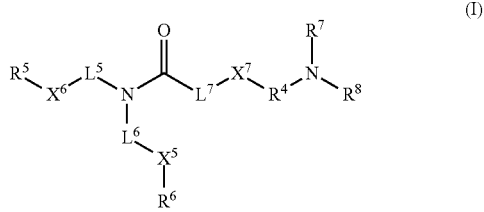

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; L is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, the ionizable cationic lipid is selected from
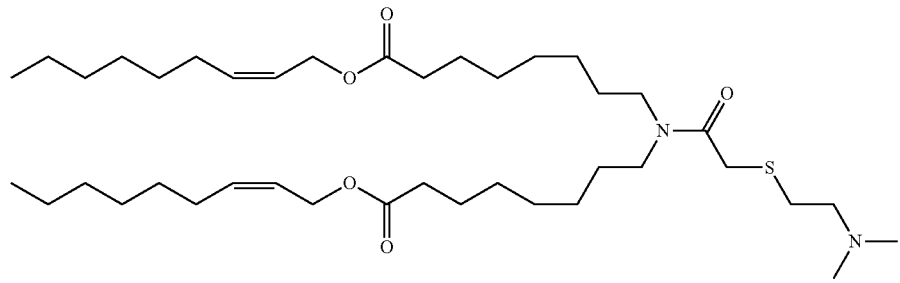
ATX-001
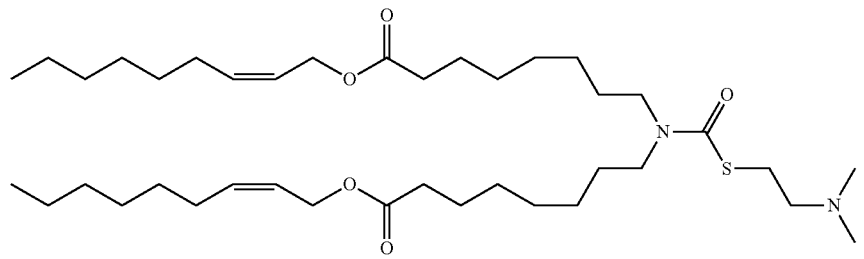
ATX-002
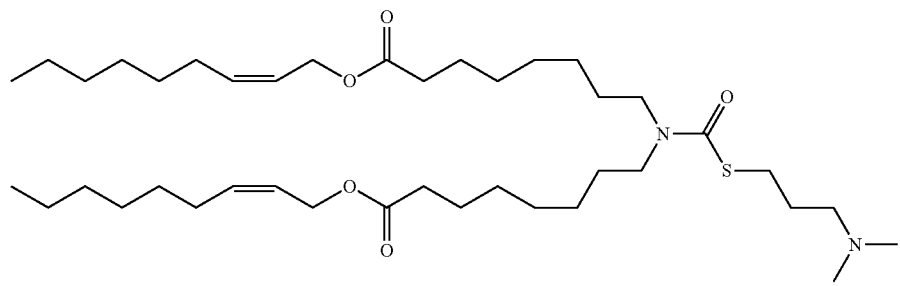
ATX-003
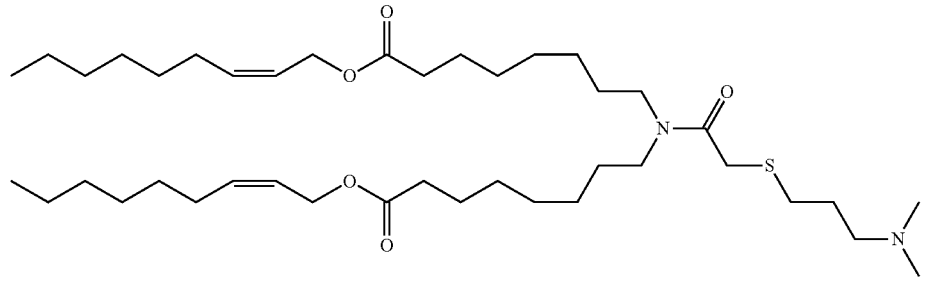
ATX-004
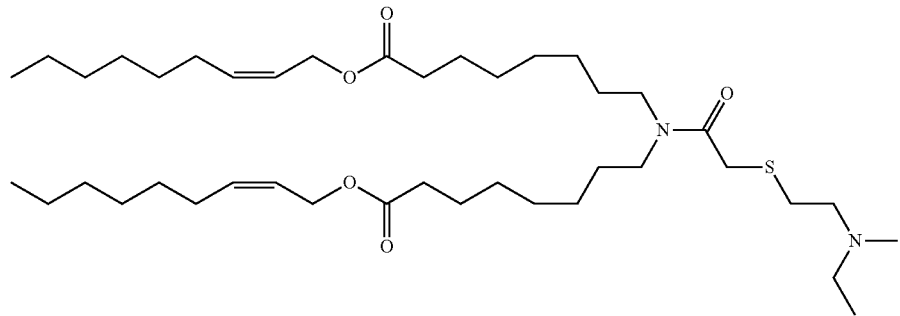
ATX-005

-continued
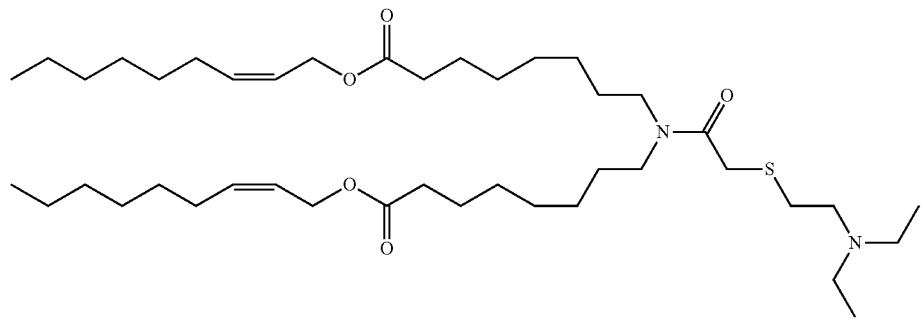
ATX-006
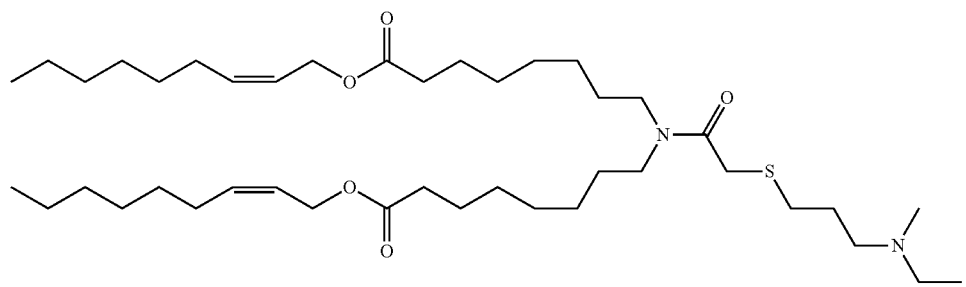
ATX-007
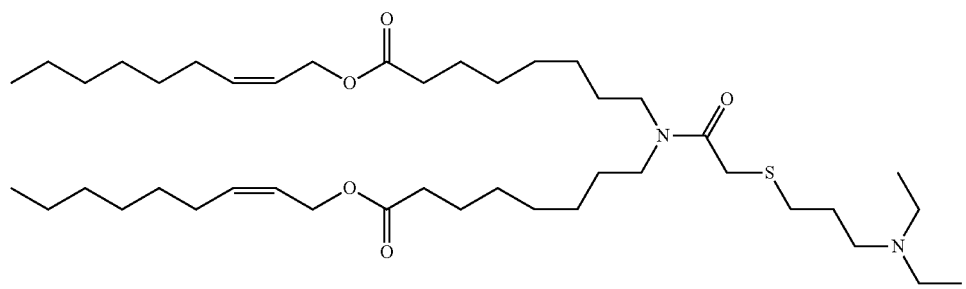
ATX-008
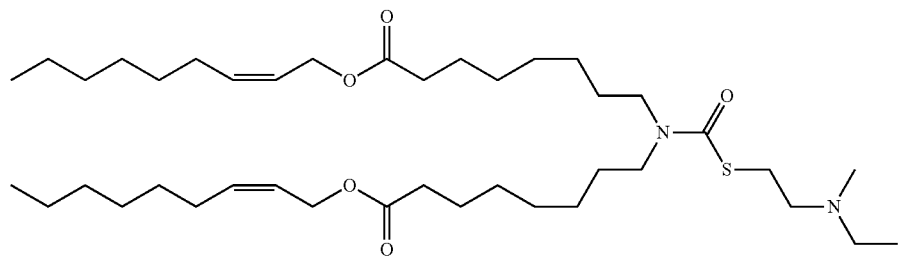
ATX-009
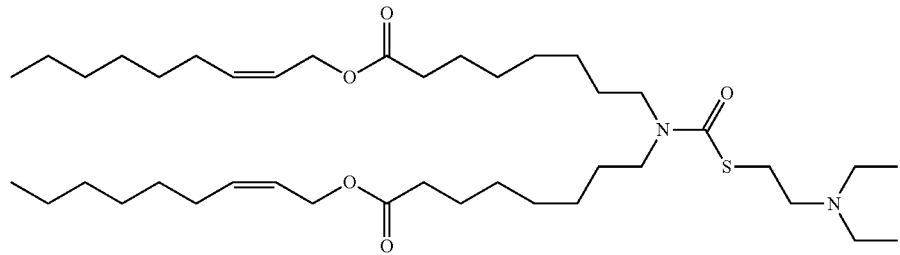
ATX-010

-continued
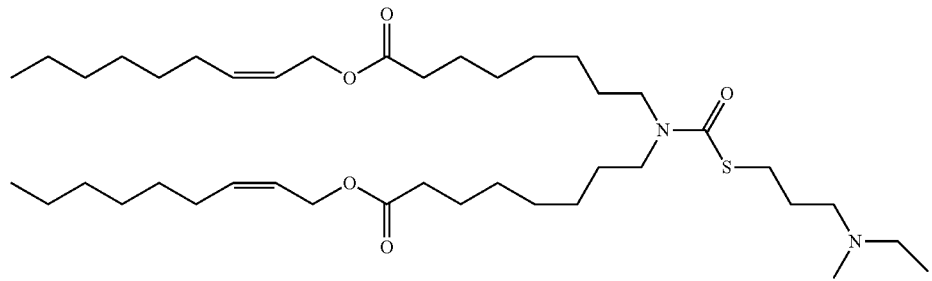
ATX-011
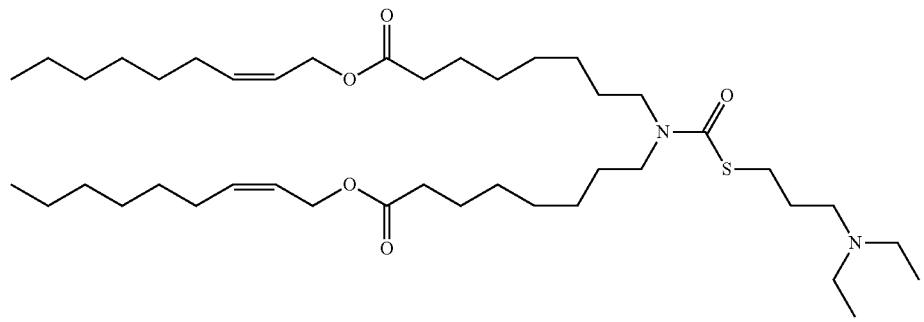
ATX-012
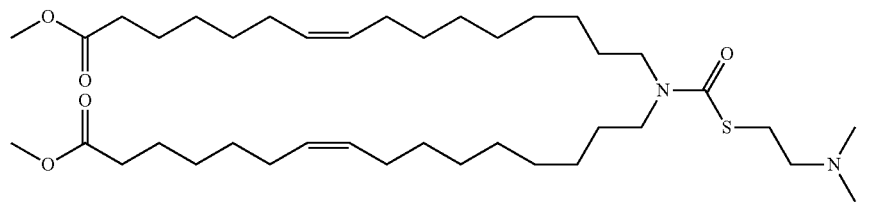
ATX-013
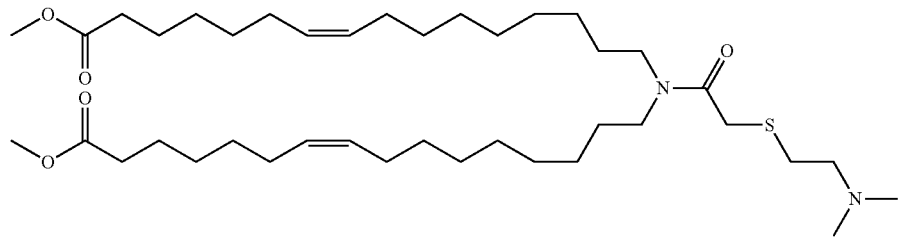
ATX-014
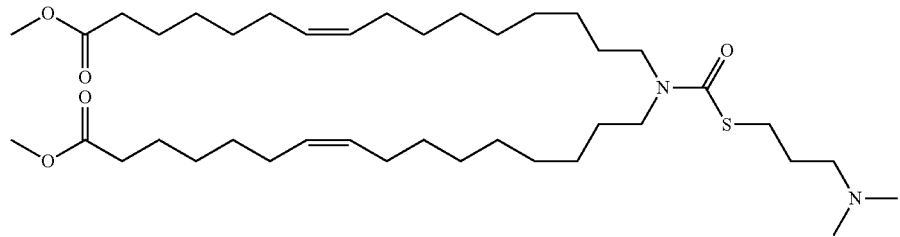
ATX-015
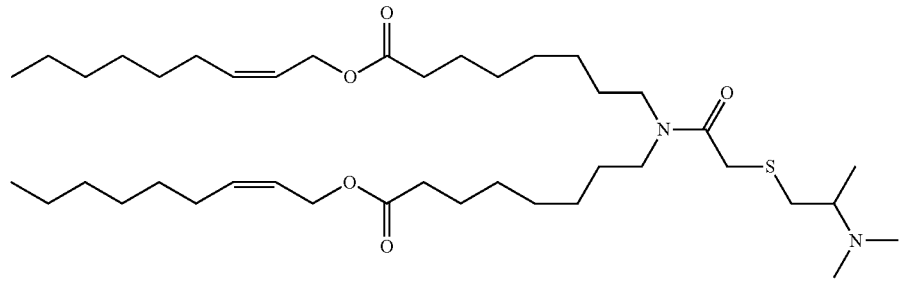
ATX-016

-continued
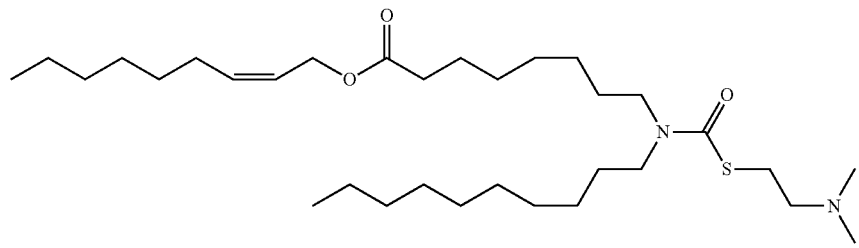
ATX-018
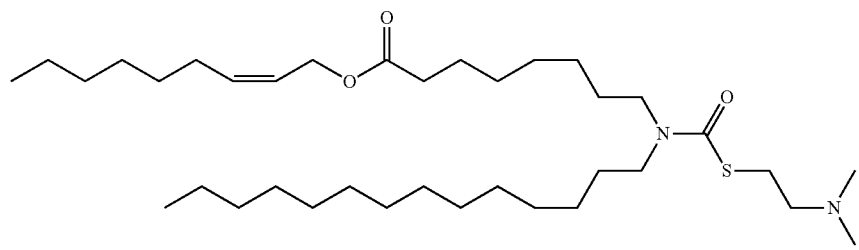
ATX-019
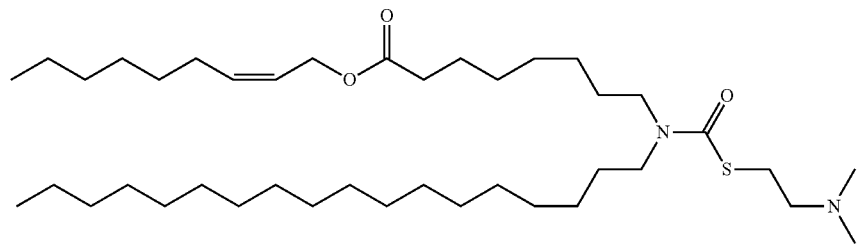
ATX-020
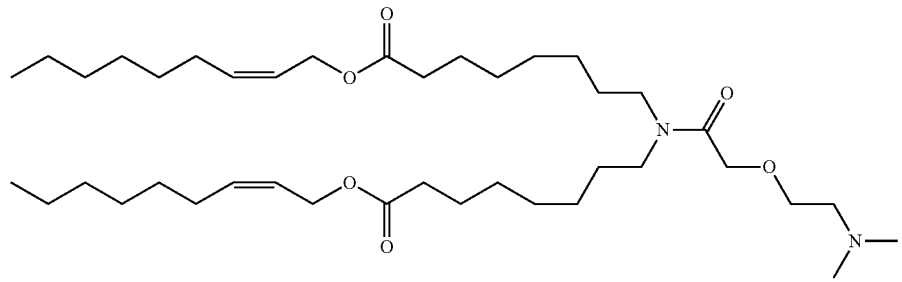
ATX-021
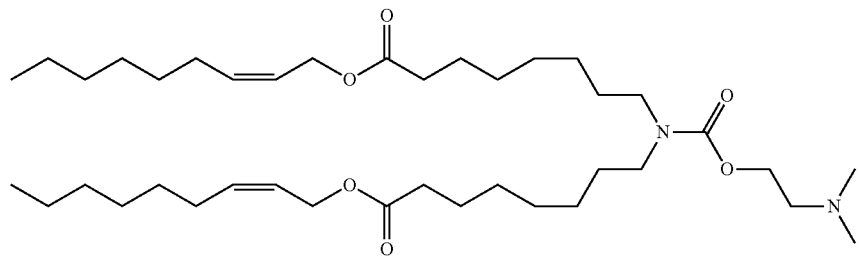
ATX-022
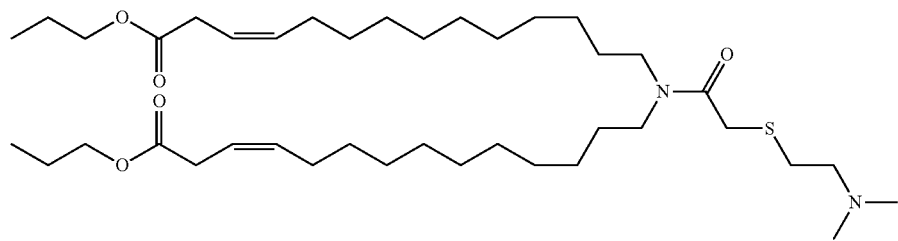
ATX-023

ATX-024
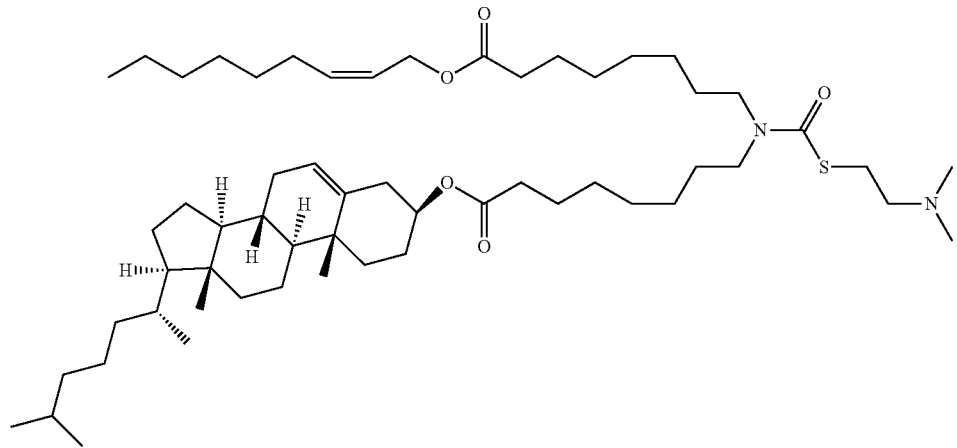
ATX-025
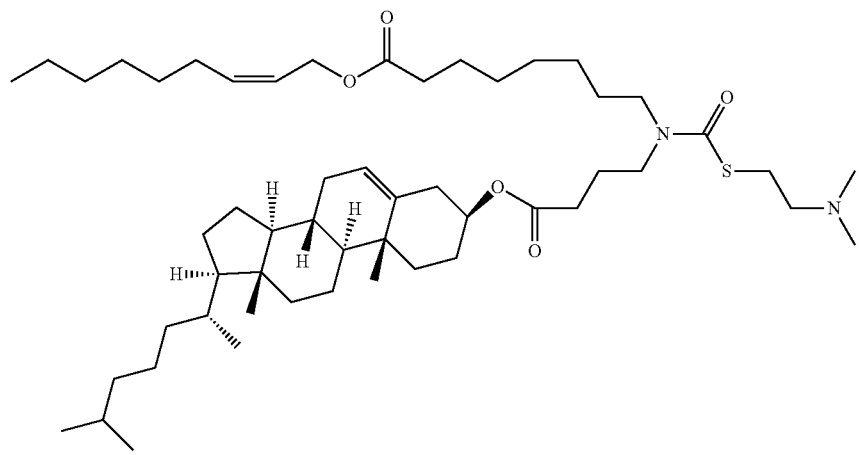
ATX-026
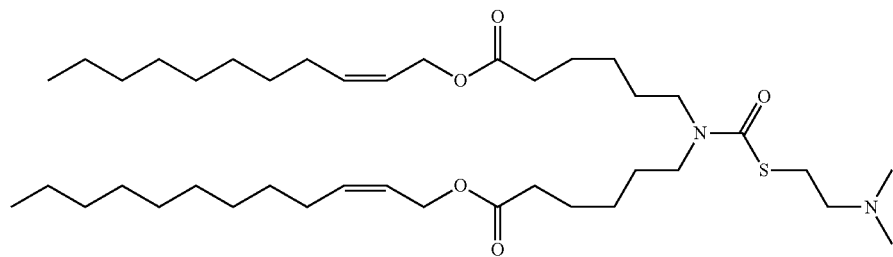
ATX-027
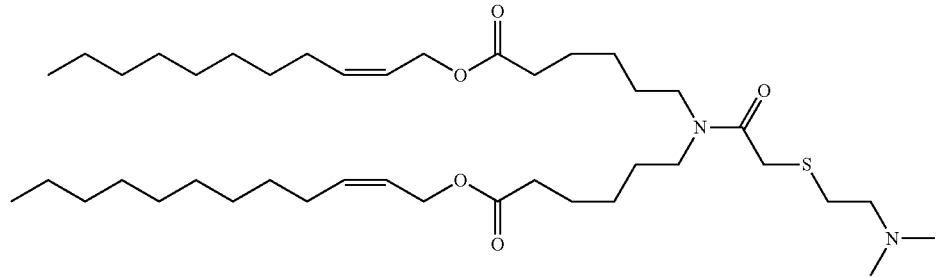

-continued
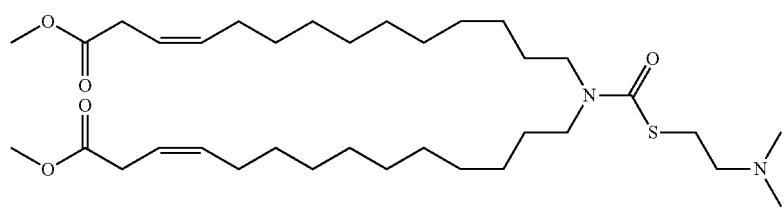
ATX-028
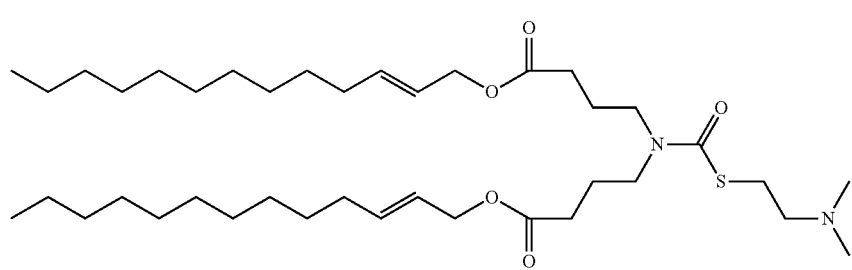
ATX-029
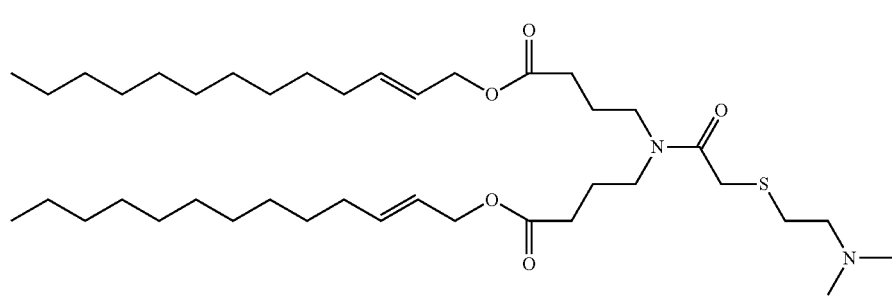
ATX-030
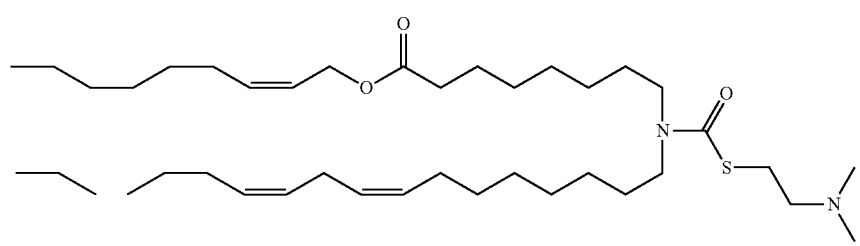
ATX-031
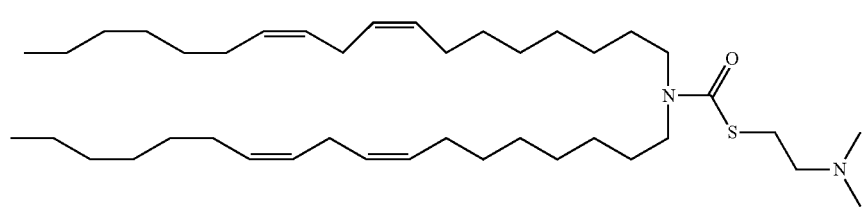
ATX-032

-continued
ATX-43
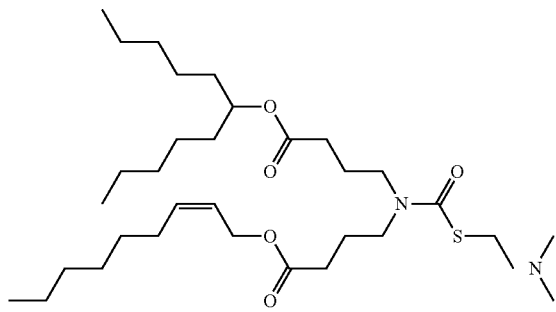
ATX-057
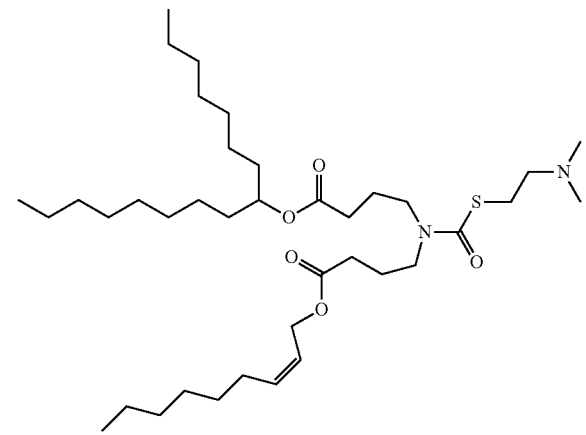
ATX-058
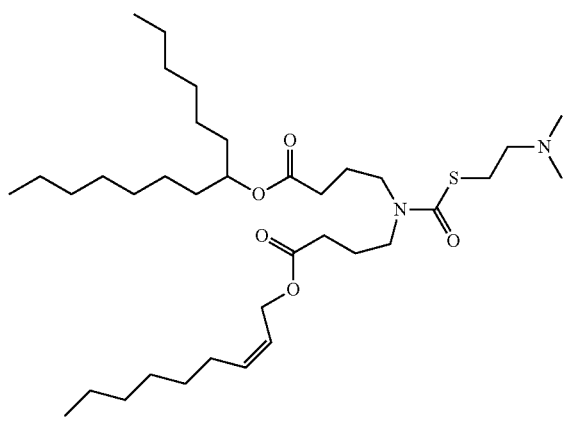
ATX-061
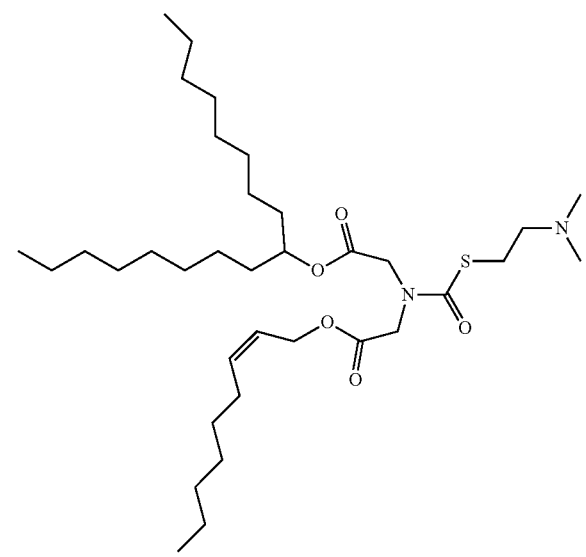
ATX-063
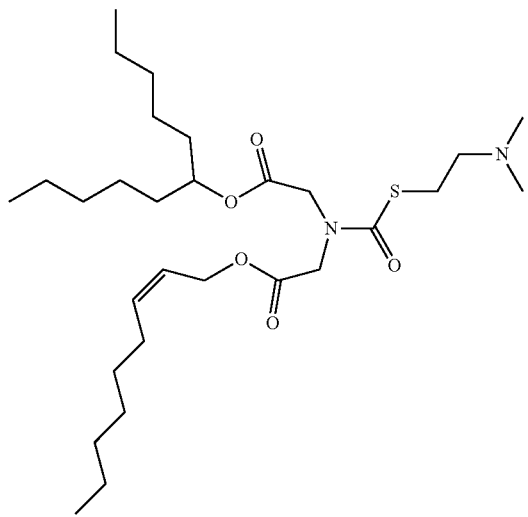
ATX-064
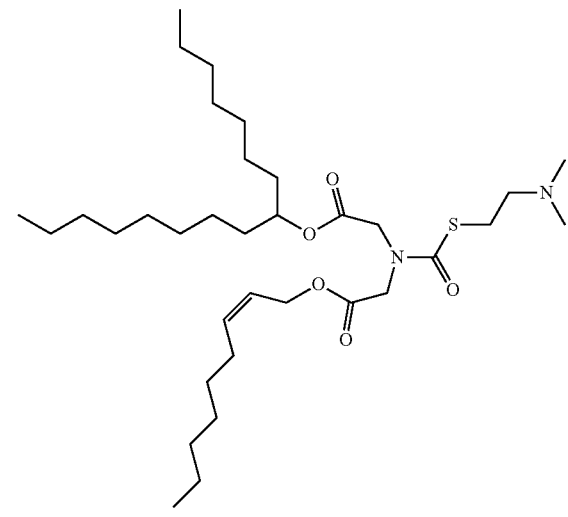

ATX-082
ATX-083
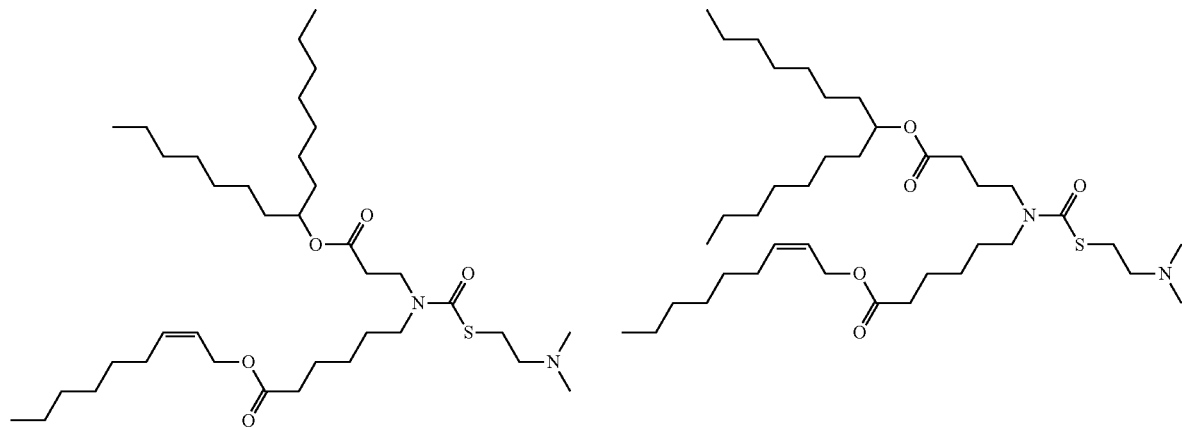
ATX-086
ATX-087
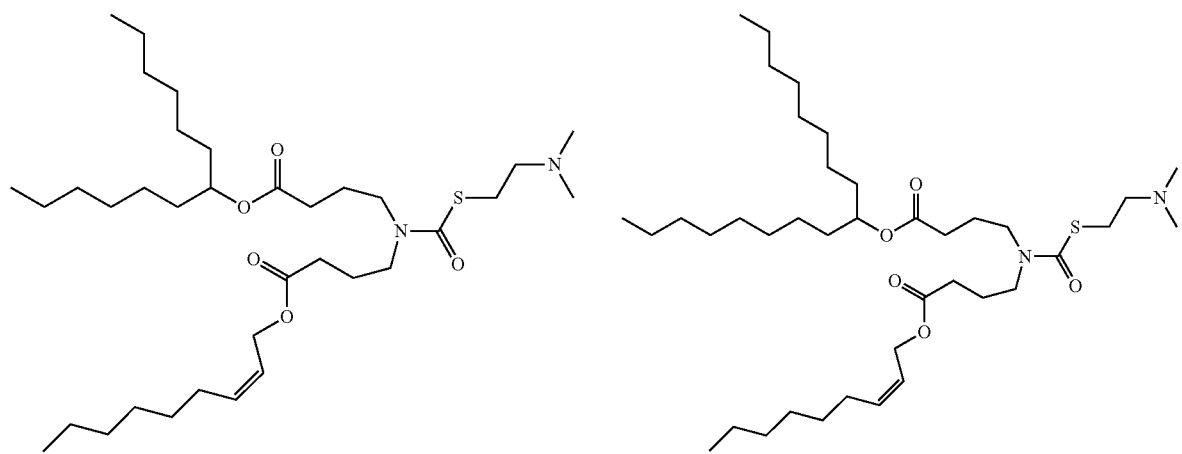
ATX-088
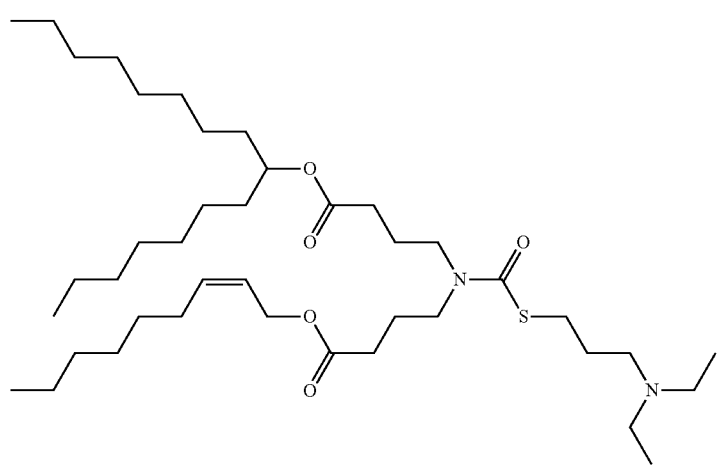

ATX-109
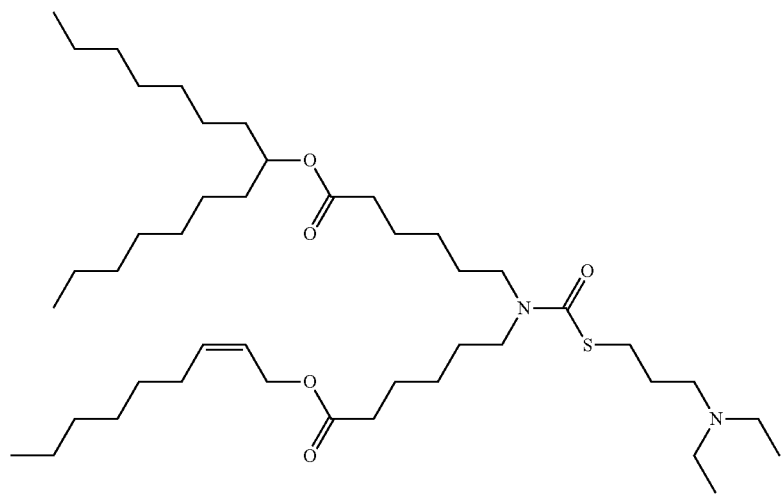
ATX-085
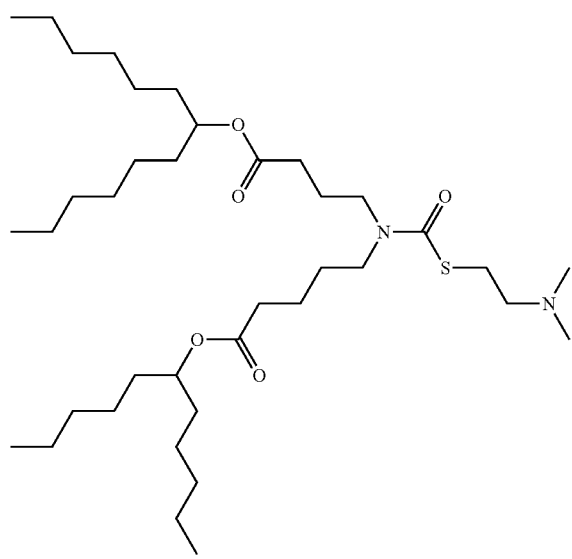
ATX-0121
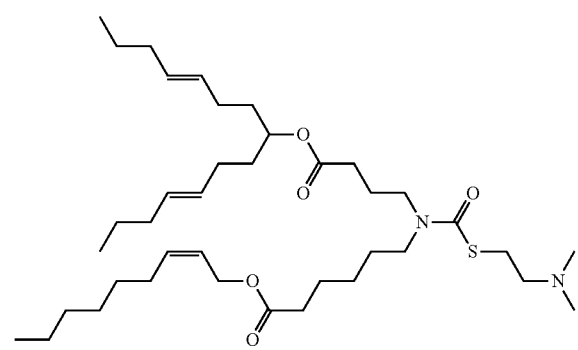
ATX-091
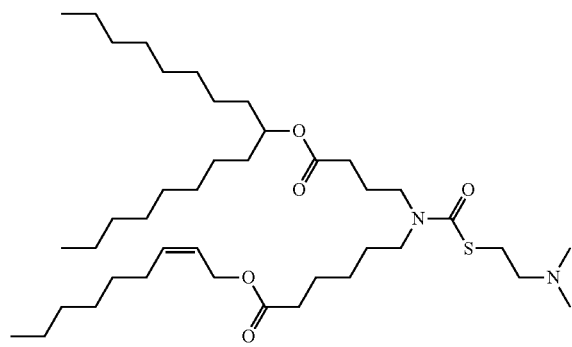
ATX-0102
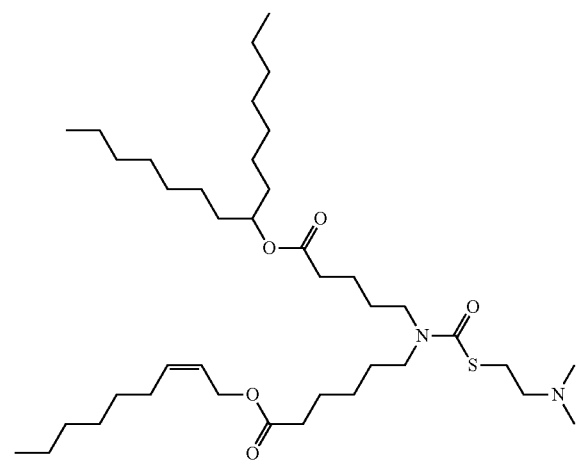

-continued
ATX-098
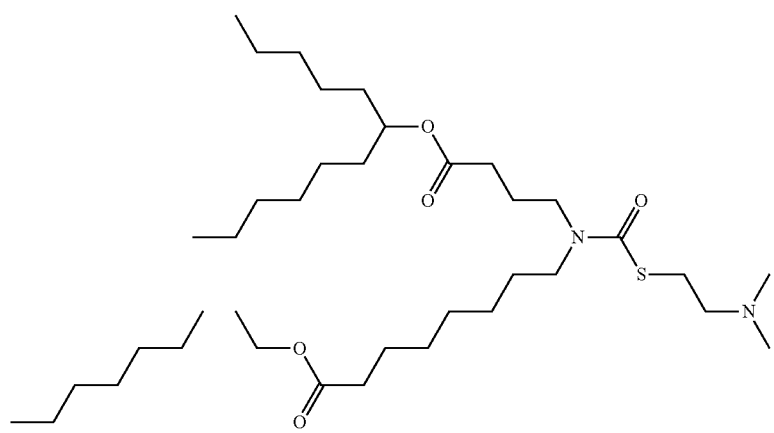
ATX-092
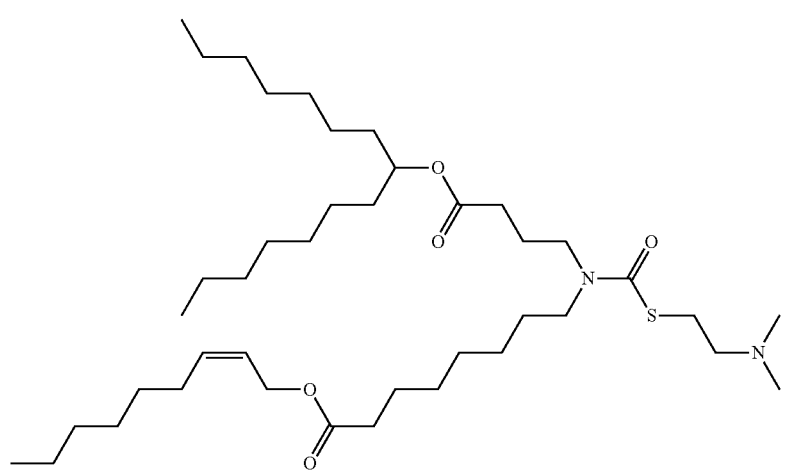
ATX-084
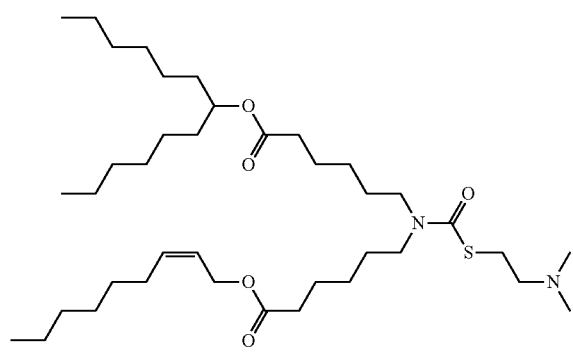
ATX-0125
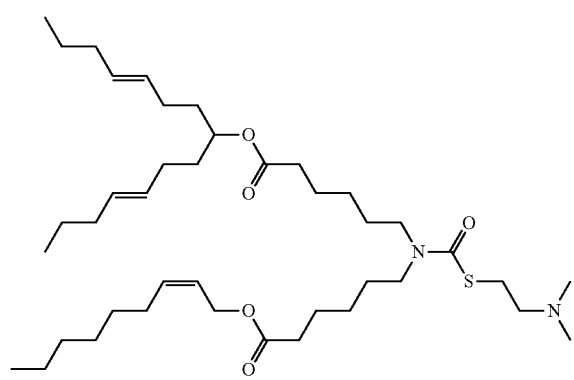

-continued
ATX-094
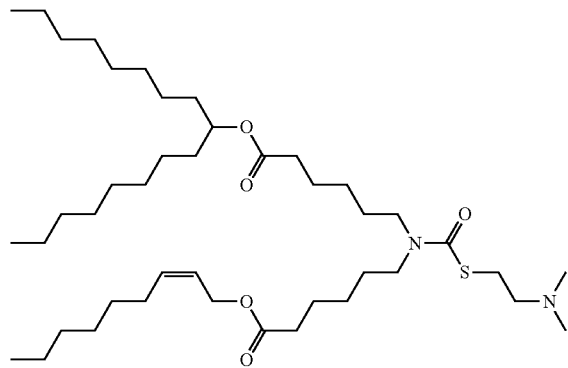
ATX-0110
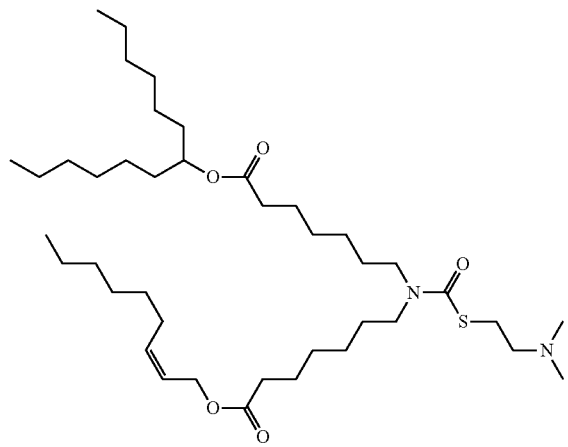
ATX-0118
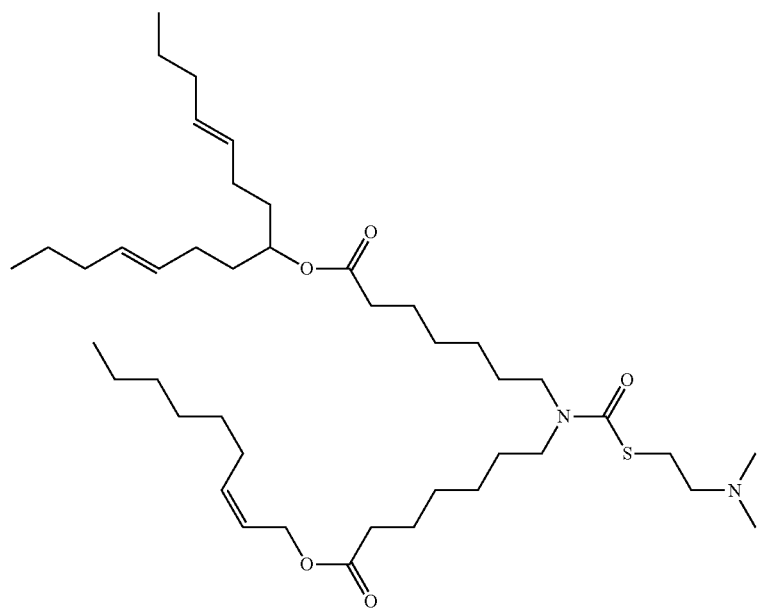
ATX-0108
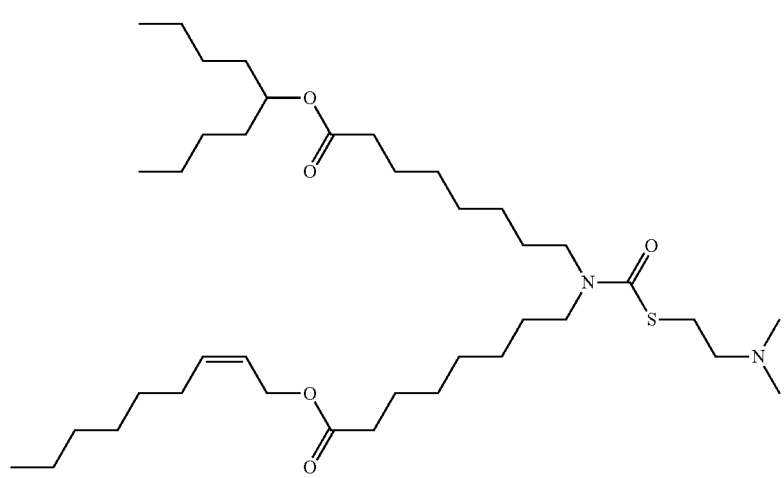

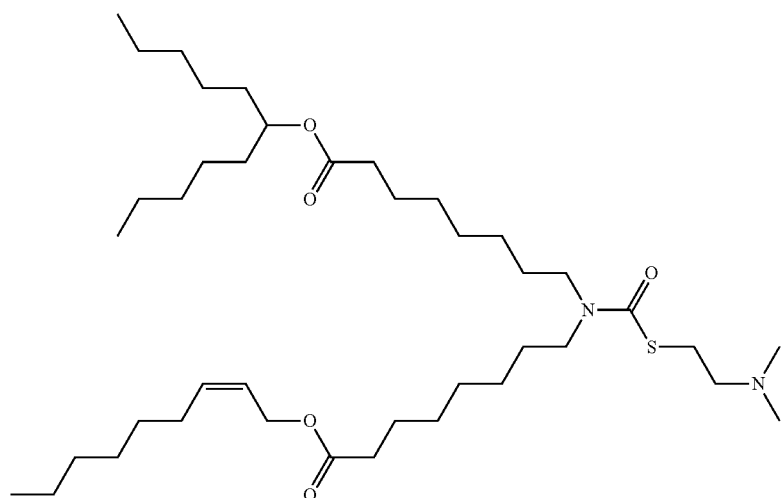
ATX-0107
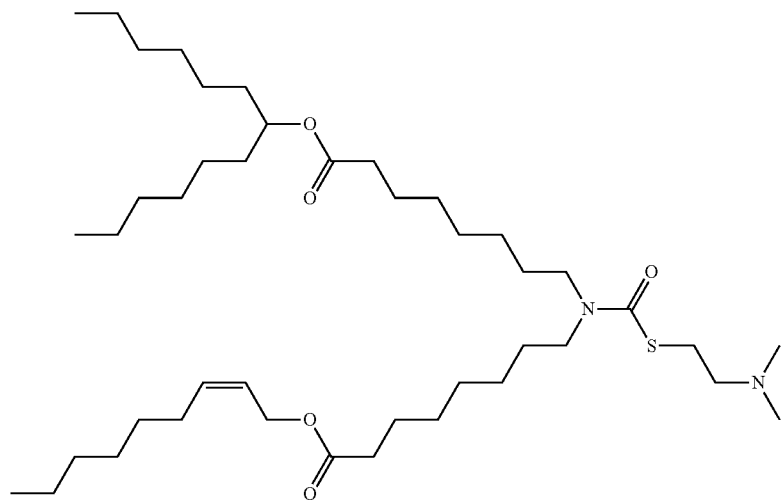
ATX-093
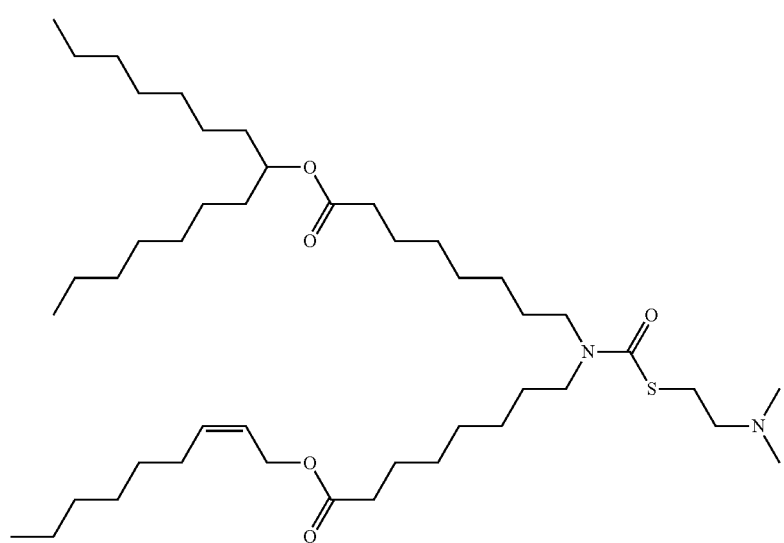
ATX-097

ATX-096
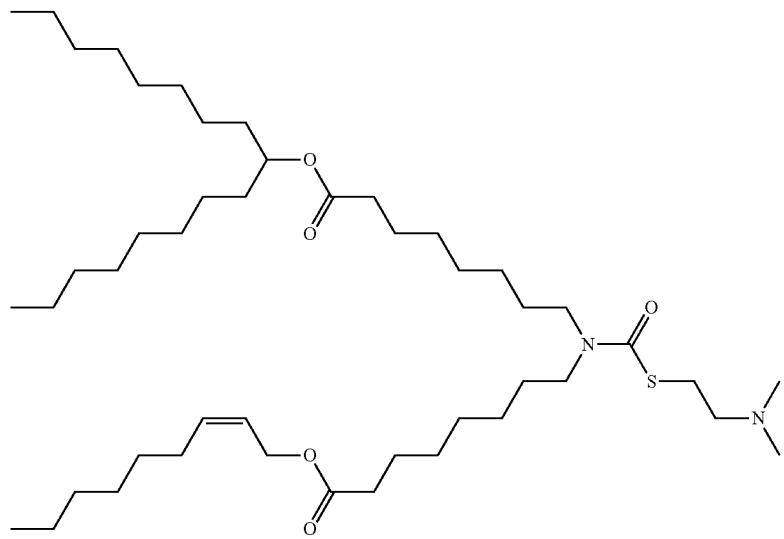
ATX-0111
ATX-0132
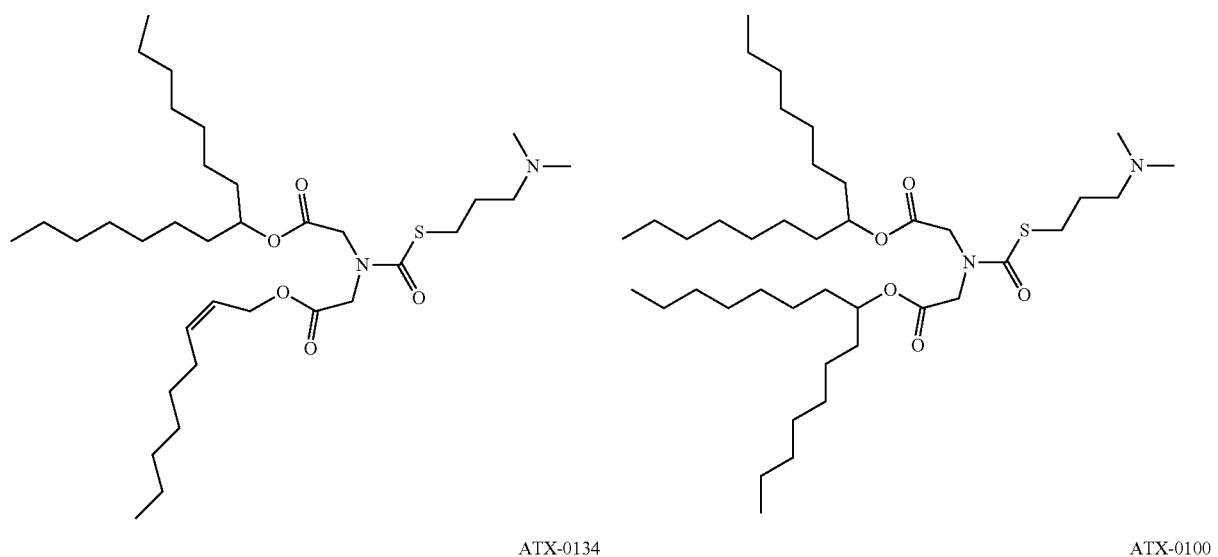
ATX-0134
ATX-0100
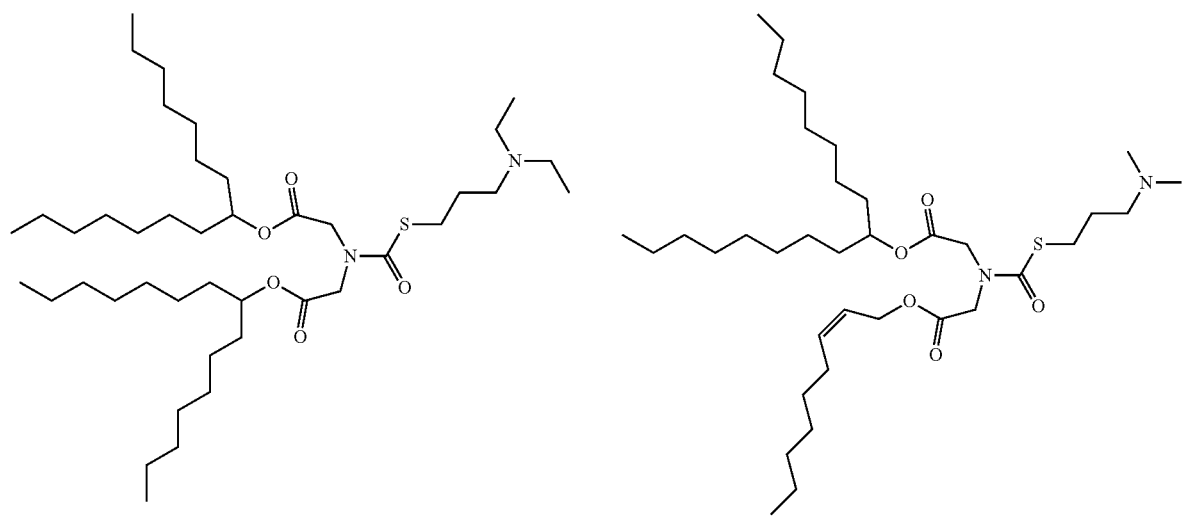

-continued
ATX-0117
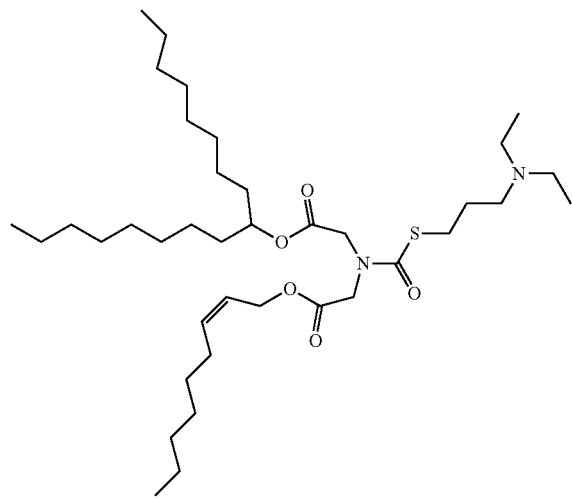
ATX-0114
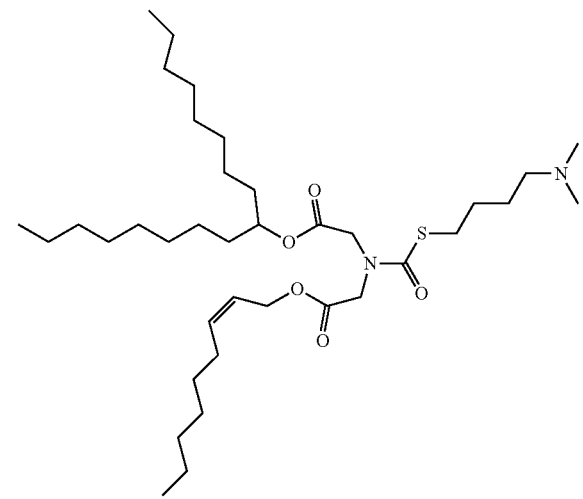
ATX-0115
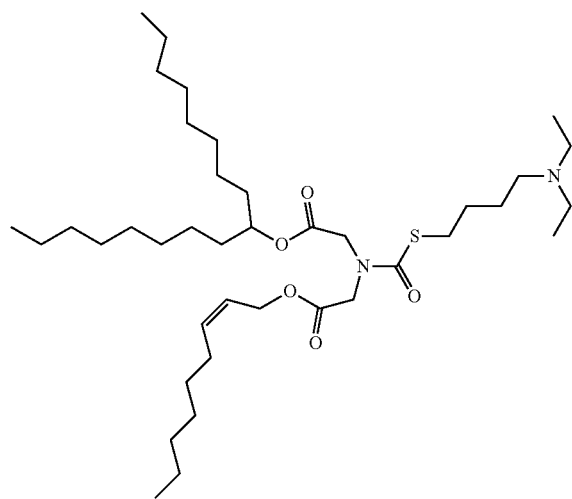
ATX-0101
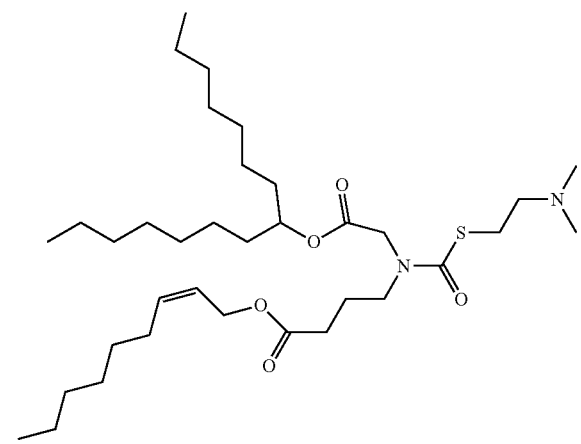
ATX-0106
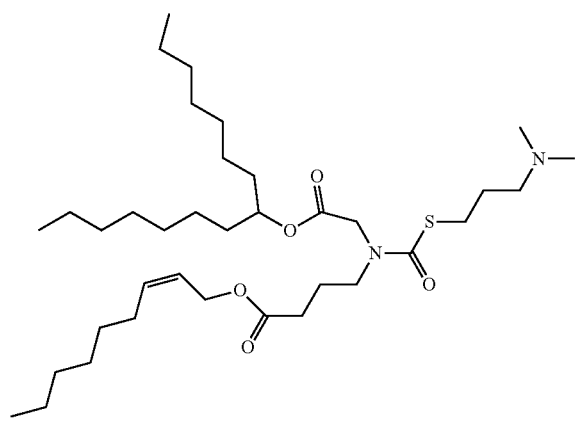
ATX-0116
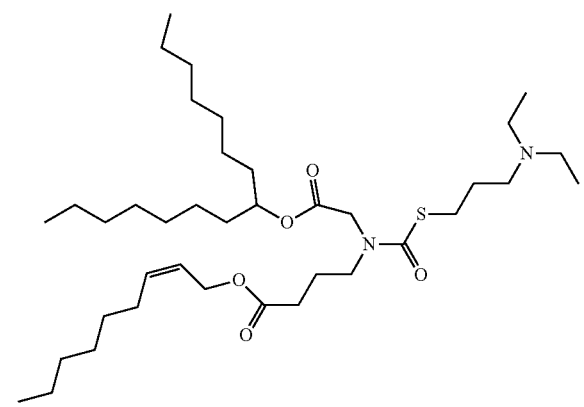

-continued
ATX-0123
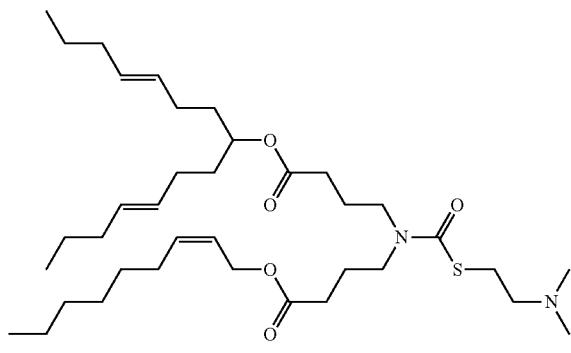
ATX-0122
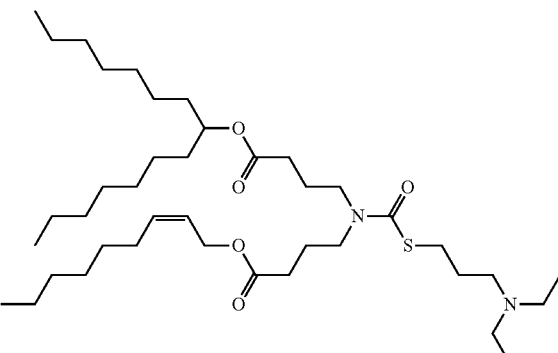
ATX-0124
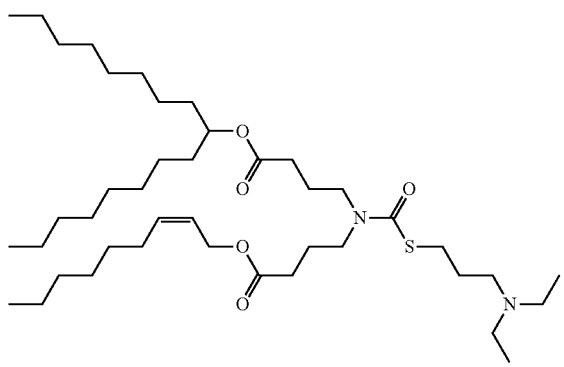
ATX-0129
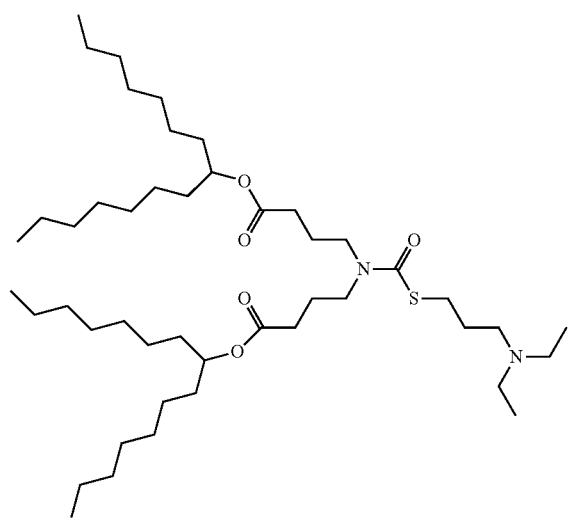
ATX-081
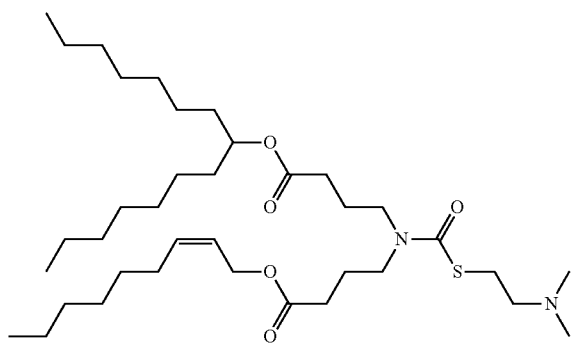
ATX-095
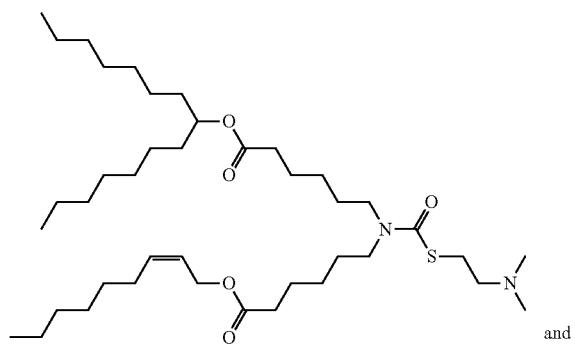
and

ATX-0126

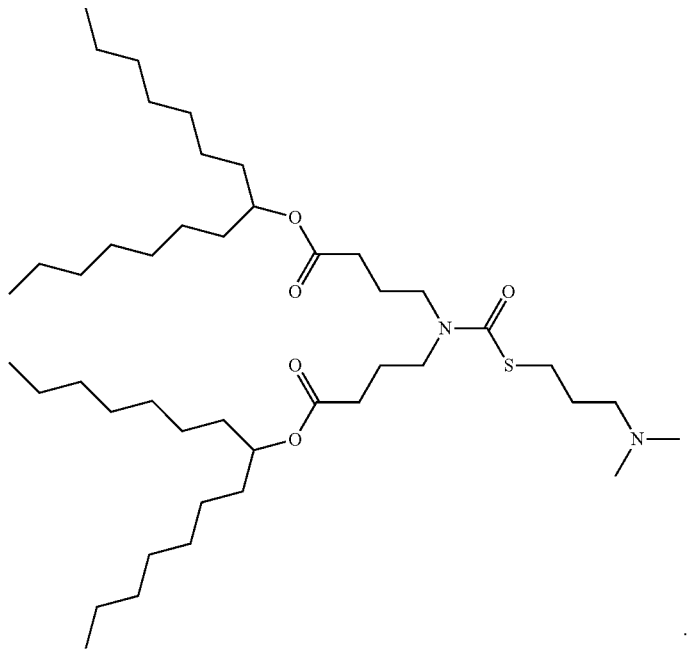

In some embodiments, the ionizable cationic lipid is ATX-126:

ATX-126

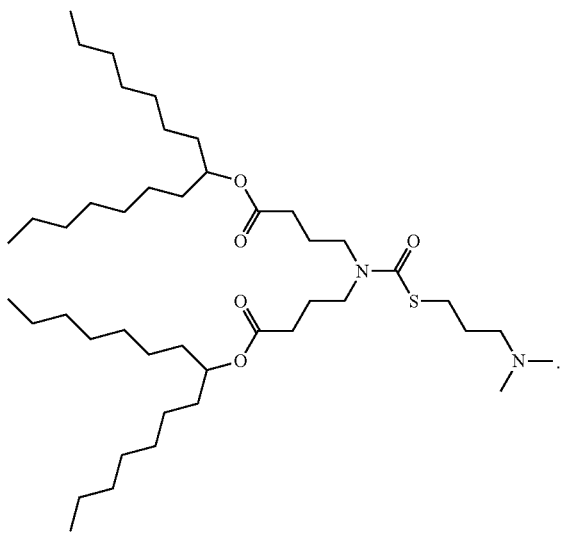

In some embodiments, the lipid formulation encapsulates the nucleic acid molecule.

In some embodiments, the lipid formulation is complexed to the nucleic acid molecule.

In some embodiments, the lipid formulation further comprises a helper lipid. In some embodiments, the helper lipid is a phospholipid. In some embodiments, the helper lipid is selected from diolcoylphosphatidyl ethanolamine (DOPE), dimyristoylphosphatidyl choline (DMPC), distearoylphosphatidyl choline (DSPC), dimyristoylphosphatidyl glycerol (DMPG), dipalmitoyl phosphatidylcholine (DPPC), and phosphatidylcholine (PC). In specific embodiments, the helper lipid is distearoylphosphatidylcholine (DSPC).

In some embodiments, the lipid formulation further comprises cholesterol.

In some embodiments, the lipid formulation further comprises a polyethylene glycol (PEG)-lipid conjugate. In some embodiments, the PEG-lipid conjugate is PEG-DMG. In some embodiments, the PEG-DMG is PEG2000-DMG.

In some embodiments, the lipid portion of the lipid formulation comprises about 40 mol % to about 60 mol % of the ionizable cationic lipid, about 4 mol % to about 16 mol % DSPC, about 30 mol % to about 47 mol % cholesterol, and about 0.5 mol % to about 3 mol % PEG2000-DMG.

In some embodiments, the lipid portion of the lipid formulation comprises about 42 mol % to about 58 mol % of the ionizable cationic lipid, about 6 mol % to about 14 mol % DSPC, about 32 mol % to about 44 mol % cholesterol, and about 1 mol % to about 2 mol % PEG2000-DMG.

In some embodiments, the lipid portion of the lipid formulation comprises about 45 mol % to about 55 mol % of the ionizable cationic lipid, about 8 mol % to about 12 mol % DSPC, about 35 mol % to about 42 mol % cholesterol, and about 1.25 mol % to about 1.75 mol % PEG2000-DMG.

In some embodiments, the composition has a total lipid:nucleic acid molecule weight ratio of about 50:1 to about 10:1. In some embodiments, the composition has a total lipid:nucleic acid molecule weight ratio of about 44:1 to about 24:1. In some embodiments, the composition has a total lipid:nucleic acid molecule weight ratio of about 40:1 to about 28:1. In some embodiments, the composition has a total lipid:nucleic acid molecule weight ratio of about 38:1 to about 30:1. In some embodiments, the composition has a total lipid:nucleic acid molecule weight ratio of about 37:1 to about 33:1. In some embodiments, the composition comprises a HEPES or TRIS buffer at a pH of about 7.0 to about 8.5.

In some embodiments, the HEPES or TRIS buffer is at a concentration of about 7 mg/mL to about 15 mg/mL.

In some embodiments, the composition further comprises about 2.0 mg/mL to about 4.0 mg/mL of NaCl.

In some embodiments, the composition further comprises one or more cryoprotectants.

In some embodiments, the one or more cryoprotectants are selected from sucrose, glycerol, or a combination of sucrose and glycerol.

In some embodiments, the composition comprises a combination of sucrose at a concentration of about 70 mg/mL to about 110 mg/mL of sucrose and glycerol at a concentration of about 50 mg/mL to about 70 mg/mL.

In some embodiments, the composition is a lyophilized composition.

In some embodiments, the lyophilized composition comprises one or more lyoprotectants.

In some embodiments, the lyophilized composition comprises a poloxamer, potassium sorbate, sucrose, or any combination thereof.

In some embodiments, the poloxamer is poloxamer 188.

In some embodiments, the lyophilized composition comprises about 0.01 to about 1.0% w/w of the nucleic acid molecule.

In some embodiments, the lyophilized composition comprises about 1.0 to about 5.0% w/w lipids.

In some embodiments, the lyophilized composition comprises about 0.5 to about 2.5% w/w of TRIS buffer.

In some embodiments, the lyophilized composition comprises about 0.75 to about 2.75% w/w of NaCl.

In some embodiments, the lyophilized composition comprises about 85 to about 95% w/w of a sugar. In some embodiments, the sugar is sucrose.

In some embodiments, the lyophilized composition comprises about 0.01 to about 1.0% w/w of a poloxamer. In some embodiments, the poloxamer is poloxamer 188.

In some embodiments, the lyophilized composition comprises about 1.0 to about 5.0% w/w of potassium sorbate.

In some embodiments, the nucleic acid molecule comprises
 (a) a sequence of SEQ ID NO:124;
 (b) a sequence of SEQ ID NO:124, wherein T is substituted with U;
 (c) a sequence of SEQ ID NO:125; or
 (d) a sequence of SEQ ID NO:125, wherein T is substituted with U.

In yet another aspect, the disclosure provides a lipid nanoparticle composition comprising
 a. a lipid formulation comprising
  i. about 45 mol % to about 55 mol % of an ionizable cationic lipid having the structure of ATX-126:

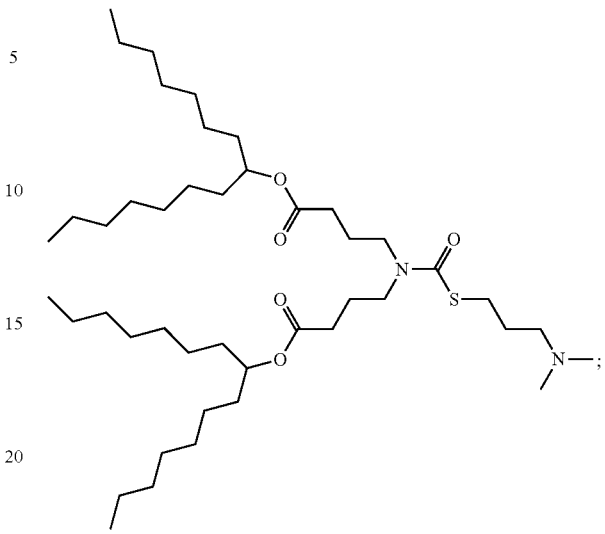

ATX-126 ii. about 8 mol % to about 12 mol % DSPC;
  iii. about 35 mol % to about 42 mol % cholesterol; and
  iv. about 1.25 mol % to about 1.75 mol % PEG2000-DMG; and
 b. a nucleic acid molecule having at least 85% sequence identity to SEQ ID NO:125;
wherein the lipid formulation encapsulates the nucleic acid molecule and the lipid nanoparticle has a size of about 60 to about 90 nm.

In yet another aspect, the disclosure provides a method for administering any of the compositions described herein to a subject in need thereof, wherein the composition is administered intramuscularly, subcutaneously, intradermally, transdermally, intranasally, orally, sublingually, intravenously, intraperitoneally, topically, by aerosol, or by a pulmonary route. In specific embodiments, n the composition is administered intramuscularly.

In yet another aspect, the disclosure provides a method of administering any of the compositions described herein to a subject in need thereof, wherein the composition is lyophilized and is reconstituted prior to administration.

In yet another aspect, the disclosure provides a method of ameliorating COVID-19, comprising administering any of the compositions described herein to a subject in need thereof.

In some embodiments, the composition is administered one time. In some embodiments, the composition is administered two times.

In yet another aspect, the disclosure provides a method of administering a booster dose to a vaccinated subject, comprising administering any of the compositions described herein to a subject who was previously vaccinated against coronavirus.

In some embodiments, the composition is administered at a dosage of about 0.01 µg to about 1,000 µg of nucleic acid.

In some embodiments, the composition is administered at a dosage of about 1, 2, 5, 7.5, or 10 µg of nucleic acid.

In yet another aspect, the disclosure provides a method of inducing an immune response in a subject comprising administering to the subject an effective amount of any of the nucleic acid molecules described herein.

In some embodiments, the nucleic acid molecule may be administered intramuscularly, subcutaneously, intradermally, transdermally, intranasally, orally, sublingually, intravenously, intraperitoneally, topically, by aerosol, or by a pulmonary route.

In yet another aspect, the disclosure provides a method of inducing an immune response in a subject comprising administering to the subject an effective amount of any of the compositions described herein.

In some embodiments, the composition may be administered intramuscularly, subcutaneously, intradermally, transdermally, intranasally, orally, sublingually, intravenously, intraperitoneally, topically, by aerosol, or by a pulmonary route.

In some embodiments, the nucleic acid molecules described herein may be used in inducing an immune response to the first antigenic protein or fragment thereof.

In some embodiments, the nucleic acid molecules described herein may be used in the manufacture of a medicament for inducing an immune response to the first antigenic protein or fragment thereof.

BRIEF DESCRIPTION OF THE DRAWINGS

FIGS. 1A-1D show design and expression of a SARS-CoV-2 vaccine in mRNA and self-replicating RNA (STARR™) platforms. (1A) Schematic diagram of the SARS-CoV-2 self-replicating STARR™ RNA and mRNA vaccine constructs. The STARR™ construct encodes for the four non-structural proteins, ns1-ns4, from Venezuelan equine encephalitis virus (VEEV) and the SARS-CoV-2 full length spike (S) protein. The mRNA construct codes for the SARS-CoV-2 full length spike S protein. (1B) Physical characteristics and RNA trapping efficiency of the LNP in the mRNA and STARR™ (self-replicating RNA corresponding to SEQ ID NO:125; referred to herein as "STARR™ SARS-CoV-2 RNA") vaccines. (1C) Western blot detection of SARS-CoV-2 S protein following transfection of HEK293 cells with the STARR™ RNA and mRNA constructs. (1D) In vivo comparison of protein expression following intramuscular (IM) administration of LNP containing luciferase-expressing STARR™ RNA or mRNA. Balb/c mice (n=3/group) were injected IM with 0.2 μg, 2.0 μg and 10.0 μg of STARR™ RNA or mRNA in lipid formulation. Luciferase expression was measured by in vivo bioluminescence on days 1, 3 and 7 post-IM administration. S domain 1=S1, S domain 2=S2, transmembrane domain=TM, cytoplasmic domain=CP.

FIGS. 2A-2I show clinical scores, mouse weights and transcriptomic analysis of immune genes following vaccination with STARR™ RNA or mRNA SARS-CoV-2 vaccine candidates. (2A) C57BL/6 mice were immunized with either PBS, mRNA or STARR™ SARS-CoV-2 RNA (doses 0.2 μg, 2 μg or 10 μg), weight and clinical scores assessed every day, bled at day 1 post-immunization, sacrificed at 7 days post-vaccination and lymph nodes harvested. Gene expression of inflammatory genes and immune genes were measured in whole blood (at day 1) and lymph nodes (at day 7), respectively. (2B) Expression of IFN and inflammatory response genes in whole blood presented as heatmap of z scores. (2C) Lymph node weights at 7 days post-vaccination. Principal component analysis (PCA) of immune gene expression following vaccination with mRNA or STARR™ SARS-CoV-2 RNA at doses (2D) 0.2 μg, (2E) 2 μg and (2F) 10 μg. Volcano plots of fold change of STARR™ SARS-CoV-2 RNA versus mRNA (x-axis) and Log 10 P-value of STARR™ SARS-CoV-2 RNA versus mRNA (y-axis) for doses (2G) 0.2 μg, (2H) 2 μg and (2I) 10 μg.

DETAILED DESCRIPTION

Figure 1C:
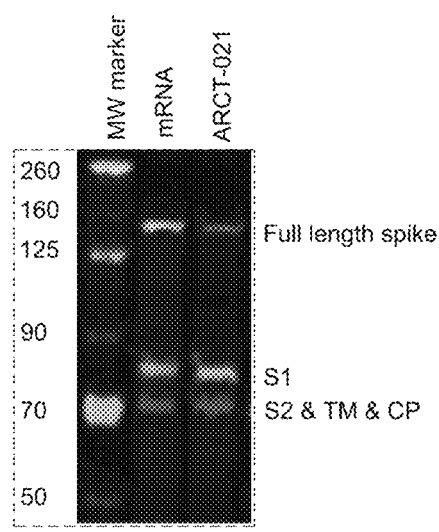

The present disclosure relates to self-replicating RNAs and nucleic acids encoding the same for expression of transgenes such as antigenic proteins and tumor antigens, for example. Also provided herein are methods of administration (e.g., to a host, such as a mammalian subject) of self-replicating RNAs, whereby the self-replicating RNA is translated in vivo and the heterologous protein-coding sequence is expressed and, e.g., can elicit an immune response to the heterologous protein-coding sequence in the recipient or provide a therapeutic effect, where the heterologous protein-coding sequence is a therapeutic protein. Self-replicating RNAs provided herein are useful as vaccines that can be rapidly generated and that can be effective at low and/or single doses. The present disclosure further relates to methods of inducing an immune response using self-replicating RNAs provided herein.

In some embodiments, an immune response can be elicited against Coronavirus: immunogens that include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Self-replicating RNAs are described, for example, in U.S. 2018/0036398, the contents of which are incorporated by reference in their entirety.

Definitions

As used herein, the term "fragment," when referring to a protein or nucleic acid, for example, means any shorter sequence than the full-length protein or nucleic acid. Accordingly, any sequence of a nucleic acid or protein other than the full-length nucleic acid or protein sequence can be a fragment. In some aspects, a protein fragment includes an epitope. In other aspects, a protein fragment is an epitope.

As used herein, the term "nucleic acid" refers to any deoxyribonucleic acid (DNA) molecule, ribonucleic acid (RNA) molecule, or nucleic acid analogues. A DNA or RNA molecule can be double-stranded or single-stranded and can be of any size. Exemplary nucleic acids include, but are not limited to, chromosomal DNA, plasmid DNA, cDNA, cell-free DNA (cfDNA), mitochondrial DNA, chloroplast DNA, viral DNA, mRNA, tRNA, rRNA, long non-coding RNA, siRNA, micro RNA (miRNA or miR), hnRNA, and viral RNA. Exemplary nucleic analogues include peptide nucleic acid, morpholino- and locked nucleic acid, glycol nucleic acid, and threose nucleic acid. As used herein, the term "nucleic acid molecule" is meant to include fragments of nucleic acid molecules as well as any full-length or non-fragmented nucleic acid molecule, for example. As used herein, the terms "nucleic acid" and "nucleic acid molecule" can be used interchangeably, unless context clearly indicates otherwise.

As used herein, the term "protein" refers to any polymeric chain of amino acids. The terms "peptide" and "polypeptide" can be used interchangeably with the term protein, unless context clearly indicates otherwise, and can also refer to a polymeric chain of amino acids. The term "protein" encompasses native or artificial proteins, protein fragments and polypeptide analogs of a protein sequence. A protein may be monomeric or polymeric. The term "protein" encompasses fragments and variants (including fragments of variants) thereof, unless otherwise contradicted by context.

In general, "sequence identity" or "sequence homology," which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby or the amino acid sequence of a polypeptide, and comparing these sequences to a second nucleotide or amino acid sequence. As used herein, the term "percent (%) sequence identity" or "percent (%) identity," also including "homology," refers to the percentage of amino acid residues or nucleotides in a sequence that are identical with the amino acid residues or nucleotides in a reference sequence after aligning the sequences and introducing gaps, if necessary, to achieve the maximum percent sequence identity, and not considering any conservative substitutions as part of the sequence identity. Thus, two or more sequences (polynucleotide or amino acid) can be compared by determining their "percent identity," also referred to as "percent homology." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul et al., J. Mol. Biol. 215:403-410 (1990); Karlin and Altschul, Proc. Natl. Acad. sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a reference sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. Additional programs and methods for comparing sequences and/or assessing sequence identity include the Needleman-Wunsch algorithm (see, e.g., the EMBOSS Needle aligner available at cbi.ac.uk/Tools/psa/emboss needle/, optionally with default settings), the Smith-Waterman algorithm (see, e.g., the EMBOSS Water aligner available at ebi.ac.uk/Tools/psa/emboss water/, optionally with default settings), the similarity search method of Pearson and Lipman, 1988, Proc. Natl. Acad. Sci. USA 85, 2444, or computer programs which use these algorithms (GAP, BESTFIT, FASTA, BLAST P, BLAST N and TFASTA in Wisconsin Genetics Software Package, Genetics Computer Group. 575 Science Drive, Madison, Wis.). In some aspects, reference to percent sequence identity refers to sequence identity as measured using BLAST (Basic Local Alignment Search Tool). In other aspects, ClustalW is used for multiple sequence alignment. Optimal alignment may be assessed using any suitable parameters of a chosen algorithm, including default parameters.

As used herein, the term "drug" or "medicament," means a pharmaceutical formulation or composition as described herein.

As used herein, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of +20%, or ±10%, or ±5%, or even ±1% from the specified value, as such variations are appropriate for the disclosed methods or to perform the disclosed methods.

The term "expression" refers to the process by which a nucleic acid sequence or a polynucleotide is transcribed from a DNA template (such as into mRNA or other RNA transcript) and/or the process by which a transcribed mRNA or other RNA is subsequently translated into peptides, polypeptides, or proteins. Transcripts and encoded polypeptides may be collectively referred to as "gene product."

As used herein, the terms "self-replicating RNA," "self-transcribing and self-replicating RNA," "self-amplifying RNA (saRNA)," and "replicon" may be used interchangeably, unless context clearly indicates otherwise. Generally, the term "replicon" or "viral replicon" refers to a self-replicating subgenomic RNA derived from a viral genome that includes viral genes encoding non-structural proteins important for viral replication and that lacks viral genes encoding structural proteins. A self-replicating RNA can encode further subgenomic RNAs that are not able to self-replicate.

As used herein, "operably linked," "operable linkage," "operatively linked," or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

Nucleic Acid Molecules

In some embodiments, provided herein are nucleic acid molecules comprising: (i) a first polynucleotide encoding one or more viral replication proteins, wherein the first polynucleotide is codon-optimized as compared to a wild-type polynucleotide encoding the one or more viral replication proteins; and (ii) a second polynucleotide comprising a first transgene encoding a first antigenic protein or a fragment thereof, wherein the first antigenic protein is a coronavirus protein.

An RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Also provided herein, in some embodiments, are nucleic acid molecules comprising: (i) a first polynucleotide comprising a sequence having at least 80% identity to a sequence of SEQ ID NO:72; and (ii) a second polynucleotide comprising a first transgene encoding a first antigenic protein or a fragment thereof.

Codon Optimization

In some embodiments, first polynucleotides of nucleic acid molecules provided herein encoding one or more viral replication proteins include codon-optimized sequences. As used herein, the term "codon-optimized" means a polynucleotide, nucleic acid sequence, or coding sequence has been redesigned as compared to a wild-type or reference polynucleotide, nucleic acid sequence, or coding sequence by choosing different codons without altering the amino acid sequence of the encoded protein. Accordingly, codon-optimization generally refers to replacement of codons with synonymous codons to optimize expression of a protein while keeping the amino acid sequence of the translated protein the same. Codon optimization of a sequence can increase protein expression levels (Gustafsson et al., Codon bias and heterologous protein expression. 2004, Trends Biotechnol 22: 346-53) of the encoded proteins, for example, and provide other advantages. Variables such as codon usage preference as measured by codon adaptation index (CAI), for example, the presence or frequency of U and other nucleotides, mRNA secondary structures, cis-regulatory sequences, GC content, and other variables may correlate with protein expression levels (Villalobos et al., Gene Designer: a synthetic biology tool for constructing artificial DNA segments. 2006, BMC Bioinformatics 7:285).

Any method of codon optimization can be used to codon optimize polynucleotides and nucleic acid molecules provided herein, and any variable can be altered by codon optimization. Accordingly, any combination of codon optimization methods can be used. Exemplary methods include the high codon adaptation index (CAI) method, the Low U method, and others. The CAI method chooses a most frequently used synonymous codon for an entire protein coding sequence. As an example, the most frequently used codon for each amino acid can be deduced from 74,218 protein-coding genes from a human genome. The Low U method targets U-containing codons that can be replaced with a synonymous codon with fewer U moieties, generally without changing other codons. If there is more than one choice for replacement, the more frequently used codon can be selected. Any polynucleotide, nucleic acid sequence, or codon sequence provided herein can be codon-optimized.

In some embodiments, the nucleotide sequence of any region of the RNA or DNA templates described herein may be codon optimized. Preferably, the primary cDNA template may include reducing the occurrence or frequency of appearance of certain nucleotides in the template strand. For example, the occurrence of a nucleotide in a template may be reduced to a level below 25% of said nucleotides in the template. In further examples, the occurrence of a nucleotide in a template may be reduced to a level below 20% of said nucleotides in the template. In some examples, the occurrence of a nucleotide in a template may be reduced to a level below 16% of said nucleotides in the template. Preferably, the occurrence of a nucleotide in a template may be reduced to a level below 15%, and preferably may be reduced to a level below 12% of said nucleotides in the template.

In some embodiments, the nucleotide reduced is uridine. For example, the present disclosure provides nucleic acids with altered uracil content wherein at least one codon in the wild-type sequence has been replaced with an alternative codon to generate a uracil-altered sequence. Altered uracil sequences can have at least one of the following properties:
  (i) an increase or decrease in global uracil content (i.e., the percentage of uracil of the total nucleotide content in the nucleic acid of a section of the nucleic acid, e.g., the open reading frame);
  (ii) an increase or decrease in local uracil content (i.e., changes in uracil content are limited to specific subsequences);
  (iii) a change in uracil distribution without a change in the global uracil content;
  (iv) a change in uracil clustering (e.g., number of clusters, location of clusters, or distance between clusters); or
  (v) combinations thereof.

In some embodiments, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the nucleic acid sequences of the disclosure. The percentage uracil content can be determined by dividing the number of uracil in a sequence by the total number of nucleotides and multiplying by 100.

In some embodiments, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure. These subsequences can also be part of the wild-type sequences of the heterologous 5' and 3' UTR sequences of the present disclosure.

In some embodiments, codons in the nucleic acid sequence of the disclosure reduce or modify, for example, the number, size, location, or distribution of uracil clusters that could have deleterious effects on protein translation. Although lower uracil content is desirable in certain aspects, the uracil content, and in particular the local uracil content, of some subsequences of the wild-type sequence can be greater than the wild-type sequence and still maintain beneficial features (e.g., increased expression).

In some embodiments, the uracil-modified sequence induces a lower Toll-Like Receptor (TLR) response when compared to the wild-type sequence. Several TLRs recognize and respond to nucleic acids. Double-stranded (ds) RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial RNA contains no nucleoside modifications, whereas mammalian RNAs have modified nucleosides such as 5-methylcytidine (m5C), N6-methyladenosine (m6A), inosine and many 2'-O-methylated nucleosides in addition to N7-methylguanosine (m7G).

In some embodiments, the uracil content of polynucleotides disclosed herein is less than about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the sequence in the reference sequence. In some embodiments, the uracil content of polynucleotides disclosed herein is between about 5% and about 25%. In some embodiments, the uracil content of polynucleotides disclosed herein is between about 15% and about 25%.

In some embodiments, first polynucleotides of nucleic acid molecules provided herein comprise a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:72. In some embodiments, first polynucleotides of nucleic acid molecules provided herein comprise a sequence of SEQ ID NO:72.

In some aspects, first polynucleotides and second polynucleotides of nucleic acid molecules provided herein are included in the same (i.e., a single) or in separate nucleic acid molecules. Generally, first polynucleotides and second polynucleotides of nucleic acid molecules provided herein are included in a single nucleic acid molecule. In one aspect, the first polynucleotide is located 5' of the second polynucleotide. In one aspect, first polynucleotides and second polynucleotides of nucleic acid molecules provided herein are included in separate nucleic acid molecules. In yet another aspect, first polynucleotides and second polynucleotides are included in two separate nucleic acid molecules.

In some aspects, first polynucleotides and second polynucleotides are included in the same (i.e., a single) nucleic acid molecule. First polynucleotides and second polynucleotides of nucleic acid molecules provided herein can be contiguous, i.e., adjacent to each other without nucleotides in between. In one aspect, an intergenic region is located between the first polynucleotide and the second polynucleotide. In another aspect, the intergenic region located between the first polynucleotide and the second polynucleotide is a second intergenic region, with a first intergenic region included in the first polynucleotide as described below. As used herein, the terms "intergenic region" and intergenic sequence" can be used interchangeably, unless context clearly indicates otherwise.

An intergenic region located between the first polynucleotide and the second polynucleotide can be of any length and can have any nucleotide sequence. As an example, the intergenic region between the first polynucleotide and the second polynucleotide can include about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, about 60 nucleotides, about 70 nucleotides, about 80 nucleotides, about 90 nucleotides, about 100 nucleotides, about 125 nucleotides, about 150 nucleotides, about 175 nucleotides, about 200 nucleotides, about 250 nucleotides, about 300 nucleotides, about 350 nucleotides, about 400 nucleotides, about 450 nucleotides, about 500 nucleotides, about 600 nucleotides, about 700 nucleotides, about 800 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 4,500 nucleotides, about 5,000 nucleotides, about 6,000 nucleotides, about 7,000 nucleotides, about 8,000 nucleotides, about 9,000 nucleotides, about 10,000 nucleotides, and any number or range in between. In one aspect, the intergenic region between first and second polynucleotides includes about 10-100 nucleotides, about 10-200 nucleotides, about 10-300 nucleotides, about 10-400 nucleotides, or about 10-500 nucleotides. In another aspect, the intergenic region between first and second polynucleotides includes about 1-10 nucleotides, about 1-20 nucleotides, about 1-30 nucleotides, about 1-40 nucleotides, or about 1-50 nucleotides. In yet another aspect, the region includes about 44 nucleotides. In one aspect, the intergenic region between first and second polynucleotides of nucleic acid molecules provided herein is a second intergenic region.

In one aspect, the intergenic region between first and second polynucleotides includes a viral sequence. The intergenic region between first and second polynucleotides can include a sequence from any virus, such as alphaviruses and rubiviruses, for example. In one aspect, the intergenic region between the first polynucleotide and the second polynucleotide comprises an alphavirus sequence, such as a sequence from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof. In another aspect, the intergenic region between first and second polynucleotides comprises a sequence from Venezuelan Equine Encephalitis Virus (VEEV). In yet another aspect, the intergenic region between first and second polynucleotides comprises a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9% h, and any number or range in between, identity to SEQ ID NO:77. In a further aspect, the intergenic region between first and second polynucleotides comprises a sequence of SEQ ID NO:77. In yet a further aspect, the intergenic region between first and second polynucleotides is a second intergenic region comprising a sequence having at least 85% identity to SEQ ID NO:77.

Natural and Modified Nucleotides

A self-replicating RNA of the disclosure can comprise one or more chemically modified nucleotides. Examples of nucleic acid monomers include non-natural, modified, and chemically-modified nucleotides, including any such nucleotides known in the art. Nucleotides can be artificially modified at either the base portion or the sugar portion. In nature, most polynucleotides comprise nucleotides that are "unmodified" or "natural" nucleotides, which include the purine bases adenine (A) and guanine (G), and the pyrimidine bases thymine (T), cytosine (C) and uracil (U). These bases are typically fixed to a ribose or deoxy ribose at the 1' position. The use of RNA polynucleotides comprising chemically modified nucleotides have been shown to improve RNA expression, expression rates, half-life and/or expressed protein concentrations. RNA polynucleotides comprising chemically modified nucleotides have also been useful in optimizing protein localization thereby avoiding deleterious bio-responses such as immune responses and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, N4-alkylcytidines, N4-aminocytidines, N4-acetylcytidines, and N4,N4-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; N4-methylcytidine, N4-aminocytidine, N4-acetylcytidine, and N4,N4-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include N6-methyladenosine, 2-aminoadenosine, 3-methyladenosine, 8-azaadenosine, 7-deazaadenosine, 8-oxoadenosine, 8-bromoadenosine, 2-methylthio-N6-methyladenosine, N6-isopentenyladenosine, 2-methylthio-N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyl-adenosine, N6-methyl-N6-threonylcarbamoyl-adenosine, 2-methylthio-N6-threonylcarbamoyl-adenosine, N6,N6-dimethyladenosine, N6-hydroxynorvalylcarbamoyladenosine, 2-methylthio-N6-hydroxynorvalylcarbamoyl-adenosine, N6-acetyl-adenosine, 7-methyl-adenine, 2-methylthio-adenine, 2-methoxy-adenine, alpha-thio-adenosine, 2'-O-methyl-adenosine, N6,2'-O-dimethyl-adenosine, N6,N6,2'-O-trimethyl-adenosine, 1,2'-O-dimethyl-adenosine, 2'-O-ribosyladenosine, 2-amino-N6-methyl-purine, 1-thio-adenosine, 2'-F-ara-adenosine, 2'-F-adenosine, 2'-OH-ara-adenosine, and N6-(19-amino-pentaoxanonadecyl)-adenosine.

Examples of modified or chemically-modified nucleotides include N1-alkylguanosines, N2-alkylguanosines, thienoguanosines, 7-deazaguanosines, 8-oxoguanosines, 8-bromoguanosines, 06-alkylguanosines, xanthosines, inosines, and N1-alkylinosines.

Examples of modified or chemically-modified nucleotides include N1-methylguanosine, N2-methylguanosine, thienoguanosine, 7-deazaguanosine, 8-oxoguanosine, 8-bromoguanosine, 06-methylguanosine, xanthosine, inosine, and N1-methylinosine.

Examples of modified or chemically-modified nucleotides include pseudouridines. Examples of pseudouridines include N1-alkylpseudouridines, N1-cycloalkylpseudouridines, N1-hydroxypseudouridines, N1-hydroxyalkylpseudouridines, N1-phenylpseudouridines, N1-phenylalkylpseudouridines, N1-aminoalkylpseudouridines, N3-alkylpseudouridines, N6-alkylpseudouridines, N6-alkoxypseudouridines, N6-hydroxypseudouridines, N6-hydroxyalkylpseudouridines, N6-morpholinopseudouridines, N6-phenylpseudouridines, and N6-halopseudouridines. Examples of pseudouridines include N1-alkyl-N6-alkylpseudouridines, N1-alkyl-N6-alkoxypseudouridines, N1-alkyl-N6-hydroxypseudouridines, N1-alkyl-N6-hydroxyalkylpseudouridines, N1-alkyl-N6-morpholinopseudouridines, N1-alkyl-N6-phenylpseudouridines, and N1-alkyl-N6-halopseudouridines. In these examples, the alkyl, cycloalkyl, and phenyl substituents may be unsubstituted, or further substituted with alkyl, halo, haloalkyl, amino, or nitro substituents.

Examples of pseudouridines include N1-methylpseudouridine (also referred to herein as "NIMPU"), N1-ethylpseudouridine, N1-propylpseudouridine, N1-cyclopropylpseudouridine, N1-phenylpseudouridine, N1-aminomethylpseudouridine, N3-methylpseudouridine, N1-hydroxypseudouridine, and N1-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include N6-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include N1-methylpseudouridine and 5-methoxyuridine.

Viral Replication Proteins and Polynucleotides Encoding them

Provided herein, in some embodiments, are nucleic acid molecules comprising a first polynucleotide encoding one or more viral replication proteins. As used herein, the term "replication protein" or "viral replication protein" refers to any protein or any protein subunit of a protein complex that functions in replication of a viral genome. Generally, viral replication proteins are non-structural proteins. Viral replication proteins encoded by nucleic acid molecules provided herein can function in the replication of any viral genome. The viral genome can be a single-stranded positive-sense RNA genome, a single-stranded negative-sense RNA genome, a double-stranded RNA genome, a single-stranded positive-sense DNA genome, a single-stranded negative-sense DNA genome, or a double-stranded DNA genome. Viral genomes can include a single nucleic acid molecule or more than one nucleic acid molecule. Nucleic acid molecules provided herein can encode one or more viral replication proteins from any virus or virus family, including animal viruses and plant viruses, for example. Viral replication proteins encoded by first polynucleotides included in nucleic acid molecules provided herein can be expressed from self-replicating RNA.

First polynucleotide sequences of nucleic acid molecules provided herein can encode one or more togavirus replication proteins. In some aspects, the one or more viral replication proteins encoded by first polynucleotides of nucleic acid molecules provided herein are alphavirus proteins. In some embodiments, the one or more viral replication proteins encoded by first polynucleotides of nucleic acid molecules provided herein are rubivirus proteins. First polynucleotide sequences of nucleic acid molecules provided herein can encode any alphavirus replication protein and any rubivirus replication protein. Exemplary replication proteins from alphaviruses include proteins from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), and any combination thereof. Exemplary rubivirus replication proteins include proteins from rubella virus.

Viral replication proteins encoded by first polynucleotides of nucleic acid molecules provided herein can be expressed as one or more polyproteins or as separate or single proteins. Generally, polyproteins are precursor proteins that are cleaved to generate individual or separate proteins. Accordingly, proteins derived from a precursor polyprotein can be expressed from a single open reading frame (ORF). As used herein, the term "ORF" refers to a nucleotide sequence that begins with a start codon, generally ATG, and that ends with a stop codon, such as TAA, TAG, or TGA, for example. It will be appreciated that T is present in DNA, while U is present in RNA. Accordingly, a start codon of ATG in DNA corresponds to AUG in RNA, and the stop codons TAA, TAG, and TGA in DNA correspond to UAA, UAG, and UGA in RNA. It will further be appreciated that for any sequence provided in the present disclosure, T is present in DNA, while U is present in RNA. Accordingly, for any sequence provided herein, T present in DNA is substituted with U for an RNA molecule, and U present in RNA is substituted with T for a DNA molecule.

The protease cleaving a polyprotein can be a viral protease or a cellular protease. In some aspects, the first polynucleotide of nucleic acid molecules provided herein encodes a polyprotein comprising an alphavirus nsP1 protein, an alphavirus nsP2 protein, an alphavirus nsP3 protein, an alphavirus nsP4 protein, or any combination thereof. In other aspects, the first polynucleotide of nucleic acid molecules provided herein encodes a polyprotein comprising an alphavirus nsP1 protein, an alphavirus nsP2 protein, an alphavirus nsP3 protein, or any combination thereof, and an alphavirus nsP4 protein. In some aspects, the polyprotein is a VEEV polyprotein. In other aspects, the alphavirus nsP1, nsP2, nsP3, and nsP4 proteins are VEEV proteins.

In one aspect, first polynucleotides of nucleic acid molecules provided herein lack a stop codon between sequences encoding an nsP3 protein and an nsP4 protein. Accordingly, in some aspects, first polynucleotides of nucleic acid molecules provided herein encode a P1234 polyprotein comprising nsP1, nsP2, nsP3, and nsP4. First polynucleotides of nucleic acid molecules provided herein can also include a stop codon between sequences encoding an nsP3 and an nsP4 protein. Accordingly, in some aspects, first polynucleotides of nucleic acid molecules provided herein encode a P123 polyprotein comprising nsP1, nsP2, and nsP3 and a P1234 polyprotein comprising nsP1, nsP2, nsP3, and nsP4 as a result of stop codon readthrough, for example. In other aspects, first polynucleotides of nucleic acid molecules provided herein encode a polyprotein having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:79. In some embodiments, first polynucleotides of nucleic acid molecules provided herein encode a polyprotein having a sequence of SEQ ID NO:79. Further exemplary polyproteins comprise a sequence of SEQ ID NO:80 or SEQ ID NO:81. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

In some aspects, first polynucleotides of nucleic acid molecules provided herein can include a first intergenic region. In some aspects, the first intergenic region is located between a sequence encoding a polyprotein comprising an alphavirus nsP1 protein, an alphavirus nsP2 protein, an alphavirus nsP3 protein, or any combination thereof, and a sequence encoding an alphavirus nsP4 protein. A first intergenic region can comprise any sequence, such as any viral or non-viral sequence. In one aspect, the first intergenic region comprises a viral sequence. In another aspect, the first intergenic region comprises an alphavirus sequence. In yet another aspect, the alphavirus is VEEV. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

In some embodiments, the first polynucleotide may comprise a sequence having at least 80% identity to a sequence of SEQ ID NO:72.

In some embodiments, the nucleic acid molecule described herein may further comprise a second polynucleotide comprising a first transgene encoding a first antigenic protein or fragment thereof, wherein the first antigenic protein is a coronavirus protein. In specific embodiments, the antigenic protein may be a SARS-CoV-2 protein. In specific embodiments, the antigenic protein is a SARS-CoV-2 spike glycoprotein. In specific embodiments, the SARS-CoV-2 spike glycoprotein is a wild-type SARS-CoV-2 spike glycoprotein having an amino acid sequence of SEQ ID NO:123.

In some embodiments, the second polynucleotide comprises a sequence having at least 85% identity to a sequence of SEQ ID NO:121 or SEQ ID NO:122.

5' Untranslated Region (5' UTR)

Nucleic acid molecules provided herein can further comprise untranslated regions (UTRs). Untranslated regions, including 5' UTRs and 3' UTRs, for example, can affect RNA stability and/or efficiency of RNA translation, such as translation of cellular and viral mRNAs, for example. 5' UTRs and 3' UTRs can also affect stability and translation of viral genomic RNAs and self-replicating RNAs, including virally derived self-replicating RNAs or replicons. Exemplary viral genomic RNAs whose stability and/or efficiency of translation can be affected by 5' UTRs and 3' UTRs include the genome nucleic acid of positive-sense RNA viruses. Both genome nucleic acid of positive-sense RNA viruses and self-replicating RNAs, including virally derived self-replicating RNAs or replicons, can be translated upon infection or introduction into a cell.

In some aspects, nucleic acid molecules provided herein further include a 5' untranslated region (5' UTR). Any 5' UTR sequence can be included in nucleic acid molecules provided herein. In some embodiments, nucleic acid molecules provided herein include a viral 5' UTR. In one aspect, nucleic acid molecules provided herein include a non-viral 5' UTR. Any non-viral 5' UTR can be included in nucleic acid molecules provided herein, such as 5' UTRs of transcripts expressed in any cell or organ, including muscle, skin, subcutaneous tissue, liver, spleen, lymph nodes, antigen-presenting cells, and others. In another aspect, nucleic acid molecules provided herein include a 5' UTR comprising viral and non-viral sequences. Accordingly, a 5' UTR included in nucleic acid molecules provided herein can comprise a combination of viral and non-viral 5' UTR sequences. In some aspects, the 5' UTR included in nucleic acid molecules provided herein is located upstream of or 5' of the first polynucleotide that encodes one or more viral replication proteins. In other aspects, the 5' UTR is located 5' of or upstream of the first polynucleotide of nucleic acid molecules provided herein that encodes one or more viral replication proteins, and the first polynucleotide is located 5' of or upstream of the second polynucleotide of nucleic acid molecules provided herein.

In one aspect, the 5' UTR of nucleic acid molecules provided herein comprises an alphavirus 5' UTR. A 5' UTR from any alphavirus can be included in nucleic acid molecules provided herein, including 5' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 5' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:73, SEQ ID NO:74, or SEQ ID NO:75. In yet another aspect, the 5' UTR comprises a sequence of SEQ ID NO:73, SEQ ID NO:74, or SEQ ID NO:75.

In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is ATIG58420. Examples of 5 UTRs and 3' UTRs are described in PCT/US2018/035419, the contents of which are herein incorporated by reference. Preferred 5' UTR sequences comprise SEQ ID NOs: 5-10 and 25-45: as shown in Table 1.

TABLE 1

5' UTR Sequences

| Name | Sequence | Seq ID No.: |
|---|---|---|
| EV | UCAACACAACAUAUACAAAACAAACGAAUCUCAAGCAAUC AAGCAUUCUACUUCUAUUGCAGCAAUUUAAAUCAUUUCU UUUAAAGCAAAAGCAAUUUUCUGAAAAUUUUCACCAUUU ACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGCGCUGCCUACGGAGGUGGCAGCCAUCUCCU UCUCGGCAUCAAGCUUACCAUGGUGCCCCAGGCCCUGCUC UUGGUCCCGCUGCUGGUGUUCCCCCUCUGCUUCGGCAAGU UCCCCAUCUACACCAUCCCCGACAAGCUGGGGCCGUGGAG CCCCAUCGACAUCCACCACCUGUCCUGCCCCAACAACCUCG UGGUCGAGGACGAGGGCUGCACCAACCUGAGCGGGUUCUC CUAC | SEQ ID NO: 7 |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UGGGCGUGC CCCCGCAAGA CUGCUAGCCG AGUAGUGUUG GGUUGCG | SEQ ID NO : 8 |

TABLE 1-continued

5' UTR Sequences

| Name | Sequence | Seq ID No.: |
|---|---|---|
| HUMAN ALBUMIN | AAUUAUUGGUUAAAGAAGUAUAUUAGUGCUAAUUUCCCU CCGUUUGUCCUAGCUUUUCUCUUCUGUCAACCCCACACGC CUUUGGCACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCCGAACC ACGGGGACGU GGUUUUCCUU UGAAAAACAC GAUGAUAAU | SEQ ID NO: 10 |
| AT1G67090 | CACAAAGAGUAAAGAAGAACA | SEQ ID NO: 25 |
| AT1G35720 | AACACUAAAAGUAGAAGAAAA | SEQ ID NO: 26 |
| AT5G45900 | CUCAGAAAGAUAAGAUCAGCC | SEQ ID NO: 27 |
| AT5G61250 | AACCAAUCGAAAGAAACCAAA | SEQ ID NO: 28 |
| AT5G46430 | CUCUAAUCACCAGGAGUAAAA | SEQ ID NO: 29 |
| AT5G47110 | GAGAGAGAUCUUAACAAAAAA | SEQ ID NO: 30 |
| AT1G03110 | UGUGUAACAACAACAACAACA | SEQ ID NO: 31 |
| AT3G12380 | CCGCAGUAGGAAGAGAAAGCC | SEQ ID NO: 32 |
| AT5G45910 | AAAAAAAAAAGAAAUCAUAAA | SEQ ID NO: 33 |
| AT1G07260 | GAGAGAAGAAAGAAGAAGACG | SEQ ID NO: 34 |
| AT3G55500 | CAAUUAAAAAUACUUACCAAA | SEQ ID NO: 35 |
| AT3G46230 | GCAAACAGAGUAAGCGAAACG | SEQ ID NO: 36 |
| AT2G36170 | GCGAAGAAGACGAACGCAAAG | SEQ ID NO: 37 |
| AT1G10660 | UUAGGACUGUAUUGACUGGCC | SEQ ID NO: 38 |
| AT4G14340 | AUCAUCGGAAUUCGGAAAAAG | SEQ ID NO: 39 |
| AT1G49310 | AAAACAAAAGUUAAAGCAGAC | SEQ ID NO: 40 |
| AT4G14360 | UUUAUCUCAAAUAAGAAGGCA | SEQ ID NO: 41 |
| AT1G28520 | GGUGGGAGGUGAGAUUUCUU | SEQ ID NO: 42 |
| AT1G20160 | UGAUUAGGAAACUACAAAGCC | SEQ ID NO: 43 |
| AT5G37370 | CAUUUUUCAAUUUCAUAAAAC | SEQ ID NO: 44 |
| AT4G11320 | UUACUUUUAAGCCCAACAAAA | SEQ ID NO: 45 |
| AT5G40850 | GGCGUGUGUGUGUGUUGUUGA | SEQ ID NO: 46 |
| AT1G06150 | GUGGUGAAGGGGAAGGUUUAG | SEQ ID NO: 47 |
| AT2G26080 | UUGUUUUUUUUUGGUUUGGUU | SEQ ID NO: 48 |

3' Untranslated Region (3' UTR)

In some aspects, nucleic acid molecules provided herein further include a 3' untranslated region (3' UTR). Any 3' UTR sequence can be included in nucleic acid molecules provided herein. In one aspect, nucleic acid molecules provided herein include a viral 3' UTR. In another aspect, nucleic acid molecules provided herein include a non-viral 3' UTR. Any non-viral 3' UTR can be included in nucleic acid molecules provided herein, such as 3' UTRs of transcripts expressed in any cell or organ, including muscle, skin, subcutaneous tissue, liver, spleen, lymph nodes, antigen-presenting cells, and others. In some aspects, nucleic acid molecules provided herein include a 3' UTR comprising viral and non-viral sequences. Accordingly, a 3' UTR included in nucleic acid molecules provided herein can comprise a combination of viral and non-viral 3' UTR sequences. In one aspect, the 3' UTR is located 3' of or downstream of the second polynucleotide of nucleic acid molecules provided herein that comprises a first transgene encoding a first antigenic protein or a fragment thereof. In another aspect, the 3' UTR is located 3' of or downstream of the second polynucleotide of nucleic acid molecules provided herein that comprises a first transgene encoding a first antigenic protein or a fragment thereof, and the second polynucleotide is located 3' of or downstream of the first polynucleotide of nucleic acid molecules provided herein.

In one aspect, the 3' UTR of nucleic acid molecules provided herein comprises an alphavirus 3' UTR. A 3' UTR from any alphavirus can be included in nucleic acid molecules provided herein, including 3' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 3' UTR comprises a sequence having at least 80%, at least 85%, at least 90%, at least 91%, at least 92%, at least 93%, at least 94%, at least 95%, at least %%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:76. In yet another aspect, the 3' UTR comprises a poly-A sequence. In a further aspect, the 3' UTR comprises a sequence of SEQ ID NO:76.

In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement $C_3$, human growth factor, human hepcidin, MALAT-1, mouse beta globin, mouse albumin, and *Xenopus* beta globin, or fragments of any of the foregoing. In some embodiments, the 3' UTR is derived from *Xenopus* beta globin. Exemplary 3' UTR sequences include SEQ ID NOs: 16-22 as shown in Table 2.

TABLE 2

3' UTR sequences.

| Name | Sequence | Seq ID No.: |
|---|---|---|
| XBG | CUAGUGACUGACUAGGAUCUGGUUACCACUAAACCAG CCUCAAGAACACCCGAAUGGAGUCUCUAAGCUACAUA AUACCAACUUACACUUACAAAAUGUUGUCCCCCAAAA UGUAGCCAUUCGUAUCUGCUCCUAAUAAAAAGAAAGU UUCUUCACAU | SEQ ID NO: 16 |
| HUMAN HAPTOGLOBIN | UGCAAGGCUGGCCGGAAGCCCUUGCCUGAAAGCAAGA UUUCAGCCUGGAAGAGGGCAAAGUGGACGGGAGUGG ACAGGAGUGGAUGCGAUAAGAUGUGGUUUGAAGCUG AUGGGUGCCAGCCCUGCAUUGCUGAGUCAAUCAAUAA AGAGCUUUCUUUUGACCCAU | SEQ ID NO: 17 |
| HUMAN APOLIPO- PROTEIN E | ACGCCGAAGCCUGCAGCCAUGCGACCCCACGCCACCCC GUGCCUCCUGCCUCCGCGCAGCCUGCAGCGGGAGACC CUGUCCCCGCCCCAGCCGUCCUCCUGGGGUGGACCCU AGUUUAAUAAAGAUUCACCAAGUUUCACGCA | SEQ ID NO: 18 |
| HCV | UAGAGCGGCAAACCCUAGCUACACUCCAUAGCUAGUU UCUUUUUUUUUGUUUUUUUUUUUUUUUUUUUUU UUUUUUUUUUUUUUUCCUUUCUUUUCCUUCUUUU UUCCUCUUUUCUUGGUGGCUCCAUCUUAGCCCUAGUC ACGGCUAGCUGUGAAAGGUCCGUGAGCCGCAUGACUG CAGAGAGUGCCGUAACUGGUCUCUCUGCAGAUCAUGU | SEQ ID NO: 19 |
| MOUSE ALBUMIN | ACACAUCACAACCACAACCUUCUCAGGCUACCCUGAG AAAAAAAGACAUGAAGACUCAGGACUCAUCUUUUCUG UUGGUGUAAAAUCAACACCCUAAGGAACACAAAUUUC UUUAAACAUUUGACUUCUUGUCUCUGUGCUGCAAUUA AUAAAAAAUGGAAAGAAUCUAC | SEQ ID NO: 20 |
| HUMAN ALPHA GLOBIN | GCUGGAGCCUCGGUAGCCGUUCCUCCUGCCCGCUGGG CCUCCCAACGGGCCCUCCUCCCCUCCUUGCACCGGCCC UUCCUGGUCUUUGAAUAAAGUCUGAGUGGGCAGCA | SEQ ID NO: 21 |

TABLE 2-continued

3' UTR sequences.

| Name | Sequence | Seq ID No.: |
|---|---|---|
| EMCV | UAGUGCAGUCAC UGGCACAACG CGUUGCCCGG UAAGCCAAUC GGGUAUACAC GGUCGUCAUACUGCAGACAG GGUUCUUCUA CUUUGCAAGA UAGUCUAGAG UAGUAAAAUA AAUAGUAUAAG | SEQ ID NO: 22 |

Triple Stop Codon

In some embodiments, the self-replicating RNA may comprise a sequence immediately downstream of a coding region (i.e., ORF) that creates a triple stop codon. A triple stop codon is a sequence of three consecutive stop codons. The triple stop codon can ensure total insulation of an expression cassette and may be incorporated to enhance the efficiency of translation. In some embodiments, a self-replicating RNA of the disclosure may comprise a triple combination of any of the sequences UAG, UGA, or UAA immediately downstream of a ORF described herein. The triple combination can be three of the same codons, three different codons, or any other permutation of the three stop codons.

Translation Enhancers and Kozak Sequences

For translation initiation, proper interactions between ribosomes and mRNAs must be established to determine the exact position of the translation initiation region. However, ribosomes also must dissociate from the translation initiation region to slide toward the downstream sequence during mRNA translation. Translation enhancers upstream from initiation sequences of mRNAs enhance the yields of protein biosynthesis. Several studies have investigated the effects of translation enhancers. In some embodiments, an mRNA described herein comprises a translation enhancer sequence. These translation enhancer sequences enhance the translation efficiency of a self-replicating RNA of the disclosure and thereby provide increased production of the protein encoded by the mRNA. The translation enhancer region may be located in the 5' or 3' UTR of an mRNA sequence. Examples of translation enhancer regions include naturally-occurring enhancer regions from the TEV 5' UTR and the Xenopus beta-globin 3' UTR. Exemplary 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID Nos: 11-15 as shown in Table 3.

TABLE 3

5' UTR Enhancers

| Name | Sequence | Seq ID No.: |
|---|---|---|
| HSP70-P2 | GUCAGCUUUCAAACUCUUUGUUUCUUGUUU GUUGAUUGAGAAUA | SEQ ID NO: 11 |
| HSP70-M1 | CUCUCGCCUGAGAAAAAAAAUCCACGAACC AAUUUCUCAGCAACCAGCAGCACG | SEQ ID NO: 12 |
| HISP72-M2 | ACCUGUGAGGGUUCGAAGGAAGUAGCAGUG UUUUUUGUUCCUAGAGGAAGAG | SEQ ID NO: 13 |
| HSP17.9 | ACACAGAAACAUUCGCAAAAACAAAAUCCC AGUAUCAAAAUUCUUCUCUUUUUUUCAUAU UUCGCAAAGAC | SEQ ID NO: 14 |
| HSP70-P1 | CAGAAAAAUUUGCUACAUUGUUUCACAAAC UUCAAAUAUUAUUCAUUUAUUU | SEQ ID NO: 15 |

In some embodiments, a self-replicating RNA of the disclosure comprises a Kozak sequence. As is understood in the art, a Kozak sequence is a short consensus sequence centered around the translational initiation site of eukaryotic mRNAs that allows for efficient initiation of translation of the mRNA. See, for example, Kozak, Marilyn (1988) Mol. and Cell Biol, 8:2737-2744; Kozak, Marilyn (1991) J. Biol. Chem, 266:19867-19870; Kozak, Marilyn (1990) Proc Natl. Acad. Sci. USA, 87:8301-8305; and Kozak, Marilyn (1989) J. Cell Biol, 108:229-241. It ensures that a protein is correctly translated from the genetic message, mediating ribosome assembly and translation initiation. The ribosomal translation machinery recognizes the AUG initiation codon in the context of the Kozak sequence. A Kozak sequence may be inserted upstream of the coding sequence for the protein of interest, downstream of a 5' UTR or inserted upstream of the coding sequence for the protein of interest and downstream of a 5' UTR. In some embodiments, a self-replicating RNA described herein comprises a Kozak sequence having the amino acid sequence GCCACC (SEQ ID NO: 23). Preferably a self-replicating RNA described herein comprises a partial Kozak sequence "p" having the amino acid sequence GCCA (SEQ ID NO: 24).

Transgenes

Transgenes included in nucleic acid molecules provided herein can encode an antigenic protein or a fragment thereof. In some embodiments, second polynucleotides of nucleic acid molecules provided herein comprise a first transgene. A first transgene included in second polynucleotides of nucleic acid molecules provided herein can encode a first antigenic protein or a fragment thereof. A transgene included in second polynucleotides of nucleic acid molecules provided herein can comprise a sequence encoding the full amino acid sequence of an antigenic protein or a sequence encoding any suitable portion or fragment of the full amino acid sequence of an antigenic protein. In some embodiments, the antigenic protein is a coronavirus protein.

In another embodiment, the antigenic protein, when administered to a mammalian subject, raises an immune response to a pathogen, such as a coronavirus. In some more particular embodiments, the antigenic protein is expressed on the outer surface of the coronavirus; while in other more particular embodiments, the antigen may be a non-surface antigen, e.g., useful as a T-cell epitope. The immunogen may elicit an immune response against a coronavirus. The immune response may comprise an antibody response (usually including IgG) and/or a cell mediated immune response. The polypeptide immunogen will typically elicit an immune response that recognizes the corresponding coronavirus The immunogen will typically be a surface polypeptide e.g. an envelope glycoprotein, a spike glycoprotein, etc.

In some aspects, the viral protein encoded by transgenes included in nucleic acid molecules provided herein is a coronavirus protein. In some embodiments, the antigenic protein is a SARS-CoV-2 protein.

In one aspect, the antigenic protein is a SARS-CoV-2 spike glycoprotein or a fragment thereof. In another aspect, the SARS-CoV-2 spike glycoprotein is a wild-type SARS-CoV-2 spike glycoprotein. In some aspects, the wild-type SARS-CoV-2 spike glycoprotein has an amino acid sequence of SEQ ID NO:123. In yet another aspect, the second polynucleotide of nucleic acid molecules provided herein comprises a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:121 or SEQ ID NO:122. In another aspect, the second polynucleotide of nucleic acid molecules provided herein comprises a sequence of SEQ ID NO:121 or SEQ ID NO:122. Accordingly, in some aspects, first transgenes included in second polynucleotides of nucleic acid molecules provided herein comprise a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, or 100% identity to a sequence of SEQ ID NO:121 or SEQ ID NO:122.

In one aspect, the second polynucleotide of nucleic acid molecules provided herein encodes a wild-type SARS-CoV-2 spike glycoprotein or a fragment thereof. In some aspects, a wild-type SARS-CoV-2 spike glycoprotein comprises a sequence of SEQ ID NO:123. In another aspect, the second polynucleotide of nucleic acid molecules provided herein encodes a SARS-CoV-2 spike protein comprising one or more mutations as compared to a wild-type SARS-CoV-2 spike glycoprotein sequence. Mutations can include substitutions, deletions, insertions, and others. Mutations can be present at any position or at any combination of positions of a SARS-CoV-2 spike glycoprotein. Any number of substitutions, insertions, deletions, or combinations thereof, can be present at any one or more positions of a SARS-CoV-2 spike glycoprotein. As an example, substitutions can include a change of a wild-type amino acid at any position or at any combination of positions to any other amino acid or combination of any other amino acids. Exemplary mutations include mutations at positions 614, 936, 320, 477, 986, 987, or any combination thereof. In one aspect, a SARS-CoV-2 spike glycoprotein or a fragment thereof encoded by transgenes of second polynucleotides included in nucleic acid molecules provided herein includes a D614G mutation, a D936Y mutation, a D936I1 mutation, a V320G mutation, an S477N mutation, an S477I mutation, an S477T mutation, a K986P mutation, a V987P mutation, or any combination thereof. Additional mutations and variants can be found in the National Bioinformatics Center 2019 Novel Coronavirus Information Database (2019nCoVR), National Genomics Data Center, China National Center for Bioinformation/ Beijing Institute of Genomics, Chinese Academy of Science at bigd.big.ac.cn/ncov/variation/annotation. In another aspect, the second polynucleotide includes a transgene encoding a SARS-CoV-2 glycoprotein having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, or 100% identity to a sequence of SEQ ID NO:123.

In some aspects, the second polynucleotide of nucleic acid molecules provided herein comprises at least two transgenes, such as a second coronavirus protein. Any number of transgenes can be included in second polynucleotides of nucleic acid molecules provided herein, such as one, two, three, four, five, six, seven, eight, nine, ten, or more transgenes. In one aspect, the second polynucleotide of nucleic acid molecules provided herein includes a second transgene encoding a second antigenic protein or a fragment thereof or an immunomodulatory protein. In one aspect, the second polynucleotide further comprises an internal ribosomal entry site (IRES), a sequence encoding a 2A peptide, or a combination thereof, located between transgenes. As used herein, the term "2A peptide" refers to a small (generally 18-22 amino acids) sequence that allows for efficient, stoichiometric production of discrete protein products within a single reading frame through a ribosomal skipping event within the 2A peptide sequence. As used herein, the term "internal ribosomal entry site" or "IRES" refers to a nucleotide sequence that allows for the initiation of protein translation of a messenger RNA (mRNA) sequence in the absence of an AUG start codon or without using an AUG start codon. An IRES can be found anywhere in an mRNA sequence, such as at or near the beginning, at or near the middle, or at or near the end of the mRNA sequence, for example.

Any number of transgenes included in second polynucleotides of nucleic acid molecules provided herein can be expressed via any combination of 2A peptide and IRES sequences. For example, a second transgene located 3' of a first transgene can be expressed via a 2A peptide sequence or via an IRES sequence. As another example, a second transgene located 3' of a first transgene and a third transgene located 3' of the second transgene can be expressed via 2A peptide sequences located between the first and second transgenes and the second and third transgenes, via an IRES sequence located between the first and second transgenes and the second and third transgenes, via a 2A peptide sequence located between the first and second transgenes and an IRES located between the second and third transgenes, or via an IRES sequence located between the first and second transgenes and a 2A peptide sequence located between the second and third transgenes. Similar configurations and combinations of 2A peptide and IRES sequences located between transgenes are contemplated for any number of transgenes included in second polynucleotides of nucleic acid molecules provided herein. In addition to expression via 2A peptide and IRES sequences, two or more transgenes included in nucleic acid molecules provided herein can also be expressed from separate subgenomic RNAs.

A second, third, fourth, fifth, sixth, seventh, eighth, ninth, tenth, etc., transgene included in second polynucleotides of nucleic acid molecules provided herein can encode an immunomodulatory protein or a functional fragment or functional variant thereof. Any immunomodulatory protein or a functional fragment or functional variant thereof can be encoded by a transgene included in second polynucleotides.

As used herein, the terms "functional variant" or "functional fragment" refer to a molecule, including a nucleic acid or protein, for example, that comprises a nucleotide and/or amino acid sequence that is altered by one or more nucleotides and/or amino acids compared to the nucleotide and/or amino acid sequences of the parent or reference molecule. For a protein, a functional variant is still able to function in a manner that is similar to the parent molecule. In other words, the modifications in the amino acid and/or nucleotide sequence of the parent molecule do not significantly affect or alter the functional characteristics of the molecule encoded by the nucleotide sequence or containing the amino acid sequence. The functional variant may have conservative sequence modifications including nucleotide and amino acid substitutions, additions and deletions. These modifications can be introduced by standard techniques known in the art, such as site-directed mutagenesis and random PCR-mediated mutagenesis. Functional variants can also include, but are not limited to, derivatives that are substantially similar in primary structural sequence, but which contain, e.g., in vitro or in vivo modifications, chemical and/or biochemical, that are not found in the parent molecule. Such modifications include, inter alia, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

In one aspect, a second transgene included in second polynucleotides of nucleic acid molecules provided herein encodes a cytokine, a chemokine, or an interleukin. Exemplary cytokines include interferons, TNF-α, TGF-β, G-CSF, and GM-CSF. Exemplary chemokines include CCL3, CCL26, and CXCL7. Exemplary interleukins include IL-1, IL-2, IL-3, IL-4, IL-5, IL-6, IL-7, IL-8, IL-10, IL-12, IL-15, IL-18, IL-21, and IL-23. Any transgene or combination of transgenes encoding any cytokine, chemokine, interleukin, or combinations thereof, can be included in second polynucleotides of nucleic acid molecules provided herein.

In some embodiments, the second transgene encodes a second coronavirus protein.

DNA and RNA Molecules

Nucleic acid molecules provided herein can be DNA molecules or RNA molecules. It will be appreciated that T present in DNA is substituted with U in RNA, and vice versa. In one aspect, nucleic acid molecules provided herein are DNA molecules. In another aspect, DNA molecules provided herein further comprise a promoter. As used herein, the term "promoter" refers to a regulatory sequence that initiates transcription. A promoter can be operably linked to first and second polynucleotides of nucleic acid molecules provided herein. Generally, promoters included in DNA molecules provided herein include promoters for in vitro transcription (IVT). Any suitable promoter for in vitro transcription can be included in DNA molecules provided herein, such as a T7 promoter, a T3 promoter, an SP6 promoter, and others. In one aspect, DNA molecules provided herein comprise a T7 promoter. In another aspect, the promoter is located 5' of the 5' UTR included in DNA molecules provided herein. In yet another aspect, the promoter is a T7 promoter located 5' of the 5' UTR included in DNA molecules provided herein. In yet another aspect, the promoter overlaps with the 5' UTR. A promoter and a 5' UTR can overlap by about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, or more nucleotides.

In some aspects, DNA molecules provided herein include a promoter for in vivo transcription. Generally, the promoter for in vivo transcription is an RNA polymerase II (RNA pol II) promoter. Any RNA pol II promoter can be included in DNA molecules provided herein, including constitutive promoters, inducible promoters, and tissue-specific promoters. Exemplary constitutive promoters include a cytomegalovirus (CMV) promoter, an EF1α promoter, an SV40 promoter, a PGK1 promoter, a Ubc promoter, a human beta actin promoter, a CAG promoter, and others. Any tissue-specific promoter can be included in DNA molecules provided herein. In one aspect, the RNA pol II promoter is a muscle-specific promoter, skin-specific promoter, subcutaneous tissue-specific promoter, liver-specific promoter, spleen-specific promoter, lymph node-specific promoter, or a promoter with any other tissue specificity. DNA molecules provided herein can also include an enhancer. Any enhancer that increases transcription can be included in DNA molecules provided herein.

In some aspects, nucleic acid molecules provided herein are RNA molecules. An RNA molecule provided herein can be generated by in vitro transcription (IVT) of DNA molecules provided herein. In one aspect, RNA molecules provided herein are self-replicating RNA molecules. In another aspect, RNA molecules provided herein further comprise a 5' cap. Any 5' cap can be included in RNA molecules provided herein, including 5' caps having a Cap 1 structure, a Cap 1 (m6A) structure, a Cap 2 structure, a Cap 0 structure, or any combination thereof. In one aspect, RNA molecules provided herein include a 5' cap having Cap 1 structure. In yet another aspect, RNA molecules provided herein are self-replicating RNA molecules comprising a 5' cap having a Cap 1 structure. In a further aspect, RNA molecules provided herein comprise a cap having a Cap 1 structure, wherein a m7G is linked via a 5'-5' triphosphate to the 5' end of the 5' UTR. In yet a further aspect, RNA molecules provided herein comprise a cap having a Cap 1 structure, wherein a m7G is linked via a 5'-5' triphosphate to the 5' end of the 5' UTR comprising a sequence of SEQ ID NO:73. Any method of capping can be used, including, but not limited to using a Vaccinia Capping enzyme (New England Biolabs, Ipswich, Mass.) and co-transcriptional capping or capping at or shortly after initiation of in vitro transcription (IVT), by for example, including a capping agent as part of an in vitro transcription (IVT) reaction. (Nuc. Acids Symp. (2009) 53:129).

Provided herein, in some embodiments, are nucleic acid molecules comprising (a) a sequence of SEQ ID NO:10; (b) a sequence of SEQ ID NO:72, SEQ ID NO:73, SEQ ID NO:76, and SEQ ID NO:77, wherein T is substituted with U; (c) a sequence of SEQ ID NO:124; (d) a sequence of SEQ ID NO:124, wherein T is substituted with U; (e) a sequence of SEQ ID NO:125; or (f) a sequence of SEQ ID NO:125, wherein T is substituted with U. In one aspect, nucleic acid molecules provided herein are RNA molecules. In another aspect, RNA molecules provided herein further comprise a 5' cap having a Cap 1 structure. Any RNA molecules provided herein can be self-replicating RNA molecules.

Only those mRNAs that carry the Cap structure are active in Cap dependent translation; "decapitation" of mRNA results in an almost complete loss of their template activity for protein synthesis (Nature, 255:33-37, (1975); J. Biol. Chem., vol. 253:5228-5231, (1978); and Proc. Natl. Acad. Sci. USA, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA provides higher efficacy of mRNA translation in vivo (Proc. Natl. Acad. Sci. USA, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (Nucleic Acid Research 43: 482-492 (2015)).

Some examples of 5' cap structures and methods for preparing mRNAs comprising the same are given in WO2015/051169A2, WO/2015/061491, US 2018/0273576, and U.S. Pat. Nos. 8,093,367, 8,304,529, and 10,487,105. In some embodiments, the 5' cap is m7GpppAmpG, which is known in the art. In some embodiments, the 5' cap is m7GpppG or m7GpppGm, which are known in the art. Structural formulas for embodiments of 5' cap structures are provided below.

In some embodiments, a self-replicating RNA of the disclosure comprises a 5' cap having the structure of Formula (Cap I).

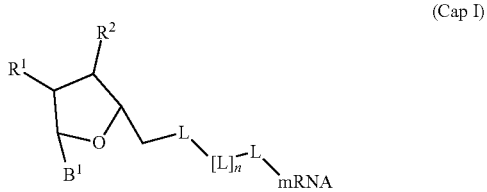

(Cap I)

wherein $B^1$ is a natural or modified nucleobase; $R^1$ and $R^2$ are each independently selected from a halogen, OH, and $OCH_3$; each L is independently selected from the group consisting of phosphate, phophorothioate, and boranophosphate wherein each L is linked by diester bonds; n is 0 or 1. and mRNA represents an mRNA of the present disclosure linked at its 5' end. In some embodiments $B^1$ is G, $m^7G$, or A. In some embodiments n is 0. In some embodiments n is 1. In some embodiments, $B^1$ is A or $m^7A$ and $R^1$ is $OCH_3$; wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap II).

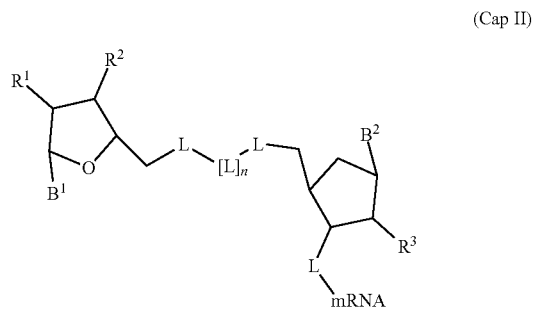

(Cap II)

wherein $B^1$ and $B^2$ are each independently a natural or modified nucleobase; $R^1$, $R^2$, and $R^3$ are each independently selected from a halogen, OH, and $OCH_3$; each L is independently selected from the group consisting of phosphate, phophorothioate, and boranophosphate wherein each L is linked by diester bonds; mRNA represents an mRNA of the present disclosure linked at its 5' end; and n is 0 or 1. In some embodiments $B^1$ is G, $m^7G$, or A. In some embodiments, n is 0. In some embodiments, n is 1. In some embodiments, $B^1$ is A or $m^6A$ and $R^1$ is $OCH_3$; wherein G is guanine, $m^7G$ is 7-methylguanine, A is adenine, and $m^7A$ is $N^6$-methyladenine.

In some embodiments, a self-replicating RNA of the disclosure comprises a 5' cap having the structure of Formula (Cap III).

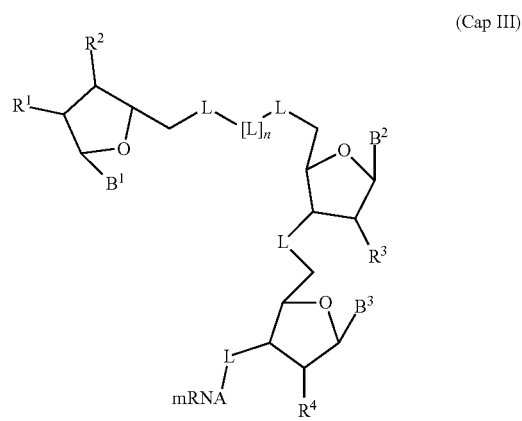

(Cap III)

wherein B1, B2, and B3 are each independently a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments B1 is G, m7G, or A. In some embodiments, B1 is A or m6A and R1 is $OCH_3$; wherein G is guanine, m7G is 7-methylguanine, A is adenine, and m6A is N6-methyladenine. In some embodiments, n is 1.

In some embodiments, a self-replicating RNA of the disclosure comprises a m7GpppG 5' cap analog having the structure of Formula (Cap IV).

(Cap IV)

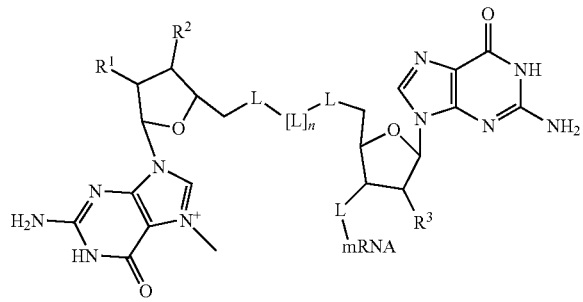

(Cap VI)

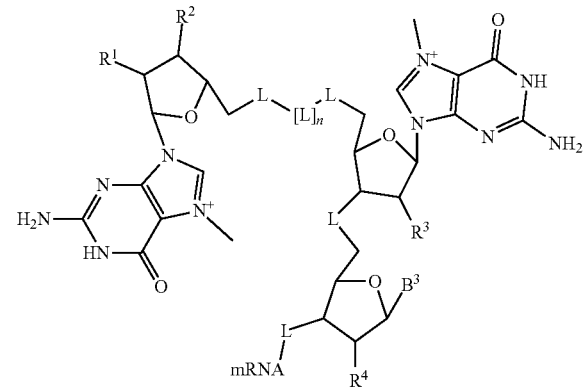

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, and $R^3$ is OH. In some embodiments, the 5' cap is m7GpppG wherein $R^1$, $R^2$, and $R^3$ are each OH, n is 1, and each L is a phosphate. In some embodiments, n is 1. In some embodiments, the 5' cap is m7GpppGm, wherein $R^1$ and $R^2$ are each OH, $R^3$ is $OCH_3$, each L is a phosphate, mRNA is the mRNA encoding an enzyme having OTC activity linked at its 5' end, and n is 1.

In some embodiments, a self-replicating RNA of the disclosure comprises a m7Gpppm7G 5' cap analog having the structure of Formula (Cap V).

wherein B3 is a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 3. In some embodiments, at least one of $R^1$, $R^2$, $R^3$, and $R^4$ is OH. In some embodiments $B^1$ is G, m7G, or A. In some embodiments, $B^1$ is A or $m^6A$ and $R^1$ is $OCH_3$; wherein G is guanine, m7G is 7-methylguanine, A is adenine, and $m^6A$ is $N^6$-methyladenine. In some embodiments, n is 1.

In some embodiments, a self-replicating RNA of the disclosure comprises a m7Gpppm7GpG 5' cap analog having the structure of Formula (Cap VII).

(Cap V)

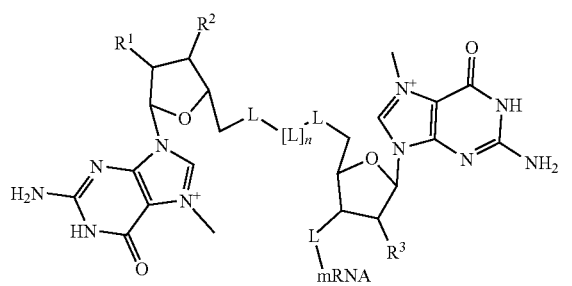

(Cap VII)

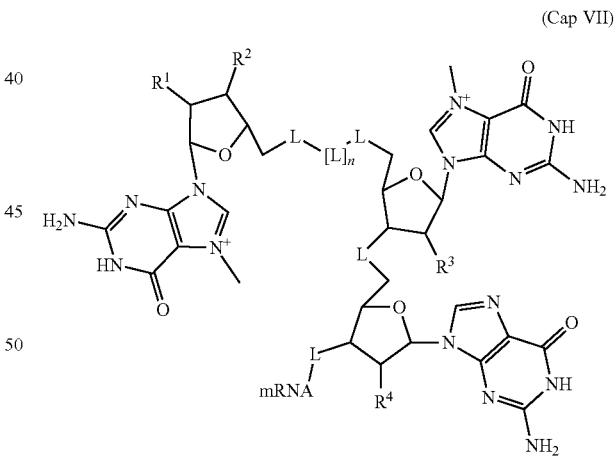

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7Gpppm7GpN, 5' cap analog, wherein N is a natural or modified nucleotide, the 5' cap analog having the structure of Formula (Cap VI).

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7Gpppm7Gpm7G 5' cap analog having the structure of Formula (Cap VIII).

(Cap VIII)

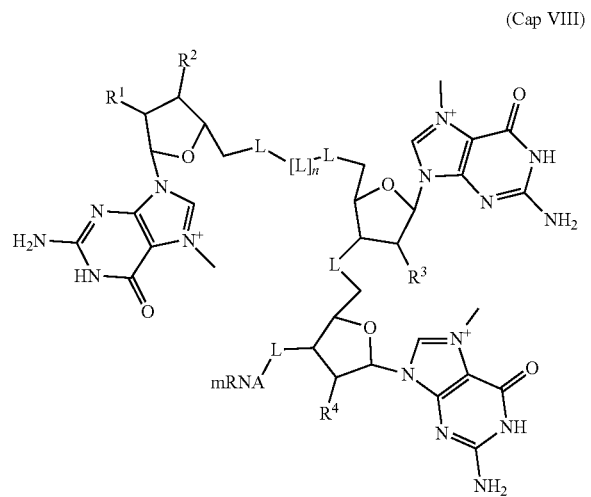

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppA 5' cap analog having the structure of Formula (Cap IX).

(Cap IX)

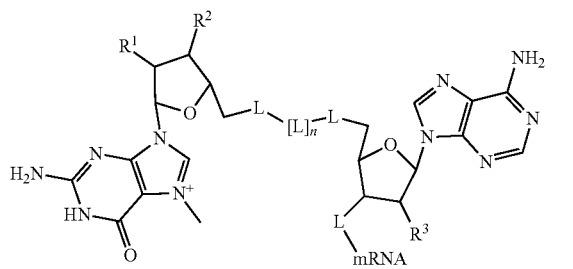

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7GpppApN 5' cap analog, wherein N is a natural or modified nucleotide, and the 5' cap has the structure of Formula (Cap X).

(Cap X)

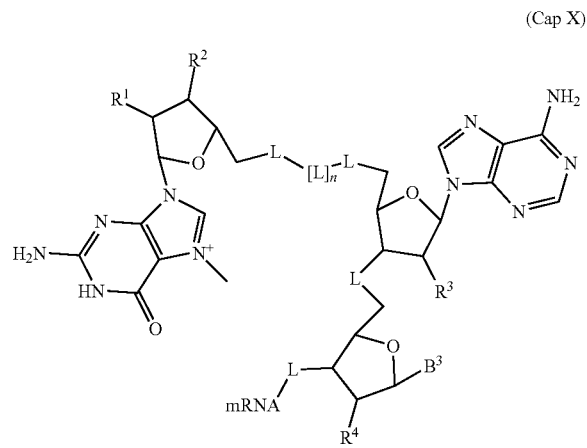

wherein $B^3$ is a natural or modified nucleobase; $R^1$, $R^2$, $R^3$, and R are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and R is OH. In some embodiments $B^3$ is G, $m^7G$, A or $m^6A$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a (Cap XI)

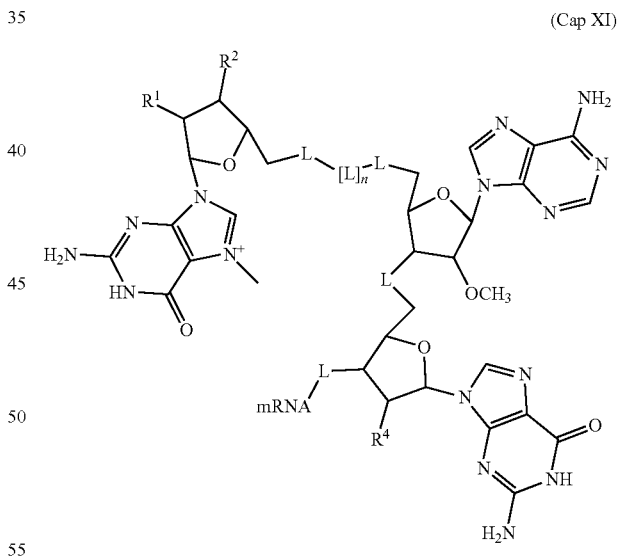

wherein, $R^1$, $R^2$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, the compound of Formula Cap XI is m7GpppAmpG, wherein $R^1$, $R^2$, and $R^4$ are each OH, n is 1, and each L is a phosphate linkage. In some embodiments, n is 1.

In some embodiments, a self-replicating RNA of the disclosure comprises a m7GpppApm7G 5' cap analog having the structure of Formula (Cap XII).

(Cap XII)

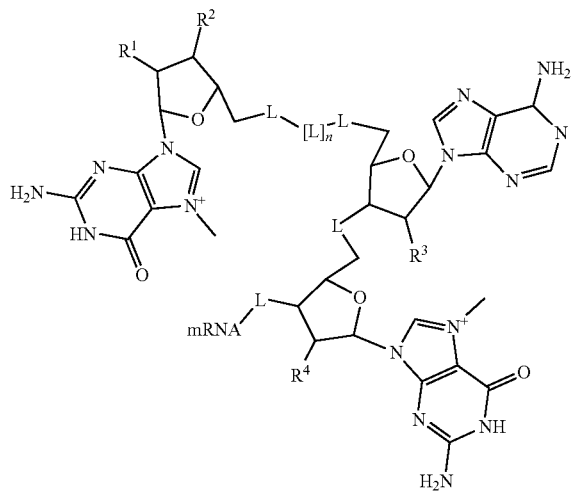

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppApm7G 5' cap analog having the structure of Formula (Cap XIII).

(Cap XIII)

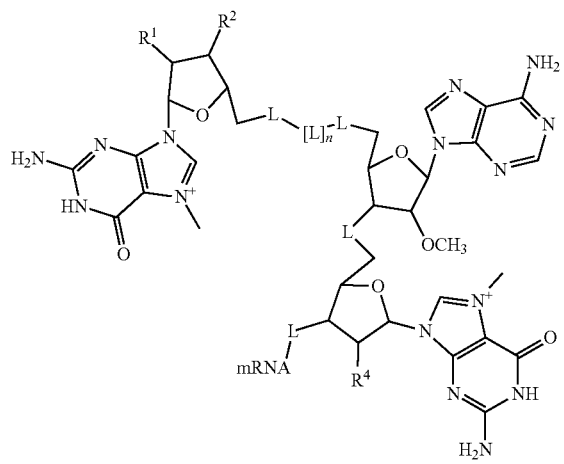

wherein, $R^1$, $R^2$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, n is 1.

Poly-Adenine (Poly-A) Tail

Polyadenylation is the addition of a poly(A) tail, a chain of adenine nucleotides usually about 100-120 monomers in length, to mRNA. In eukaryotes, polyadenylation is part of the process that produces mature mRNA for translation and begins as the transcription of a gene terminates. The 3'-most segment of a newly made pre-mRNA is first cleaved off by a set of proteins; these proteins then synthesize the poly(A) tail at the 3' end. The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol.

Preferably, a self-replicating RNA of the disclosure comprises a 3' tail region, which can serve to protect the RNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; 112-121 sequential adenine nucleotides; 114-121 adenine sequential nucleotides; or 115 to 121 sequential adenine nucleotides. Preferably, a 3' poly(A) tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly(A) tails or the use of a ligase (e.g., via splint ligation using a T4 RNA ligase and/or T4 DNA ligase), wherein poly(A) may be ligated to the 3 end of a sense RNA. In some embodiments, a combination of any of the above methods is utilized.

Design and Synthesis of Self-Replicating RNA

The constructs for exemplary self-replicating RNA sequences of the present disclosure are provided in Tables 4-5.

TABLE 4

Comparison of STARR™ self-replicating RNA of the disclosure with comparative self-replicating RNA as described

| Construct | Position | Sequence Type | Sequence |
|---|---|---|---|
| STARR™ (SEQ ID NO: 49) | 5' UTR | nucleotide | ATGGGCGGCGCATGAGAGAAGCCCAGACCAATTACCT ACCCAAA |

TABLE 4-continued

Comparison of STARR™ self-replicating
RNA of the disclosure with comparative
self-replicating RNA as described

| Construct | Position | Sequence Type | Sequence |
|---|---|---|---|
| STARR™ (SEQ ID NO: 50) | non-structural gene ORF | nucleotide | ATGGAGAAAGTTCACGTTGACATCGAGGAAGACAGCC<br>CATTCCTCAGAGCTTTGCAGCGGAGCTTCCCGCAGTTT<br>GAGGTAGAAGCCAAGCAGGTCACTGATAATGACCATG<br>CTAATGCCAGAGCGTTTTCGCATCTGGCTTCAAAACTG<br>ATCGAAACGGAGGTGGACCCATCCGACACGATCCTTG<br>ACATTGGAAGTGCGCCCGCCCGCAGAATGTATTCTAA<br>GCACAAGTATCOATTGTATCTGTCCGATGAGATGTGCGG<br>AAGATCCGGACAGATTGTATAAGTATGCAACTAAGCT<br>GAAGAAAAACTGTAAGGAAATAACTGATAAGGAATTG<br>ACAAGAAAATGAAGGAGCTGGCCGCCGTCATGAGCG<br>ACCCTGACCTGGAAACTGAGACTATGTGCCTCCACGA<br>CGACGAGTCGTGTCGCTACGAAGGGCAAGTCGCTGTT<br>TACCAGGATGTATACGCCGTCGACGGCCCCACCAGCC<br>TGTACCACCAGGCCAACAAGGGCGTGAGGGTGGCCTA<br>CTGGATCGGCTTCGACACCACACCCTTCATGTTCAAGA<br>ACCTGGCCGGCGCCTACCCCAGCTACAGCACCAACTG<br>GGCCGACGAGACCGTGCTGACCGCCAGGAACATCGGC<br>CTGTGCAGCAGCGACGTGATGGAGAGGAGCCGGAGAG<br>GCATGAGCATCCTGAGGAAGAAATACCTGAAGCCCAG<br>CAACAACGTGCTGTTCAGCGTGGGCAGCACCATCTAC<br>CACGAGAAGAGGGACCTGCTCAGGAGCTGGCACCTGC<br>CCAGCGTGTTCCACCTGAGGGGCAAGCAGAACTACAC<br>CTGCAGGTGCGAGACCATCGTGAGCTGCGACGGCTAC<br>GTGGTGAAGAGGATCGCCATCAGCCCCGGCCTGTACG<br>GCAAGCCCAGCGGCTACGCCGCTACAATGCACAGGGA<br>GGGCTTCCTGTGCTGCAAGGTGACCGACACCCTGAAC<br>GGCGAGAGGGTGAGCTTCCCCGTGTGCACCTACGTGC<br>CCGCCACCCTGTGCGACCAGATGACCGGCATCCTGGC<br>CACCGACGTGAGCGCCGACGACGCCCAGAAGCTGCTC<br>GTGGGCCTGAACCAGAGGATCGTGGTCAACGGCAGGA<br>CCCAGAGGAACACCAACACAATGAAGAACTACCTGCT<br>GCCCGTGGTGGCCCAGGCTTTCGCCAGGTGGGCCAAG<br>GAGTACAAGGAGGACCAGGAAGACGAGAGGCCCCTG<br>GGCCTGAGGGACAGGCAGCTGGTGATGGGCTGCTGCT<br>GGGCCTTCAGGCGGCACAAGATCACCAGCATCTACAA<br>GAGGGCCCGACACCCAGACCATCATCAAGGTGAACAGC<br>GACTTCCACAGCTTCGTGCTGCCCAGGATCGGCAGCA<br>ACACCCTGGAGATCGGCCTGAGGACCCGGATCAGGAA<br>GATGCTGGAGGAACACAAGGAGCCCAGCCCACTGATC<br>ACCGCCGAGGACGTGCAGGAGGCCAAGTGCGCTGCCG<br>ACGAGGCCAAGGAGGTGAGGGAGGCCGAGGAACTGA<br>GGGCCGCCCTGCCACCCCTGGCTGCCGACGTGGAGGA<br>ACCCACCCTGGAAGCCGACGTGGACCTGATGCTGCAG<br>GAGGCCGGCGCCGGAAGCGTGGAGACACCCAGGGGC<br>CTGATCAAGGTGACCAGCTACGACGGCGAGGACAAGA<br>TCGGCAGCTACGCCGTGCTGAGCCCACAGGCCGTGCT<br>GAAGTCCGAGAAGCTGAGCTGCATCCACCCACTGGCC<br>GAGCAGGTGATCGTGATCACCCACAGCGGCAGGAAGG<br>GCAGGTACGCCGTGGAGCCCTACCACGGCAAGGTGGT<br>CGTGCCCGAGGGCCACGCCATCCCCGTGCAGGACTTC<br>CAGGCCCTGAGCGAGAGCGCCACCATCGTGTACAACG<br>AGAGGGAGTTCGTGAACAGGTACCTGCACCATATCGC<br>CACCCACGGCGGAGCCCTGAACACCGACGAGGAATAC<br>TACAAGACCGTGAAGCCCAGCGAGCACGACGGCGAGT<br>ACCTGTACGACATCGACAGGAAGCAGTGCGTGAAGAA<br>AGAGCTGGTGACCGGCCTGGGACTGACCGGCGAGCTG<br>GTGGACCCACCCTTCCACGAGTTCGCCTACGAGAGCCT<br>GAGGACCAGACCCGCCGCTCCCTACCAGGTGCCCACC<br>ATCGGCGTGTACGGCGTGCCCGGCAGCGGAAAGAGCG<br>GCATCATCAAGAGCGCCGTGACCAAGAAAGACCTGGT<br>GGTCAGCGCCAAGAAAGAGAACTGCGCCGAGATCATC<br>AGGGACGTGAAGAAGATGAAAGGCCTGGACGTGAAC<br>GCGCGCACCGTGGACAGCGTGCTGCTGAACGGCTGCA<br>AGCACCCCGTGGAGACCCTGTACATCGACGAGGCCTT<br>CGCTTGCCACGCCGGCACCCTGAGGGCCCTGATCGCC<br>ATCATCAGGCCCAAGAAAGCCGTGCTGTGCGGCGACC<br>CCAAGCAGTGCGGCTTCTTCAACATGATGTGCCTGAAG<br>GTGCACTTCAACCACGAGATCTGCACCCAGGTGTTCCA<br>CAAGAGCATCAGCAGGCGGTGCACCAAGAGCGTGACC<br>AGCGTCGTGAGCACCCTGTTCTACGACAAGAAAATGA<br>GGACCACCAACCCCAAGGAGACCAAAATCGTGATCGA<br>CACCACAGGCAGCACCAAGCCCAAGCAGGACGACCTG |

TABLE 4-continued

Comparison of STARR™ self-replicating
RNA of the disclosure with comparative
self-replicating RNA as described

| Construct | Position | Sequence Type | Sequence |
|---|---|---|---|
| | | | ATCCTGACCTGCTTCAGGGGCTGGGTGAAGCAGCTGC |
| | | | AGATCGACTACAAGGGCAACGAGATCATGACCGCCGC |
| | | | TGCCAGCCAGGGCCTGACCAGGAAGGGCGTGTACGCC |
| | | | GTGAGGTACAAGGTGAACGAGAACCCACTGTACGCTC |
| | | | CCACCAGCGAGCACGTGAACGTGCTGCTGACCAGGAC |
| | | | CGAGGACAGGATCGTGTGGAAGACCCTGGCCGGCGAC |
| | | | CCCTGGATCAAGACCCTGACCGCCAAGTACCCCGGCA |
| | | | ACTTCACCGCCACCATCGAAGAGTGGCAGGCCGAGCA |
| | | | CGACGCCATCATGAGGCACATCCTGGAGAGGCCCGAC |
| | | | CCCACCGACGTGTTCCAGAACAAGGCCAACGTGTGCT |
| | | | GGGCCAAGGCCCTGGTGCCCGTGCTGAAGACCGCCGG |
| | | | CATCGACATGACCACAGAGCAGTGGAACACCGTGGAC |
| | | | TACTTCGAGACCGACAAGGCCCACAGCGCCGAGATCG |
| | | | TGCTGAACCAGCTGTGCGTGAGGTTCTTCGGCCTGGAC |
| | | | CTGGACAGCGGCCTGTTCAGCGCCCCCACCGTGCCACT |
| | | | GAGCATCAGGAACAACCACTGGGACAACAGCCCCAGC |
| | | | CCAAACATGTACGGCCTGAACAAGGAGGTGGTCAGGC |
| | | | AGCTGAGCAGGCGGTACCCACAGCTGCCCAGGGCCGT |
| | | | GGCCACCGGCAGGGTGTACGACATGAACACCGGCACC |
| | | | CTGAGGAACTACGACCCCAGGATCAACCTGGTGCCCG |
| | | | TGAACAGGCGGCTGCCCCACGCCCTGGTGCTGCACCA |
| | | | CAACGAGCACCCACAGAGCGACTTCAGCTCCTTCGTG |
| | | | AGCAAGCTGAAAGGCAGGACCGTGCTGGTCGTGGGCG |
| | | | AGAAGCTGAGCGTGCCCGGCAAGATGGTGGACTGGCT |
| | | | GAGCGACAGGCCCGAGGCCACCTTCCGGGCCAGGCTG |
| | | | GACCTCGGCATCCCCGGCGACGTGCCCAAGTACGACA |
| | | | TCATCTTCGTGAACGTCAGGACCCCATACAAGTACCAC |
| | | | CATTACCAGCAGTGCGAGGACCACGCCATCAAGCTGA |
| | | | GCATGCTGACCAAGAAGGCCTGCCTGCACCTGAACCC |
| | | | CGGAGGCACCTGCGTGAGCATCGGCTACGGCTACGCC |
| | | | GACAGGGCCAGCGAGAGCATCATTGGCGCCATCGCCA |
| | | | GGCTGTTCAAGTTCAGCAGGGTGTGCAAACCCAAGAG |
| | | | CAGCCTGGAGGAAACCGAGGTGCTGTTCGTGTTCATC |
| | | | GGCTACGACCGGAAGGCCAGGACCCACAACCCCTACA |
| | | | AGCTGAGCAGCACCCTGACAAACATCTACACCGGCAG |
| | | | CAGGCTGCACGAGGCCGGCTGCGCCCCCAGCTACCAC |
| | | | GTGGTCAGGGGCGATATCGCCACCGCCACCGAGGGCG |
| | | | TGATCATCAACGCTGCCAACAGCAAGGGCCAGCCCGG |
| | | | AGGCGGAGTGTGCGGCGCCCTGTACAAGAAGTTCCCC |
| | | | GAGAGCTTCGACCTGCAGCCCATCGAGGTGGGCAAGG |
| | | | CCAGGCTGGTGAAGGGCGCCGCTAAGCACATCATCCA |
| | | | CGCCGTGGGCCCCAACTTCAACAAGGTGAGCGAGGTG |
| | | | GAAGGCGACAAGCAGCTGGCCGAAGCCTACGAGAGC |
| | | | ATCGCCAAGATCGTGAACGACAATAACTACAAGAGCG |
| | | | TGGCCATCCCACTGCTCAGCACCGGCATCTTCAGCGGC |
| | | | AACAAGGACAGGCTGACCCAGAGCCTGAACCACCTGC |
| | | | TCACCGCCCTGGACACCACCGATGCCGACGTGGCCAT |
| | | | CTACTGCAGGGACAAGAAGTGGGAGATGACCCTGAAG |
| | | | GAGGCCGTGGCCAGGCGGGAGGCCGTGGAAGAGATCT |
| | | | GCATCAGCGACGACTCCAGCGTGACCGAGCCCGACGC |
| | | | CGAGCTGGTGAGGGTGCACCCCAAGAGCTCCCTGGCC |
| | | | GGCAGGAAGGGCTACAGCACCAGCGACGGCAAGACCT |
| | | | TCAGCTACCTGGAGGGCACCAAGTTCCACCAGGCCGC |
| | | | TAAGGACATCGCCGAGATCAACGCTATGTGGCCCGTG |
| | | | GCCACCGAGGCCAACGAGCAGGTGTGCATGTACATCC |
| | | | TGGGCGAGAGCATGTCCAGCATCAGGAGCAAGTGCCC |
| | | | CGTGGAGGAAAGCGAGGCCAGCACACCACCCAGCACC |
| | | | CTGCCCTGCCTGTGCATCCACGCTATGACACCCGAGAG |
| | | | GGTGCAGCGGCTGAAGGCCAGCAGGCCCGAGCAGATC |
| | | | ACCGTGTGCAGCTCCTTCCCACTGCCCAAGTACAGGAT |
| | | | CACCGGCGTGCAGAAGATCCAGTGCAGCCAGCCCATC |
| | | | CTGTTCAGCCCAAAGGTGCCCGCCTACATCCACCCCAG |
| | | | GAAGTACCTGGTGGAGACCCCACCCGTGGACGAGACA |
| | | | CCCGAGCCAAGCGCCGAGAACCAGAGCACCGAGGGC |
| | | | ACACCCGAGCAGCCACCCCTGATCACCGAGGACGAGA |
| | | | CAAGGACCCGGACCCCAGAGCCCATCATTATCGAGGA |
| | | | AGAGGAAGAGGACAGCATCAGCCTGCTGAGCGACGGC |
| | | | CCCACCCACCAGGTGCTGCAGGTGGAGGCCGACATCC |
| | | | ACGGCCCACCCAGCGTGTCCAGCTCCAGCTGGAGCAT |
| | | | CCCACACGCCAGCGACTTCGACGTGGACAGCCTGAGC |
| | | | ATCCTGGACACCCTGGAGGGCGCCAGCGTGACCTCCG |
| | | | GCGCCACCAGCGCCGAGACCAACAGCTACTTCGCCAA |
| | | | GAGCATGGAGTTCCTGGCCAGGCCCGTGCCAGCTCCC |

TABLE 4-continued

Comparison of STARR™ self-replicating
RNA of the disclosure with comparative
self-replicating RNA as described

| Construct | Position | Sequence Type | Sequence |
|---|---|---|---|
| | | | AGGACCGTGTTCAGGAACCCACCCCACCCAGCTCCCA
GGACCAGGACCCCAAGCCTGGCTCCCAGCAGGGCCTG
CAGCAGGACCAGCCTGGTGAGCACCCCACCCGGCGTG
AACAGGGTGATCACCAGGGAGGAACTGGAGGCCCTGA
CACCCAGCAGGACCCCCAGCAGGTCCGTGAGCAGGAC
TAGTCTGGTGTCCAACCCACCCGGCGTGAACAGGGTG
ATCACCAGGGAGGAATTCGAGGCCTTCGTGGCCCAGC
AACAGAGACGGTTCGACGCCGGCGCCTACATCTTCAG
CAGCGACACCGGCCAGGGACACCTGCAGCAAAAGAGC
GTGAGGCAGACCGTGCTGAGCGAGGTGGTGCTGGAGA
GGACCGAGCTGGAAATCAGCTACGCCCCCAGGCTGGA
CCAGGAGAAGGAGGAACTGCTCAGGAAGAAACTGCA
GCTGAACCCCACCCCAGCCAACAGGAGCAGGTACCAG
AGCAGGAAGGTGGAGAACATGAAGGCCATCACCGCCA
GGCGGATCCTGCAGGGCCTGGGACACTACCTGAAGGC
CGAGGGCAAGGTGGAGTGCTACAGGACCCTGCACCCC
GTGCCACTGTACAGCTCCAGCGTGAACAGGGCCTTCTC
CAGCCCCAAGGTGGCCGTGGAGGCCTGCAACGCTATG
CTGAAGGAGAACTTCCCCACCGTGGCCAGCTACTGCA
TCATCCCCGAGTACGACGCCTACCTGGACATGGTGGA
CGGCGCCAGCTGCTGCCTGGACACCGCCAGCTTCTGCC
CCGCCAAGCTGAGGAGCTTCCCCAAGAAACACAGCTA
CCTGGAGCCCACCATCAGGAGCGCCGTGCCCAGCGCC
ATCCAGAACACCCTGCAGAACGTGCTGGCCGCTGCCA
CCAAGAGGAACTGCAACGTGACCCAGATGAGGGAGCT
GCCCGTGCTGGACAGCGCTGCCTTCAACGTGGAGTGCT
TCAAGAAATACGCCTGCAACAACGAGTACTGGGAGAC
CTTCAAGGAGAACCCCATCAGGCTGACCGAAGAGAAC
GTGGTGAACTACATCACCAAGCTGAAGGGCCCCAAGG
CCGCTGCCCTGTTCGCTAAGACCCACAACCTGAACATG
CTGCAGGACATCCCAATGGACAGGTTCGTGATGGACC
TGAAGAGGGACGTGAAGGTGACACCCGGCACCAAGCA
CACCGAGGAGAGGCCCAAGGTGCAGGTGATCCAGGCC
GCTGACCCACTGGCCACCGCCTACCTGTGCGGCATCCA
CAGGGAGCTGGTGAGGCGGCTGAACGCCGTGCTGCTG
CCCAACATCCACACCCTGTTCGACATGAGCGCCGAGG
ACTTCGACGCCATCATCGCCGAGCACTTCCAGCCCGGC
GACTGCGTGCTGGAGACCGACATCGCCAGCTTCGACA
AGAGCGAGGATGACGCTATGGCCCTGACCGCTCTGAT
GATCCTGGAGGACCTGGGCGTGGACGCCGAGCTGCTC
ACCCTGATCGAGGCTGCCTTCGGCGAGATCAGCTCCAT
CCACCTGCCCACCAAGACCAAGTTCAAGTTCGGCGCT
ATGATGAAAAGCGGAATGTTCCTGACCCTGTTCGTGA
ACACCGTGATCAACATTGTGATCGCCAGCAGGGTGCT
GCGGGAGAGGCTGACCGGCAGCCCCTGCGCTGCCTTC
ATCGGCGACGACAACATCGTGAAGGGCGTGAAAAGCG
ACAAGCTGATGGCCGACAGGTGCGCCACCTGGCTGAA
CATGGAGGTGAAGATCATCGACGCCGTGGTGGGCGAG
AAGGCCCCCTACTTCTGCGGCGGATTCATCCTGTGCGA
CAGCGTGACCGGCACCGCCTGCAGGGTGGCCGACCCC
CTGAAGAGGCTGTTCAAGCTGGGCAAGCCACTGGCCG
CTGACGATGAGCACGACGATGACAGGCGGAGGGCCCT
GCACGAGGAAAGCACCAGGTGGAACAGGGTGGGCAT
CCTGAGCGAGCTGTGCAAGGCCGTGGAGAGCAGGTAC
GAGACCGTGGGCACCAGCATCATCGTGATGGCTATGA
CCACACTGGCCAGCTCCGTCAAGAGCTTCTCCTACCTG
AGGGGGGCCCCTATAACTCTCTACGGCTAA |
| STARR™ (SEQ ID NO: 51) | non-structural gene ORF | amino acid | MEKVHVDIEEDSPFLRALQRSFPQFEVEAKQVTDNDHAN
ARAFSHLASKLIETEVDPSDTILDIGSAPARRMYSKHKYH
CICPMRCAEDPDRLYKYATKLKKNCKEITDKELDKKMK
ELAAVMSDPDLETETMCLHDDESCRYEGQVAVYQDVY
AVDGPTSLYHQANKGVRVAYWIGFDTTPFMFKNLAGAY
PSYSTNWADETVLTARNIGLCSSDVMERSRRGMSILRKK
YLKPSNNVLFSVGSTIYHEKRDLLRSWHLPSVFHLRGKQ
NYTCRCETIVSCDGYVVKRIAISPGLYGKPSGYAATMHR
EGFLCCKVTDTLNGERVSFPVCTYVPATLCDQMTGILAT
DVSADDAQKLLVGLNQRIVVNGRTQRNTNTMKNYLLPV
VAQAFARWAKEYKEDQEDERPLGLRDRQLVMGCCWAF
RRHKITSIYKRPDTQTIIKVNSDFHSFVLPRIGSNTLEIGLR
TRIRKMLEEHKEPSPLITAEDVQEAKCAADEAKEVREAE
ELRAALPPLAADVEEPTLEADVDLMLQEAGAGSVETPRG
LIKVTSYDGEDKIGSYAVLSPQAVLKSEKLSCIHPLAEQVI |

TABLE 4-continued

Comparison of STARR™ self-replicating
RNA of the disclosure with comparative
self-replicating RNA as described

| Construct | Position | Sequence Type | Sequence |
|---|---|---|---|
| | | | VITHSGRKGRYAVEPYHGKVVVPEGHAIPVQDFQALSES
ATIVYNEREFVNRYLHHIATHGGALNTDEEYYKTVKPSE
HDGEYLYDIDRKQCVKKELVTGLGLTGELVDPPFHEFAY
ESLRTRPAAPYQVPTIGVYGVPGSGKSGIIKSAVTKKDLV
VSAKKENCAEIIRDVKKMKGLDVNARTVDSVLLNGCKH
PVETLYIDEAFACHAGTLRALIAIIRPKKAVLCGDPKQCG
FFNMMCLKVHFNHEICTQVFHKSISRRCTKSVTSVVSTLF
YDKKMRTTNPKETKIVIDTTGSTKPKQDDLILTCFRGWV
KQLQIDYKGNEIMTAAASQGLTRKGVYAVRYKVNENPL
YAPTSEHVNVLLTRTEDRIVWKTLAGDPWIKTLTAKYPG
NFTATIEEWQAEHDAIMRHILERPDPTDVFQNKANVCWA
KALVPVLKTAGIDMTTEQWNTVDYFETDKAHSAEIVLN
QLCVRFFGLDLDSGLFSAPTVPLSIRNNHWDNSPSPNMY
GLNKEVVRQLSRRYPQLPRAVATGRVYDMNTGTLRNYD
PRINLVPVNRRLPHALVLHHNEHPQSDFSSFVSKLKGRTV
LVVGEKLSVPGKMVDWLSDRPEATFRARLDLGIPGDVP
KYDIIFVNVRTPYKYHHYQQCEDHAIKLSMLTKKACLHL
NPGGTCVSIGYGYADRASESIIGAIARLFKFSRVCKPKSSL
EETEVLFVFIGYDRKARTHNPYKLSSTLTNIYTGSRLHEA
GCAPSYHVVRGDIATATEGVIINAANSKGQPGGGVCGAL
YKKFPESFDLQPIEVGKARLVKGAAKHIIHAVGPNFNKVS
EVEGDKQLAEAYESIAKIVNDNNYKSVAIPLLSTGIFSGN
KDRLTQSLNHLLTALDTTDADVAIYCRDKKWEMTLKEA
VARREAVEEICISDDSSVTEPDAELVRVHPKSSLAGRKGY
STSDGKTFSYLEGTKFHQAAKDIAEINAMWPVATEANEQ
VCMYILGESMSSIRSKCPVEESEASTPPSTLPCLCIHAMTP
ERVQRLKASRPEQITVCSSFPLPKYRITGVQKIQCSQPILFS
PKVPAYIHPRKYLVETPPVDETPEPSAENQSTEGTPEQPPL
ITEDEDTRTRTPEPIIIEEEEEDSISLLSDGPTHQVLQVEADIH
GPPSVSSSSWSIPHASDFDVDSLSILDTLEGASVTSGATSA
ETNSYFAKSMEFLARPVPAPRTVFRNPPHPAPRTRTPSLA
PSRACSRTSLVSTPPGVNRVITREELEALTPSRTPSRSVSR
TSLVSNPPGVNRVITREEFEAFVAQQQRRFDAGAYIFSSD
TGQGHLQQKSVRQTVLSEVVLERTELEISYAPRLDQEKE
ELLRKKLQLNPTPANRSRYQSRKVENMKAITARRILQGL
GHYLKAEGKVECYRTLHPVPLYSSSVNRAFSSPKVAVEA
CNAMLKENFPTVASYCIIPEYDAYLDMVDGASCCLDTAS
FCPAKLRSFPKKHSYLEPTIRSAVPSAIQNTLQNVLAAAT
KRNCNVTQMRELPVLDSAAFNVECFKKYACNNEYWETF
KENPIRLTEENVVNYITKLKGPKAAALFAKTHNLNMLQD
IPMDRFVMDLKRDVKVTPGTKHTEERPKVQVIQAADPL
ATAYLCGIHRELVRRLNAVLLPNIHTLFDMSAEDFDAIIA
EHFQPGDCVLETDIASFDKSEDDAMALTALMILEDLGVD
AELLTLIEAAFGEISSIHLPTKTKFKFGAMMKSGMFLTLF
VNTVINIVIASRVLRERLTGSPCAAFIGDDNIVKGVKSDK
LMADRCATWLNMEVKIIDAVVGEKAPYFCGGFILCDSVT
GTACRVADPLKRLFKLGKPLAADDEHDDDRRRALHEES
TRWNRVGILSELCKAVESRYETVGTSIIVMAMTTLASSV
KSFSYLRGAPITLYG* |
| STARR™ (SEQ ID NO: 52) | intergenic region | nucleotide | CCTGAATGGACTACGACATAGTCTAGTCCGCCAAGGC
CGCCACC |
| STARR™ | transgene ORF | nucleotide | n/a (depends on gene of our interest) |
| STARR™ (SEQ ID NO: 53) | 3' UTR | nucleotide | ACTCGAGTATGTTACGTGCAAAGGTGATTGTCACCCCC
CGAAAGACCATATTGTGACACACCCTCAGTATCACGC
CCAAACATTTACAGCCGCGGTGTCAAAAACCGCGTGG
ACGTGGTTAACATCCCTGCTGGGAGGATCAGCCGTAA
TTATTATAATTGGCTTGGTGCTGGCTACTATTGTGGCC
ATGTACGTGCTGACCAACCAGAAACATAATTGAATAC
AGCAGCAATTGGCAAGCTGCTTACATAGAACTCGCGG
CGATTGGCATGCCGCCTTAAAATTTTTATTTTATTTTTT
CTTTTCTTTTCCGAATCGGATTTTGTTTTTAATATTTCA
AAAAAAAAAAAAAAAAAAAATCTAGAAAAAAA
AAAAAAAAAAAAAAAAAAAAAAAAAAAAAAA
AAAAAAAAAAAAAAAAAAAAAAAAAAAAAAA
AAAAAAAAAAAAAAAAAAAAAA |

TABLE 4-continued

Comparison of STARR™ self-replicating RNA of the disclosure with comparative self-replicating RNA as described

| Construct | Position | Sequence Type | Sequence |
|---|---|---|---|
| Comparitive | 5' UTR | nucleotide | unknown |
| Original (SEQ ID NO: 54) | non-structural gene ORF | nucleotide | ATGCCCGAGAAGGTGCACGTGGACATCGAGGAGGACA GCCCCTTCCTGAGGGCCCTGCAGAGGAGCTTCCCACA GTTCGAAGTGGAGGCCAAGCAGGTGACCGACAACGAC CACGCCAACGCCAGGGCCTTCAGCCACCTGGCCAGCA AGCTGATCGAGACCGAGGTGGACCCCAGCGACACCAT CCTGGACATCGGCAGCGCCCCAGCCAGGAGAATGTAC AGCAAGCACAAGTACCACTGCATCTGCCCCATGAGGT GCGCCGAGGACCCCGACAGGCTGTACAAGTACGCCAC CAAACTGAAGAAGAACTGCAAGGAGATCACCGACAA GGAGCTGGACAAGAAAATGAAGGAGCTGGCCGCCGTG ATGAGCGACCCCGACCTGGAGACCGAGACAATGTGCC TGCACGACGACGAGAGCTGCAGGTACGAGGGCCAGGT GGCCGTCTACCAGGACGTGTACGCCGTCGACGGCCCC ACCAGCCTGTACCACCAGGCCAACAAGGGCGTGAGGG TGGCCTACTGGATCGGCTTCGACACCACACCCTTCATG TTCAAGAACCTGGCCGGCGCCTACCCCAGCTACAGCA CCAACTGGGCCGACGAGACCGTGCTGACCGCCAGGAA CATCGGCCTGTGCAGCAGCGACGTGATGGAGAGGAGC CGGAGAGGCATGAGCATCCTGAGGAAGAAATACCTGA AGCCCAGCAACAACGTGCTGTTCAGCGTGGGCAGCAC CATCTACCACGAGAAGAGGGACCTGCTCAGGAGCTGG CACCTGCCCAGCGTGTTCCACCTGAGGGGCAAGCAGA ACTACACCTGCAGGTGCGAGACCATCGTGAGCTGCGA CGGCTACGTGGTGAAGAGGATCGCCATCAGCCCCGGC CTGTACGGCAAGCCCAGCGGCTACGCCGCTACAATGC ACAGGGAGGGCTTCCTGTGCTGCAAGGTGACCGACAC CCTGAACGGCGAGAGGGTGAGCTTCCCCGTGTGCACC TACGTGCCCGCCACCCTGTGCGACCAGATGACCGGCA TCCTGGCCACCGACGTGAGCGCCGACGACGCCCAGAA GCTGCTCGTGGGCCTGAACCAGAGGATCGTGGTCAAC GGCAGGACCCAGAGGAACACCAACACAATGAAGAAC TACCTGCTGCCCGTGGTGGCCCAGGCTTTCGCCAGGTG GGCCAAGGAGTACAAGGAGGACCAGGAAGACGAGAG GCCCCTGGGCCTGAGGGACAGGCAGCTGGTGATGGGC TGCTGCTGGGCCTTCAGGCGGCACAAGATCACCAGCA TCTACAAGAGGCCCGACACCCAGACCATCATCAAGGT GAACAGCGACTTCCACAGCTTCGTGCTGCCCAGGATC GGCAGCAACACCCTGGAGATCGGCCTGAGGACCCGGA TCAGGAAGATGCTGGAGGAACACAAGGAGCCCAGCCC ACTGATCACCGCCGAGGACGTGCAGGAGGCCAAGTGC GCTGCCGACGAGGCCAAGGAGGTGAGGGAGGCCGAG GAACTGAGGGCCGCCCTGCCACCCCTGGCTGCCGACG TGGAGGAACCCACCCTGGAAGCCGACGTGGACCTGAT GCTGCAGGAGGCCGGCGCCGGAAGCGTGGAGACACCC AGGGGCCTGATCAAGGTGACCAGCTACGACGGCGAGG ACAAGATCGGCAGCTACGCCGTGCTGAGCCCACAGGC CGTGCTGAAGTCCGAGAAGCTGAGCTGCATCCACCCA CTGGCCGAGCAGGTGATCGTGATCACCCACAGCGGCA GGAAGGGCAGGTACGCCGTGGAGCCCTACCACGGCAA GGTGGTCGTGCCCGAGGGCCACGCCATCCCCGTGCAG GACTTCCAGGCCCTGAGCGAGAGCGCCACCATCGTGT ACAACGAGAGGGAGTTCGTGAACAGGTACCTGCACCA TATCGCCACCCACGGCGGAGCCCTGAACACCGACGAG GAATACTACAAGACCGTGAAGCCCAGCGAGCACGACG GCGAGTACCTGTACGACATCGACAGGAAGCAGTGCGT GAAGAAAGAGCTGGTGACCGGCCTGGGACTGACCGGC GAGCTGGTGGACCCACCCTTCCACGAGTTCGCCTACGA GAGCCTGAGGACCAGACCCGCCGCTCCCTACCAGGTG CCCACCATCGGCGTGTACGGCGTGCCCGGCAGCGGAA AGAGCGGCATCATCAAGAGCGCCGTGACCAAGAAAGA CCTGGTGGTCAGCGCCAAGAAAGAGAACTGCGCCGAG ATCATCAGGGACGTGAAGAAGATGAAAGGCCTGGACG TGAACGCGCGCACCGTGGACAGCGTGCTGCTGAACGG CTGCAAGCACCCCGTGGAGACCCTGTACATCGACGAG GCCTTCGCTTGCCACGCCGGCACCCTGAGGGCCCTGAT CGCCATCATCAGGCCCAAGAAGGCCGTGCTGTGCGGC GACCCCAAGCAGTGCGGCTTCTTCAACATGATGTGCCT GAAGGTGCACTTCAACCACGAGATCTGCACCCAGGTG TTCCACAAGAGCATCAGCAGGCGGTGCACCAAGAGCG TGACCAGCGTCGTGAGCACCCTGTTCTACGACAAGAA AATGAGGACCACCAACCCCAAGGAGACCAAAATCGTG |

TABLE 4-continued

Comparison of STARR™ self-replicating
RNA of the disclosure with comparative
self-replicating RNA as described

| Construct | Position | Sequence Type | Sequence |
|---|---|---|---|
| | | | ATCGACACCACAGGCAGCACCAAGCCCAAGCAGGACG |
| | | | ACCTGATCCTGACCTGCTTCAGGGGCTGGGTGAAGCA |
| | | | GCTGCAGATCGACTACAAGGGCAACGAGATCATGACC |
| | | | GCCGCTGCCAGCCAGGGCCTGACCAGGAAGGGCGTGT |
| | | | ACGCCGTGAGGTACAAGGTGAACGAGAACCCACTGTA |
| | | | CGCTCCCACCAGCGAGCACGTGAACGTGCTGCTGACC |
| | | | AGGACCGAGGACAGGATCGTGTGGAAGACCCTGGCCG |
| | | | GCGACCCCTGGATCAAGACCCTGACCGCCAAGTACCC |
| | | | CGGCAACTTCACCGCCACCATCGAAGAGTGGCAGGCC |
| | | | GAGCACGACGCCATCATGAGGCACATCCTGGAGAGGC |
| | | | CCGACCCCACCGACGTGTTCCAGAACAAGGCCAACGT |
| | | | GTGCTGGGCCAAGGCCCTGGTGCCCGTGCTGAAGACC |
| | | | GCCGGCATCGACATGACCACAGAGCAGTGGAACACCG |
| | | | TGGACTACTTCGAGACCGACAAGGCCCACAGCGCCGA |
| | | | GATCGTGCTGAACCAGCTGTGCGTGAGGTTCTTCGGCC |
| | | | TGGACCTGGACAGCGGCCTGTTCAGCGCCCCCACCGT |
| | | | GCCACTGAGCATCAGGAACAACCACTGGGACAACAGC |
| | | | CCCAGCCCAAACATGTACGGCCTGAACAAGGAGGTGG |
| | | | TCAGGCAGCTGAGCAGGCGGTACCCACAGCTGCCCAG |
| | | | GGCCGTGGCCACCGGCAGGGTGTACGACATGAACACC |
| | | | GGCACCCTGAGGAACTACGACCCCAGGATCAACCTGG |
| | | | TGCCCGTGAACAGGCGGCTGCCCCACGCCCTGGTGCT |
| | | | GCACCACAACGAGCACCCACAGAGCGACTTCAGCTCC |
| | | | TTCGTGAGCAAGCTGAAAGGCAGGACCGTGCTGGTCG |
| | | | TGGGCGAGAAGCTGAGCGTGCCCGGCAAGATGGTGGA |
| | | | CTGGCTGAGCGACAGGCCCGAGGCCACCTTCCGGGCC |
| | | | AGGCTGGACCTCGGCATCCCCGGCGACGTGCCCAAGT |
| | | | ACGACATCATCTTCGTGAACGTCAGGACCCCATACAA |
| | | | GTACCACCATTACCAGCAGTGCGAGGACCACGCCATC |
| | | | AAGCTGAGCATGCTGACCAAGAAGGCCTGCCTGCACC |
| | | | TGAACCCCGGAGGCACCTGCGTGAGCATCGGCTACGG |
| | | | CTACGCCGACAGGGCCAGCGAGAGCATCATTGGCGCC |
| | | | ATCGCCAGGCTGTTCAAGTTCAGCAGGGTGTGCAAAC |
| | | | CCAAGAGCAGCCTGGAGGAAACCGAGGTGCTGTTCGT |
| | | | GTTCATCGGCTACGACCGGAAGGCCAGGACCCACAAC |
| | | | CCCTACAAGCTGAGCAGCACCCTGACAAACATCTACA |
| | | | CCGGCAGCAGGCTGCACGAGGCCGGCTGCGCCCCCAG |
| | | | CTACCACGTGGTCAGGGGCGATATCGCCACCGCCACC |
| | | | GAGGGCGTGATCATCAACGCTGCCAACAGCAAGGGCC |
| | | | AGCCCGGAGGCGGAGTGTGCGGCGCCCTGTACAAGAA |
| | | | GTTCCCCGAGAGCTTCGACCTGCAGCCCATCGAGGTG |
| | | | GGCAAGGCCAGGCTGGTGAAGGGCGCCGCTAAGCACA |
| | | | TCATCCACGCCGTGGGCCCCAACTTCAACAAGGTGAG |
| | | | CGAGGTGGAAGGCGACAAGCAGCTGGCCGAAGCCTAC |
| | | | GAGAGCATCGCCAAGATCGTGAACGACAATAACTACA |
| | | | AGAGCGTGGCCATCCCACTGCTCAGCACCGGCATCTTC |
| | | | AGCGGCAACAAGGACAGGCTGACCCAGAGCCTGAACC |
| | | | ACCTGCTCACCGCCCTGGACACCACCGATGCCGACGT |
| | | | GGCCATCTACTGCAGGGACAAGAAGTGGGAGATGACC |
| | | | CTGAAGGAGGCCGTGGCCAGGCGGGAGGCCGTGGAA |
| | | | GAGATCTGCATCAGCGACGACTCCAGCGTGACCGAGC |
| | | | CCGACGCCGAGCTGGTGAGGGTGCACCCCAAGAGCTC |
| | | | CCTGGCCGGCAGGAAGGGCTACAGCACCAGCGACGGC |
| | | | AAGACCTTCAGCTACCTGGAGGGCACCAAGTTCCACC |
| | | | AGGCCGCTAAGGACATCGCCGAGATCAACGCTATGTG |
| | | | GCCCGTGGCCACCGAGGCCAACGAGCAGGTGTGCATG |
| | | | TACATCCTGGGCGAGAGCATGTCCAGCATCAGGAGCA |
| | | | AGTGCCCCGTGGAGGAAAGCGAGGCCAGCACACCACC |
| | | | CAGCACCCTGCCCTGCCTGTGCATCCACGCTATGACAC |
| | | | CCGAGAGGGTGCAGCGGCTGAAGGCCAGCAGGCCCGA |
| | | | GCAGATCACCGTGTGCAGCTCCTTCCCACTGCCCAAGT |
| | | | ACAGGATCACCGGCGTGCAGAAGATCCAGTGCAGCCA |
| | | | GCCCATCCTGTTCAGCCCAAAGGTGCCCGCCTACATCC |
| | | | ACCCCAGGAAGTACCTGGTGGAGACCCCACCCGTGGA |
| | | | CGAGACACCCGAGCCAAGCGCCGAGAACCAGAGCACC |
| | | | GAGGGCACACCCGAGCAGCCACCCCTGATCACCGAGG |
| | | | ACGAGACAAGGACCCGGACCCCAGAGCCCATCATTAT |
| | | | CGAGGAAGAGGAAGAGGACAGCATCAGCCTGCTGAG |
| | | | CGACGGCCCCACCCACCAGGTGCTGCAGGTGGAGGCC |
| | | | GACATCCACGGCCCACCCAGCGTGTCCAGCTCCAGCT |
| | | | GGAGCATCCCACACGCCAGCGACTTCGACGTGGACAG |
| | | | CCTGAGCATCCTGGACACCCTGGAGGGCGCCAGCGTG |
| | | | ACCTCCGGCGCCACCAGCGCCGAGACCAACAGCTACT |

TABLE 4-continued

Comparison of STARR™ self-replicating RNA of the disclosure with comparative self-replicating RNA as described

| Construct | Position | Sequence Type | Sequence |
|---|---|---|---|
| | | | TCGCCAAGAGCATGGAGTTCCTGGCCAGGCCCGTGCC<br>AGCTCCCAGGACCGTGTTCAGGAACCCACCCCACCCA<br>GCTCCCAGGACCAGGACCCCAAGCCTGGCTCCCAGCA<br>GGGCCTGCAGCAGGACCAGCCTGGTGAGCACCCCACC<br>CGGCGTGAACAGGGTGATCACCAGGGAGGAACTGGAG<br>GCCCTGACACCCAGCAGGACCCCCAGCAGGTCCGTGA<br>GCAGGACTAGTCTGGTGTCCAACCCACCCGGCGTGAA<br>CAGGGTGATCACCAGGGAGGAATTCGAGGCCTTCGTG<br>GCCCAGCAACAGAGACGGTTCGACGCCGGCGCCTACA<br>TCTTCAGCAGCGACACCGGCCAGGGACACCTGCAGCA<br>AAAGAGCGTGAGGCAGACCGTGCTGAGCGAGGTGGTG<br>CTGGAGAGGACCGAGCTGGAAATCAGCTACGCCCCCA<br>GGCTGGACCAGGAGAAGGAGGAACTGCTCAGGAAGA<br>AACTGCAGCTGAACCCCACCCCAGCCAACAGGAGCAG<br>GTACCAGAGCAGGAAGGTGGAGAACATGAAGGCCATC<br>ACCGCCAGGCGGATCCTGCAGGGCCTGGGACACTACC<br>TGAAGGCCGAGGGCAAGGTGGAGTGCTACAGGACCCT<br>GCACCCCGTGCCACTGTACAGCTCCAGCGTGAACAGG<br>GCCTTCTCCAGCCCCAAGGTGGCCGTGGAGGCCTGCA<br>ACGCTATGCTGAAGGAGAACTTCCCCACCGTGGCCAG<br>CTACTGCATCATCCCCGAGTACGACGCCTACCTGGACA<br>TGGTGGACGGCGCCAGCTGCTGCCTGGACACCGCCAG<br>CTTCTGCCCCGCCAAGCTGAGGAGCTTCCCCAAGAAA<br>CACAGCTACCTGGAGCCCACCATCAGGAGCGCCGTGC<br>CCAGCGCCATCCAGAACACCCTGCAGAACGTGCTGGC<br>CGCTGCCACCAAGAGGAACTGCAACGTGACCCAGATG<br>AGGGAGCTGCCCGTGCTGGACAGCGCTGCCTTCAACG<br>TGGAGTGCTTCAAGAAATACGCCTGCAACAACGAGTA<br>CTGGGAGACCTTCAAGGAGAACCCCATCAGGCTGACC<br>GAAGAGAACGTGGTGAACTACATCACCAAGCTGAAGG<br>GCCCCAAGGCCGCTGCCCTGTTCGCTAAGACCCACAA<br>CCTGAACATGCTGCAGGACATCCCAATGGACAGGTTC<br>GTGATGGACCTGAAGAGGGACGTGAAGGTGACACCCG<br>GCACCAAGCACACCGAGGAGAGGCCCAAGGTGCAGGT<br>GATCCAGGCCGCTGACCCACTGGCCACCGCCTACCTGT<br>GCGGCATCCACAGGGAGCTGGTGAGGCGGCTGAACGC<br>CGTGCTGCTGCCCAACATCCACACCCTGTTCGACATGA<br>GCGCCGAGGACTTCGACGCCATCATCGCCGAGCACTT<br>CCAGCCCGGCGACTGCGTGCTGGAGACCGACATCGCC<br>AGCTTCGACAAGAGCGAGGATGACGCTATGGCCCTGA<br>CCGCTCTGATGATCCTGGAGGACCTGGGCGTGGACGC<br>CGAGCTGCTCACCCTGATCGAGGCTGCCTTCGGCGAG<br>ATCAGCTCCATCCACCTGCCCACCAAGACCAAGTTCAA<br>GTTCGGCGCTATGATGAAAAGCGGAATGTTCCTGACC<br>CTGTTCGTGAACACCGTGATCAACATTGTGATCGCCAG<br>CAGGGTGCTGCGGGAGAGGCTGACCGGCAGCCCCTGC<br>GCTGCCTTCATCGGCGACGACAACATCGTGAAGGGCG<br>TGAAAAGCGACAAGCTGATGGCCGACAGGTGCGCCAC<br>CTGGCTGAACATGGAGGTGAAGATCATCGACGCCGTG<br>GTGGGCGAGAAGGCCCCCTACTTCTGCGGCGGATTCA<br>TCCTGTGCGACAGCGTGACCGGCACCGCCTGCAGGGT<br>GGCCGACCCCCTGAAGAGGCTGTTCAAGCTGGGCAAG<br>CCACTGGCCGCTGACGATGAGCACGACGATGACAGGC<br>GGAGGGCCCTGCACGAGAAAGCACCAGGTGGAACA<br>GGGTGGGCATCCTGAGCGAGCTGTGCAAGGCCGTGGA<br>GAGCAGGTACGAGACCGTGGGCACCAGCATCATCGTG<br>ATGGCTATGACCACACTGGCCAGCTCCGTCAAGAGCTT<br>CTCCTACCTGAGGGGGGCCCCTATAACTCTCTACGGCT<br>AA |
| Comparitive<br>(SEQ ID<br>NO: 55) | non-<br>structural<br>gene ORF | amino acid | MPEKVHVDIEEDSPFLRALQRSFPQFEVEAKQVTDNDHA<br>NARAFSHLASKLIETEVDPSDTILDIGSAPARRMYSKHKY<br>HCICPMRCAEDPDRLYKYATKLKKNCKEITDKELDKKM<br>KELAAVMSDPDLETETMCLHDDESCRYEGQVAVYQDV<br>YAVDGPTSLYHQANKGVRVAYWIGFDTTPFMFKNLAGA<br>YPSYSTNWADETVLTARNIGLCSSDVMERSRRGMSILRK<br>KYLKPSNNVLFSVGSTIYHEKRDLLRSWHLPSVFHLRGK<br>QNYTCRCETIVSCDGYVVKRIAISPGLYGKPSGYAATMH<br>REGFLCCKVTDTLNGERVSFPVCTYVPATLCDQMTGILA<br>TDVSADDAQKLLVGLNQRIVVNGRTQRNTNTMKNYLLP<br>VVAQAFARWAKEYKEDQEDERPLGLRDRQLVMGCCWA<br>FRRHKITSIYKRPDTQTIIKVNSDFHSFVLPRIGSNTLEIGL<br>RTRIRKMLEEHKEPSPLITAEDVQEAKCAADEAKEVREA |

TABLE 4-continued

Comparison of STARR™ self-replicating
RNA of the disclosure with comparative
self-replicating RNA as described

| Construct | Position | Sequence Type | Sequence |
|---|---|---|---|
| | | | EELRAALPPLAADVEEPTLEADVDLMLQEAGAGSVETPR GLIKVTSYDGEDKIGSYAVLSPQAVLKSEKLSCIHPLAEQ VIVITHSGRKGRYAVEPYHGKVVVPEGHAIPVQDFQALS ESATIVYNEREFVNRYLHHIATHGGALNTDEEYYKTVKP SEHDGEYLYDIDRKQCVKKELVTGLGLTGELVDPPFHEF AYESLRTRPAAPYQVPTIGVYGVPGSGKSGIIKSAVTKKD LVVSAKKENCAEIIRDVKKMKGLDVNARTVDSVLLNGC KHPVETLYIDEAFACHAGTLRALIAIIRPKKAVLCGDPKQ CGFFNMMCLKVHFNHEICTQVFHKSISRRCTKSVTSVVS TLFYDKKMRTTNPKETKIVIDTTGSTKPKQDDLILTCFRG WVKQLQIDYKGNEIMTAAASQGLTRKGVYAVRYKVNE NPLYAPTSEHVNVLLTRTEDRIVWKTLAGDPWIKTLTAK YPGNFTATIEEWQAEHDAIMRHILERPDPTDVFQNKANV CWAKALVPVLKTAGIDMTTEQWNTVDYFETDKAHSAEI VLNQLCVRFFGLDLDSGLFSAPTVPLSIRNNHWDNSPSPN MYGLNKEVVRQLSRRYPQLPRAVATGRVYDMNTGTLR NYDPRINLVPVNRRLPHALVLHHNEHPQSDFSSFVSKLK GRTVLVVGEKLSVPGKMVDWLSDRPEATFRARLDLGIP GDVPKYDIIFVNVRTPYKYHHYQQCEDHAIKLSMLTKKA CLHLNPGGTCVSIGYGYADRASESIIGAIARLFKFSRVCKP KSSLEETEVLFVFIGYDRKARTHNPYKLSSTLTNIYTGSRL HEAGCAPSYHVVRGDIATATEGVIINAANSKGQPGGGVC GALYKKFPESFDLQPIEVGKARLVKGAAKHIIHAVGPNF NKVSEVEGDKQLAEAYESIAKIVNDNNYKSVAIPLLSTGI FSGNKDRLTQSLNHLLTALDTTDADVAIYCRDKKWEMT LKEAVARREAVEEICISDDSSVTEPDAELVRVHPKSSLAG RKGYSTSDGKTFSYLEGTKFHQAAKDIAEINAMWPVATE ANEQVCMYILGESMSSIRSKCPVEESEASTPPSTLPCLCIH AMTPERVQRLKASRPEQITVCSSFPLPKYRITGVQKIQCS QPILFSPKVPAYIHPRKYLVETPPVDETPEPSAENQSTEGT PEQPPLITEDETRTRTPEPINIEEEEEDSISLLSDGPTHQVLQ VEADIHGPPSVSSSSWSIPHASDFDVDSLSILDTLEGASVT SGATSAETNSYFAKSMEFLARPVPAPRTVFRNPPHPAPRT RTPSLAPSRACSRTSLVSTPPGVNRVITREELEALTPSRTP SRSVSRTSLVSNPPGVNRVITREEFEAFVAQQQRRFDAGA YIFSSDTGQGHLQQKSVRQTVLSEVVLERTELEISYAPRL DQEKEELLRKKLQLNPTPANRSRYQSRKVENMKAITARR ILQGLGHYLKAEGKVECYRTLHPVPLYSSSVNRAFSSPK VAVEACNAMLKENFPTVASYCIIPEYDAYLDMVDGASC CLDTASFCPAKLRSFPKKHSYLEPTIRSAVPSAIQNTLQNV LAAATKRNCNVTQMRELPVLDSAAFNVECFKKYACNNE YWETFKENPIRLTEENVVNYITKLKGPKAAALFAKTHNL NMLQDIPMDRFVMDLKRDVKVTPGTKHTEERPKVQVIQ AADPLATAYLCGIHRELVRRLNAVLLPNIHTLFDMSAED FDAIIAEHFQPGDCVLETDIASFDKSEDDAMALTALMILE DLGVDAELLTLIEAAFGEISSIHLPTKTKFKFGAMMKSGM FLTLFVNTVINIVIASRVLRERLTGSPCAAFIGDDNIVKGV KSDKLMADRCATWLNMEVKIIDAVVGEKAPYFCGGFIL CDSVTGTACRVADPLKRLFKLGKPLAADDEHDDDRRRA LHEESTRWNRVGILSELCKAVESRYETVGTSIIVMAMTTL ASSVKSFSYLRGAPITLYG* |
| Comparitive | intergenic region | nucleotide | unknown |
| Comparitive | 3' UTR | nucleotide | unknown |

TABLE 5

ORF of Peptide of Interest for
Self-Replicating RNAs of the Disclosure

| ORF Identity | Sequence Type | Sequence |
|---|---|---|
| 2019-nCoV Spike gene (SEQ ID NO: 117) | nucleotide | ATGTTTGTTTT TABLE 5-continued ORF of Peptide of Interest for
Self-Replicating RNAs of the Disclosure

| ORF Identity | Sequence Type | Sequence |
|---|---|---|
| | | GAGGTTTGATAACCCTGTCCTACCATTTAATGATGGTGTTTATTTT
GCTTCCACTGAGAAGTCTAACATAATAAGAGGCTGGATTTTTGGT
ACTACTTTAGATTCGAAGACCCAGTCCCTACTTATTGTTAATAAC
GCTACTAATGTTGTTATTAAAGTCTGTGAATTTCAATTTTGTAATG
ATCCATTTTTGGGTGTTTATTACCACAAAAACAACAAAAGTTGGA
TGGAAAGTGAGTTCAGAGTTTATTCTAGTGCGAATAATTGCACTT
TTGAATATGTCTCTCAGCCTTTTCTTATGGACCTTGAAGGAAAAC
AGGGTAATTTCAAAAATCTTAGGGAATTTGTGTTTAAGAATATTG
ATGGTTATTTTAAAATATATTCTAAGCACACGCCTATTAATTTAGT
GCGTGATCTCCCTCAGGGTTTTTCGGCTTTAGAACCATTGGTAGAT
TTGCCAATAGGTATTAACATCACTAGGTTTCAAACTTTACTTGCTT
TACATAGAAGTTATTTGACTCCTGGTGATTCTTCTTCAGGTTGGAC
AGCTGGTGCTGCAGCTTATTATGTGGGTTATCTTCAACCTAGGAC
TTTTCTATTAAAATATAATGAAAATGGAACCATTACAGATGCTGT
AGACTGTGCACTTGACCCTCTCTCAGAAACAAAGTGTACGTTGAA
ATCCTTCACTGTAGAAAAAGGAATCTATCAAACTTCTAACTTTAG
AGTCCAACCAACAGAATCTATTGTTAGATTTCCTAATATTACAAA
CTTGTGCCCTTTTGGTGAAGTTTTTAACGCCACCAGATTTGCATCT
GTTTATGCTTGGAACAGGAAGAGAATCAGCAACTGTGTTGCTGAT
TATTCTGTCCTATATAATTCCGCATCATTTTCCACTTTTAAGTGTT
ATGGAGTGTCTCCTACTAAATTAAATGATCTCTGCTTTACTAATGT
CTATGCAGATTCATTTGTAATTAGAGGTGATGAAGTCAGACAAAT
CGCTCCAGGGCAAACTGGAAAGATTGCTGATTATAATTATAAATT
ACCAGATGATTTTACAGGCTGCGTTATAGCTTGGAATTCTAACAA
TCTTGATTCTAAGGTTGGTGGTAATTATAATTACCTGTATAGATTG
TTTAGGAAGTCTAATCTCAAACCTTTTGAGAGAGATATTTCAACT
GAAATCTATCAGGCCGGTAGCACACCTTGTAATGGTGTTGAAGGT
TTTAATTGTTACTTTCCTTTACAATCATATGGTTTCCAACCCACTA
ATGGTGTTGGTTACCAACCATACAGAGTAGTAGTACTTTCTTTTG
AACTTCTACATGCACCAGCAACTGTTTGTGGACCTAAAAAGTCTA
CTAATTTGGTTAAAAACAAATGTGTCAATTTCAACTTCAATGGTTT
AACAGGCACAGGTGTTCTTACTGAGTCTAACAAAAAGTTTCTGCC
TTTCCAACAATTTGGCAGAGACATTGCTGACACTACTGATGCTGT
CCGTGATCCACAGACACTTGAGATTCTTGACATTACACCATGTTC
TTTTGGTGGTGTCAGTGTTATAACACCAGGAACAAATACTTCTAA
CCAGGTTGCTGTTCTTTATCAGGATGTTAACTGCACAGAAGTCCC
TGTTGCTATTCATGCAGATCAACTTACTCCTACTTGGCGTGTTTAT
TCTACAGGTTCTAATGTTTTTCAAACACGTGCAGGCTGTTTAATAG
GGGCTGAACATGTCAACAACTCATATGAGTGTGACATACCCATTG
GTGCAGGTATATGCGCTAGTTATCAGACTCAGACTAATTCTCCTC
GGCGGGCACGTAGTGTAGCTAGTCAATCCATCATTGCCTACACTA
TGTCACTTGGTGCAGAAAATTCAGTTGCTTACTCTAATAACTCTAT
TGCCATACCCACAAATTTTACTATTAGTGTTACCACAGAAATTCT
ACCAGTGTCTATGACCAAGACATCAGTAGATTGTACAATGTACAT
TTGTGGTGATTCAACTGAATGCAGCAATCTTTTGTTGCAATATGG
CAGTTTTTGTACACAATTAAACCGTGCTTTAACTGGAATAGCTGTT
GAACAAGACAAAAACACCCAAGAAGTTTTTGCACAAGTCAAACA
AATTTACAAAACACCACCAATTAAAGATTTTGGTGGTTTTAATTTT
TCACAAATATTACCAGATCCATCAAAACCAAGCAAGAGGTCATTT
ATTGAAGATCTACTTTTCAACAAAGTGACACTTGCAGATGCTGGC
TTCATCAAACAATATGGTGATTGCCTTGGTGATATTGCTGCTAGA
GACCTCATTTGTGCACAAAAGTTTAACGGCCTTACTGTTTTGCCAC
CTTTGCTCACAGATGAAATGATTGCTCAATACACTTCTGCACTGTT
AGCGGGTACAATCACTTCTGGTTGGACCTTTGGTGCAGGTGCTGC
ATTACAAATACCATTTGCTATGCAAATGGCTTATAGGTTTAATGG
TATTGGAGTTACACAGAATGTTCTCTATGAGAACCAAAAATTGAT
TGCCAACCAATTTAATAGTGCTATTGGCAAAATTCAAGACTCACT
TTCTTCCACAGCAAGTGCACTTGGAAAACTTCAAGATGTGGTCAA
CCAAAATGCACAAGCTTTAAACACGCTTGTTAAACAACTTAGCTC
CAATTTTGGTGCAATTTCAAGTGTTTTAAATGATATCCTTTCACGT
CTTGACAAAGTTGAGGCTGAAGTGCAAATTGATAGGTTGATCACA
GGCAGACTTCAAAGTTTGCAGACATATGTGACTCAACAATTAATT
AGAGCTGCAGAAATCAGAGCTTCTGCTAATCTTGCTGCTACTAAA
ATGTCAGAGTGTGTACTTGGACAATCAAAAAGAGTTGATTTTTGT
GGAAAGGGCTATCATCTTATGTCCTTCCCTCAGTCAGCACCTCAT
GGTGTAGTCTTCTTGCATGTGACTTATGTCCCTGCACAAGAAAAG
AACTTCACAACTGCTCCTGCCATTTGTCATGATGGAAAAGCACAC
TTTCCTCGTGAAGGTGTCTTTGTTTCAAATGGCACACACTGGTTTG
TAACACAAAGGAATTTTATGAACCACAAATCATTACTACAGACA
ACACATTTGTGTCTGGTAACTGTGATGTTGTAATAGGAATTGTCA
ACAACACAGTTTATGATCCTTTGCAACCTGAATTAGACTCATTCA
AGGAGGAGTTAGATAAATATTTTAAGAATCATACATCACCAGATG
TTGATTTAGGTGACATCTCTGGCATTAATGCTTCAGTTGTAAACAT
TCAAAAAGAAATTGACCGCCTCAATGAGGTTGCCAAGAATTTAA |

TABLE 5-continued

ORF of Peptide of Interest for
Self-Replicating RNAs of the Disclosure

| ORF Identity | Sequence Type | Sequence |
|---|---|---|
| | | ATGAATCTCTCATCGATCTCCAAGAACTTGGAAAGTATGAGCAGT<br>ATATAAAATGGCCATGGTACATTTGGCTAGGTTTTATAGCTGGCT<br>TGATTGCCATAGTAATGGTGACAATTATGCTTTGCTGTATGACCA<br>GTTGCTGTAGTTGTCTCAAGGGCTGTTGTTCTTGTGGATCCTGCTG<br>CAAATTTGATGAAGACGACTCTGAGCCAGTGCTCAAAGGAGTCA<br>AATTACATTACACATAA |
| 2019-nCoV Spike gene (SEQ ID NO: 118) | amino acid | MFVFLVLLPLVSSQCVNLTTRTQLPPAYTNSFTRGVYYPDKVFRSSV<br>LHSTQDLFLPFFSNVTWFHAIHVSGTNGTKRFDNPVLPFNDGVYFAS<br>TEKSNIIRGWIFGTTLDSKTQSLLIVNNATNVVIKVCEFQFCNDPFLG<br>VYYHKNNKSWMESEFRVYSSANNCTFEYVSQPFLMDLEGKQGNFK<br>NLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENG<br>TITDAVDCALDPLSETKCTLKSFTVEKGIYQTSNFRVQPTESIVRFPNI<br>TNLCPFGEVFNATRFASVYAWNRKRISNCVADYSVLYNSASFSTFKC<br>YGVSPTKLNDLCFTNVYADSFVIRGDEVRQIAPGQTGKIADYNYKLP<br>DDFTGCVIAWNSNNLDSKVGGNYNYLYRLFRKSNLKPFERDISTEIY<br>QAGSTPCNGVEGFNCYFPLQSYGFQPTNGVGYQPYRVVVLSFELLH<br>APATVCGPKKSTNLVKNKCVNFNFNGLTGTGVLTESNKKFLPFQQF<br>GRDIADTTDAVRDPQTLEILDITPCSFGGVSVITPGTNTSNQVAVLYQ<br>DVNCTEVPVAIHADQLTPTWRVYSTGSNVFQTRAGCLIGAEHVNNS<br>YECDIPIGAGICASYQTQTNSPRRARSVASQSIIAYTMSLGAENSVAY<br>SNNSIAIPTNFTISVTTEILPVSMTKTSVDCTMYICGDSTECSNLLLQY<br>GSFCTQLNRALTGIAVEQDKNTQEVFAQVKQIYKTPPIKDFGGFNFS<br>QILPDPSKPSKRSFIEDLLFNKVTLADAGFIKQYGDCLGDIAARDLICA<br>QKFNGLTVLPPLLTDEMIAQYTSALLAGTITSGWTFGAGAALQIPFA<br>MQMAYRFNGIGVTQNVLYENQKLIANQFNSAIGKIQDSLSSTASALG<br>KLQDVVNQNAQALNTLVKQLSSNFGAISSVLNDILSRLDKVEAEVQI<br>DRLITGRLQSLQTYVTQQLIRAAEIRASANLAATKMSECVLGQSKRV<br>DFCGKGYHLMSFPQSAPHGVVFLHVTYVPAQEKNFTTAPAICHDGK<br>AHFPREGVFVSNGTHWFVTQRNFYEPQIITTDNTFVSGNCDVVIGIVN<br>NTVYDPLQPELDSFKEELDKYFKNHTSPDVDLGDISGINASVVNIQKE<br>IDRLNEVAKNLNESLIDLQELGKYEQYIKWPWYIWLGFIAGLIAIVM<br>VTIMLCCMTSCCSCLKGCCSCGSCCKFDEDDSEPVLKGVKLHYT* |
| 2019-nCoV Spike gene (SEQ ID NO: 119) | nucleotide | ATGTTCGTCTTCCTGGTCCTGCTGCCTCTGGTCTCCTCACAGTGCG<br>TCAATCTGACAACTCGGACTCAGCTGCCACCTGCTTATACTAATA<br>GCTTCACCAGAGGCGTGTACTATCCTGACAAGGTGTTTAGAAGCT<br>CCGTGCTGCACTCTACACAGGATCTGTTTCTGCCATTCTTTAGCAA<br>CGTGACCTGGTTCCACGCCATCCACGTGAGCGGCACCAATGGCAC<br>AAAGCGGTTCGACAATCCCGTGCTGCCTTTTAACGATGGCGTGTA<br>CTTCGCCTCTACCGAGAAGAGCAACATCATCAGAGGCTGGATCTT<br>TGGCACCACACTGGACTCCAAGACACAGTCTCTGCTGATCGTGAA<br>CAATGCCACCAACGTGGTCATCAAGGTGTGCGAGTTCCAGTTTTG<br>TAATGATCCCTTCCTGGGCGTGTACTATCACAAGAACAATAAGAG<br>CTGGATGGAGTCCGAGTTTAGAGTGTATTCTAGCGCCAACAACTG<br>CACATTTGAGTACGTGAGCCAGCCTTTCCTGATGGACCTGGAGGG<br>CAAGCAGGGCAATTTCAAGAACCTGAGGGAGTTCGTGTTTAAGA<br>ATATCGACGGCTACTTCAAAATCTACTCTAAGCACACCCCCATCA<br>ACCTGGTGCGCGACCTGCCTCAGGGCTTCAGCGCCCTGGAGCCCC<br>TGGTGGATCTGCCTATCGGCATCAACATCACCCGGTTTCAGACAC<br>TGCTGGCCCTGCACAGAAGCTACCTGACACCCGGCGACTCCTCTA<br>GCGGATGGACCGCCGGCGCTGCCGCCTACTATGTGGGCTACCTCC<br>AGCCCCGGACCTTCCTGCTGAAGTACAACGAGAATGGCACCATCA<br>CAGACGCAGTGGATTGCGCCCTGGACCCCCTGAGCGAGACAAAG<br>TGTACACTGAAGTCCTTTACCGTGGAGAAGGGCATCTATCAGACA<br>TCCAATTTCAGGGTGCAGCCAACCGAGTCTATCGTGCGCTTTCCT<br>AATATCACAAACCTGTGCCCATTTGGCGAGGTGTTCAACGCAACC<br>CGCTTCGCCAGCGTGTACGCCTGGAATAGGAAGCGGATCAGCAA<br>CTGCGTGGCCGACTATAGCGTGCTGTACAACTCCGCCTCTTTCAG<br>CACCTTTAAGTGCTATGGCGTGTCCCCCACAAAGCTGAATGACCT<br>GTGCTTTACCAACGTCTACGCCGATTCTTTCGTGATCAGGGGCGA<br>CGAGGTGCGCCAGATCGCCCCGGCCAGACAGGCAAGATCGCAG<br>ACTACAATTATAAGCTGCCAGACGATTTCACCGGCTGCGTGATCG<br>CCTGGAACAGCAACAATCTGGATTCCAAAGTGGGCGGCAACTAC<br>AATTATCTGTACCGGCTGTTTAGAAAGAGCAATCTGAAGCCCTTC<br>GAGAGGGACATCTCTACAGAAATCTACCAGGCCGGCAGCACCCC<br>TTGCAATGGCGTGGAGGGCTTTAACTGTTATTTCCCACTCCAGTCC<br>TACGGCTTCCAGCCCACAAACGGCGTGGGCTATCAGCCTTACCGC<br>GTGGTGGTGCTGAGCTTTGAGCTGCTGCACGCCCCAGCAACAGTG<br>TGCGGCCCCAAGAAGTCCACCAATCTGGTGAAGAACAAGTGCGT<br>GAACTTCAACTTCAACGGCCTGACCGGCACAGGCGTGCTGACCGA<br>GTCCAACAAGAAGTTCCTGCCATTTCAGCAGTTCGGCAGGGACAT<br>CGCAGATACCACAGACGCCGTGCGCGACCCACAGACCCTGGAGA |

TABLE 5-continued

ORF of Peptide of Interest for Self-Replicating RNAs of the Disclosure

| ORF Identity | Sequence Type | Sequence |
|---|---|---|
| | | TCCTGGACATCACACCCTGCTCTTTCGGCGGCGTGAGCGTGATCA<br>CACCCGGCACCAATACAAGCAACCAGGTGGCCGTGCTGTATCAG<br>GACGTGAATTGTACCGAGGTGCCCGTGGCTATCCACGCCGATCAG<br>CTGACCCCAACATGGCGGGTGTACAGCACCGGCTCCAACGTCTTC<br>CAGACAAGAGCCGGATGCCTGATCGGAGCAGAGCACGTGAACAA<br>TTCCTATGAGTGCGACATCCCAATCGGCGCCGGCATCTGTGCCTC<br>TTACCAGACCCAGACAAACTCTCCCAGAAGAGCCCGGAGCGTGG<br>CCTCCCAGTCTATCATCGCCTATACCATGTCCCTGGGCGCCGAGA<br>ACAGCGTGGCCTACTCTAACAATAGCATCGCCATCCCAACCAACT<br>TCACAATCTCTGTGACCACAGAGATCCTGCCCGTGTCCATGACCA<br>AGACATCTGTGGACTGCACAATGTATATCTGTGGCGATTCTACCG<br>AGTGCAGCAACCTGCTGCTCCAGTACGGCAGCTTTTGTACCCAGC<br>TGAATAGAGCCCTGACAGGCATCGCCGTGGAGCAGGATAAGAAC<br>ACACAGGAGGTGTTCGCCCAGGTGAAGCAAATCTACAAGACCCC<br>CCCTATCAAGGACTTTGGCGGCTTCAATTTTTCCCAGATCCTGCCT<br>GATCCATCCAAGCCTTCTAAGCGGAGCTTTATCGAGGACCTGCTG<br>TTCAACAAGGTGACCCTGGCCGATGCCGGCTTCATCAAGCAGTAT<br>GGCGATTGCCTGGGCGACATCGCAGCCAGGGACCTGATCTGCGCC<br>CAGAAGTTTAATGGCCTGACCGTGCTGCCACCCCTGCTGACAGAT<br>GAGATGATCGCACAGTACACAAGCGCCCTGCTGGCCGGCACCAT<br>CACATCCGGATGGACCTTCGGCGCAGGAGCCGCCCTCCAGATCCC<br>CTTTGCCATGCAGATGGCCTATAGGTTCAACGGCATCGGCGTGAC<br>CCAGAATGTGCTGTACGAGAACCAGAAGCTGATCGCCAATCAGTT<br>TAACTCCGCCATCGGCAAGATCCAGGACAGCCTGTCCTCTACAGC<br>CAGCGCCCTGGGCAAGCTCCAGGATGTGGTGAATCAGAACGCCC<br>AGGCCCTGAATACCCTGGTGAAGCAGCTGAGCAGCAACTTCGGC<br>GCCATCTCTAGCGTGCTGAATGACATCCTGAGCCGGCTGGACAAG<br>GTGGAGGCAGAGGTGCAGATCGACCGGCTGATCACCGGCCGGCT<br>CCAGAGCCTCCAGACCTATGTGACACAGCAGCTGATCAGGGCCG<br>CCGAGATCAGGGCCAGCGCCAATCTGGCAGCAACCAAGATGTCC<br>GAGTGCGTGCTGGGCCAGTCTAAGAGAGTGGACTTTTGTGGCAAG<br>GGCTATCACCTGATGTCCTTCCCTCAGTCTGCCCCACACGGCGTG<br>GTGTTTCTGCACGTGACCTACGTGCCCGCCCAGGAGAAGAACTTC<br>ACCACAGCCCCTGCCATCTGCCACGATGGCAAGGCCCACTTTCCA<br>AGGGAGGGCGTGTTCGTGTCCAACGGCACCCACTGGTTTGTGACA<br>CAGCGCAATTTCTACGAGCCCCAGATCATCACCACAGACAACACC<br>TTCGTGAGCGGCAACTGTGACGTGGTCATCGGCATCGTGAACAAT<br>ACCGTGTATGATCCACTCCAGCCCGAGCTGGACAGCTTTAAGGAG<br>GAGCTGGATAAGTATTTCAAGAATCACACCTCCCCTGACGTGGAT<br>CTGGGCGACATCAGCGGCATCAATGCCTCCGTGGTGAACATCCAG<br>AAGGAGATCGACCGCCTGAACGAGGTGGCTAAGAATCTGAACGA<br>GAGCCTGATCGACCTCCAGGAGCTGGGCAAGTATGAGCAGTACA<br>TCAAGTGGCCCTGGTACATCTGGCTGGGCTTCATCGCCGGCCTGA<br>TCGCCATCGTGATGGTGACCATCATGCTGTGCTGTATGACATCCT<br>GCTGTTCTTGCCTGAAGGGCTGCTGTAGCTGTGGCTCCTGCTGTA<br>AGTTTGACGAGGATGACTCTGAACCTGTGCTGAAGGGCGTGAAG<br>CTGCATTACACCTAA |
| 2019-nCoV Spike gene (SEQ ID NO: 120) | amino acid | MFVFLVLLPLVSSQCVNLTTRTQLPPAYTNSFTRGVYYPDKVFRSSV<br>LHSTQDLFLPFFSNVTWFHAIHVSGTNGTKRFDNPVLPFNDGVYFAS<br>TEKSNIIRGWIFGTTLDSKTQSLLIVNNATNVVIKVCEFQFCNDPFLG<br>VYYHKNNKSWMESEFRVYSSANNCTFEYVSQPFLMDLEGKQGNFK<br>NLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENG<br>TITDAVDCALDPLSETKCTLKSFTVEKGIYQTSNFRVQPTESIVRFPNI<br>TNLCPFGEVFNATRFASVYAWNRKRISNCVADYSVLYNSASFSTFKC<br>YGVSPTKLNDLCFTNVYADSFVIRGDEVRQIAPGQTGKIADYNYKLP<br>DDFTGCVIAWNSNNLDSKVGGNYNYLYRLFRKSNLKPFERDISTEIY<br>QAGSTPCNGVEGFNCYFPLQSYGFQPTNGVGYQPYRVVVLSFELLH<br>APATVCGPKKSTNLVKNKCVNFNFNGLTGTGVLTESNKKFLPFQQF<br>GRDIADTTDAVRDPQTLEILDITPCSFGGVSVITPGTNTSNQVAVLYQ<br>DVNCTEVPVAIHADQLTPTWRVYSTGSNVFQTRAGCLIGAEHVNNS<br>YECDIPIGAGICASYQTQTNSPRRARSVASQSIIAYTMSLGAENSVAY<br>SNNSIAIPTNFTISVTTEILPVSMTKTSVDCTMYICGDSTECSNLLLQY<br>GSFCTQLNRALTGIAVEQDKNTQEVFAQVKQIYKTPPIKDFGGFNFS<br>QILPDPSKPSKRSFIEDLLFNKVTLADAGFIKQYGDCLGDIAARDLICA<br>QKFNGLTVLPPLLTDEMIAQYTSALLAGTITSGWTFGAGAALQIPFA<br>MQMAYRFNGIGVTQNVLYENQKLIANQFNSAIGKIQDSLSSTASALG<br>KLQDVVNQNAQALNTLVKQLSSNFGAISSVLNDILSRLDKVEAEVQI<br>DRLITGRLQSLQTYVTQQLIRAAEIRASANLAATKMSECVLGQSKRV |

TABLE 5-continued

ORF of Peptide of Interest for
Self-Replicating RNAs of the Disclosure

| ORF Identity | Sequence Type | Sequence |
|---|---|---|
| | | DFCGKGYHLMSFPQSAPHGVVFLHVTYVPAQEKNFTTAPAICHDGK AHFPREGVFVSNGTHWFVTQRNFYEPQUITTDNTFVSGNCDVVIGIVN NTVYDPLQPELDSFKEELDKYFKNHTSPDVDLGDISGINASVVNIQKE IDRLNEVAKNLNESLIDLQELGKYEQYIKWPWYIWLGFIAGLIAIVM VTIMLCCMTSCCSCLKGCCSCGSCCKFDEDDSEPVLKGVKLHYT* |

RNA sequences can include any combination of the RNA sequences listed in Tables 4 and 5. In some embodiments, RNA sequences of the present disclosure include any combination of the RNA sequences listed in Tables 4 and 5 in which 0% to 100%, 1% to 100%, 25% to 100%, 50% to 100% and 75% to 100% of the uracil nucleotides of the mRNA sequences are modified. In some embodiments, 1% to 100% of the uracil nucleotides are N1-methylpseudouridine or 5-methoxyuridine. In some embodiments, 100/% of the uracil nucleotides are N1-methylpseudouridine. In some embodiments, 100% of the uracil nucleotides are 5-methoxyuridine.

A self-replicating RNA of the disclosure may be obtained by any suitable means. Methods for the manufacture of self-replicating RNA are known in the art and would be readily apparent to a person of ordinary skill. A self-replicating RNA of the disclosure may be prepared according to any available technique including, but not limited to chemical synthesis, in vitro transcription (IVT) or enzymatic or chemical cleavage of a longer precursor, etc.

In some embodiments, a self-replicating RNA of the disclosure is produced from a primary complementary DNA (cDNA) construct. The cDNA constructs can be produced on an RNA template by the action of a reverse transcriptase (e.g., RNA-dependent DNA-polymerase). The process of design and synthesis of the primary cDNA constructs described herein generally includes the steps of gene construction, RNA production (either with or without modifications) and purification. In the IVT method, a target polynucleotide sequence encoding a self-replicating RNA of the disclosure is first selected for incorporation into a vector which will be amplified to produce a cDNA template. Optionally, the target polynucleotide sequence and/or any flanking sequences may be codon optimized. The cDNA template is then used to produce a self-replicating RNA of the disclosure through in vitro transcription (IVT). After production, the self-replicating RNA of the disclosure may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a protein of interest is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

The cDNA templates may be transcribed to produce a self-replicating RNA of the disclosure using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed RNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or capping at initiation of in vitro transcription, by for example, including a capping agent as part of the IVT reaction. (Nuc. Acids Symp. (2009) 53:129). A poly(A) tailing reaction may be performed by methods known in the art, such as, but not limited to, 2' O-methyltransferase and by methods as described herein. If the primary construct generated from cDNA does not include a poly-T, it may be beneficial to perform the poly(A)-tailing reaction before the primary construct is cleaned.

Codon optimized cDNA constructs encoding the non-structural proteins and the transgene for a self-replicating RNA protein are particularly suitable for generating self-replicating RNA sequences described herein. For example, such cDNA constructs may be used as the basis to transcribe, in vitro, a polyribonucleotide encoding a protein of interest as part of a self-replicating RNA.

The present disclosure also provides expression vectors comprising a nucleotide sequence encoding a self-replicating RNA that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides polynucleotides (e.g. DNA, RNA, cDNA, mRNA, etc.) directed to a self-replicating RNA of the disclosure that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

The present disclosure also provides a host cell transfected with a self-replicating RNA or DNA described herein. The self-replicating RNA or DNA can encode any coronavirus protein of interest, for example an antigen, including the S-antigen of the COVID-19 virus. The host cell may be any prokaryotic or eukaryotic cell. For example, a polypeptide encoded by a self-replicating RNA may be expressed in bacterial cells such as *E. coli*, insect cells (e.g., using a baculovirus expression system), yeast, or mammalian cells. Other suitable host cells are known to those skilled in the art.

A host cell transfected with an expression vector comprising a self-replicating RNA of the disclosure can be cultured under appropriate conditions to allow expression of the amplification of the self-replicating RNA and translation of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide.

Compostions and Pharmaceutical Compostions

Provided herein, in some embodiments, are compositions comprising any of the nucleic acid molecules provided herein. Compositions provided herein can include a lipid. Any lipid can be included in compositions provided herein. In one aspect, the lipid is an ionizable cationic lipid. Any ionizable cationic lipid can be included in compositions comprising nucleic acid molecules provided herein.

The compositions and polynucleotides of the present disclosure may be used to immunize or vaccinate a subject against a viral infection. In some embodiments, the compositions and polynucleotides of the present disclosure may be used to vaccinate or immunize a subject against COVID-19 virus.

Also provided herein, in some embodiments, are pharmaceutical compositions comprising any of the nucleic acid molecules provided herein and a lipid formulation. Any lipid can be included in lipid formulations of pharmaceutical compositions provided herein. In one aspect, lipid formulations of pharmaceutical compositions provided herein include an ionizable cationic lipid. Exemplary ionizable cationic lipids of compositions and pharmaceutical compositions provided herein include the following:

ATX-001

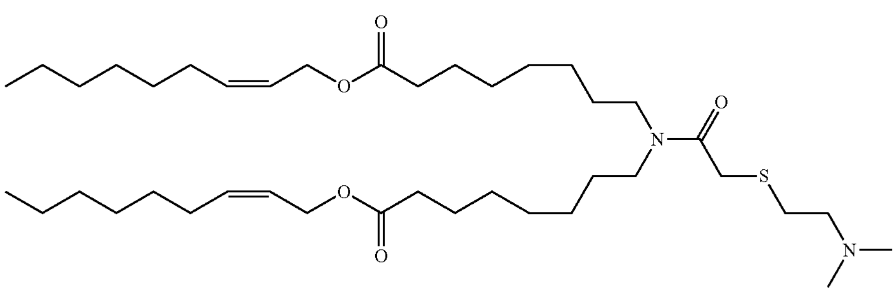

ATX-002

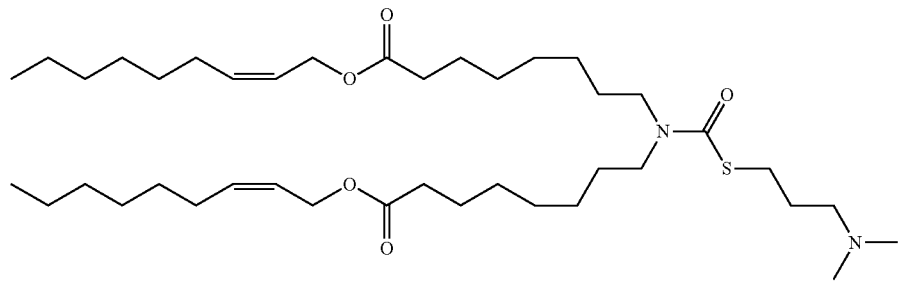
ATX-003
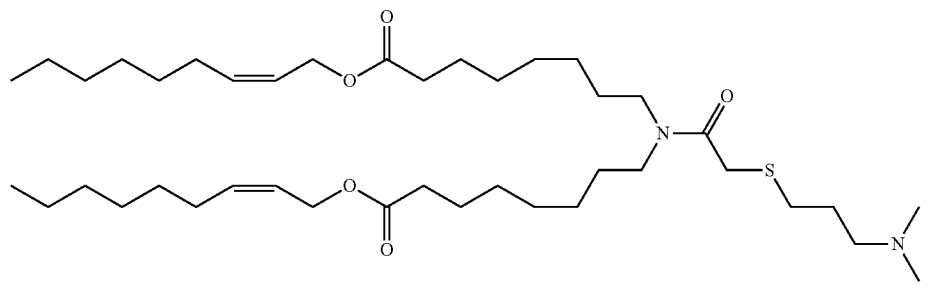
ATX-004
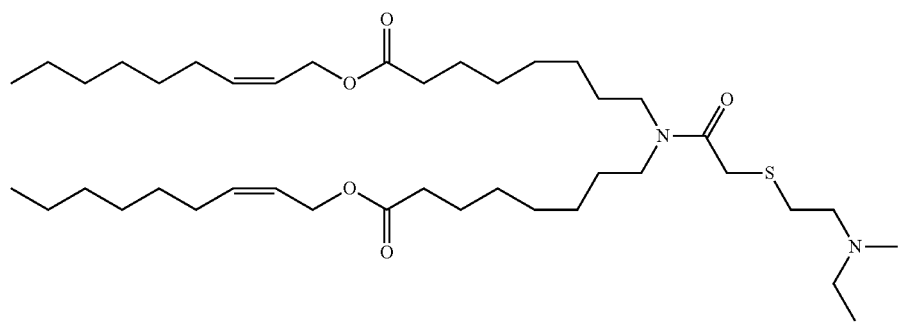
ATX-005
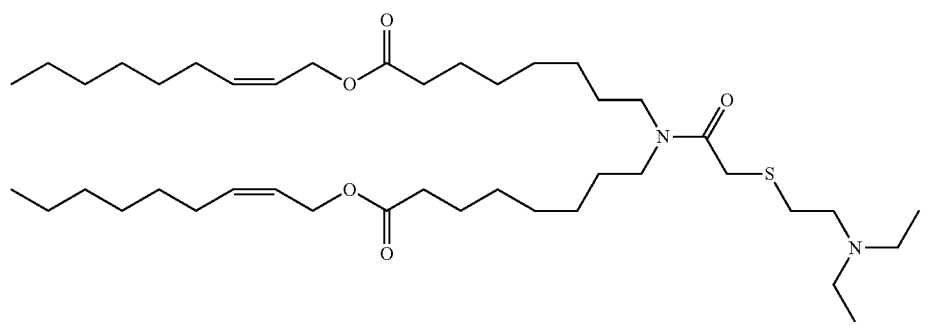
ATX-006
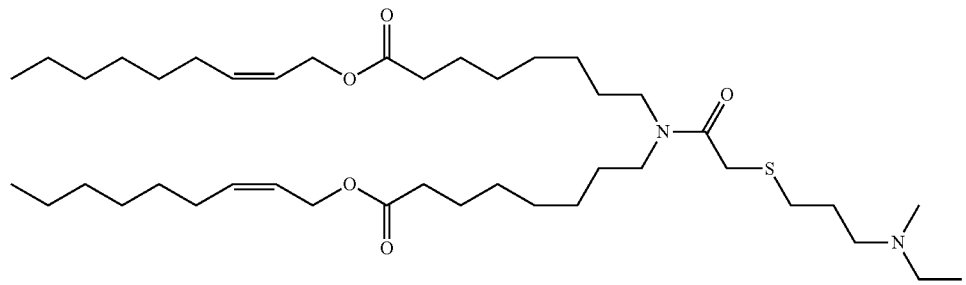
ATX-007

-continued
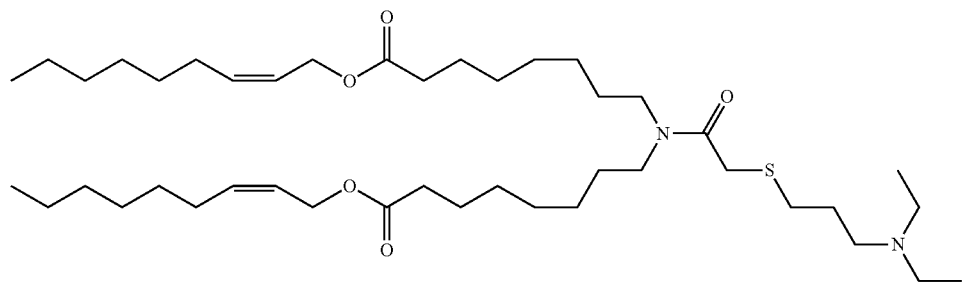
ATX-008
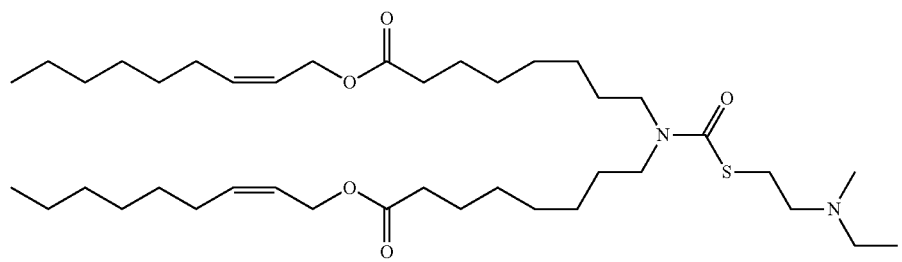
ATX-009
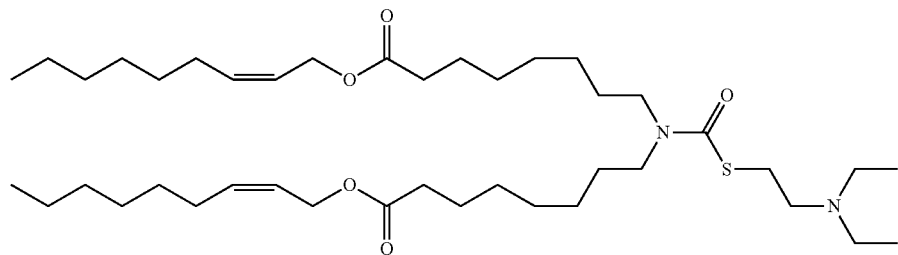
ATX-010
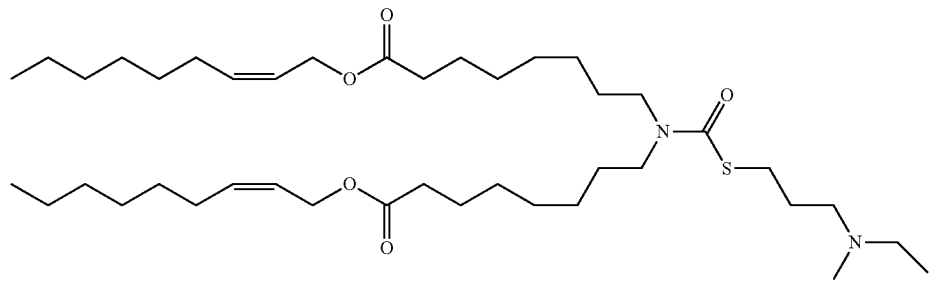
ATX-011
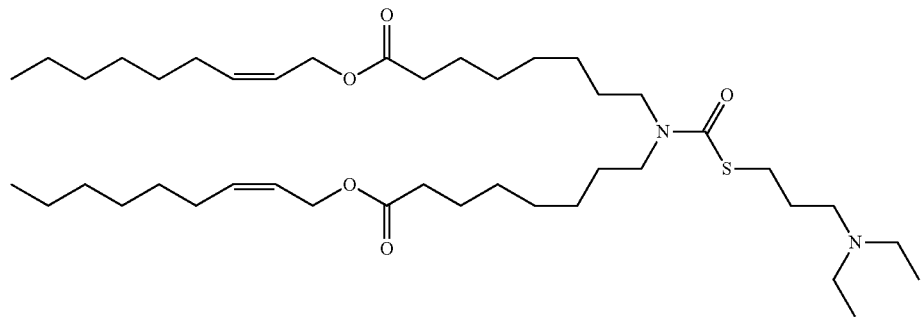
ATX-012
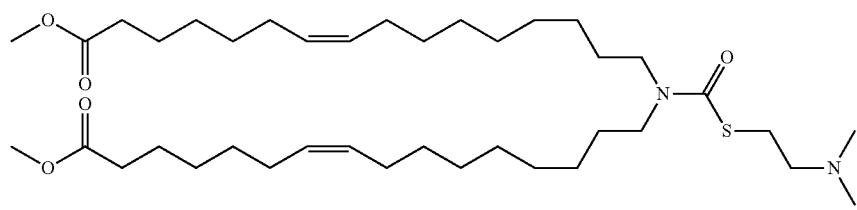
ATX-013

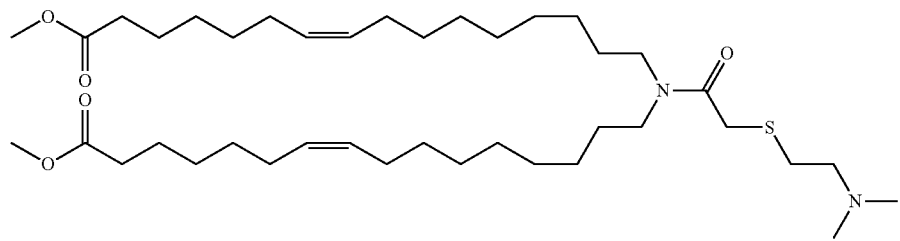
ATX-014
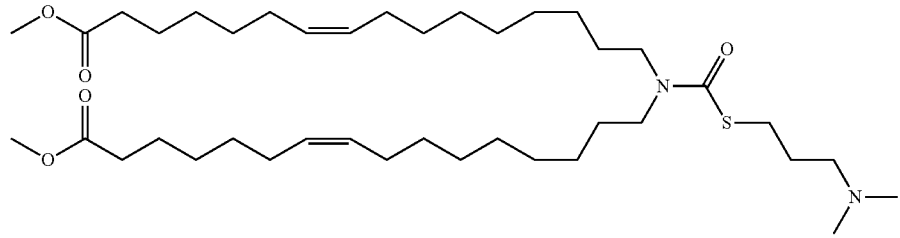
ATX-015
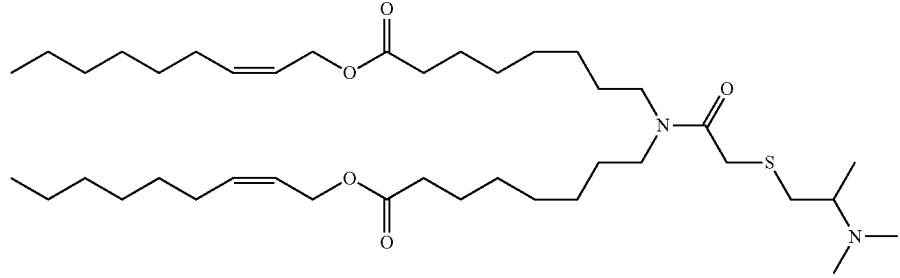
ATX-016
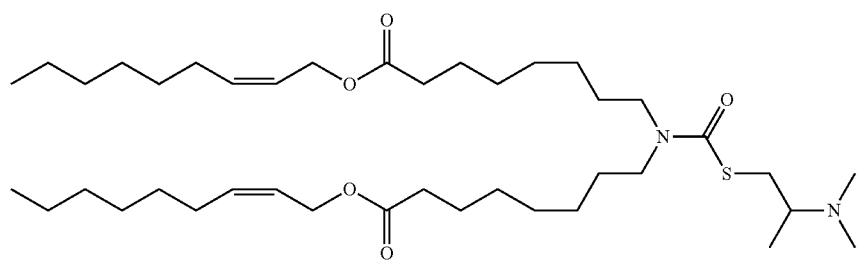
ATX-018
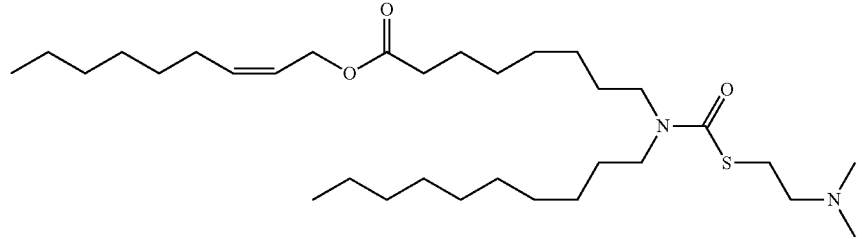
ATX-019
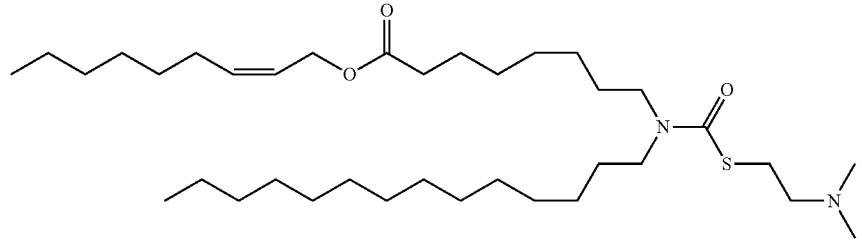

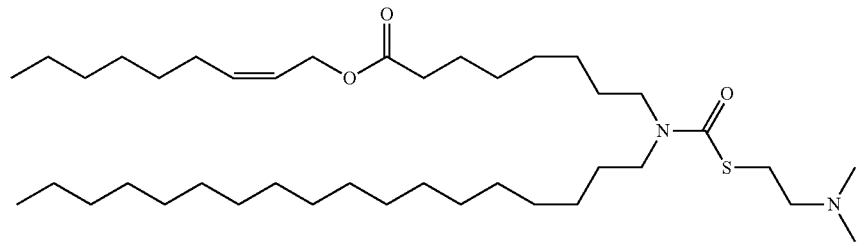
ATX-020
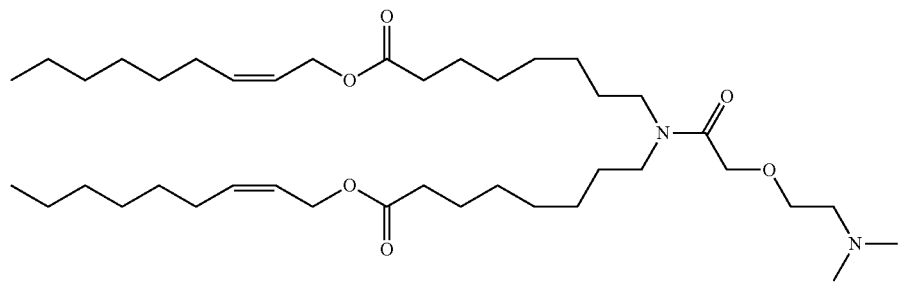
ATX-021
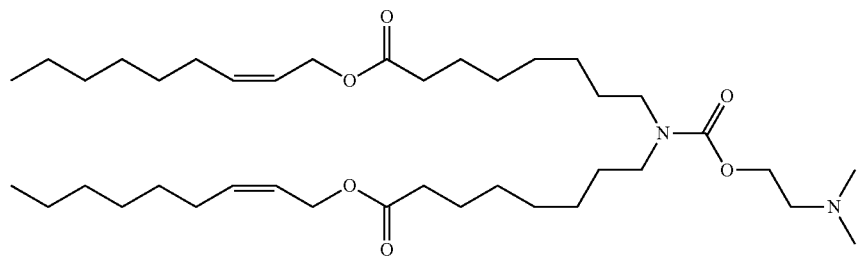
ATX-022
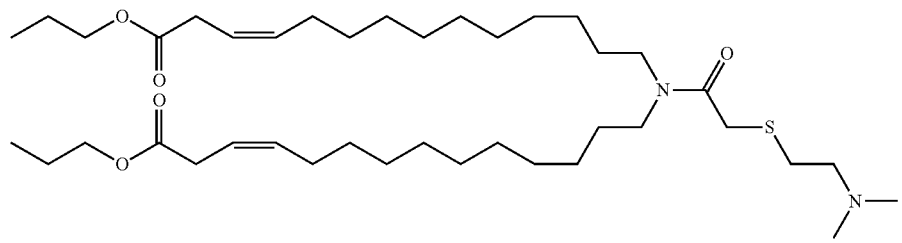
ATX-023
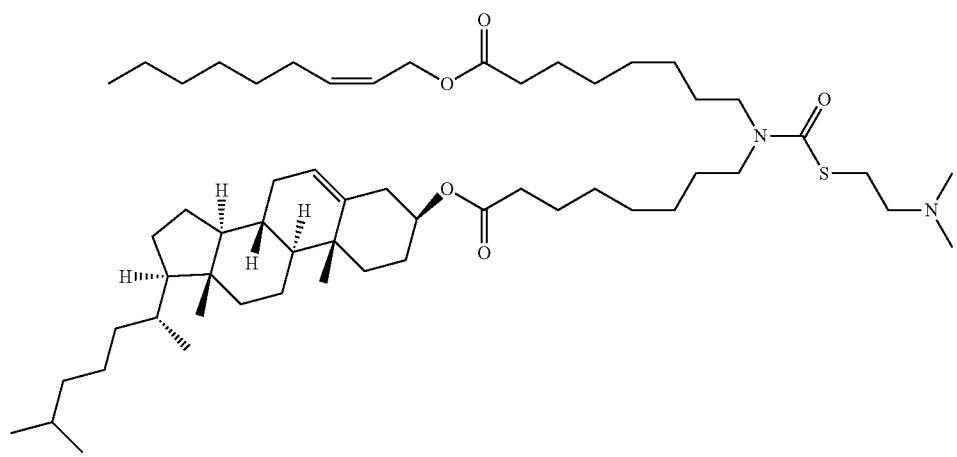
ATX-024

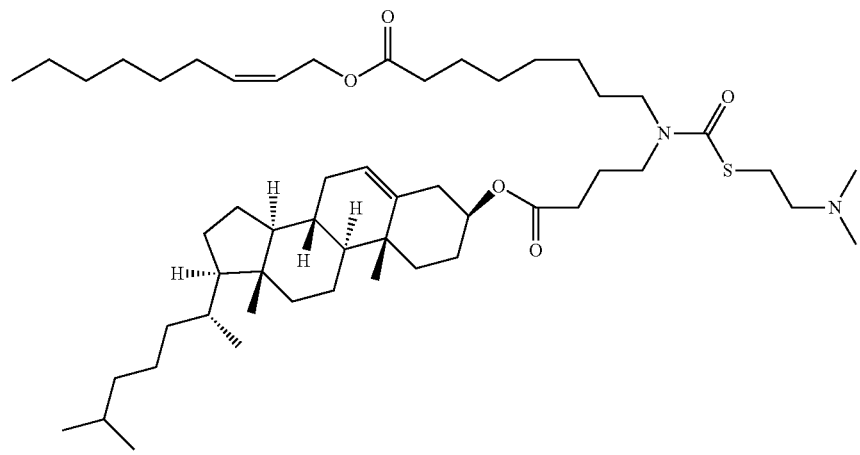
ATX-025
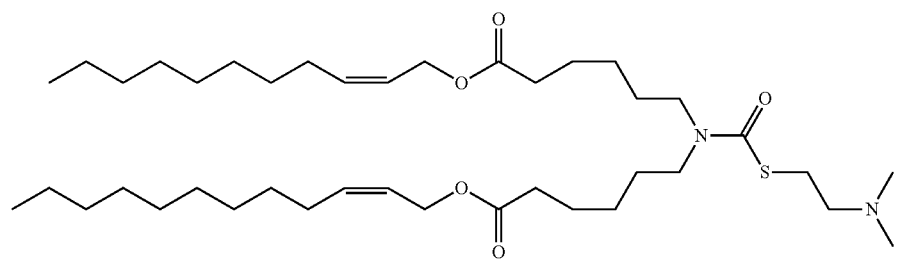
ATX-026
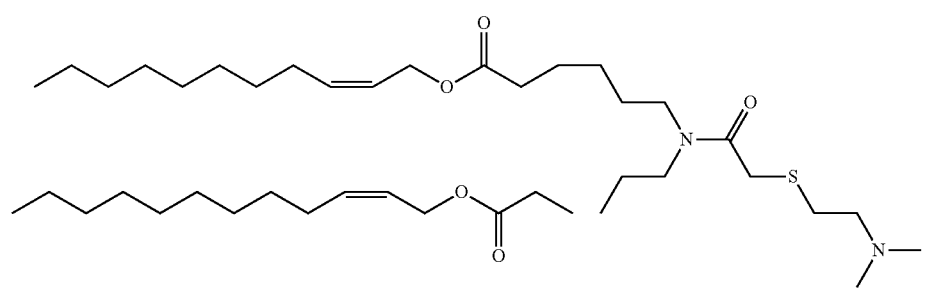
ATX-027
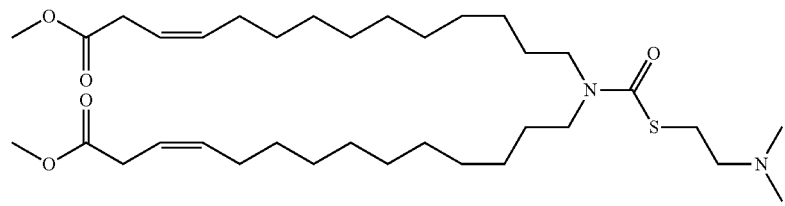
ATX-028
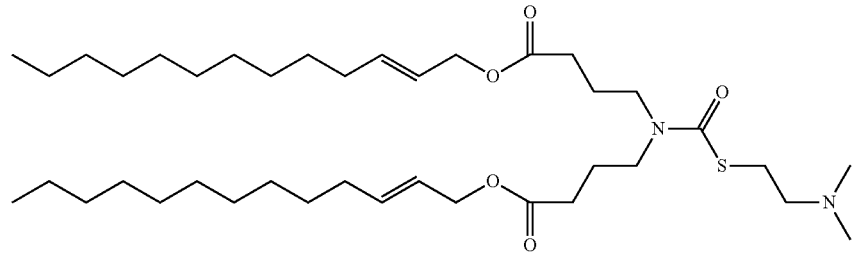
ATX-029

-continued
ATX-030
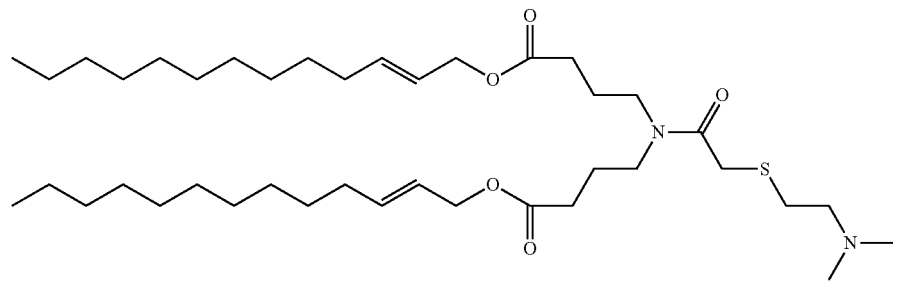
ATX-031
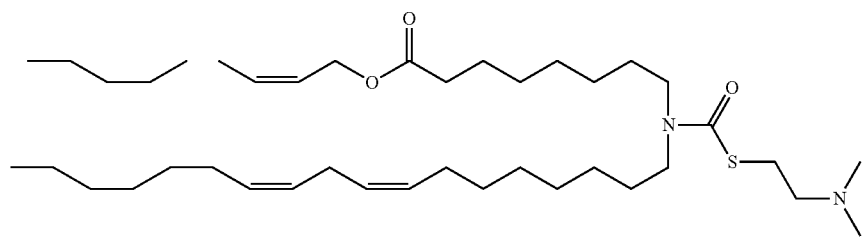
ATX-032
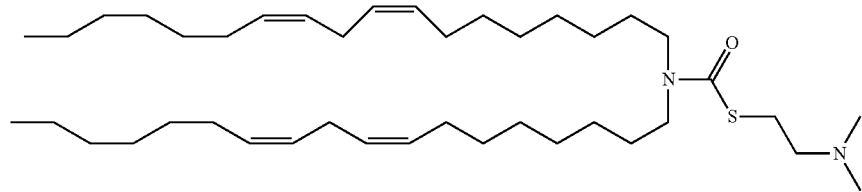
ATX-086
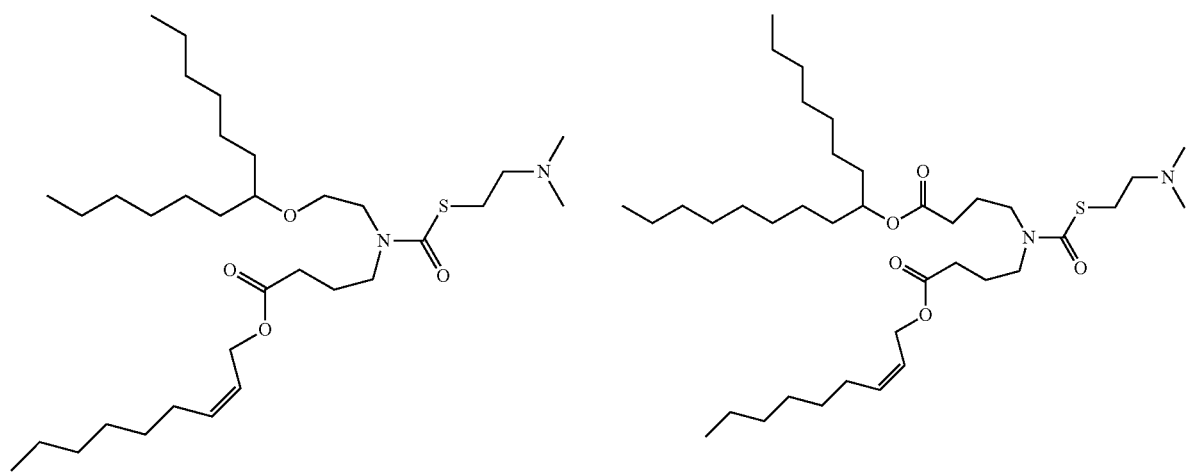

-continued
ATX-058
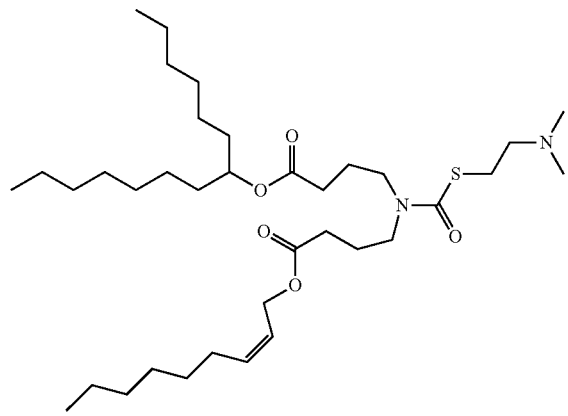
ATX-061
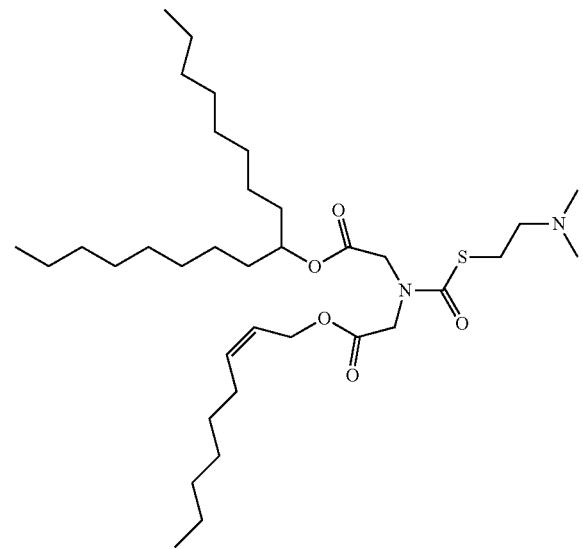
ATX-063
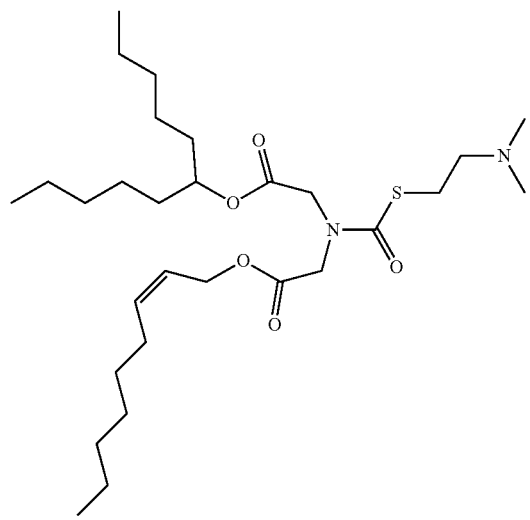
ATX-064
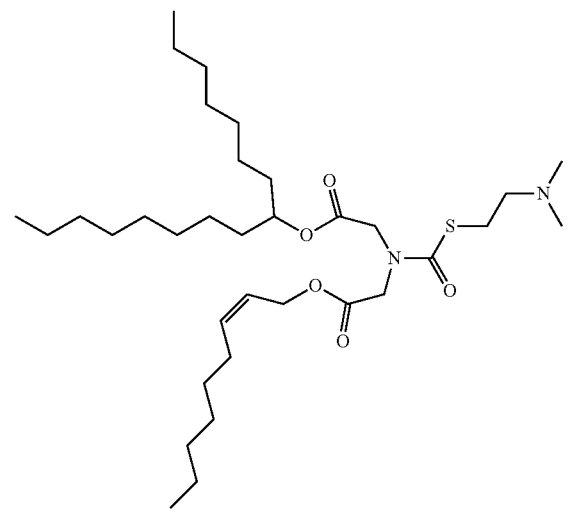
ATX-082
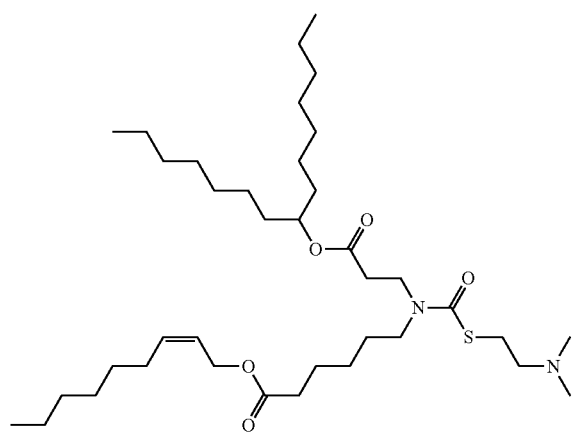
ATX-043
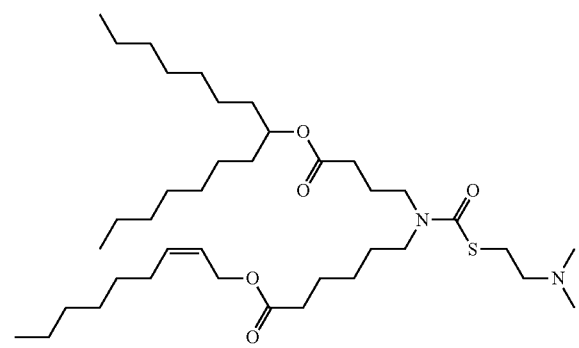

119
120
-continued
ATX-057
ATX-087
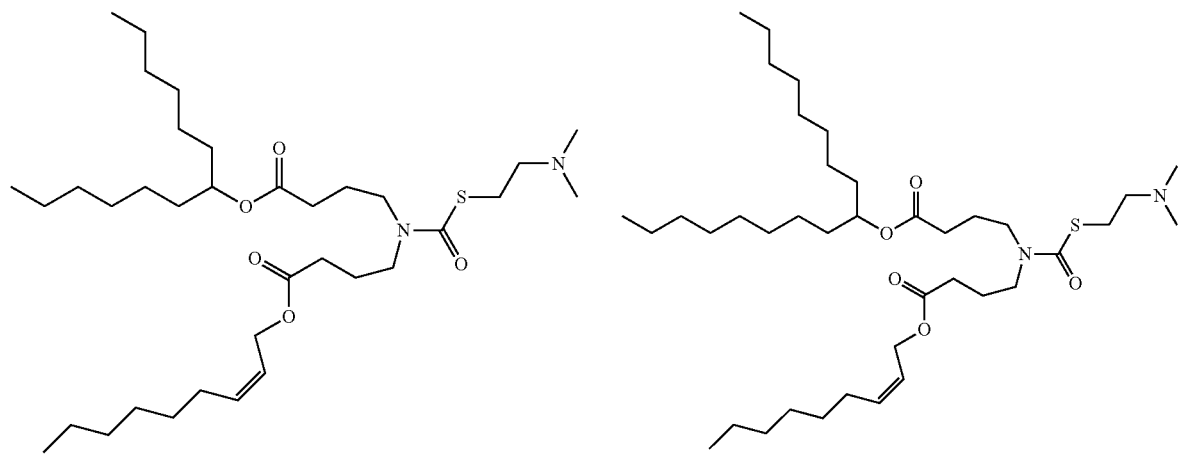
ATX-088
ATX-085
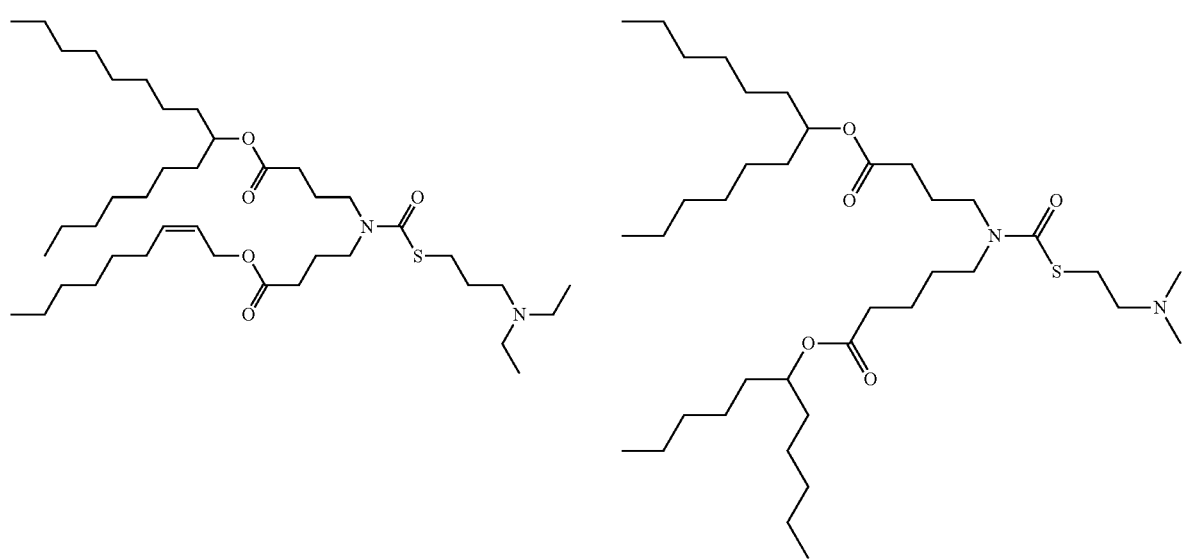
ATX-083
ATX-091
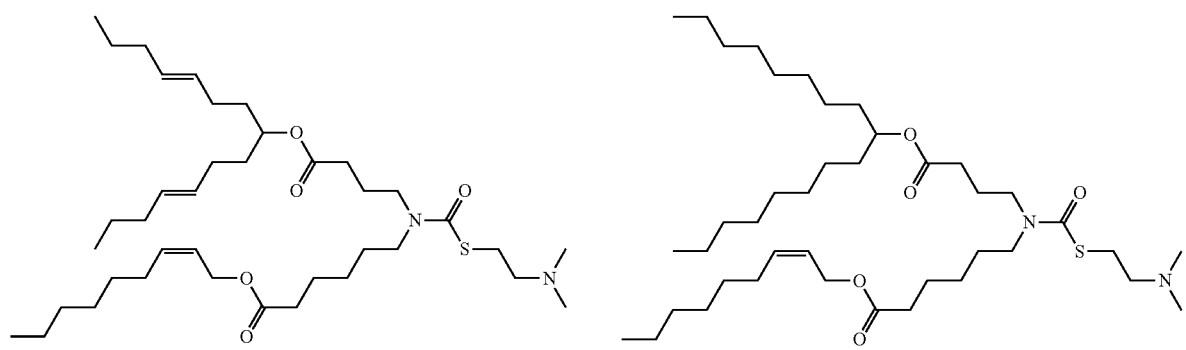

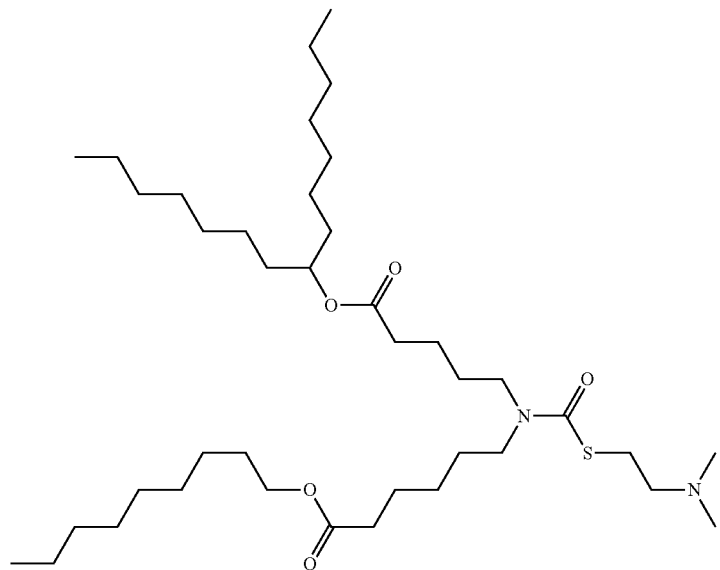
ATX-0102
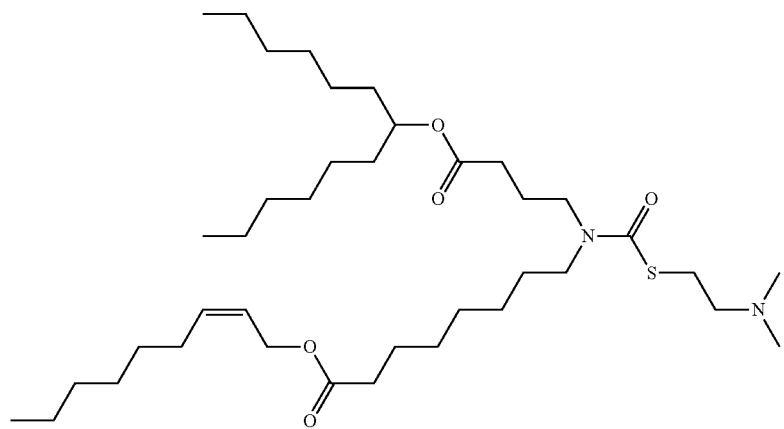
ATX-098
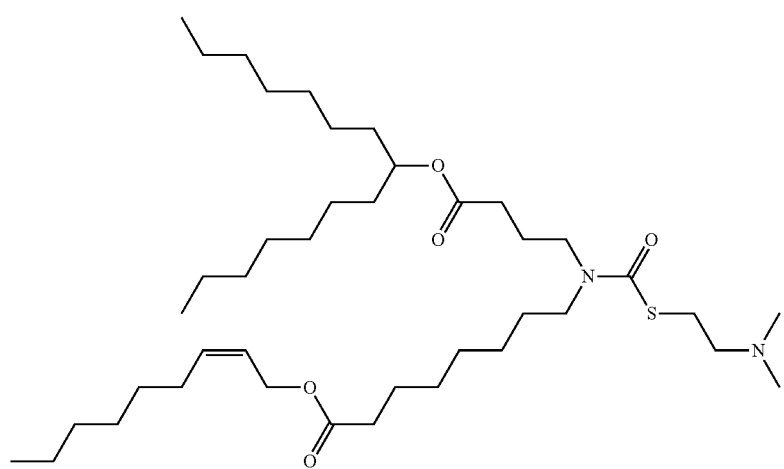
ATX-092

-continued
ATX-084
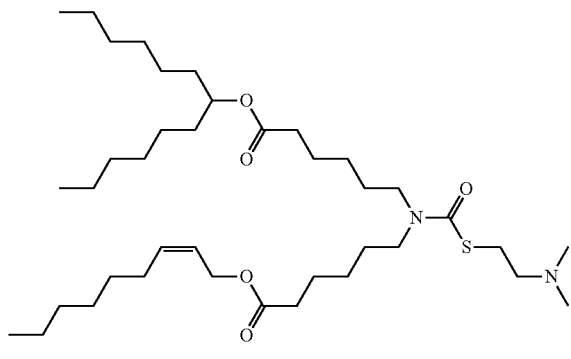
ATX-0125
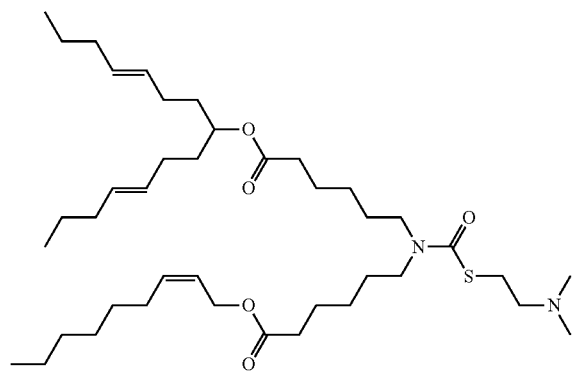
ATX-094
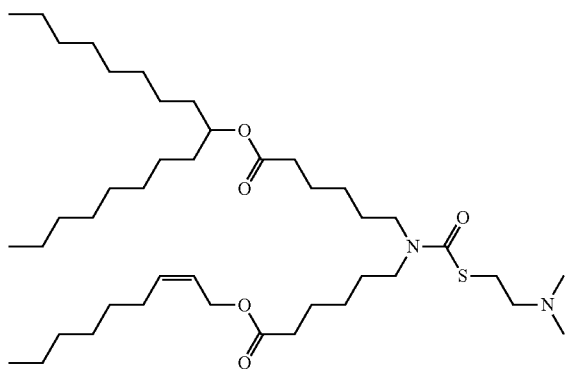
ATX-0110
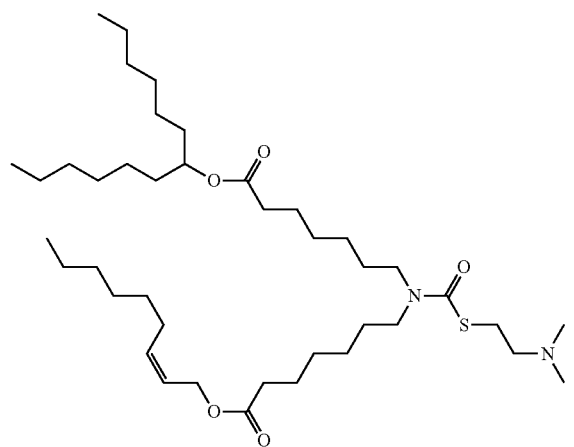
ATX-0118
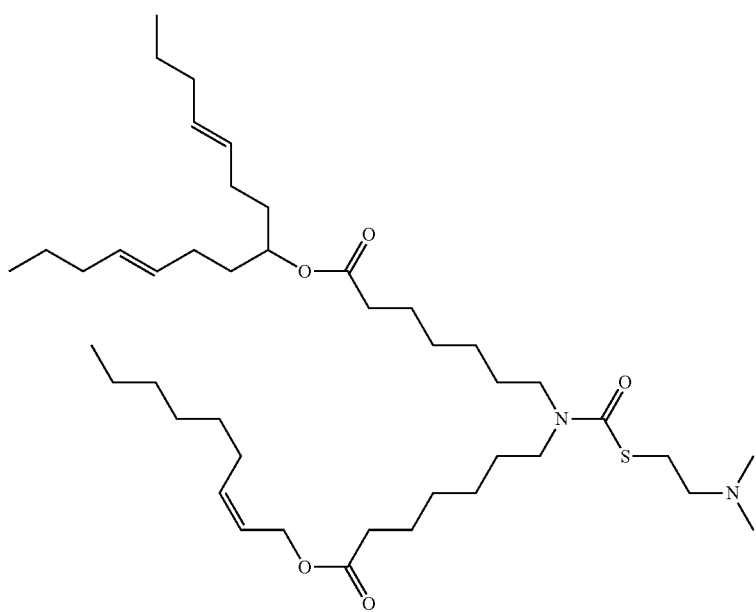

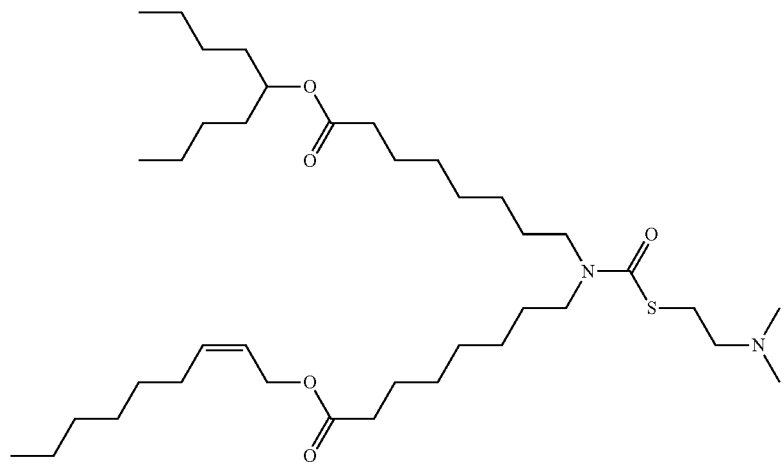
ATX-0108
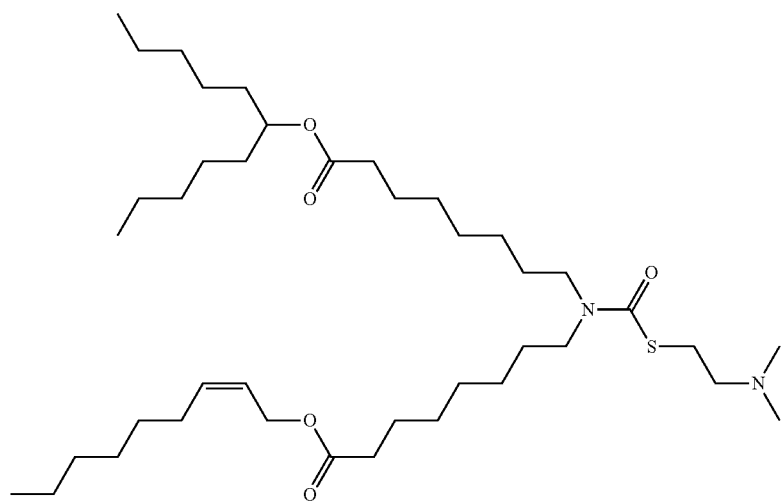
ATX-0107
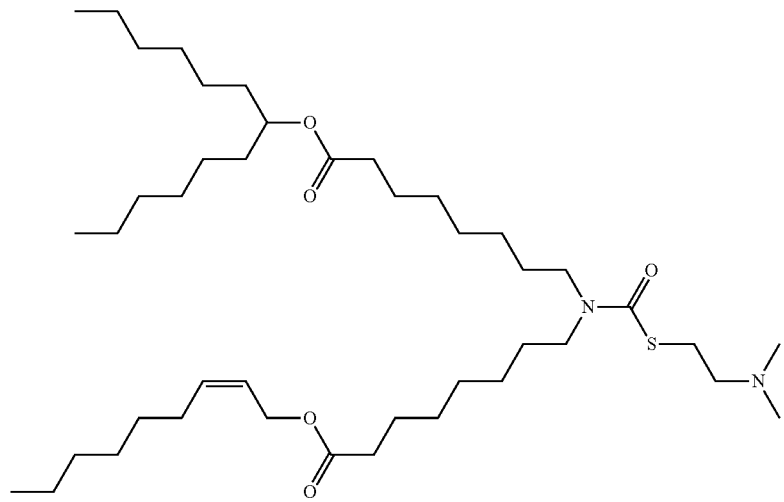
ATX-093

-continued
ATX-097
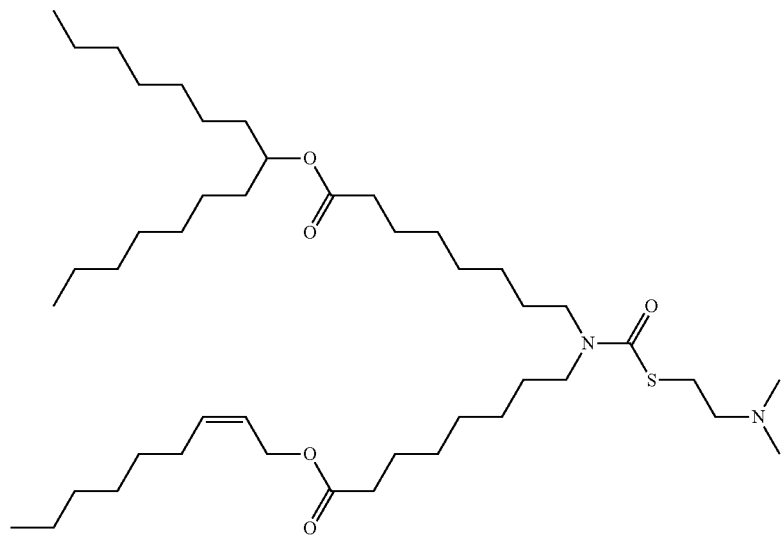
ATX-096
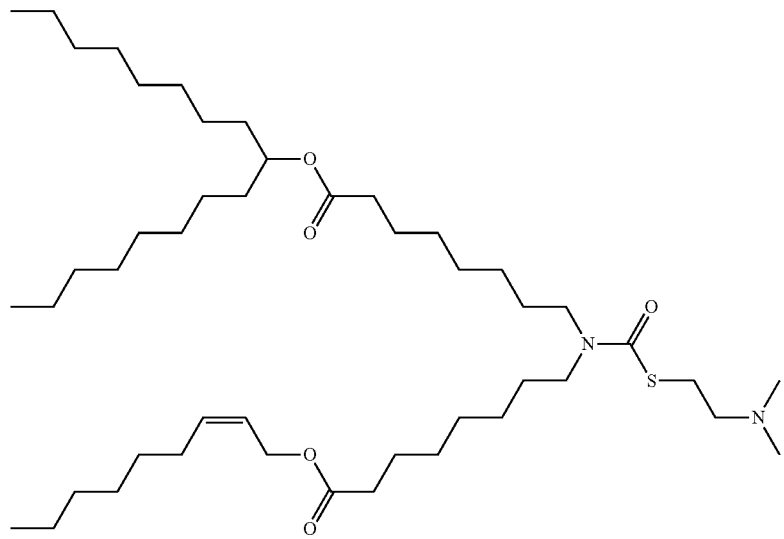
ATX-0111
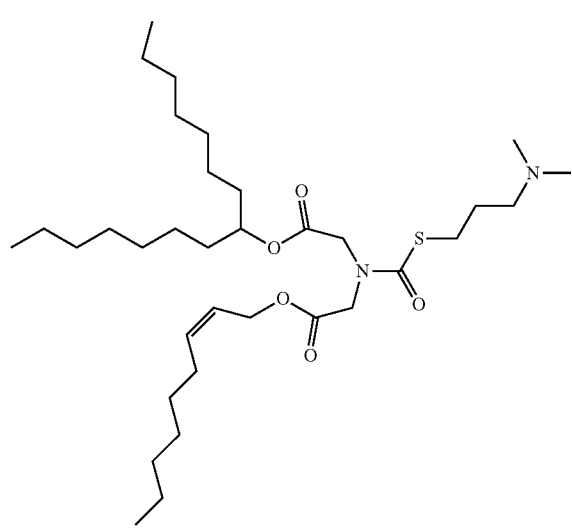
ATX-0132
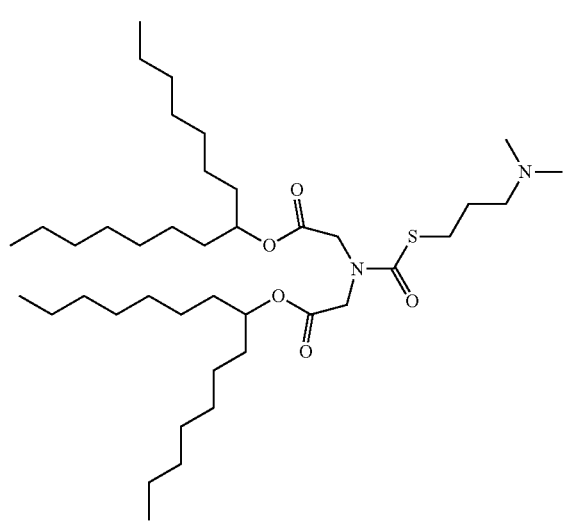

129 130
-continued
ATX-0134
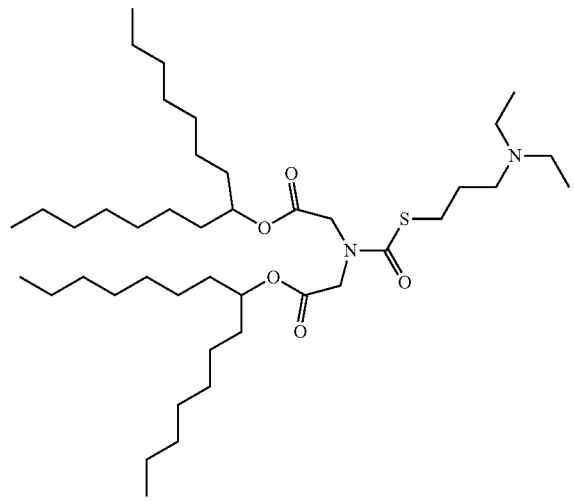
ATX-0100
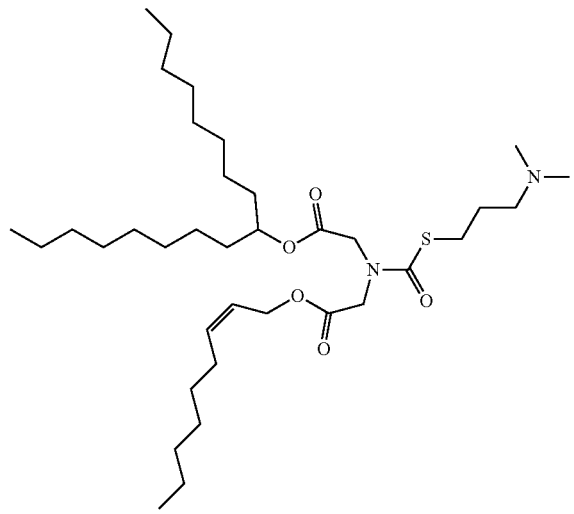
ATX-0117
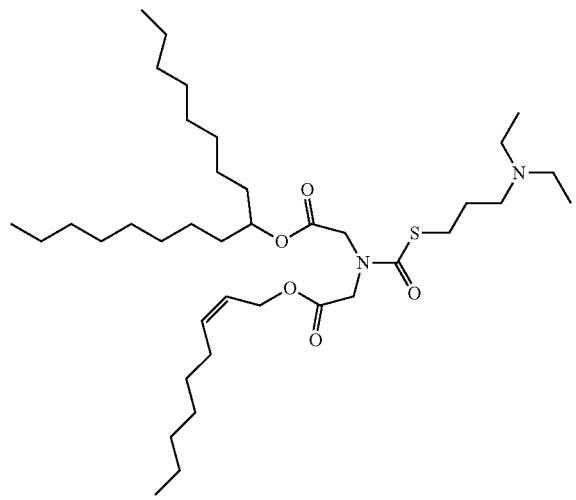
ATX-0114
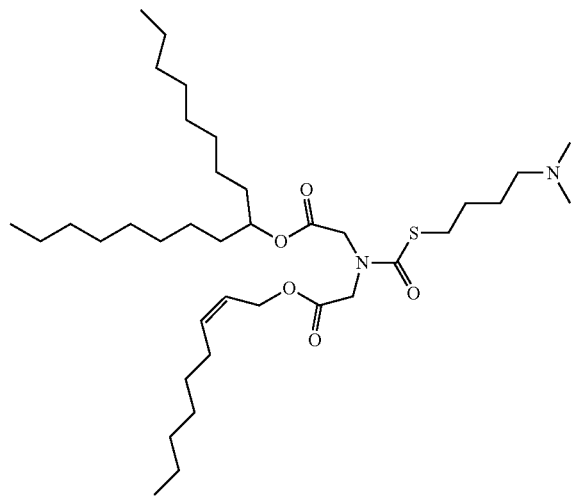
ATX-0115
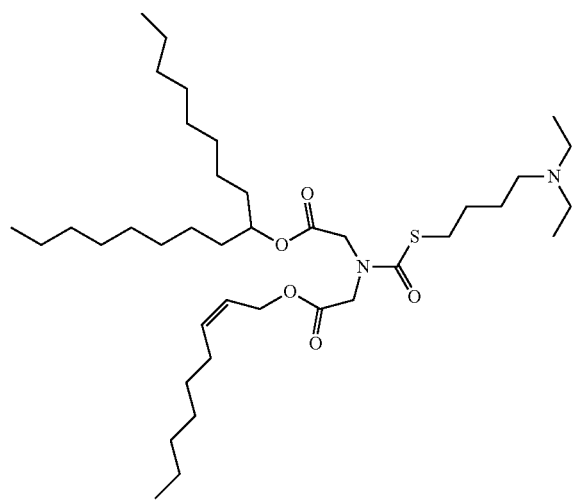
ATX-0101
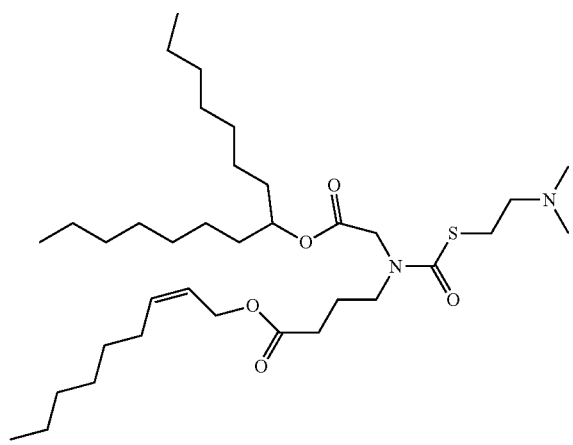

131
-continued
ATX-0106
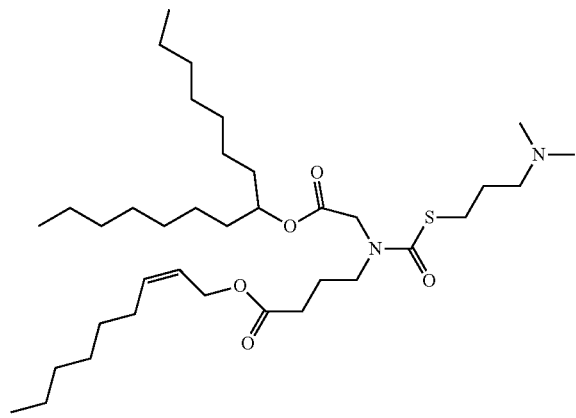
ATX-0116
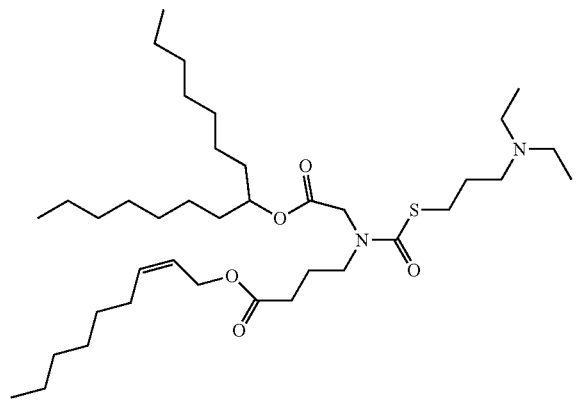
132
ATX-0123
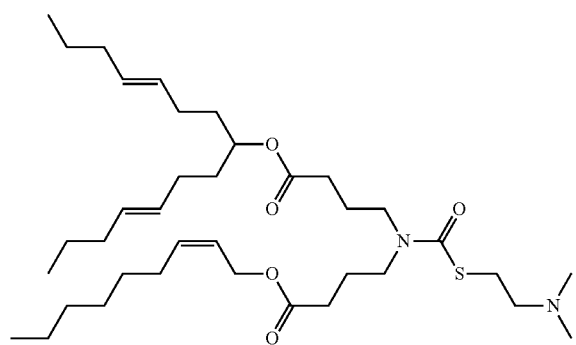
ATX-0122
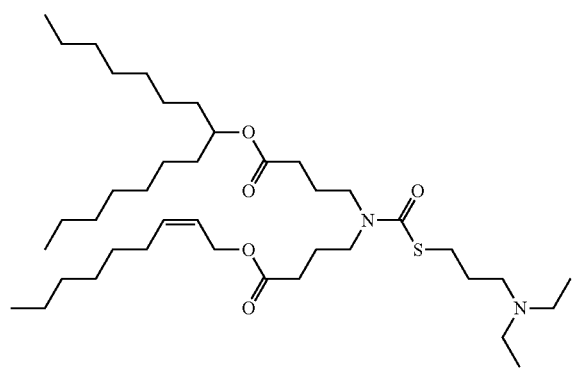
ATX-0124
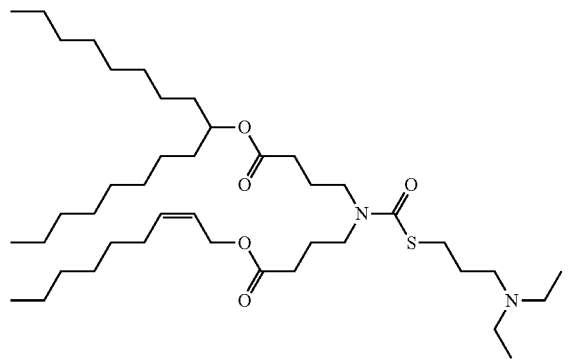
ATX-0129
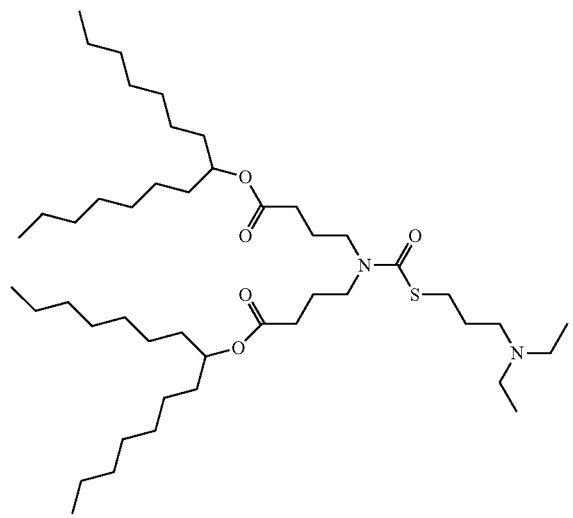

-continued
ATX-081
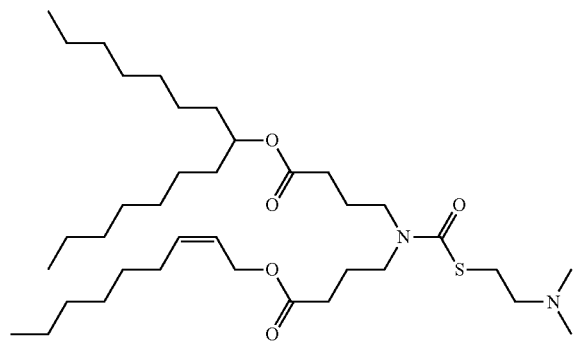
ATX-095
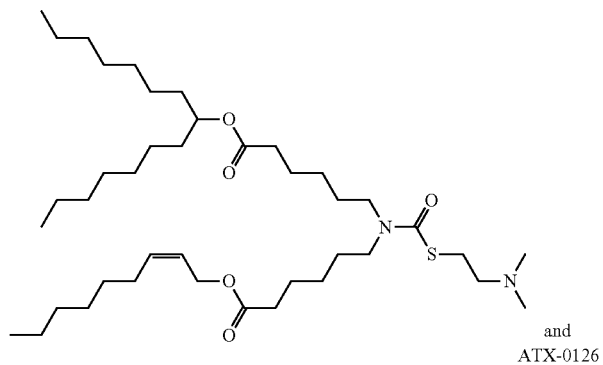
and
ATX-0126
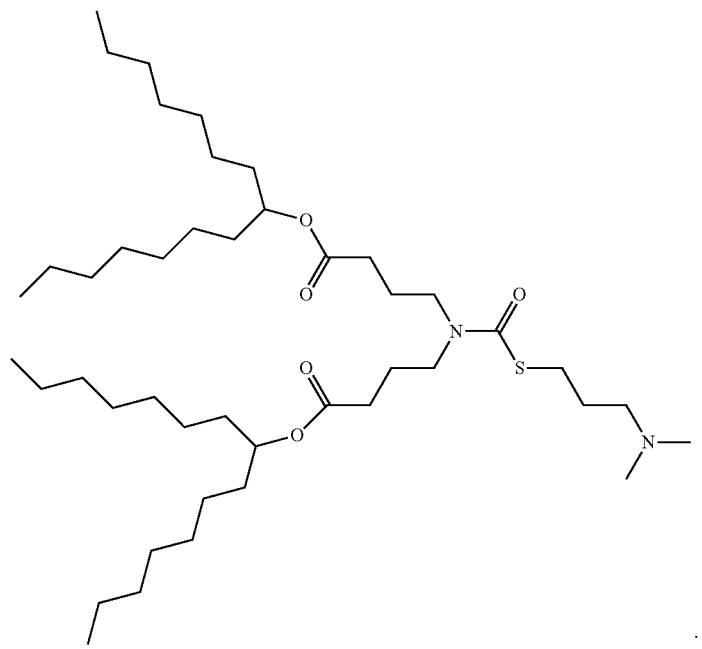
In one aspect, the ionizable cationic lipid of compositions provided herein has a structure of
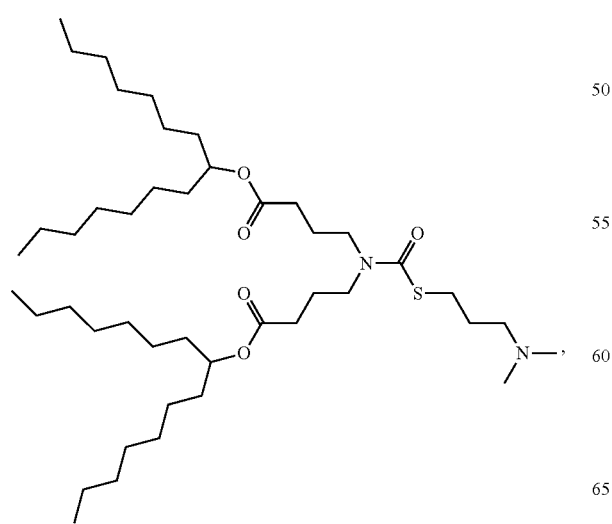
-continued
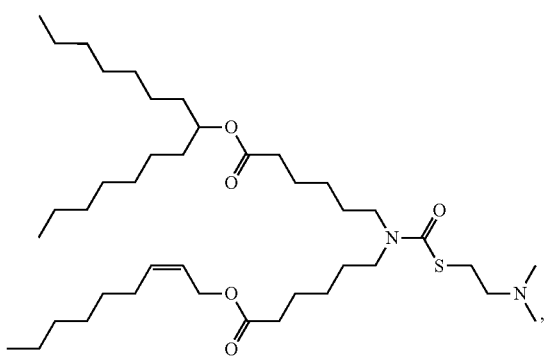

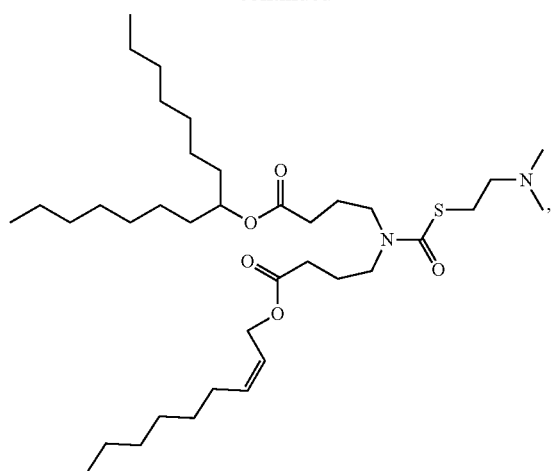

or a pharmaceutically acceptable salt thereof.

In another aspect, the ionizable cationic lipid of compositions provided herein has a structure of

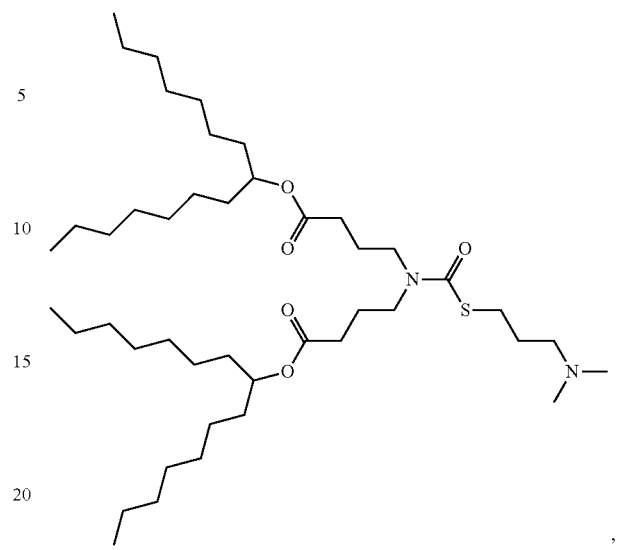

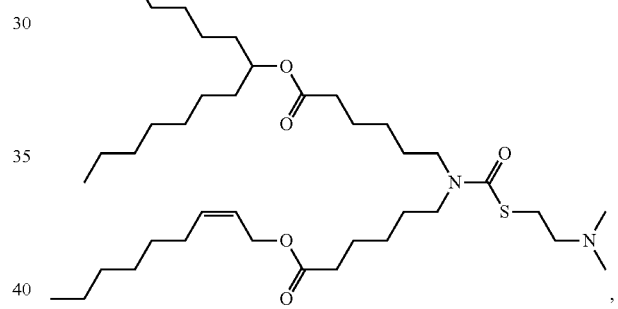

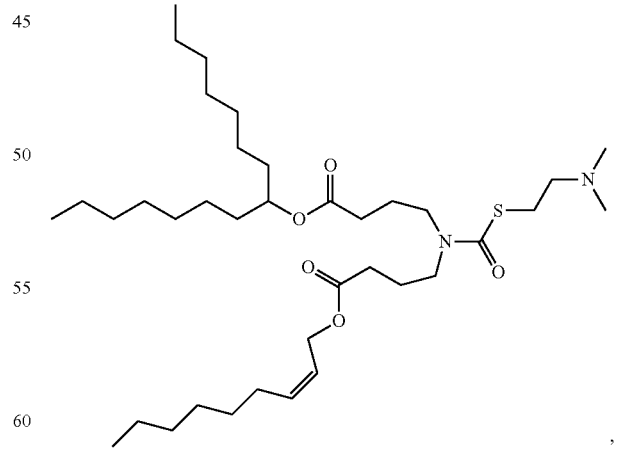

or a pharmaceutically acceptable salt thereof.

In one aspect, the ionizable cationic lipid included in lipid formulations of pharmaceutical compositions provided herein has a structure of or a pharmaceutically acceptable salt thereof.

In another aspect, the ionizable cationic lipid included in lipid formulations of pharmaceutical compositions provided herein has a structure of

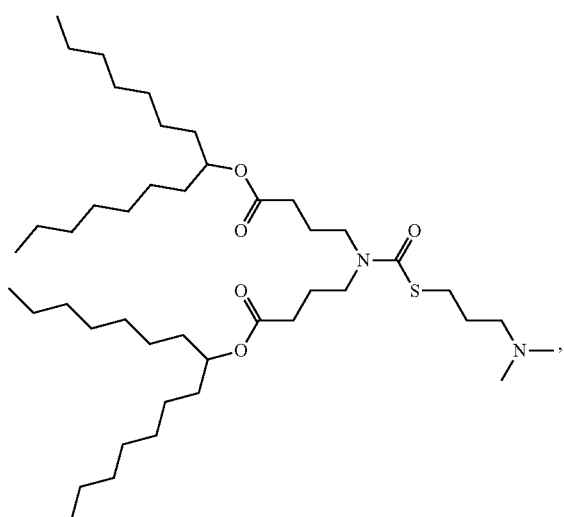

or a pharmaceutically acceptable salt thereof.

Lipid Formulations/LNPs

Therapies based on the intracellular delivery of nucleic acids to target cells face both extracellular and intracellular barriers. Indeed, naked nucleic acid materials cannot be easily systemically administered due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida MPharm Res. 1995 June; 12(6):825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), release at the cytoplasm (for RNA), and so on. Successful nucleic acid-based therapy thus depends upon the ability of the vector to deliver the nucleic acids to the target sites inside of the cells in order to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still under ongoing development.

Some art-recognized lipid-formulated delivery vehicles for nucleic acid therapeutics include, according to various embodiments, polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. These lipid formulations can vary in their structure and composition, and as can be expected in a rapidly evolving field, several different terms have been used in the art to describe a single type of delivery vehicle. At the same time, the terms for lipid formulations have varied as to their intended meaning throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns. Liposomal formulations can be prepared as a colloidal dispersion or they can be lyophilized to reduce stability risks and to improve the shelf-life for liposome-based drugs. Methods of preparing liposomal compositions are known in the art and would be within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicle (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several nonconcentric lipid bilayers.

Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9:1833-1843). In their use as drug delivery vehicles, because a liposome has an aqueous solution core surrounded by a hydrophobic membrane, hydrophilic solutes dissolved in the core cannot readily pass through the bilayer, and hydrophobic compounds will associate with the bilayer. Thus, a liposome can be loaded with hydrophobic and/or hydrophilic molecules. When a liposome is used to carry a nucleic acid such as RNA, the nucleic acid will be contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed herein below.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell is formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the Lipofectamine® reagent, have found considerable utility for in vitro transfection. However, these first-generation lipoplexes have not proven useful in vivo. The large particle size and positive charge (Imparted by the cationic lipid) result in rapid plasma clearance, hemolytic and other toxicities, as well as immune system activation. In some aspects, nucleic acid molecules provided herein and lipids or lipid formulations provided herein form a lipid nanoparticle (LNP).

In other aspects, nucleic acid molecules provided herein are incorporated into a lipid formulation (i.e., a lipid-based delivery vehicle).

In the context of the present disclosure, a lipid-based delivery vehicle typically serves to transport a desired RNA to a target cell or tissue. The lipid-based delivery vehicle can be any suitable lipid-based delivery vehicle known in the art. In some aspects, the lipid-based delivery vehicle is a liposome, a cationic liposome, or a lipid nanoparticle containing a self-replicating RNA of the disclosure. In some aspects, the lipid-based delivery vehicle comprises a nanoparticle or a bilayer of lipid molecules and a self-replicating RNA of the disclosure. In some aspects, the lipid bilayer further comprises a neutral lipid or a polymer. In some aspects, the lipid formulation comprises a liquid medium. In some aspects, the formulation further encapsulates a nucleic acid. In some aspects, the lipid formulation further comprises a nucleic acid and a neutral lipid or a polymer. In some aspects, the lipid formulation encapsulates the nucleic acid.

The description provides lipid formulations comprising one or more self-replicating RNA molecules encapsulated within the lipid formulation. In some aspects, the lipid formulation comprises liposomes. In some aspects, the lipid formulation comprises cationic liposomes. In some aspects, the lipid formulation comprises lipid nanoparticles.

In some aspects, the self-replicating RNA is fully encapsulated within the lipid portion of the lipid formulation such that the RNA in the lipid formulation is resistant in aqueous solution to nuclease degradation. In other aspects, the lipid formulations described herein are substantially non-toxic to animals such as humans and other mammals.

The lipid formulations of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 45:1, or from about 10:1 to about 40:1, or from about 15:1 to about 40:1, or from about 20:1 to about 40:1; or from about 25:1 to about 45:1; or from about 30:1 to about 45:1; or from about 32:1 to about 42:1; or from about 34:1 to about 42:1. In some aspects, the total lipid:RNA ratio (mass/mass ratio) is from about 30:1 to about 45:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, generally are resistant in aqueous solution to degradation with a nuclease.

In some embodiments, the lipid nanoparticle has a size of less than about 500 nm, less than about 400 nm, less than about 300 nm, less than about 200 nm, less than about 100 nm, or less than about 50 nm. In specific embodiments, the lipid nanoparticle has a size of about 55 nm to about 90 nm.

In some aspects, the lipid formulations comprise a self-replicating RNA, a cationic lipid (e.g., one or more cationic lipids or salts thereof described herein), a phospholipid, and a conjugated lipid that inhibits aggregation of the particles (e.g., one or more PEG-lipid conjugates). The lipid formulations can also include cholesterol. In one aspect, the cationic lipid is an ionizable cationic lipid.

In the nucleic acid-lipid formulations, the RNA may be fully encapsulated within the lipid portion of the formulation, thereby protecting the nucleic acid from nuclease degradation. In some aspects, a lipid formulation comprising an RNA is fully encapsulated within the lipid portion of the lipid formulation, thereby protecting the nucleic acid from nuclease degradation. In certain aspects, the RNA in the lipid formulation is not substantially degraded after exposure of the particle to a nuclease at 37° C. for at least 20, 30, 45, or 60 minutes. In certain other aspects, the RNA in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In some aspects, the RNA is complexed with the lipid portion of the formulation. One of the benefits of the formulations of the present disclosure is that the nucleic acid-lipid compositions are substantially non-toxic to animals such as humans and other mammals.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as $E=(10-1)/10$, where/and 10 refers to the fluorescence intensities before and after the addition of detergent.

In some aspects, the present disclosure provides a nucleic acid-lipid composition comprising a plurality of nucleic acid-liposomes, nucleic acid-cationic liposomes, or nucleic acid-lipid nanoparticles. In some aspects, the nucleic acid-lipid composition comprises a plurality of RNA-liposomes. In some aspects, the nucleic acid-lipid composition comprises a plurality of RNA-cationic liposomes. In some aspects, the nucleic acid-lipid composition comprises a plurality of RNA-lipid nanoparticles.

In some aspects, the lipid formulations comprise RNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% h to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the RNA encapsulated therein. The amount may be any value or subvalue within the recited ranges, including endpoints. The RNA included in any RNA-lipid composition or RNA-lipid formulation provided herein can be a self-replicating RNA.

Depending on the intended use of the lipid formulation, the proportions of the components can be varied, and the delivery efficiency of a particular formulation can be measured using assays known in the art.

In some aspects, nucleic acid molecules provided herein are lipid formulated. The lipid formulation is preferably selected from, but not limited to, liposomes, cationic liposomes, and lipid nanoparticles. In one aspect, a lipid formulation is a cationic liposome or a lipid nanoparticle (LNP) comprising:
  (a) an RNA of the present disclosure,
  (b) a cationic lipid,
  (c) an aggregation reducing agent (such as polyethylene glycol (PEG) lipid or PEG-modified lipid),
  (d) optionally a non-cationic lipid (such as a neutral lipid), and
  (e) optionally, a sterol.

In another aspect, the cationic lipid is an ionizable cationic lipid. Any ionizable cationic lipid can be included in lipid formulations, including exemplary cationic lipids provided herein.

Cationic Lipids

In one aspect, the lipid nanoparticle formulation comprises (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation comprises (i) at least one cationic lipid; (ii) a helper lipid; (iii) a sterol (e.g., cholesterol); and (iv) a PEG-lipid, in a molar ratio of about 40-70% ionizable cationic lipid:about 2-15% helper lipid:about 20-45% sterol; about 0.5-5% PEG-lipid. In a further aspect, the cationic lipid is an ionizable cationic lipid.

In one aspect, the lipid nanoparticle formulation consists of (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation consists of (i) at least one cationic lipid; (ii) a helper lipid; (iii) a sterol (e.g., cholesterol); and (iv) a PEG-lipid, in a molar ratio of about 40-70% ionizable cationic lipid:about 2-15% helper lipid:about 20-45% sterol; about 0.5-5% PEG-lipid. In a further aspect, the cationic lipid is an ionizable cationic lipid.

In the presently disclosed lipid formulations, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), I-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C$_2$-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P—(N—(N',N'-dimethylaminoethane)-carbamoyl)cholesterol (DC-Choi), N-(1-(2,3-dioleyloxy)propyl)-N-2-(sperminecarboxamido) ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

The RNA-lipid formulations of the present disclosure can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylcthanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. As a helper lipid, cholesterol increases the spacing of the charges of the lipid layer interfacing with the nucleic acid making the charge distribution match that of the nucleic acid more closely. (J. R. Soc. Interface. 2012 Mar. 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In some aspects, the cholesterol derivative is a polar analogue such as cholesteryl-(4'-hydroxy)-butyl ether.

In some aspects, the helper lipid present in the lipid formulation comprises or consists of a mixture of one or more phospholipids and cholesterol or a derivative thereof. In other aspects, the neutral lipid present in the lipid formulation comprises or consists of one or more phospholipids, e.g., a cholesterol-free lipid formulation. In yet other aspects, the neutral lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In some embodiments, the lipid formulation comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH1 at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises an ionizable cationic lipid of Formula I:

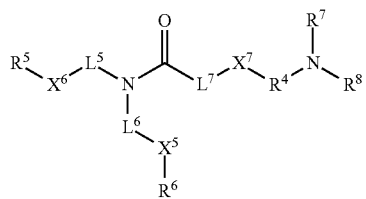

(I)

or a pharmaceutically acceptable salt or solvate thereof, wherein R5 and R6 are each independently selected from the group consisting of a linear or branched C1-C31 alkyl, C2-C31 alkenyl or C2-C31 alkynyl and cholesteryl; L5 and L6 are each independently selected from the group consisting of a linear C1-C20 alkyl and C2-C20 alkenyl; X5 is —C(O)O—, whereby —C(O)O—R6 is formed or —OC(O)— whereby —OC(O)—R6 is formed; X6 is —C(O)O— whereby —C(O)O—R5 is formed or —OC(O)— whereby —OC(O)—R5 is formed; X7 is S or O; L7 is absent or lower alkyl; R4 is a linear or branched C1-C6 alkyl; and R7 and R8 are each independently selected from the group consisting of a hydrogen and a linear or branched C1-C6 alkyl.

In some embodiments, X7 is S.

In some embodiments, X5 is —C(O)O—, whereby —C(O)O—R6 is formed and X6 is —C(O)O— whereby —C(O)O—R5 is formed.

In some embodiments, R7 and R8 are each independently selected from the group consisting of methyl, ethyl and isopropyl.

In some embodiments, L5 and L6 are each independently a C1-C10 alkyl. In some embodiments, L5 is C1-C3 alkyl, and L6 is C1-C5 alkyl. In some embodiments, L6 is C1-C2 alkyl. In some embodiments, L5 and L6 are each a linear C7 alkyl. In some embodiments, L5 and L6 are each a linear C9 alkyl.

In some embodiments, R5 and R6 are each independently an alkenyl. In some embodiments, R6 is alkenyl. In some embodiments, R6 is C2-C9 alkenyl. In some embodiments, the alkenyl comprises a single double bond. In some embodiments, R5 and R6 are each alkyl. In some embodiments, R5 is a branched alkyl. In some embodiments, R5 and R6 are each independently selected from the group consisting of a C9 alkyl, C9 alkenyl and C9 alkynyl. In some embodiments, R5 and R6 are each independently selected from the group consisting of a C11 alkyl, C11 alkenyl and C11 alkynyl. In some embodiments, R5 and R6 are each independently selected from the group consisting of a C7 alkyl, C7 alkenyl and C7 alkynyl. In some embodiments, R5 is —CH((CH2)pCH3)2 or —CH((CH2)pCH3)((CH2)p-1CH3), wherein p is 4-8. In some embodiments, p is 5 and L5 is a C1-C3 alkyl. In some embodiments, p is 6 and L5 is a C3 alkyl. In some embodiments, p is 7. In some embodiments, p is 8 and L5 is a C1-C3 alkyl. In some embodiments, R5 consists of —CH((CH2)pCH3)((CH2)p-1CH3), wherein p is 7 or 8.

In some embodiments, R4 is ethylene or propylene. In some embodiments, R4 is n-propylene or isobutylene.

In some embodiments, L7 is absent, R4 is ethylene, X7 is S and R7 and R8 are each methyl. In some embodiments, L7 is absent, R4 is n-propylene, X7 is S and R7 and R8 are each methyl. In some embodiments, L7 is absent, R4 is ethylene, X7 is S and R7 and R8 are each ethyl.

In some embodiments, X7 is S, X5 is —C(O)O—, whereby —C(O)O—R6 is formed, X6 is —C(O)O— whereby —C(O)O—R5 is formed, L5 and L6 are each independently a linear C3-C7 alkyl, L7 is absent, R5 is —CH((CH2)pCH3)2, and R6 is C7-C12 alkenyl. In some further embodiments, p is 6 and R6 is C9 alkenyl.

In some embodiments, the lipid formulation can comprise an ionizable cationic lipid selected from the group consisting of LIPID #1 to LIPID #8:

TABLE 6

| LIPID # | STRUCTURE |
|---|---|
| 1 | 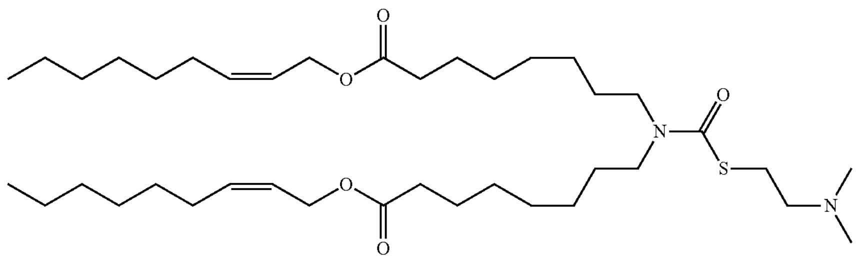 [SMILES: CCCCCC/C=C\COC(=O)CCCCCCCN(CCCCCCCC(=O)OC/C=C\CCCCCC)C(=O)SCCN(C)C] |
| 2 | 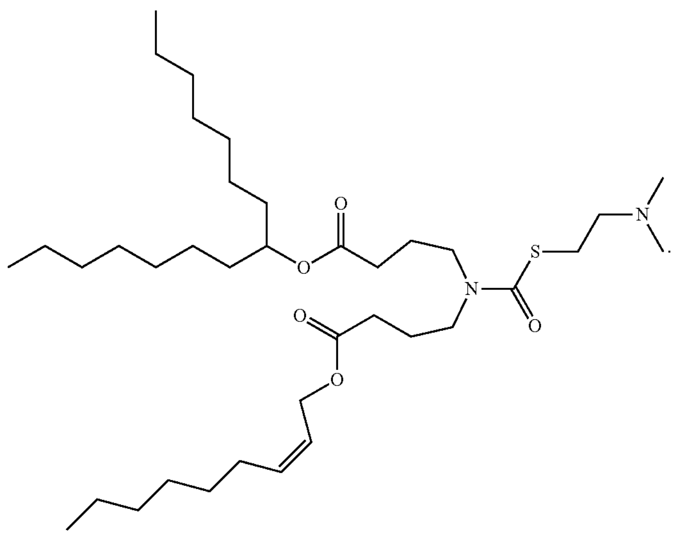 [SMILES: CCCCCC/C=C\COC(=O)CCCN(CCCC(=O)OC(CCCCCCC)CCCCCCC)C(=O)SCCN(C)C] |
| 3 | 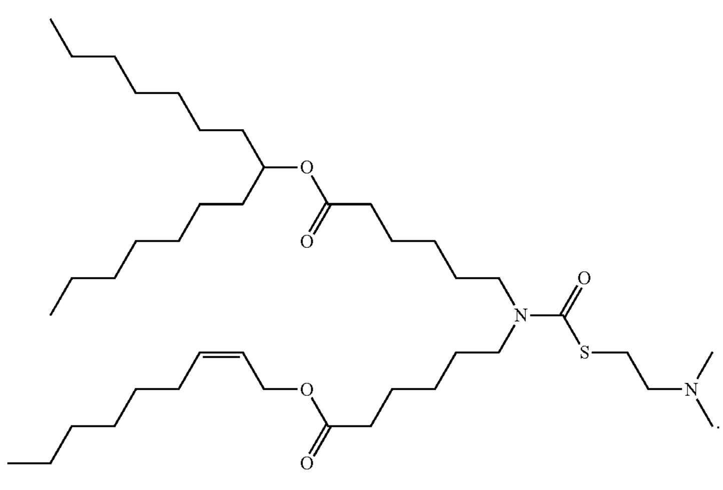 [SMILES: CCCCCC/C=C\COC(=O)CCCCCN(CCCCCC(=O)OC(CCCCCCC)CCCCCCC)C(=O)SCCN(C)C] |

TABLE 6-continued
| LIPID # | STRUCTURE |
|---|---|
| 4 | 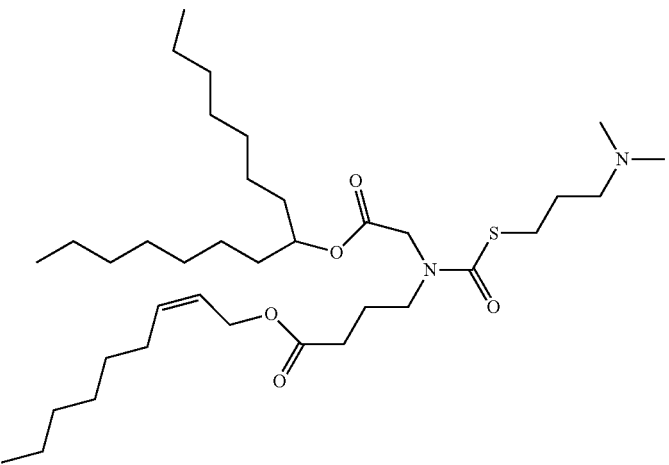 [SMILES: CCCCCC/C=C\COC(=O)CCCN(CC(=O)OC(CCCCCCC)CCCCCCC)C(=O)SCCCN(C)C] |
| 5 | 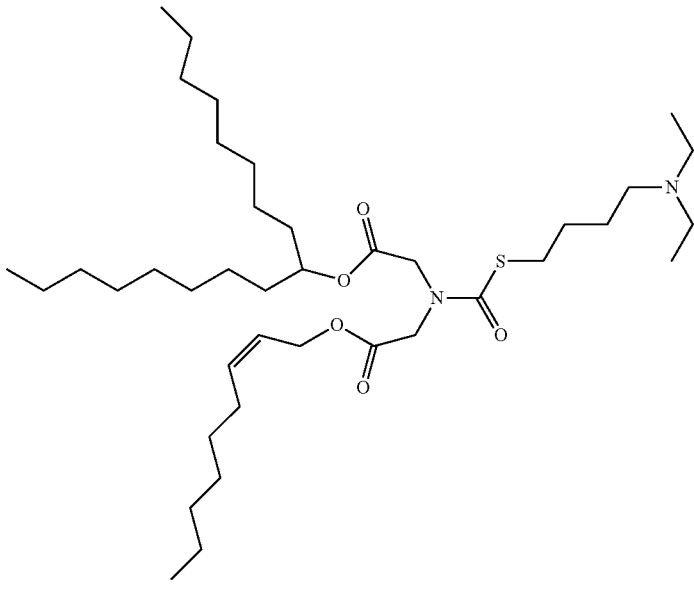 [SMILES: CCCCCC/C=C\COC(=O)CN(CC(=O)OC(CCCCCCCC)CCCCCCCC)C(=O)SCCCCN(CC)CC] |
| 6 | 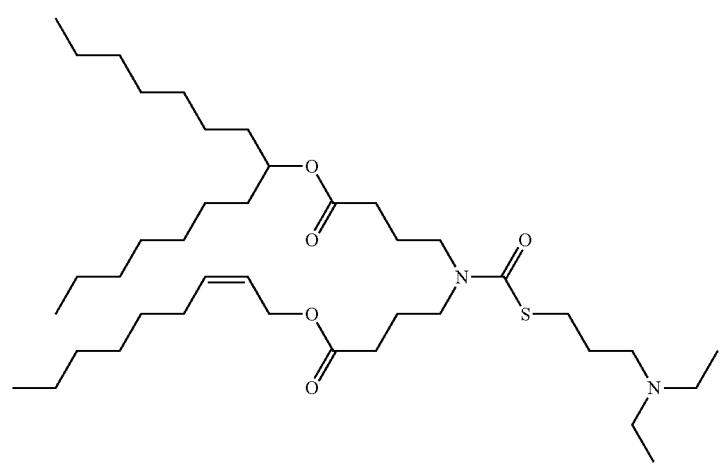 [SMILES: CCCCCC/C=C\COC(=O)CCCN(CCCC(=O)OC(CCCCCCC)CCCCCCC)C(=O)SCCCN(CC)CC] |

TABLE 6-continued
| LIPID # | STRUCTURE |
|---|---|
| 7 | 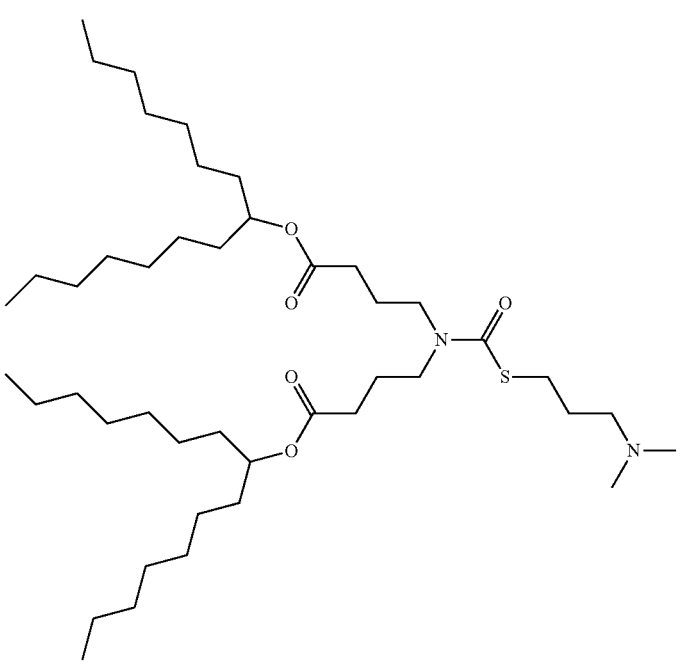 [SMILES: CCCCCCCC(CCCCCCC)OC(=O)CCCN(CCCC(=O)OC(CCCCCCC)CCCCCCC)C(=O)SCCCN(C)C] |
| 8 | 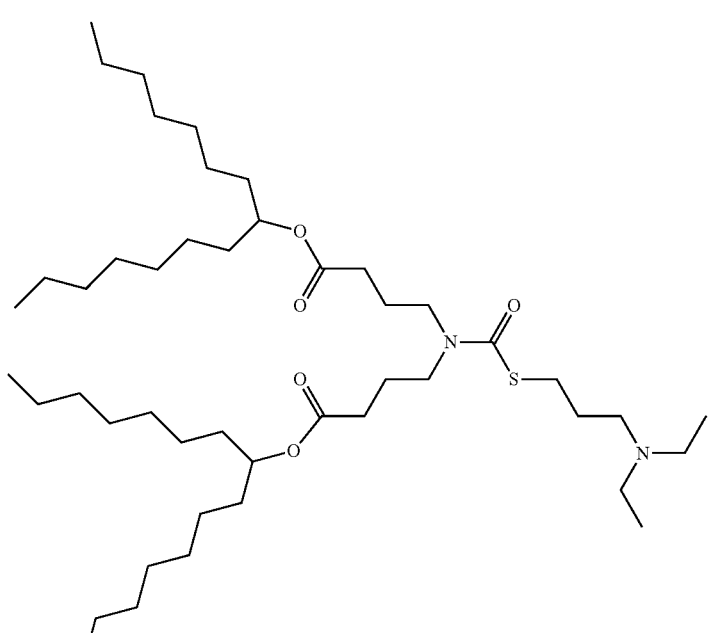 |

In some embodiments, the lipid formulation comprises an ionizable cationic lipid having a structure selected from

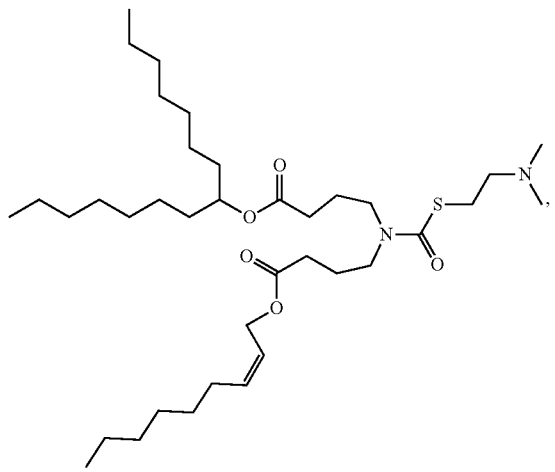 [SMILES: CCCCCC/C=C\COC(=O)CCCN(CCCC(=O)OC(CCCCCCC)CCCCCCC)C(=O)SCCN(C)C]

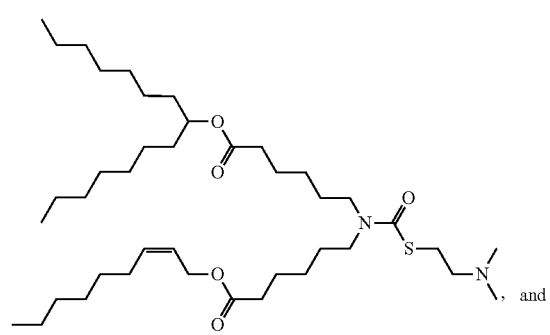

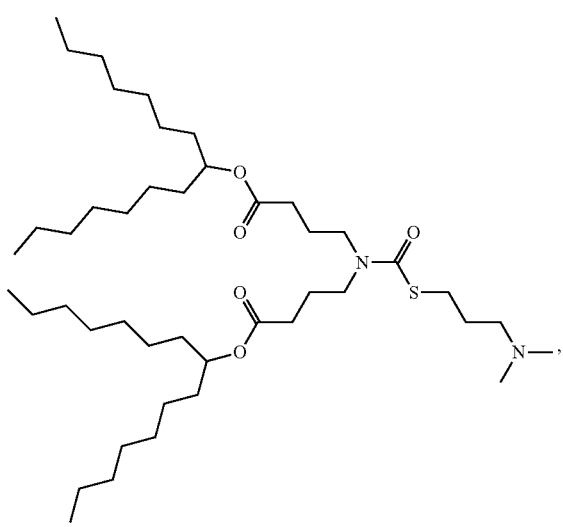 [SMILES: CCCCCCCC(CCCCCCC)OC(=O)CCCN(CCCC(=O)OC(CCCCCCC)CCCCCCC)C(=O)SCCCN(C)C]

or a pharmaceutically acceptable salt thereof.

In some preferred embodiments, the lipid formulation comprises an ionizable cationic lipid having the structure

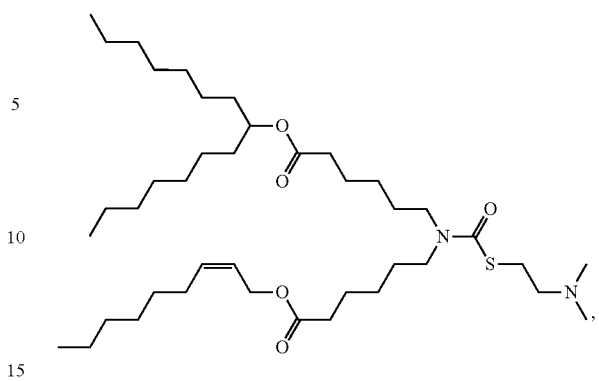

or a pharmaceutically acceptable salt thereof.

In embodiments, any one or more lipids recited herein may be expressly excluded.

In some aspects, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The lipid portion, or the cholesterol or cholesterol derivative in the lipid formulation may comprise up to about 40 mol %, about 45 mol %, about 50 mol %, about 55 mol %, or about 60 mol % of the total lipid present in the lipid formulation. In some aspects, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol/a, or about 37 mol % of the total lipid present in the lipid formulation.

In specific embodiments, the lipid portion of the lipid formulation is about 35 mol % to about 42 mol % cholesterol.

In some aspects, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

In certain embodiments, the lipid portion of the lipid formulation comprises about, but is not necessarily limited to, 40 mol % to about 60 mol % of the ionizable cationic lipid, about 4 mol % to about 16 mol % DSPC, about 30 mol % to about 47 mol % cholesterol, and about 0.5 mol % to about 3 mol % PEG2000-DMG.

In certain embodiments, the lipid portion of the lipid formulation may comprise, but is not necessarily limited to, about 42 mol % to about 58 mol % of the ionizable cationic lipid, about 6 mol % to about 14 mol % DSPC, about 32 mol % to about 44 mol % cholesterol, and about 1 mol % to about 2 mol % PEG2000-DMG.

In certain embodiments, the lipid portion of the lipid formulation may comprise, but is not necessarily limited to, about 45 mol % to about 55 mol % of the ionizable cationic lipid, about 8 mol % to about 12 mol % DSPC, about 35 mol % to about 42 mol % cholesterol, and about 1.25 mol % to about 1.75 mol % PEG2000-DMG.

The percentage of helper lipid present in the lipid formulation is a target amount, and the actual amount of helper lipid present in the formulation may vary, for example, by ±5 mol %.

A lipid formulation that includes a cationic lipid compound or ionizable cationic lipid compound may be on a molar basis about 30-70% cationic lipid compound, about 25-40% cholesterol, about 2-15% helper lipid, and about 0.5-5% of a polyethylene glycol (PEG) lipid, wherein the percent is of the total lipid present in the formulation. In some aspects, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid formulations described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In some aspects, the lipid conjugate is a PEG-lipid. The inclusion of polyethylene glycol (PEG) in a lipid formulation as a coating or surface ligand, a technique referred to as PEGylation, helps to protect nanoparticles from the immune system and their escape from RES uptake (Nanomedicine (Lond). 2011 June; 6(4):715-28). PEGylation has been used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). PEGylation leads to a significant increase in the circulation half-life of lipid formulations (Annu. Rev. Biomed. Eng. 2011 Aug. 15; 13( ):507-30; J. Control Release. 2010 Aug. 3; 145(3):178-81).

Examples of PEG-lipids include, but are not limited to, PEG coupled to dialkyloxypropyls (PEG-DAA), PEG coupled to diacylglycerol (PEG-DAG), methoxypolyethyleneglycol (PEG-DMG or PEG2000-DMG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH2).

The PEG moiety of the PEG-lipid conjugates described herein may comprise an average molecular weight ranging from about 550 daltons to about 10,000 daltons. In certain aspects, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In some aspects, the PEG moiety has an average molecular weight of about 2,000 daltons or about 750 daltons. The average molecular weight may be any value or subvalue within the recited ranges, including endpoints.

In certain aspects, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In one aspect, the linker moiety is a non-ester-containing linker moiety. Exemplary non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH2CH2C(O)—), succinamidyl (—NHC(O)CH2CH2C(O)NH—), ether, as well as combinations thereof (such as a linker containing both a carbamate linker moiety and an amido linker moiety). In one aspect, a carbamate linker is used to couple the PEG to the lipid.

In some aspects, an ester-containing linker moiety is used to couple the PEG to the lipid. Exemplary ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

In some aspects, the PEG-DAA conjugate is a PEG-didecyloxypropyl (C10) conjugate, a PEG-dilauryloxypropyl (C12) conjugate, a PEG-dimyristyloxypropyl (C14) conjugate, a PEG-dipalmityloxypropyl (C16) conjugate, or a PEG-distearyloxypropyl (C18) conjugate. In some aspects, the PEG has an average molecular weight of about 750 or about 2,000 daltons. In some aspects, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some aspects, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%/o, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation. The amount may be any value or subvalue within the recited ranges, including endpoints.

The percentage of lipid conjugate (e.g., PEG-lipid) present in the lipid formulations of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid formulation is to become fusogenic.

In some embodiments, the lipid formulation for any of the compositions described herein comprises a lipoplex, a liposome, a lipid nanoparticle, a polymer-based particle, an exosome, a lamellar body, a micelle, or an emulsion.

Mechanism of Action for Cellular Uptake of Lipid Formulations

In some aspects, lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28(3):146-157, 2018). Prior to endocytosis, functionalized ligands such as PEG-lipid at the surface of the lipid delivery vehicle are shed from the surface, which triggers internalization into the target cell. During endocytosis, some part of the plasma membrane of the cell surrounds the vector and engulfs it into a vesicle that then pinches off from the cell membrane, enters the cytosol and ultimately enters and moves through the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For RNA payloads, the cell's own internal translation processes will then translate the RNA into the encoded protein. The encoded protein can further undergo postranslational processing, including transportation to a targeted organelle or location within the cell or excretion from the cell.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual assymetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

Encapsulation in Preformed Liposomes

The entrapment of nucleic acids can also be obtained starting with preformed liposomes through two different methods: (1) A simple mixing of cationic liposomes with nucleic acids which gives electrostatic complexes called "lipoplexes", where they can be successfully used to transfect cell cultures, but are characterized by their low encapsulation efficiency and poor performance in vivo; and (2) a liposomal destabilization, slowly adding absolute ethanol to a suspension of cationic vesicles up to a concentration of 40% v/v followed by the dropwise addition of nucleic acids achieving loaded vesicles; however, the two main steps characterizing the encapsulation process are too sensitive, and the particles have to be downsized.

Excipients

The pharmaceutical compositions disclosed herein can be formulated using one or more excipients to: (1) increase stability; (2) increase cell transfection; (3) permit a sustained or delayed release (e.g., from a depot formulation of the polynucleotide, primary construct, or RNA); (4) alter the biodistribution (e.g., target the polynucleotide, primary construct, or RNA to specific tissues or cell types); (5) increase the translation of encoded protein in vivo; and/or (6) alter the release profile of encoded protein in vivo.

The pharmaceutical compositions described herein may be prepared by any method known or hereafter developed in the art of pharmacology. In general, such preparatory methods include the step of associating the active ingredient (i.e., nucleic acid) with an excipient and/or one or more other accessory ingredients. A pharmaceutical composition in accordance with the present disclosure may be prepared, packaged, and/or sold in bulk, as a single unit dose, and/or as a plurality of single unit doses.

Pharmaceutical compositions may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or RNA (e.g., for transplantation into a subject), hyaluronidase, nanoparticle mimics and combinations thereof.

Accordingly, the pharmaceutical compositions described herein can include one or more excipients, each in an amount that together increases the stability of the nucleic acid in the lipid formulation, increases cell transfection by the nucleic acid, increases the expression of the encoded protein, and/or alters the release profile of encoded proteins. Further, the RNA of the present disclosure may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

The pharmaceutical compositions of this disclosure may further contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the RNA-lipid formulation may be administered in a time release formulation, for example in a composition which includes a slow release polymer. The active agent can be prepared with carriers that will protect against rapid release, for example a controlled release vehicle such as a polymer, microencapsulated delivery system, or a bioadhesive gel. Prolonged delivery of the RNA, in various compositions of the disclosure can be brought about by including in the composition agents that delay absorption, for example, aluminum monostearate hydrogels and gelatin.

Methods of Inducing Immune Responses

Provided herein, in some embodiments, are methods of inducing an immune response in a subject. Any type of immune response can be induced using the methods provided herein, including adaptive and innate immune responses. In one aspect, immune responses induced using the methods provided herein include an antibody response, a cellular immune response, or both an antibody response and a cellular immune response.

Methods of inducing an immune response provided herein include administering to a subject an effective amount of any nucleic acid molecule provided herein. In one aspect, methods of inducing an immune response include administering to a subject an effective amount of any composition comprising a nucleic acid molecule and a lipid provided herein. In another aspect, methods of inducing an immune response include administering to a subject an effective amount of any pharmaceutical composition comprising a nucleic acid molecule and a lipid formulation provided herein. In some aspects, nucleic acid molecules, compositions, and pharmaceutical composition provided here are vaccines that can elicit a protective or a therapeutic immune response, for example.

As used herein, the term "subject" refers to any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. As used herein, the term "effective amount" or "therapeutically effective amount" refers to that amount of a nucleic acid molecule, composition, or pharmaceutical composition described herein that is sufficient to effect the intended application, including but not limited to inducing an immune response and/or disease treatment, as defined herein. The therapeutically effective amount may vary depending upon the intended application (e.g., inducing an immune response, treatment, application in vivo), or the subject or patient and disease condition being treated, e.g., the weight and age of the subject, the species, the severity of the disease condition, the manner of administration and the like, which can readily be determined by one of ordinary skill in the art. The term also applies to a dose that will induce a particular response in a target cell. The specific dose will vary depending on the particular nucleic acid molecule, composition, or pharmaceutical composition chosen, the dosing regimen to be followed, whether it is administered in combination with other compounds, timing of administration, the tissue to which it is administered, and the physical delivery system in which it is carried.

Exemplary doses of nucleic acid molecules that can be administered include about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 10 µg, about 11 µg, about 12 µg, about 13µ, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1,000 µg, or more, and any number or range in between. In one aspect, the nucleic acid molecules are RNA molecules. In another aspect, the nucleic acid molecules are DNA molecules. Nucleic acid molecules can have a unit dosage comprising about 0.01 µg to about 1,000 µg or more nucleic acid in a single dose.

In some aspects, compositions provided herein that can be administered include about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1,000 µg, or more, and any number or range in between, nucleic acid and lipid. In other aspects, pharmaceutical compositions provided herein that can be administered include about 0.01 µg, about 0.02 µg, about 0.03 µg, about 0.04 µg, about 0.05 µg, about 0.06 µg, about 0.07 µg, about 0.08 µg, about 0.09 µg, about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.5 µg, about 2.0 µg, about 2.5 µg, about 3.0 µg, about 3.5 µg, about 4.0 µg, about 4.5 µg, about 5.0 µg, about 5.5 µg, about 6.0 µg, about 6.5 µg, about 7.0 µg, about 7.5 µg, about 8.0 µg, about 8.5 µg, about 9.0 µg, about 9.5 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 600 µg, about 700 µg, about 800 µg, about 900 µg, about 1,000 μg, or more, and any number or range in between, nucleic acid and lipid formulation.

In one aspect, compositions provided herein can have a unit dosage comprising about 0.01 μg to about 1,000 μg or more nucleic acid and lipid in a single dose. In another aspect, pharmaceutical compositions provided herein can have a unit dosage comprising about 0.01 μg to about 1,000 μg or more nucleic acid and lipid formulation in a single dose. A vaccine unit dosage can correspond to the unit dosage of nucleic acid molecules, compositions, or pharmaceutical compositions provided herein and that can be administered to a subject. In one aspect, vaccine compositions of the instant disclosure have a unit dosage comprising about 0.01 μg to about 1,000 μg or more nucleic acid and lipid formulation in a single dose. In another aspect, vaccine compositions of the instant disclosure have a unit dosage comprising about 0.01 μg to about 50 μg nucleic acid and lipid formulation in a single dose. In yet another aspect, vaccine compositions of the instant disclosure have a unit dosage comprising about 0.2 μg to about 20 μg nucleic acid and lipid formulation in a single dose.

A dosage form of the composition of this disclosure can be solid, which can be reconstituted in a liquid prior to administration. The solid can be administered as a powder. The solid can be in the form of a capsule, tablet, or gel. In some embodiments, the pharmaceutical composition comprises a nucleic acid lipid formulation that has been lyophilized. In some embodiments, the lyophilized composition may comprise one or more lyoprotectants, such as, including but not necessarily limited to, glucose, trehalose, sucrose, maltose, lactose, mannitol, inositol, hydroxypropyl-p-cyclodextrin, and/or polyethylene glycol. In some embodiments, the lyophilized composition comprises a poloxamer, potassium sorbate, sucrose, or any combination thereof. In specific embodiments, the poloxamer is poloxamer 188. In some embodiments, the lyophilized compositions described herein may comprise about 0.01 to about 1.0% w/w of a poloxamer. In some embodiments, the lyophilized compositions described herein may comprise about 1.0 to about 5.0% w/w of potassium sorbate. The percentages may be any value or subvalue within the recited ranges, including endpoints.

In some embodiments, the lyophilized composition may comprise about 0.01 to about 1.0% w/w of the nucleic acid molecule. In some embodiments, the composition may comprise about 1.0 to about 5.0% w/w lipids. In some embodiments, the composition may comprise about 0.5 to about 2.5% w/w of TRIS buffer. In some embodiments, the composition may comprise about 0.75 to about 2.75% w/w of NaCl. In some embodiments, the composition may comprise about 85 to about 95% w/w of a sugar. The percentages may be any value or subvalue within the recited ranges, including endpoints.

In a preferred embodiment, the dosage form of the pharmaceutical compositions described herein can be a liquid suspension of self-replicating RNA lipid nanoparticles described herein. In some embodiments, the liquid suspension is in a buffered solution. In some embodiments, the buffered solution comprises a buffer selected from the group consisting of HEPES, MOPS, TES, and TRIS. In some embodiments, the buffer has a pH of about 7.4. In some preferred embodiments, the buffer is HEPES. In some further embodiments, the buffered solution further comprises a cryoprotectant. In some embodiments, the cryoprotectant is selected from a sugar and glycerol or a combination of a sugar and glycerol. In some embodiments, the sugar is a dimeric sugar. In some embodiments, the sugar is sucrose. In some preferred embodiments, the buffer comprises HEPES, sucrose, and glycerol at a pH of 7.4. In certain embodiments, the composition comprises a HEPES, MOPS, TES, or TRIS buffer at a pH of about 7.0 to about 8.5. In some embodiments, the HEPES, MOPS, TES, or TRIS buffer may at a concentration ranging from 7 mg/ml to about 15 mg/ml. The pH or concentration may be any value or subvalue within the recited ranges, including endpoints.

In some embodiments, the suspension is frozen during storage and thawed prior to administration. In some embodiments, the suspension is frozen at a temperature below about 70° C. In some embodiments, the suspension is diluted with sterile water during intravenous administration. In some embodiments, intravenous administration comprises diluting the suspension with about 2 volumes to about 6 volumes of sterile water. In some embodiments, the suspension comprises about 0.1 mg to about 3.0 mg self-replicating RNA/mL, about 15 mg/mL to about 25 mg/mL of an ionizable cationic lipid, about 0.5 mg/mL to about 2.5 mg/mL of a PEG-lipid, about 1.8 mg/mL to about 3.5 mg/mL of a helper lipid, about 4.5 mg/mL to about 7.5 mg/mL of a cholesterol, about 7 mg/mL to about 15 mg/mL of a buffer, about 2.0 mg/mL to about 4.0 mg/mL of NaCl, about 70 mg/mL to about 110 mg/mL of sucrose, and about 50 mg/mL to about 70 mg/mL of glycerol. In some embodiments, a lyophilized self-replicating RNA-lipid nanoparticle formulation can be resuspended in a buffer as described herein.

In some embodiments, the compositions of the disclosure are administered to a subject such that a self-replicating RNA concentration of at least about 0.05 mg/kg, at least about 0.1 mg/kg, at least about 0.5 mg/kg, at least about 1.0 mg/kg, at least about 2.0 mg/kg, at least about 3.0 mg/kg, at least about 4.0 mg/kg, at least about 5.0 mg/kg of body weight is administered in a single dose or as part of single treatment cycle. In some embodiments, the compositions of the disclosure are administered to a subject such that a total amount of at least about 0.1 mg, at least about 0.5 mg, at least about 1.0 mg, at least about 2.0 mg, at least about 3.0 mg, at least about 4.0 mg, at least about 5.0 mg, at least about 6.0 mg, at least about 7.0 mg, at least about 8.0 mg, at least about 9.0 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, or at least about 125 mg self-replicating RNA is administered in one or more doses up to a maximum dose of about 300 mg, about 350 mg, about 400 mg, about 450 mg, or about 500 mg self-replicating RNA.

Any route of administration can be included in methods provided herein. In some aspects, nucleic acid molecules, compositions, and pharmaceutical compositions provided herein are administered intramuscularly, subcutaneously, intradermally, transdermally, intranasally, orally, sublingually, intravenously, intraperitoneally, topically, by aerosol, or by a pulmonary route, such as by inhalation or by nebulization, for example. In some embodiments, the pharmaceutical compositions described are administered systemically. Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments, the pharmaceutical composition is administered intravenously.

Pharmaceutical compositions may be administered to any desired tissue. In some embodiments, the self-replicating RNA delivered is expressed in a tissue different from the tissue in which the lipid formulation or pharmaceutical composition was administered. In preferred embodiments, self-replicating RNA is delivered and expressed in the liver.

In other aspects, nucleic acid molecules, compositions, and pharmaceutical compositions provided herein are administered intramuscularly.

In some aspects, the subject in which an immune response is induced is a healthy subject. As used herein, the term "healthy subject" refers to a subject not having a condition or disease, including an infectious disease or cancer, for example, or not having a condition or disease against which an immune response is induced. Accordingly, in some aspects, a nucleic acid molecule, composition, or pharmaceutical composition provided herein is administered prophylactically to prevent an infectious disease or cancer, for example. In other aspects, the subject in which an immune response is induced has cancer. The subject may suffer from any cancer or have any tumor, including solid and liquid tumors. In one aspect, the cancer is kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma. Accordingly, a nucleic acid molecule, composition, or pharmaceutical composition provided herein can be administered therapeutically, i.e., to treat a condition or disease, such as cancer, after the onset of the condition or disease.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, includes any treatment of a disease in a mammal, particularly in a human, and includes: (a) preventing the disease from occurring in a subject, including a subject which is predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some aspects, for prophylactic benefit, treatment or compositions for treatment, including pharmaceutical compositions, are administered to a subject at risk of developing a particular disease, or to a subject reporting one or more of the physiological symptoms of a disease, even though a diagnosis of this disease may not have been made. The methods of the present disclosure may be used with any mammal or other animal. In some aspects, treatment results in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

Nucleic acid molecules, compositions, and pharmaceutical compositions provided herein can be administered once or multiple times. Accordingly, nucleic acid molecules, compositions, and pharmaceutical compositions provided herein can be administered one, two, three, four, five, six, seven, eight, nine, ten, or more times. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. In one aspect, nucleic acid molecules, compositions, or pharmaceutical compositions provided herein are administered once.

More than one nucleic acid molecule, composition, or pharmaceutical composition can be administered in the methods provided herein. In one aspect, two or more nucleic acid molecules, compositions, or pharmaceutical compositions provided herein are administered simultaneously. In another aspect, two or more nucleic acid molecules, compositions, or pharmaceutical compositions provided herein are administered sequentially. Simultaneous and sequential administrations can include any number and any combination of nucleic acid molecules, compositions, or pharmaceutical compositions provided herein. Multiple nucleic acid molecules, compositions, or pharmaceutical compositions that are administered together or sequentially can include transgenes encoding different antigenic proteins or fragments thereof. In this manner, immune responses against different antigenic targets can be induced. Two, three, four, five, six, seven, eight, nine, ten, or more nucleic acid molecules, compositions, or pharmaceutical compositions including transgenes encoding different antigenic proteins or fragments thereof can be administered simultaneously or sequentially. Any combination of nucleic acid molecules, compositions, and pharmaceutical compositions including any combination of transgenes can be administered simultaneously or sequentially. In some aspects, administration is simultaneous. In other aspects, administration is sequential. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. Nucleic acid molecules, compositions, and pharmaceutical compositions provided herein can be administered with any other vaccine or treatment.

Following administration of the composition to the subject, the protein product encoded by the self-replicating RNA of the disclosure (e.g., an antigen) is detectable in the target tissues for at least about one to seven days or longer. The amount of protein product necessary to achieve a therapeutic effect will vary depending on antibody titer necessary to generate an immunity to COVID-19 in the patient. For example, the protein product may be detectable in the target tissues at a concentration (e.g., a therapeutic concentration) of at least about 0.025-1.5 µg/ml (e.g., at least about 0.050 µg/ml, at least about 0.075 µg/ml, at least about 0.1 µg/ml, at least about 0.2 µg/ml, at least about 0.3 pig/ml, at least about 0.4 pig/ml, at least about 0.5 µg/ml, at least about 0.6 µg/ml, at least about 0.7 µg/ml, at least about 0.8 µg/ml, at least about 0.9 µg/ml, at least about 1.0 µg/ml, at least about 1.1 µg/ml, at least about 1.2 µg/ml, at least about 1.3 µg/ml, at least about 1.4 µg/ml, or at least about 1.5 µg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the composition to the subject.

In some embodiments, the composition described herein may be administered one time. In some embodiments, the composition described herein may be administered two times.

In some embodiments, the composition may be administered in the form of a booster dose, to a subject who was previously vaccinated against coronavirus.

In some embodiments, a pharmaceutical composition of the present disclosure is administered to a subject once per month. In some embodiments, a pharmaceutical composition of the present disclosure is administered to a subject twice per month. In some embodiments, a pharmaceutical composition of the present disclosure is administered to a subject three times per month. In some embodiments, a pharmaceutical composition of the present disclosure is administered to a subject four times per month.

Alternatively, the compositions of the present disclosure may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present disclosure can be inhaled (for nasal, tracheal, or bronchial delivery); compositions of the present disclosure can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present disclosure complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Combinations

The self-replicating RNA, formulations thereof, or encoded proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, a self-replicating RNA of the disclosure may be used in combination with a pharmaceutical agent for immunizing or vaccinating a subject. In general, it is expected that agents utilized in combination with the presently disclosed self-replicating RNA and formulations thereof be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

Ranges

Throughout this disclosure, various aspects can be presented in range format. It should be understood that any description in range format is merely for convenience and brevity and not meant to be limiting. Accordingly, the description of a range should be considered to have specifically disclosed all possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example 1, 2, 2.1, 2.2, 2.5, 3, 4, 4.75, 4.8, 4.85, 4.95, 5, 5.5, 5.75, 5.9, 5.00, and 6. This applies to a range of any breadth.

Example 1

This example describes a comparison of design and expression of mRNA and self-replicating RNA (STARR™) platforms.

Figure 1D:
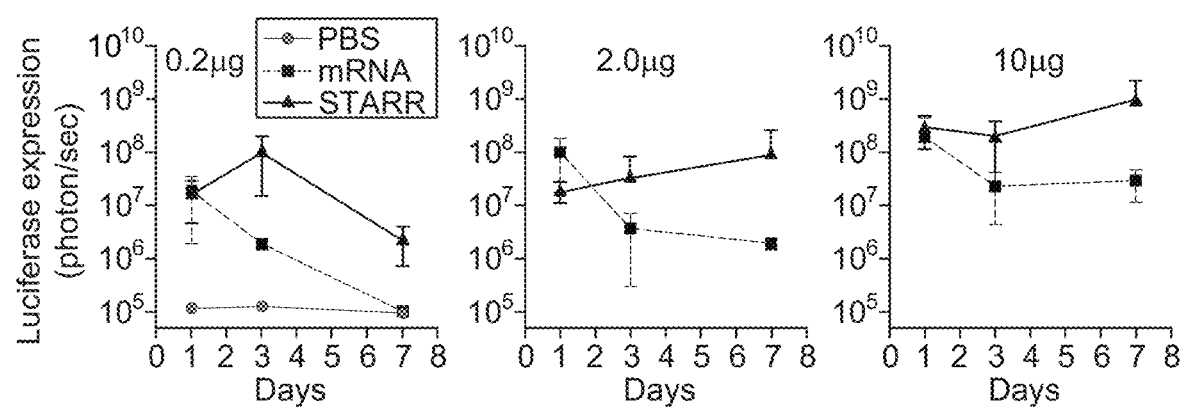

Both mRNA and STARR™ vaccine constructs were designed to encode the full-length SARS-CoV-2 S protein (1273 aa), with the STARR™ self-replicating RNA additionally encoding for the Venezuelan equine encephalitis virus (VEEV) replicase genes (FIG. 1A; STARR™ vaccine construct corresponding to an RNA having a sequence of SEQ ID NO:125, with U in place of T, referred to herein as "STARR™ SARS-CoV-2 RNA"; mRNA corresponding to a sequence of SEQ ID NO:126, with U in place of T and including a tobacco etch virus (TEV) 5' UTR, a *Xenopus* beta-globin (Xbg) 3' UTR, and a codon-optimized open reading frame encoding the SARS-CoV-2 glycoprotein). The characteristics of these different constructs was studied first. Constructs were encapsulated in the same LNP composition. Briefly, RNA constructs were encapsulated into lipid nanoparticles (LNPs) that included four lipid excipients (an ionizable cationic lipid, 1,2-distearoyl-sn-glycero-3-phosphocholine (DSPC), cholesterol, and PEG2000-DMG) dispersed in HEPES buffer (pH 8.0) containing sodium chloride and the cryoprotectants sucrose and glycerol. The ionizable cationic lipid had the following structure:

Despite differences in RNA lengths of mRNA and the STARR™ SARS-CoV-2 RNA construct, the LNP diameter, polydispersity index and RNA trapping efficiency were similar (FIG. 1B). In vitro expression of the mRNA vaccine and the STARR™ SARS-CoV-2 RNA construct were confirmed in cell lysate 24 hours post-transfection through positive western blot detection of the S protein (FIG. 1C). It was also observed that both mRNA and STARR™ vaccines expressed a mixture of full-length S protein and cleaved S protein, i.e., S was cleaved into S1 and S2 transmembrane and cytoplasmic membrane domains (FIG. 1C). In vivo protein expression of the two RNA platforms in BALB/c mice was compared by using mRNA and STARR™ constructs that expressed a luciferase reporter (FIG. 1D). Animals injected with the mRNA vaccine construct showed high in vivo luciferase expression at day 1, although the expression levels declined over time. In contrast, luciferase expression in STARR™ injected mice showed sustained or even increased signals, apart from those given the 0.2 µg dose, until day 7 post-inoculation (FIG. 1D).

These data show that dose-for-dose, antigen expression was more prolonged with the STARR™ compared to the mRNA vaccine.

Example 2

This example describes immune gene expression following the STARR™ construct and mRNA vaccination.

Figure 2A:
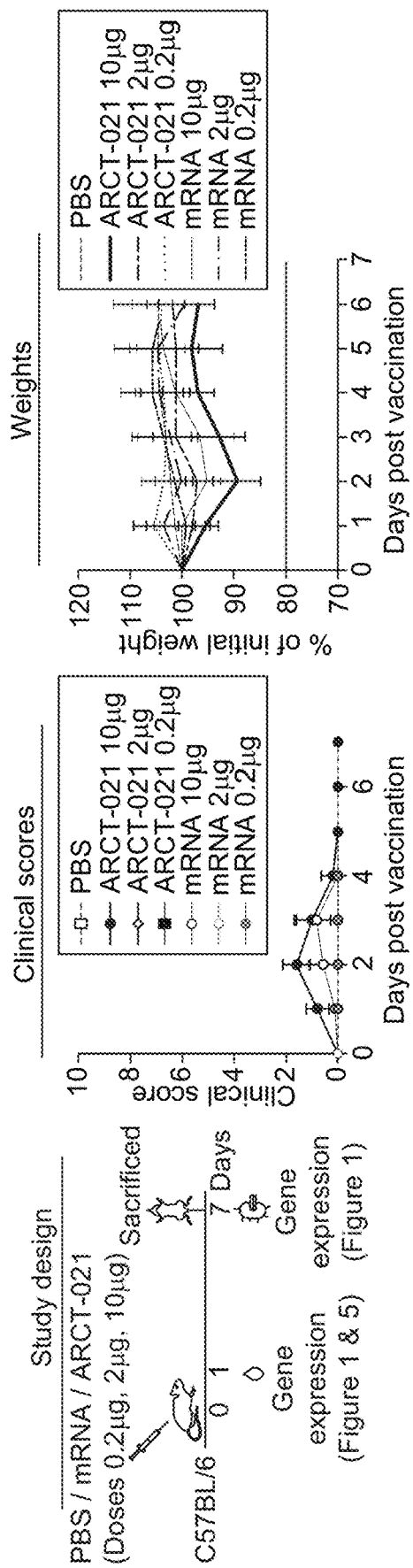

C57BL/6J mice were inoculated with STARR™ SARS-CoV-2 RNA (encoding the SARS-CoV-2 glycoprotein as described above (Example 1)) and mRNA vaccines at 0.2 µg, 2 µg and 10 µg doses or PBS control. No significant mean loss in animal weight occurred over the first 4 days, except for those that received 10 µg of STARR™ SARS-CoV-2 RNA (FIG. 2A). However, apart from weight loss, there were few other clinical signs as indicated by the minimal differences in clinical scores. Both weight and clinical scores improved after day 3 post vaccination.

Figure 2B:
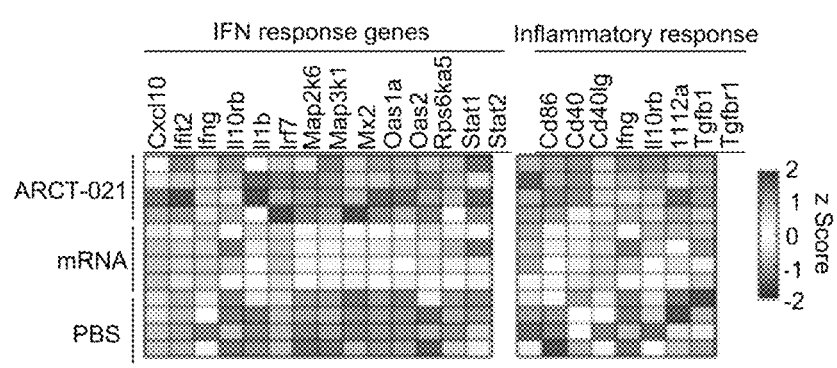
Figure 8A:
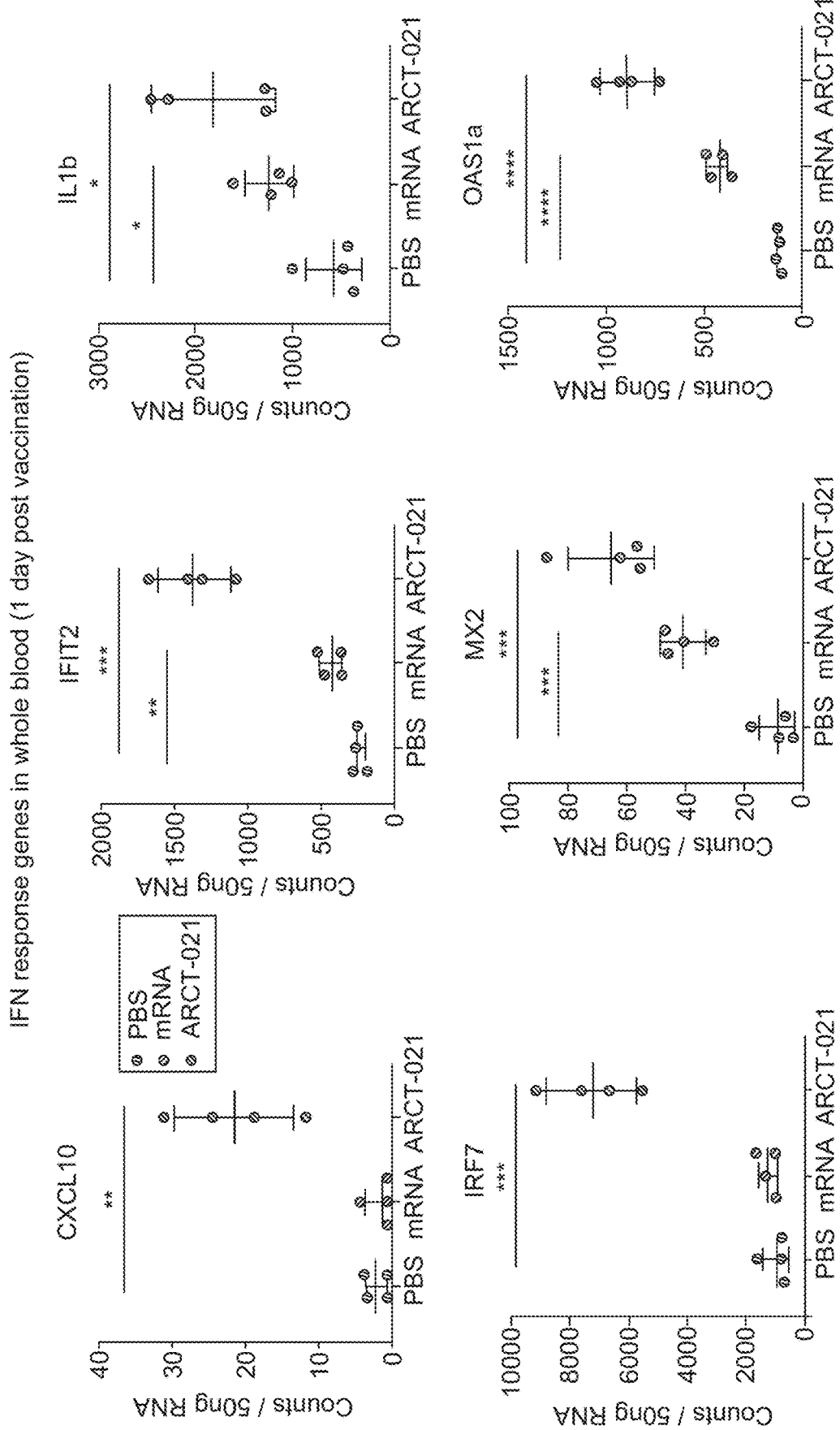
FIGS. 8A-8B show whole blood transcriptomic data at 1-day post-prime vaccination showing Nanostring counts per 50 ng RNA of selected (8A) IFN and (8B) inflammatory genes.
Figure 8B:
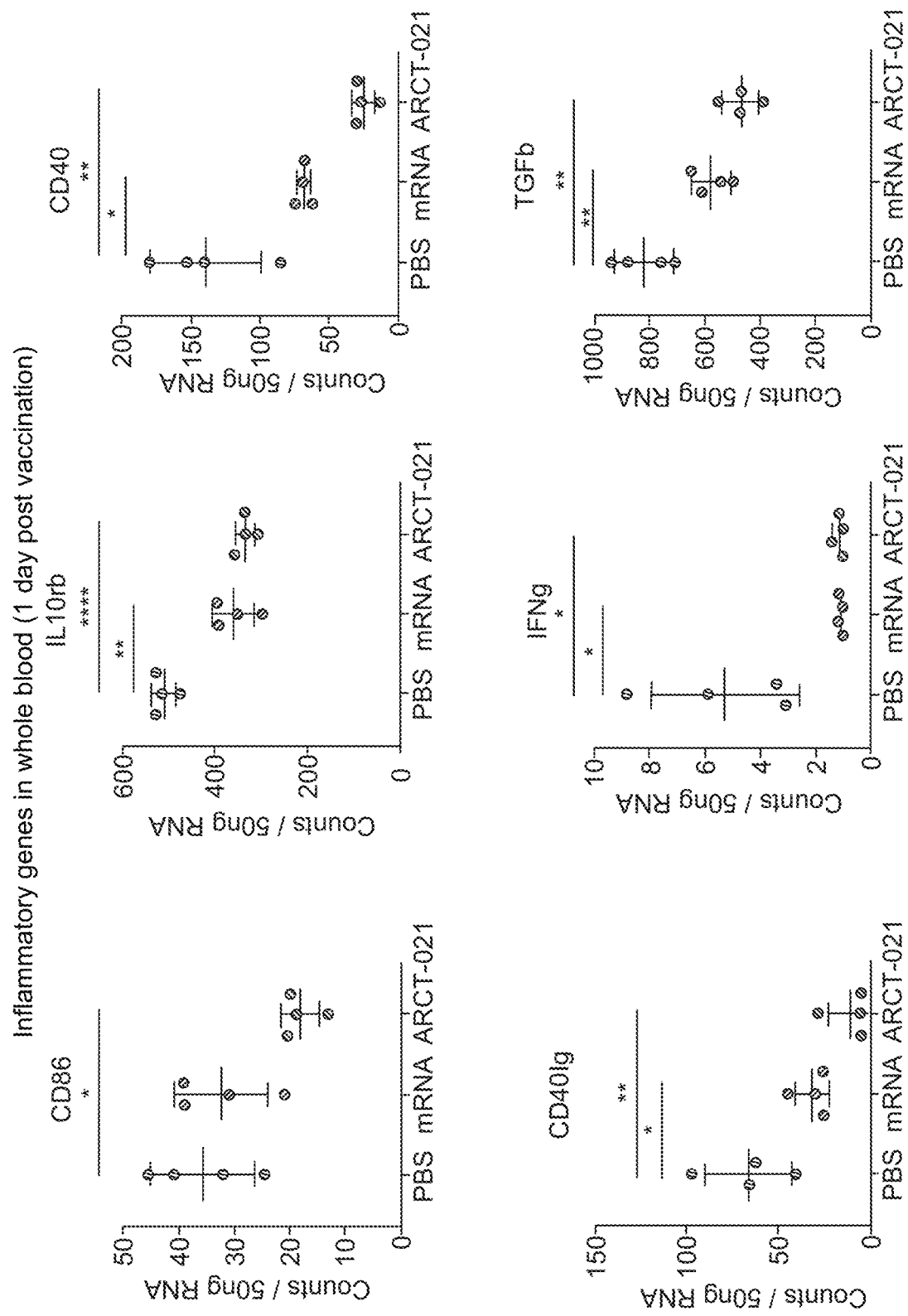

The innate immune response, such as the type-I interferon (IFN) response, has previously been shown to be associated with vaccine immunogenicity following yellow fever vaccination, for example. Furthermore, reactive oxygen species-driven pro-inflammatory responses have been shown to underpin systemic adverse events in yellow fever vaccination. Therefore, the expression of innate immune and pro-inflammatory genes in whole blood of C57BL/6 mice inoculated was measured with either PBS, mRNA vaccine, or the STARR™ SARS-CoV-2 RNA construct. Genes in the type-I IFN pathway were the most highly expressed in animals inoculated with STARR™ SARS-CoV-2 RNA compared to either mRNA vaccine or PBS (FIG. 2B and FIG. 8). By contrast, genes associated with pro-inflammatory responses were mostly reduced in abundance following vaccination STARR™ SARS-CoV-2 RNA compared with either mRNA vaccine or PBS (FIG. 2B and FIG. 8).

Figure 2C:
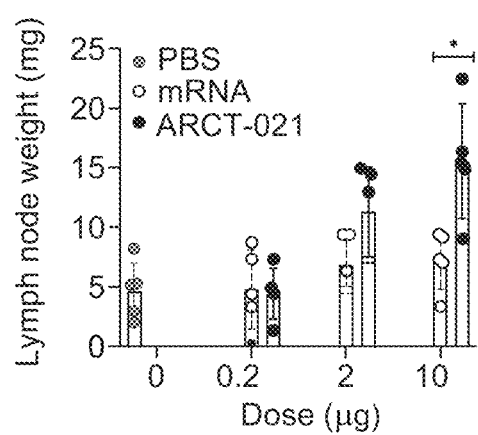

Since adaptive immune responses develop in germinal centers in the draining lymph nodes, the draining lymph nodes were dissected at day 7 post-inoculation (study schematic in FIG. 2A). The inguinal lymph nodes of mice inoculated with STARR™ SARS-CoV-2 RNA showed a dose-dependent increase in weight, unlike those from mice inoculated with either mRNA vaccine or PBS; the mean weight of lymph nodes from mice given 10 µg of STARR™ SARS-CoV-2 RNA was significantly higher than those given the equivalent mRNA vaccine (FIG. 2C). Principal component analysis (PCA) of immune gene expression showed clustering of responses to each of the 3 doses of STARR™ SARS-CoV-2 RNA away from the PBS control (STARR™ RNA): depicted as lower sphere in FIG. 2D, smallest sphere in FIG. 2E, and lower sphere in FIG. 2F; PBS control: depicted as upper sphere in FIG. 2D, lower elongated and narrow sphere in FIG. 2E, and upper sphere in FIG. 2F) indicating clear differences in immune gene expression between STARR™ SARS-CoV-2 RNA vaccinated and placebo groups. These trends were also dissimilar to those from mice given mRNA vaccine where at all tested doses, the PCA displayed substantial overlap with placebo (mRNA: shown as center sphere in FIG. 2D, large upright sphere in FIG. 2E, and as flat line with four data points along the bottom of the center square in FIG. 2F; placebo (PBS control): shown as upper sphere in FIG. 2D, lower elongated and narrow sphere in FIG. 2E, and upper sphere in FIG. 2F).

Differentially expressed genes in the lymph nodes of mice given STARR™ SARS-CoV-2 RNA compared to those inoculated with mRNA vaccine were assessed next. Volcano plot analysis identified significant upregulation of several innate, B cell, and T cells genes in STARR™ SARS-CoV-2 RNA immunized animals (FIG. 2G-2I). Some of the most highly differentially expressed genes included, for example, GZMB (important for target cell killing by cytotoxic immune cells), S100A8 and S100A9 (factors that regulate immune responses via TLR4), TNFRSF17 (also known as BCMA and regulates humoral immunity), CXCR3 (chemokine receptor involved in T cell trafficking and function) and AICDA (mediates antibody class switching and somatic hypermutation in B cells).

These findings collectively indicate that the adaptive immune responses in the draining lymph nodes of mice inoculated with STARR™ SARS-CoV-2 RNA appeared to be significantly different compared to immune responses in mice inoculated with a non-replicating mRNA vaccine.

Example 3

This example describes STARR™ SARS-CoV-2 RNA-induced T cell responses.

Figure 3A:
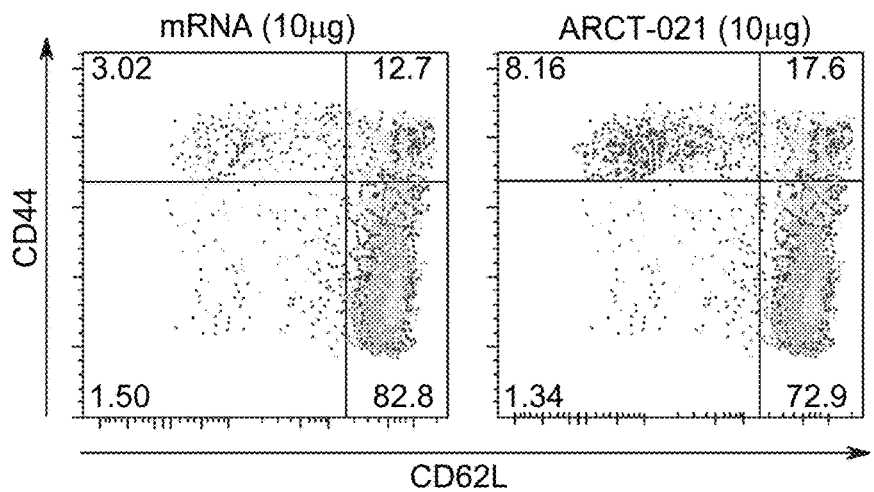
FIGS. 3A-3J show cellular immune responses following vaccination with SARS-CoV-2 STARR™ RNA and mRNA. C57BL/6 mice (n=5 per group) were immunized with 0.2 μg, 2 μg, or 10 μg of STARR™ RNA or mRNA via IM, sacrificed at day 7 post-vaccination and spleens analyzed for cellular T cell responses by flow-cytometry and ELISPOT. (3A-3B) CD8+ and C) CD4+ T effector cells were assessed in vaccinated animals using surface staining for T cell markers and flow-cytometry. (3D-3E) IFNγ+ CD8+ T cells and (3F) Ratio of IFNγ+/IL4+CD4+ T cells in spleens of immunized mice were assessed following ex vivo stimulation with PMA/ionomycin (IO) and intracellular staining. (3G-3I) SARS-CoV-2 S protein-specific responses to pooled S protein peptides were assessed using IFNγ ELISPOT assays following vaccination with mRNA (3H) or STARR™ RNA (3I). A schematic of S protein domains is shown in (3J).
Figure 3B:
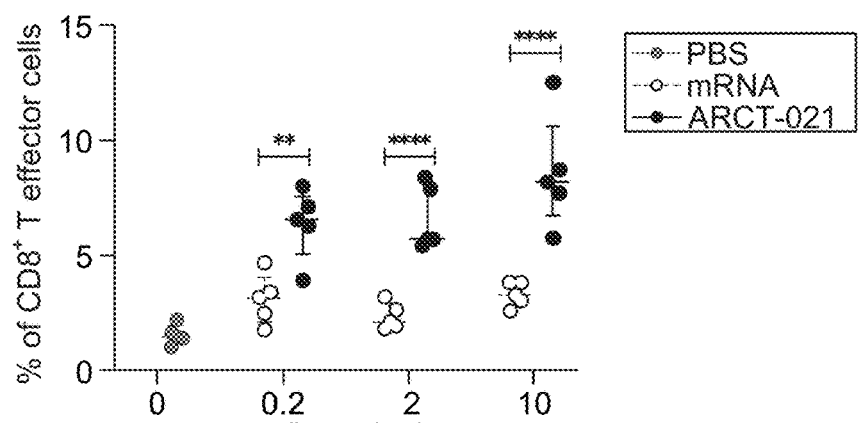
Figure 3C:
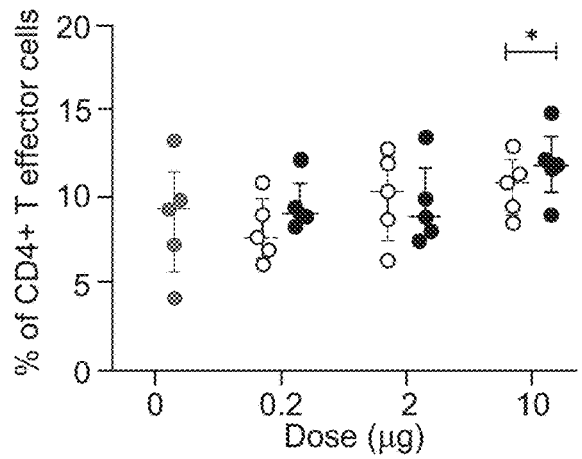
Figure 3D:
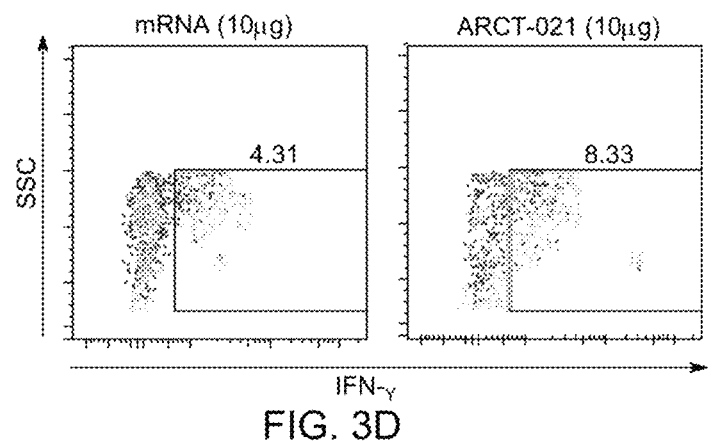
Figure 3E:
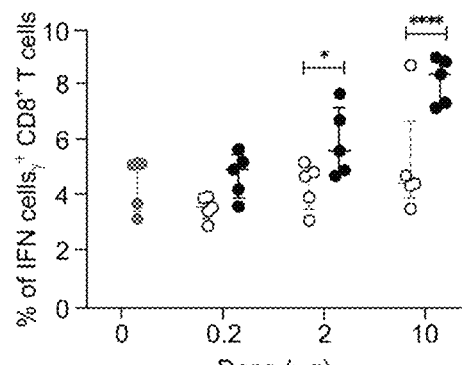
Figure 3F:
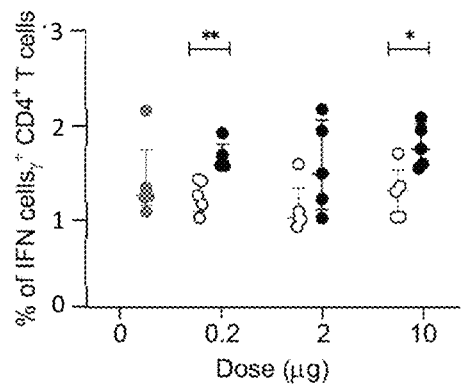

The cellular immune response following vaccination of C57BL/6 mice (n=5 per group) with mRNA or the STARR™ SARS-CoV-2 RNA construct encoding the SARS-CoV-2 glycoprotein described above (Example 1) was investigated next. At day 7 post-vaccination, spleens were harvested and assessed for CD8 and CD4 T cells by flow-cytometry. The CD8+ T cell CD44+CD62L− effector/memory subset was significantly expanded in STARR™ SARS-CoV-2 RNA vaccinated mice compared to those given either PBS or mRNA vaccine (FIG. 3A-B). There was no statistically significant difference in the proportion of CD4+ T effector cells of these animals (FIG. 3C). IFNγ+ CD8+ T cells (with 2 µg and 10 µg doses) and IFNγ+CD4+ T cells (in 0.2 µg and 10 µg) were proportionately higher, as found using intracellular staining (ICS) with flow cytometry, in STARR™ SARS-CoV-2 RNA as compared to mRNA vaccinated animals (FIG. 3D-3F).

Figure 3G:
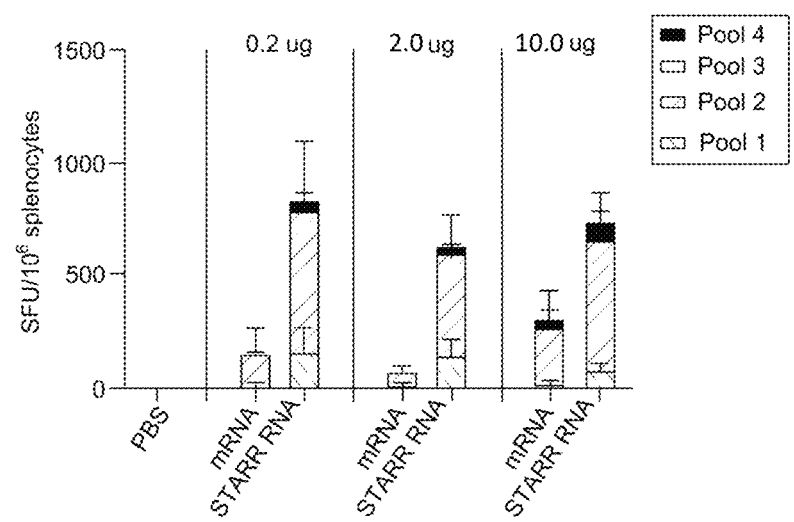
Figure 3H:
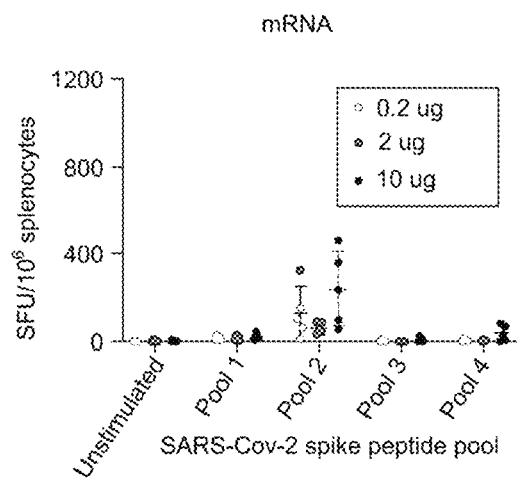
Figure 3I:
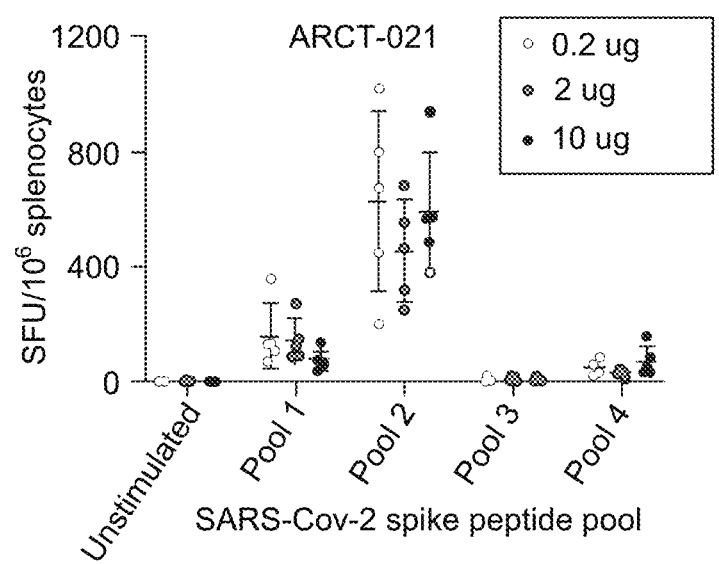
Figure 3J:
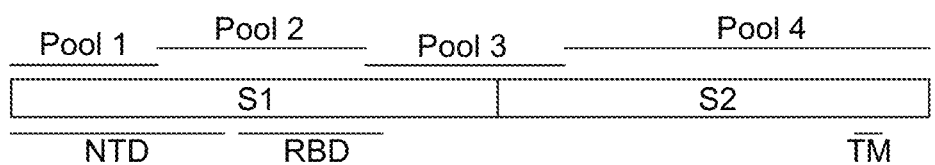

SARS-CoV-2 specific cellular responses were assessed in vaccinated animals by ELISPOT. A set of 15-mer peptides covering the SARS-CoV-2 S protein were divided into 4 pools and tested for IFNγ+ responses in splenocytes of vaccinated and non-vaccinated animals. SARS-CoV-2-specific cellular responses (displayed as IFNγ+ SFU/106 cells) were detected by ELISPOT in both STARR™ SARS-CoV-2 RNA and mRNA vaccine immunized animals compared to PBS control (FIG. 3G-3I). These responses were higher across the doses in STARR™ SARS-CoV-2 RNA compared to mRNA vaccinated groups (FIG. 3G-3I). Even the highest tested dose (10 µg) of mRNA vaccine produced IFNγ+ ELISPOT responses that were appreciably lower than those by the lowest dose (0.2 µg) of STARR™ SARS-CoV-2 RNA.

These results show that the STARR™ SARS-CoV-2 RNA construct induced strong T cell responses.

Example 4

This example illustrates humoral responses following vaccination with STARR™ SARS-CoV-2 RNA.

Figure 4A:
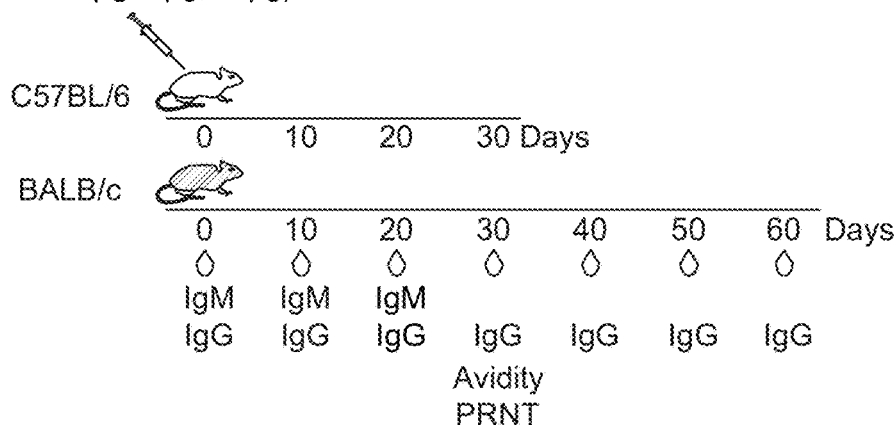
FIGS. 4A-4G show humoral responses in multiple mouse strains following immunization with mRNA and STARR™ vaccine candidates. (4A) BALB/c and C57BL/6J mice were immunized via IM with 0.2 μg, 2 μg, or 10 Hg of STARR™ RNA or mRNA (n=5/group). Blood sampling was conducted at baseline, and days 10, 19, 30, 40, 50 and 60 post-vaccination for BALB/c and days 10, 20 and 30 for C57BL/6J. (4B-4C) IgM and (4D-4E) IgG against the SARS-CoV-2 S protein over time, assessed using insect cell-derived whole S protein in a Luminex immuno-assay (measured as MFI). IgG endpoint titers to mammalian-derived whole S protein, S1, S2 and receptor binding domain (RBD) proteins at day 30 post-vaccination were assessed in (4F) BALB/c and (4G) C57BL/6J.
Figure 4B:
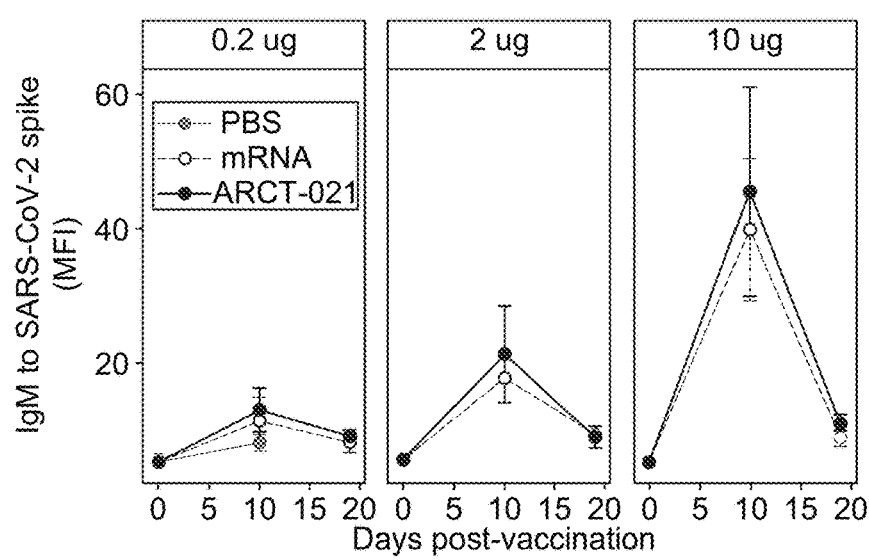
Figure 4C:
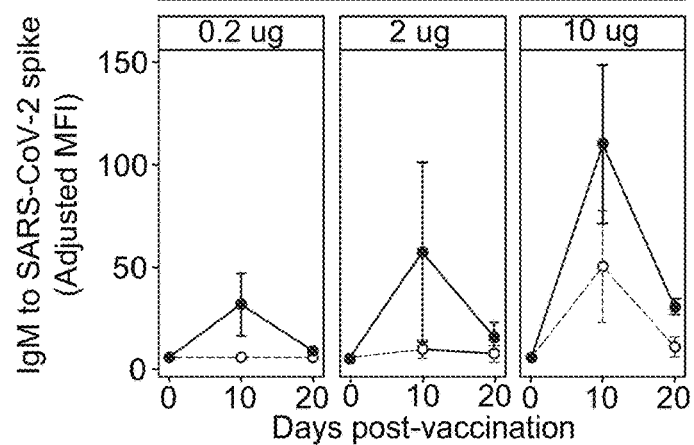
Figure 4D:
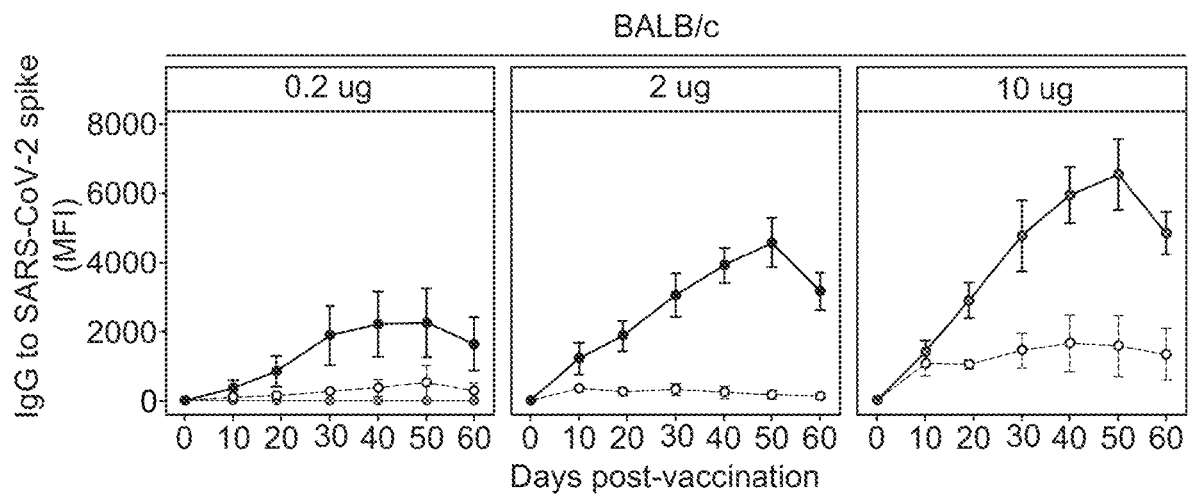
Figure 4E:
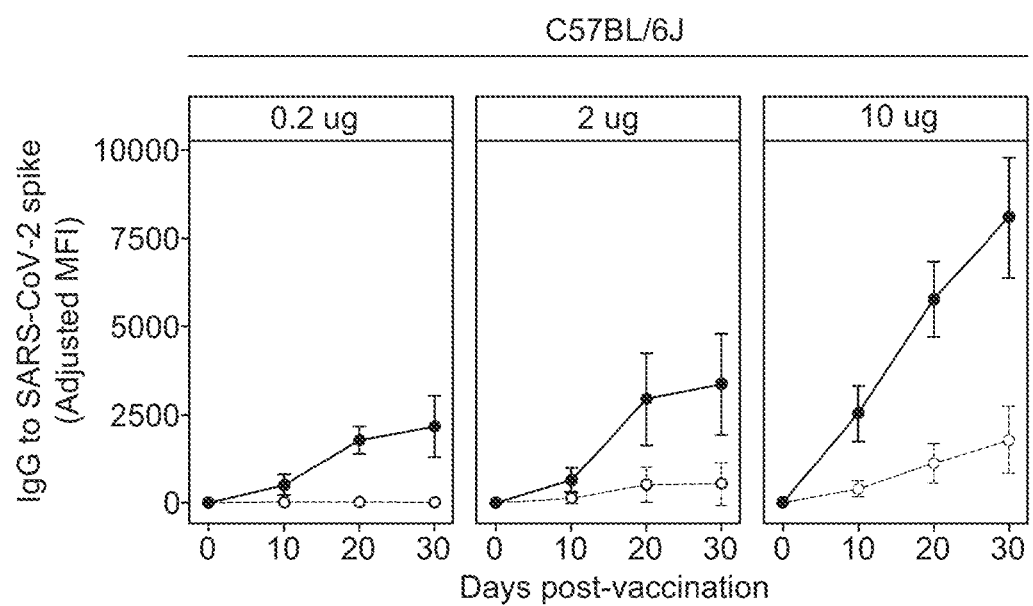

SARS-CoV-2-specific humoral responses following vaccination were characterized in two different mouse models, BALB/c and C57BL/6. Female mice (n=5 per group) were vaccinated at day 0 and bled every 10 days, up to day 60 for BALB/c and day 30 for C57BL/6 (FIG. 4A). SARS-CoV-2 S-specific IgM responses were tested at 1:2000 serum dilution using an in-house Luminex immuno-assay. All tested doses of mRNA vaccine and STARR™ SARS-CoV-2 RNA (corresponding to SEQ ID NO:125, as described in Example 1 above) produced detectable S-specific IgM responses in both mouse models (FIG. 4B-4C). When comparing mRNA to STARR™ SARS-CoV-2 RNA vaccinated BALC/c mice, no difference in IgM responses was observed; IgM levels in C57BL/6 mice were higher in STARR™ SARS-CoV-2 RNA vaccinated C57BL/6 mice at day 10 post vaccination. In contrast, SARS-CoV-2 S-specific IgG (at 1:2000 serum dilution) levels were higher from day 20 onwards in animals inoculated with STARR™ SARS-CoV-2 RNA compared to mRNA vaccine (FIG. 4D-4E). Remarkably, the IgG levels continued to show an increasing trend in STARR™ SARS-CoV-2 RNA vaccinated mice, both BALB/c and C57BL/6, until day 50 post-vaccination with a single inoculation across all the doses. This trend contrasted with mice that received the mRNA vaccine where in BALB/c mice antibody levels plateaued after day 10 post-vaccination; increasing S-specific IgG levels were observed in mRNA-vaccinated C57BL/6 mice but these were lower than those seen in mice that received STARR™ SARS-CoV-2 RNA.

Figure 4F:
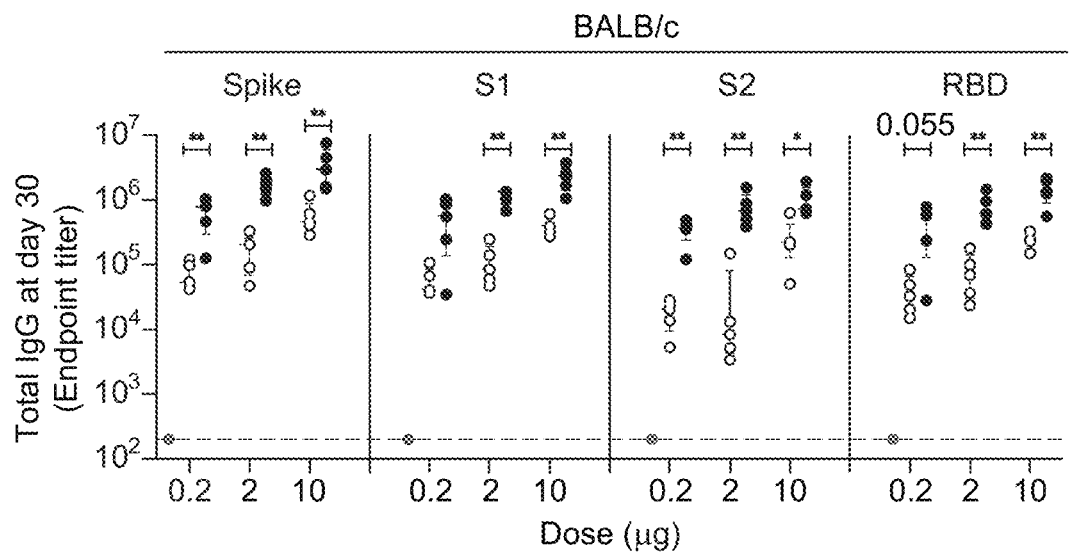
Figure 4G:
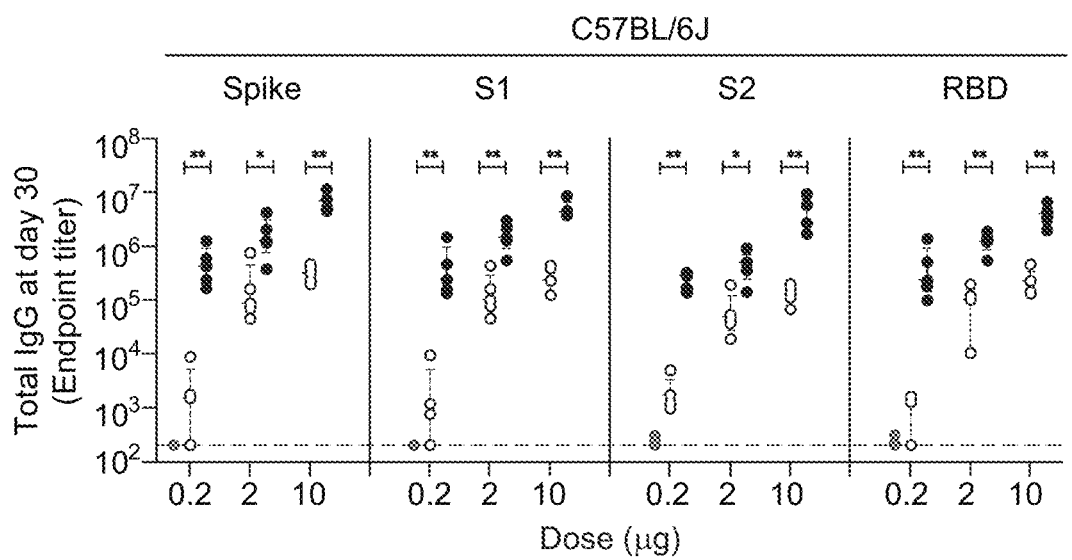

Further characterization of the SARS-CoV-2 specific IgG response in vaccinated animals was conducted at day 30 post-immunization to assess which regions of the S protein are targeted. IgG endpoint titers were estimated to full ectodomain S protein, S1, S2 and receptor binding domain (RBD) regions. For both vaccine candidates the majority of SARS-CoV-2 specific IgG recognized S1, although high IgG endpoint titers were also detected to S2 protein (FIG. 4F-4G). However, STARR™ SARS-CoV-2 RNA elicited IgG endpoint titers were significantly higher compared to those produced by mRNA vaccination (FIG. 4F-4G). Notably, IgG that bind the receptor binding domain (RBD) of S protein, which is an immunodominant site of neutralizing antibodies, were also higher in STARR™ SARS-CoV-2 RNA compared to mRNA vaccinated animals. Furthermore, at lower doses, mRNA vaccine but not STARR™ SARS-CoV-2 RNA struggled to elicit high SARS-CoV-2 specific IgG titers in the more Th1 dominant C57BL/6 mouse strain (FIG. 4G). Taken collectively, a single dose of STARR™ SARS-CoV-2 RNA induced significant differences in immune gene expression and superior cellular immune responses in draining lymph nodes compared to mRNA vaccine and consequently humoral immune responses.

These data show that STARR™ SARS-CoV-2 RNA vaccination induced elevated humoral responses as compared to mRNA vaccination.

Example 5

This example illustrates reduced risk of immune enhancement upon STARR™ SARS-CoV-2 RNA vaccination.

Figure 5A:
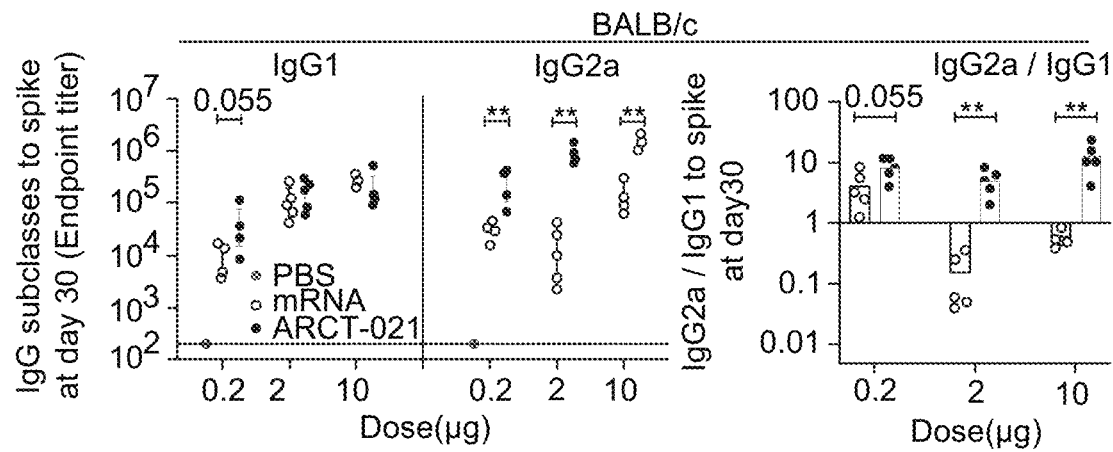
FIGS. 5A-5D show that STARR™ SARS-CoV-2 RNA elicits Th1 skewed immune responses. SARS-CoV-2 spike-specific IgG subclasses and the ratio of IgG2a/c/IgG1 at 30 days post-vaccination with STARR™ RNA and mRNA in (5A) BALB/c and (5B) C57BL/6J mice. Th2 cytokine and Th1/Th2 skew in CD4 T cells at day 7 post-vaccination in C57BL/6J mice measured by ICS as (5C) percentage of IL4+CD4 T cells and (5D) ratio of IFNγ+/IL4+ CD4+ T cells.
Figure 5B:
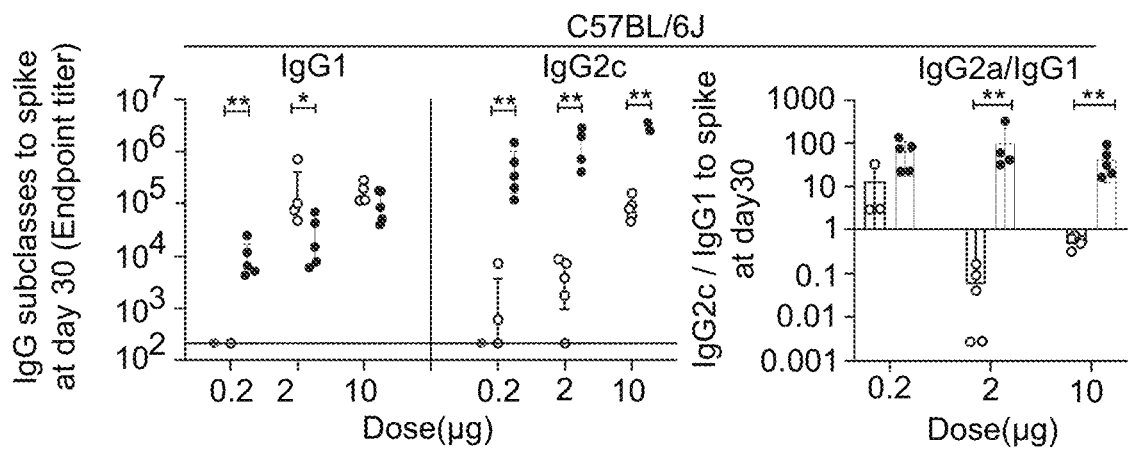

A safety consideration for coronavirus vaccine is a risk of vaccine-mediate immune enhancement of respiratory disease. Indeed, SARS-CoV and MERS-CoV vaccine development have highlighted the importance of Th1 skewed responses to avoid vaccine-induced immune enhancement. Therefore, the Th1/Th2 balance elicited by both mRNA and STARR™ SARS-CoV-2 RNA (self-replicating RNA construct as described in Example 1 above) vaccination was investigated. The IgG subclass fate of plasma cells is influenced by T helper (Th) cells. At day 30 post-vaccination, both mRNA and STARR™ SARS-CoV-2 RNA, except the 0.2 µg dose in C56BL/6J mice, induced comparable amounts of SARS-CoV-2 S-specific IgG1, a Th2-associated IgG subclass in mice (FIG. 5A-5B). In contrast, the Th1-associated IgG subclasses—IgG2a in BALB/c and IgG2c in C56BL/6J—were significantly greater in STARR™ SARS-CoV-2 RNA vaccinated animals. The ratios of S protein-specific IgG2a/IgG1 (BALBc) and IgG2c/IgG1 (C57BL/6) were greater than 1 in STARR™ SARS-CoV-2 RNA vaccinated animals (FIG. 5A-5B). Except for the 0.2 ug dose, these ratios were all significantly greater with STARR™ SARS-CoV-2 RNA compared to mRNA vaccinated animals.

Figures 5C, 5D:
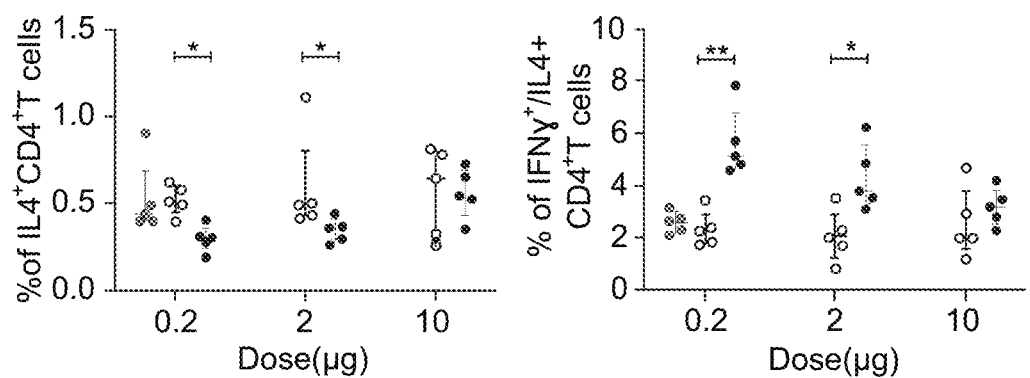

ICS was used to investigate the production of IFNγ (Th1 cytokine) and IL4 (Th2 cytokine) by CD4+ T cells in spleens of day 7 vaccinated C56BL/6J mice. As shown above (Example 3), compared to mRNA vaccination, IFNγ levels were significantly greater in STARR™ SARS-CoV-2 RNA vaccinated animals (FIG. 3F). IL4 expression in CD4 T cells was slightly higher in mRNA as compared to STARR™ SARS-CoV-2 RNA at 0.2 μg and 2 μg doses (FIG. 5C). In comparing the IFNγ and IL4 levels in individual mice, the ratios of IFNγ/IL4 in CD4+ T cells for both STARR™ SARS-CoV-2 RNA and mRNA vaccinated mice were above 1 (FIG. 5D). The ratio of IFNγ/IL4 in CD4+ T cells in mice given the 0.2 μg and 2 μg doses were significantly greater with STARR™ SARS-CoV-2 RNA than mRNA vaccination (FIG. 5F). However, without being limited by theory, the elevated ratios in these doses appeared to be due to the lowered IL4 expression at levels below background (i.e., PBS control mice), rather than reduced IFNγ and hence Th1 activity.

Taken collectively, these data show that STARR™ SARS-CoV-2 RNA produced Th1 instead of Th2 skewed adaptive immune responses.

Example 6

This example illustrates the quality of STARR™ SARS-CoV-2 RNA-induced humoral immune responses.

Figure 6A:
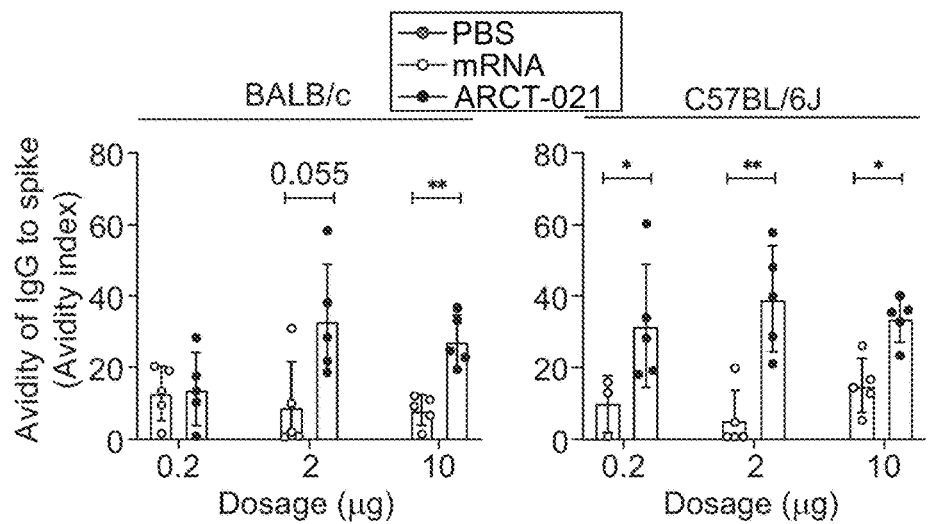
FIGS. 6A-6E show that STARR™ SARS-CoV-2 RNA elicits a higher quality humoral response than mRNA platform. (6A) Avidity of SARS-CoV-2 S protein-specific IgG at day 30 post-immunization was measured using 8M urea washes. (6B) Neutralizing antibody (PRNT50 titers) at day 30 post-vaccination against a clinically isolated live SARS-CoV-2 virus measured in both BALB/c and C57BL/6J. Dashed lines depict the serum dilution range (i.e. from 1:20 to 1:320) tested by PRNT. (6C) PRNT50 and (6D) PRNT70 of SARS-CoV-2 neutralization at day 60 post-vaccination and convalescent sera from COVID-19 patients. (6E) Correlation analysis of Spike-specific IgG endpoint titers against SARS-CoV-2 neutralization (PRNT50). PRNT—plaque reduction neutralization test.

The binding strength (avidity) and the neutralizing ability of the antibody response elicited by the self-replicating STARR™ SARS-CoV-2 RNA (construct as described in Example 1 above) and mRNA vaccine constructs was assessed next. Serum IgG avidity was measured at day 30 post-vaccination using a modified Luminex immuno-assay with 8M urea washes. STARR™ SARS-CoV-2 RNA elicited higher avidity S protein-specific IgG than mRNA in both mouse models at all tested doses (FIG. 6A). These differences were observed, with the exception of 0.2 μg in BALB/c, across all doses (FIG. 6A), indicating that STARR™ SARS-CoV-2 RNA elicited better quality antibodies than conventional mRNA.

Figure 6B:
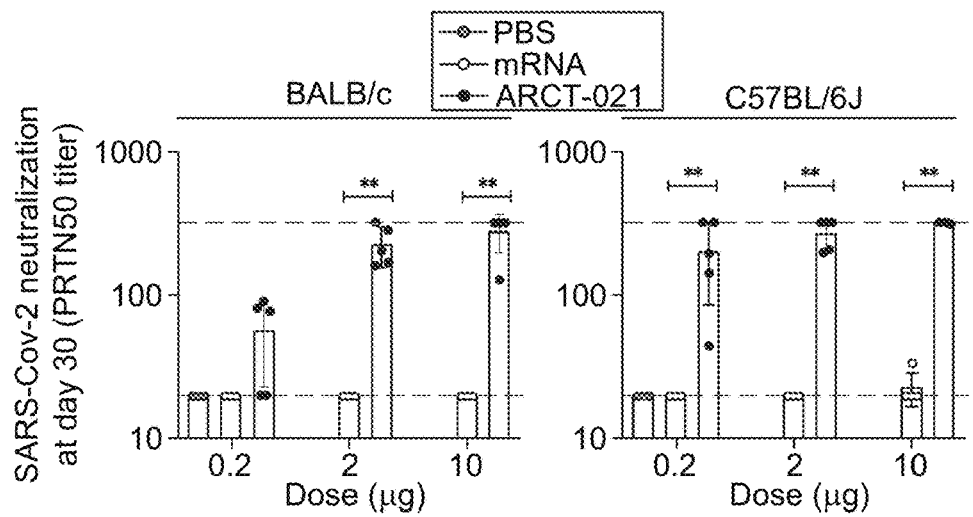
Figure 6C:
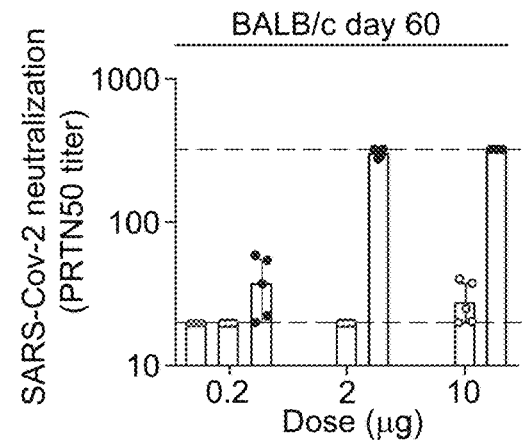
Figure 6D:
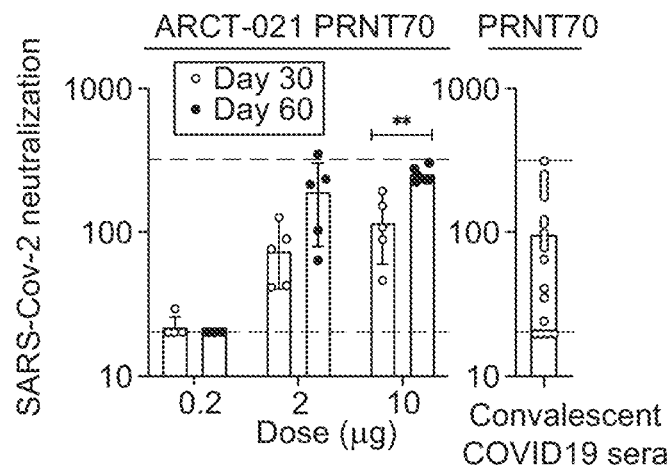

Neutralization of live SARS-CoV-2 by serum from vaccinated animals was assessed using the plaque reduction neutralization test (PRNT). At day 30 STARR™ SARS-CoV-2 RNA vaccinated BALB/c showed a clear dose dependent elevation in PRNT50 titers; 4 out of 5 (80%) of mice in the 10 μg STARR™ SARS-CoV-2 RNA group showed PRNT50 titers above the 320 upper limit (FIG. 6B). Similar dose-dependent trends in PRNT50 titers were also found in C57B/6 mice, although in these animals, the PRNT50 titers of several animals exceeded the 320 upper limit even with a low 0.2 μg dose vaccination (FIG. 6B). In contrast, PRNT50 titers in animals inoculated with mRNA vaccine construct were, except for one C57BL/6J mouse that received 10 μg dose, all <20 (FIG. 6B). Unexpectedly and surprisingly, PRNT50 and PRNT70 titers of STARR™ SARS-CoV-2 RNA vaccinated BALBc mice continued to rise between day 30 and day 60 after a single dose of vaccination (FIG. 6C-6D). These titers were also comparable to PRNT70 titers in sera from convalescent COVID-19 patients (FIG. 6D).

Figure 6E:
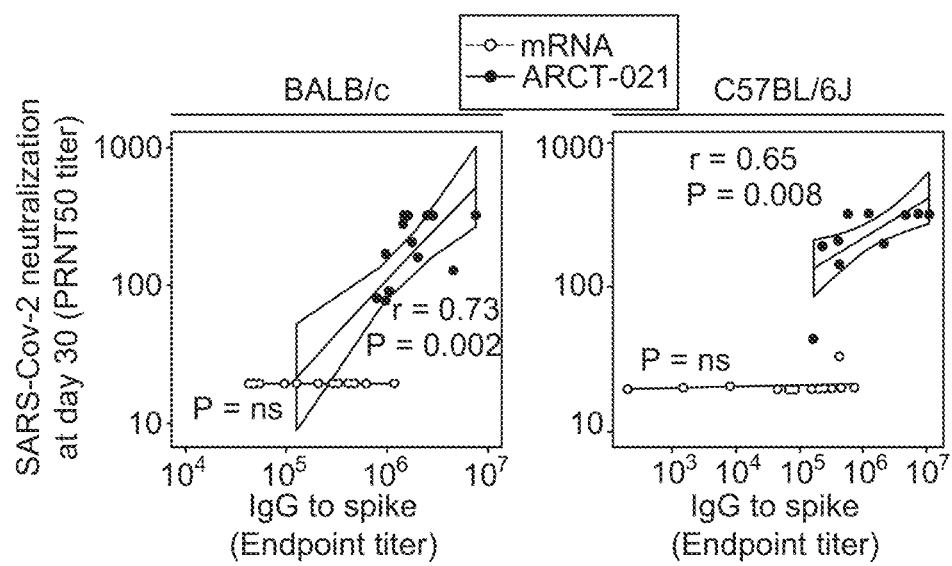
Figure 9A:
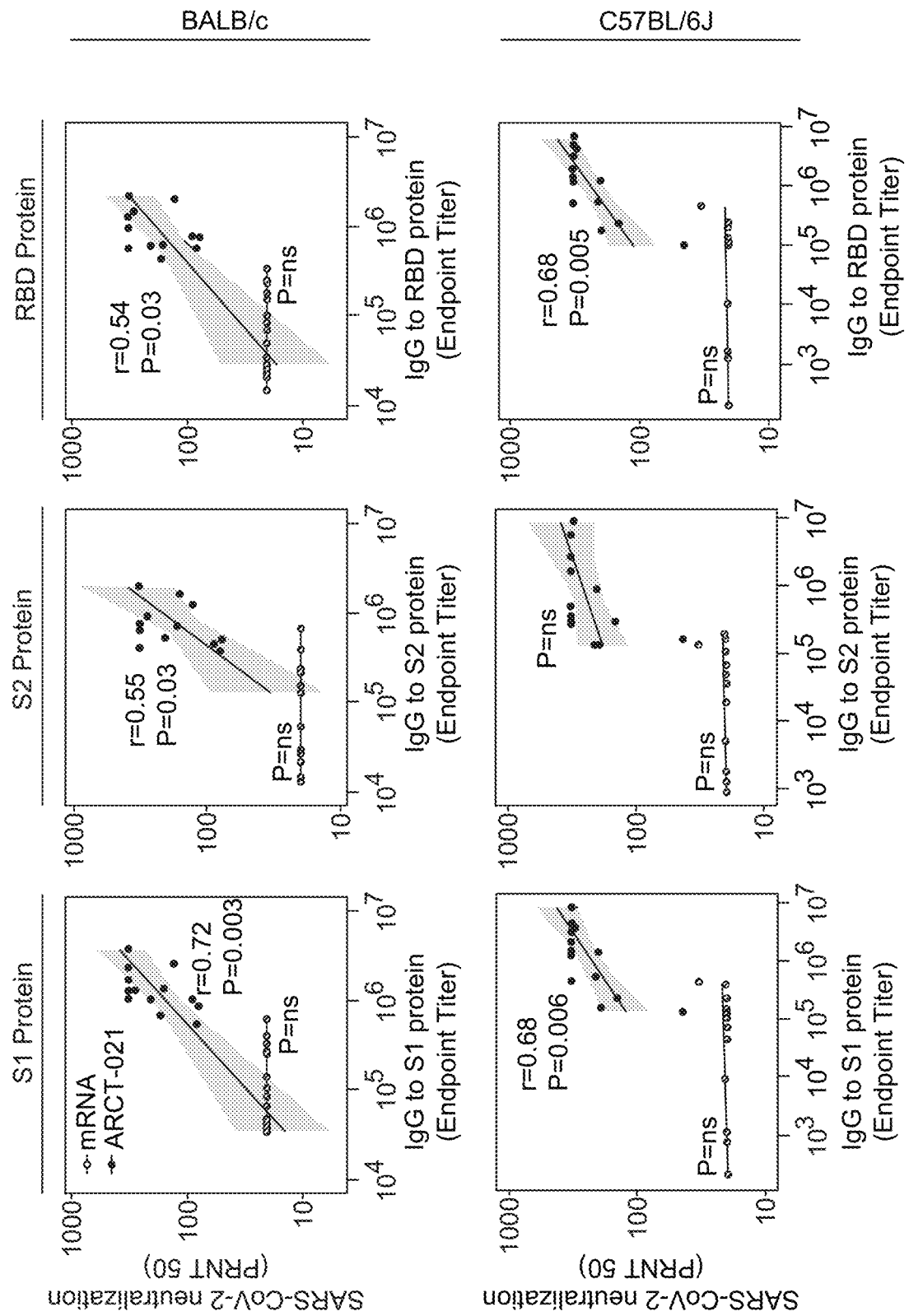
FIGS. 9A-9B show correlation analysis of live SARS-CoV-2 neutralization against binding IgG and IgG subclasses in BALB/c and C57BL/6J mouse strains. (9A) Spearman correlation analysis of SARS-CoV-2 neutralization (PRNT50) against total IgG specific to several SARS-CoV-2 antigens, including S, S1, and RBD recombinant proteins. (9B) Spearman correlation analysis of SARS-CoV-2 neutralization (PRNT50) against SARS-CoV-2 S-specific IgG subclasses (IgG1 and IgG2a or IgG2c).
Figure 9B:
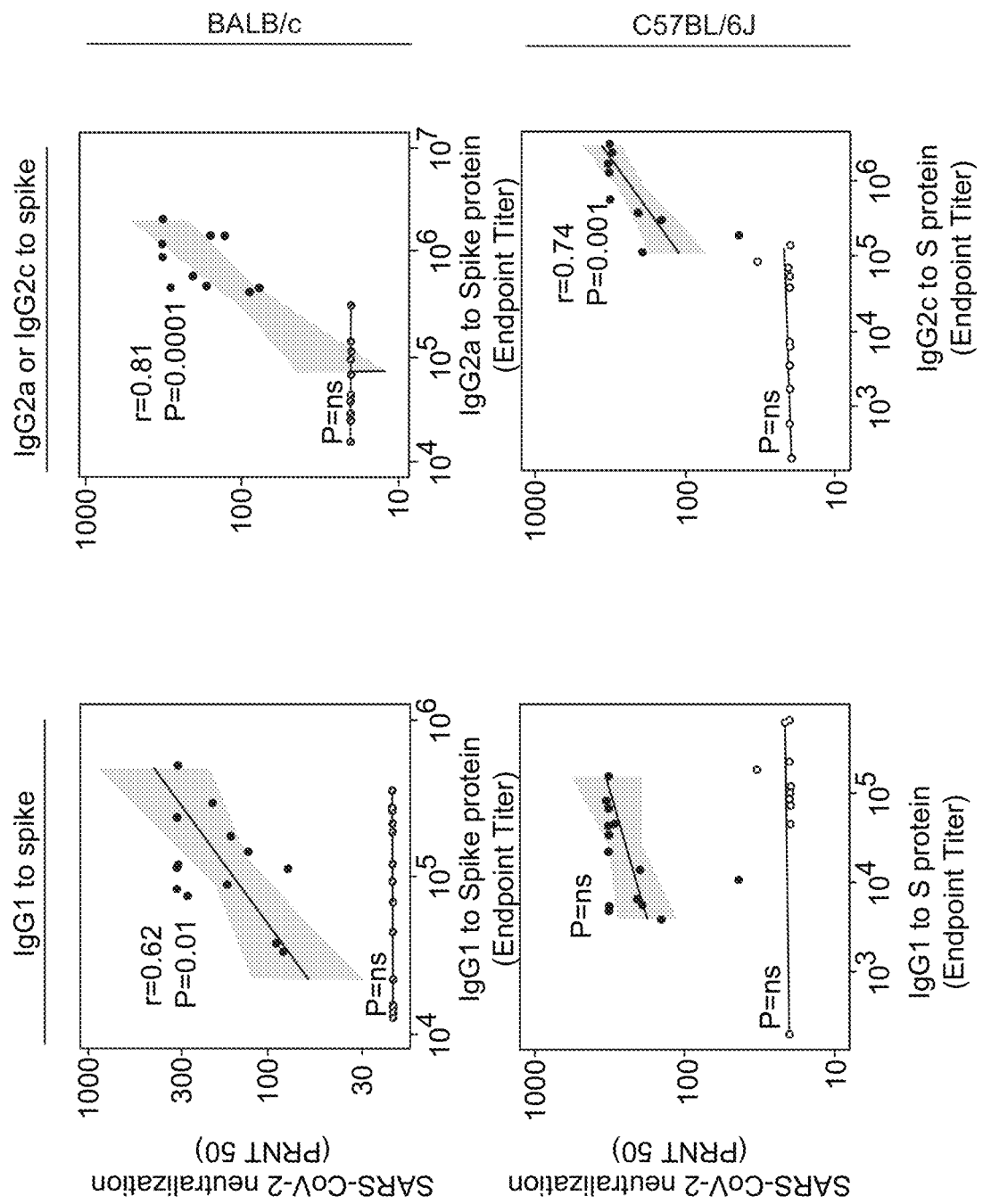

S protein IgG titers also positively correlated with PRNT50 titers in both mouse models (FIG. 6E). Similar positive correlations were also observed with IgG against S1 and RBD (FIG. 9). By contrast, no correlation was found between IgG and PRNT50 titers in mRNA vaccinated mice (FIG. 6E). Taken collectively, without being limited by theory, these antibody response analyses indicate that the higher PRNT50 titers following STARR™ SARS-CoV-2 RNA vaccination are not only attributable to the amount of IgG produced but also due to superiority of the quality of the anti-SARS-CoV-2 antibodies.

In summary, STARR™ SARS-CoV-2 RNA induced qualitatively superior humoral immune response than conventional mRNA.

Example 7

This example illustrates the effect of a second dose of STARR™ SARS-CoV-2 RNA.

Figure 7A:
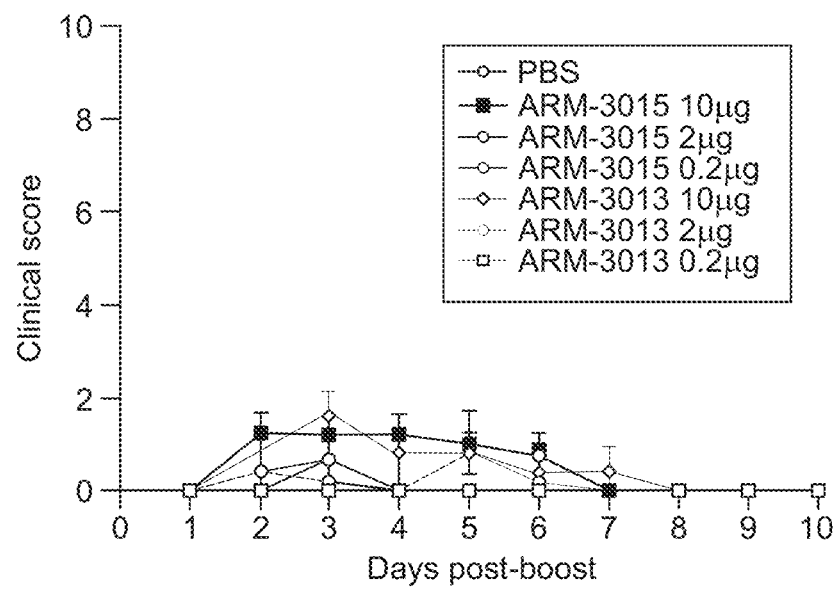
FIGS. 7A-7E show clinical scores, body weight and immune responses to STARR™ SARS-CoV-2 RNA and mRNA following boost at day 30 post-prime in C57BL/6J. (7A) Clinical scores and (7B) percentage of initial body weight following boost vaccinations. (7C) Anti-Spike IgG responses following boost by mRNA and STARR™ SARS-CoV-2 RNA. Grey dashed line marks the experimental assay saturation point. IFN γ+ CD8+ T effector cells responses (fold change over PBS) in animals either primed or prime & boosted with either (7D) mRNA or (7E) STARR™ SARS-CoV-2 RNA vaccine candidates.
Figure 7B:
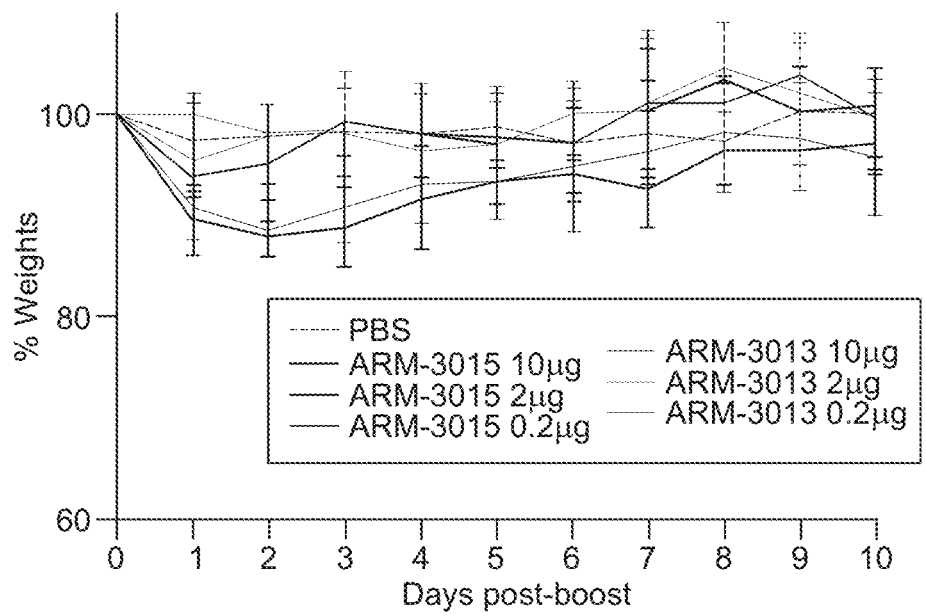
Figure 7C:
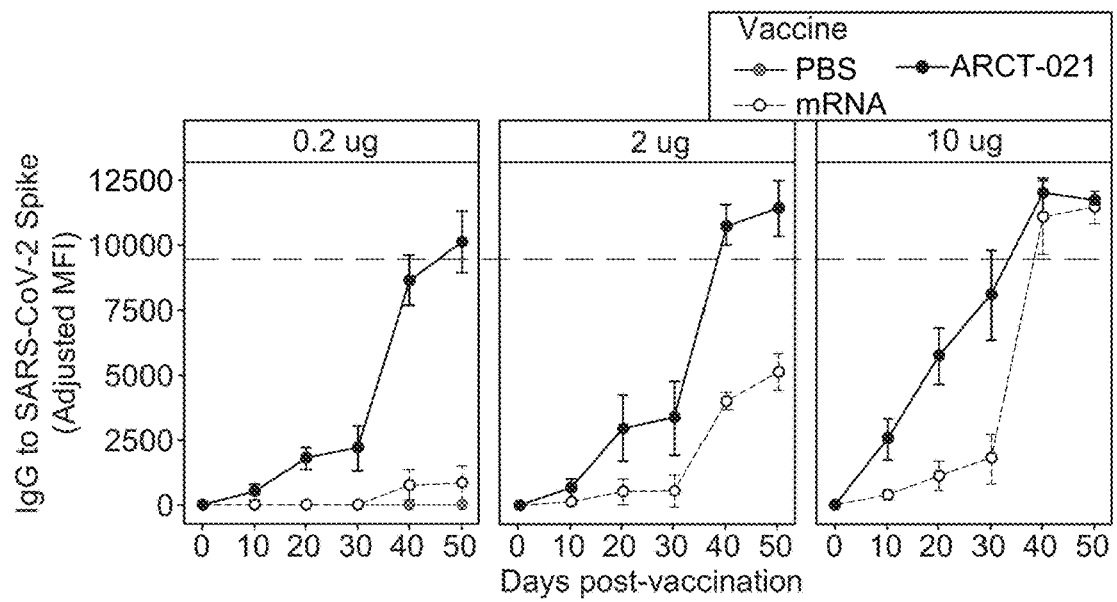

A possible added benefit of a second dose of STARR™ SARS-CoV-2 RNA (self-replicating RNA construct as described in Example 1 above) to the cellular and humoral immune responses to the S protein of SARS-CoV-2 was explored next. The clinical scores after the second dose were higher than after the first dose (FIG. 7A). Like the first dose, mice that received 2 μg and 10 μg of STARR™ SARS-CoV-2 RNA experienced weight loss (FIG. 7B). The IgG response to a second dose of STARR™ SARS-CoV-2 RNA produced an appreciable boost in S protein-specific IgG levels, but only with 0.2 μg and 2 μg of STARR™ SARS-CoV-2 RNA (FIG. 7C). Without being limited by theory, a likely reason for the lack of increase in the anti-S protein specific IgG levels for the 10 μg dose is that the amount of fluorescence is near the saturation point of the detector and sera was not further diluted to observe and increase. However, in a subsequent Balb/c mouse study, the sera from mice vaccinated with a 5 μg RNA dose administered unilaterally in a 0.05 mL injection volume produced a significant increase in neutralizing antibody titers as assayed using a 96 well microneutralization assay format. Mice were bled every 14 days and a second vaccination of 5 μg was administered on day 28. 4 mice were injected with a VEEV replicon RNA expressing luciferase as a negative control and 6 mice were vaccinated with STARR™ SARS-CoV-2 RNA. The results are shown in Table 8 below.

TABLE 7

Microneutralization Titers (MN50) in Balb/c Mice

| Mouse No. | Treatment | Microneutralization Titers (MN50) | | | | |
|---|---|---|---|---|---|---|
| | | Wk 0 | Wk2 | Wk4 | Wk6 | Wk8 |
| 1 | Luciferase | <10 | <10 | <10 | <10 | <10 |
| 2 | Luciferase | <10 | <10 | <10 | <10 | <10 |
| 3 | Luciferase | <10 | <10 | <10 | <10 | <10 |
| 4 | Luciferase | <10 | <10 | <10 | <10 | <10 |
| 5 | STARR ™ SARS-CoV-2 RNA | <10 | 1,280 | 5,120 | 327,680 | 81,920 |
| 6 | STARR ™ SARS-CoV-2 RNA | <10 | 640 | 20,480 | 327,680 | 327,680 |
| 7 | STARR ™ SARS-CoV-2 RNA | <10 | 1,280 | 2,560 | 163,840 | 163,840 |
| 8 | STARR ™ SARS-CoV-2 RNA | <10 | 1,280 | 10,240 | 327,680 | 163,840 |
| 9 | STARR ™ SARS-COV-2 RNA | <10 | 640 | 40,960 | 327,680 | 327,680 |

TABLE 7-continued

Microneutralization Titers (MN50) in Balb/c Mice

| Mouse No. | Treatment | Microneutralization Titers (MN50) | | | | |
|---|---|---|---|---|---|---|
| | | Wk 0 | Wk2 | Wk4 | Wk6 | Wk8 |
| 10 | STARR™ SARS-CoV-2 RNA | <10 | 1,280 | 10,240 | 327,680 | 327,680 |
| Avg Geometric Mean | | | 1,016 | 10,240 | 29,1930 | 206,426 |

The neutralization titers increased ~10 fold between day 14 and day 28 post vaccination. Following the boost on day 28, the neutralization titers increased an additional 20 fold 14 days post boost.

Figure 7D:
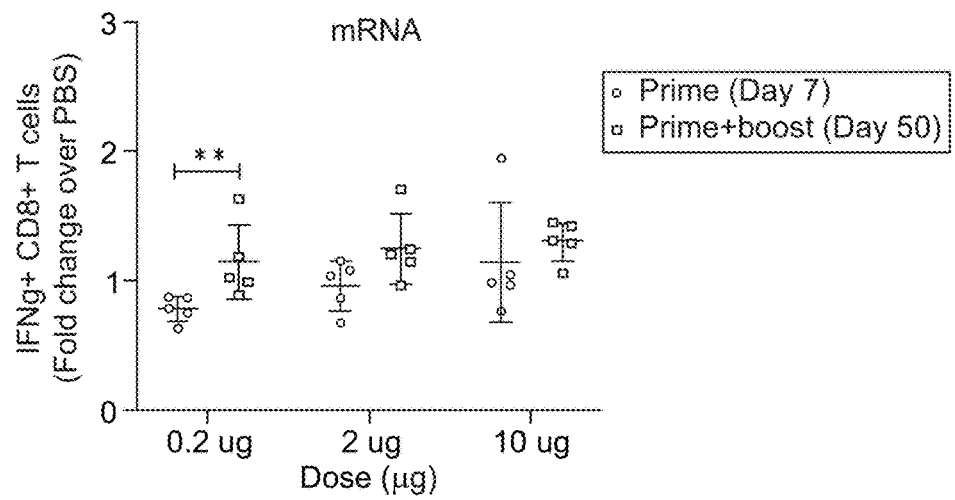
Figure 7E:
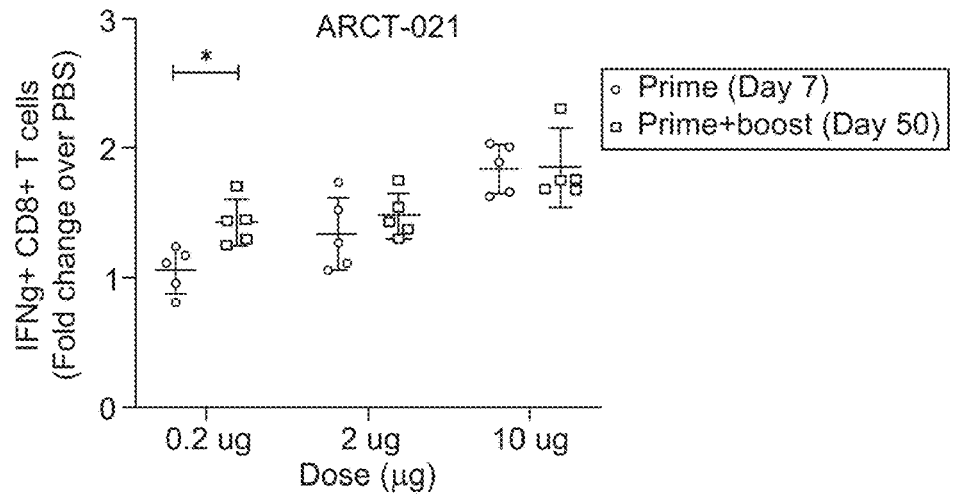

To determine if there was added benefit in IFNγ+CD8+ T cell counts from a second dose vaccination, CD8 T cell IFNγ responses in mice given only a prime were compared to responses of mice given a prime and a boost. Fold change in IFNγ+CD8+ T cells in the vaccinated over PBS control mice was calculated for mice given either a prime only or given a prime and boost. The fold change of IFNγ+CD8+ T cells was similar following the prime and prime+boost for 2 μg and 10 μg doses of STARR™ SARS-CoV-2 RNA (FIG. 7D-7E); the 0.2 μg dose showed higher fold change of IFNγ+CD8+ T cells between prime (at day 7) and prime+boost (day 50). Vaccination with 0.2 μg of mRNA also showed increased IFNγ+CD8+ T cells relative to PBS control after two doses of vaccination. Without being limited by theory, these findings suggest that a second 10 μg dose of STARR™ SARS-CoV-2 RNA did not produce superior cellular immunity compared to single dose vaccination. Thus, there was no apparent benefit from a second 10 μg dose of STARR™ SARS-CoV-2 RNA.

Taken collectively, these data suggest that 10 μg STARR™ SARS-CoV-2 RNA offers the opportunity of a single dose vaccination to protect against COVID-19.

Example 8

This example illustrates protection from SARS-CoV-2 viral challenge in mice following vaccination with STARR™ SARS-CoV-2 self-replicating RNA.

A mouse viral challenge study was conducted with human ACE2 transgenic mice. Mice were immunized with 2 μg and 10 μg RNA doses of STARR™ SARS-CoV-2 RNA (RNA construct as described in Example 1 above) or injected with PBS. There were three different cohorts with 5 mice in each treatment group. Cohorts 1 and 3 received a lethal SARS-CoV-2 virus challenge load of 5×105 TCID50. Cohort 1 was monitored for survival and Cohort 3 was euthanized 5 days after challenge. Lungs were assayed for viral load and processed for histopathology. Cohorts 2 received a sublethal viral load of 5×104 TCID50. Cohort 2 was euthanized 5 days after virus challenge and lungs were assayed for infectious virus and processed for histopathology. All mice were inoculated intratracheally 30 days post-vaccination with a single dose of STARR™ SARS-CoV-2 RNA.

Figure 10:
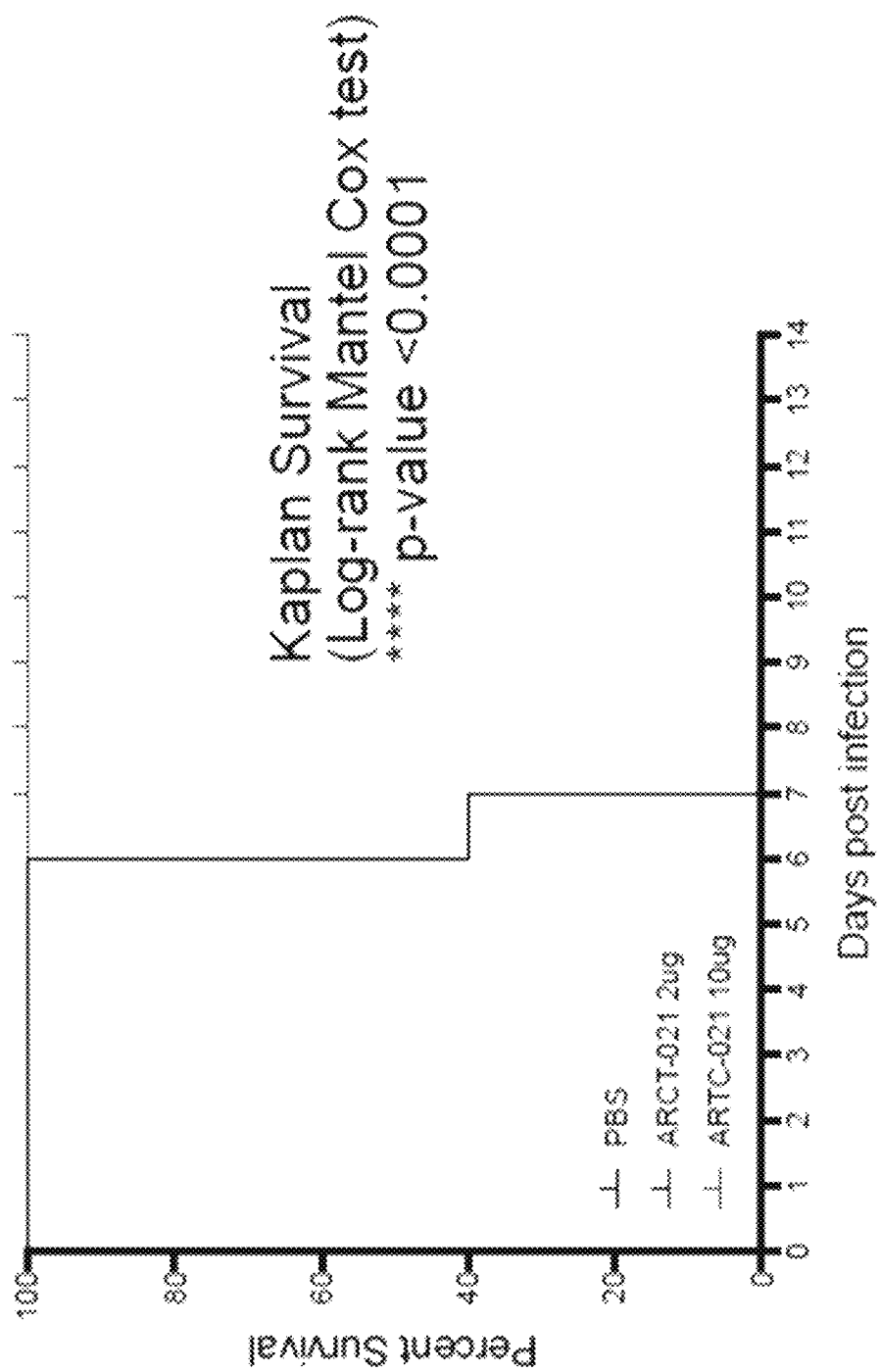
FIG. 10 shows Kaplan-Meier survival curves for unvaccinated mice (PBS) and mice vaccinated with STARR™ SARS-CoV-2 RNA following challenge with a lethal dose of SARS-CoV-2 virus. Upper line—STARR™ SARS-CoV-2 RNA (2 µg, 0 µg); dropping line—PBS.
Figure 11:
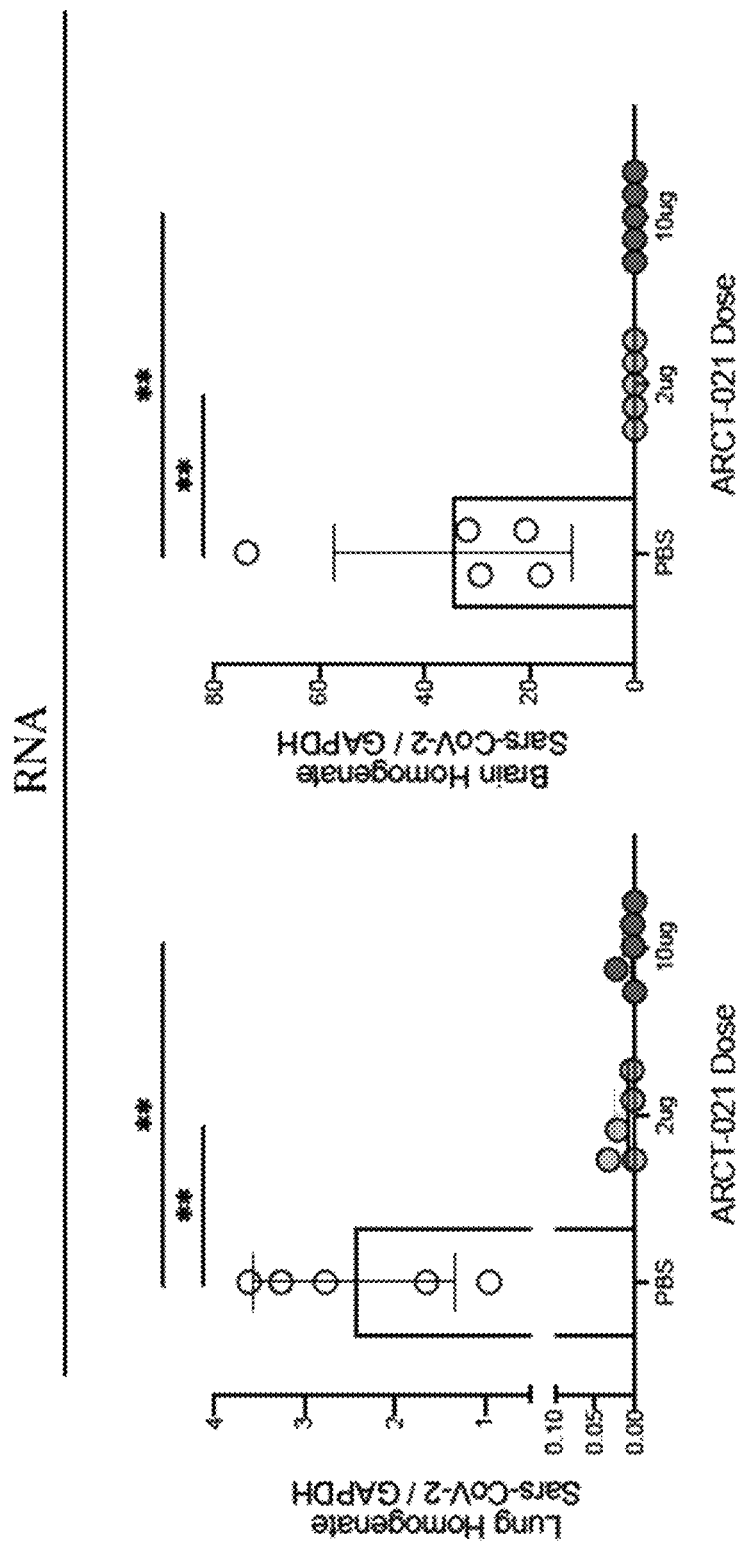
FIG. 11 shows that STARR™ SARS-CoV-2 RNA vaccination protects against lung and brain SARS-CoV-2 infection. Viral RNA levels in lungs (FIG. 11, left) and in brains (FIG. 11, right) of unvaccinated mice (PBS) and mice vaccinated with the indicated dose of STARR™ SARS-CoV-2 RNA are shown.
Figure 12:
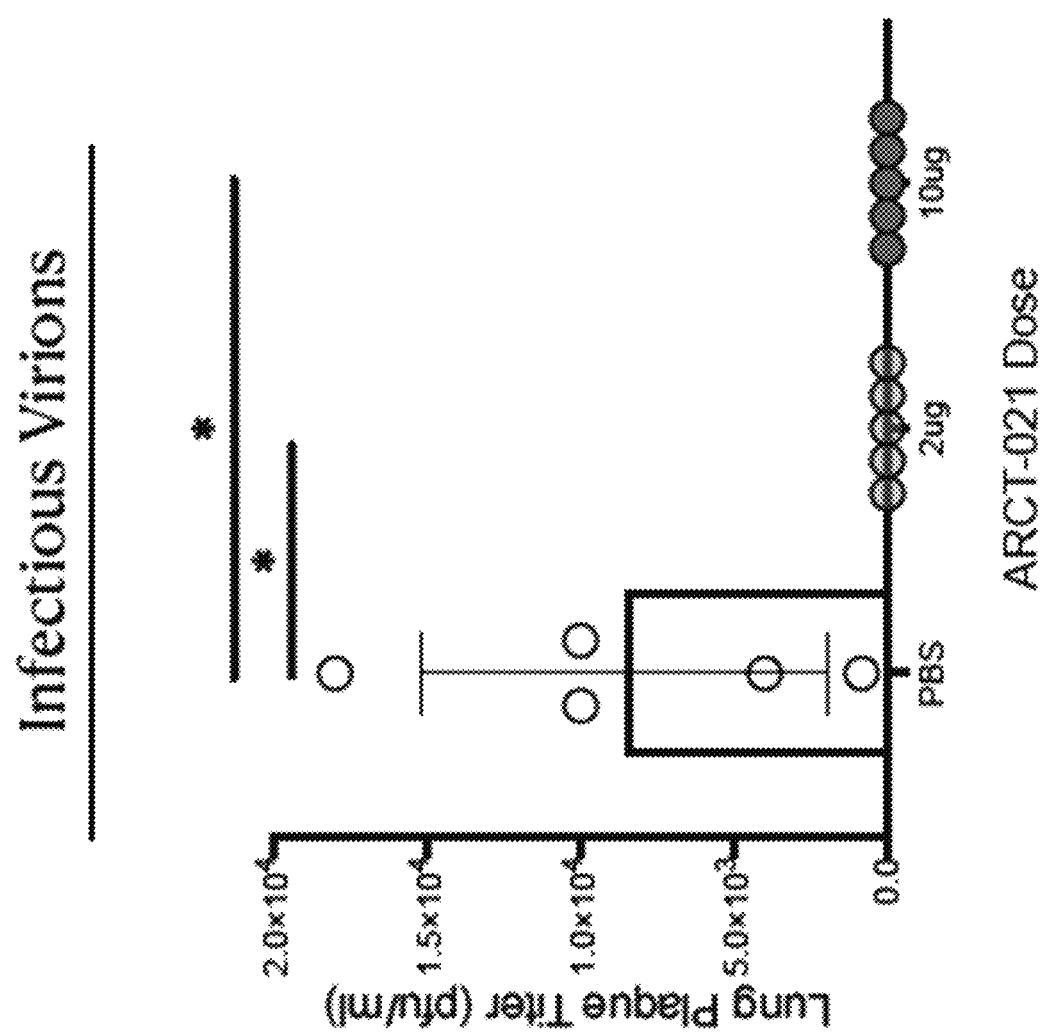
FIG. 12 shows viral titers in lungs of unvaccinated mice (PBS) and mice vaccinated with the indicated dose of STARR™ SARS-CoV-2 RNA following challenge with SARS-CoV-2.

All mice injected with PBS in cohort 1 were dead by day 7, whereas all vaccinated mice showed no signs of infection 15 days after viral challenge (FIG. 10). For Cohort 2 receiving a sublethal viral load, 10 to 3,300 copies of virus was measured by RT-PCR in the lungs with an average of 1,200 copies, whereas no copies of viral RNA were measured in mice vaccinated with ARTC-021 at 2 μg and 10 μg RNA doses (LOD was 0.1 copies; FIG. 11, left). Copies of viral RNA were also observed in the brain ranging from 20 to 80 in the PBS treatment group, whereas no viral RNA copies were measured in the brains of mice vaccinated with either 2.0 μg or 10.0 μg RNA doses (FIG. 11, right). Lastly, lungs were carefully processed and assayed for lung plaque titers. The average plaque titers for the group injected with PBS was 8×103/mL of lung homogenate, whereas no plaques were detected for mice vaccinated with either 2.0 μg or 10.0 μg or STARR™ SARS-CoV-2 RNA (FIG. 12). Lung and brain tissues from Cohort 3 are being assayed for viral copy number and infectious virus. Histopathology of lungs for cohorts 2 and 3 is in progress.

These results show that vaccination with STARR™ SARS-CoV-2 self-replicating RNA protected mice from a lethal SARS-CoV-2 infection and protected against lung and brain infection upon challenge with a sublethal dose of SARS-CoV-2.

Example 9

Figure 13:
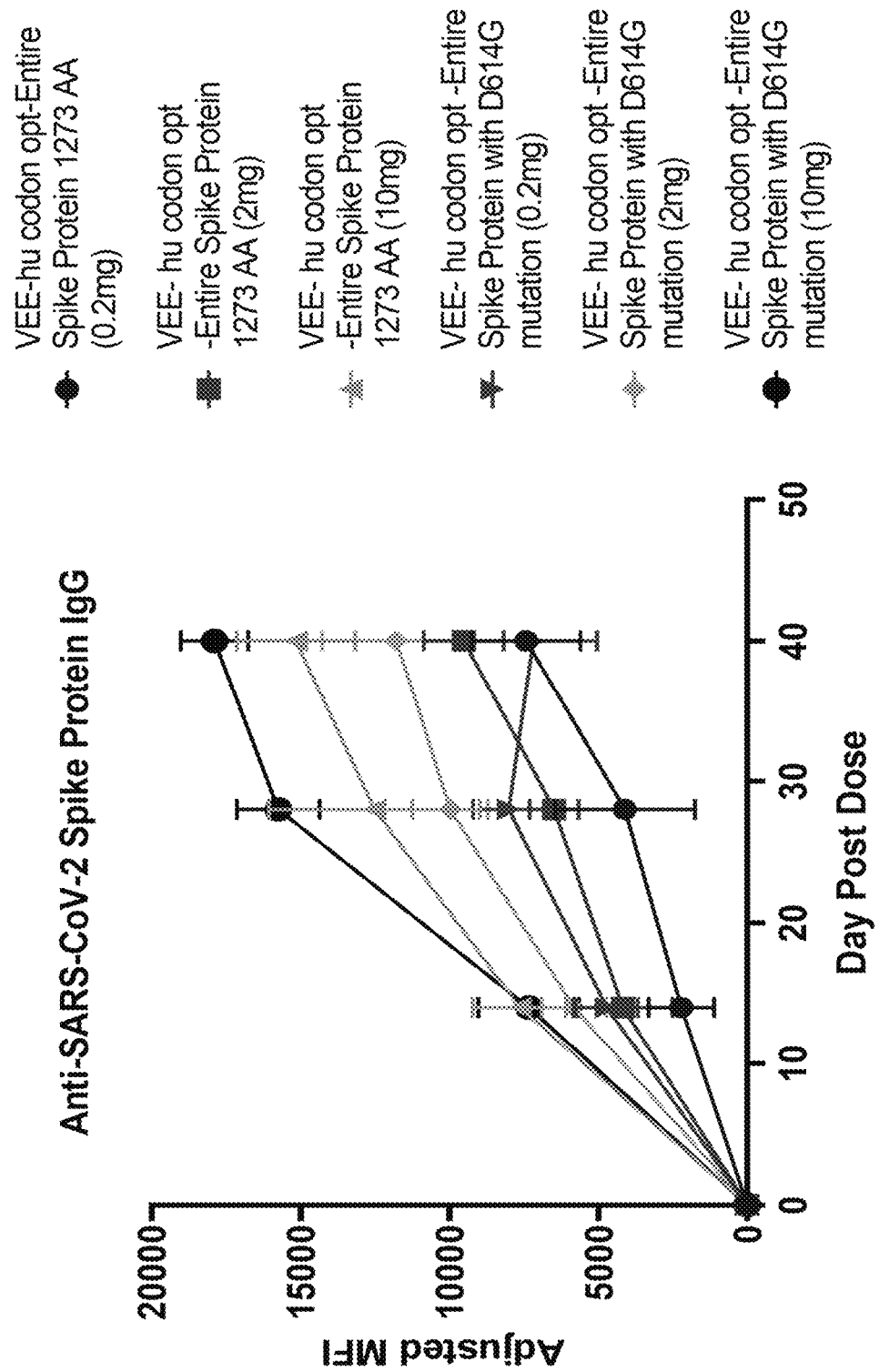
FIG. 13 shows an RNA dose-dependent immunogenicity comparison between G614 and D614 SARS CoV-2 glycoprotein expressed from self-replicating RNA.
Figure 14:
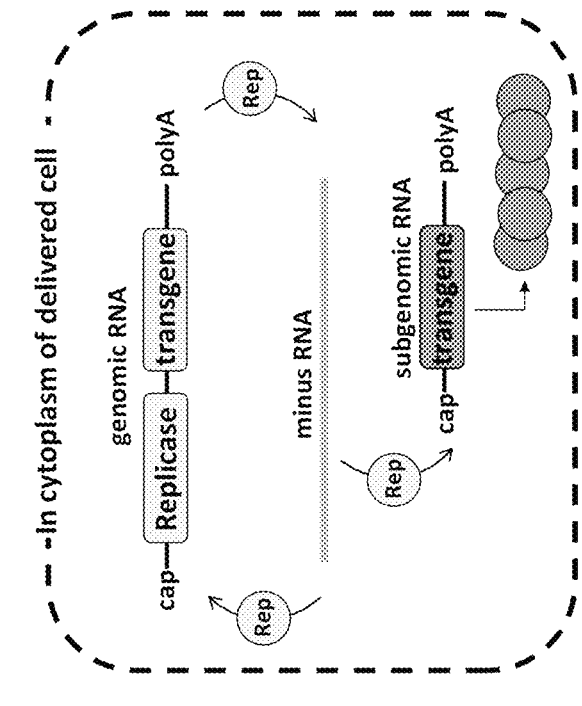
FIG. 14 shows a schematic illustrating one aspect of STARR™ technology and lipid-mediated delivery.
Figure 14:
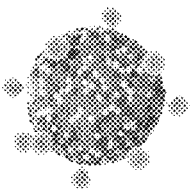
Figure 14:
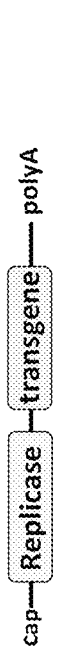

The COVID-19 pandemic is caused by infection with the SARS-CoV-2 virus. A major mutation detected to date in the SARS-CoV-2 viral envelope spike protein, which is responsible for virus attachment to the host and is also the main target for host antibodies, is a mutation of an aspartate (D) at position 614 found frequently in Chinese strains to a glycine (G). VEEV Replicon transcripts expressing the D614 and G614 versions of the SARS-CoV-2 spike glycoprotein were formulated with the exact same lipid formulation as studies described in Examples 1-8. Balb/c mice were vaccinated with a single RNA administration of 0.2 μg, 2.0 μg and 10.0 μg of RNA. There were 5 mice per dose. Mice were bled on days, 14, 28 and 42 post vaccination. Sera was diluted 1/2000 and incubated with Luminex beads derivatized with the SARS-CoV-2 spike glycoprotein containing the D614 amino acid sequence. A secondary mouse antibody derivatized with a fluorophore was used to assay for bound antibody to the beads and adjusted mean fluorescence intensity (MFI) was measured as a function of RNA dose, shown in FIG. 13. The results showed that MFI increased as a function of RNA dose with slightly higher MFI observed for the serum from mice immunized with the G614 spike glycoprotein. This slight elevation is attributed to a lower percentage of full length RNA with the D614 amino acid sequence. An important conclusion is that the serum from mice immunized with the G614 spike glycoprotein RNA construct was able to bind to spike glycoprotein with the D614 amino acid sequence, indicative of cross reactivity.

These results show that immunization with a G614 spike glycoprotein expressed from self-replicating RNA results in production of antibodies that are able to bind to a D614 spike glycoprotein.

Discussion of Examples 1-9

The pandemic of COVID-19 has necessitated rapid development of vaccines, as physical distancing to prevent SARS-CoV-2 transmission is not a sustainable long-term solution. Several COVID-19 vaccine candidates are now in clinical trials and more are entering first-in-human trials. However, a majority of vaccine candidates being developed require two doses for sufficient adaptive immunity. A single dose vaccine that generates both cellular and humoral immunity, without elevating the risk of vaccine-mediated immune enhancement, remains an unmet need. Without being limited by theory, deployment of a single dose vaccine would enable greater level of compliance and enable distribution of finite production of vaccines to more susceptible people globally.

Among licensed vaccines, live attenuated vaccines can offer durable protection against viral diseases. Live vaccines infect and replicate at sites of inoculation and some even in draining lymph nodes. Replication enables endogenous expression of viral antigens that enables antigen presentation to stimulate cytotoxic CD8+ T cells. Expressed antigens would also be taken up by antigen presenting cells to trigger CD4+ T cell help that drive affinity maturation in B cells. Studies on the live attenuated yellow fever vaccine have shown that a longer period of stimulation of the adaptive immune response results in superior adaptive immune responses. Without being limited by theory, simulating the processes of live vaccination could offer a chance of durable immunity against COVID-19.

In a crisis such as COVID-19, a nucleic acid vaccine platform offers opportunities for accelerated development. In studies described herein, a side-by-side comparison of the immunogenicity elicited by two SARS-CoV-2 vaccines candidates was conducted, a non-replicative mRNA construct and STARR™ SARS-CoV-2 RNA. Compared to an mRNA vaccine, STARR™ SARS-CoV-2 RNA produced higher and longer protein expression in vivo and upregulated gene expression of several innate, B cell, and T cell response genes in the blood and draining lymph nodes. These properties translated into significantly greater CD8+ T cell responses, IFNγ+ ELISPOT responses, and SARS-CoV-2 specific IgG and Th1 skewed responses. Interestingly, despite the highest tested dose of mRNA eliciting comparable S protein-specific antibodies as the lowest tested dose of STARR™ SARS-CoV-2 RNA, mRNA-elicited IgG did not show similar avidity or neutralization activity as those from STARR™ SARS-CoV-2 RNA vaccination. These findings thus highlight the immunological advantages of self-replicating RNA over mRNA platforms. In addition, mouse challenge studies with SARS-CoV-2 virus showed that vaccination with a single high dose (10 µg) or a single low dose (2 µg) of STARR™ SARS-CoV-2 self-replicating RNA protected mice from a lethal SARS-CoV-2 infection and protected from lung and brain infection upon challenge with a sublethal SARS-CoV-2 dose.

The extent to which STARR™ vaccines reproduce the features of live vaccines remain to be experimentally defined. Without being limited by theory, the superior quality of immune responses elicited by STARR™ SARS-CoV-2 RNA over the mRNA vaccine construct could be attributable to multiple factors, all of which have been found to be associated with live vaccination. For example, higher and longer expression of immunogens produce better immunity, likely through better engagement of T follicular helper cells and thereby leading to more diverse antibody targets and more neutralizing antibody responses. Replication of STARR™ SARS-CoV-2 RNA would result in the formation of a negative-strand template for production of more positive-strand mRNA and sub-genomic mRNA expressing the S transgene. Interaction between the negative- and positive-strands would form double stranded RNA (dsRNA), which would interact with TLR3 and RIG-I-like receptors to stimulate interferon responses, which has been shown to correlate with superior adaptive immune responses. Production of IFNγ can then stimulate development of cytotoxic CD8+ T cells. Importantly, the S protein does contain human CD8+ T cell epitopes. Without being limited by theory, the development of T cell memory could be important for long-term immunity, as suggested by recent findings on T cell responses to SARS-CoV-2 and other coronavirus infections.

It is unclear whether the VEEV nsP1-4 forming the replication complex contains any immunogenic properties, although mutations in the nsP proteins have been shown to affect induction of type I IFN. VEEV replicons have also been shown to adjuvant immune responses at mucosal sites, further illustrating the advantages of using the STARR™ platform to develop a COVID-19 vaccine. Without being limited by theory, there does not appear to be an immune response to replicon non-structural proteins, as indicated by an increase in antigen-specific IgG production upon a second administration of replicon to animals. In the presence of an immune response to non-structural proteins, a limited or no increase in antigen-specific IgG production may have resulted following a second administration. The RNA is encapsulated in lipid nanoparticles (LNP), which together can form potent adjuvants leading to robust immune responses. In addition, using the genetic sequence of an antigen, including a viral antigen such as the spike protein from SARS-CoV-2, for example, STARR™ vaccines can be rapidly generated and manufactured using cell-free and rapidly scalable techniques.

In conclusion, a STARR™ vaccine as exemplified by STARR™ SARS-CoV-2 RNA offers an approach to simulate several of the properties of live vaccination and offers a potential for single-dose vaccination against COVID-19.

SEQUENCES

SEQ ID NO: 72

ATGGAGAAAGTTCACGTTGACATCGAGGAAGACAGCCCATTCCTCAGAGCTTTG

CAGCGGAGCTTCCCGCAGTTTGAGGTAGAAGCCAAGCAGGTCACTGATAATGAC

CATGCTAATGCCAGAGCGTTTTCGCATCTGGCTTCAAAACTGATCGAAACGGAGG

TGGACCCATCCGACACGATCCTTGACATTGGAAGTGCGCCCGCCCGCAGAATGT

ATTCTAAGCACAAGTATCATTGTATCTGTCCGATGAGATGTGCGGAAGATCCGGA

CAGATTGTATAAGTATGCAACTAAGCTGAAGAAAAACTGTAAGGAAATAACTGA

TAAGGAATTGGACAAGAAAATGAAGGAGCTGGCCGCCGTCATGAGCGACCCTGA

CCTGGAAACTGAGACTATGTGCCTCCACGACGACGAGTCGTGTCGCTACGAAGG

GCAAGTCGCTGTTTACCAGGATGTATACGCCGTCGACGGCCCCACCAGCCTGTAC

CACCAGGCCAACAAGGGCGTGAGGGTGGCCTACTGGATCGGCTTCGACACCACA

-continued

| SEQUENCES |
|---|
| CCCTTCATGTTCAAGAACCTGGCCGGCGCCTACCCCAGCTACAGCACCAACTGGG |
| CCGACGAGACCGTGCTGACCGCCAGGAACATCGGCCTGTGCAGCAGCGACGTGA |
| TGGAGAGGAGCCGGAGAGGCATGAGCATCCTGAGGAAGAAATACCTGAAGCCC |
| AGCAACAACGTGCTGTTCAGCGTGGGCAGCACCATCTACCACGAGAAGAGGGAC |
| CTGCTCAGGAGCTGGCACCTGCCCAGCGTGTTCCACCTGAGGGGCAAGCAGAAC |
| TACACCTGCAGGTGCGAGACCATCGTGAGCTGCGACGGCTACGTGGTGAAGAGG |
| ATCGCCATCAGCCCCGGCCTGTACGGCAAGCCCAGCGGCTACGCCGCTACAATG |
| CACAGGGAGGGCTTCCTGTGCTGCAAGGTGACCGACACCCTGAACGGCGAGAGG |
| GTGAGCTTCCCCGTGTGCACCTACGTGCCCGCCACCCTGTGCGACCAGATGACCG |
| GCATCCTGGCCACCGACGTGAGCGCCGACGACGCCCAGAAGCTGCTCGTGGGCC |
| TGAACCAGAGGATCGTGGTCAACGGCAGGACCCAGAGGAACACCAACACAATG |
| AAGAACTACCTGCTGCCCGTGGTGGCCCAGGCTTTCGCCAGGTGGGCCAAGGAG |
| TACAAGGAGGACCAGGAAGACGAGAGGCCCCTGGGCCTGAGGGACAGGCAGCT |
| GGTGATGGGCTGCTGCTGGGCCTTCAGGCGGCACAAGATCACCAGCATCTACAA |
| GAGGCCCGACACCCAGACCATCATCAAGGTGAACAGCGACTTCCACAGCTTCGT |
| GCTGCCCAGGATCGGCAGCAACACCCTGGAGATCGGCCTGAGGACCCGGATCAG |
| GAAGATGCTGGAGGAACACAAGGAGCCCAGCCCACTGATCACCGCCGAGGACGT |
| GCAGGAGGCCAAGTGCGCTGCCGACGAGGCCAAGGAGGTGAGGGAGGCCGAGG |
| AACTGAGGGCCGCCCTGCCACCCCTGGCTGCCGACGTGGAGGAACCCACCCTGG |
| AAGCCGACGTGGACCTGATGCTGCAGGAGGCCGGCGCCGAAGCGTGGAGACA |
| CCCAGGGGCCTGATCAAGGTGACCAGCTACGACGGCGAGGACAAGATCGGCAGC |
| TACGCCGTGCTGAGCCCACAGGCCGTGCTGAAGTCCGAGAAGCTGAGCTGCATC |
| CACCCACTGGCCGAGCAGGTGATCGTGATCACCCACAGCGGCAGGAAGGGCAGG |
| TACGCCGTGGAGCCCTACCACGGCAAGGTGGTCGTGCCCGAGGGCCACGCCATC |
| CCCGTGCAGGACTTCCAGGCCCTGAGCGAGAGCGCCACCATCGTGTACAACGAG |
| AGGGAGTTCGTGAACAGGTACCTGCACCATATCGCCACCCACGGCGGAGCCCTG |
| AACACCGACGAGGAATACTACAAGACCGTGAAGCCCAGCGAGCACGACGGCGA |
| GTACCTGTACGACATCGACAGGAAGCAGTGCGTGAAGAAAGAGCTGGTGACCGG |
| CCTGGGACTGACCGGCGAGCTGGTGGACCCACCCTTCCACGAGTTCGCCTACGA |
| GAGCCTGAGGACCAGACCCGCCGCTCCCTACCAGGTGCCCACCATCGGCGTGTA |
| CGGCGTGCCCGGCAGCGGAAAGAGCGGCATCATCAAGAGCGCCGTGACCAAGA |
| AAGACCTGGTGGTCAGCGCCAAGAAAGAGAACTGCGCCGAGATCATCAGGGAC |
| GTGAAGAAGATGAAAGGCCTGGACGTGAACGCGCGCACCGTGGACAGCGTGCTG |
| CTGAACGGCTGCAAGCACCCCGTGGAGACCCTGTACATCGACGAGGCCTTCGCTT |
| GCCACGCCGGCACCCTGAGGGCCCTGATCGCCATCATCAGGCCCAAGAAAGCCG |
| TGCTGTGCGGCGACCCCAAGCAGTGCGGCTTCTTCAACATGATGTGCCTGAAGGT |
| GCACTTCAACCACGAGATCTGCACCCAGGTGTTCCACAAGAGCATCAGCAGGCG |
| GTGCACCAAGAGCGTGACCAGCGTCGTGAGCACCCTGTTCTACGACAAGAAAAT |
| GAGGACCACCAACCCCAAGGAGACCAAAATCGTGATCGACACCACAGGCAGCA |

| SEQUENCES |
|---|
| CCAAGCCCAAGCAGGACGACCTGATCCTGACCTGCTTCAGGGGCTGGGTGAAGC |
| AGCTGCAGATCGACTACAAGGGCAACGAGATCATGACCGCCGCTGCCAGCCAGG |
| GCCTGACCAGGAAGGGCGTGTACGCCGTGAGGTACAAGGTGAACGAGAACCCAC |
| TGTACGCTCCCACCAGCGAGCACGTGAACGTGCTGCTGACCAGGACCGAGGACA |
| GGATCGTGTGGAAGACCCTGGCCGGCGACCCCTGGATCAAGACCCTGACCGCCA |
| AGTACCCCGGCAACTTCACCGCCACCATCGAAGAGTGGCAGGCCGAGCACGACG |
| CCATCATGAGGCACATCCTGGAGAGGCCCGACCCCACCGACGTGTTCCAGAACA |
| AGGCCAACGTGTGCTGGGCCAAGGCCCTGGTGCCCGTGCTGAAGACCGCCGGCA |
| TCGACATGACCACAGAGCAGTGGAACACCGTGGACTACTTCGAGACCGACAAGG |
| CCCACAGCGCCGAGATCGTGCTGAACCAGCTGTGCGTGAGGTTCTTCGGCCTGGA |
| CCTGGACAGCGGCCTGTTCAGCGCCCCCACCGTGCCACTGAGCATCAGGAACAA |
| CCACTGGGACAACAGCCCCAGCCCAAACATGTACGGCCTGAACAAGGAGGTGGT |
| CAGGCAGCTGAGCAGGCGGTACCCACAGCTGCCCAGGGCCGTGGCCACCGGCAG |
| GGTGTACGACATGAACACCGGCACCCTGAGGAACTACGACCCCAGGATCAACCT |
| GGTGCCCGTGAACAGGCGGCTGCCCCACGCCCTGGTGCTGCACCACAACGAGCA |
| CCCACAGAGCGACTTCAGCTCCTTCGTGAGCAAGCTGAAAGGCAGGACCGTGCT |
| GGTCGTGGGCGAGAAGCTGAGCGTGCCCCGGCAAGATGGTGGACTGGCTGAGCGA |
| CAGGCCCGAGGCCACCTTCCGGGCCAGGCTGGACCTCGGCATCCCCGGCGACGT |
| GCCCAAGTACGACATCATCTTCGTGAACGTCAGGACCCCATACAAGTACCACCAT |
| TACCAGCAGTGCGAGGACCACGCCATCAAGCTGAGCATGCTGACCAAGAAGGCC |
| TGCCTGCACCTGAACCCCGGAGGCACCTGCGTGAGCATCGGCTACGGCTACGCC |
| GACAGGGCCAGCGAGAGCATCATTGGCGCCATCGCCAGGCTGTTCAAGTTCAGC |
| AGGGTGTGCAAACCCAAGAGCAGCCTGGAGGAAACCGAGGTGCTGTTCGTGTTC |
| ATCGGCTACGACCGGAAGGCCAGGACCCACAACCCCTACAAGCTGAGCAGCACC |
| CTGACAAACATCTACACCGGCAGCAGGCTGCACGAGGCCGGCTGCGCCCCCAGC |
| TACCACGTGGTCAGGGGCGATATCGCCACCGCCACCGAGGGCGTGATCATCAAC |
| GCTGCCAACAGCAAGGGCCAGCCCGGAGGCGGAGTGTGCGGCGCCCTGTACAAG |
| AAGTTCCCCGAGAGCTTCGACCTGCAGCCCATCGAGGTGGGCAAGGCCAGGCTG |
| GTGAAGGGCGCCGCTAAGCACATCATCCACGCCGTGGGCCCCAACTTCAACAAG |
| GTGAGCGAGGTGGAAGGCGACAAGCAGCTGGCCGAAGCCTACGAGAGCATCGC |
| CAAGATCGTGAACGACAATAACTACAAGAGCGTGGCCATCCCACTGCTCAGCAC |
| CGGCATCTTCAGCGGCAACAAGGACAGGCTGACCCAGAGCCTGAACCACCTGCT |
| CACCGCCCTGGACACCACCGATGCCGACGTGGCCATCTACTGCAGGGACAAGAA |
| GTGGGAGATGACCCTGAAGGAGGCCGTGGCCAGGCGGGAGGCCGTGGAAGAGA |
| TCTGCATCAGCGACGACTCCAGCGTGACCGAGCCCGACGCCGAGCTGGTGAGGG |
| TGCACCCCAAGAGCTCCCTGGCCGGCAGGAAGGGCTACAGCACCAGCGACGGCA |
| AGACCTTCAGCTACCTGGAGGGCACCAAGTTCCACCAGGCCGCTAAGGACATCG |
| CCGAGATCAACGCTATGTGGCCCGTGGCCACCGAGGCCAACGAGCAGGTGTGCA |

| SEQUENCES |
|---|
| TGTACATCCTGGGCGAGAGCATGTCCAGCATCAGGAGCAAGTGCCCCGTGGAGG |
| AAAGCGAGGCCAGCACACCACCCAGCACCCTGCCCTGCCTGTGCATCCACGCTA |
| TGACACCCGAGAGGGTGCAGCGGCTGAAGGCCAGCAGGCCCGAGCAGATCACC |
| GTGTGCAGCTCCTTCCCACTGCCCAAGTACAGGATCACCGGCGTGCAGAAGATCC |
| AGTGCAGCCAGCCCATCCTGTTCAGCCCAAAGGTGCCCGCCTACATCCACCCCAG |
| GAAGTACCTGGTGGAGACCCCACCCGTGGACGAGACACCCGAGCCAAGCGCCGA |
| GAACCAGAGCACCGAGGGCACACCCGAGCAGCCACCCCTGATCACCGAGGACG |
| AGACAAGGACCCGGACCCCAGAGCCCATCATTATCGAGGAAGAGGAAGAGGAC |
| AGCATCAGCCTGCTGAGCGACGGCCCCACCCACCAGGTGCTGCAGGTGGAGGCC |
| GACATCCACGGCCCACCCAGCGTGTCCAGCTCCAGCTGGAGCATCCCACACGCC |
| AGCGACTTCGACGTGGACAGCCTGAGCATCCTGGACACCCTGGAGGGCGCCAGC |
| GTGACCTCCGGCGCCACCAGCGCCGAGACCAACAGCTACTTCGCCAAGAGCATG |
| GAGTTCCTGGCCAGGCCCGTGCCAGCTCCCAGGACCGTGTTCAGGAACCCACCCC |
| ACCCAGCTCCCAGGACCAGGACCCCAAGCCTGGCTCCCAGCAGGGCCTGCAGCA |
| GGACCAGCCTGGTGAGCACCCCACCCGGCGTGAACAGGGTGATCACCAGGGAGG |
| AACTGGAGGCCCTGACACCCAGCAGGACCCCCAGCAGGTCCGTGAGCAGGACTA |
| GTCTGGTGTCCAACCCACCCGGCGTGAACAGGGTGATCACCAGGGAGGAATTCG |
| AGGCCTTCGTGGCCCAGCAACAGAGACGGTTCGACGCCGGCGCCTACATCTTCA |
| GCAGCGACACCGGCCAGGGACACCTGCAGCAAAAGAGCGTGAGGCAGACCGTG |
| CTGAGCGAGGTGGTGCTGGAGAGGACCGAGCTGGAAATCAGCTACGCCCCCAGG |
| CTGGACCAGGAGAAGGAGGAACTGCTCAGGAAGAAACTGCAGCTGAACCCCAC |
| CCCAGCCAACAGGAGCAGGTACCAGAGCAGGAAGGTGGAGAACATGAAGGCCA |
| TCACCGCCAGGCGGATCCTGCAGGGCCTGGGACACTACCTGAAGGCCGAGGGCA |
| AGGTGGAGTGCTACAGGACCCTGCACCCCGTGCCACTGTACAGCTCCAGCGTGA |
| ACAGGGCCTTCTCCAGCCCCAAGGTGGCCGTGGAGGCCTGCAACGCTATGCTGA |
| AGGAGAACTTCCCCACCGTGGCCAGCTACTGCATCATCCCCGAGTACGACGCCTA |
| CCTGGACATGGTGGACGGCGCCAGCTGCTGCCTGGACACCGCCAGCTTCTGCCCC |
| GCCAAGCTGAGGAGCTTCCCCAAGAAACACAGCTACCTGGAGCCCACCATCAGG |
| AGCGCCGTGCCCAGCGCCATCCAGAACACCCTGCAGAACGTGCTGGCCGCTGCC |
| ACCAAGAGGAACTGCAACGTGACCCAGATGAGGGAGCTGCCCGTGCTGGACAGC |
| GCTGCCTTCAACGTGGAGTGCTTCAAGAAATACGCCTGCAACAACGAGTACTGG |
| GAGACCTTCAAGGAGAACCCCATCAGGCTGACCGAAGAGAACGTGGTGAACTAC |
| ATCACCAAGCTGAAGGGCCCCAAGGCCGCTGCCCTGTTCGCTAAGACCCACAAC |
| CTGAACATGCTGCAGGACATCCCAATGGACAGGTTCGTGATGGACCTGAAGAGG |
| GACGTGAAGGTGACACCCGGCACCAAGCACACCGAGGAGAGGCCCAAGGTGCA |
| GGTGATCCAGGCCGCTGACCCACTGGCCACCGCCTACCTGTGCGGCATCCACAG |
| GGAGCTGGTGAGGCGGCTGAACGCCGTGCTGCTGCCCAACATCCACACCCTGTTC |
| GACATGAGCGCCGAGGACTTCGACGCCATCATCGCCGAGCACTTCCAGCCCGGC |
| GACTGCGTGCTGGAGACCGACATCGCCAGCTTCGACAAGAGCGAGGATGACGCT |

-continued

| SEQUENCES |
| --- |
| ATGGCCCTGACCGCTCTGATGATCCTGGAGGACCTGGGCGTGGACGCCGAGCTG |
| CTCACCCTGATCGAGGCTGCCTTCGGCGAGATCAGCTCCATCCACCTGCCCACCA |
| AGACCAAGTTCAAGTTCGGCGCTATGATGAAAAGCGGAATGTTCCTGACCCTGTT |
| CGTGAACACCGTGATCAACATTGTGATCGCCAGCAGGGTGCTGCGGGAGAGGCT |
| GACCGGCAGCCCCTGCGCTGCCTTCATCGGCGACGACAACATCGTGAAGGGCGT |
| GAAAAGCGACAAGCTGATGGCCGACAGGTGCGCCACCTGGCTGAACATGGAGGT |
| GAAGATCATCGACGCCGTGGTGGGCGAGAAGGCCCCCTACTTCTGCGGCGGATT |
| CATCCTGTGCGACAGCGTGACCGGCACCGCCTGCAGGGTGGCCGACCCCCTGAA |
| GAGGCTGTTCAAGCTGGGCAAGCCACTGGCCGCTGACGATGAGCACGACGATGA |
| CAGGCGGAGGGCCCTGCACGAGGAAAGCACCAGGTGGAACAGGGTGGGCATCC |
| TGAGCGAGCTGTGCAAGGCCGTGGAGAGCAGGTACGAGACCGTGGGCACCAGC |
| ATCATCGTGATGGCTATGACCACACTGGCCAGCTCCGTCAAGAGCTTCTCCTACC |
| TGAGGGGGGCCCCTATAACTCTCTACGGCTAA |

SEQ ID NO: 73
ATGGGCGGCGCATGAGAGAAGCCCAGACCAATTACCTACCCAAA

SEQ ID NO: 74
GATGGGCGGCGCATGAGAGAAGCCCAGACCAATTACCTACCCAAA

SEQ ID NO: 75
GATAGGCGGCGCATGAGAGAAGCCCAGACCAATTACCTACCCAAA

SEQ ID NO: 76
ACTCGAGTATGTTACGTGCAAAGGTGATTGTCACCCCCCGAAAGACC

ATATTGTGACACACCCTCAGTATCACGCCCAAACATTTACAGCCGCG

-continued

GTGTCAAAAACCGCGTGGACGTGGTTAACATCCCTGCTGGGAGGATC

AGCCGTAATTATTATAATTGGCTTGGTGCTGGCTACTATTGTGGCCA

TGTACGTGCTGACCAACCAGAAACATAATTGAATACAGCAGCAATTG

GCAAGCTGCTTACATAGAACTCGCGGCGATTGGCATGCCGCCTTAAA

ATTTTTATTTTATTTTTTCTTTTCTTTTCCGAATCGGATTTTGTTTT

TAATATTTCAAAAAAAAAAAAAAAAAAAAAAAAAAATCTAGAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAA

SEQ ID NO: 121

ATGTTTGTTTTTCTTGTTTTATTGCCACTAGTCTCTAGTCAGTGTGTTAATCTTACA

ACCAGAACTCAATTACCCCCTGCATACACTAATTCTTTCACACGTGGTGTTTATTA

CCCTGACAAAGTTTTCAGATCCTCAGTTTTACATTCAACTCAGGACTTGTTCTTAC

CTTTCTTTTCCAATGTTACTTGGTTCCATGCTATACATGTCTCTGGGACCAATGGT

ACTAAGAGGTTTGATAACCCTGTCCTACCATTTAATGATGGTGTTTATTTTGCTTC

CACTGAGAAGTCTAACATAATAAGAGGCTGGATTTTTGGTACTACTTTAGATTCG

AAGACCCAGTCCCTACTTATTGTTAATAACGCTACTAATGTTGTTATTAAAGTCTG

TGAATTTCAATTTTGTAATGATCCATTTTTGGGTGTTTATTACCACAAAAACAACA

AAAGTTGGATGGAAAGTGAGTTCAGAGTTTATTCTAGTGCGAATAATTGCACTTT

TGAATATGTCTCTCAGCCTTTTCTTATGGACCTTGAAGGAAAACAGGGTAATTTC

AAAAATCTTAGGGAATTTGTGTTTAAGAATATTGATGGTTATTTTAAAATATATT

CTAAGCACACGCCTATTAATTTAGTGCGTGATCTCCCTCAGGGTTTTTCGGCTTTA

-continued

```
GAACCATTGGTAGATTTGCCAATAGGTATTAACATCACTAGGTTTCAAACTTTAC

TTGCTTTACATAGAAGTTATTTGACTCCTGGTGATTCTTCTTCAGGTTGGACAGCT

GGTGCTGCAGCTTATTATGTGGGTTATCTTCAACCTAGGACTTTTCTATTAAAATA

TAATGAAAATGGAACCATTACAGATGCTGTAGACTGTGCACTTGACCCTCTCTCA

GAAACAAAGTGTACGTTGAAATCCTTCACTGTAGAAAAAGGAATCTATCAAACT

TCTAACTTTAGAGTCCAACCAACAGAATCTATTGTTAGATTTCCTAATATTACAA

ACTTGTGCCCTTTTGGTGAAGTTTTTAACGCCACCAGATTTGCATCTGTTTATGCT

TGGAACAGGAAGAGAATCAGCAACTGTGTTGCTGATTATTCTGTCCTATATAATT

CCGCATCATTTTCCACTTTTAAGTGTTATGGAGTGTCTCCTACTAAATTAAATGAT

CTCTGCTTTACTAATGTCTATGCAGATTCATTTGTAATTAGAGGTGATGAAGTCA

GACAAATCGCTCCAGGGCAAACTGGAAAGATTGCTGATTATAATTATAAATTAC

CAGATGATTTTACAGGCTGCGTTATAGCTTGGAATTCTAACAATCTTGATTCTAA

GGTTGGTGGTAATTATAATTACCTGTATAGATTGTTTAGGAAGTCTAATCTCAAA

CCTTTTGAGAGAGATATTCAACTGAAATCTATCAGGCCGGTAGCACACCTTGTA

ATGGTGTTGAAGGTTTTAATTGTTACTTTCCTTTACAATCATATGGTTTCCAACCC

ACTAATGGTGTTGGTTACCAACCATACAGAGTAGTAGTACTTTCTTTTGAACTTCT

ACATGCACCAGCAACTGTTTGTGGACCTAAAAAGTCTACTAATTTGGTTAAAAAC

AAATGTGTCAATTTCAACTTCAATGGTTTAACAGGCACAGGTGTTCTTACTGAGT

CTAACAAAAGTTTCTGCCTTTCCAACAATTTGGCAGAGACATTGCTGACACTAC

TGATGCTGTCCGTGATCCACAGACACTTGAGATTCTTGACATTACACCATGTTCTT

TTGGTGGTGTCAGTGTTATAACACCAGGAACAAATACTTCTAACCAGGTTGCTGT

TCTTTATCAGGATGTTAACTGCACAGAAGTCCCTGTTGCTATTCATGCAGATCAA

CTTACTCCTACTTGGCGTGTTTATTCTACAGGTTCTAATGTTTTTCAAACACGTGC

AGGCTGTTTAATAGGGGCTGAACATGTCAACAACTCATATGAGTGTGACATACCC

ATTGGTGCAGGTATATGCGCTAGTTATCAGACTCAGACTAATTCTCCTCGGCGGG

CACGTAGTGTAGCTAGTCAATCCATCATTGCCTACACTATGTCACTTGGTGCAGA

AAATTCAGTTGCTTACTCTAATAACTCTATTGCCATACCCACAAATTTTACTATTA

GTGTTACCACAGAAATTCTACCAGTGTCTATGACCAAGACATCAGTAGATTGTAC

AATGTACATTTGTGGTGATTCAACTGAATGCAGCAATCTTTTGTTGCAATATGGC

AGTTTTTGTACACAATTAAACCGTGCTTTAACTGGAATAGCTGTTGAACAAGACA

AAAACACCCAAGAAGTTTTTGCACAAGTCAAACAAATTTACAAAACACCACCAA

TTAAAGATTTTGGTGGTTTTAATTTTTCACAAATATTACCAGATCCATCAAAACCA

AGCAAGAGGTCATTTATTGAAGATCTACTTTTCAACAAAGTGACACTTGCAGATG

CTGGCTTCATCAAACAATATGGTGATTGCCTTGGTGATATTGCTGCTAGAGACCT

CATTTGTGCACAAAAGTTTAACGGCCTTACTGTTTTGCCACCTTTGCTCACAGATG

AAATGATTGCTCAATACACTTCTGCACTGTTAGCGGGTACAATCACTTCTGGTTG

GACCTTTGGTGCAGGTGCTGCATTACAAATACCATTTGCTATGCAAATGGCTTAT

AGGTTTAATGGTATTGGAGTTACACAGAATGTTCTCTATGAGAACCAAAAATTGA

TTGCCAACCAATTTAATAGTGCTATTGGCAAAATTCAAGACTCACTTTCTTCCAC

AGCAAGTGCACTTGGAAAACTTCAAGATGTGGTCAACCAAAATGCACAAGCTTT
```

-continued

```
AAACACGCTTGTTAAACAACTTAGCTCCAATTTTGGTGCAATTTCAAGTGTTTTA
AATGATATCCTTTCACGTCTTGACAAAGTTGAGGCTGAAGTGCAAATTGATAGGT
TGATCACAGGCAGACTTCAAAGTTTGCAGACATATGTGACTCAACAATTAATTAG
AGCTGCAGAAATCAGAGCTTCTGCTAATCTTGCTGCTACTAAAATGTCAGAGTGT
GTACTTGGACAATCAAAAGAGTTGATTTTTGTGGAAAGGGCTATCATCTTATGT
CCTTCCCTCAGTCAGCACCTCATGGTGTAGTCTTCTTGCATGTGACTTATGTCCCT
GCACAAGAAAAGAACTTCACAACTGCTCCTGCCATTTGTCATGATGGAAAAGCA
CACTTTCCTCGTGAAGGTGTCTTTGTTTCAAATGGCACACACTGGTTTGTAACAC
AAAGGAATTTTTATGAACCACAAATCATTACTACAGACAACACATTTGTGTCTGG
TAACTGTGATGTTGTAATAGGAATTGTCAACAACACAGTTTATGATCCTTTGCAA
CCTGAATTAGACTCATTCAAGGAGGAGTTAGATAAATATTTTAAGAATCATACAT
CACCAGATGTTGATTTAGGTGACATCTCTGGCATTAATGCTTCAGTTGTAAACAT
TCAAAAAGAAATTGACCGCCTCAATGAGGTTGCCAAGAATTTAAATGAATCTCTC
ATCGATCTCCAAGAACTTGGAAAGTATGAGCAGTATATAAAATGGCCATGGTAC
ATTTGGCTAGGTTTTATAGCTGGCTTGATTGCCATAGTAATGGTGACAATTATGCT
TTGCTGTATGACCAGTTGCTGTAGTTGTCTCAAGGGCTGTTGTTCTTGTGGATCCT
GCTGCAAATTTGATGAAGACGACTCTGAGCCAGTGCTCAAAGGAGTCAAATTAC
ATTACACATAA
```

SEQ ID NO: 122
```
ATGTTCGTCTTCCTGGTCCTGCTGCCTCTGGTCTCCTCACAGTGCGTCAATCTGAC
AACTCGGACTCAGCTGCCACCTGCTTATACTAATAGCTTCACCAGAGGCGTGTAC
TATCCTGACAAGGTGTTTAGAAGCTCCGTGCTGCACTCTACACAGGATCTGTTTC
TGCCATTCTTTAGCAACGTGACCTGGTTCCACGCCATCCACGTGAGCGGCACCAA
TGGCACAAAGCGGTTCGACAATCCCGTGCTGCCTTTTAACGATGGCGTGTACTTC
GCCTCTACCGAGAAGTCCAACATCATCAGAGGCTGGATCTTTGGCACCACACTGG
ACTCCAAGACACAGTCTCTGCTGATCGTGAACAATGCCACCAACGTGGTCATCAA
GGTGTGCGAGTTCCAGTTTTGTAATGATCCCTTCCTGGGCGTGTACTATCACAAG
AACAATAAGAGCTGGATGGAGTCCGAGTTTAGAGTGTATTCTAGCGCCAACAAC
TGCACATTTGAGTACGTGAGCCAGCCTTTCCTGATGGACCTGGAGGGCAAGCAG
GGCAATTTCAAGAACCTGAGGGAGTTCGTGTTTAAGAATATCGACGGCTACTTCA
AAATCTACTCTAAGCACACCCCCATCAACCTGGTGCGCGACCTGCCTCAGGGCTT
CAGCGCCCTGGAGCCCCTGGTGGATCTGCCTATCGGCATCAACATCACCCGGTTT
CAGACACTGCTGGCCCTGCACAGAAGCTACCTGACACCCGGCGACTCCTCTAGC
GGATGGACCGCCGGCGCTGCCGCCTACTATGTGGGCTACCTCCAGCCCCGGACCT
TCCTGCTGAAGTACAACGAGAATGGCACCATCACAGACGCAGTGGATTGCGCCC
TGGACCCCCTGAGCGAGACAAAGTGTACACTGAAGTCCTTTACCGTGGAGAAGG
GCATCTATCAGACATCCAATTTCAGGGTGCAGCCAACCGAGTCTATCGTGCGCTT
TCCTAATATCACAAACCTGTGCCCATTTGGCGAGGTGTTCAACGCAACCCGCTTC
GCCAGCGTGTACGCCTGGAATAGGAAGCGGATCAGCAACTGCGTGGCCGACTAT
AGCGTGCTGTACAACTCCGCCTCTTTCAGCACCTTTAAGTGCTATGGCGTGTCCC
```

-continued

```
CCACAAAGCTGAATGACCTGTGCTTTACCAACGTCTACGCCGATTCTTTCGTGAT

CAGGGGCGACGAGGTGCGCCAGATCGCCCCCGGCCAGACAGGCAAGATCGCAG

ACTACAATTATAAGCTGCCAGACGATTTCACCGGCTGCGTGATCGCCTGGAACAG

CAACAATCTGGATTCCAAAGTGGGCGGCAACTACAATTATCTGTACCGGCTGTTT

AGAAAGAGCAATCTGAAGCCCTTCGAGAGGGACATCTCTACAGAAATCTACCAG

GCCGGCAGCACCCCTTGCAATGGCGTGGAGGGCTTTAACTGTTATTTCCCACTCC

AGTCCTACGGCTTCCAGCCCACAAACGGCGTGGGCTATCAGCCTTACCGCGTGGT

GGTGCTGAGCTTTGAGCTGCTGCACGCCCCAGCAACAGTGTGCGGCCCCAAGAA

GTCCACCAATCTGGTGAAGAACAAGTGCGTGAACTTCAACTTCAACGGCCTGAC

CGGCACAGGCGTGCTGACCGAGTCCAACAAGAAGTTCCTGCCATTTCAGCAGTTC

GGCAGGGACATCGCAGATACCACAGACGCCGTGCGCGACCCACAGACCCTGGAG

ATCCTGGACATCACACCCTGCTCTTTCGGCGGCGTGAGCGTGATCACACCCGGCA

CCAATACAAGCAACCAGGTGGCCGTGCTGTATCAGGACGTGAATTGTACCGAGG

TGCCCGTGGCTATCCACGCCGATCAGCTGACCCCAACATGGCGGGTGTACAGCA

CCGGCTCCAACGTCTTCCAGACAAGAGCCGGATGCCTGATCGGAGCAGAGCACG

TGAACAATTCCTATGAGTGCGACATCCCAATCGGCGCCGGCATCTGTGCCTCTTA

CCAGACCCAGACAAACTCTCCCAGACGGGCCCGGAGCGTGGCCTCCCAGTCTAT

CATCGCCTATACCATGTCCCTGGGCGCCGAGAACAGCGTGGCCTACTCTAACAAT

AGCATCGCCATCCCAACCAACTTCACAATCTCTGTGACCACAGAGATCCTGCCCG

TGTCCATGACCAAGACATCTGTGGACTGCACAATGTATATCTGTGGCGATTCTAC

CGAGTGCAGCAACCTGCTGCTCCAGTACGGCAGCTTTTGTACCCAGCTGAATAGA

GCCCTGACAGGCATCGCCGTGGAGCAGGATAAGAACACACAGGAGGTGTTCGCC

CAGGTGAAGCAAATCTACAAGACCCCCCCTATCAAGGACTTTGGCGGCTTCAATT

TTTCCCAGATCCTGCCTGATCCATCCAAGCCTTCTAAGCGGAGCTTTATCGAGGA

CCTGCTGTTCAACAAGGTGACCCTGGCCGATGCCGGCTTCATCAAGCAGTATGGC

GATTGCCTGGGCGACATCGCAGCCAGGGACCTGATCTGCGCCCAGAAGTTTAAT

GGCCTGACCGTGCTGCCACCCCTGCTGACAGATGAGATGATCGCACAGTACACA

AGCGCCCTGCTGGCCGGCACCATCACATCCGGATGGACCTTCGGCGCAGGAGCC

GCCCTCCAGATCCCCTTTGCCATGCAGATGGCCTATAGGTTCAACGGCATCGGCG

TGACCCAGAATGTGCTGTACGAGAACCAGAAGCTGATCGCCAATCAGTTTAACT

CCGCCATCGGCAAGATCCAGGACAGCCTGTCCTCTACAGCCAGCGCCCTGGGCA

AGCTCCAGGATGTGGTGAATCAGAACGCCCAGGCCCTGAATACCCTGGTGAAGC

AGCTGAGCAGCAACTTCGGCGCCATCTCTAGCGTGCTGAATGACATCCTGAGCCG

GCTGGACAAGGTGGAGGCAGAGGTGCAGATCGACCGGCTGATCACCGGCCGGCT

CCAGAGCCTCCAGACCTATGTGACACAGCAGCTGATCAGGGCCGCCGAGATCAG

GGCCAGCGCCAATCTGGCAGCAACCAAGATGTCCGAGTGCGTGCTGGGCCAGTC

TAAGAGAGTGGACTTTTGTGGCAAGGGCTATCACCTGATGTCCTTCCCTCAGTCT

GCCCCACACGGCGTGGTGTTTCTGCACGTGACCTACGTGCCCGCCCAGGAGAAG

AACTTCACCACAGCCCCTGCCATCTGCCACGATGGCAAGGCCCACTTTCCAAGGG

AGGGCGTGTTCGTGTCCAACGGCACCCACTGGTTTGTGACACAGCGCAATTTCTA
```

-continued

CGAGCCCCAGATCATCACCACAGACAACACCTTCGTGAGCGGCAACTGTGACGT

GGTCATCGGCATCGTGAACAATACCGTGTATGATCCACTCCAGCCCGAGCTGGAC

AGCTTTAAGGAGGAGCTGGATAAGTATTTCAAGAATCACACCTCCCCTGACGTG

GATCTGGGCGACATCAGCGGCATCAATGCCTCCGTGGTGAACATCCAGAAGGAG

ATCGACCGCCTGAACGAGGTGGCTAAGAATCTGAACGAGAGCCTGATCGACCTC

CAGGAGCTGGGCAAGTATGAGCAGTACATCAAGTGGCCCTGGTACATCTGGCTG

GGCTTCATCGCCGGCCTGATCGCCATCGTGATGGTGACCATCATGCTGTGCTGTA

TGACATCCTGCTGTTCTTGCCTGAAGGGCTGCTGTAGCTGTGGCTCCTGCTGTAA

GTTTGACGAGGATGACTCTGAACCTGTGCTGAAGGGCGTGAAGCTGCATTACAC

CTAA

SEQ ID NO: 123

MFVFLVLLPLVSSQCVNLTTRTQLPPAYTNSFTRGVYYPDKVFRSSVLHSTQDLFLPF

FSNVTWFHAIHVSGTNGTKRFDNPVLPFNDGVYFASTEKSNIIRGWIFGTTLDSKTQS

LLIVNNATNVVIKVCEFQFCNDPFLGVYYHKNNKSWMESEFRVYSSANNCTFEYVS

QPFLMDLEGKQGNFKNLREFVFKNIDGYFKIYSKHTPINLVRDLPQGFSALEPLVDLP

IGINITRFQTLLALHRSYLTPGDSSSGWTAGAAAYYVGYLQPRTFLLKYNENGTITDA

VDCALDPLSETKCTLKSFTVEKGIYQTSNFRVQPTESIVRFPNITNLCPFGEVFNATRF

ASVYAWNRKRISNCVADYSVLYNSASFSTFKCYGVSPTKLNDLCFTNVYADSFVIRG

DEVRQIAPGQTGKIADYNYKLPDDFTGCVIAWNSNNLDSKVGGNYNYLYRLFRKSN

LKPFERDISTEIYQAGSTPCNGVEGFNCYFPLQSYGFQPTNGVGYQPYRVVVLSFELL

HAPATVCGPKKSTNLVKNKCVNFNFNGLTGTGVLTESNKKFLPFQQFGRDIADTTD

AVRDPQTLEILDITPCSFGGVSVITPGTNTSNQVAVLYQDVNCTEVPVAIHADQLTPT

WRVYSTGSNVFQTRAGCLIGAEHVNNSYECDIPIGAGICASYQTQTNSPRRARSVAS

QSIIAYTMSLGAENSVAYSNNSIAIPTNFTISVTTEILPVSMTKTSVDCTMYICGDSTEC

SNLLLQYGSFCTQLNRALTGIAVEQDKNTQEVFAQVKQIYKTPPIKDFGGFNFSQILP

DPSKPSKRSFIEDLLFNKVTLADAGFIKQYGDCLGDIAARDLICAQKFNGLTVLPPLLT

DEMIAQYTSALLAGTITSGWTFGAGAALQIPFAMQMAYRFNGIGVTQNVLYENQKLI

ANQFNSAIGKIQDSLSSTASALGKLQDVVNQNAQALNTLVKQLSSNFGAISSVLNDIL

SRLDKVEAEVQIDRLITGRLQSLQTYVTQQLIRAAEIRASANLAATKMSECVLGQSK

RVDFCGKGYHLMSFPQSAPHGVVFLHVTYVPAQEKNFTTAPAICHDGKAHFPREGV

FVSNGTHWFVTQRNFYEPQIITTDNTFVSGNCDVVIGIVNNTVYDPLQPELDSFKEEL

DKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKG

VKLHYT

SEQ ID NO: 77
CCTGAATGGACTACGACATAGTCTAGTCCGCCAAGGCCGCCACC

SEQ ID NO: 78

```
ATGGGCGGCGCATGAGAGAAGCCCAGACCAATTACCTACCCAAAATGGAGAAA
GTTCACGTTGACATCGAGGAAGACAGCCCATTCCTCAGAGCTTTGCAGCGGAGCT
TCCCGCAGTTTGAGGTAGAAGCCAAGCAGGTCACTGATAATGACCATGCTAATG
CCAGAGCGTTTTCGCATCTGGCTTCAAAACTGATCGAAACGGAGGTGGACCCATC
CGACACGATCCTTGACATTGGAAGTGCGCCCGCCCGCAGAATGTATTCTAAGCAC
AAGTATCATTGTATCTGTCCGATGAGATGTGCGGAAGATCCGGACAGATTGTATA
AGTATGCAACTAAGCTGAAGAAAAACTGTAAGGAAATAACTGATAAGGAATTGG
ACAAGAAAATGAAGGAGCTGGCCGCCGTCATGAGCGACCCTGACCTGGAAACTG
AGACTATGTGCCTCCACGACGACGAGTCGTGTCGCTACGAAGGGCAAGTCGCTG
TTTACCAGGATGTATACGCCGTCGACGGCCCCACCAGCCTGTACCACCAGGCCAA
CAAGGGCGTGAGGGTGGCCTACTGGATCGGCTTCGACACCACACCCTTCATGTTC
AAGAACCTGGCCGGCGCCTACCCCAGCTACAGCACCAACTGGGCCGACGAGACC
GTGCTGACCGCCAGGAACATCGGCCTGTGCAGCAGCGACGTGATGGAGAGGAGC
CGGAGAGGCATGAGCATCCTGAGGAAGAAATACCTGAAGCCCAGCAACAACGT
GCTGTTCAGCGTGGGCAGCACCATCTACCACGAGAAGAGGGACCTGCTCAGGAG
CTGGCACCTGCCCAGCGTGTTCCACCTGAGGGGCAAGCAGAACTACACCTGCAG
GTGCGAGACCATCGTGAGCTGCGACGGCTACGTGGTGAAGAGGATCGCCATCAG
CCCCGGCCTGTACGGCAAGCCCAGCGGCTACGCCGCTACAATGCACAGGGAGGG
CTTCCTGTGCTGCAAGGTGACCGACACCCTGAACGGCGAGAGGGTGAGCTTCCC
CGTGTGCACCTACGTGCCCGCCACCCTGTGCGACCAGATGACCGGCATCCTGGCC
ACCGACGTGAGCGCCGACGACGCCCAGAAGCTGCTCGTGGGCCTGAACCAGAGG
ATCGTGGTCAACGGCAGGACCCAGAGGAACACCAACACAATGAAGAACTACCTG
CTGCCCGTGGTGGCCCAGGCTTTCGCCAGGTGGGCCAAGGAGTACAAGGAGGAC
CAGGAAGACGAGAGGCCCCTGGGCCTGAGGGACAGGCAGCTGGTGATGGGCTG
CTGCTGGGCCTTCAGGCGGCACAAGATCACCAGCATCTACAAGAGGCCCGACAC
CCAGACCATCATCAAGGTGAACAGCGACTTCCACAGCTTCGTGCTGCCCAGGATC
GGCAGCAACACCCTGGAGATCGGCCTGAGGACCCGGATCAGGAAGATGCTGGAG
GAACACAAGGAGCCCAGCCCACTGATCACCGCCGAGGACGTGCAGGAGGCCAA
GTGCGCTGCCGACGAGGCCAAGGAGGTGAGGGAGGCCGAGGAACTGAGGGCCG
CCCTGCCACCCCTGGCTGCCGACGTGGAGGAACCCACCCTGGAAGCCGACGTGG
ACCTGATGCTGCAGGAGGCCGGCGCCGGAAGCGTGGAGACACCCAGGGGCCTGA
TCAAGGTGACCAGCTACGACGGCGAGGACAAGATCGGCAGCTACGCCGTGCTGA
GCCCACAGGCCGTGCTGAAGTCCGAGAAGCTGAGCTGCATCCACCCACTGGCCG
AGCAGGTGATCGTGATCACCCACAGCGGCAGGAAGGGCAGGTACGCCGTGGAGC
CCTACCACGGCAAGGTGGTCGTGCCCGAGGGCCACGCCATCCCCGTGCAGGACT
TCCAGGCCCTGAGCGAGAGCGCCACCATCGTGTACAACGAGAGGGAGTTCGTGA
ACAGGTACCTGCACCATATCGCCACCCACGGCGGAGCCCTGAACACCGACGAGG
AATACTACAAGACCGTGAAGCCCAGCGAGCACGACGGCGAGTACCTGTACGACA
TCGACAGGAAGCAGTGCGTGAAGAAAGAGCTGGTGACCGGCCTGGGACTGACCG
GCGAGCTGGTGGACCCACCCTTCCACGAGTTCGCCTACGAGAGCCTGAGGACCA
```

-continued

```
GACCCGCCGCTCCCTACCAGGTGCCCACCATCGGCGTGTACGGCGTGCCCGGCA
GCGGAAAGAGCGGCATCATCAAGAGCGCCGTGACCAAGAAAGACCTGGTGGTC
AGCGCCAAGAAAGAGAACTGCGCCGAGATCATCAGGGACGTGAAGAAGATGAA
AGGCCTGGACGTGAACGCGCGCACCGTGGACAGCGTGCTGCTGAACGGCTGCAA
GCACCCCGTGGAGACCCTGTACATCGACGAGGCCTTCGCTTGCCACGCCGGCACC
CTGAGGGCCCTGATCGCCATCATCAGGCCCAAGAAAGCCGTGCTGTGCGGCGAC
CCCAAGCAGTGCGGCTTCTTCAACATGATGTGCCTGAAGGTGCACTTCAACCACG
AGATCTGCACCCAGGTGTTCCACAAGAGCATCAGCAGGCGGTGCACCAAGAGCG
TGACCAGCGTCGTGAGCACCCTGTTCTACGACAAGAAAATGAGGACCACCAACC
CCAAGGAGACCAAAATCGTGATCGACACCACAGGCAGCACCAAGCCCAAGCAG
GACGACCTGATCCTGACCTGCTTCAGGGGCTGGGTGAAGCAGCTGCAGATCGAC
TACAAGGGCAACGAGATCATGACCGCCGCTGCCAGCCAGGGCCTGACCAGGAAG
GGCGTGTACGCCGTGAGGTACAAGGTGAACGAGAACCCACTGTACGCTCCCACC
AGCGAGCACGTGAACGTGCTGCTGACCAGGACCGAGGACAGGATCGTGTGGAAG
ACCCTGGCCGGCGACCCCTGGATCAAGACCCTGACCGCCAAGTACCCCGGCAAC
TTCACCGCCACCATCGAAGAGTGGCAGGCCGAGCACGACGCCATCATGAGGCAC
ATCCTGGAGAGGCCCGACCCCACCGACGTGTTCCAGAACAAGGCCAACGTGTGC
TGGGCCAAGGCCCTGGTGCCCGTGCTGAAGACCGCCGGCATCGACATGACCACA
GAGCAGTGGAACACCGTGGACTACTTCGAGACCGACAAGGCCCACAGCGCCGAG
ATCGTGCTGAACCAGCTGTGCGTGAGGTTCTTCGGCCTGGACCTGGACAGCGGCC
TGTTCAGCGCCCCCACCGTGCCACTGAGCATCAGGAACAACCACTGGGACAACA
GCCCCAGCCCAAACATGTACGGCCTGAACAAGGAGGTGGTCAGGCAGCTGAGCA
GGCGGTACCCACAGCTGCCCAGGGCCGTGGCCACCGGCAGGGTGTACGACATGA
ACACCGGCACCCTGAGGAACTACGACCCCAGGATCAACCTGGTGCCCGTGAACA
GGCGGCTGCCCCACGCCCTGGTGCTGCACCACAACGAGCACCCACAGAGCGACT
TCAGCTCCTTCGTGAGCAAGCTGAAAGGCAGGACCGTGCTGGTCGTGGGCGAGA
AGCTGAGCGTGCCCGGCAAGATGGTGGACTGGCTGAGCGACAGGCCCGAGGCCA
CCTTCCGGGCCAGGCTGGACCTCGGCATCCCCGGCGACGTGCCCAAGTACGACA
TCATCTTCGTGAACGTCAGGACCCCATACAAGTACCACCATTACCAGCAGTGCGA
GGACCACGCCATCAAGCTGAGCATGCTGACCAAGAAGGCCTGCCTGCACCTGAA
CCCCGGAGGCACCTGCGTGAGCATCGGCTACGGCTACGCCGACAGGGCCAGCGA
GAGCATCATTGGCGCCATCGCCAGGCTGTTCAAGTTCAGCAGGGTGTGCAAACC
CAAGAGCAGCCTGGAGGAAACCGAGGTGCTGTTCGTGTTCATCGGCTACGACCG
GAAGGCCAGGACCCACAACCCCTACAAGCTGAGCAGCACCCTGACAAACATCTA
CACCGGCAGCAGGCTGCACGAGGCCGGCTGCGCCCCCAGCTACCACGTGGTCAG
GGGCGATATCGCCACCGCCACCGAGGGCGTGATCATCAACGCTGCCAACAGCAA
GGGCCAGCCCGGAGGCGGAGTGTGCGGCGCCCTGTACAAGAAGTTCCCCGAGAG
CTTCGACCTGCAGCCCATCGAGGTGGGCAAGGCCAGGCTGGTGAAGGGCGCCGC
TAAGCACATCATCCACGCCGTGGGCCCCAACTTCAACAAGGTGAGCGAGGTGGA
AGGCGACAAGCAGCTGGCCGAAGCCTACGAGAGCATCGCCAAGATCGTGAACG
ACAATAACTACAAGAGCGTGGCCATCCCACTGCTCAGCACCGGCATCTTCAGCG
```

-continued

```
GCAACAAGGACAGGCTGACCCAGAGCCTGAACCACCTGCTCACCGCCCTGGACA
CCACCGATGCCGACGTGGCCATCTACTGCAGGGACAAGAAGTGGGAGATGACCC
TGAAGGAGGCCGTGGCCAGGCGGGAGGCCGTGGAAGAGATCTGCATCAGCGAC
GACTCCAGCGTGACCGAGCCCGACGCCGAGCTGGTGAGGGTGCACCCCAAGAGC
TCCCTGGCCGGCAGGAAGGGCTACAGCACCAGCGACGGCAAGACCTTCAGCTAC
CTGGAGGGCACCAAGTTCCACCAGGCCGCTAAGGACATCGCCGAGATCAACGCT
ATGTGGCCCGTGGCCACCGAGGCCAACGAGCAGGTGTGCATGTACATCCTGGGC
GAGAGCATGTCCAGCATCAGGAGCAAGTGCCCCGTGGAGGAAAGCGAGGCCAG
CACACCACCCAGCACCCTGCCCTGCCTGTGCATCCACGCTATGACACCCGAGAGG
GTGCAGCGGCTGAAGGCCAGCAGGCCCGAGCAGATCACCGTGTGCAGCTCCTTC
CCACTGCCCAAGTACAGGATCACCGGCGTGCAGAAGATCCAGTGCAGCCAGCCC
ATCCTGTTCAGCCCAAAGGTGCCCGCCTACATCCACCCCAGGAAGTACCTGGTGG
AGACCCCACCCGTGGACGAGACACCCGAGCCAAGCGCCGAGAACCAGAGCACC
GAGGGCACACCCGAGCAGCCACCCCTGATCACCGAGGACGAGACAAGGACCCG
GACCCCAGAGCCCATCATTATCGAGGAAGAGGAAGAGGACAGCATCAGCCTGCT
GAGCGACGGCCCCACCCACCAGGTGCTGCAGGTGGAGGCCGACATCCACGGCCC
ACCCAGCGTGTCCAGCTCCAGCTGGAGCATCCCACACGCCAGCGACTTCGACGT
GGACAGCCTGAGCATCCTGGACACCCTGGAGGGCGCCAGCGTGACCTCCGGCGC
CACCAGCGCCGAGACCAACAGCTACTTCGCCAAGAGCATGGAGTTCCTGGCCAG
GCCCGTGCCAGCTCCCAGGACCGTGTTCAGGAACCCACCCCACCCAGCTCCCAG
GACCAGGACCCCAAGCCTGGCTCCCAGCAGGGCCTGCAGCAGGACCAGCCTGGT
GAGCACCCCACCCGGCGTGAACAGGGTGATCACCAGGGAGGAACTGGAGGCCCT
GACACCCAGCAGGACCCCCAGCAGGTCCGTGAGCAGGACTAGTCTGGTGTCCAA
CCCACCCGGCGTGAACAGGGTGATCACCAGGGAGGAATTCGAGGCCTTCGTGGC
CCAGCAACAGAGACGGTTCGACGCCGGCGCCTACATCTTCAGCAGCGACACCGG
CCAGGGACACCTGCAGCAAAAGAGCGTGAGGCAGACCGTGCTGAGCGAGGTGG
TGCTGGAGAGGACCGAGCTGGAAATCAGCTACGCCCCCAGGCTGGACCAGGAGA
AGGAGGAACTGCTCAGGAAGAAACTGCAGCTGAACCCCACCCCAGCCAACAGG
AGCAGGTACCAGAGCAGGAAGGTGGAGAACATGAAGGCCATCACCGCCAGGCG
GATCCTGCAGGGCCTGGGACACTACCTGAAGGCCGAGGGCAAGGTGGAGTGCTA
CAGGACCCTGCACCCCGTGCCACTGTACAGCTCCAGCGTGAACAGGGCCTTCTCC
AGCCCCAAGGTGGCCGTGGAGGCCTGCAACGCTATGCTGAAGGAGAACTTCCCC
ACCGTGGCCAGCTACTGCATCATCCCCGAGTACGACGCCTACCTGGACATGGTGG
ACGGCGCCAGCTGCTGCCTGGACACCGCCAGCTTCTGCCCCGCCAAGCTGAGGA
GCTTCCCCAAGAAACACAGCTACCTGGAGCCCACCATCAGGAGCGCCGTGCCCA
GCGCCATCCAGAACACCCTGCAGAACGTGCTGGCCGCTGCCACCAAGAGGAACT
GCAACGTGACCCAGATGAGGGAGCTGCCCGTGCTGGACAGCGCTGCCTTCAACG
TGGAGTGCTTCAAGAAATACGCCTGCAACAACGAGTACTGGGAGACCTTCAAGG
AGAACCCCATCAGGCTGACCGAAGAGAACGTGGTGAACTACATCACCAAGCTGA
AGGGCCCCAAGGCCGCTGCCCTGTTCGCTAAGACCCACAACCTGAACATGCTGC
```

-continued
AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCACTCGAGTATGTTACGTGCAAAGGTGATTGTCACCCCCCGAAAGACCATA

TTGTGACACACCCTCAGTATCACGCCCAAACATTTACAGCCGCGGTGTCAAAAAC

CGCGTGGACGTGGTTAACATCCCTGCTGGGAGGATCAGCCGTAATTATTATAATT

GGCTTGGTGCTGGCTACTATTGTGGCCATGTACGTGCTGACCAACCAGAAACATA

ATTGAATACAGCAGCAATTGGCAAGCTGCTTACATAGAACTCGCGGCGATTGGC

ATGCCGCCTTAAAATTTTTATTTTATTTTTTCTTTTCTTTTCCGAATCGGATTTTGT

TTTTAATATTTCAAAAAAAAAAAAAAAAAAAAAAAAATCTAGAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

SEQ ID NO: 124
ATGGGCGGCGCATGAGAGAAGCCCAGACCAATTACCTACCCAAAATGGAGAAA

GTTCACGTTGACATCGAGGAAGACAGCCCATTCCTCAGAGCTTTGCAGCGGAGCT

TCCCGCAGTTTGAGGTAGAAGCCAAGCAGGTCACTGATAATGACCATGCTAATG

CCAGAGCGTTTTCGCATCTGGCTTCAAAACTGATCGAAACGGAGGTGGACCCATC

CGACACGATCCTTGACATTGGAAGTGCGCCCGCCCGCAGAATGTATTCTAAGCAC

AAGTATCATTGTATCTGTCCGATGAGATGTGCGGAAGATCCGGACAGATTGTATA

AGTATGCAACTAAGCTGAAGAAAAACTGTAAGGAAATAACTGATAAGGAATTGG

ACAAGAAAATGAAGGAGCTGGCCGCCGTCATGAGCGACCCTGACCTGGAAACTG

AGACTATGTGCCTCCACGACGACGAGTCGTGTCGCTACGAAGGGCAAGTCGCTG

TTTACCAGGATGTATACGCCGTCGACGGCCCCACCAGCCTGTACCACCAGGCCAA

CAAGGGCGTGAGGGTGGCCTACTGGATCGGCTTCGACACCACACCCTTCATGTTC

-continued

```
AAGAACCTGGCCGGCGCCTACCCCAGCTACAGCACCAACTGGGCCGACGAGACC

GTGCTGACCGCCAGGAACATCGGCCTGTGCAGCAGCGACGTGATGGAGAGGAGC

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

CCTACCACGGCAAGGTGGTCGTGCCCGAGGGCCACGCCATCCCCGTGCAGGACT

TCCAGGCCCTGAGCGAGAGCGCCACCATCGTGTACAACGAGAGGGAGTTCGTGA

ACAGGTACCTGCACCATATCGCCACCCACGGCGGAGCCCTGAACACCGACGAGG

AATACTACAAGACCGTGAAGCCCAGCGAGCACGACGGCGAGTACCTGTACGACA

TCGACAGGAAGCAGTGCGTGAAGAAAGAGCTGGTGACCGGCCTGGGACTGACCG

GCGAGCTGGTGGACCCACCCTTCCACGAGTTCGCCTACGAGAGCCTGAGGACCA

GACCCGCCGCTCCCTACCAGGTGCCCACCATCGGCGTGTACGGCGTGCCCGGCA

GCGGAAAGAGCGGCATCATCAAGAGCGCCGTGACCAAGAAAGACCTGGTGGTC

AGCGCCAAGAAAGAGAACTGCGCCGAGATCATCAGGGACGTGAAGAAGATGAA

AGGCCTGGACGTGAACGCGCGCACCGTGGACAGCGTGCTGCTGAACGGCTGCAA

GCACCCCGTGGAGACCCTGTACATCGACGAGGCCTTCGCTTGCCACGCCGGCACC

CTGAGGGCCCTGATCGCCATCATCAGGCCCAAGAAAGCCGTGCTGTGCGGCGAC

CCCAAGCAGTGCGGCTTCTTCAACATGATGTGCCTGAAGGTGCACTTCAACCACG

AGATCTGCACCCAGGTGTTCCACAAGAGCATCAGCAGGCGGTGCACCAAGAGCG

TGACCAGCGTCGTGAGCACCCTGTTCTACGACAAGAAAATGAGGACCACCAACC

CCAAGGAGACCAAAATCGTGATCGACACCACAGGCAGCACCAAGCCCAAGCAG

GACGACCTGATCCTGACCTGCTTCAGGGGCTGGGTGAAGCAGCTGCAGATCGAC
```

-continued

```
TACAAGGGCAACGAGATCATGACCGCCGCTGCCAGCCAGGGCCTGACCAGGAAG
GGCGTGTACGCCGTGAGGTACAAGGTGAACGAGAACCCACTGTACGCTCCCACC
AGCGAGCACGTGAACGTGCTGCTGACCAGGACCGAGGACAGGATCGTGTGGAAG
ACCCTGGCCGGCGACCCCTGGATCAAGACCCTGACCGCCAAGTACCCCGGCAAC
TTCACCGCCACCATCGAAGAGTGGCAGGCCGAGCACGACGCCATCATGAGGCAC
ATCCTGGAGAGGCCCGACCCCACCGACGTGTTCCAGAACAAGGCCAACGTGTGC
TGGGCCAAGGCCCTGGTGCCCGTGCTGAAGACCGCCGGCATCGACATGACCACA
GAGCAGTGGAACACCGTGGACTACTTCGAGACCGACAAGGCCCACAGCGCCGAG
ATCGTGCTGAACCAGCTGTGCGTGAGGTTCTTCGGCCTGGACCTGGACAGCGGCC
TGTTCAGCGCCCCCACCGTGCCACTGAGCATCAGGAACAACCACTGGGACAACA
GCCCCAGCCCAAACATGTACGGCCTGAACAAGGAGGTGGTCAGGCAGCTGAGCA
GGCGGTACCCACAGCTGCCCAGGGCCGTGGCCACCGGCAGGGTGTACGACATGA
ACACCGGCACCCTGAGGAACTACGACCCCAGGATCAACCTGGTGCCCGTGAACA
GGCGGCTGCCCCACGCCCTGGTGCTGCACCACAACGAGCACCCACAGAGCGACT
TCAGCTCCTTCGTGAGCAAGCTGAAAGGCAGGACCGTGCTGGTCGTGGGCGAGA
AGCTGAGCGTGCCCGGCAAGATGGTGGACTGGCTGAGCGACAGGCCCGAGGCCA
CCTTCCGGGCCAGGCTGGACCTCGGCATCCCCGGCGACGTGCCCAAGTACGACA
TCATCTTCGTGAACGTCAGGACCCCATACAAGTACCACCATTACCAGCAGTGCGA
GGACCACGCCATCAAGCTGAGCATGCTGACCAAGAAGGCCTGCCTGCACCTGAA
CCCCGGAGGCACCTGCGTGAGCATCGGCTACGGCTACGCCGACAGGGCCAGCGA
GAGCATCATTGGCGCCATCGCCAGGCTGTTCAAGTTCAGCAGGGTGTGCAAACC
CAAGAGCAGCCTGGAGGAAACCGAGGTGCTGTTCGTGTTCATCGGCTACGACCG
GAAGGCCAGGACCCACAACCCCTACAAGCTGAGCAGCACCCTGACAAACATCTA
CACCGGCAGCAGGCTGCACGAGGCCGGCTGCGCCCCCAGCTACCACGTGGTCAG
GGGCGATATCGCCACCGCCACCGAGGGCGTGATCATCAACGCTGCCAACAGCAA
GGGCCAGCCCGGAGGCGGAGTGTGCGGCGCCCTGTACAAGAAGTTCCCCGAGAG
CTTCGACCTGCAGCCCATCGAGGTGGGCAAGGCCAGGCTGGTGAAGGGCGCCGC
TAAGCACATCATCCACGCCGTGGGCCCCAACTTCAACAAGGTGAGCGAGGTGGA
AGGCGACAAGCAGCTGGCCGAAGCCTACGAGAGCATCGCCAAGATCGTGAACG
ACAATAACTACAAGAGCGTGGCCATCCCACTGCTCAGCACCGGCATCTTCAGCG
GCAACAAGGACAGGCTGACCCAGAGCCTGAACCACCTGCTCACCGCCCTGGACA
CCACCGATGCCGACGTGGCCATCTACTGCAGGGACAAGAAGTGGGAGATGACCC
TGAAGGAGGCCGTGGCCAGGCGGGAGGCCGTGGAAGAGATCTGCATCAGCGAC
GACTCCAGCGTGACCGAGCCCGACGCCGAGCTGGTGAGGGTGCACCCCAAGAGC
TCCCTGGCCGGCAGGAAGGGCTACAGCACCAGCGACGGCAAGACCTTCAGCTAC
CTGGAGGGCACCAAGTTCCACCAGGCCGCTAAGGACATCGCCGAGATCAACGCT
ATGTGGCCCGTGGCCACCGAGGCCAACGAGCAGGTGTGCATGTACATCCTGGGC
GAGAGCATGTCCAGCATCAGGAGCAAGTGCCCCGTGGAGGAAAGCGAGGCCAG
CACACCACCCAGCACCCTGCCCTGCCTGTGCATCCACGCTATGACACCCGAGAGG
GTGCAGCGGCTGAAGGCCAGCAGGCCCGAGCAGATCACCGTGTGCAGCTCCTTC
CCACTGCCCAAGTACAGGATCACCGGCGTGCAGAAGATCCAGTGCAGCCAGCCC
```

-continued

```
ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA

GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA

AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC
```

-continued

```
TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCATGTTTGTTTTTCTTGTTTTATTGCCACTAGTCTCTAGTCAGTGTGTTAATC

TTACAACCAGAACTCAATTACCCCCTGCATACACTAATTCTTTCACACGTGGTGT

TTATTACCCTGACAAAGTTTTCAGATCCTCAGTTTTACATTCAACTCAGGACTTGT

TCTTACCTTTCTTTTCCAATGTTACTTGGTTCCATGCTATACATGTCTCTGGGACC

AATGGTACTAAGAGGTTTGATAACCCTGTCCTACCATTTAATGATGGTGTTTATTT

TGCTTCCACTGAGAAGTCTAACATAATAAGAGGCTGGATTTTTGGTACTACTTTA

GATTCGAAGACCCAGTCCCTACTTATTGTTAATAACGCTACTAATGTTGTTATTAA

AGTCTGTGAATTTCAATTTTGTAATGATCCATTTTTGGGTGTTTATTACCACAAAA

ACAACAAAAGTTGGATGGAAAGTGAGTTCAGAGTTTATTCTAGTGCGAATAATT

GCACTTTTGAATATGTCTCTCAGCCTTTTCTTATGGACCTTGAAGGAAAACAGGG

TAATTTCAAAAATCTTAGGGAATTTGTGTTTAAGAATATTGATGGTTATTTTAAA

ATATATTCTAAGCACACGCCTATTAATTTAGTGCGTGATCTCCCTCAGGGTTTTTC

GGCTTTAGAACCATTGGTAGATTTGCCAATAGGTATTAACATCACTAGGTTTCAA

ACTTTACTTGCTTTACATAGAAGTTATTTGACTCCTGGTGATTCTTCTTCAGGTTG

GACAGCTGGTGCTGCAGCTTATTATGTGGGTTATCTTCAACCTAGGACTTTTCTAT

TAAAATATAATGAAAATGGAACCATTACAGATGCTGTAGACTGTGCACTTGACC

CTCTCTCAGAAACAAAGTGTACGTTGAAATCCTTCACTGTAGAAAAAGGAATCTA

TCAAACTTCTAACTTTAGAGTCCAACCAACAGAATCTATTGTTAGATTTCCTAAT

ATTACAAACTTGTGCCCTTTTGGTGAAGTTTTTAACGCCACCAGATTTGCATCTGT

TTATGCTTGGAACAGGAAGAGAATCAGCAACTGTGTTGCTGATTATTCTGTCCTA

TATAATTCCGCATCATTTTCCACTTTTAAGTGTTATGGAGTGTCTCCTACTAAATT

AAATGATCTCTGCTTTACTAATGTCTATGCAGATTCATTTGTAATTAGAGGTGATG

AAGTCAGACAAATCGCTCCAGGGCAAACTGGAAAGATTGCTGATTATAATTATA

AATTACCAGATGATTTTACAGGCTGCGTTATAGCTTGGAATTCTAACAATCTTGA

TTCTAAGGTTGGTGGTAATTATAATTACCTGTATAGATTGTTTAGGAAGTCTAATC

TCAAACCTTTTGAGAGAGATATTCAACTGAAATCTATCAGGCCGGTAGCACACC

TTGTAATGGTGTTGAAGGTTTTAATTGTTACTTTCCTTTACAATCATATGGTTTCC

AACCCACTAATGGTGTTGGTTACCAACCATACAGAGTAGTAGTACTTTCTTTTGA

ACTTCTACATGCACCAGCAACTGTTTGTGGACCTAAAAAGTCTACTAATTTGGTT

AAAAACAAATGTGTCAATTTCAACTTCAATGGTTTAACAGGCACAGGTGTTCTTA

CTGAGTCTAACAAAAAGTTTCTGCCTTTCCAACAATTTGGCAGAGACATTGCTGA

CACTACTGATGCTGTCCGTGATCCACAGACACTTGAGATTCTTGACATTACACCA

TGTTCTTTTGGTGGTGTCAGTGTTATAACACCAGGAACAAATACTTCTAACCAGG
```

-continued

```
TTGCTGTTCTTTATCAGGATGTTAACTGCACAGAAGTCCCTGTTGCTATTCATGCA
GATCAACTTACTCCTACTTGGCGTGTTTATTCTACAGGTTCTAATGTTTTTCAAAC
ACGTGCAGGCTGTTTAATAGGGGCTGAACATGTCAACAACTCATATGAGTGTGA
CATACCCATTGGTGCAGGTATATGCGCTAGTTATCAGACTCAGACTAATTCTCCT
CGGCGGGCACGTAGTGTAGCTAGTCAATCCATCATTGCCTACACTATGTCACTTG
GTGCAGAAAATTCAGTTGCTTACTCTAATAACTCTATTGCCATACCCACAAATTT
TACTATTAGTGTTACCACAGAAATTCTACCAGTGTCTATGACCAAGACATCAGTA
GATTGTACAATGTACATTTGTGGTGATTCAACTGAATGCAGCAATCTTTTGTTGC
AATATGGCAGTTTTTGTACACAATTAAACCGTGCTTTAACTGGAATAGCTGTTGA
ACAAGACAAAAACACCCAAGAAGTTTTTGCACAAGTCAAACAAATTTACAAAAC
ACCACCAATTAAAGATTTTGGTGGTTTTAATTTTTCACAAATATTACCAGATCCAT
CAAAACCAAGCAAGAGGTCATTTATTGAAGATCTACTTTTCAACAAAGTGACACT
TGCAGATGCTGGCTTCATCAAACAATATGGTGATTGCCTTGGTGATATTGCTGCT
AGAGACCTCATTTGTGCACAAAAGTTTAACGGCCTTACTGTTTTGCCACCTTTGCT
CACAGATGAAATGATTGCTAATACACTTCTGCACTGTTAGCGGGTACAATCACT
TCTGGTTGGACCTTTGGTGCAGGTGCTGCATTACAAATACCATTTGCTATGCAAA
TGGCTTATAGGTTTAATGGTATTGGAGTTACACAGAATGTTCTCTATGAGAACCA
AAAATTGATTGCCAACCAATTTAATAGTGCTATTGGCAAAATTCAAGACTCACTT
TCTTCCACAGCAAGTGCACTTGGAAAACTTCAAGATGTGGTCAACCAAAATGCA
CAAGCTTTAAACACGCTTGTTAAACAACTTAGCTCCAATTTTGGTGCAATTTCAA
GTGTTTTAAATGATATCCTTTCACGTCTTGACAAAGTTGAGGCTGAAGTGCAAAT
TGATAGGTTGATCACAGGCAGACTTCAAAGTTTGCAGACATATGTGACTCAACA
ATTAATTAGAGCTGCAGAAATCAGAGCTTCTGCTAATCTTGCTGCTACTAAAATG
TCAGAGTGTGTACTTGGACAATCAAAAAGAGTTGATTTTTGTGGAAAGGGCTATC
ATCTTATGTCCTTCCCTCAGTCAGCACCTCATGGTGTAGTCTTCTTGCATGTGACT
TATGTCCCTGCACAAGAAAAGAACTTCACAACTGCTCCTGCCATTTGTCATGATG
GAAAAGCACACTTTCCTCGTGAAGGTGTCTTTGTTTCAAATGGCACACACTGGTT
TGTAACACAAAGGAATTTTTATGAACCACAAATCATTACTACAGACAACACATTT
GTGTCTGGTAACTGTGATGTTGTAATAGGAATTGTCAACAACACAGTTTATGATC
CTTTGCAACCTGAATTAGACTCATTCAAGGAGGAGTTAGATAAATATTTTAAGAA
TCATACATCACCAGATGTTGATTTAGGTGACATCTCTGGCATTAATGCTTCAGTTG
TAAACATTCAAAAAGAAATTGACCGCCTCAATGAGGTTGCCAAGAATTTAAATG
AATCTCTCATCGATCTCCAAGAACTTGGAAAGTATGAGCAGTATATAAAATGGCC
ATGGTACATTTGGCTAGGTTTTATAGCTGGCTTGATTGCCATAGTAATGGTGACA
ATTATGCTTTGCTGTATGACCAGTTGCTGTAGTTGTCTCAAGGGCTGTTGTTCTTG
TGGATCCTGCTGCAAATTTGATGAAGACGACTCTGAGCCAGTGCTCAAAGGAGT
CAAATTACATTACACATAAACTCGAGTATGTTACGTGCAAAGGTGATTGTCACCC
CCCGAAAGACCATATTGTGACACACCCTCAGTATCACGCCCAAACATTTACAGCC
GCGGTGTCAAAAACCGCGTGGACGTGGTTAACATCCCTGCTGGGAGGATCAGCC
GTAATTATTATAATTGGCTTGGTGCTGGCTACTATTGTGGCCATGTACGTGCTGAC
```

-continued

CAACCAGAAACATAATTGAATACAGCAGCAATTGGCAAGCTGCTTACATAGAAC

TCGCGGCGATTGGCATGCCGCCTTAAAATTTTTATTTTATTTTTTCTTTTCTTTTCC

GAATCGGATTTTGTTTTTAATATTTCAAAAAAAAAAAAAAAAAAAAAAAAAATCT

AGAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA

SEQ ID NO: 125

ATGGGCGGCGCATGAGAGAAGCCCAGACCAATTACCTACCCAAAATGGAGAAA

GTTCACGTTGACATCGAGGAAGACAGCCCATTCCTCAGAGCTTTGCAGCGGAGCT

TCCCGCAGTTTGAGGTAGAAGCCAAGCAGGTCACTGATAATGACCATGCTAATG

CCAGAGCGTTTTCGCATCTGGCTTCAAAACTGATCGAAACGGAGGTGGACCCATC

CGACACGATCCTTGACATTGGAAGTGCGCCCGCCCGCAGAATGTATTCTAAGCAC

AAGTATCATTGTATCTGTCCGATGAGATGTGCGGAAGATCCGGACAGATTGTATA

AGTATGCAACTAAGCTGAAGAAAAACTGTAAGGAAATAACTGATAAGGAATTGG

ACAAGAAAATGAAGGAGCTGGCCGCCGTCATGAGCGACCCTGACCTGGAAACTG

AGACTATGTGCCTCCACGACGACGAGTCGTGTCGCTACGAAGGGCAAGTCGCTG

TTTACCAGGATGTATACGCCGTCGACGGCCCCACCAGCCTGTACCACCAGGCCAA

CAAGGGCGTGAGGGTGGCCTACTGGATCGGCTTCGACACCACACCCTTCATGTTC

AAGAACCTGGCCGGCGCCTACCCCAGCTACAGCACCAACTGGGCCGACGAGACC

GTGCTGACCGCCAGGAACATCGGCCTGTGCAGCAGCGACGTGATGGAGAGGAGC

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

-continued

```
CCTACCACGGCAAGGTGGTCGTGCCCGAGGGCCACGCCATCCCCGTGCAGGACT
TCCAGGCCCTGAGCGAGAGCGCCACCATCGTGTACAACGAGAGGGAGTTCGTGA
ACAGGTACCTGCACCATATCGCCACCCACGGCGGAGCCCTGAACACCGACGAGG
AATACTACAAGACCGTGAAGCCCAGCGAGCACGACGGCGAGTACCTGTACGACA
TCGACAGGAAGCAGTGCGTGAAGAAAGAGCTGGTGACCGGCCTGGGACTGACCG
GCGAGCTGGTGGACCCACCCTTCCACGAGTTCGCCTACGAGAGCCTGAGGACCA
GACCCGCCGCTCCCTACCAGGTGCCCACCATCGGCGTGTACGGCGTGCCCGGCA
GCGGAAAGAGCGGCATCATCAAGAGCGCCGTGACCAAGAAAGACCTGGTGGTC
AGCGCCAAGAAAGAGAACTGCGCCGAGATCATCAGGGACGTGAAGAAGATGAA
AGGCCTGGACGTGAACGCGCGCACCGTGGACAGCGTGCTGCTGAACGGCTGCAA
GCACCCCGTGGAGACCCTGTACATCGACGAGGCCTTCGCTTGCCACGCCGGCACC
CTGAGGGCCCTGATCGCCATCATCAGGCCCAAGAAAGCCGTGCTGTGCGGCGAC
CCCAAGCAGTGCGGCTTCTTCAACATGATGTGCCTGAAGGTGCACTTCAACCACG
AGATCTGCACCCAGGTGTTCCACAAGAGCATCAGCAGGCGGTGCACCAAGAGCG
TGACCAGCGTCGTGAGCACCCTGTTCTACGACAAGAAAATGAGGACCACCAACC
CCAAGGAGACCAAAATCGTGATCGACACCACAGGCAGCACCAAGCCCAAGCAG
GACGACCTGATCCTGACCTGCTTCAGGGGCTGGGTGAAGCAGCTGCAGATCGAC
TACAAGGGCAACGAGATCATGACCGCCGCTGCCAGCCAGGGCCTGACCAGGAAG
GGCGTGTACGCCGTGAGGTACAAGGTGAACGAGAACCCACTGTACGCTCCCACC
AGCGAGCACGTGAACGTGCTGCTGACCAGGACCGAGGACAGGATCGTGTGGAAG
ACCCTGGCCGGCGACCCCTGGATCAAGACCCTGACCGCCAAGTACCCCGGCAAC
TTCACCGCCACCATCGAAGAGTGGCAGGCCGAGCACGACGCCATCATGAGGCAC
ATCCTGGAGAGGCCCGACCCCACCGACGTGTTCCAGAACAAGGCCAACGTGTGC
TGGGCCAAGGCCCTGGTGCCCGTGCTGAAGACCGCCGGCATCGACATGACCACA
GAGCAGTGGAACACCGTGGACTACTTCGAGACCGACAAGGCCCACAGCGCCGAG
ATCGTGCTGAACCAGCTGTGCGTGAGGTTCTTCGGCCTGGACCTGGACAGCGGCC
TGTTCAGCGCCCCCACCGTGCCACTGAGCATCAGGAACAACCACTGGGACAACA
GCCCCAGCCCAAACATGTACGGCCTGAACAAGGAGGTGGTCAGGCAGCTGAGCA
GGCGGTACCCACAGCTGCCCAGGGCCGTGGCCACCGGCAGGGTGTACGACATGA
ACACCGGCACCCTGAGGAACTACGACCCCAGGATCAACCTGGTGCCCGTGAACA
GGCGGCTGCCCCACGCCCTGGTGCTGCACCACAACGAGCACCCACAGAGCGACT
TCAGCTCCTTCGTGAGCAAGCTGAAAGGCAGGACCGTGCTGGTCGTGGGCGAGA
AGCTGAGCGTGCCCGGCAAGATGGTGGACTGGCTGAGCGACAGGCCCGAGGCCA
CCTTCCGGGCCAGGCTGGACCTCGGCATCCCCGGCGACGTGCCCAAGTACGACA
TCATCTTCGTGAACGTCAGGACCCCATACAAGTACCACCATTACCAGCAGTGCGA
GGACCACGCCATCAAGCTGAGCATGCTGACCAAGAAGGCCTGCCTGCACCTGAA
CCCCGGAGGCACCTGCGTGAGCATCGGCTACGGCTACGCCGACAGGGCCAGCGA
GAGCATCATTGGCGCCATCGCCAGGCTGTTCAAGTTCAGCAGGGTGTGCAAACC
CAAGAGCAGCCTGGAGGAAACCGAGGTGCTGTTCGTGTTCATCGGCTACGACCG
GAAGGCCAGGACCCACAACCCCTACAAGCTGAGCAGCACCCTGACAAACATCTA
```

-continued

```
CACCGGCAGCAGGCTGCACGAGGCCGGCTGCGCCCCAGCTACCACGTGGTCAG

GGGCGATATCGCCACCGCCACCGAGGGCGTGATCATCAACGCTGCCAACAGCAA

GGGCCAGCCCGGAGGCGGAGTGTGCGGCGCCCTGTACAAGAAGTTCCCCGAGAG

CTTCGACCTGCAGCCCATCGAGGTGGGCAAGGCCAGGCTGGTGAAGGGCGCCGC

TAAGCACATCATCCACGCCGTGGGCCCCAACTTCAACAAGGTGAGCGAGGTGGA

AGGCGACAAGCAGCTGGCCGAAGCCTACGAGAGCATCGCCAAGATCGTGAACG

ACAATAACTACAAGAGCGTGGCCATCCCACTGCTCAGCACCGGCATCTTCAGCG

GCAACAAGGACAGGCTGACCCAGAGCCTGAACCACCTGCTCACCGCCCTGGACA

CCACCGATGCCGACGTGGCCATCTACTGCAGGGACAAGAAGTGGGAGATGACCC

TGAAGGAGGCCGTGGCCAGGCGGGAGGCCGTGGAAGAGATCTGCATCAGCGAC

GACTCCAGCGTGACCGAGCCCGACGCCGAGCTGGTGAGGGTGCACCCCAAGAGC

TCCCTGGCCGGCAGGAAGGGCTACAGCACCAGCGACGGCAAGACCTTCAGCTAC

CTGGAGGGCACCAAGTTCCACCAGGCCGCTAAGGACATCGCCGAGATCAACGCT

ATGTGGCCCGTGGCCACCGAGGCCAACGAGCAGGTGTGCATGTACATCCTGGGC

GAGAGCATGTCCAGCATCAGGAGCAAGTGCCCCGTGGAGGAAAGCGAGGCCAG

CACACCACCCAGCACCCTGCCCTGCCTGTGCATCCACGCTATGACACCCGAGAGG

GTGCAGCGGCTGAAGGCCAGCAGGCCCGAGCAGATCACCGTGTGCAGCTCCTTC

CCACTGCCCAAGTACAGGATCACCGGCGTGCAGAAGATCCAGTGCAGCCAGCCC

ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA
```

-continued

```
GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA

AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCATGTTCGTCTTCCTGGTCCTGCTGCCTCTGGTCTCCTCACAGTGCGTCAAT

CTGACAACTCGGACTCAGCTGCCACCTGCTTATACTAATAGCTTCACCAGAGGCG

TGTACTATCCTGACAAGGTGTTTAGAAGCTCCGTGCTGCACTCTACACAGGATCT

GTTTCTGCCATTCTTTAGCAACGTGACCTGGTTCCACGCCATCCACGTGAGCGGC

ACCAATGGCACAAAGCGGTTCGACAATCCCGTGCTGCCTTTTAACGATGGCGTGT

ACTTCGCCTCTACCGAGAAGTCCAACATCATCAGAGGCTGGATCTTTGGCACCAC

ACTGGACTCCAAGACACAGTCTCTGCTGATCGTGAACAATGCCACCAACGTGGTC

ATCAAGGTGTGCGAGTTCCAGTTTTGTAATGATCCCTTCCTGGGCGTGTACTATC

ACAAGAACAATAAGAGCTGGATGGAGTCCGAGTTTAGAGTGTATTCTAGCGCCA

ACAACTGCACATTTGAGTACGTGAGCCAGCCTTTCCTGATGGACCTGGAGGGCA

AGCAGGGCAATTTCAAGAACCTGAGGGAGTTCGTGTTTAAGAATATCGACGGCT

ACTTCAAAATCTACTCTAAGCACACCCCCATCAACCTGGTGCGCGACCTGCCTCA

GGGCTTCAGCGCCCTGGAGCCCCTGGTGGATCTGCCTATCGGCATCAACATCACC

CGGTTTCAGACACTGCTGGCCCTGCACAGAAGCTACCTGACACCCGGCGACTCCT

CTAGCGGATGGACCGCCGGCGCTGCCGCCTACTATGTGGGCTACCTCCAGCCCCG
```

-continued

```
GACCTTCCTGCTGAAGTACAACGAGAATGGCACCATCACAGACGCAGTGGATTG

CGCCCTGGACCCCCTGAGCGAGACAAAGTGTACACTGAAGTCCTTTACCGTGGA

GAAGGGCATCTATCAGACATCCAATTTCAGGGTGCAGCCAACCGAGTCTATCGT

GCGCTTTCCTAATATCACAAACCTGTGCCCATTTGGCGAGGTGTTCAACGCAACC

CGCTTCGCCAGCGTGTACGCCTGGAATAGGAAGCGGATCAGCAACTGCGTGGCC

GACTATAGCGTGCTGTACAACTCCGCCTCTTTCAGCACCTTTAAGTGCTATGGCG

TGTCCCCCACAAAGCTGAATGACCTGTGCTTTACCAACGTCTACGCCGATTCTTT

CGTGATCAGGGGCGACGAGGTGCGCCAGATCGCCCCCGGCCAGACAGGCAAGAT

CGCAGACTACAATTATAAGCTGCCAGACGATTTCACCGGCTGCGTGATCGCCTGG

AACAGCAACAATCTGGATTCCAAAGTGGGCGGCAACTACAATTATCTGTACCGG

CTGTTTAGAAAGAGCAATCTGAAGCCCTTCGAGAGGGACATCTCTACAGAAATC

TACCAGGCCGGCAGCACCCCTTGCAATGGCGTGGAGGGCTTTAACTGTTATTTCC

CACTCCAGTCCTACGGCTTCCAGCCCACAAACGGCGTGGGCTATCAGCCTTACCG

CGTGGTGGTGCTGAGCTTTGAGCTGCTGCACGCCCCAGCAACAGTGTGCGGCCCC

AAGAAGTCCACCAATCTGGTGAAGAACAAGTGCGTGAACTTCAACTTCAACGGC

CTGACCGGCACAGGCGTGCTGACCGAGTCCAACAAGAAGTTCCTGCCATTTCAG

CAGTTCGGCAGGGACATCGCAGATACCACAGACGCCGTGCGCGACCCACAGACC

CTGGAGATCCTGGACATCACACCCTGCTCTTTCGGCGGCGTGAGCGTGATCACAC

CCGGCACCAATACAAGCAACCAGGTGGCCGTGCTGTATCAGGACGTGAATTGTA

CCGAGGTGCCCGTGGCTATCCACGCCGATCAGCTGACCCCAACATGGCGGGTGT

ACAGCACCGGCTCCAACGTCTTCCAGACAAGAGCCGGATGCCTGATCGGAGCAG

AGCACGTGAACAATTCCTATGAGTGCGACATCCCAATCGGCGCCGGCATCTGTGC

CTCTTACCAGACCCAGACAAACTCTCCCAGACGGGCCCGGAGCGTGGCCTCCCA

GTCTATCATCGCCTATACCATGTCCCTGGGCGCCGAGAACAGCGTGGCCTACTCT

AACAATAGCATCGCCATCCCAACCAACTTCACAATCTCTGTGACCACAGAGATCC

TGCCCGTGTCCATGACCAAGACATCTGTGGACTGCACAATGTATATCTGTGGCGA

TTCTACCGAGTGCAGCAACCTGCTGCTCCAGTACGGCAGCTTTTGTACCCAGCTG

AATAGAGCCCTGACAGGCATCGCCGTGGAGCAGGATAAGAACACACAGGAGGT

GTTCGCCCAGGTGAAGCAAATCTACAAGACCCCCCCTATCAAGGACTTTGGCGG

CTTCAATTTTTCCCAGATCCTGCCTGATCCATCCAAGCCTTCTAAGCGGAGCTTTA

TCGAGGACCTGCTGTTCAACAAGGTGACCCTGGCCGATGCCGGCTTCATCAAGCA

GTATGGCGATTGCCTGGGCGACATCGCAGCCAGGGACCTGATCTGCGCCCAGAA

GTTTAATGGCCTGACCGTGCTGCCACCCCTGCTGACAGATGAGATGATCGCACAG

TACACAAGCGCCCTGCTGGCCGGCACCATCACATCCGGATGGACCTTCGGCGCA

GGAGCCGCCCTCCAGATCCCCTTTGCCATGCAGATGGCCTATAGGTTCAACGGCA

TCGGCGTGACCCAGAATGTGCTGTACGAGAACCAGAAGCTGATCGCCAATCAGT

TTAACTCCGCCATCGGCAAGATCCAGGACAGCCTGTCCTCTACAGCCAGCGCCCT

GGGCAAGCTCCAGGATGTGGTGAATCAGAACGCCCAGGCCCTGAATACCCTGGT

GAAGCAGCTGAGCAGCAACTTCGGCGCCATCTCTAGCGTGCTGAATGACATCCT

GAGCCGGCTGGACAAGGTGGAGGCAGAGGTGCAGATCGACCGGCTGATCACCG

GCCGGCTCCAGAGCCTCCAGACCTATGTGACACAGCAGCTGATCAGGGCCGCCG
```

-continued

AGATCAGGGCCAGCGCCAATCTGGCAGCAACCAAGATGTCCGAGTGCGTGCTGG

GCCAGTCTAAGAGAGTGGACTTTTGTGGCAAGGGCTATCACCTGATGTCCTTCCC

TCAGTCTGCCCCACACGGCGTGGTGTTTCTGCACGTGACCTACGTGCCCGCCCAG

GAGAAGAACTTCACCACAGCCCCTGCCATCTGCCACGATGGCAAGGCCCACTTTC

CAAGGGAGGGCGTGTTCGTGTCCAACGGCACCCACTGGTTTGTGACACAGCGCA

ATTTCTACGAGCCCCAGATCATCACCACAGACAACACCTTCGTGAGCGGCAACTG

TGACGTGGTCATCGGCATCGTGAACAATACCGTGTATGATCCACTCCAGCCCGAG

CTGGACAGCTTTAAGGAGGAGCTGGATAAGTATTTCAAGAATCACACCTCCCCTG

ACGTGGATCTGGGCGACATCAGCGGCATCAATGCCTCCGTGGTGAACATCCAGA

AGGAGATCGACCGCCTGAACGAGGTGGCTAAGAATCTGAACGAGAGCCTGATCG

ACCTCCAGGAGCTGGGCAAGTATGAGCAGTACATCAAGTGGCCCTGGTACATCT

GGCTGGGCTTCATCGCCGGCCTGATCGCCATCGTGATGGTGACCATCATGCTGTG

CTGTATGACATCCTGCTGTTCTTGCCTGAAGGGCTGCTGTAGCTGTGGCTCCTGCT

GTAAGTTTGACGAGGATGACTCTGAACCTGTGCTGAAGGGCGTGAAGCTGCATT

ACACCTAAACTCGAGTATGTTACGTGCAAAGGTGATTGTCACCCCCCGAAAGAC

CATATTGTGACACACCCTCAGTATCACGCCCAAACATTTACAGCCGCGGTGTCAA

AAACCGCGTGGACGTGGTTAACATCCCTGCTGGGAGGATCAGCCGTAATTATTAT

AATTGGCTTGGTGCTGGCTACTATTGTGGCCATGTACGTGCTGACCAACCAGAAA

CATAATTGAATACAGCAGCAATTGGCAAGCTGCTTACATAGAACTCGCGGCGAT

TGGCATGCCGCCTTAAAATTTTTATTTTATTTTTTCTTTTCTTTTCCGAATCGGATT
TTGTTTTTAATATTTCAAAAAAAAAAAAAAAAAAAAAAAAATCTAGAAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

SEQ ID NO: 79

MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK

GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRHKITSIYKRPDTQTIIKVNSDFHSFV

LPRIGSNTLEIGLRTRIRKMLEEHKEPSPLITAEDVQEAKCAADEAKEVREAEELRAA

LPPLAADVEEPTLEADVDLMLQEAGAGSVETPRGLIKVTSYDGEDKIGSYAVLSPQA

VLKSEKLSCIHPLAEQVIVITHSGRKGRYAVEPYHGKVVVPEGHAIPVQDFQALSESA

TIVYNEREFVNRYLHHIATHGGALNTDEEYYKTVKPSEHDGEYLYDIDRKQCVKKEL

VTGLGLTGELVDPPFHEFAYESLRTRPAAPYQVPTIGVYGVPGSGKSGIIKSAVTKKD

LVVSAKKENCAEIIRDVKKMKGLDVNARTVDSVLLNGCKHPVETLYIDEAFACHAG

TLRALIAIIRPKKAVLCGDPKQCGFFNMMCLKVHFNHEICTQVFHKSISRRCTKSVTS

-continued

VVSTLFYDKKMRTTNPKETKIVIDTTGSTKPKQDDLILTCFRGWVKQLQIDYKGNEI
MTAAASQGLTRKGVYAVRYKVNENPLYAPTSEHVNVLLTRTEDRIVWKTLAGDPW
KTAGIDMTTEQWNTVDYFETDKAHSAEIVLNQLCVRFFGLDLDSGLFSAPTVPLSIR
NNHWDNSPSPNMYGLNKEVVRQLSRRYPQLPRAVATGRVYDMNTGTLRNYDPRIN
LVPVNRRLPHALVLHHNEHPQSDFSSFVSKLKGRTVLVVGEKLSVPGKMVDWLSDR
PEATFRARLDLGIPGDVPKYDIIFVNVRTPYKYHHYQQCEDHAIKLSMLTKKACLHL
NPGGTCVSIGYGYADRASESIIGAIARLFKFSRVCKPKSSLEETEVLFVFIGYDRKART
HNPYKLSSTLTNIYTGSRLHEAGCAPSYHVVRGDIATATEGVIINAANSKGQPGGGV
CGALYKKFPESFDLQPIEVGKARLVKGAAKHIIHAVGPNFNKVSEVEGDKQLAEAYE
SIAKIVNDNNYKSVAIPLLSTGIFSGNKDRLTQSLNHLLTALDTTDADVAIYCRDKKW
EMTLKEAVARREAVEEICISDDSSVTEPDAELVRVHPKSSLAGRKGYSTSDGKTFSYL
EGTKFHQAAKDIAEINAMWPVATEANEQVCMYILGESMSSIRSKCPVEESEASTPPST
LPCLCIHAMTPERVQRLKASRPEQITVCSSFPLPKYRITGVQKIQCSQPILFSPKVPAYI
HPRKYLVETPPVDETPEPSAENQSTEGTPEQPPLITEDETRTRTPEPINIEEEEEDSISLLS
DGPTHQVLQVEADIHGPPSVSSSSWSIPHASDFDVDSLSILDTLEGASVTSGATSAETN
SYFAKSMEFLARPVPAPRTVFRNPPHPAPRTRTPSLAPSRACSRTSLVSTPPGVNRVIT
REELEALTPSRTPSRSVSRTSLVSNPPGVNRVITREEFEAFVAQQQRRFDAGAYIFSSD
TGQGHLQQKSVRQTVLSEVVLERTELEISYAPRLDQEKEELLRKKLQLNPTPANRSR
YQSRKVENMKAITARRILQGLGHYLKAEGKVECYRTLHPVPLYSSSVNRAFSSPKVA
VEACNAMLKENFPTVASYCIIPEYDAYLDMVDGASCCLDTASFCPAKLRSFPKKHSY
LEPTIRSAVPSAIQNTLQNVLAAATKRNCNVTQMRELPVLDSAAFNVECFKKYACNN
EYWETFKENPIRLTEENVVNYITKLKGPKAAALFAKTHNLNMLQDIPMDRFVMDLK
RDVKVTPGTKHTEERPKVQVIQAADPLATAYLCGIHRELVRRLNAVLLPNIHTLFDM
SAEDFDAIIAEHFQPGDCVLETDIASFDKSEDDAMALTALMILEDLGVDAELLTLIEA
AFGEISSIHLPTKTKFKFGAMMKSGMFLTLFVNTVINIVIASRVLRERLTGSPCAAFIG
DDNIVKGVKSDKLMADRCATWLNMEVKIIDAVVGEKAPYFCGGFILCDSVTGTACR
VADPLKRLFKLGKPLAADDEHDDDRRRALHEESTRWNRVGILSELCKAVESRYETV
GTSIIVMAMTTLASSVKSFSYLRGAPITLYG

SEQ ID NO: 80
MPEKVHVDIEEDSPFLRALQRSFPQFEVEAKQVTDNDHANARAFSHLASKLIETEVD
PSDTILDIGSAPARRMYSKHKYHCICPMRCAEDPDRLYKYATKLKKNCKEITDKELD
KKMKELAAVMSDPDLETETMCLHDDESCRYEGQVAVYQDVYAVDGPTSLYHQAN
KGVRVAYWIGFDTTPFMFKNLAGAYPSYSTNWADETVLTARNIGLCSSDVMERSRR
GMSILRKKYLKPSNNVLFSVGSTIYHEKRDLLRSWHLPSVFHLRGKQNYTCRCETIVS
CDGYVVKRIAISPGLYGKPSGYAATMHREGFLCCKVTDTLNGERVSFPVCTYVPATL
CDQMTGILATDVSADDAQKLLVGLNQRIVVNGRTQRNTNTMKNYLLPVVAQAFAR
WAKEYKEDQEDERPLGLRDRQLVMGCCWAFRRHKITSIYKRPDTQTIIKVNSDFHSF
VLPRIGSNTLEIGLRTRIRKMLEEHKEPSPLITAEDVQEAKCAADEAKEVREAEELRA
ALPPLAADVEEPTLEADVDLMLQEAGAGSVETPRGLIKVTSYDGEDKIGSYAVLSPQ
AVLKSEKLSCIHPLAEQVIVITHSGRKGRYAVEPYHGKVVVPEGHAIPVQDFQALSES

-continued

ATIVYNEREFVNRYLHHIATHGGALNTDEEYYKTVKPSEHDGEYLYDIDRKQCVKK

ELVTGLGLTGELVDPPFHEFAYESLRTRPAAPYQVPTIGVYGVPGSGKSGIIKSAVTK

KDLVVSAKKENCAEIIRDVKKMKGLDVNARTVDSVLLNGCKHPVETLYIDEAFACH

AGTLRALIAIIRPKKAVLCGDPKQCGFFNMMCLKVHFNHEICTQVFHKSISRRCTKSV

TSVVSTLFYDKKMRTTNPKETKIVIDTTGSTKPKQDDLILTCFRGWVKQLQIDYKGN

EIMTAAASQGLTRKGVYAVRYKVNENPLYAPTSEHVNVLLTRTEDRIVWKTLAGDP

LKTAGIDMTTEQWNTVDYFETDKAHSAEIVLNQLCVRFFGLDLDSGLFSAPTVPLSIR

NNHWDNSPSPNMYGLNKEVVRQLSRRYPQLPRAVATGRVYDMNTGTLRNYDPRIN

LVPVNRRLPHALVLHHNEHPQSDFSSFVSKLKGRTVLVVGEKLSVPGKMVDWLSDR

PEATFRARLDLGIPGDVPKYDIIFVNVRTPYKYHHYQQCEDHAIKLSMLTKKACLHL

NPGGTCVSIGYGYADRASESIIGAIARLFKFSRVCKPKSSLEETEVLFVFIGYDRKART

HNPYKLSSTLTNIYTGSRLHEAGCAPSYHVVRGDIATATEGVIINAANSKGQPGGGV

CGALYKKFPESFDLQPIEVGKARLVKGAAKHIIHAVGPNFNKVSEVEGDKQLAEAYE

SIAKIVNDNNYKSVAIPLLSTGIFSGNKDRLTQSLNHLLTALDTTDADVAIYCRDKKW

EMTLKEAVARREAVEEICISDDSSVTEPDAELVRVHPKSSLAGRKGYSTSDGKTFSYL

EGTKFHQAAKDIAEINAMWPVATEANEQVCMYILGESMSSIRSKCPVEESEASTPPST

LPCLCIHAMTPERVQRLKASRPEQITVCSSFPLPKYRITGVQKIQCSQPILFSPKVPAYI

HPRKYLVETPPVDETPEPSAENQSTEGTPEQPPLITEDETRTRTPEPIIIEEEEEDSISLLS

DGPTHQVLQVEADIHGPPSVSSSSWSIPHASDFDVDSLSILDTLEGASVTSGATSAETN

SYFAKSMEFLARPVPAPRTVFRNPPHPAPRTRTPSLAPSRACSRTSLVSTPPGVNRVIT

TGQGHLQQKSVRQTVLSEVVLERTELEISYAPRLDQEKEELLRKKLQLNPTPANRSR

YQSRKVENMKAITARRILQGLGHYLKAEGKVECYRTLHPVPLYSSSVNRAFSSPKVA

VEACNAMLKENFPTVASYCHIPEYDAYLDMVDGASCCLDTASFCPAKLRSFPKKHSY

LEPTIRSAVPSAIQNTLQNVLAAATKRNCNVTQMRELPVLDSAAFNVECFKKYACNN

EYWETFKENPIRLTEENVVNYITKLKGPKAAALFAKTHNLNMLQDIPMDRFVMDLK

RDVKVTPGTKHTEERPKVQVIQAADPLATAYLCGIHRELVRRLNAVLLPNIHTLFDM

AFGEISSIHLPTKTKFKFGAMMKSGMFLTLFVNTVINIVIASRVLRERLTGSPCAAFIG

DDNIVKGVKSDKLMADRCATWLNMEVKIIDAVVGEKAPYFCGGFILCDSVTGTACR

VADPLKRLFKLGKPLAADDEHDDDRRRALHEESTRWNRVGILSELCKAVESRYETV

GTSIIVMAMTTLASSVKSFSYLRGAPITLYG

SEQ ID NO: 81
MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK

GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRHKITSIYKRPDTQTIIKVNSDFHSFV

-continued

LPRIGSNTLEIGLRTRIRKMLEEHKEPSPLITAEDIQEAKCAADEAKEVREAEELRAAL
PPLAADFEEPTLEADVDLMLQEAGAGSVETPRGLIKVTSYAGEDKIGSYAVLSPQAV
LKSEKLSCIHPLAEQVIVITHSGRKGRYAVEPYHGKVVVPEGHAIPVQDFQALSESAT
IVYNEREFVNRYLHHIATHGGALNTDEEYYKTVKPSEHDGEYLYDIDRKQCVKKEL
VTGLGLTGELVDPPFHEFAYESLRTRPAAPYQVPTIGVYGVPGSGKSGIIKSAVTKKD
LVVSAKKENCAEIIRDVKKMKGLDVNARTVDSVLLNGCKHPVETLYIDEAFACHAG
TLRALIAIIRPKKAVLCGDPKQCGFFNMMCLKVHFNHEICTQVFHKSISRRCTKSVTS
VVSTLFYDKRMRTTNPKETKIVIDTTGSTKPKQDDLILTCFRGWVKQLQIDYKGNEI
MTAAASQGLTRKGVYAVRYKVNENPLYAPTSEHVNVLLTRTEDRIVWKTLAGDPW
TAGIDMTTEQWNTVDYFETDKAHSAEIVLNQLCVRFFGLDLDSGLFSAPTVPLSIRN
NHWDNSPSPNMYGLNKEVVRQLSRRYPQLPRAVATGRVYDMNTGTLRNYDPRINL
VPVNRRLPHALVLHHNEHPQSDFSSFVSKLKGRTVLVVGEKLSVPGKKVDWLSDQP
EATFRARLDLGIPGDVPKYDIVFINVRTPYKYHHYQQCEDHAIKLSMLTKKACLHLN
PGGTCVSIGYGYADRASESIIGAIARQFKFSRVCKPKSSHEETEVLFVFIGYDRKARTH
NPYKLSSTLTNIYTGSRLHEAGCAPSYHVVRGDIATATEGVIINAANSKGQPGGGVC
GALYKKFPESFDLQPIEVGKARLVKGAAKHIIHAVGPNFNKVSEVEGDKQLAEAYES
IAKIVNDNNYKSVAIPLLSTGIFSGNKDRLTQSLNHLLTALDTTDADVAIYCRDKKWE
MTLKEAVARREAVEEICISDDSSVTEPDAELVRVHPKSSLAGRKGYSTSDGKTFSYLE
GTKFHQAAKDIAEINAMWPVATEANEQVCMYILGESMSSIRSKCPVEESEASTPPSTL
PCLCIHAMTPERVQRLKASRPEQITVCSSFPLPKYRITGVQKIQCSQPILFSPKVPAYIH
PRKYLVETPPVEETPESPAENQSTEGTPEQPALVNVDATRTRMPEPIIIEEEEEDSISLL
SDGPTHQVLQVEADIHGSPSVSSSSWSIPHASDFDVDSLSILDTLDGASVTSGAVSAET
NSYFARSMEFRARPVPAPRTVFRNPPHPAPRTRTPPLAHSRASSRTSLVSTPPGVNRVI
TREELEALTPSRAPSRSASRTSLVSNPPGVNRVITREEFEAFVAQQQ*RFDAGAYIFSS
DTGQGHLQQKSVRQTVLSEVVLERTELEISYAPRLDQEKEELLRKKLQLNPTPANRS
RYQSRRVENMKAITARRILQGLGHYLKAEGKVECYRTLHPVPLYSSSVNRAFSSPKV
AVEACNAMLKENFPTVASYCIIPEYDAYLDMVDGASCCLDTASFCPAKLRSFPKKHS
YLEPTIRSAVPSAIQNTLQNVLAAATKRNCNVTQMRELPVLDSAAFNVECFKKYACN
NEYWETFKENPIRLTEENVVNYITKLKGPKAAALFAKTHNLNMLQDIPMDRFVMDL
KRDVKVTPGTKHTEERPKVQVIQAADPLATADLCGIHRELVRRLNAVLLPNIHTLFD
MSAEDFDAIIAEHFQPGDCVLETDIASFDKSEDDAMALTALMILEDLGVDAELLTLIE
AAFGEISSIHLPTKTKFKFGAMMKSGMFLTLFVNTVINIVIASRVLRERLTGSPCAAFI
GDDNIVKGVKSDKLMADRCATWLNMEVKIIDAVVGEKAPYFCGGFILCDSVTGTAC
RVADPLKRLFKLGKPLAVDDEHDDDRRRALHEESTRWNRVGILPELCKAVESRYET
VGTSIIVMAMTTLASSVKSFSYLRGAPITLYG*

SEQ ID NO: 126
AGGAAACTTAAGTCAACACAACATATACAAAACAAACGAATCTCAAGCAATCAA
GCATTCTACTTCTATTGCAGCAATTTAAATCATTTCTTTTAAAGCAAAAGCAATTT
TCTGAAAATTTTCACCATTTACGAACGATAGCCACCATGTTCGTCTTCCTGGTCCT
GCTGCCTCTGGTCTCCTCACAGTGCGTCAATCTGACAACTCGGACTCAGCTGCCA

-continued

```
CCTGCTTATACTAATAGCTTCACCAGAGGCGTGTACTATCCTGACAAGGTGTTTA

GAAGCTCCGTGCTGCACTCTACACAGGATCTGTTTCTGCCATTCTTTAGCAACGT

GACCTGGTTCCACGCCATCCACGTGAGCGGCACCAATGGCACAAAGCGGTTCGA

CAATCCCGTGCTGCCTTTTAACGATGGCGTGTACTTCGCCTCTACCGAGAAGTCC

AACATCATCAGAGGCTGGATCTTTGGCACCACACTGGACTCCAAGACACAGTCTC

TGCTGATCGTGAACAATGCCACCAACGTGGTCATCAAGGTGTGCGAGTTCCAGTT

TTGTAATGATCCCTTCCTGGGCGTGTACTATCACAAGAACAATAAGAGCTGGATG

GAGTCCGAGTTTAGAGTGTATTCTAGCGCCAACAACTGCACATTTGAGTACGTGA

GCCAGCCTTTCCTGATGGACCTGGAGGGCAAGCAGGGCAATTTCAAGAACCTGA

GGGAGTTCGTGTTTAAGAATATCGACGGCTACTTCAAAATCTACTCTAAGCACAC

CCCCATCAACCTGGTGCGCGACCTGCCTCAGGGCTTCAGCGCCCTGGAGCCCCTG

GTGGATCTGCCTATCGGCATCAACATCACCCGGTTTCAGACACTGCTGGCCCTGC

ACAGAAGCTACCTGACACCCGGCGACTCCTCTAGCGGATGGACCGCCGGCGCTG

CCGCCTACTATGTGGGCTACCTCCAGCCCCGGACCTTCCTGCTGAAGTACAACGA

GAATGGCACCATCACAGACGCAGTGGATTGCGCCCTGGACCCCCTGAGCGAGAC

AAAGTGTACACTGAAGTCCTTTACCGTGGAGAAGGGCATCTATCAGACATCCAA

TTTCAGGGTGCAGCCAACCGAGTCTATCGTGCGCTTTCCTAATATCACAAACCTG

TGCCCATTTGGCGAGGTGTTCAACGCAACCCGCTTCGCCAGCGTGTACGCCTGGA

ATAGGAAGCGGATCAGCAACTGCGTGGCCGACTATAGCGTGCTGTACAACTCCG

CCTCTTTCAGCACCTTTAAGTGCTATGGCGTGTCCCCCACAAAGCTGAATGACCT

GTGCTTTACCAACGTCTACGCCGATTCTTTCGTGATCAGGGGCGACGAGGTGCGC

CAGATCGCCCCCGGCCAGACAGGCAAGATCGCAGACTACAATTATAAGCTGCCA

GACGATTTCACCGGCTGCGTGATCGCCTGGAACAGCAACAATCTGGATTCCAAA

GTGGGCGGCAACTACAATTATCTGTACCGGCTGTTTAGAAAGAGCAATCTGAAG

CCCTTCGAGAGGGACATCTCTACAGAAATCTACCAGGCCGGCAGCACCCCTTGC

AATGGCGTGGAGGGCTTTAACTGTTATTTCCCACTCCAGTCCTACGGCTTCCAGC

CCACAAACGGCGTGGGCTATCAGCCTTACCGCGTGGTGGTGCTGAGCTTTGAGCT

GCTGCACGCCCCAGCAACAGTGTGCGGCCCCAAGAAGTCCACCAATCTGGTGAA

GAACAAGTGCGTGAACTTCAACTTCAACGGCCTGACCGGCACAGGCGTGCTGAC

CGAGTCCAACAAGAAGTTCCTGCCATTTCAGCAGTTCGGCAGGGACATCGCAGA

TACCACAGACGCCGTGCGCGACCCACAGACCCTGGAGATCCTGGACATCACACC

CTGCTCTTTCGGCGGCGTGAGCGTGATCACACCCGGCACCAATACAAGCAACCA

GGTGGCCGTGCTGTATCAGGACGTGAATTGTACCGAGGTGCCCGTGGCTATCCAC

GCCGATCAGCTGACCCCAACATGGCGGGTGTACAGCACCGGCTCCAACGTCTTCC

AGACAAGAGCCGGATGCCTGATCGGAGCAGAGCACGTGAACAATTCCTATGAGT

GCGACATCCCAATCGGCGCCGGCATCTGTGCCTCTTACCAGACCCAGACAAACTC

TCCCAGACGGGCCCGGAGCGTGGCCTCCCAGTCTATCATCGCCTATACCATGTCC

CTGGGCGCCGAGAACAGCGTGGCCTACTCTAACAATAGCATCGCCATCCCAACC

AACTTCACAATCTCTGTGACCACAGAGATCCTGCCCGTGTCCATGACCAAGACAT

CTGTGGACTGCACAATGTATATCTGTGGCGATTCTACCGAGTGCAGCAACCTGCT
```

-continued

GCTCCAGTACGGCAGCTTTTGTACCCAGCTGAATAGAGCCCTGACAGGCATCGCC

GTGGAGCAGGATAAGAACACACAGGAGGTGTTCGCCCAGGTGAAGCAAATCTAC

AAGACCCCCCCTATCAAGGACTTTGGCGGCTTCAATTTTTCCCAGATCCTGCCTG

ATCCATCCAAGCCTTCTAAGCGGAGCTTTATCGAGGACCTGCTGTTCAACAAGGT

GACCCTGGCCGATGCCGGCTTCATCAAGCAGTATGGCGATTGCCTGGGCGACATC

GCAGCCAGGGACCTGATCTGCGCCCAGAAGTTTAATGGCCTGACCGTGCTGCCA

CCCCTGCTGACAGATGAGATGATCGCACAGTACACAAGCGCCCTGCTGGCCGGC

ACCATCACATCCGGATGGACCTTCGGCGCAGGAGCCGCCCTCCAGATCCCCTTTG

CCATGCAGATGGCCTATAGGTTCAACGGCATCGGCGTGACCCAGAATGTGCTGT

ACGAGAACCAGAAGCTGATCGCCAATCAGTTTAACTCCGCCATCGGCAAGATCC

AGGACAGCCTGTCCTCTACAGCCAGCGCCCTGGGCAAGCTCCAGGATGTGGTGA

ATCAGAACGCCCAGGCCCTGAATACCCTGGTGAAGCAGCTGAGCAGCAACTTCG

GCGCCATCTCTAGCGTGCTGAATGACATCCTGAGCCGGCTGGACAAGGTGGAGG

CAGAGGTGCAGATCGACCGGCTGATCACCGGCCGGCTCCAGAGCCTCCAGACCT

ATGTGACACAGCAGCTGATCAGGGCCGCCGAGATCAGGGCCAGCGCCAATCTGG

CAGCAACCAAGATGTCCGAGTGCGTGCTGGGCCAGTCTAAGAGAGTGGACTTTT

GTGGCAAGGGCTATCACCTGATGTCCTTCCCTCAGTCTGCCCCACACGGCGTGGT

GTTTCTGCACGTGACCTACGTGCCCGCCCAGGAGAAGAACTTCACCACAGCCCCT

GCCATCTGCCACGATGGCAAGGCCCACTTTCCAAGGGAGGGCGTGTTCGTGTCCA

ACGGCACCCACTGGTTTGTGACACAGCGCAATTTCTACGAGCCCCAGATCATCAC

CACAGACAACACCTTCGTGAGCGGCAACTGTGACGTGGTCATCGGCATCGTGAA

CAATACCGTGTATGATCCACTCCAGCCCGAGCTGGACAGCTTTAAGGAGGAGCT

GGATAAGTATTTCAAGAATCACACCTCCCCTGACGTGGATCTGGGCGACATCAGC

GGCATCAATGCCTCCGTGGTGAACATCCAGAAGGAGATCGACCGCCTGAACGAG

GTGGCTAAGAATCTGAACGAGAGCCTGATCGACCTCCAGGAGCTGGGCAAGTAT

GAGCAGTACATCAAGTGGCCCTGGTACATCTGGCTGGGCTTCATCGCCGGCCTGA

TCGCCATCGTGATGGTGACCATCATGCTGTGCTGTATGACATCCTGCTGTTCTTGC

CTGAAGGGCTGCTGTAGCTGTGGCTCCTGCTGTAAGTTTGACGAGGATGACTCTG

AACCTGTGCTGAAGGGCGTGAAGCTGCATTACACCTAAACTCGAGCTAGTGACT

GACTAGGATCTGGTTACCACTAAACCAGCCTCAAGAACACCCGAATGGAGTCTC

TAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SEQ ID NO: 82

AGGAAACTTAAGTCAACACAACATATACAAAACAAACGAATCTCAAG

CAATCAAGCATTCTACTTCTATTGCAGCAATTTAAATCATTTCTTTT

AAAGCAAAAGCAATTTTCTGAAAATTTTCACCATTTACGAACGATAG

CCACC

SEQ ID NO: 83

ACTCGAGCTAGTGACTGACTAGGATCTGGTTACCACTAAACCAGCCT

CAAGAACACCCGAATGGAGTCTCTAAGCTACATAATACCAACTTACA

CTTACAAAATGTTGTCCCCCAAAATGTAGCCATTCGTATCTGCTCCT

AATAAAAAGAAAGTTTCTTCACATTCTAGAAAAAAAAAAAAAAAAAA

-continued

AAAAAAAAAAAAAAAAAAAAAAAAAAAAAAAAAAAAAAAAAAAAAAAAA

AAAAAAAAAAAAAAAAAAAAAAAAAAAAAAAAAAAAA

SEQ ID NO: 1

GAGGAAACTT AAGAUGGG

SEQ ID NO:2
GGAUGGG

SEQ ID NO:3
GGAUAGG

SEQ ID NO:4
GGAGAGG

SEQ ID NO:58
GGGAUGGG

SEQ ID NO:59
GAGAGG

SEQ ID NO:60
GAGGG

SEQ ID NO:61
GAGAUGGG

SEQ ID NO:62
GAGUGG

SEQ ID NO:63
GAGGGG

SEQ ID NO:64
GAGUAGG

SEQ ID NO:65
GAGUGGG (RNA sequence for a construct with two subgenomic promoters, Luc, and E3L)

SEQ ID NO:127 atgggoggcgcatgagagaagcccagaccaattacctacccaaaatggagaaagttcacgttgacatcgaggaagacagcccatt cctcagagctttgcagcggagcttcccgcagtttgaggtagaagccaagcaggtcactgataatgaccatgctaatgccagagcgtt ttcgcatctggcttcaaaactgatcgaaacggaggtggacccatccgacacgatccttgacattggaagtgcgcccgcccgcagaat gtattctaagcacaagtatcattgtatctgtccgatgagatgtgcggaagatccggacagattgtataagtatgcaactaagctgaa gaaaaactgtaaggaaataactgataaggaattggacaagaaaatgaaggagctggccgccgtcatgagcgaccctgacctgga aactgagactatgtgcctccacgacgacgagtcgtgtcgctacgaagggcaagtcgctgtttaccaggatgtatacgcCGTCGAC

GGCCCCACCAGCCTGTACCACCAGGCCAACAAGGGCGTGAGGGTGGCCTACTGGATCGGCTTCGAC

ACCACACCCTTCATGTTCAAGAACCTGGCCGGCGCCTACCCCAGCTACAGCACCAACTGGGCCGACG

AGACCGTGCTGACCGCCAGGAACATCGGCCTGTGCAGCAGCGACGTGATGGAGAGGAGCCGGAGA

GGCATGAGCATCCTGAGGAAGAAATACCTGAAGCCCAGCAACAACGTGCTGTTCAGCGTGGGCAGC

ACCATCTACCACGAGAAGAGGGACCTGCTCAGGAGCTGGCACCTGCCCAGCGTGTTCCACCTGAGG

GGCAAGCAGAACTACACCTGCAGGTGCGAGACCATCGTGAGCTGCGACGGCTACGTGGTGAAGAG

GATCGCCATCAGCCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCCCGTGTGCACCTA

CGTGCCCGCCACCCTGTGCGACCAGATGACCGGCATCCTGGCCACCGACGTGAGCGCCGACGACGC

CCAGAAGCTGCTCGTGGGCCTGAACCAGAGGATCGTGGTCAACGGCAGGACCCAGAGGAACACCA

ACACAATGAAGAACTACCTGCTGCCCGTGGTGGCCCAGGCTTTCGCCAGGTGGGCCAAGGAGTACA

AGGAGGACCAGGAAGACGAGAGGCCCCTGGGCCTGAGGGACAGGCAGCTGGTGATGGGCTGCTG

CTGGGCCTTCAGGCGGCACAAGATCACCAGCATCTACAAGAGGCCCGACACCCAGACCATCATCAA

GGTGAACAGCGACTTCCACAGCTTCGTGCTGCCCAGGATCGGCAGCAACACCCTGGAGATCGGCCT

GAGGACCCGGATCAGGAAGATGCTGGAGGAACACAAGGAGCCCAGCCCACTGATCACCGCCGAGG

-continued

```
ACGTGCAGGAGGCCAAGTGCGCTGCCGACGAGGCCAAGGAGGTGAGGGAGGCCGAGGAACTGAG

GGCCGCCCTGCCACCCCTGGCTGCCGACGTGGAGGAACCCACCCTGGAAGCCGACGTGGACCTGAT

GCTGCAGGAGGCCGGCGCCGGAAGCGTGGAGACACCCAGGGGCCTGATCAAGGTGACCAGCTACG

ACGGCGAGGACAAGATCGGCAGCTACGCCGTGCTGAGCCCACAGGCCGTGCTGAAGTCCGAGAAG

CTGAGCTGCATCCACCCACTGGCCGAGCAGGTGATCGTGATCACCCACAGCGGCAGGAAGGGCAG

GTACGCCGTGGAGCCCTACCACGGCAAGGTGGTCGTGCCCGAGGGCCACGCCATCCCCGTGCAGGA

CTTCCAGGCCCTGAGCGAGAGCGCCACCATCGTGTACAACGAGAGGGAGTTCGTGAACAGGTACCT

GCACCATATCGCCACCCACGGCGGAGCCCTGAACACCGACGAGGAATACTACAAGACCGTGAAGCC

CAGCGAGCACGACGGCGAGTACCTGTACGACATCGACAGGAAGCAGTGCGTGAAGAAAGAGCTGG

TGACCGGCCTGGGACTGACCGGCGAGCTGGTGGACCCACCCTTCCACGAGTTCGCCTACGAGAGCC

TGAGGACCAGACCCGCCGCTCCCTACCAGGTGCCCACCATCGGCGTGTACGGCGTGCCCGGCAGCG

GAAAGAGCGGCATCATCAAGAGCGCCGTGACCAAGAAAGACCTGGTGGTCAGCGCCAAGAAAGAG

AACTGCGCCGAGATCATCAGGGACGTGAAGAAGATGAAAGGCCTGGACGTGAACGCGCGCACCGT

GGACAGCGTGCTGCTGAACGGCTGCAAGCACCCCGTGGAGACCCTGTACATCGACGAGGCCTTCGC

TTGCCACGCCGGCACCCTGAGGGCCCTGATCGCCATCATCAGGCCCAAGAAAGCCGTGCTGTGCGG

CGACCCCAAGCAGTGCGGCTTCTTCAACATGATGTGCCTGAAGGTGCACTTCAACCACGAGATCTGC

ACCCAGGTGTTCCACAAGAGCATCAGCAGGCGGTGCACCAAGAGCGTGACCAGCGTCGTGAGCACC

CTGTTCTACGACAAGAAAATGAGGACCACCAACCCCAAGGAGACCAAAATCGTGATCGACACCACA

GGCAGCACCAAGCCCAAGCAGGACGACCTGATCCTGACCTGCTTCAGGGGCTGGGTGAAGCAGCTG

CAGATCGACTACAAGGGCAACGAGATCATGACCGCCGCTGCCAGCCAGGGCCTGACCAGGAAGGG

CGTGTACGCCGTGAGGTACAAGGTGAACGAGAACCCACTGTACGCTCCCACCAGCGAGCACGTGAA

CGTGCTGCTGACCAGGACCGAGGACAGGATCGTGTGGAAGACCCTGGCCGGCGACCCCTGGATCA

AGACCCTGACCGCCAAGTACCCCGGCAACTTCACCGCCACCATCGAAGAGTGGCAGGCCGAGCACG

ACGCCATCATGAGGCACATCCTGGAGAGGCCCGACCCCACCGACGTGTTCCAGAACAAGGCCAACG

TGTGCTGGGCCAAGGCCCTGGTGCCCGTGCTGAAGACCGCCGGCATCGACATGACCACAGAGCAGT

GGAACACCGTGGACTACTTCGAGACCGACAAGGCCCACAGCGCCGAGATCGTGCTGAACCAGCTGT

GCGTGAGGTTCTTCGGCCTGGACCTGGACAGCGGCCTGTTCAGCGCCCCCACCGTGCCACTGAGCAT

CAGGAACAACCACTGGGACAACAGCCCCAGCCCAAACATGTACGGCCTGAACAAGGAGGTGGTCA

GGCAGCTGAGCAGGCGGTACCCACAGCTGCCCAGGGCCGTGGCCACCGGCAGGGTGTACGACATG

AACACCGGCACCCTGAGGAACTACGACCCCAGGATCAACCTGGTGCCCGTGAACAGGCGGCTGCCC

CACGCCCTGGTGCTGCACCACAACGAGCACCCACAGAGCGACTTCAGCTCCTTCGTGAGCAAGCTGA

AAGGCAGGACCGTGCTGGTCGTGGGCGAGAAGCTGAGCGTGCCCGGCAAGATGGTGGACTGGCTG

AGCGACAGGCCCGAGGCCACCTTCCGGGCCAGGCTGGACCTCGGCATCCCCGGCGACGTGCCCAAG

TACGACATCATCTTCGTGAACGTCAGGACCCCATACAAGTACCACCATTACCAGCAGTGCGAGGACC

ACGCCATCAAGCTGAGCATGCTGACCAAGAAGGCCTGCCTGCACCTGAACCCCGGAGGCACCTGCG

TGAGCATCGGCTACGGCTACGCCGACAGGGCCAGCGAGAGCATCATTGGCGCCATCGCCAGGCTGT

TCAAGTTCAGCAGGGTGTGCAAACCCAAGAGCAGCCTGGAGGAAACCGAGGTGCTGTTCGTGTTCA

TCGGCTACGACCGGAAGGCCAGGACCCACAACCCCTACAAGCTGAGCAGCACCCTGACAAACATCT

ACACCGGCAGCAGGCTGCACGAGGCCGGCTGCGCCCCCAGCTACCACGTGGTCAGGGGCGATATC

GCCACCGCCACCGAGGGCGTGATCATCAACGCTGCCAACAGCAAGGGCCAGCCCGGAGGCGGAGT

GTGCGGCGCCCTGTACAAGAAGTTCCCCGAGAGCTTCGACCTGCAGCCCATCGAGGTGGGCAAGGC
```

-continued

```
CAGGCTGGTGAAGGGCGCCGCTAAGCACATCATCCACGCCGTGGGCCCCAACTTCAACAAGGTGAG
CGAGGTGGAAGGCGACAAGCAGCTGGCCGAAGCCTACGAGAGCATCGCCAAGATCGTGAACGACA
ATAACTACAAGAGCGTGGCCATCCCACTGCTCAGCACCGGCATCTTCAGCGGCAACAAGGACAGGC
TGACCCAGAGCCTGAACCACCTGCTCACCGCCCTGGACACCACCGATGCCGACGTGGCCATCTACTG
CAGGGACAAGAAGTGGGAGATGACCCTGAAGGAGGCCGTGGCCAGGCGGGAGGCCGTGGAAGAG
ATCTGCATCAGCGACGACTCCAGCGTGACCGAGCCCGACGCCGAGCTGGTGAGGGTGCACCCCAAG
AGCTCCCTGGCCGGCAGGAAGGGCTACAGCACCAGCGACGGCAAGACCTTCAGCTACCTGGAGGG
CACCAAGTTCCACCAGGCCGCTAAGGACATCGCCGAGATCAACGCTATGTGGCCCGTGGCCACCGA
GGCCAACGAGCAGGTGTGCATGTACATCCTGGGCGAGAGCATGTCCAGCATCAGGAGCAAGTGCCC
CGTGGAGGAAAGCGAGGCCAGCACACCACCCAGCACCCTGCCCTGCCTGTGCATCCACGCTATGAC
ACCCGAGAGGGTGCAGCGGCTGAAGGCCAGCAGGCCCGAGCAGATCACCGTGTGCAGCTCCTTCCC
ACTGCCCAAGTACAGGATCACCGGCGTGCAGAAGATCCAGTGCAGCCAGCCCATCCTGTTCAGCCCA
AAGGTGCCCGCCTACATCCACCCCAGGAAGTACCTGGTGGAGACCCCACCCGTGGACGAGACACCC
GAGCCAAGCGCCGAGAACCAGAGCACCGAGGGCACACCCGAGCAGCCACCCCTGATCACCGAGGA
CGAGACAAGGACCCGGACCCCAGAGCCCATCATTATCGAGGAAGAGGAAGAGGACAGCATCAGCC
TGCTGAGCGACGGCCCCACCCACCAGGTGCTGCAGGTGGAGGCCGACATCCACGGCCCACCCAGCG
TGTCCAGCTCCAGCTGGAGCATCCCACACGCCAGCGACTTCGACGTGGACAGCCTGAGCATCCTGG
ACACCCTGGAGGGCGCCAGCGTGACCTCCGGCGCCACCAGCGCCGAGACCAACAGCTACTTCGCCA
AGAGCATGGAGTTCCTGGCCAGGCCCGTGCCAGCTCCCAGGACCGTGTTCAGGAACCCACCCCACC
CAGCTCCCAGGACCAGGACCCCAAGCCTGGCTCCCAGCAGGGCCTGCAGCAGGACCAGCCTGGTGA
GCACCCCACCCGGCGTGAACAGGGTGATCACCAGGGAGGAACTGGAGGCCCTGACACCCAGCAGG
ACCCCCAGCAGGTCCGTGAGCAGGACTAGTCTGGTGTCCAACCCACCCGGCGTGAACAGGGTGATC
ACCAGGGAGGAATTCGAGGCCTTCGTGGCCCAGCAACAGAGACGGTTCGACGCCGGCGCCTACATC
TTCAGCAGCGACACCGGCCAGGGACACCTGCAGCAAAAGAGCGTGAGGCAGACCGTGCTGAGCGA
GGTGGTGCTGGAGAGGACCGAGCTGGAAATCAGCTACGCCCCCAGGCTGGACCAGGAGAAGGAG
GAACTGCTCAGGAAGAAACTGCAGCTGAACCCCACCCCAGCCAACAGGAGCAGGTACCAGAGCAG
GAAGGTGGAGAACATGAAGGCCATCACCGCCAGGCGGATCCTGCAGGGCCTGGGACACTACCTGA
AGGCCGAGGGCAAGGTGGAGTGCTACAGGACCCTGCACCCCGTGCCACTGTACAGCTCCAGCGTGA
ACAGGGCCTTCTCCAGCCCCAAGGTGGCCGTGGAGGCCTGCAACGCTATGCTGAAGGAGAACTTCC
CCACCGTGGCCAGCTACTGCATCATCCCCGAGTACGACGCCTACCTGGACATGGTGGACGGCGCCA
GCTGCTGCCTGGACACCGCCAGCTTCTGCCCCGCCAAGCTGAGGAGCTTCCCCAAGAAACACAGCTA
CCTGGAGCCCACCATCAGGAGCGCCGTGCCCAGCGCCATCCAGAACACCCTGCAGAACGTGCTGGC
CGCTGCCACCAAGAGGAACTGCAACGTGACCCAGATGAGGGAGCTGCCCGTGCTGGACAGCGCTG
CCTTCAACGTGGAGTGCTTCAAGAAATACGCCTGCAACAACGAGTACTGGGAGACCTTCAAGGAGA
ACCCCATCAGGCTGACCGAAGAGAACGTGGTGAACTACATCACCAAGCTGAAGGGCCCCAAGGCCG
CTGCCCTGTTCGCTAAGACCCACAACCTGAACATGCTGCAGGACATCCCAATGGACAGGTTCGTGAT
GGACCTGAAGAGGGACGTGAAGGTGACACCCGGCACCAAGCACACCGAGGAGAGGCCCAAGGTG
CAGGTGATCCAGGCCGCTGACCCACTGGCCACCGCCTACCTGTGCGGCATCCACAGGGAGCTGGTG
AGGCGGCTGAACGCCGTGCTGCTGCCCAACATCCACACCCTGTTCGACATGAGCGCCGAGGACTTC
GACGCCATCATCGCCGAGCACTTCCAGCCCGGCGACTGCGTGCTGGAGACCGACATCGCCAGCTTC
```

```
GACAAGAGCGAGGATGACGCTATGGCCCTGACCGCTCTGATGATCCTGGAGGACCTGGGCGTGGA
CGCCGAGCTGCTCACCCTGATCGAGGCTGCCTTCGGCGAGATCAGCTCCATCCACCTGCCCACCAAG
ACCAAGTTCAAGTTCGGCGCTATGATGAAAAGCGGAATGTTCCTGACCCTGTTCGTGAACACCGTGA
TCAACATTGTGATCGCCAGCAGGGTGCTGCGGGAGAGGCTGACCGGCAGCCCCTGCGCTGCCTTCA
TCGGCGACGACAACATCGTGAAGGGCGTGAAAAGCGACAAGCTGATGGCCGACAGGTGCGCCACC
TGGCTGAACATGGAGGTGAAGATCATCGACGCCGTGGTGGGCGAGAAGGCCCCCTACTTCTGCGGC
GGATTCATCCTGTGCGACAGCGTGACCGGCACCGCCTGCAGGGTGGCCGACCCCCTGAAGAGGCTG
TTCAAGCTGGGCAAGCCACTGGCCGCTGACGATGAGCACGACGATGACAGGCGGAGGGCCCTGCA
CGAGGAAAGCACCAGGTGGAACAGGGTGGGCATCCTGAGCGAGCTGTGCAAGGCCGTGGAGAGC
AGGTACGAGACCGTGGGCACCAGCATCATCGTGATGGCTATGACCACACTGGCCAGCTCCGTCAAG
AGCTTCTCCTACCTGAGGGGGGCCCCTATAACTCTCTACGGCTAACCTGAATGGACTACGACATAGT
CTAgccaccATGagcaagatctacatcgacgagcggagcaacgccgagatcgtgtgcgaggccatcaagaccatcggcatcga
gggcgccaccgccgcccagctgaccaggcagctgaacatggagaagcgggaggtgaacaaggccctgtacgacctgcagaggag
cgctatggtgtactccagcgacgacatccctccccggtggttcatgaccaccgaggccgacaagcccgacgccgacgctatggccg
acgtgatcatcgacgacgtgagcagggagaagtccatgagggaggaccacaagagcttcgacgacgtgatccccgccaagaaga
tcatcgactggaagggcgccaaccccgtgaccgtgatcaacgagtactgccagatcaccaggagggactggagcttccggatcga
gagcgtgggccccagcaacagccccaccttctacgcctgcgtggacatcgacggcagggtgttcgacaaggccgacggcaagagc
aagcgggacgccaagaacaacgccgccaagctggccgtggacaagctgctgggctacgtgatcatccggttcTAActcgagcta
gtgactgactaggatctggttaccactaaaccagcctcaagaacacccgaatggagtctctaagctacataataccaacttacactt
acaaaatgttgtcccccaaaatgtagccattcgtatctgctcctaataaaaagaaagtttcttcacattctagAGCTCCGTCAAG
AGCTTCTCCTACCTGAGGGGGGCCCCTATAACTCTCTACGGCTAACCTGAATGGACTACGACATAGT
CTAGCCACCATGGAAGATGCCAAAAACATTAAGAAGGGCCCAGCGCCATTCTACCCACTCGAAGAC
GGGACCGCCGGCGAGCAGCTGCACAAAGCCATGAAGCGCTACGCCCTGGTGCCCGGCACCATCGCC
TTTACCGACGCACATATCGAGGTGGACATTACCTACGCCGAGTACTTCGAGATGAGCGTTCGGCTGG
CAGAAGCTATGAAGCGCTATGGGCTGAATACAAACCATCGGATCGTGGTGTGCAGCGAGAATAGCT
TGCAGTTCTTCATGCCCGTGTTGGGTGCCCTGTTCATCGGTGTGGCTGTGGCCCCAGCTAACGACAT
CTACAACGAGCGCGAGCTGCTGAACAGCATGGGCATCAGCCAGCCCACCGTCGTATTCGTGAGCAA
GAAAGGGCTGCAAAAGATCCTCAACGTGCAAAAGAAGCTACCGATCATACAAAAGATCATCATCAT
GGATAGCAAGACCGACTACCAGGGCTTCCAAAGCATGTACACCTTCGTGACTTCCCATTTGCCACCC
GGCTTCAACGAGTACGACTTCGTGCCCGAGAGCTTCGACCGGGACAAAACCATCGCCCTGATCATGA
ACAGTAGTGGCAGTACCGGATTGCCCAAGGGCGTAGCCCTACCGCACCGCACCGCTTGTGTCCGATT
CAGTCATGCCCGCGACCCCATCTTCGGCAACCAGATCATCCCCGACACCGCTATCCTCAGCGTGGTG
CCATTTCACCACGGCTTCGGCATGTTCACCACGCTGGGCTACTTGATCTGCGGCTTTCGGGTCGTGCT
CATGTACCGCTTCGAGGAGGAGCTATTCTTGCGCAGCTTGCAAGACTATAAGATTCAATCTGCCCTG
CTGGTGCCCACACTATTTAGCTTCTTCGCTAAGAGCACTCTCATCGACAAGTACGACCTAAGCAACTT
GCACGAGATCGCCAGCGGCGGGGCGCCGCTCAGCAAGGAGGTAGGTGAGGCCGTGGCCAAACGC
TTCCACCTACCAGGCATCCGACAGGGCTACGGCCTGACAGAAACAACCAGCGCCATTCTGATCACCC
CCGAAGGGGACGACAAGCCTGGCGCAGTAGGCAAGGTGGTGCCCTTCTTCGAGGCTAAGGTGGTG
GACTTGGACACCGGTAAGACACTGGGTGTGAACCAGCGCGGCGAGCTGTGCGTCCGTGGCCCCATG
ATCATGAGCGGCTACGTTAACAACCCCGAGGCTACAAACGCTCTCATCGACAAGGACGGCTGGCTG
CACAGCGGCGACATCGCCTACTGGGACGAGGACGAGCACTTCTTCATCGTGGACCGGCTGAAGTCC
```

-continued

CTGATCAAATACAAGGGCTACCAGGTAGCCCCAGCCGAACTGGAGAGCATCCTGCTGCAACACCCC
AACATCTTCGACGCCGGGGTCGCCGGCCTGCCCGACGACGATGCCGGCGAGCTGCCCGCCGCAGTC
GTCGTGCTGGAACACGGTAAAACCATGACCGAGAAGGAGATCGTGGACTATGTGGCCAGCCAGGTT
ACAACCGCCAAGAAGCTGCGCGGTGGTGTTGTGTTCGTGGACGAGGTGCCTAAAGGACTGACCGG
CAAGTTGGACGCCCGCAAGATCCGCGAGATTCTCATTAAGGCCAAGAAGGGCGGCAAGATCGCCGT
GTAACTCGAGTATGTTACGTGCAAAGGTGATTGTCACCCCCCGAAAGACCATATTGTGACACACCCT
CAGTATCACGCCCAAACATTTACAGCCGCGGTGTCAAAAACCGCGTGGACGTGGTTAACATCCCTGC
TGGGAGGATCAGCCGTAATTATTATAATTGGCTTGGTGCTGGCTACTATTGTGGCCATGTACGTGCT
GACCAACCAGAAACATAATTGAATACAGCAGCAATTGGCAAGCTGCTTACATAGAACTCGCGGCGA
TTGGCATGCCGCCTTAAAATTTTTATTTTATTTTTTCTTTTCTTTTCCGAATCGGATTTTGTTTTTAATAT

TTCAAAAAAAAAAAAAAAAAAAAAAAAAATctagAAAAAAAAAAAAAAAAAAAAAAAAAAAAAAAA

AAAAAAAAAAAAAAAAAAAAAAAAAAAAAAAAAAAAAAAAAAAAAaaaaaaaaaaaaaaaaaaaa (RNA sequence for STARR Fluc IRES-E3L)

SEQ ID NO:128

AUGGGCGGCGCAUGAGAGAAGCCCAGACCAAUUACCUACCCAAAAUGGAGAAA
GUUCACGUUGACAUCGAGGAAGACAGCCCAUUCCUCAGAGCUUUGCAGCGGAG
CUUCCCGCAGUUUGAGGUAGAAGCCAAGCAGGUCACUGAUAAUGACCAUGCUA
AUGCCAGAGCGUUUUCGCAUCUGGCUUCAAAACUGAUCGAAACGGAGGUGGA
CCCAUCCGACACGAUCCUUGACAUUGGAAGUGCGCCCGCCCGCAGAAUGUAUU
CUAAGCACAAGUAUCAUUGUAUCUGUCCGAUGAGAUGUGCGGAAGAUCCGGA
CAGAUUGUAUAAGUAUGCAACUAAGCUGAAGAAAAACUGUAAGGAAAUAACU
GAUAAGGAAUUGGACAAGAAAAUGAAGGAGCUGGCCGCCGUCAUGAGCGACC
CUGACCUGGAAACUGAGACUAUGUGCCUCCACGACGACGAGUCGUGUCGCUAC
GAAGGGCAAGUCGCUGUUUACCAGGAUGUAUACGCCGUCGACGGCCCCACCAG
CCUGUACCACCAGGCCAACAAGGGCGUGAGGGUGGCCUACUGGAUCGGCUUCG
ACACCACACCCUUCAUGUUCAAGAACCUGGCCGGCGCCUACCCCAGCUACAGC
ACCAACUGGGCCGACGAGACCGUGCUGACCGCCAGGAACAUCGGCCUGUGCAG
CAGCGACGUGAUGGAGAGGAGCCGGAGAGGCAUGAGCAUCCUGAGGAAGAAA
UACCUGAAGCCCAGCAACAACGUGCUGUUCAGCGUGGGCAGCACCAUCUACCA
CGAGAAGAGGGACCUGCUCAGGAGCUGGCACCUGCCCAGCGUGUUCCACCUGA
GGGGCAAGCAGAACUACACCUGCAGGUGCGAGACCAUCGUGAGCUGCGACGGC
UACGUGGUGAAGAGGAUCGCCAUCAGCCCCGGCCUGUACGGCAAGCCCAGCGG
CUACGCCGCUACAAUGCACAGGGAGGGCUUCCUGUGCUGCAAGGUGACCGACA
CCCUGAACGGCGAGAGGGUGAGCUUCCCCGUGUGCACCUACGUGCCCGCCACC
CUGUGCGACCAGAUGACCGGCAUCCUGGCCACCGACGUGAGCGCCGACGACGC
CCAGAAGCUGCUCGUGGGCCUGAACCAGAGGAUCGUGGUCAACGGCAGGACCC
AGAGGAACACCAACACAAUGAAGAACUACCUGCUGCCCGUGGUGGCCCAGGCU
UUCGCCAGGUGGGCCAAGGAGUACAAGGAGGACCAGGAAGACGAGAGGCCCCU
GGGCCUGAGGGACAGGCAGCUGGUGAUGGGCUGCUGCUGGGCCUUCAGGCGGC
ACAAGAUCACCAGCAUCUACAAGAGGCCCGACACCCAGACCAUCAUCAAGGUG

-continued

AACAGCGACUUCCACAGCUUCGUGCUGCCCAGGAUCGGCAGCAACACCCUGGA
GAUCGGCCUGAGGACCCGGAUCAGGAAGAUGCUGGAGGAACACAAGGAGCCCA
GCCCACUGAUCACCGCCGAGGACGUGCAGGAGGCCAAGUGCGCUGCCGACGAG
GCCAAGGAGGUGAGGGAGGCCGAGGAACUGAGGGCCGCCCUGCCACCCCUGGC
UGCCGACGUGGAGGAACCCACCCUGGAAGCCGACGUGGACCUGAUGCUGCAGG
AGGCCGGCGCCGGAAGCGUGGAGACACCCAGGGGCCUGAUCAAGGUGACCAGC
UACGACGGCGAGGACAAGAUCGGCAGCUACGCCGUGCUGAGCCCACAGGCCGU
GCUGAAGUCCGAGAAGCUGAGCUGCAUCCACCCACUGGCCGAGCAGGUGAUCG
UGAUCACCCACAGCGGCAGGAAGGGCAGGUACGCCGUGGAGCCCUACCACGGC
AAGGUGGUCGUGCCCGAGGGCCACGCCAUCCCCGUGCAGGACUUCCAGGCCCU
GAGCGAGAGCGCCACCAUCGUGUACAACGAGAGGGAGUUCGUGAACAGGUACC
UGCACCAUAUCGCCACCCACGGCGGAGCCCUGAACACCGACGAGGAAUACUAC
AAGACCGUGAAGCCCAGCGAGCACGACGGCGAGUACCUGUACGACAUCGACAG
GAAGCAGUGCGUGAAGAAAGAGCUGGUGACCGGCCUGGGACUGACCGGCGAG
CUGGUGGACCCACCCUUCCACGAGUUCGCCUACGAGAGCCUGAGGACCAGACC
CGCCGCUCCCUACCAGGUGCCCACCAUCGGCGUGUACGGCGUGCCCGGCAGCG
GAAAGAGCGGCAUCAUCAAGAGCGCCGUGACCAAGAAAGACCUGGUGGUCAGC
GCCAAGAAAGAGAACUGCGCCGAGAUCAUCAGGGACGUGAAGAAGAUGAAAG
GCCUGGACGUGAACGCGCGCACCGUGGACAGCGUGCUGCUGAACGGCUGCAAG
CACCCCGUGGAGACCCUGUACAUCGACGAGGCCUUCGCUUGCCACGCCGGCAC
CCUGAGGGCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCACUUCAAC
CACGAGAUCUGCACCCAGGUGUUCCACAAGAGCAUCAGCAGGCGGUGCACCAA
GAGCGUGACCAGCGUCGUGAGCACCCUGUUCUACGACAAGAAAAUGAGGACCA
CCAACCCCAAGGAGACCAAAAUCGUGAUCGACACCACAGGCAGCACCAAGCCC
AAGCAGGACGACCUGAUCCUGACCUGCUUCAGGGGCUGGGUGAAGCAGCUGCA
GAUCGACUACAAGGGCAACGAGAUCAUGACCGCCGCUGCCAGCCAGGGCCUGA
CCAGGAAGGGCGUGUACGCCGUGAGGUACAAGGUGAACGAGAACCCACUGUAC
GCUCCCACCAGCGAGCACGUGAACGUGCUGCUGACCAGGACCGAGGACAGGAU
CGUGUGGAAGACCCUGGCCGGCGACCCCUGGAUCAAGACCCUGACCGCCAAGU
ACCCCGGCAACUUCACCGCCACCAUCGAAGAGUGGCAGGCCGAGCACGACGCC
AUCAUGAGGCACAUCCUGGAGAGGCCCGACCCCACCGACGUGUUCCAGAACAA
GGCCAACGUGUGCUGGGCCAAGGCCCUGGUGCCCGUGCUGAAGACCGCCGGCA
UCGACAUGACCACAGAGCAGUGGAACACCGUGGACUACUUCGAGACCGACAAG
GCCCACAGCGCCGAGAUCGUGCUGAACCAGCUGUGCGUGAGGUUCUUCGGCCU
GGACCUGGACAGCGGCCUGUUCAGCGCCCCCACCGUGCCACUGAGCAUCAGGA
ACAACCACUGGGACAACAGCCCCAGCCCAAACAUGUACGGCCUGAACAAGGAG
GUGGUCAGGCAGCUGAGCAGGCGGUACCCACAGCUGCCCAGGGCCGUGGCCAC
CGGCAGGGUGUACGACAUGAACACCGGCACCCUGAGGAACUACGACCCCAGGA
UCAACCUGGUGCCCGUGAACAGGCGGCUGCCCCACGCCCUGGUGCUGCACCAC

-continued

AACGAGCACCCACAGAGCGACUUCAGCUCCUUCGUGAGCAAGCUGAAAGGCAG
GACCGUGCUGGUCGUGGGCGAGAAGCUGAGCGUGCCCGGCAAGAUGGUGGAC
UGGCUGAGCGACAGGCCCGAGGCCACCUUCCGGGCCAGGCUGGACCUCGGCAU
CCCCGGCGACGUGCCCAAGUACGACAUCAUCUUCGUGAACGUCAGGACCCCAU
ACAAGUACCACCAUUACCAGCAGUGCGAGGACCACGCCAUCAAGCUGAGCAUG
CUGACCAAGAAGGCCUGCCUGCACCUGAACCCCGGAGGCACCUGCGUGAGCAU
CGGCUACGGCUACGCCGACAGGGCCAGCGAGAGCAUCAUUGGCGCCAUCGCCA
GGCUGUUCAAGUUCAGCAGGGUGUGCAAACCCAAGAGCAGCCUGGAGGAAACC
GAGGUGCUGUUCGUGUUCAUCGGCUACGACCGGAAGGCCAGGACCCACAACCC
CUACAAGCUGAGCAGCACCCUGACAAACAUCUACACCGGCAGCAGGCUGCACG

AGGCCGGCUGCGCCCCCAGCUACCACGUGGUCAGGGGCGAUAUCGCCACCGCC

ACCGAGGGCGUGAUCAUCAACGCUGCCAACAGCAAGGGCCAGCCCGGAGGCGG
AGUGUGCGGCGCCCUGUACAAGAAGUUCCCCGAGAGCUUCGACCUGCAGCCCA
UCGAGGUGGGCAAGGCCAGGCUGGUGAAGGGCGCCGCUAAGCACAUCAUCCAC
GCCGUGGGCCCCAACUUCAACAAGGUGAGCGAGGUGGAAGGCGACAAGCAGCU
GGCCGAAGCCUACGAGAGCAUCGCCAAGAUCGUGAACGACAAUAACUACAAGA
GCGUGGCCAUCCCACUGCUCAGCACCGGCAUCUUCAGCGGCAACAAGGACAGG
CUGACCCAGAGCCUGAACCACCUGCUCACCGCCCUGGACACCACCGAUGCCGA
CGUGGCCAUCUACUGCAGGGACAAGAAGUGGGAGAUGACCCUGAAGGAGGCC
GUGGCCAGGCGGGAGGCCGUGGAAGAGAUCUGCAUCAGCGACGACUCCAGCGU
GACCGAGCCCGACGCCGAGCUGGUGAGGGUGCACCCCAAGAGCUCCCUGGCCG
GCAGGAAGGGCUACAGCACCAGCGACGGCAAGACCUUCAGCUACCUGGAGGGC
ACCAAGUUCCACCAGGCCGCUAAGGACAUCGCCGAGAUCAACGCUAUGUGGCC
CGUGGCCACCGAGGCCAACGAGCAGGUGUGCAUGUACAUCCUGGGCGAGAGCA
UGUCCAGCAUCAGGAGCAAGUGCCCCGUGGAGGAAAGCGAGGCCAGCACACCA
CCCAGCACCCUGCCCUGCCUGUGCAUCCACGCUAUGACACCCGAGAGGGUGCA
GCGGCUGAAGGCCAGCAGGCCCGAGCAGAUCACCGUGUGCAGCUCCUUCCCAC
UGCCCAAGUACAGGAUCACCGGCGUGCAGAAGAUCCAGUGCAGCCAGCCCAUC
CUGUUCAGCCCAAAGGUGCCCGCCUACAUCCACCCCAGGAAGUACCUGGUGGA
GACCCCACCCGUGGACGAGACACCCGAGCCAAGCGCCGAGAACCAGAGCACCG
AGGGCACACCCGAGCAGCCACCCCUGAUCACCGAGGACGAGACAAGGACCCGG
ACCCCAGAGCCCAUCAUUAUCGAGGAAGAGGAAGAGGACAGCAUCAGCCUGCU
GAGCGACGGCCCCACCCACCAGGUGCUGCAGGUGGAGGCCGACAUCCACGGCC
CACCCAGCGUGUCCAGCUCCAGCUGGAGCAUCCCACACGCCAGCGACUUCGAC
GUGGACAGCCUGAGCAUCCUGGACACCCUGGAGGGCGCCAGCGUGACCUCCGG
CGCCACCAGCGCCGAGACCAACAGCUACUUCGCCAAGAGCAUGGAGUUCCUGG
CCAGGCCCGUGCCAGCUCCCAGGACCGUGUUCAGGAACCCACCCCACCCAGCUC
CCAGGACCAGGACCCCAAGCCUGGCUCCCAGCAGGGCCUGCAGCAGGACCAGC
CUGGUGAGCACCCCACCCGGCGUGAACAGGGUGAUCACCAGGGAGGAACUGGA
GGCCCUGACACCCAGCAGGACCCCCAGCAGGUCCGUGAGCAGGACUAGUCUGG
UGUCCAACCCACCCGGCGUGAACAGGGUGAUCACCAGGGAGGAAUUCGAGGCC

```
UUCGUGGCCCAGCAACAGAGACGGUUCGACGCCGGCGCCUACAUCUUCAGCAG

CGACACCGGCCAGGGACACCUGCAGCAAAAGAGCGUGAGGCAGACCGUGCUGA

GCGAGGUGGUGCUGGAGAGGACCGAGCUGGAAAUCAGCUACGCCCCCAGGCUG

GACCAGGAGAAGGAGGAACUGCUCAGGAAGAAACUGCAGCUGAACCCCACCCC

AGCCAACAGGAGCAGGUACCAGAGCAGGAAGGUGGAGAACAUGAAGGCCAUC

ACCGCCAGGCGGAUCCUGCAGGGCCUGGGACACUACCUGAAGGCCGAGGGCAA

GGUGGAGUGCUACAGGACCCUGCACCCCGUGCCACUGUACAGCUCCAGCGUGA

ACAGGGCCUUCUCCAGCCCCAAGGUGGCCGUGGAGGCCUGCAACGCUAUGCUG

AAGGAGAACUUCCCCACCGUGGCCAGCUACUGCAUCAUCCCCGAGUACGACGC

CUACCUGGACAUGGUGGACGGCGCCAGCUGCUGCCUGGACACCGCCAGCUUCU

GCCCCGCCAAGCUGAGGAGCUUCCCCAAGAAACACAGCUACCUGGAGCCCACC

AUCAGGAGCGCCGUGCCCAGCGCCAUCCAGAACACCCUGCAGAACGUGCUGGC

CGCUGCCACCAAGAGGAACUGCAACGUGACCCAGAUGAGGGAGCUGCCCGUGC

UGGACAGCGCUGCCUUCAACGUGGAGUGCUUCAAGAAAUACGCCUGCAACAAC

GAGUACUGGGAGACCUUCAAGGAGAACCCCAUCAGGCUGACCGAAGAGAACGU

GGUGAACUACAUCACCAAGCUGAAGGGCCCCAAGGCCGCUGCCCUGUUCGCUA

AGACCCACAACCUGAACAUGCUGCAGGACAUCCCAAUGGACAGGUUCGUGAUG

GACCUGAAGAGGGACGUGAAGGUGACACCCGGCACCAAGCACACCGAGGAGAG

GCCCAAGGUGCAGGUGAUCCAGGCCGCUGACCCACUGGCCACCGCCUACCUGU

GCGGCAUCCACAGGGAGCUGGUGAGGCGGCUGAACGCCGUGCUGCUGCCCAAC

AUCCACACCCUGUUCGACAUGAGCGCCGAGGACUUCGACGCCAUCAUCGCCGA

GCACUUCCAGCCCGGCGACUGCGUGCUGGAGACCGACAUCGCCAGCUUCGACA

AGAGCGAGGAUGACGCUAUGGCCCUGACCGCUCUGAUGAUCCUGGAGGACCUG

GGCGUGGACGCCGAGCUGCUCACCCUGAUCGAGGCUGCCUUCGGCGAGAUCAG

CUCCAUCCACCUGCCCACCAAGACCAAGUUCAAGUUCGGCGCUAUGAUGAAAA

GCGGAAUGUUCCUGACCCUGUUCGUGAACACCGUGAUCAACAUUGUGAUCGCC

AGCAGGGUGCUGCGGGAGAGGCUGACCGGCAGCCCCGCGCUGCCUUCAUCGG

CGACGACAACAUCGUGAAGGGCGUGAAAAGCGACAAGCUGAUGGCCGACAGG

UGCGCCACCUGGCUGAACAUGGAGGUGAAGAUCAUCGACGCCGUGGUGGGCGA

GAAGGCCCCCUACUUCUGCGGCGGAUUCAUCCUGUGCGACAGCGUGACCGGCA

CCGCCUGCAGGGUGGCCGACCCCCUGAAGAGGCUGUUCAAGCUGGGCAAGCCA

CUGGCCGCUGACGAUGAGCACGACGAUGACAGGCGGAGGGCCCUGCACGAGGA

AAGCACCAGGUGGAACAGGGUGGGCAUCCUGAGCGAGCUGUGCAAGGCCGUG

GAGAGCAGGUACGAGACCGUGGGCACCAGCAUCAUCGUGAUGGCUAUGACCAC

ACUGGCCAGCUCCGUCAAGAGCUUCUCCUACCUGAGGGGGGCCCCUAUAACUC

UCUACGGCUAACCUGAAUGGACUACGACAUAGUCUAGUCCGCCAAGGCCGCCA

CCAUGGAAGAUGCCAAAAACAUUAAGAAGGGCCCAGCGCCAUUCUACCCACUC

GAAGACGGGACCGCCGGCGAGCAGCUGCACAAAGCCAUGAAGCGCUACGCCCU

GGUGCCCGGCACCAUCGCCUUUACCGACGCACAUAUCGAGGUGGACAUUACCU

ACGCCGAGUACUUCGAGAUGAGCGUUCGGCUGGCAGAAGCUAUGAAGCGCUA
```

-continued

```
UGGGCUGAAUACAAACCAUCGGAUCGUGGUGUGCAGCGAGAAUAGCUUGCAG

UUCUUCAUGCCCGUGUUGGGUGCCCUGUUCAUCGGUGUGGCUGUGGCCCAGC

UAACGACAUCUACAACGAGCGCGAGCUGCUGAACAGCAUGGGCAUCAGCCAGC

CCACCGUCGUAUUCGUGAGCAAGAAAGGGCUGCAAAAGAUCCUCAACGUGCAA

AAGAAGCUACCGAUCAUACAAAAGAUCAUCAUCAUGGAUAGCAAGACCGACU

ACCAGGGCUUCCAAAGCAUGUACACCUUCGUGACUUCCCAUUUGCCACCCGGC

UUCAACGAGUACGACUUCGUGCCCGAGAGCUUCGACCGGGACAAAACCAUCGC

CCUGAUCAUGAACAGUAGUGGCAGUACCGGAUUGCCCAAGGGCGUAGCCCUAC

CGCACCGCACCGCUUGUGUCCGAUUCAGUCAUGCCCGCGACCCCAUCUUCGGC

AACCAGAUCAUCCCCGACACCGCUAUCCUCAGCGUGGUGCCAUUUCACCACGG

CUUCGGCAUGUUCACCACGCUGGGCUACUUGAUCUGCGGCUUUCGGGUCGUGC

UCAUGUACCGCUUCGAGGAGGAGCUAUUCUUGCGCAGCUUGCAAGACUAUAA

GAUUCAAUCUGCCCUGCUGGUGCCCACACUAUUUAGCUUCUUCGCUAAGAGCA

CUCUCAUCGACAAGUACGACCUAAGCAACUUGCACGAGAUCGCCAGCGGCGGG

GCGCCGCUCAGCAAGGAGGUAGGUGAGGCCGUGGCCAAACGCUUCCACCUACC

AGGCAUCCGACAGGGCUACGGCCUGACAGAAACAACCAGCGCCAUUCUGAUCA

CCCCCGAAGGGGACGACAAGCCUGGCGCAGUAGGCAAGGUGGUGCCCUUCUUC

GAGGCUAAGGUGGUGGACUUGGACACCGGUAAGACACUGGGUGUGAACCAGC

GCGGCGAGCUGUGCGUCCGUGGCCCCAUGAUCAUGAGCGGCUACGUUAACAAC

CCCGAGGCUACAAACGCUCUCAUCGACAAGGACGGCUGGCUGCACAGCGGCGA

CAUCGCCUACUGGGACGAGGACGAGCACUUCUUCAUCGUGGACCGGCUGAAGU

CCCUGAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCGACGA

CGAUGCCGGCGAGCUGCCCGCCGCAGUCGUCGUGCUGGAACACGGUAAAACCA

UGACCGAGAAGGAGAUCGUGGACUAUGUGGCCAGCCAGGUUACAACCGCCAAG

AAGCUGCGCGGUGGUGUUGUGUUCGUGGACGAGGUGCCUAAAGGACUGACCG

GCAAGUUGGACGCCCGCAAGAUCCGCGAGAUUCUCAUUAAGGCCAAGAAGGGC

GGCAAGAUCGCCGUGUAACUCGAGCCGGAAACGCAAUAGCCGAAAAACAAAAA

ACAAAAAAAACAAAAAAAAAACCAAAAAAACAAAACACAUUAAAACAGCCUG

UGGGUUGAUCCCACCCACAGGCCCAUUGGGCGCUAGCACUCUGGUAUCACGGU

ACCUUUGUGCGCCUGUUUUAUACCCCUCCCCCAACUGUAACUUAGAAGUAAC

ACACACCGAUCAACAGUCAGCGUGGCACACCAGCCACGUUUUGAUCAAGCACU

UCUGUUACCCCGGACUGAGUAUCAAUAGACUGCUCACGCGGUUGAAGGAGAA

AGCGUUCGUUAUCCGGCCAACUACUUCGAAAAACCUAGUAACACCGUGGAAGU

UGCAGAGUGUUUCGCUCAGCACUACCCCAGUGUAGAUCAGGUCGAUGAGUCAC

CGCAUUCCCCACGGGCGACCGUGGCGGUGGCUGCGUUGGCGGCCUGCCCAUGG

GGAAACCCAUGGGACGCUCUAAUACAGACAUGGUGCGAAGAGUCUAUUGAGC

UAGUUGGUAGUCCUCCGGCCCCUGAAUGCGGCUAAUCCUAACUGCGGAGCACA

CACCCUCAAGCCAGAGGGCAGUGUGUCGUAACGGGCAACUCUGCAGCGGAACC

GACUACUUUGGGUGUCCGUGUUUCAUUUUAUUCCUAUACUGGCUGCUUUAUGG

UGACAAUUGAGAGAUCGUUACCAUAUAGCUAUUGGAUUGGCCAUCCGGUGAC
```

-continued

UAAUAGAGCUAUUAUAUAUCCCUUUGUUGGGUUUAUACCACUUAGCUUGAAA

GAGGUUAAAACAUUACAAUUCAUUGUUAAGUUGAAUACAGCAAAAUGAGCAA

GAUCUACAUCGACGAGCGGAGCAACGCCGAGAUCGUGUGCGAGGCCAUCAAGA

CCAUCGGCAUCGAGGGCGCCACCGCCGCCCAGCUGACCAGGCAGCUGAACAUG

GAGAAGCGGGAGGUGAACAAGGCCCUGUACGACCUGCAGAGGAGCGCUAUGG

UGUACUCCAGCGACGACAUCCCUCCCCGGUGGUUCAUGACCACCGAGGCCGAC

AAGCCCGACGCCGACGCUAUGGCCGACGUGAUCAUCGACGACGUGAGCAGGGA

GAAGUCCAUGAGGGAGGACCACAAGAGCUUCGACGACGUGAUCCCCGCCAAGA

AGAUCAUCGACUGGAAGGGCGCCAACCCCGUGACCGUGAUCAACGAGUACUGC

CAGAUCACCAGGAGGGACUGGAGCUUCCGGAUCGAGAGCGUGGGCCCCAGCAA

CAGCCCCACCUUCUACGCCUGCGUGGACAUCGACGGCAGGGUGUUCGACAAGG

CCGACGGCAAGAGCAAGCGGGACGCCAAGAACAACGCCGCCAAGCUGGCCGUG

GACAAGCUGCUGGGCUACGUGAUCAUCCGGUUCUAAACGUAUGUUACGUGCA

AAGGUGAUUGUCACCCCCCGAAAGACCAUAUUGUGACACACCCUCAGUAUCAC

GCCCAAACAUUUACAGCCGCGGUGUCAAAAACCGCGUGGACGUGGUUAACAUC

CCUGCUGGGAGGAUCAGCCGUAAUUAUUAUAAUUGGCUUGGUGCUGGCUACU

AUUGUGGCCAUGUACGUGCUGACCAACCAGAAACAUAAUUGAAUACAGCAGC

AAUUGGCAAGCUGCUUACAUAGAACUCGCGGCGAUUGGCAUGCCGCCUUAAAA

UUUUUAUUUUAUUUUUUCUUUUCUUUUCCGAAUCGGAUUUUGUUUUUAAUAU

UUCAAAAAAAAAAAAAAAAAAAAAAAAAAUCUAGAAAAAAAAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAA (RNA sequence for STARR Fluc IRES-E3L (short 3' UTR))
SEQ ID NO:129

AUGGGCGGCGCAUGAGAGAAGCCCAGACCAAUUACCUACCCAAAAUGGAGAAA

GUUCACGUUGACAUCGAGGAAGACAGCCCAUUCCUCAGAGCUUUGCAGCGGAG

CUUCCCGCAGUUUGAGGUAGAAGCCAAGCAGGUCACUGAUAAUGACCAUGCUA

AUGCCAGAGCGUUUUCGCAUCUGGCUUCAAAACUGAUCGAAACGGAGGUGGA

CCCAUCCGACACGAUCCUUGACAUUGGAAGUGCGCCCGCCCGCAGAAUGUAUU

CUAAGCACAAGUAUCAUUGUAUCUGUCCGAUGAGAUGUGCGGAAGAUCCGGA

CAGAUUGUAUAAGUAUGCAACUAAGCUGAAGAAAAACUGUAAGGAAAUAACU

GAUAAGGAAUUGGACAAGAAAAUGAAGGAGCUGGCCGCCGUCAUGAGCGACC

CUGACCUGGAAACUGAGACUAUGUGCCUCCACGACGACGAGUCGUGUCGCUAC

GAAGGGCAAGUCGCUGUUUACCAGGAUGUAUACGCCGUCGACGGCCCCACCAG

CCUGUACCACCAGGCCAACAAGGGCGUGAGGGUGGCCUACUGGAUCGGCUUCG

ACACCACACCCUUCAUGUUCAAGAACCUGGCCGGCGCCUACCCCAGCUACAGC

ACCAACUGGGCCGACGAGACCGUGCUGACCGCCAGGAACAUCGGCCUGUGCAG

CAGCGACGUGAUGGAGAGGAGCCGGAGAGGCAUGAGCAUCCUGAGGAAGAAA

UACCUGAAGCCCAGCAACAACGUGCUGUUCAGCGUGGGCAGCACCAUCUACCA

CGAGAAGAGGGACCUGCUCAGGAGCUGGCACCUGCCCAGCGUGUUCCACCUGA

-continued

GGGGCAAGCAGAACUACACCUGCAGGUGCGAGACCAUCGUGAGCUGCGACGGC
UACGUGGUGAAGAGGAUCGCCAUCAGCCCCGGCCUGUACGGCAAGCCCAGCGG
CUACGCCGCUACAAUGCACAGGGAGGGCUUCCUGUGCUGCAAGGUGACCGACA
CCCUGAACGGCGAGAGGGUGAGCUUCCCCGUGUGCACCUACGUGCCCGCCACC
CUGUGCGACCAGAUGACCGGCAUCCUGGCCACCGACGUGAGCGCCGACGACGC
CCAGAAGCUGCUCGUGGGCCUGAACCAGAGGAUCGUGGUCAACGGCAGGACCC
AGAGGAACACCAACACAAUGAAGAACUACCUGCUGCCCGUGGUGGCCCAGGCU
UUCGCCAGGUGGGCCAAGGAGUACAAGGAGGACCAGGAAGACGAGAGGCCCCU
GGGCCUGAGGGACAGGCAGCUGGUGAUGGGCUGCUGCUGGGCCUUCAGGCGGC
ACAAGAUCACCAGCAUCUACAAGAGGCCCGACACCCAGACCAUCAUCAAGGUG
AACAGCGACUUCCACAGCUUCGUGCUGCCCAGGAUCGGCAGCAACACCCUGGA
GAUCGGCCUGAGGACCCGGAUCAGGAAGAUGCUGGAGGAACACAAGGAGCCCA
GCCCACUGAUCACCGCCGAGGACGUGCAGGAGGCCAAGUGCGCUGCCGACGAG
GCCAAGGAGGUGAGGGAGGCCGAGGAACUGAGGGCCGCCCUGCCACCCCUGGC
UGCCGACGUGGAGGAACCCACCCUGGAAGCCGACGUGGACCUGAUGCUGCAGG
AGGCCGGCGCCGGAAGCGUGGAGACACCCAGGGGCCUGAUCAAGGUGACCAGC
UACGACGGCGAGGACAAGAUCGGCAGCUACGCCGUGCUGAGCCCACAGGCCGU
GCUGAAGUCCGAGAAGCUGAGCUGCAUCCACCCACUGGCCGAGCAGGUGAUCG
UGAUCACCCACAGCGGCAGGAAGGGCAGGUACGCCGUGGAGCCCUACCACGGC
AAGGUGGUCGUGCCCGAGGGCCACGCCAUCCCCGUGCAGGACUUCCAGGCCCU
GAGCGAGAGCGCCACCAUCGUGUACAACGAGAGGGAGUUCGUGAACAGGUACC
UGCACCAUAUCGCCACCCACGGCGGAGCCCUGAACACCGACGAGGAAUACUAC
AAGACCGUGAAGCCCAGCGAGCACGACGGCGAGUACCUGUACGACAUCGACAG
GAAGCAGUGCGUGAAGAAAGAGCUGGUGACCGGCCUGGGACUGACCGGCGAG
CUGGUGGACCCACCCUUCCACGAGUUCGCCUACGAGAGCCUGAGGACCAGACC
CGCCGCUCCCUACCAGGUGCCCACCAUCGGCGUGUACGGCGUGCCCGGCAGCG
GAAAGAGCGGCAUCAUCAAGAGCGCCGUGACCAAGAAAGACCUGGUGGUCAGC
GCCAAGAAAGAGAACUGCGCCGAGAUCAUCAGGGACGUGAAGAAGAUGAAAG
GCCUGGACGUGAACGCGCGCACCGUGGACAGCGUGCUGCUGAACGGCUGCAAG
CACCCCGUGGAGACCCUGUACAUCGACGAGGCCUUCGCUUGCCACGCCGGCAC
CCUGAGGGCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCACUUCAAC
CACGAGAUCUGCACCCAGGUGUUCCACAAGAGCAUCAGCAGGCGGUGCACCAA
GAGCGUGACCAGCGUCGUGAGCACCCUGUUCUACGACAAGAAAAUGAGGACCA
CCAACCCCAAGGAGACCAAAAUCGUGAUCGACACCACAGGCAGCACCAAGCCC
AAGCAGGACGACCUGAUCCUGACCUGCUUCAGGGGCUGGGUGAAGCAGCUGCA
GAUCGACUACAAGGGCAACGAGAUCAUGACCGCCGCUGCCAGCCAGGGCCUGA
CCAGGAAGGGCGUGUACGCCGUGAGGUACAAGGUGAACGAGAACCCACUGUAC
GCUCCCACCAGCGAGCACGUGAACGUGCUGCUGACCAGGACCGAGGACAGGAU
CGUGUGGAAGACCCUGGCCGGCGACCCCUGGAUCAAGACCCUGACCGCCAAGU

-continued

ACCCCGGCAACUUCACCGCCACCAUCGAAGAGUGGCAGGCCGAGCACGACGCC

AUCAUGAGGCACAUCCUGGAGAGGCCCGACCCCACCGACGUGUUCCAGAACAA

GGCCAACGUGUGCUGGGCCAAGGCCCUGGUGCCCGUGCUGAAGACCGCCGGCA

UCGACAUGACCACAGAGCAGUGGAACACCGUGGACUACUUCGAGACCGACAAG

GCCCACAGCGCCGAGAUCGUGCUGAACCAGCUGUGCGUGAGGUUCUUCGGCCU

GGACCUGGACAGCGGCCUGUUCAGCGCCCCCACCGUGCCACUGAGCAUCAGGA

ACAACCACUGGGACAACAGCCCCAGCCCAAACAUGUACGGCCUGAACAAGGAG

GUGGUCAGGCAGCUGAGCAGGCGGUACCCACAGCUGCCCAGGGCCGUGGCCAC

CGGCAGGGUGUACGACAUGAACACCGGCACCCUGAGGAACUACGACCCCAGGA

UCAACCUGGUGCCCGUGAACAGGCGGCUGCCCCACGCCCUGGUGCUGCACCAC

AACGAGCACCCACAGAGCGACUUCAGCUCCUUCGUGAGCAAGCUGAAAGGCAG

GACCGUGCUGGUCGUGGGCGAGAAGCUGAGCGUGCCCGGCAAGAUGGUGGAC

UGGCUGAGCGACAGGCCCGAGGCCACCUUCCGGGCCAGGCUGGACCUCGGCAU

CCCCGGCGACGUGCCCAAGUACGACAUCAUCUUCGUGAACGUCAGGACCCCAU

ACAAGUACCACCAUUACCAGCAGUGCGAGGACCACGCCAUCAAGCUGAGCAUG

CUGACCAAGAAGGCCUGCCUGCACCUGAACCCCGGAGGCACCUGCGUGAGCAU

CGGCUACGGCUACGCCGACAGGGCCAGCGAGAGCAUCAUUGGCGCCAUCGCCA

GGCUGUUCAAGUUCAGCAGGGUGUGCAAACCCAAGAGCAGCCUGGAGGAAACC

GAGGUGCUGUUCGUGUUCAUCGGCUACGACCGGAAGGCCAGGACCCACAACCC

CUACAAGCUGAGCAGCACCCUGACAAACAUCUACACCGGCAGCAGGCUGCACG

AGGCCGGCUGCGCCCCCAGCUACCACGUGGUCAGGGGCGAUAUCGCCACCGCC

ACCGAGGGCGUGAUCAUCAACGCUGCCAACAGCAAGGGCCAGCCCGGAGGCGG

AGUGUGCGGCGCCCUGUACAAGAAGUUCCCCGAGAGCUUCGACCUGCAGCCCA

UCGAGGUGGGCAAGGCCAGGCUGGUGAAGGGCGCCGCUAAGCACAUCAUCCAC

GCCGUGGGCCCCAACUUCAACAAGGUGAGCGAGGUGGAAGGCGACAAGCAGCU

GGCCGAAGCCUACGAGAGCAUCGCCAAGAUCGUGAACGACAAUAACUACAAGA

GCGUGGCCAUCCCACUGCUCAGCACCGGCAUCUUCAGCGGCAACAAGGACAGG

CUGACCCAGAGCCUGAACCACCUGCUCACCGCCCUGGACACCACCGAUGCCGA

CGUGGCCAUCUACUGCAGGGACAAGAAGUGGGAGAUGACCCUGAAGGAGGCC

GUGGCCAGGCGGGAGGCCGUGGAAGAGAUCUGCAUCAGCGACGACUCCAGCGU

GACCGAGCCCGACGCCGAGCUGGUGAGGGUGCACCCCAAGAGCUCCCUGGCCG

GCAGGAAGGGCUACAGCACCAGCGACGGCAAGACCUUCAGCUACCUGGAGGGC

ACCAAGUUCCACCAGGCCGCUAAGGACAUCGCCGAGAUCAACGCUAUGUGGCC

CGUGGCCACCGAGGCCAACGAGCAGGUGUGCAUGUACAUCCUGGGCGAGAGCA

UGUCCAGCAUCAGGAGCAAGUGCCCCGUGGAGGAAAGCGAGGCCAGCACACCA

CCCAGCACCCUGCCCUGCCUGUGCAUCCACGCUAUGACACCCGAGAGGGUGCA

GCGGCUGAAGGCCAGCAGGCCCGAGCAGAUCACCGUGUGCAGCUCCUUCCCAC

UGCCCAAGUACAGGAUCACCGGCGUGCAGAAGAUCCAGUGCAGCCAGCCCAUC

CUGUUCAGCCCAAAGGUGCCCGCCUACAUCCACCCCAGGAAGUACCUGGUGGA

GACCCCACCCGUGGACGAGACACCCGAGCCAAGCGCCGAGAACCAGAGCACCG

AGGGCACACCCGAGCAGCCACCCCUGAUCACCGAGGACGAGACAAGGACCCGG

-continued

```
ACCCCAGAGCCCAUCAUUAUCGAGGAAGAGGAAGAGGACAGCAUCAGCCUGCU
GAGCGACGGCCCCACCCACCAGGUGCUGCAGGUGGAGGCCGACAUCCACGGCC
CACCCAGCGUGUCCAGCUCCAGCUGGAGCAUCCCACACGCCAGCGACUUCGAC
GUGGACAGCCUGAGCAUCCUGGACACCCUGGAGGGCGCCAGCGUGACCUCCGG
CGCCACCAGCGCCGAGACCAACAGCUACUUCGCCAAGAGCAUGGAGUUCCUGG
CCAGGCCCGUGCCAGCUCCCAGGACCGUGUUCAGGAACCCACCCCACCCAGCUC
CCAGGACCAGGACCCCAAGCCUGGCUCCCAGCAGGGCCUGCAGCAGGACCAGC
CUGGUGAGCACCCCACCCGGCGUGAACAGGGUGAUCACCAGGGAGGAACUGGA
GGCCCUGACACCCAGCAGGACCCCCAGCAGGUCCGUGAGCAGGACUAGUCUGG
UGUCCAACCCACCCGGCGUGAACAGGGUGAUCACCAGGGAGGAAUUCGAGGCC
UUCGUGGCCCAGCAACAGAGACGGUUCGACGCCGGCGCCUACAUCUUCAGCAG
CGACACCGGCCAGGGACACCUGCAGCAAAAGAGCGUGAGGCAGACCGUGCUGA
GCGAGGUGGUGCUGGAGAGGACCGAGCUGGAAAUCAGCUACGCCCCCAGGCUG
GACCAGGAGAAGGAGGAACUGCUCAGGAAGAAACUGCAGCUGAACCCCACCCC
AGCCAACAGGAGCAGGUACCAGAGCAGGAAGGUGGAGAACAUGAAGGCCAUC
ACCGCCAGGCGGAUCCUGCAGGGCCUGGGACACUACCUGAAGGCCGAGGGCAA
GGUGGAGUGCUACAGGACCCUGCACCCCGUGCCACUGUACAGCUCCAGCGUGA
ACAGGGCCUUCUCCAGCCCCAAGGUGGCCGUGGAGGCCUGCAACGCUAUGCUG
AAGGAGAACUUCCCCACCGUGGCCAGCUACUGCAUCAUCCCCGAGUACGACGC
CUACCUGGACAUGGUGGACGGCGCCAGCUGCUGCCUGGACACCGCCAGCUUCU
GCCCCGCCAAGCUGAGGAGCUUCCCCAAGAAACACAGCUACCUGGAGCCCACC
AUCAGGAGCGCCGUGCCCAGCGCCAUCCAGAACACCCUGCAGAACGUGCUGGC
CGCUGCCACCAAGAGGAACUGCAACGUGACCCAGAUGAGGGAGCUGCCCGUGC
UGGACAGCGCUGCCUUCAACGUGGAGUGCUUCAAGAAAUACGCCCUGCAACAAC
GAGUACUGGGAGACCUUCAAGGAGAACCCCAUCAGGCUGACCGAAGAGAACGU
GGUGAACUACAUCACCAAGCUGAAGGGCCCCAAGGCCGCUGCCCUGUUCGCUA
AGACCCACAACCUGAACAUGCUGCAGGACAUCCCAAUGGACAGGUUCGUGAUG
GACCUGAAGAGGGACGUGAAGGUGACACCCGGCACCAAGCACACCGAGGAGAG
GCCCAAGGUGCAGGUGAUCCAGGCCGCUGACCCACUGGCCACCGCCUACCUGU
GCGGCAUCCACAGGGAGCUGGUGAGGCGGCUGAACGCCGUGCUGCUGCCCAAC
AUCCACACCCUGUUCGACAUGAGCGCCGAGGACUUCGACGCCAUCAUCGCCGA
GCACUUCCAGCCCGGCGACUGCGUGCUGGAGACCGACAUCGCCAGCUUCGACA
AGAGCGAGGAUGACGCUAUGGCCCUGACCGCUCUGAUGAUCCUGGAGGACCUG
GGCGUGGACGCCGAGCUGCUCACCCUGAUCGAGGCUGCCUUCGGCGAGAUCAG
CUCCAUCCACCUGCCCACCAAGACCAAGUUCAAGUUCGGCGCUAUGAUGAAAA
GCGGAAUGUUCCUGACCCUGUUCGUGAACACCGUGAUCAACAUUGUGAUCGCC
AGCAGGGUGCUGCGGGAGAGGCUGACCGGCAGCCCCGCGCUGCCUUCAUCGG
CGACGACAACAUCGUGAAGGGCGUGAAAAGCGACAAGCUGAUGGCCGACAGG
UGCGCCACCUGGCUGAACAUGGAGGUGAAGAUCAUCGACGCCGUGGUGGGCGA
GAAGGCCCCCUACUUCUGCGGCGGAUUCAUCCUGUGCGACAGCGUGACCGGCA
```

-continued

```
CCGCCUGCAGGGUGGCCGACCCCCUGAAGAGGCUGUUCAAGCUGGGCAAGCCA

CUGGCCGCUGACGAUGAGCACGACGAUGACAGGCGGAGGGCCCUGCACGAGGA

AAGCACCAGGUGGAACAGGGUGGGCAUCCUGAGCGAGCUGUGCAAGGCCGUG

GAGAGCAGGUACGAGACCGUGGGCACCAGCAUCAUCGUGAUGGCUAUGACCAC

ACUGGCCAGCUCCGUCAAGAGCUUCUCCUACCUGAGGGGGGCCCCUAUAACUC

UCUACGGCUAACCUGAAUGGACUACGACAUAGUCUAGUCCGCCAAGGCCGCCA

CCAUGGAAGAUGCCAAAAACAUUAAGAAGGGCCCAGCGCCAUUCUACCCACUC

GAAGACGGGACCGCCGGCGAGCAGCUGCACAAAGCCAUGAAGCGCUACGCCCU

GGUGCCCGGCACCAUCGCCUUUACCGACGCACAUAUCGAGGUGGACAUUACCU

ACGCCGAGUACUUCGAGAUGAGCGUUCGGCUGGCAGAAGCUAUGAAGCGCUA

UGGGCUGAAUACAAACCAUCGGAUCGUGGUGUGCAGCGAGAAUAGCUUGCAG

UUCUUCAUGCCCGUGUUGGGUGCCCUGUUCAUCGGUGUGGCUGUGGCCCCAGC

UAACGACAUCUACAACGAGCGCGAGCUGCUGAACAGCAUGGGCAUCAGCCAGC

CCACCGUCGUAUUCGUGAGCAAGAAAGGGCUGCAAAAGAUCCUCAACGUGCAA

AAGAAGCUACCGAUCAUACAAAAGAUCAUCAUCAUGGAUAGCAAGACCGACU

ACCAGGGCUUCCAAAGCAUGUACACCUUCGUGACUUCCCAUUUGCCACCCGGC

UUCAACGAGUACGACUUCGUGCCCGAGAGCUUCGACCGGGACAAAACCAUCGC

CCUGAUCAUGAACAGUAGUGGCAGUACCGGAUUGCCCAAGGGCGUAGCCCUAC

CGCACCGCACCGCUUGUGUCCGAUUCAGUCAUGCCCGCGACCCCAUCUUCGGC

AACCAGAUCAUCCCCGACACCGCUAUCCUCAGCGUGGUGCCAUUUCACCACGG

CUUCGGCAUGUUCACCACGCUGGGCUACUUGAUCUGCGGCUUUCGGGUCGUGC

UCAUGUACCGCUUCGAGGAGGAGCUAUUCUUGCGCAGCUUGCAAGACUAUAA

GAUUCAAUCUGCCCUGCUGGUGCCCACACUAUUUAGCUUCUUCGCUAAGAGCA

CUCUCAUCGACAAGUACGACCUAAGCAACUUGCACGAGAUCGCCAGCGGCGGG

GCGCCGCUCAGCAAGGAGGUAGGUGAGGCCGUGGCCAAACGCUUCCACCUACC

AGGCAUCCGACAGGGCUACGGCCUGACAGAAACAACCAGCGCCAUUCUGAUCA

CCCCCGAAGGGGACGACAAGCCUGGCGCAGUAGGCAAGGUGGUGCCCUUCUUC

GAGGCUAAGGUGGUGGACUUGGACACCGGUAAGACACUGGGGUGUGAACCAGC

GCGGCGAGCUGUGCGUCCGUGGCCCCAUGAUCAUGAGCGGCUACGUUAACAAC

CCCGAGGCUACAAACGCUCUCAUCGACAAGGACGGCUGGCUGCACAGCGGCGA

CAUCGCCUACUGGGACGAGGACGAGCACUUCUUCAUCGUGGACCGGCUGAAGU

CCCUGAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCGACGA

CGAUGCCGGCGAGCUGCCCGCCGCAGUCGUCGUGCUGGAACACGGUAAAACCA

UGACCGAGAAGGAGAUCGUGGACUAUGUGGCCAGCCAGGUUACAACCGCCAAG

AAGCUGCGCGGUGGUGUUUGUUCGUGGACGAGGUGCCUAAAGGACUGACCG

GCAAGUUGGACGCCCGCAAGAUCCGCGAGAUUCUCAUUAAGGCCAAGAAGGGC

GGCAAGAUCGCCGUGUAACUCGAGCCGGAAACGCAAUAGCCGAAAAACAAAAA

ACAAAAAAAACAAAAAAAAAACCAAAAAAAACAAAACACAUUAAAACAGCCUG

UGGGUUGAUCCCACCCACAGGCCCAUUGGGCGCUAGCACUCUGGUAUCACGGU

ACCUUUGUGCGCCUGUUUUAUACCCCCUCCCCCAACUGUAACUUAGAAGUAAC
```

-continued

ACACACCGAUCAACAGUCAGCGUGGCACACCAGCCACGUUUUGAUCAAGCACU
UCUGUUACCCCGGACUGAGUAUCAAUAGACUGCUCACGCGGUUGAAGGAGAA
AGCGUUCGUUAUCCGGCCAACUACUUCGAAAAACCUAGUAACACCGUGGAAGU
UGCAGAGUGUUUCGCUCAGCACUACCCCAGUGUAGAUCAGGUCGAUGAGUCAC
CGCAUUCCCCACGGGCGACCGUGGCGGUGGCUGCGUUGGCGGCCUGCCCAUGG
GGAAACCCAUGGGACGCUCUAAUACAGACAUGGUGCGAAGAGUCUAUUGAGC
UAGUUGGUAGUCCUCCGGCCCCUGAAUGCGGCUAAUCCUAACUGCGGAGCACA
CACCCUCAAGCCAGAGGGCAGUGUGUCGUAACGGGCAACUCUGCAGCGGAACC
GACUACUUUGGGUGUCCGUGUUUCAUUUUAUUCCUAUACUGGCUGCUUAUGG
UGACAAUUGAGAGAUCGUUACCAUAUAGCUAUUGGAUUGGCCAUCCGGUGAC
UAAUAGAGCUAUUAUAUAUCCCUUUGUUGGGUUUAUACCACUUAGCUUGAAA

GAGGUUAAAACAUUACAAUUCAUUGUUAAGUUGAAUACAGCAAAAUGAGCAA

GAUCUACAUCGACGAGCGGAGCAACGCCGAGAUCGUGUGCGAGGCCAUCAAGA

CCAUCGGCAUCGAGGGCGCCACCGCCGCCCAGCUGACCAGGCAGCUGAACAUG

GAGAAGCGGGAGGUGAACAAGGCCCUGUACGACCUGCAGAGGAGCGCUAUGG

UGUACUCCAGCGACGACAUCCCUCCCCGGUGGUUCAUGACCACCGAGGCCGAC

AAGCCCGACGCCGACGCUAUGGCCGACGUGAUCAUCGACGACGUGAGCAGGGA

GAAGUCCAUGAGGGAGGACCACAAGAGCUUCGACGACGUGAUCCCCGCCAAGA

AGAUCAUCGACUGGAAGGGCGCCAACCCCGUGACCGUGAUCAACGAGUACUGC

CAGAUCACCAGGAGGGACUGGAGCUUCCGGAUCGAGAGCGUGGGCCCCAGCAA

CAGCCCCACCUUCUACGCCUGCGUGGACAUCGACGGCAGGGUGUUCGACAAGG

CCGACGGCAAGAGCAAGCGGGACGCCAAGAACAACGCCGCCAAGCUGGCCGUG

GACAAGCUGCUGGGCUACGUGAUCAUCCGGUUCUAAACAAUUGGCAAGCUGCU

UACAUAGAACUCGCGGCGAUUGGCAUGCCGCCUUAAAAUUUUUAUUUUAUUU

UUUCUUUUCUUUUCCGAAUCGGAUUUUGUUUUUAAUAUUUCAAAAAAAAAAA

AAAAAAAAAAAAAAUCUAGAAAAAAAAAAAAAAAAAAAAAAAAAAAAAAAAAA

AAAAAAAAAAAAAAAAAAAAAAAAAAAAAAAAAAAAAAAAAAAAAAAAAAAAA

AAAAAAAAAAAAAAA

TABLE 8

| SEQ ID NO | Description |
|---|---|
| SEQ ID NO: 72 | nsP1-4 ORF, codon-optimized |
| SEQ ID NO: 73 | 5' UTR |
| SEQ ID NO: 74 | 5' UTR |
| SEQ ID NO: 75 | 5' UTR |
| SEQ ID NO: 76 | 3' UTR |
| SEQ ID NO: 121 | SARS-CoV-2 spike glycoprotein (non-codon optimized nucleic acid) |
| SEQ ID NO: 122 | SARS-CoV-2 spike glycoprotein (codon-optimized nucleic acid) |
| SEQ ID NO: 123 | SARS-CoV-2 spike glycoprotein (wild-type protein) |
| SEQ ID NO: 77 | Intergenic region between nsP1-4 ORF and antigenic protein ORF |
| SEQ ID NO: 78 | Replicon sequence comprising SEQ ID NO: 72, SEQ ID NO: 73, SEQ ID NO: 76, and SEQ ID NO: 77 |
| SEQ ID NO: 124 | Replicon sequence comprising SEQ ID NO: 72, SEQ ID NO: 73, SEQ ID NO: 76, SEQ ID NO: 121, and SEQ ID NO: 77 |
| SEQ ID NO: 125 | Replicon sequence comprising SEQ ID NO: 72, SEQ ID NO: 73, SEQ ID NO: 76, SEQ ID NO: 122, and SEQ ID NO: 77 (ARCT-021; aka “STARR ™ SARS-CoV-2 RNA) |

TABLE 8-continued

| SEQ ID NO | Description |
|---|---|
| SEQ ID NO: 79 | nsP1-4 protein sequence |
| SEQ ID NO: 80 | nsP1-4 protein sequence |
| SEQ ID NO: 81 | nsP1-4 protein sequence |
| SEQ ID NO: 126 | mRNA encoding SARS-CoV-2 glycoprotein |
| SEQ ID NO: 82 | 5' UTR (TEV) |
| SEQ ID NO: 83 | 3' UTR (Xbg) |

Example 10

This example describes characterization of self-replicating (STARR™) technology using firefly luciferase transgene expression.

In vitro transcripts were formulated with lipid nanoparticles (LNP) at a concentration of 0.1 mg/ml, and injected intramuscularly in both legs of female BALB/C mice (n=3) at a dose of 5 ug per leg. Expression of firefly luciferase (FLuc) was measured by IVIS Lumina LT Series III (PerkinElmer) by administering 100 ul of 1.5 mg Xenolight D-luciferin (PerkinElmer) in PBS via intraperitoneal injection ~10 min prior to the measurement. Six data points per group of mice were obtained at each time point (FIGS. 18A-18D).

Figure 18A:
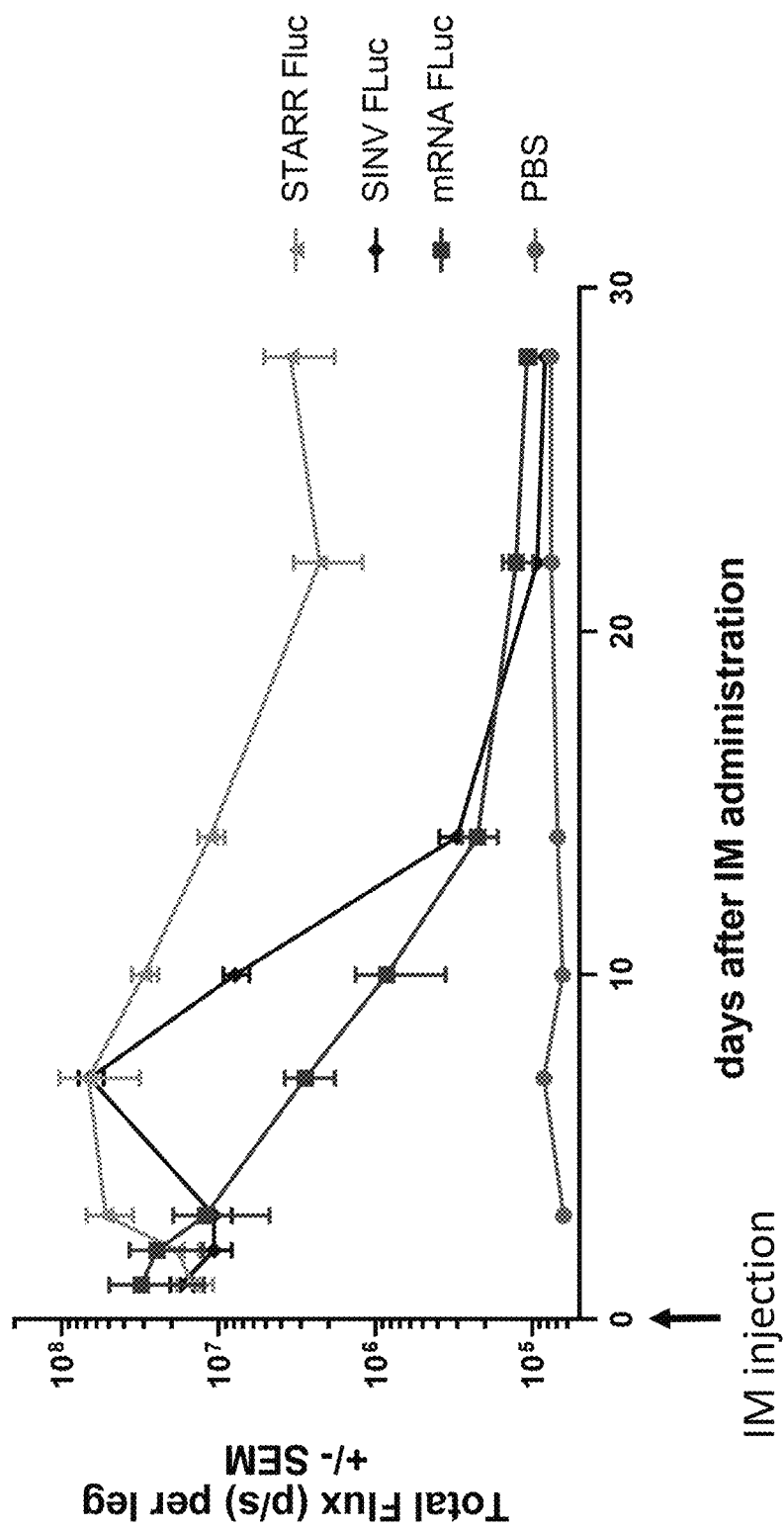
FIGS. 18A-18D shows characterization of STARR™ technology with firefly luciferase transgene expression. (18A) Firefly luciferase (FLuc) expression from STARR™ FLuc, SINV FLuc, and mRNA FLuc was monitored up to day 28 by In Vivo Imaging System (IVIS). The average of total flux (p/s) from 6 injection sites in a mouse group was plotted at each time point with a standard error of mean, SEM. (18B) IVIS picture of three mice (6 injection sites) per group on day 14 is shown for each group that was administered with the test article labeled below the picture. (18C) Luciferase expression from mice that were intramuscularly injected with STARR™ FLuc was monitored by IVIS up to 63 days post administration. (18D) Effect of prior administration of replicon backbone was examined for STARR™ (upper panel) and SINV (lower panel). Replicon encoding FLuc was IM injected at 7 days post dose of replicon with homologous backbone with an irrelevant gene/sequence (labeled STARR™ irr or SINV irr) at day 0. As a reference, a mouse group with PBS administration at day 0 was included in each of STARR™ and SINV group.
Figure 18B:
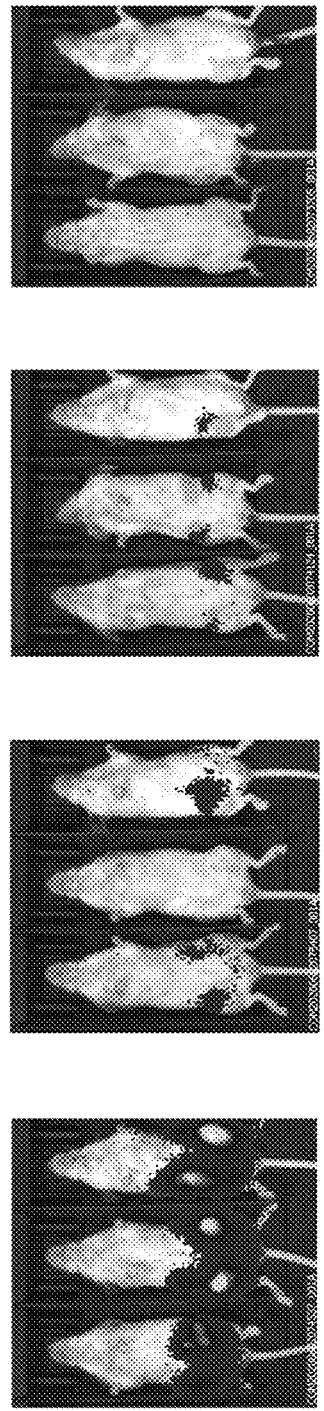
Figure 18C:
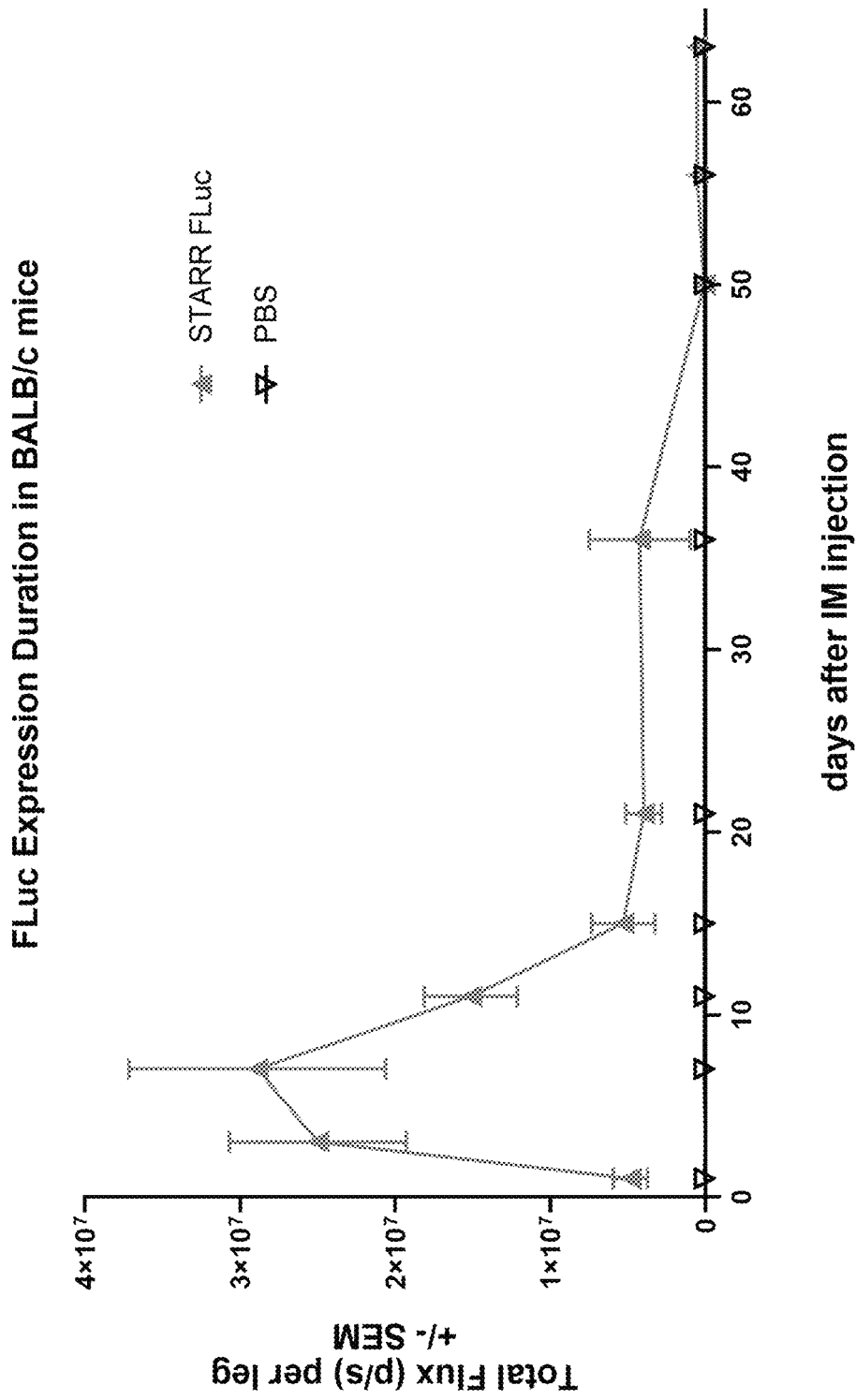
Figure 18D:
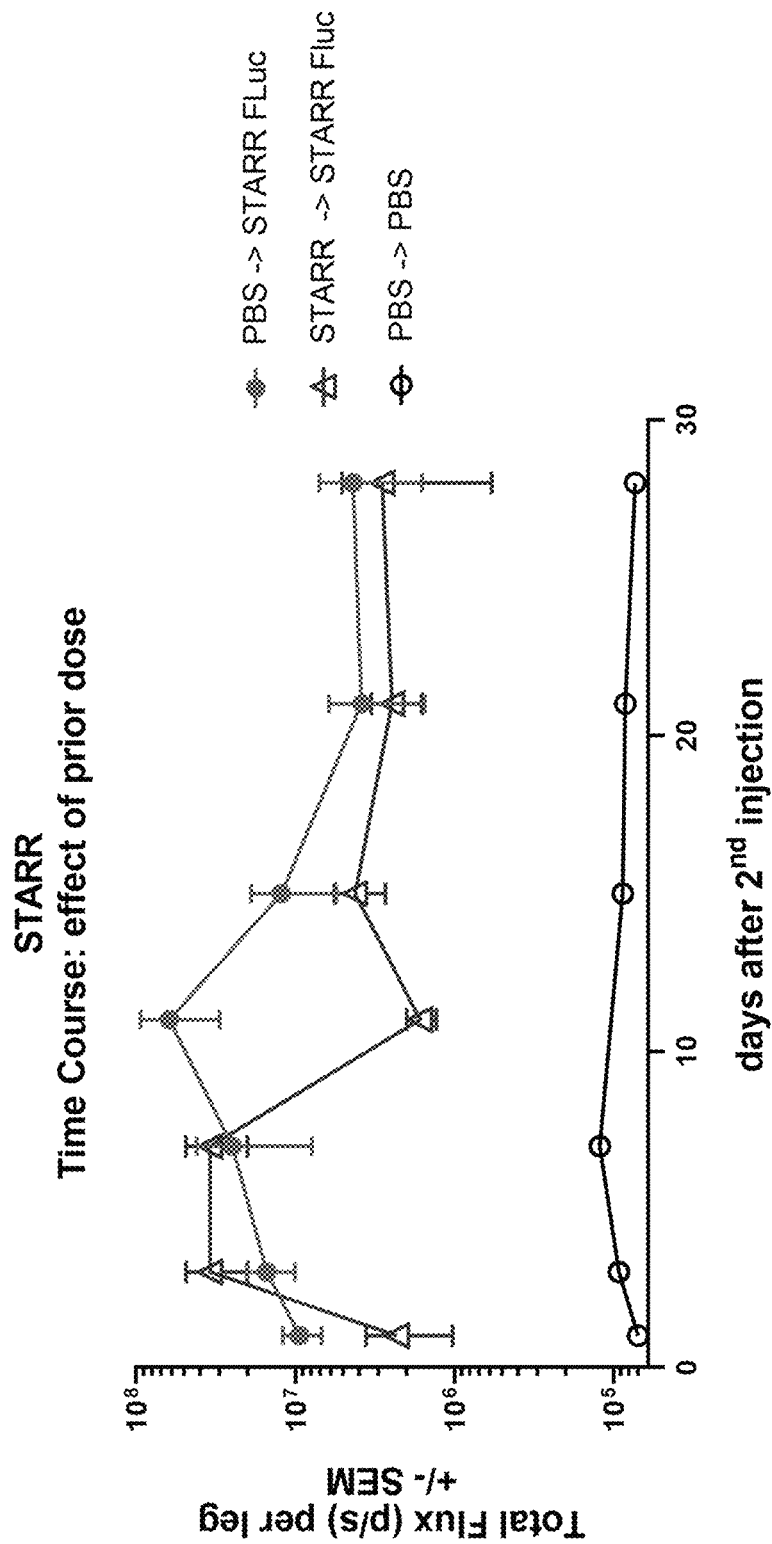

Firefly luciferase (FLuc) expression was monitored from STARR™ Fluc, SINV FLuc, and mRNA FLuc up to day 28 by In Vivo Imaging System (IVIS). Enhanced levels and durations of transgene expression from STARR™ were observed. The expression from STARR™ Fluc peaked around day 3 to 7 and declined until day 22. Fluc expression from SINV FLuc also peaked on day 10, however, the expression was reduced at a significantly faster rate than STARR™ FLuc. Additionally, the expression on day 3 was significantly lower than STARR™ FLuc. FLuc expression from the conventional mRNA backbone was highest at day 1, the earliest time point in this study, and declined at a slightly faster rate than that of STARR™-Fluc (FIG. 18A). FIG. 18B shows that at 14 days post dosing, FLuc expression from STARR™ FLuc was higher than the other groups by about two orders of magnitude. FIG. 18D shows that the effect of the STARR™ backbone remained minimal throughout the experimental period (up to day 28), while prior administration of SINV replicon backbone resulted in a reduction of FLuc transgene expression by ~2 orders of magnitude.

Figure 19:
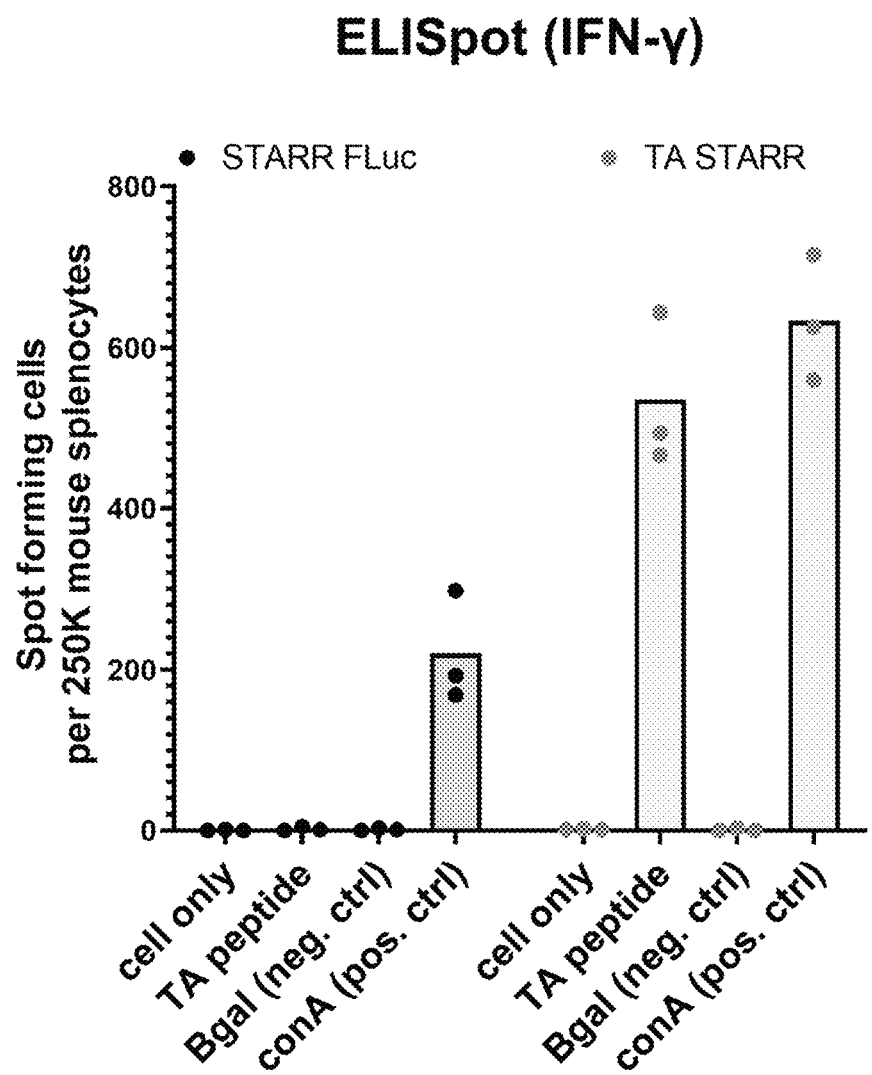
FIG. 19 shows that STARR™ elicits antigen-specific IFN-gamma response. Enzyme-linked immune absorbent spot ELISpot was used to count the number of splenocytes that were specifically stimulated by an antigen peptide of the same amino acid sequence encoded in TA STARR™. Neither no peptide (cell only) nor irrelevant peptide (Bgal) did not elicit significant IFN-gamma from splenocytes from mice vaccinated with STARR™ FLuc or TA STARR™. Stimulation with AH1-A5 peptide resulted in the detection of IFN-gamma-producing cells specifically from the mice that were vaccinated with TASTARR™. Concanavalin A (ConA) was used as a positive control of IFN-gamma production.
Figure 20A:
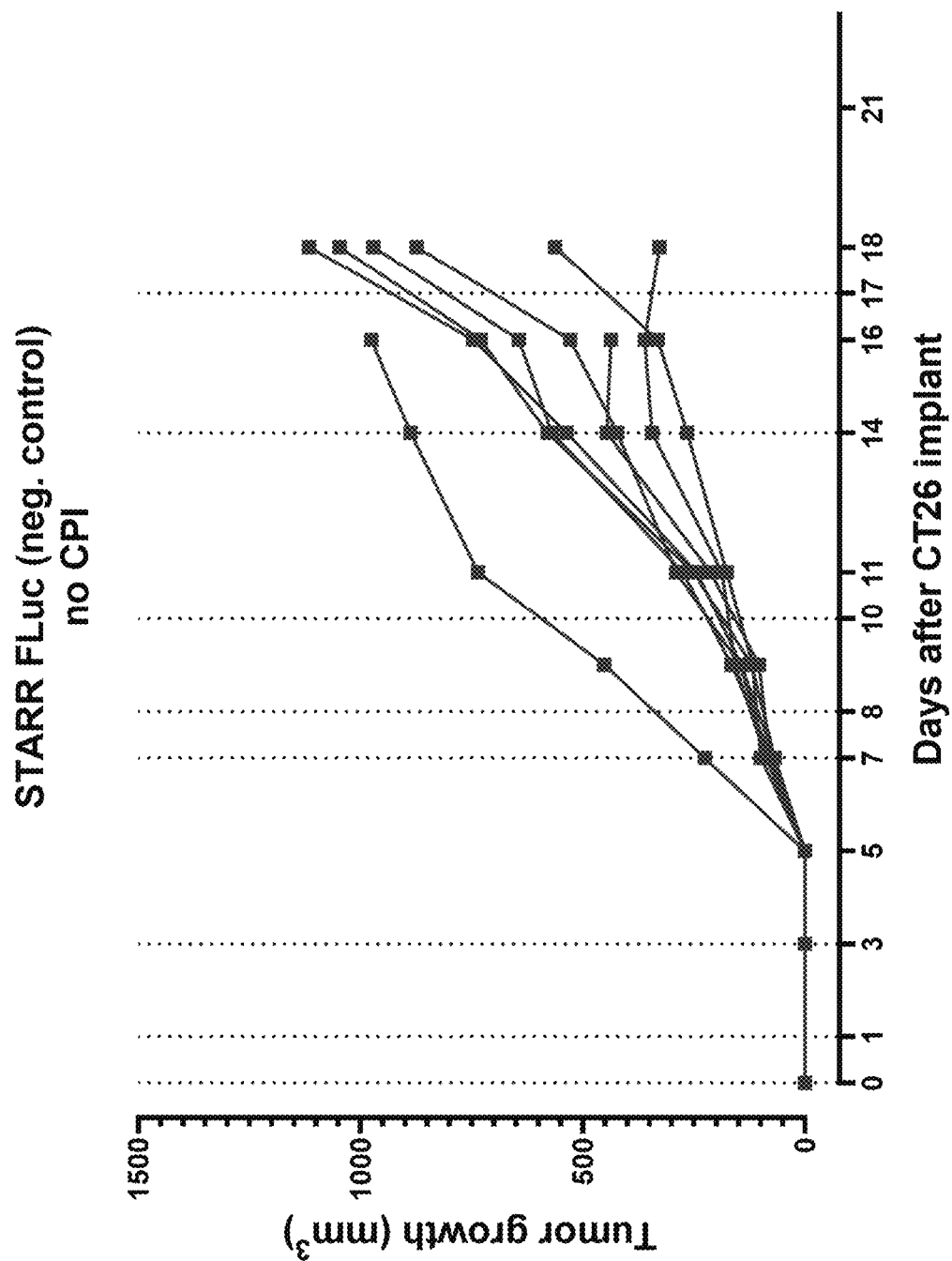
FIGS. 20A-20F illustrate reduced tumor growth rate by TA STARR™ vaccination in a CT26 syngeneic mouse model. CT26 murine colorectal carcinoma cells ($5 \times 10^5$) were subcutaneously implanted in 10-week old female BALB/c mice (n=8 per group). On days 1 and 8, the mice were vaccinated with STARR™ FLuc, a negative control, or TA STARR™, which encodes AH1A5 epitope. Tumor growth was monitored in mice vaccinated with (20A) STARR™ FLuc without checkpoint inhibitor treatment; (20B) STARR™ FLuc with a combination anti-PD1/PDL1 treatment; (20C) STARR™ FLuc with a combination anti-CTLA4 treatment; (20D) STARR™ vaccine without checkpoint inhibitor treatment; (20E) STARR™ vaccine with a combination treatment of anti-PD1 and anti-PDL1; and (20F) STARR™ vaccine with a combination treatment of anti-CTLA4. The individual tumor growth curves from a mouse group that were administered with STARR™ FLuc and TA STARR™ are shown in upper and lower panels, respectively.
Figure 20B:
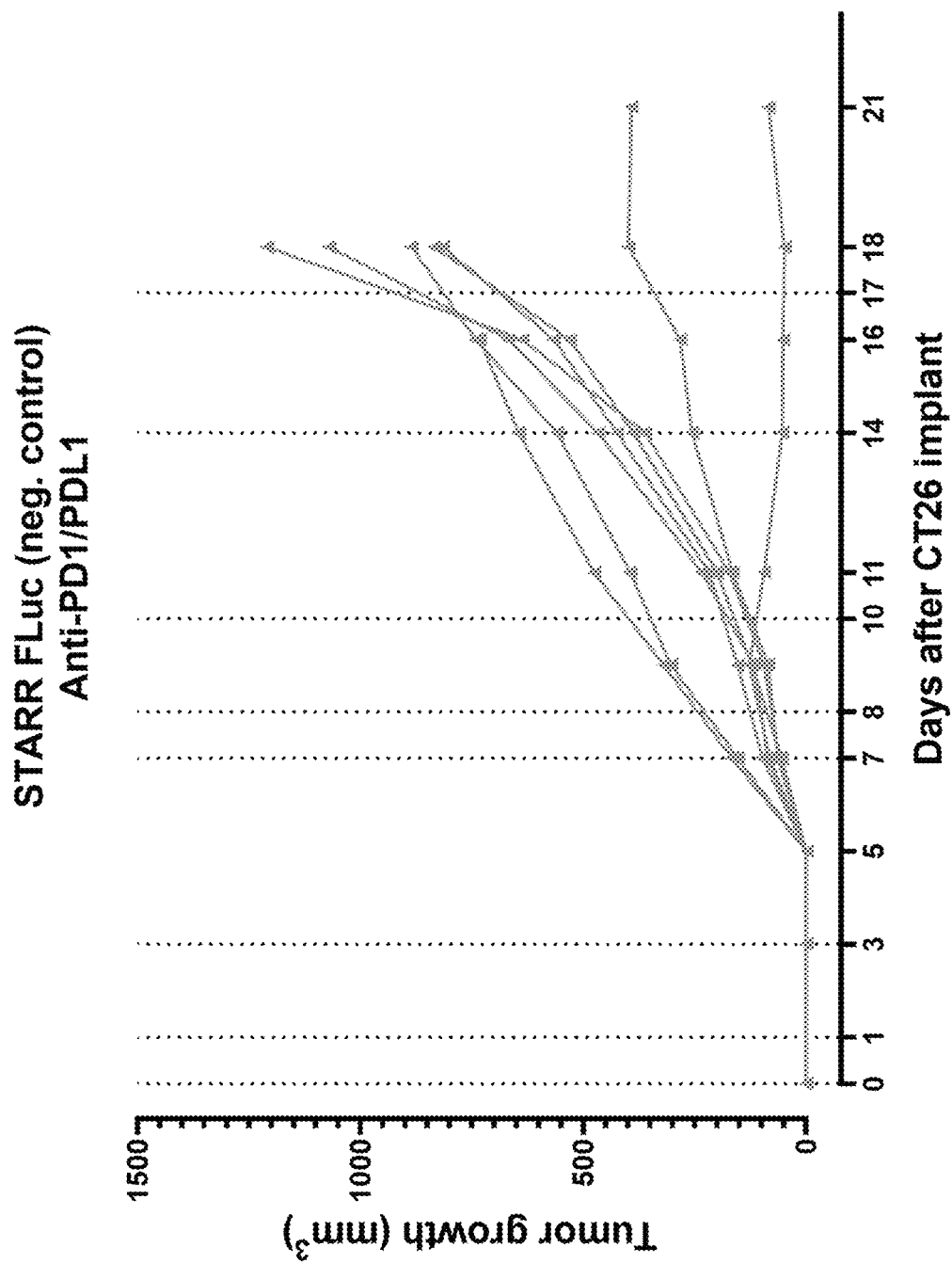
Figure 20C:
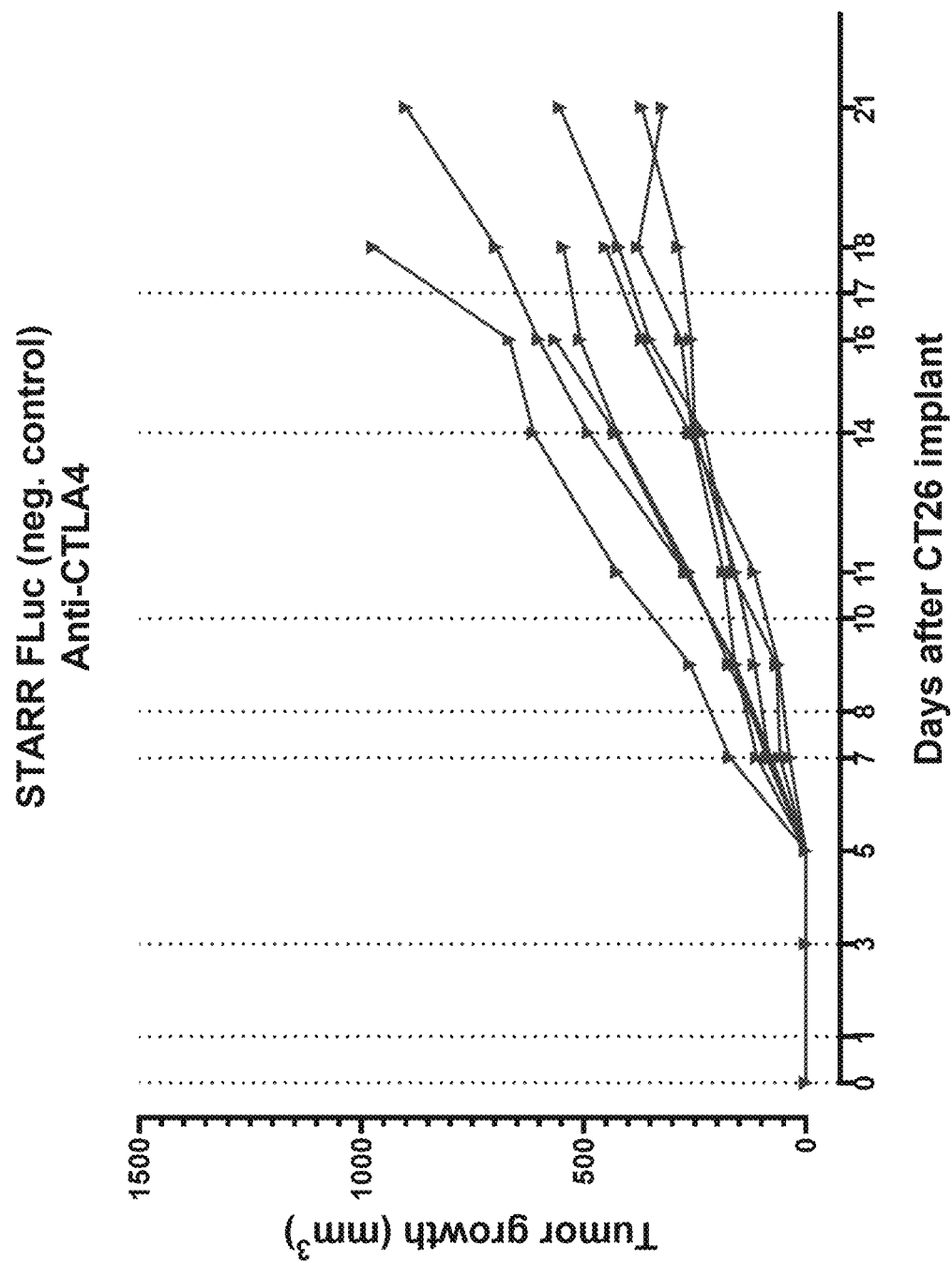
Figure 20D:
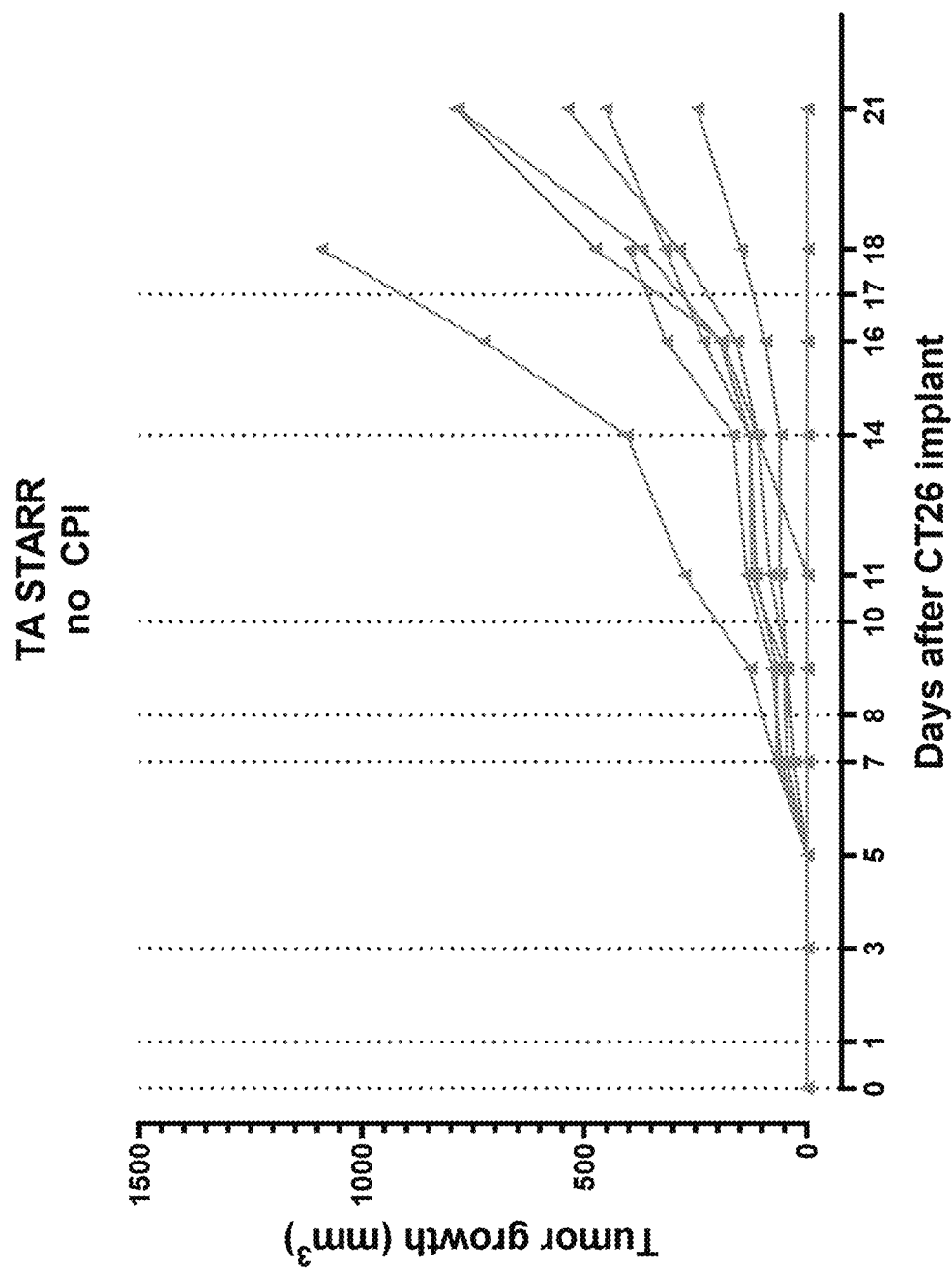
Figure 20E:
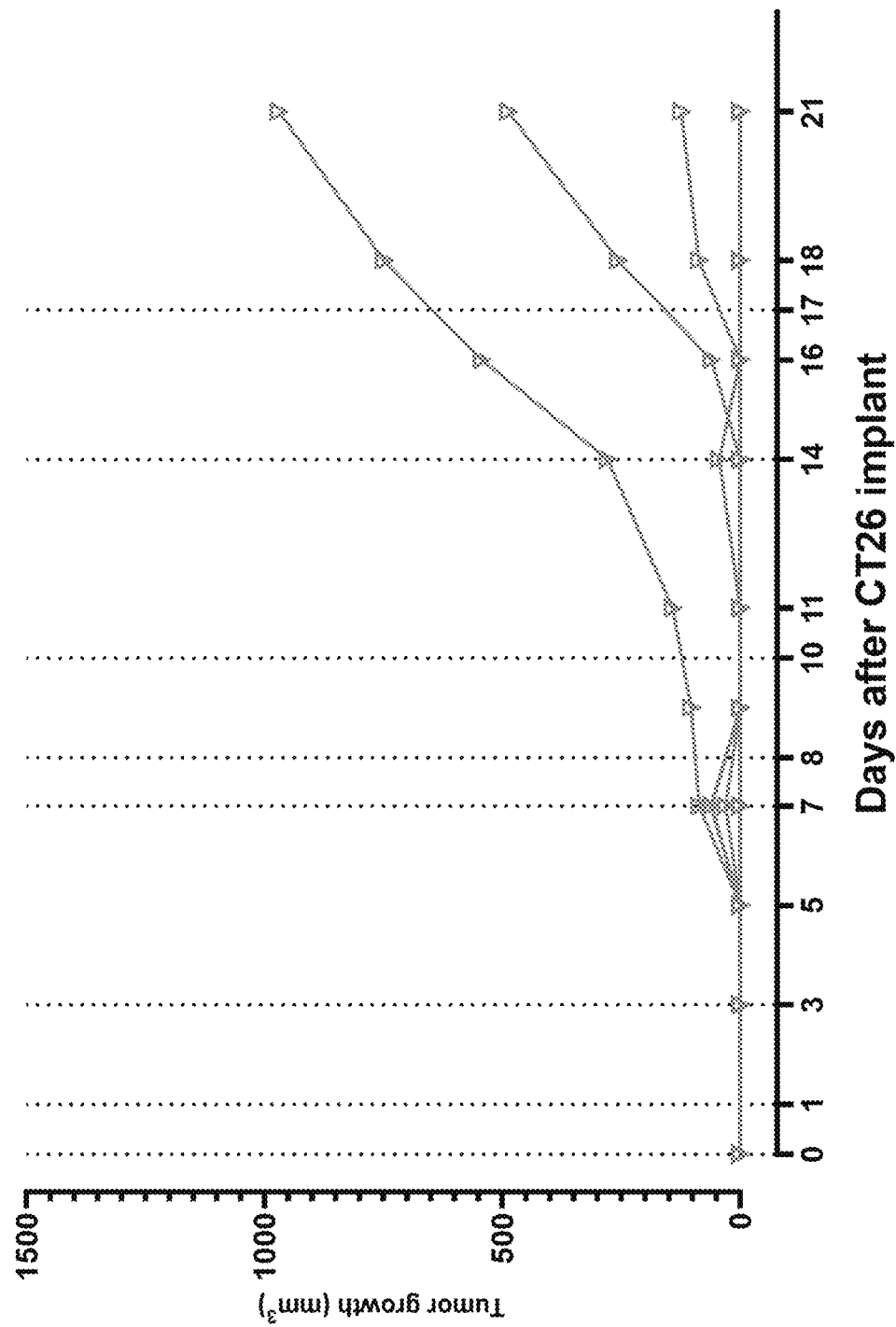
Figure 20F:
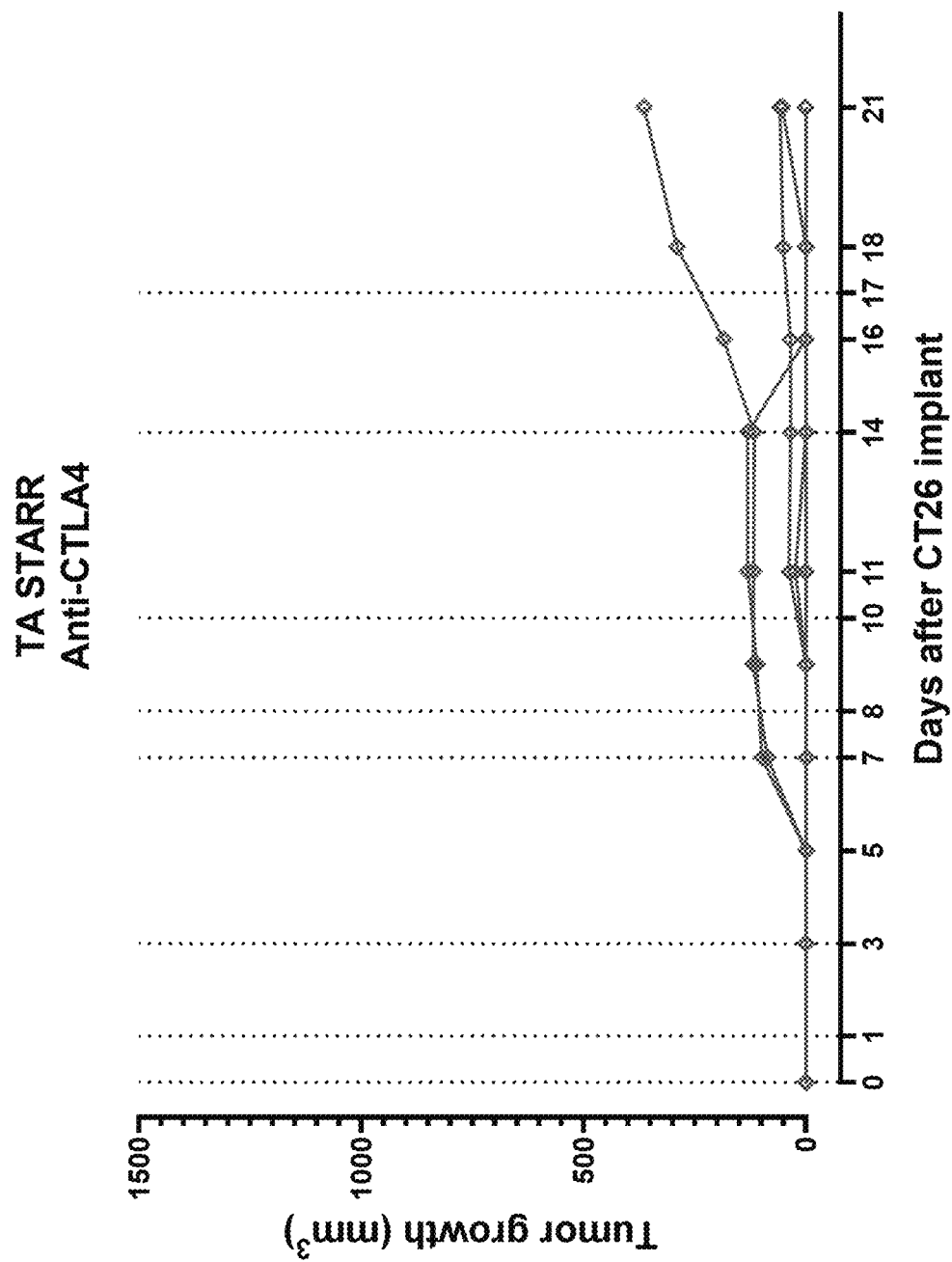

A cancer vaccine substrate, TA STARR™, was constructed next with the STARR™ backbone that encodes AH1A5 epitope from gp70, an envelope glycoprotein of endogenous Murine leukemia virus. AH1 (SPSYVYHQF) (SEQ ID NO:110) is an H-2Ld-restricted antigen of gp70423-431, which is expressed in tumor cells such as the CT26 colorectal cancer cell line, but not expressed in most of the normal tissues. AH1-A5 is a mutated sequence with SPSYAYHQF (SEQ ID NO:111) (the mutation underlined) with enhanced affinity to the T cell receptor (Slansky, et al., 2000, Immunity 13: 529-538). The open reading frame of the TA STARR™ subgenomic RNA contains a cassette with a signal peptide from the HLA class I antigen, gp70 sequence containing AH1A5 epitope, ovalbumin epitope (OVA323-339), and MHC class I trafficking signal (Kreiter, et al. 2008, J Immunol 180: 309-318). Three female BALB/c mice were intramuscularly injected with 10 ug of LNP formulated STARR™ transcripts, STARR™ FLuc or TA STARR™, on day 0 and day 7. On day 16, the spleens were harvested and the splenocytes were isolated. Splenocytes (2.5×105 cells) were incubated with or without AH1A5 (SPSYAYHQF) (SEQ ID NO: 111), beta-gal peptide (TPHPARIGL) (SEQ ID NO:112) at 1 ug/ml, and 1× Concanavalin A (Life Technologies). ELiSpot detecting murine IFN-gamma (ImmunoSpot) was performed according to the manufacturer's instructions. As can be seen in FIG. 19, TA STARR™ elicited antigen-specific IFN-gamma responses.

Figure 21:
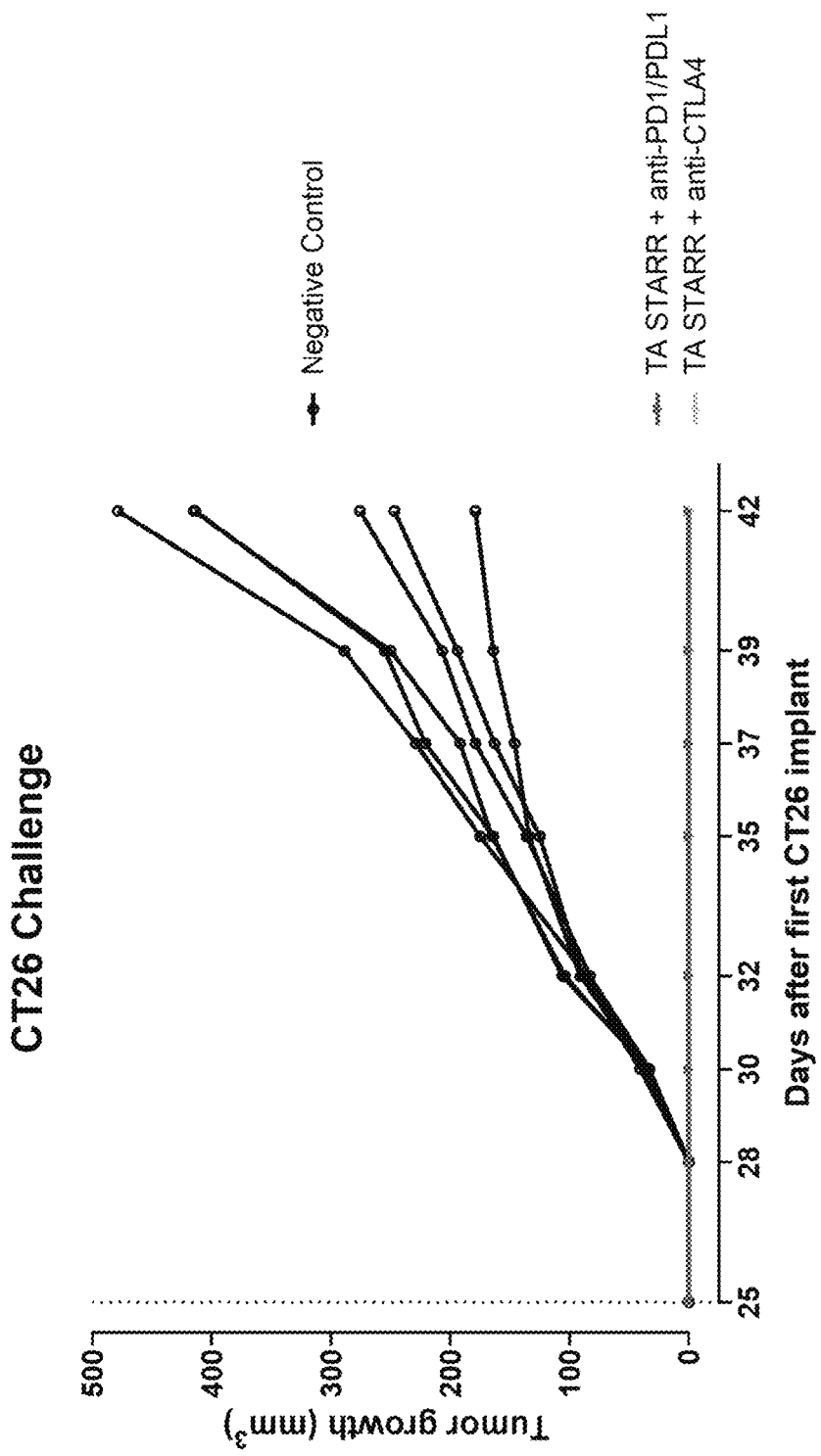
FIG. 21 illustrates prolonged protection by combination treatment of TA STARR™ Vaccine with checkpoint inhibitors. Mice that were treated with TA STARR™ combined with anti-PD1/PDL1 or anti-CTLA4 were found to be resistant to tumor growth following the CT26 challenge at day 25 to 42. Naïve mice were used as a control for the CT26 tumor growth.

BALB/c mice, 10 week-old female, were subcutaneously implanted in the right flank with 5×105 cells of CT26 cells in PBS. A day later, LNP-formulated STARR™ RNA was injected intramuscularly in the left leg at a dose of 10 ug in 100 ul. The mice were administered another booster shot on day 8 with the same dose. For a group with combination treatment of anti-mouse PD1 (RMP1-14, BioXCell) and anti-mouse PDL1 (10F.9G2, BioXcell), the combined checkpoint inhibitor (100 ug each) was administered via intraperitoneal injection in the right quadrant twice weekly for two weeks starting on day 3. For a group with the treatment of anti-mouse CTLA4 (9H10, BioxCell), 200 ug of the checkpoint inhibitor was administered in the same manner but starting on day 7. Five mice of the group with the combo treatment of TA STARR™ vaccine and the checkpoint inhibitors remained tumor-free on day 25, and were further challenged by subcutaneous implantation of CT26 (5×105 cells) in the right flank where the implantation site was slightly above the first implantation site. Naïve mice were used as a control group. The tumor growth was monitored for another 17 days (i.e. up to day 42 since the first CT26 implantation) before euthanization. FIGS. 20A-20F illustrates reduced tumor growth resulting from TA STARR™ vaccination and FIG. 21 shows prolonged protection resulting from treatment with the TA STARR™ vaccine in combination with checkpoint inhibitors.

Figure 22A:
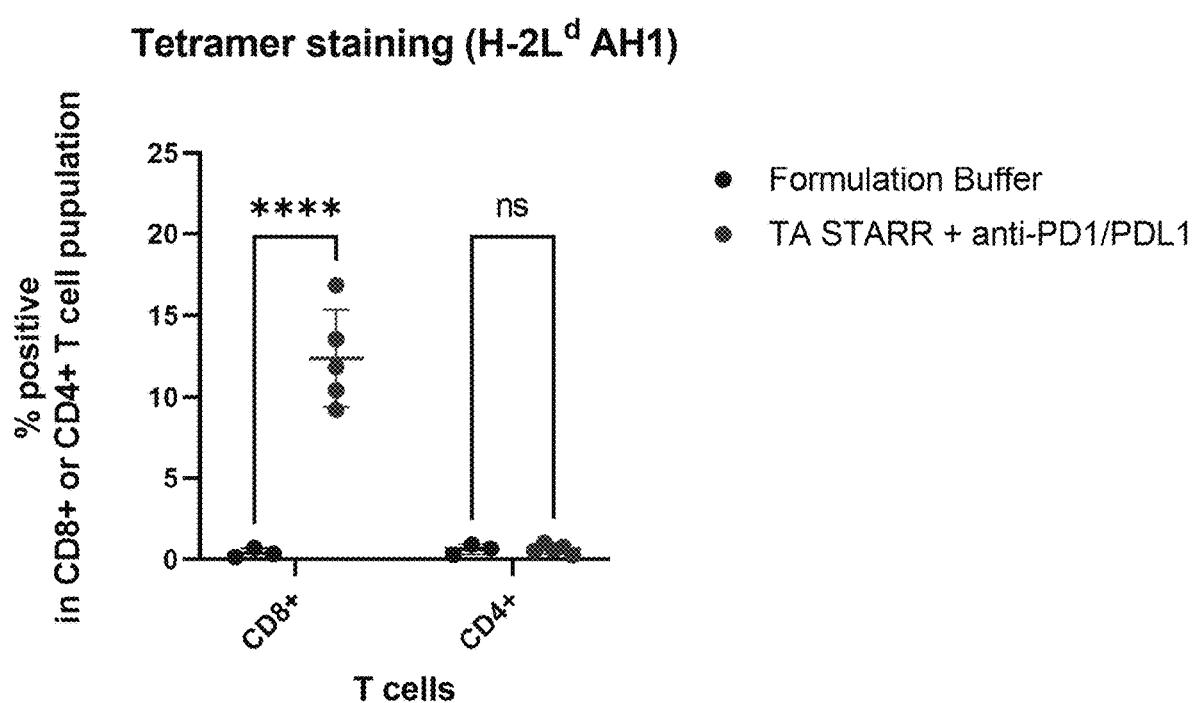
FIGS. 22A-22C show results from AH1-tetramer staining of CD8+ T-cells in the form of (22A) a graph and (22B and 22C) plots. Splenocytes from the mice group with combination treatment of TA STARR™ and anti-PD1/PDL1 at day 42 were stained with AH1 (H-2Ld)-tetramer. The staining was specific to CD8+ T cells from the mouse group with TA STARR™ treatment, and the population represented 9-17% of total CD8+ T cells from the splenocytes.
Figure 22B:
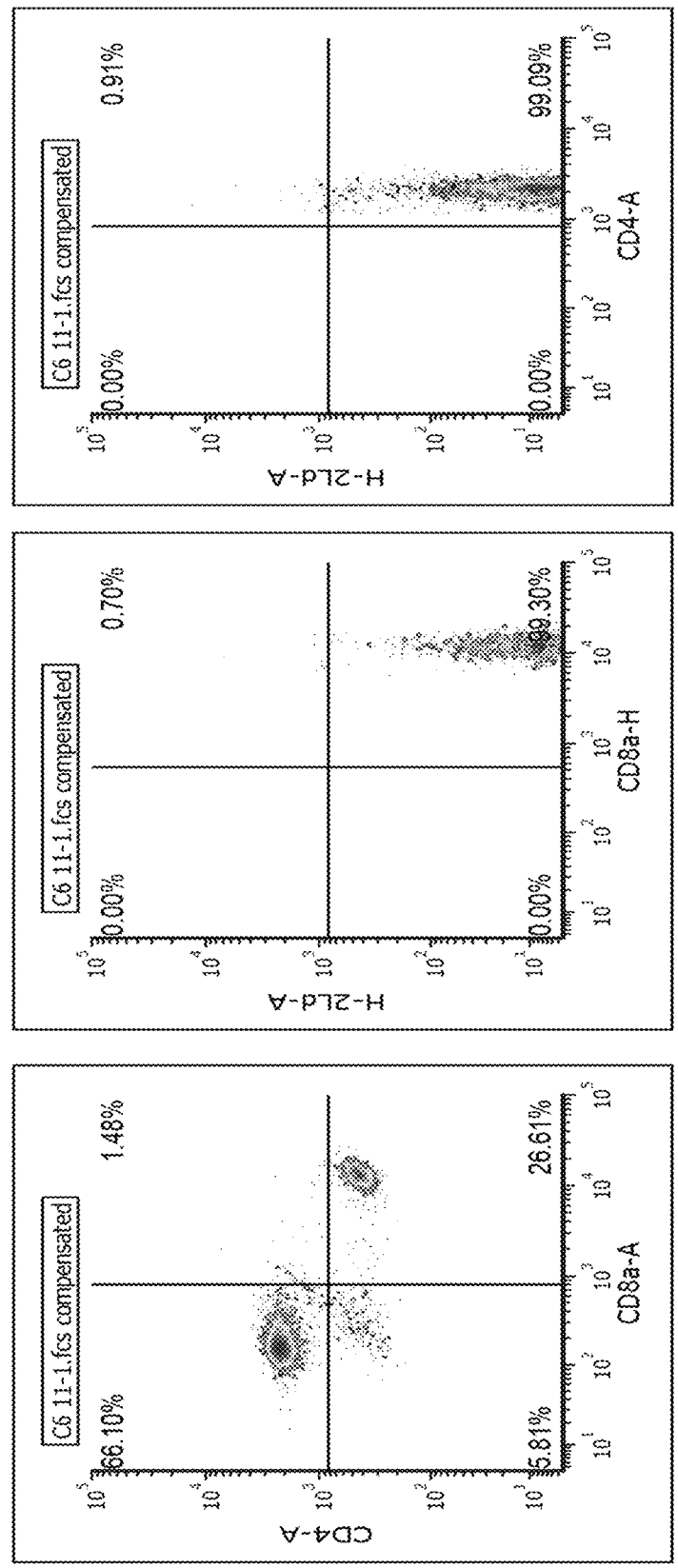
Figure 22C:
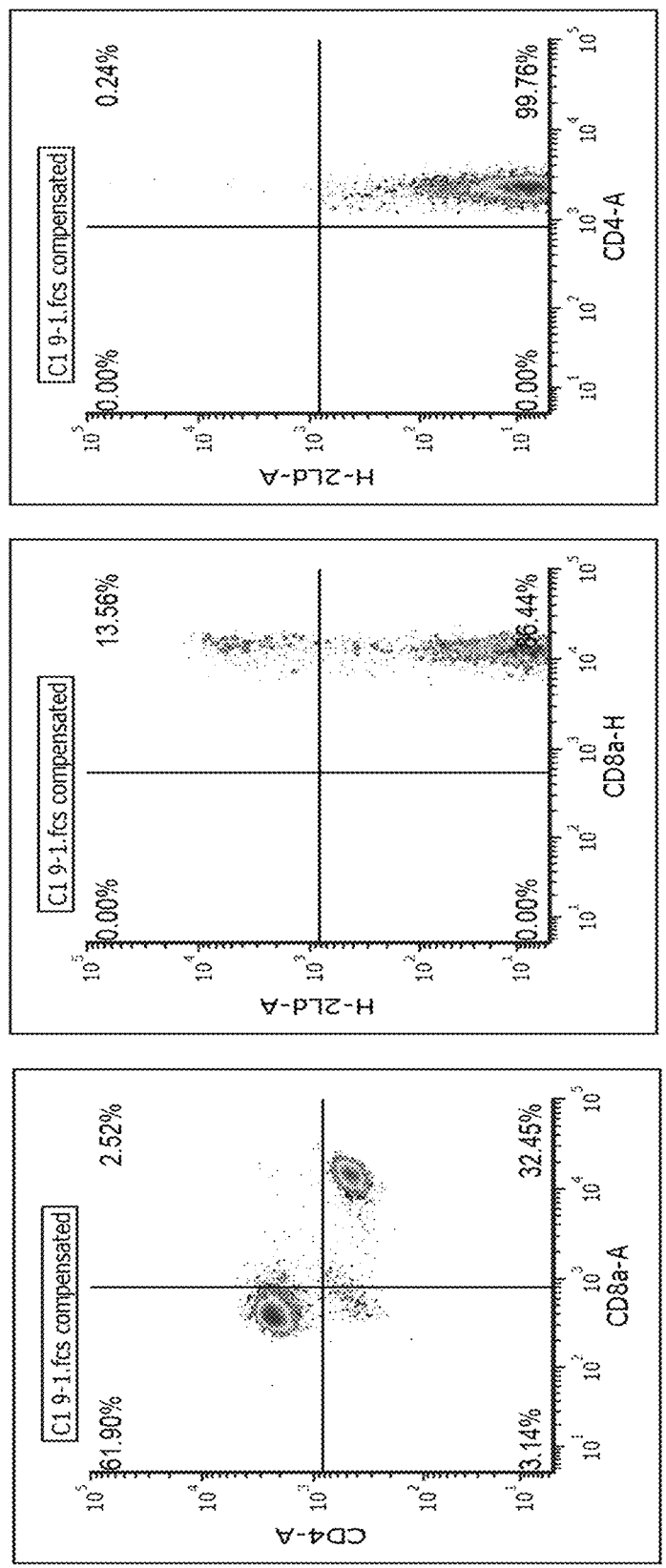

Splenocytes from the combination treatment group with TA STARR™ and anti-PD1/PDL1 were harvested for tetramer staining with AH1 peptide. Splenocytes from the control group with the LNP formulation buffer with the same dosing schedule were used as a negative control. The splenocytes (2×106 cells) were incubated with AH1 (H-2Ld)-tetramer (MBL) followed by appropriate fluorescent-labeled antibodies (Alexa Fluor 488 anti-CD8a (53-6.7), Pacific Orange anti-CD4 (RM4-5), and Pacific Blue anti-mouse CD3ε (145-2C11), eBioscience) and DRAQ7 (Invitrogen) by following the manufacture's recommendation, and 500K events were analyzed by ZE5 Cell Analyzer (Bio-Rad). Results are shown in FIGS. 22A-22C.

TABLE 9

Transgene ORF nucleotide sequence

| mARM # | RNA backbone | Transgene | Sequence |
|---|---|---|---|
| 2809 (SEQ ID NO:84) | STARR™ | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUUGUGUUCUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 2842 (SEQ ID NO:85) | SINV replicon | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUUGUGUUCUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |

TABLE 9-continued

| | | | |
|---|---|---|---|
| 1782 (SEQ ID NO:86) | mRNA (TEV-XbG) | Fluc | AUGGAAGAUGCCAAAAACAUUAAGAAGGGCCCAGCGCCAUUCUACC
CACUCGAAGACGGGACCGCCGGCGAGCAGCUGCACAAAGCCAUGAA
GCGCUACGCCCUGGUGCCCGGCACCAUCGCCUUUACCGACGCACAU
AUCGAGGUGGACAUUACCUACGCCGAGUACUUCGAGAUGAGCGUUC
GGCUGGCAGAAGCUAUGAAGCGCUAUGGGCUGAAUACAAACCAUCG
GAUCGUGGUGUGCAGCGAGAAUAGCUUGCAGUUCUUCAUGCCCGUG
UUGGGUGCCCUGUUCAUCGGUGUGGCUGUGGCCCCAGCUAACGACA
UCUACAACGAGCGCGAGCUGCUGAACAGCAUGGGCAUCAGCCAGCC
CACCGUCGUAUUCGUGAGCAAGAAAGGGCUGCAAAAGAUCCUCAAC
GUGCAAAAGAAGCUACCGAUCAUACAAAAGAUCAUCAUCAUGGAUA
GCAAGACCGACUACCAGGGCUUCCAAAGCAUGUACACCUUCGUGAC
UUCCCAUUUGCCACCGGCUUCAACGAGUACGACUUCGUGCCCGAG
AGCUUCGACCGGGACAAAACCAUCGCCCUGAUCAUGAACAGUAGUG
GCAGUACCGGAUUGCCCAAGGGCGUAGCCCUACCGCACCGCACCGC
UUGUGUCCGAUUCAGUCAUGCCCGCGACCCCAUCUUCGGCAACCAG
AUCAUCCCCGACACCGCUAUCCUCAGCGUGGUGCCAUUUCACCACG
GCUUCGGCAUGUUCACCACGCUGGGCUACUUGAUCUGCGGCUUUCG
GGUCGUGCUCAUGUACCGCUUCGAGGAGGAGCUAUUCUUGCGCAGC
UUGCAAGACUAUAAGAUUCAAUCUGCCCUGCUGGUGCCCACACUAU
UUAGCUUCUUCGCUAAGAGCACACUCAUCGACAAGUACGACCUAAG
CAACUUGCACGAGAUCGCCAGCGGCGGGGCGCCUCAGCAAGGAG
GUAGGUGAGGCCGUGGCCAAACGCUUCCACCUACCAGGCAUCCGAC
AGGGCUACGGCCUGACAGAAACAACCAGCGCCAUUCUGAUCACCCC
CGAAGGGGACGACAAGCCUGGCGCAGUAGGCAAGGUGGUGCCCUUC
UUCGAGGCUAAGGUGGUUGGACACCGGUAAGACACUGGGUG
UGAACCAGCGCGGCGAGCUGUGCGUCCGUGGCCCCAUGAUCAUGAG
CGGCUACGUUAACAACCCCGAGGCUACAAACGCUCUCAUCGACAAG
GACGGCUGGCUGCACAGCGGCGACAUCGCCUACUGGGACGAGGACG
AGCACUUCUUCAUCGUGGACCGGCUGAAGUCCCUGAUCAAAUACAA
GGGCUACCAGGUAGCCCCAGCCGAACUGGAGAGCAUCCUGCUGCAA
CACCCCAACAUCUUCGACGCCGGGUCGCCGGCCUGCCCGACGACG
AUGCCGGCGAGCUGCCCGCCGCAGUCGUCGUGCUGGAACACGGUAA
AACCAUGACCGAGAAGGAGAUCGUGGACUAUGUGGCCAGCCAGGUU
ACAACCGCCAAGAAGCUGCGCGGUGUGUUUGUGUUCGUGGACGAGG
UGCCUAAAGGACUGACCGGCAAGUUGGACGCCCGCAAGAUCCGCGA
GAUUCUCAUUAAGGCCAAGAAGGGCGGCAAGAUCGCCGUGUAA |
| 2847 (SEQ ID NO:87) | STARR™ | KRAS epitope wt | AUGAAGUUGGUGGUUGUGGGGGCCGGGGGUGUUGGCAAAAGCGCCC
UUACAAUUUGA |
| 2862 (SEQ ID NO:88) | SINV replicon | Empty | AUGGAUCCUAGACGCUACGCCCCAAUGAUCCGACCAGCAAAACUCG
AUGUACUUCCGAGGAACUGA |
| 3060 (SEQ ID NO:89) | STARR™ | Signal peptide-gp70 with AH1A5-MITD | AUGAGAGUGACAGCCCCUAGAACCUUACUGCUUCUGCUUUGGGGAG
CUGUUGCUCUGACAGAGACAUGGGCUGGAUCUCUGAGCGAGGUGAC
CGGCCAGGGCCUGUGCAUCGGCGCCGUGCCCAAGACCCACCAGGUG
CUGUGCAACACCACCCAGAAGACCAGCGACGGCAGCUACUACUGG
CCGCUCCCACCGGCACCACCUGGGCCUGCAGCACCGGCCUGACCCC
UUGCAUCAGCACCACCAUCCUGAACCUGACCACCGACUACUGCGUG
CUGGUGGAGCUGUGGCCCAGGGUGACCUACCACAGCCCCAGCUACG
CCUACCACCAGUUCGAGAGGAGGGCCAAGUACAAGAGGGAGCCCGU
GAGCCUGACCCUGGCCCUGCUGCUGGGCGGCCUGACAAUGGGCGGC
AUCGCCGCCGGCGUGGGCACCGGCACCACCGCCCUGGUGGCCACCC
AGCAGUUCCAGCAGCUGCAGGCCGCCAUGCACGACGACCUGAAGGA
GGUGGAGAAGUCCAUCACCAACCUGGAGAAGUCCCUGACCAGCCUG
AGCGAGGUGGUGCUGCAGAACAGGAGGGGCCUGGACCUGCUGUUCC
UGAAGGAGGGCGGCCUGUGCGCCGCCCUGAAGGAGGAGUGCUGCCU
GUACGCCGACCACACCGGCCUGGUGAGAGACAGCAUGGCUGCUGGC
CUGGCCGUCCUCGCCGUGGUGGUGAUUGGAGCUGUGGUCGCAGCUG
UUAUGUGCAGAAGAAAGUCAUCCGGCGGAAAGGGAGGCUCCUACUC
UCAGGCUGCUUCUGCUACAGUGCCUAGAGCUCUUUAUGUGUUUAUCU
CAGCUGUAA |
| 3061 (SEQ ID NO:90) | STARR™ | Signal peptide-AH1A5 OVA-MITD | AUGAGAGUGACAGCCCCUAGAACCUUACUGCUUCUGCUUUGGGGAG
CUGUUGCUCUGACAGAGACAUGGGCUGGAUCUUACCACAGCCCCAG
CUACGCCUACCACCAGUUCGAGAGGGGGAGGAGGCUCCGGGGA
GGAGGCUCCCUGAAGAUCAGCCAGGCCGUGCACGCCGCCCACGCCG
AGAUCAACGAGGCCGGCCGGGAGGUGAUCGUGGGCAUGUCGCUGG
CCUGGCCGUCCUCGCCGUGGUGGUGAUUGGAGCUGUGGUCGCAGCU
GUUAUGUGCAGAAGAAAGUCAUCCGGCGGAAAGGGAGGCUCCUACU
CUCAGGCUGCUUCUGCUACAGUGCCUAGAGCUCUUUAUGUGUUUAUC
UCAGCUGUAA |
| 3076 (SEQ ID | STARR™ | Signal peptide-gp70 with | AUGAGAGUGACAGCCCCUAGAACCUUACUGCUUCUGCUUUGGGGAG
CUGUUGCUCUGACAGAGACAUGGGCUGGAUCUCUGAGCGAGGUGAC
CGGCCAGGGCCUGUGCAUCGGCGCCGUGCCCAAGACCCACCAGGUG |

TABLE 9-continued

| | | | |
|---|---|---|---|
| NO:91) | | AH1A5-<br>MITD-FLAG | CUGUGCAACACCACCCAGAAGACCAGCGACGGCAGCUACUACCUGG<br>CCGCUCCCACCGGCACCACCUGGGCCUGCAGCACCGGCCUGACCCC<br>UUGCAUCAGCACCACCAUCCUGAACCUGACCACCGACUACUGCGUG<br>CUGGUGGAGCUGUGGCCCAGGGUGACCUACCACAGCCCCAGCUACG<br>CCUACCACCAGUUCGAGAGGAGGGCCAAGUACAAGAGGGAGCCCGU<br>GAGCCUGACCCUGGCCCUGCUGCUGGGCGGCCUGACAAUGGGCGGC<br>AUCGCCGCCGGCGUGGGCACCGGCACCACCGCCCUGGUGGCCACCC<br>AGCAGUUCCAGCAGCUGCAGGCCGCCAUGCACGACGACCUGAAGGA<br>GGUGGAGAAGUCCAUCACCAACCUGGAGAAGUCCCUGACCAGCCUG<br>AGCGAGGUGGUGCUGCAGAACAGGAGGGGCCUGGACCUGCUGUUCC<br>UGAAGGAGGGCGGCCUGUGCGCCGCCCUGAAGGAGGAGUGCUGCCU<br>GUACGCCGACCACACCGGCCUGGUGAUCGUGGGCAUUGUCGCUGGC<br>CUGGCCGUCCUCGCCGUGGUGGUGAUUGGAGCUGUGGUCGCAGCUG<br>UUAUGUGCAGAAGAAAGUCAUCCGGCGGAAAGGGAGGCUCCUACUC<br>UCAGGCUGCUUCUGCUACAGUGCCUAGAGCUCUUAUGUGUUUAUCU<br>CAGCUGGGCGGCGGAGGCAGCGACUACAAGGACGACGAUGACAAGU<br>AA |
| 3068<br>(SEQ<br>ID<br>NO:92) | STARR | Signal<br>peptide-<br>AH1A5 OVA-<br>MITD-FLAG | AUGAGAGUGACAGCCCCUAGAACCUUACUGCUUCUGCUUUGGGGAG<br>CUGUUGCUCUGACAGAGACAUGGGCUGGAUCUUACCACAGCCCCAG<br>CUACGCCUACCACCAGUUCGAGAGGGGAGGGCUCCCCACGCCG<br>AGAUCAACGAGGCCGGCCGGGAGGUGAUCGUGGGCAUUGUCGCUGG<br>CCUGGCCGUCCUCGCCGUGGUGGUGAUUGGAGCUGUGGUCGCAGCU<br>GUUAUGUGCAGAAGAAAGUCAUCCGGCGGAAAGGGAGGCUCCUACU<br>CUCAGGCUGCUUCUGCUACAGUGCCUAGAGCUCUUAUGUGUUUAUC<br>UCAGCUGGGCGGCGGAGGCAGCGACUACAAGGACGACGAUGACAAG<br>UAA |

| Transgene ORF amino acid sequence | | |
|---|---|---|
| mARM<br># | transgene<br>description | Sequence |
| 2809,<br>2842,<br>1782<br>(SEQ<br>ID<br>NO:93) | Fluc | MEDAKNIKKGPAPFYPLEDGTAGEQLHKAMKRYALVPGTIAFTDAH<br>IEVDITYAEYFEMSVRLAEAMKRYGLNTNHRIVVCSENSLQFFMPV<br>LGALFIGVAVAPANDIYNERELLNSMGISQPTVVFVSKKGLQKILN<br>VQKKLPIIQKIIIMDSKTDYQGFQSMYTFVTSHLPPGFNEYDFVPE<br>SFDRDKTIALIMNSSGSTGLPKGVALPHRTACVRFSHARDPIFGNQ<br>IIPDTAILSVVPFHHGFGMFTTLGYLICGFRVVLMYRFEEELFLRS<br>LQDYKIQSALLVPTLFSFFAKSTLIDKYDLSNLHEIASGGAPLSKE<br>VGEAVAKRFHLPGIRQGYGLTETTSAILITPEGDDKPGAVGKVVPF<br>FEAKVVDLDTGKTLGVNQRGELCVRGPMIMSGYVNNPEATNALIDK<br>DGWLHSGDIAYWDEDEHFFIVDRLKSLIKYKGYQVAPAELESILLQ<br>HPNIFDAGVAGLPDDDAGELPAAVVVLEHGKTMTEKEIVDYVASQV<br>TTAKKLRGGVVFVDEVPKGLTGKLDARKIREILIKAKKGGKIAV* |
| 2847<br>(SEQ<br>ID<br>NO:94) | KRAS<br>epitope wt | MKLVVVGAGGVGKSALTI* |
| 2862<br>(SEQ<br>ID<br>NO:95) | Empty | MDPRRYAPMIRPAKLDVLPRN* |
| 3060<br>(SEQ<br>ID<br>NO:96) | Signal<br>peptide-<br>gp70 with<br>AH1A5-<br>MITD | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAAVMCRRKSSGGKGGSYSQAASATVPRALMCLS<br>QL* |
| 3061<br>(SEQ<br>ID<br>NO:97) | Signal<br>peptide-<br>AH1A5 OVA-<br>MITD | MRVTAPRTLLLLLWGAVALTETWAGSYHSPSYAYHQFERGGGGSGG<br>GGSLKISQAVHAAHAEINEAGREVIVGIVAGLAVLAVVVIGAVVAA<br>VMCRRKSSGGKGGSYSQAASATVPRALMCLSQL* |
| 3076<br>(SEQ<br>ID<br>NO:98) | Signal<br>peptide-<br>gp70 with<br>AH1A5-<br>MITD-FLAG | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAAVMCRRKSSGGKGGSYSQAASATVPRALMCLS<br>QLGGGGSDYKDDDDK* |

TABLE 9-continued

| 3068 (SEQ NO:99) | Signal peptide-AH1A5 OVA-MITD-FLAG | MRVTAPRTLLLLLWGAVALTETWAGSYHSPSYAYHQFERGGGGSGG GGSLKISQAVHAAHAEINEAGREVIVGIVAGLAVLAVVVIGAVVAA VMCRRKSSGGKGGSYSQAASATVPRALMCLSQLGGGGSDYKDDDDK * | whole RNA sequence

| mARM # | brief name | Sequence |
|---|---|---|
| 2809 (SEQ ID NO:100) | STARR™ Fluc 2809 | AUGGGCGGCGCAUGAGAGAAGCCCAGACCAAUUACCUACCCAAAAU GGAGAAAGUUCACGUUGACAUCGAGGAAGACAGCCCAUUCCUCAGA GCUUUGCAGCGGAGCUUCCCGCAGUUUGAGGUAGAAGCCAAGCAGG UCACUGAUAAUGACCAUGCUAAUGCCAGAGCGUUUUCGCAUCGGC UUCAAAACUGAUCGAAACGGAGGUGGACCCAUCCGACACGAUCCUU GACAUUGGAAGUGCGCCCGCCCGCAGAAUGUAUUCUAAGCACAAGU AUCAUUGUAUCUGUCCGAUGAGAUGUGCGGAAGAUCCGGACAGAUU GUAUAAGUAUGCAACUAAGCUGAAGAAAAACUGUAAGGAAAUAACU GAUAAGGAAUUGGACAAGAAAAUGAAGGAGCUGGCCGCCGUCAUGA GCGACCCUGACCUGGAAACUGAGACUAUGUGCCUCCACGACGACGA GUCGUGUCGCUACGAAGGGCAAGUCGCUGUUUACCAGGAUGUAUAC GCCGUCGACGGCCCCACCAGCCUGUACCACCAGGCCAACAAGGGCG UGAGGGUGGCCUACUGGAUCGGCUUCGACACCACACCCUUCAUGUU CAAGAACCUGGCCGGCGCCUACCCCAGCUACAGCACCAACUGGGCC GACGAGACCGUGCUGACCGCCAGGAACAUCGGCCUGUGCAGCAGCG ACGUGAUGGAGAGGAGCCGGAGAGGCAUGAGCAUCCUGAGGAAGAA AUACCUGAAGCCCAGCAACAACGUGCUGUUCAGCUGGGCAGCACC AUCUACCACGAGAAGAGGGACCUGCUCAGGAGCUGGCACCUGCCCA GCGUGUUCCACCUGAGGGGCAAGCAGAACUACACCUGCAGGUGCGA GACCAUCGUGAGCUGCGACGGCUACGUGGUGAAGAGGAUCGCCAUC AGCCCCGGCCUGUACGGCAAGCCCAGCGGCUACGCCGCUACAAUGC ACAGGGAGGGCUUCCUGUGCUGCAAGGUGACCGACACCCUGAACGG CGAGAGGGUGAGCUUCCCCGUGUGCACCUACGUGCCGCCACCCUG UGCGACCAGAUGACCGGCAUCCUGGCCACCGACGUGAGCGCCGACG ACGCCCAGAAGCUGCUCGUGGGCCUGAACCAGAGGAUCUGGUCAA CGGCAGGACCCAGAGGAACACCAACACAUGAAGAACUACCUGCUG CCCGUGGUGGCCCAGGCUUUCGCCAGGUGGGCCAAGGAGUACAAGG AGGACCAGGAAGACGAGAGGCCCCUGGGCCUGAGGGACAGGCAGCU GGUGAUGGGCUGCUGCUGGGCCUUCAGGCGGCACAAGAUCACCAGC AUCUACAAGAGGCCCGACACCCAGACCAUCAUCAAGGUGAACAGCG ACUUCCACAGCUUCGUGCUGCCCAGGAUCGGCAGCAACACCCUGGA GAUCGGCCUGAGGACCCGGAUCAGGAAGAUGCUGGAGGAACACAAG GAGCCCAGCCCACUGAUCACCGCCGAGGACGUGCAGGAGGCCAAGU GCGCUGCCGACGAGGCCAAGGAGGUGAGGGAGGCCGAGGAACUGAG GGCCGCCCUGCCACCCCUGGCUGCCGACGUGGAGGAACCCACCCUG GAAGCCGACGUGGACCUGAUGCUGCAGGAGGCCGGCGCCGGAAGCG UGGAGACACCCAGGGGCCUGAUCAAGGUGACCAGCUACGACGGCGA GGACAAGAUCGGCAGCUACGCCGUGCUGAGCCCACAGGCCGUGCUG AAGUCCGAGAAGCUGAGCUGCAUCCACCCACUGGCCGAGCAGGUGA UCGUGAUCACCCACAGCGGCAGGAAGGGCAGGUACGCCGUGGAGCC CUACCACGGCAAGGUGGUCGUGCCCGAGGGCCACGCCAUCCCCGUG CAGGACUUCCAGGCCCUGAGCGAGAGCGCCACCAUCGUGUACAACG AGAGGGAGUUCGUGAACAGGUACCUGCACAUAUCGCCACCCACGG CGGAGCCCUGAACACCGACGAGGAAUACUACAAGACCGUGAAGCCC AGCGAGCACGACGGCGAGUACCUGUACGACAUCGACAGGAAGCAGU GCGUGAAGAAAGAGCUGGUGACCGGCCUGGGACUGACCGGCGAGCU GGUGGACCCACCCUUCCACGAGUUCGCCUACGAGAGCCUGAGGACC AGACCCGCCGCUCCCUACCAGGUGCCCACCAUCGGCGUGUACGGCG UGCCCGGCAGCGGAAAGAGCGGCAUCAUCAAGAGCGCCGUGACCAA GAAAGACCUGGUGGUCAGCGCCAAGAAAGAGAACUGCGCCGAGAUC AUCAGGGACGUGAAGAAGAUGAAAGGCCUGGACGUGAACGCGCGCA CCGUGGACAGCGUGCUGCUGAACGGCUGCAAGCACCUCCGUGGAGAC CCUGUACAUCGACGAGGCCUUCGCUUGCCACGCCGGCACCCUGAGG GCCCUGAUCGCCAUCAUCAGGCCCAAGAAAGCCGUGCUGUGCGGCG ACCCCAAGCAGUGCGGCUUCUUCAACAUGAUGUGCCUGAAGGUGCA CUUCAACCACGAGAUCUGCACCCAGGUGUUCCACAAGAGCAUCAGC AGGCGGUGCACCAAGAGCGUGACCAGCGUCGUGAGCACCCUGUUCU ACGACAAGAAAUGAGGACCACCAACCCCAAGGAGACCAAAAUCGU GAUCGACACCACAGGCAGCACCAAGCCCAAGCAGGACGACCUGAUC CUGACCUGCUUCAGGGGCUGGGUGAAGCAGCUGCAGAUCGACUACA AGGGCAACGAGAUCAUGACCGCCGUGCCAGCCAGGGCCUGACCAG GAAGGGCGUGUACGCCGUGAGGUACAAGGUGAACGAGAACCCACUG UACGCUCCCACCAGCGAGCACGUGAACGUGCUGCUGACCAGGACCG AGGACAGGAUCGUGUGGAAGACCCUGGCCGGCGACCCCUGGAUCAA GACCCUGACCGCCAAGUACCCCGGCAACUUCACCGCCACCAUCGAA GAGUGGCAGGCCGAGCACGACGCCAUCAUGAGGCACAUCCUGGAGA GGCCCGACCCCACCGACGUGUUCCAGAACAAGGCCAACGUGUGCUG GGCCAAGGCCCUGGUGCCCGUGCUGAAGACCGCCGGCAUCGACAUG ACCACAGAGCAGUGGAACACCGUGGACUACUUCGAGACCGACAAGG CCCACAGCGCCGAGAUCGUGCUGAACCAGCUGUGCGUGAGGUUCUU |

TABLE 9-continued

CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC

TABLE 9-continued

| | | | |
|---|---|---|---|
| | | | UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGGAAGAUGCCAAAAACAU
UAAGAAGGGCCCAGCGCCAUUCUACCCACUCGAAGACGGGACCGCC
GGCGAGCAGCUGCACAAAGCCAUGAAGCGCUACGCCCUGGUGCCG
GCACCAUCGCCUUUACCGACGCACAUAUCGAGGUGGACAUUACCUA
CGCCGAGUACUUCGAGAUGAGCGUUCGGCUGGCAGAAGCUAUGAAG
CGCUAUGGGCUGAAUACAAACCAUCGGAUCGUGGUGUGCAGCGAGA
AUAGCUUGCAGUUCUUCAUGCCCGUGUUGGGUGCCCUGUUCAUCGG
UGUGGCUGUGGCCCCAGCUAACGACAUCUACAACGAGCGCGAGCUG
CUGAACAGCAUGGGCAUCAGCCAGCCCACCGUCGUAUUCGUGAGCA
AGAAAGGGCUGCAAAAGAUCCUCAACGUGCAAAAGAAGCUACCGAU
CAUACAAAAGAUCAUCAUGGAUAGCAAGACCGACUACCAGGGC
UUCCAAAGCAUGUACACCUUCGUGACUUCCCAUUUG

TABLE 9-continued

```
AGAGCUGGCAUCUUCCAUCGUGUUCCACUUGAAUGGAAAGCAGUC
GUACACUUGCCGCUGUGAUACAGUGGUGAGUUGCGAAGGCUACGUA
GUGAAGAAAAUCACCAUCAGUCCCGGGAUCACGGGAGAAACCGUGG
GAUACGCGGUUACACACAAUAGCGAGGGCUUCUUGCUAUGCAAAGU
UACUGACACAGUAAAGGAGAACGGGUAUCGUUCCCUGUGUGCACG
UACAUCCCGGCCACCAUAUGCGAUCAGAUGACUGGUAUAAUGGCCA
CGGAUAUAUCACCUGACGAUGCACAAAAACUUCUGGUUGGGCUCAA
CCAGCGAAUUGUCAUUAACGGUAGGACUAACAGGAACACCAACACC
AUGCAAAAUUACCUUCUGCCGAUCAUAGCACAAGGGUUCAGCAAAU
GGGCUAAGGAGCGCAAGGAUGAUCUUGAUAACGAGAAAAUGCUGGG
UACUAGAGAACGCAAGCUUACGUAUGGCUGCUUGUGGGCGUUUCGC
ACUAAGAAAGUACAUUCGUUUUAUCGCCCACCUGGAACGCAGACCU
GCGUAAAAGUCCCAGCCUCUUUUUAGCGCUUUUCCCAUGUCGUCCGU
AUGGACGACCUCUUUGCCCAUGUCGCUGAGGCAGAAAUUGAAACUG
GCAUUGCAACCAAAGAAGGAGGAAAAACUGCUGCAGGUCUCGGAGG
AAUUAGUCAUGGAGGCCAAGGCUGCUUUUGAGGAUGCUCAGGAGGA
AGCCAGAGCGGAGAAGCUCCGAGAAGCACUUCCACCAUUAGUGGCA
GACAAAGGCAUCGAGGCAGCCGCAGAAGUUGUCUGCGAAGUGGAGG
GGCUCCAGGCGGACAUCGGAGCAGCAUUAGUUGAAACCCCGCGCGG
UCACGUAAGGAUAAUACCUCAAGCAAAUGACCGUAUGAUCGGACAG
UAUAUCGUUGUCUCGCCAAACUCUGUGCUGAAGAAUGCCAAACUCG
CACCAGCGCACCCGCUAGCAGAUCAGGUUAAGAUCAUAACACACUC
CGGAAGAUCAGGAAGGUACGCGGUCGAACCAUACGACGCUAAAGUA
CUGAUGCCAGCAGGAGGUGCCGUACCAUGGCCAGAAUUCCUAGCAC
UGAGUGAGAGCGCCACGUUAGUGUACAACGAAAGAGAGUUUGUGAA
CCGCAAACUAUACCACAUUGCCAUGCAUGGCCCCGCCAAGAAUACA
GAAGAGGAGCAGUACAAGGUUACAAAGGCAGAGCUUGCAGAAACAG
AGUACGUGUUUGACGUGGACAAGAAGCGUUGCGUUAAGAAGGAAGA
AGCCUCAGGUCUGGUCCUCUCGGGAGAACUGACCAACCCUCCCUAU
CAUGAGCUAGCUCUGGAGGGACUGAAGACCCGACCUGCGGUCCCGU
ACAAGGUCGAAACAAUAGGAGUGAUAGGCACACCGGGGUCGGGCAA
GUCAGCUAUUAUCAAGUCAACUGUCACGGCACGAGAUCUUGUUACC
AGCGGAAAGAAAGAAAAUUGUCGCGAAAUUGAGGCCGACGUGCUAA
GACUGAGGGGUAUGCAGAUUACGUCGAAGACAGUAGAUUCGGUUAU
GCUCAACGGAUGCCACAAAGCCUAGAAGUGCUGUACGUUGACGAA
GCGUUCGCGUGCCACGCAGGAGCACUACUUGCCUUGAUUGCUAUCG
UCAGGCCCCGCAAGAAGGUAGUACUAUGCGGAGACCCCAUGCAAUG
CGGAUUCUUCAACAUGAUGCAACUAAAGGUACAUUUCAAUCACCCU
GAAAAAGACAUAUGCACCAAGACAUUCUACAAGUAUAUCUCCCGGC
GUUGCACACAGCCAGUUACAGCUAUUGUAUCGACACUGCAUUACGA
UGGAAAGAUGAAAACCACGAACCCGUGCAAGAAGAACAUUGAAAUC
GAUAUUACAGGGGCCACAAAGCCGAAGCCAGGGGAUAUCAUCCUGA
CAUGUUUCCGCGGGUGGGUUAAGCAAUUGCAAAUCGACUAUCCCGG
ACAUGAAGUAAUGCAGCCGCGGCCUCACAAGGGCUAACCAGAAAA
GGAGUGUAUGCCGUCCGGCAAAAAGUCAAUGAAAAACCCACUGUACG
CGAUCACAUCAGAGCAUGUGAACGUGUUGCUCACCCGCACUGAGGA
CAGGCUAGUGUGGAAAACCUUGCAGGGCGACCCAUGGAUUAAGCAG
CUCACUAACAUACCUAAAGGAAACUUUCAGGCUACUAUAGAGGACU
GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
```

TABLE 9-continued

```
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU
CCACCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG
GAUAUGGAUGACAGUAGCGAAGGCUCACUUUUUUCGAGCUUUAGCG
GAUCGGACAACUCUAUUACUAGUAUGGACAGUUGGUCGUCAGGACC
UAGUUCACUAGAGAUAGUAGACCGAAGGCAGGUGGUGGUGGCUGAC
GUUCAUGCCGUCCAAGAGCCUGCCCCUAUUCCACCGCCAAGGCUAA
AGAAGAUGGCCCGCCUGGCAGCGGCAAGAAAAGAGCCCACUCCACC
GGCAAGCAAUAGCUCUGAGUCCCUCCCACCUCUCUUUUGGUGGGGUA
UCCAUGUCCCUCGGAUCAAUUUUCGACGGAGAGACGGCCCGCCAGG
CAGCGGUACAACCCCUGGCAACAGGCCCCACGGAUGUGCCUAUGUC
UUUCGGAUCGUUUUCCGACGGAGAGAUUGAUGAGCUGAGCCGCAGA
GUAACUGAGUCCGAACCCGUCCUGUUUGGAUCAUUUGAACCGGGCG
AAGUGAACUCAAUUAUAUCGUCCCGAUCAGCCGUAUCUUUUCCUCU
ACGCAAGCAGAGACGUAGACGCAGGAGCAGGAGGACUGAAUACUGA
CUAACCGGGGUAGGUGGGUACAUAUUUUCGACGGACACAGGCCCUG
GGCACUUGCAAAAGAAGUCCGUUCUGCAGAACCAGCUUACAGAACC
GACCUUGGAGCGCAAUGUCCUGGAAAGAAUUCAUGCCCCGGUGCUC
GACACGUCGAAAGAGGAACAACUCAAACUCAGGUACCAGAUGAUGC
CCACCGAAGCCAACAAAAGUAGGUACCAGUCUCGUAAAGUAGAAAA
UCAGAAAGCCAUAACCACUGAGCGACUACUGUCAGGACUACGACUG
UAUAACUCUGCCACAGAUCAGCCAGAAUGCUAUAAGAUCACCUAUC
CGAAACCAUUGUACUCCAGUAGCGUACCGGCGAACUACUCCGAUCC
ACAGUUCGCUGUAGCUGUCUGUAACAACUAUCUGCAUGAGAACUAU
CCGACAGUAGCAUCUUAUCAGAUUACUGACGAGUACGAUGCUUACU
UGGAUAUGGUAGACGGGACAGUCGCCUGCCUGGACACUGCAACCUU
CUGCCCCGCUAAGCUUAGAAGUUACCCGAAAAAACAUGAGUAUAGA
GCCCCGAAUAUCCGCAGUGCGGUUCCAUCAGCGAUGCAGAACACGC
UACAAAAUGUGCUCAUUGCCGCAACUAAAAGAAAUUGCAACGUCAC
GCAGAUGCGUGAACUGCCAACACUGGACUCAGCGACAUUCAAUGUC
GAAUGCUUUCGAAAAUAUGCAUGUAAUGACGAGUAUUGGGAGGAGU
UCGCUCGGAAGCCAAUUAGGAUUACCACUGAGUUUGUCACCGCAUA
UGUAGCUAGACUGAAAGGCCCUAAGGCCGCCGCACUAUUUGCAAAG
ACGUAUAAAUUUGGUCCCAUUGCAAGAAGUGCCUAUGGAUAGAUUCG
UCAUGGACAUGAAAAGAGACGUGAAAGUUACACCAGGCACGAAACA
CACAGAAGAAAGACCGAAAGUACAAGUGAUACAAGCCGCAGAACCC
CUGGCGACUGCUUACUUUAUGCGGGAUUCACCGGGAAUUAGUGCGUA
GGCUUACGGCCGUCUUGCUUCCAAACAUUCACACGCUUUUUGACAU
GUCGGCGGAGGAUUUUGAUGCAAUCAUAGCAGAACACUUCAAGCAA
GGCGACCCGGUACUGGAGACGGAUAUCGCAUCAUUCGACAAAAGCC
AAGACGACGCUAUGGCGUUAACCGGUCUGAUGAUCUUGGAGGACCU
GGGUGUGGAUCAACCACUACUCGACUUGAUCGAGUGCGCCUUUGGA
GAAAUAUCAUCCACCCAUCUACCUACGGGUACUCGUUUUAAAUUCG
GGGCGAUGAUGAAAUCCGGAAUGUUCCUCACACUUUUUGUCAACAC
AGUUUUGAAUGUCGUUAUCGCCAGCAGAGUACUAGAGGAGCGGCUU
AAAACGUCCAGAUGUGCAGCGUUCAUUGGCGACGACAACAUCAUAC
AUGGAGUAGUAUCUGACAAAGAAAUGGCUGAGAGGUGCGCCACCUG
GCUCAACAUGGAGGUUAAGAUCAUCGACGCAGUCAUCGUGAGAGA
CCACCUUACUUCUGCGGCGGAUUUAUCUUGCAAGAUUCGGUUACUU
CCACAGCGUGCCGCGUGGCGGAUCCCCUGAAAAGGCUGUUUAAGUU
GGGUAAACCGCUCCCAGCCGACGACGAGCAAGACGAAGACAGAAGA
CGCGCUCUGCUAGAUGAAACAAAGGCGUGGUUUAGAGUAGGUAUAA
CAGGCACUUUAGCAGUGGCCGUGACGACCCGGUAUGAGGUAGACAA
UAUUACACCUGUCCUACUGGCAUUGAGAACUUUUGCCCAGAGCAAA
AGAGCAUUCCAAGCCAUCAGAGGGGAAAUAAAGCAUCUCUACGGUG
GUCCUAAAUAGUCAGCAUAGUACAUUUCAUCUGACUAAUACUACAA
CACCACCACCAUGGAAGAUGCCAAAAACAUUAAGAAGGGCCCAGCG
CCAUUCUACCCACUCGAAGACGGGACCGCCGGCGAGCAGCUGCACA
AAGCCAUGAAGCGCUACGCCCUGGUGCCCGGCACCAUCGCCUUUAC
CGACGCACAUAUCGAGGUGGACAUUACCUACGCCGAGUACUUCGAG
AUGAGCGUUCGGCUGGCAGAAGCUAUGAAGCGCUAUGGGCUGAAUA
CAAACCAUCGGAUCGUGGUGUGCAGCGAGAAUAGCUUGCAGUUCUU
CAUGCCCGUGUUGGGUGCCCUGUUCAUCGGUGUGGCCGUGGCCCCA
GCUAACGACAUCUACAACGAGCGCGAGCUGCUGAACAGCAUGGGCA
UCAGCCAGCCCACCGUCGUAUUCGUGAGCAAGAAAGGGCUGCAAAA
GAUCCUCAACGUGCAAAAGAAGCUACCGAUCAUACAAAAGAUCAUC
AUCAUGGAUAGCAAGACCGACUACCAGGGCUUCCAAAGCAUGUACA
CCUUCGUGACUUCCCAUUUGCCACCCGGCUUCAACGAGUACGACUU
```

TABLE 9-continued

| | | | |
|---|---|---|---|
| | | | CGUGCCCGAGAGCUUCGACCGGGACAAAACCAUCGCCCUGAUCAUG<br>AACAGUAGUGGCAGUACCGGAUUGCCCAAGGGCGUAGCCCUACCGC<br>ACCGCACCGCUUGUGUCCGAUUCAGUCAUGCCCGCGACCCCAUCUU<br>CGGCAACCAGAUCAUCCCCGACACCGCUAUCCUCAGCGUGGUGCCA<br>UUUCACCACGGCUUCGGCAUGUUCACCACGCUGGGCUACUUGAUCU<br>GCGGCUUUCGGGUCGUGCUCAUGUACCGCUUCGAGGAGGAGCUAUU<br>CUUGCGCAGCUUGCAAGACUAUAAGAUUCAAUCUGCCCUGCUGGUG<br>CCCACACUAUUUAGCUUCUUCGCUAAGAGCACUCUCAUCGACAAGU<br>ACGACCUAAGCAACUUGCACGAGAUCGCCAGCGGCGGGGCGCCGCU<br>CAGCAAGGAGGUAGGUGAGGCCGUGGCCAAACGCUUCCACCUACCA<br>GGCAUCCGACAGGGCUACGGCCUGACAGAAACAACCAGCGCCAUUC<br>UGAUCACCCCCGAAGGGGACGACAAGCCUGGCGCAGUAGGCAAGGU<br>GGUGCCCUUCUUCGAGGCUAAGGUGGUGGACUUGGACACCGGUAAG<br>ACACUGGGUGUGAACCAGCGCGGCGAGCUGUGCGUCCGUGGCCCCA<br>UGAUCAUGAGCGGCUACGUUAACAACCCCGAGGCUACAAACGCUCU<br>CAUCGACAAGGACGGCUGGCUGCACAGCGGCGACAUCGCCUACUGG<br>GACGAGGACGAGCACUUCUUCAUCGUGGACCGGCUGAAGUCCCUGA<br>UCAAAUACAAGGGCUACCAGGUAGCCCCAGCCGAACUGGAGAGCAU<br>CCUGCUGCAACACCCCAACAUCUUCGACGCCGGGGUCGCCGGCCUG<br>CCCGACGACGAUGCCGGCGAGCUGCCCGCCGCAGUCGUCGUGCUGG<br>AACACGGUAAAACCAUGACCGAGAAGGAGAUCGUGGACUAUGUGGC<br>CAGCCAGGUUACAACCGCCAAGAAGCUGCGCGGUGGUGUUGUGUUC<br>GUGGACGAGGUGCCUAAAGGACUGACCGGCAAGUUGGACGCCCGCA<br>AGAUCCGCGAGAUUCUCAUUAAGGCCAAGAAGGGCGGCAAGAUCGC<br>CGUGUAAACGCGUGCUAGACCAUGGAUCCUAGACGCUACGCCCCAA<br>UGAUCCGACCAGCAAAACUCGAUGUACUUCCGAGGAACUGAUGUGC<br>AUAAUGCAUCAGGCUGGUACAUUAGAUCCCCGCUUACCGCGGGCAA<br>UAUAGCAACACUAAAAACUCGAUGUACUUCCGAGGAAGCGCAGUGC<br>AUAAUGCUGCGCAGUGUUGCCACAUAACCACUAUAUUAACCAUUUA<br>UCUAGCGGACGCCAAAAACUCAAUGUAUUUCUGAGGAAGCGUGGUG<br>CAUAAUGCCACGCAGCGUCUGCAUAACUUUUAUUAUUUCUUUUAUU<br>AAUCAACAAAAUUUGUUUUUAACAUUUCAAAAAAAAAAAAAAAAAA<br>AAAAAAAAUCUAGAAAAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAAAAAAA |
| 1782<br>(SEQ<br>ID<br>NO:102) | mRNA<br>Fluc | 1782 | AGGAAACUUAAGUCAACACAACAUAUACAAAACAAACGAAUCUCAA<br>GCAAUCAAGCAUUCUACUUCUAUUGCAGCAAUUUAAAUCAUUUCUU<br>UUAAAGCAAAAGCAAUUUUCUGAAAAUUUUCACCAUUUACGAACGA<br>UAGCCAUGGAAGAUGCCAAAAACAUUAAGAAGGGCCCAGCGCCAUU<br>CUACCCACUCGAAGACGGGACCGCCGGCGAGCAGCUGCACAAAGCC<br>AUGAAGCGCUACGCCCUGGUGCCCGGCACCAUCGCCUUUACCGACG<br>CACAUAUCGAGGUGGACAUUACCUACGCCGAGUACUUCGAGAUGAG<br>CGUUCGGCUGGCAGAAGCUAUGAAGCGCUAUGGGCUGAAUACAAAC<br>CAUCGGAUCGUGGUGUGCAGCGAGAAUAGCUUGCAGUUCUUCAUGC<br>CCGUGUUGGGUGCCCUGUUCAUCGGUGUGGCUGUGGCCCCAGCUAA<br>CGACAUCUACAACGAGCGCGAGCUGCUGAACAGCAUGGGCAUCAGC<br>CAGCCCACCGUCGUAUUCGUGAGCAAGAAAGGGCUGCAAAAGAUCC<br>UCAACGUGCAAAAGAAGCUACCGAUCAUACAAAAGAUCAUCAUCAU<br>GGAUAGCAAGACCGACUACCAGGGCUUCCAAAGCAUGUACACCUUC<br>GUGACUUCCCAUUUGCCACCCGGCUUCAACGAGUACGACUUCGUGC<br>CCGAGAGCUUCGACCGGGACAAAACCAUCGCCCUGAUCAUGAACAG<br>UAGUGGCAGUACCGGAUUGCCCAAGGGCGUAGCCCUACCGCACCGC<br>ACCGCUUGUGUCCGAUUCAGUCAUGCCCGCGACCCCAUCUUCGGCA<br>ACCAGAUCAUCCCCGACACCGCUAUCCUCAGCGUGGUGCCAUUUCA<br>CCACGGCUUCGGCAUGUUCACCACGCUGGGCUACUUGAUCUGCGGC<br>UUUCGGGUCGUGCUCAUGUACCGCUUCGAGGAGGAGCUAUUCUUGC<br>GCAGCUUGCAAGACUAUAAGAUUCAAUCUGCCCUGCUGGUGCCCAC<br>ACUAUUUAGCUUCUUCGCUAAGAGCACUCUCAUCGACAAGUACGAC<br>CUAAGCAACUUGCACGAGAUCGCCAGCGGCGGGGCGCCGCUCAGCA<br>AGGAGGUAGGUGAGGCCGUGGCCAAACGCUUCCACCUACCAGGCAU<br>CCGACAGGGCUACGGCCUGACAGAAACAACCAGCGCCAUUCUGAUC<br>ACCCCCGAAGGGGACGACAAGCCUGGCGCAGUAGGCAAGGUGGUGC<br>CCUUCUUCGAGGCUAAGGUGGUGGACUUGGACACCGGUAAGACACU<br>GGGUGUGAACCAGCGCGGCGAGCUGUGCGUCCGUGGCCCCAUGAUC<br>AUGAGCGGCUACGUUAACAACCCCGAGGCUACAAACGCUCUCAUCG<br>ACAAGGACGGCUGGCUGCACAGCGGCGACAUCGCCUACUGGGACGA<br>GGACGAGCACUUCUUCAUCGUGGACCGGCUGAAGUCCCUGAUCAAA<br>UACAAGGGCUACCAGGUAGCCCCAGCCGAACUGGAGAGCAUCCUGC<br>UGCAACACCCCAACAUCUUCGACGCCGGGGUCGCCGGCCUGCCCGA<br>CGACGAUGCCGGCGAGCUGCCCGCCGCAGUCGUCGUGCUGGAACAC<br>GGUAAAACCAUGACCGAGAAGGAGAUCGUGGACUAUGUGGCCAGCC<br>AGGUUACAACCGCCAAGAAGCUGCGCGGUGGUGUUGUGUUCGUGGA<br>CGAGGUGCCUAAAGGACUGACCGGCAAGUUGGACGCCCGCAAGAUC<br>CGCGAGAUUCUCAUUAAGGCCAAGAAGGGCGGCAAGAUCGCCGUGU<br>AACUCGAGCUAGUGACUGACUAGGAUCUGGUUACCACUAAACCAGC<br>CUCAAGAACACCCGAAUGGAGUCUCUAAGCUACAUAAUACCAACUU |

TABLE 9-continued

| | | |
|---|---|---|
| | | ACACUUACAAAAUGUUGUCCCCCAAAAUGUAGCCAUUCGUAUCUGC<br>UCCUAAUAAAAAGAAAGUUUCUUCACAUUCUAGAAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAA |
| 2847 (SEQ ID NO:103) | STARR$^{TM}$ 2847 KRAS wt | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC<br>AUCAGGGACGUGAAGAAGAUGAAAGGCCUGGACGUGAACGCGCGCA<br>CCGUGGACAGCGUGCUGCUGAACGGCUGCAAGCACCCCGUGGAGAC<br>CCUGUACAUCGACGAGGCCUUCGCUUGCCACGCCGGCACCCUGAGG<br>GCCCUGAUCGCCAUCAUCAGGCCCAAGAAAGCCGUGCUGUGCGGCG<br>ACCCCAAGCAGUGCGGCUUCUUCAACAUGAUGUGCCUGAAGGUGCA<br>CUUCAACCACGAGAUCUGCACCCAGGUGUUCCACAAGAGCAUCAGC<br>AGGCGGUGCACCAAGAGCGUGACCAGCGUCGUGAGCACCCUGUUCU<br>ACGACAAGAAAAUGAGGACCACCAACCCCAAGGAGACCAAAAUCGU<br>GAUCGACACCACAGGCAGCACCAAGCCCAAGCAGGACGACCUGAUC<br>CUGACCUGCUUCAGGGGCUGGGUGAAGCAGCUGCAGAUCGACUACA<br>AGGGCAACGAGAUCAUGACCGCCGCUGCCAGCCAGGGCCUGACCAG<br>GAAGGGCGUGUACGCCGUGAGGUACAAGGUGAACGAGAACCCACUG<br>UACGCUCCCACCAGCGAGCACGUGAACGUGCUGCUGACCAGGACCG<br>AGGACAGGAUCGUGUGGAAGACCCUGGCCGGCGACCCCUGGAUCAA<br>GACCCUGACCGCCAAGUACCCCGGCAACUUCACCGCCACCAUCGAA<br>GAGUGGCAGGCCGAGCACGACGCCAUCAUGAGGCACAUCCUGGAGA<br>GGCCCGACCCCACCGACGUGUUCCAGAACAAGGCCAACGUGUGCUG<br>GGCCAAGGCCCUGGUGCCCGUGCUGAAGACCGCCGGCAUCGACAUG<br>ACCACAGAGCAGUGGAACACCGUGGACUACUUCGAGACCGACAAGG<br>CCCACAGCGCCGAGAUCGUGCUGAACCAGCUGUGCGUGAGGUUCUU<br>CGGCCUGGACCUGGACAGCGGCCUGUUCAGCGCCCCCACCGUGCCA<br>CUGAGCAUCAGGAACAACCACUGGGACAACAGCCCCAGCCCAAACA<br>UGUACGGCCUGAACAAGGAGGUGGUCAGGCAGCUGAGCAGGCGGUA<br>CCCACAGCUGCCCAGGGCCGUGGCCACCGGCAGGGUGUACGACAUG |

TABLE 9-continued

AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC

TABLE 9-continued

|  |  |  |  |
|---|---|---|---|
|  |  |  | CUUCAUCGGCGACGACAACAUCGUGAAGGGCGUGAAAAGCGACAAG |
|  |  |  | CUGAUGGCCGACAGGUGCGCCACCUGGCUGAACAUGGAGGUGAAGA |
|  |  |  | UCAUCGACGCCGUGGUGGGCGAGAAGGCCCCCUACUUCUGCGGCGG |
|  |  |  | AUUCAUCCUGUGCGACAGCGUGACCGGCACCGCCUGCACGGUGGCC |
|  |  |  | GACCCCCUGAAGAGGCUGUUCAAGCUGGGCAAGCCACUGGCCGCUG |
|  |  |  | ACGAUGAGCACGACGAUGACAGGCGGAGGGCCCUGCACGAGGAAAG |
|  |  |  | CACCAGGUGGAACAGGGUGGGCAUCCUGAGCGAGCUGUGCAAGGCC |
|  |  |  | GUGGAGAGCAGGUACGAGACCGUGGGCACCAGCAGCAUCAUCGUGAUGG |
|  |  |  | CUAUGACCACACUGGCCAGCUCCGUCAAGAGCUUCUCCUACCUGAG |
|  |  |  | GGGGGCCCCUAUAACUCUCUACGGCUAACCUGAAUGGACUACGACA |
|  |  |  | UAGUCUAGUCCGCAAGGCCGCCACCCAUGAAGUUGGUGGUUGUGG |
|  |  |  | GGGCCGGGGGUGUUGGCAAAAGCGCCCUUACAAUUUGACUCGAGUA |
|  |  |  | UGUUACGUGCAAAGGUGAUUGUCACCCCCGAAAGACCAUAUUGUG |
|  |  |  | ACACACCCUCAGUAUCACGCCCAAACAUUUACAGCCGCGGUGUCAA |
|  |  |  | AAACCGCUGGACGUGGUUAACAUCCCUGCUGGGAGGAUCAGCCGU |
|  |  |  | AAUUAUUAUAAUUGGCUUGGUGCUGGCUACUAUUGUGGCCAUGUAC |
|  |  |  | GUGCUGACCAACCAGAAACAUAAUUGAAUACAGCAGCAAUUGGCAA |
|  |  |  | GCUGCUUACAUAGAACUCGCGGCGAUUGGCAUGCCGCCUUAAAAUU |
|  |  |  | UUUAUUUAUUUUUUCUUUUCUUUUCCGAAUCGGAUUUUGUUUUUA |
|  |  |  | AUAUUUCAAAAAAAAAAAAAAAAAAAAAAAAUCUAGAAAAAAAAA |
|  |  |  | AAAAAAAAAAAAAAAAAAAAAAAAAAAAAAAAAAAAAAAAAAAAA |
|  |  |  | AAAAAAAAAAAAAAAAAAAAAAAAAAAAAAAAAAAAAAAAA |
| 2862 (SEQ ID NO:104) | SINV empty | 2862 | AUUGACGGCGUAGUACACACUAUUGAAUCAAACAGCCGACCAAUUG CACUACCAUCACAAUGGAGAAGCCAGUAGUAAACGUAGACGUAGAC CCCCAGAGUCCGUUUGUCGUGCAACUGCAAAAAAGCUUCCCGCAAU UUGAGGUAGUAGCACAGCAGGUCACUCCAAAUGACCAUGCUAAUGC CAGAGCAUUUUCGCAUCUGGCCAGUAAACUAAUCGAGCUGGAGGUU CCUACCACAGCGACGAUCUUGGACAUAGGCAGCGCACCGGCUCGUA GAAUGUUUUCCGAGCACCAGUAUCAUUGUGUCUGCCCCAUGCGUAG UCCAGAAGACCCGGACCGCAUGAUGAAAUAUGCCAGUAAACUGGCG GAAAAAGCGUGCAAGAUUACAAACAAGAACUUGCAUGAGAAGAUUA AGGAUCUCCGGACCGUACUUGAUACGCCGGAUGCUGAAACACCAUC GCUCUGCUUUCACAACGAUGUUACCUGCAACAUGCGUGCCGAAUAU UCCGUCAUGCAGGACGUGUAUAUCAACGCUCCCGGAACUAUCUAUC AUCAGGCUAUGAAAGGCGUGCGGACCCUGUACUGGAUUGGCUUCGA CACCACCCAGUUCAUGUUCUCGGCUAUGGCAGGUUCGUACCCUGCG UACAACACCAACUGGGCCGACGAGAAAGUCCUUGAAGCGCGUAACA UCGGACUUUGCAGCACAAAGCUGAGUGAAGGUAGGACAGGAAAAUU GUCGAUAAUGAGGAAGAAGGAGUUGAAGCCCGGGUCGCGGGUUUAU UUCUCCGUAGGAUCGACACUUUAUCCAGAACACAGAGCCAGCUUGC AGAGCUGGCAUCUUCCAUCGGUGUUCACUUGAAUGGAAAGCAGUC GUACACUUGCCGCUGUGAUACAGUGGUGAGUUGCGAAGGCUACGUA GUGAAGAAAAUCACCAUCAGUCCCGGGAUCACGGGAGAAACCGUGG GAUACGCGGUUACACACAAUAGCGAGGGCUUCUUGCUAUGCAAAGU UACUGACACAGUAAAAGGAGAACGGGUAUCGUUCCCUGUGUGCACG UACAUCCCGGCCACCAUAUGCGAUCAGAUGACUGGUAUAAUGGCCA CGGAUAUAUCACCUGACGAUGCACAAAAACUUCUGGUUGGGCUCAA CCAGCGAAUUGUCAUUAACG TABLE 9-continued GUUGCACACAGCCAGUUACAGCUAUUGUAUCGACACUGCAUUACGA
UGGAAAGAUGAAAACCACGAACCCGUGCAAGAAGAACAUUGAAAUC
GAUAUUACAGGGGCCACAAAGCCGAAGCCAGGGGAUAUCAUCCUGA
CAUGUUUCCGCGGGUGGGUUAAGCAAUUGCAAAUCGACUAUCCCGG
ACAUGAAGUAAUGACAGCCGCGGCCUCACAAGGGCUAACCAGAAAA
GGAGUGUAUGCCGUCCGGCAAAAAGUCAAUGAAAACCCACUGUACG
CGAUCACAUCAGAGCAUGUGAACGUGUUGCUCACCCGCACUGAGGA
CAGGCUAGUGUGGAAAACCUUGCAGGGCGACCCAUGGAUUAAGCAG
CUCACUAACAUACCUAAAGGAAACUUUCAGGCUACUAUAGAGGACU
GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU
CCACCCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG
GAUAUGGAUGACAGUAGCGAAGGCUCACUUUUUUCGAGCUUUAGCG
GAUCGGACAACUCUAUUACUAGUAUGGACAGUUGGUCGUCAGGACC
UAGUUCACUAGAGAUAGUAGACCGAAGGCAGGUGGUGGUGGCUGAC
GUUCAUGCCGUCCAAGAGCCUGCCCCUAUUCCACCGCCAAGGCUAA
AGAAGAUGGCCCGCCUGGCAGCGGCAAGAAAAGAGCCCACUCCACC
GGCAAGCAAUAGCUCUGAGUCCCUCCACCUCUCUUUUGGUGGGGUA
UCCAUGUCCCUCGGAUCAAUUUUCGACGGAGAGACGGCCCGCCAGG
CAGCGGUACAACCCCUGGCAACAGGCCCCACGGAUGUGCCUAUGUC
UUUCGGAUCGUUUUCCGACGGAGAGAUUGAUGAGCUGAGCCGCAGA
GUAACUGAGUCCGAACCCGUCCUGUUUGGAUCAUUUGAACCGGGCG
AAGUGAACUCAAUUAUAUCGUCCCGAUCAGCCGUAUCUUUUCCUCU
ACGCAAGCAGAGACGUAGACGCAGGAGCAGGAGGACUGAAUACUGA
CUAACCGGGGUAGGUGGGUACAUAUUUUCGACGGACACAGGCCCUG
GGCACUUGCAAAAGAAGUCCGUUCUGCAGAACCAGCUUACAGAACC
GACCUUGGAGCGCAAUGUCCUGGAAAGAAUUCAUGCCCCGGUGCUC
GACACGUCGAAAGAGGAACAACUCAAACUCAGGUACCAGAUGAUGC
CCACCGAAGCCAACAAAAGUAGGUACCAGUCUCGUAAAGUAGAAAA
UCAGAAAGCCAUAACCACUGAGCGACUACUGUCAGGACUACGACUG
UAUAACUCUGCCACAGAUCAGCCAGAAUGCUAUAAGAUCACCUAUC
CGAAACCAUUGUACUCCAGUAGCGUACCGGCGAACUACUCCGAUCC
ACAGUUCGCUGUAGCUGUCUGUAACAACUAUCUGCAUGAGAACUAU
CCGACAGUAGCAUCUUAUCAGAUUACUGACGAGUACGAUGCUUACU
UGGAUAUGGUAGACGGGACAGUCGCCUGCCUGGACACUGCAACCUU
CUGCCCCGCUAAGCUUAGAAGUUACCCGAAAAAACAUGAGUAUAGA TABLE 9-continued

| | | | |
|---|---|---|---|
| | | | GCCCCGAAUAUCCGCAGUGCGGUUCCAUCAGCGAUGCAGAACACGC<br>UACAAAAUGUGCUCAUUGCCGCAACUAAAAGAAAUUGCAACGUCAC<br>GCAGAUGCGUGAACUGCCAACACUGGACUCAGCGACAUUCAAUGUC<br>GAAUGCUUUCGAAAAUAUGCAUGUAAUGACGAGUAUUGGGAGGAGU<br>UCGCUCGGAAGCCAAUUAGGAUUACCACUGAGUUUGUCACCGCAUA<br>UGUAGCUAGACUGAAAGGCCCUAAGGCCGCCGCACUAUUUGCAAAG<br>ACGUAUAAUUUGGUCCCAUUGCAAGAAGUGCCUAUGGAUAGAUUCG<br>UCAUGGACAUGAAAAGAGACGUGAAAGUUACACCAGGCACGAAACA<br>CACAGAAGAAAGACCGAAAGUACAAGUGAUACAAGCCGCAGAACCC<br>CUGGCGACUGCUUACUUAUGCGGGAUUCACCGGGAAUUAGUGCGUA<br>GGCUUACGGCCGUCUUGCUUCCAAACAUUCACACGCUUUUUGACAU<br>GUCGGCGGAGGAUUUUGAUGCAAUCAUAGCAGAACACUUCAAGCAA<br>GGCGACCCGGUACUGGAGACGGAUAUCGCAUCAUUCGACAAAAGCC<br>AAGACGACGCUAUGGCGUUAACCGGUCUGAUGAUCUUGGAGGACCU<br>GGGUGUGGAUCAACCACUACUCGACUUGAUCGAGUGCGCCUUUGGA<br>GAAAUAUCAUCCACCCAUCUACCUACGGGUACUCGUUUUAAAUUCG<br>GGGCGAUGAUGAAAUCCGGAAUGUUCCUCACACUUUUUGUCAACAC<br>AGUUUUGAAUGUCGUUAUCGCCAGCAGAGUACUAGAGGAGCGGCUU<br>AAAACGUCCAGAUGUGCAGCGUUCAUUGGCGACGACAACAUCAUAC<br>AUGGAGUAGUAUCUGACAAAGAAAUGGCUGAGAGGUGCGCCACCUG<br>GCUCAACAUGGAGGUUAAGAUCAUCGACGCAGUCAUCGGUGAGAGA<br>CCACCUUACUUCUGCGGCGGAUUUAUCUUGCAAGAUUCGGUUACUU<br>CCACAGCGUGCCGCGUGGCGGAUCCCCUGAAAAGGCUGUUUAAGUU<br>GGGUAAACCGCUCCCAGCCGACGACGAGCAAGACGAAGACAGAAGA<br>CGCGCUCUGCUAGAUGAAACAAAGGCGUGGUUUAGAGUAGGUAUAA<br>CAGGCACUUUAGCAGUGGCCGUGACGACCCGGUAUGAGGUAGACAA<br>UAUUACACCUGUCCUACUGGCAUUGAGAACUUUUGCCCAGAGCAAA<br>AGAGCAUUCCAAGCCAUCAGAGGGGAAAUAAAGCAUCUCUACGGUG<br>GUCCUAAAUAGUCAGCAUAGUACAUUUCAUCUGACUAAUACUACAA<br>CACCACCACCACGCGUGCUAGACCAUGGAUCCUAGACGCUACGCCC<br>CAAUGAUCCGACCAGCAAAACUCGAUGUACUUCCGAGGAACUGAUG<br>UGCAUAAUGCAUCAGGCUGGUACAUUAGAUCCCCGCUUACCGCGGG<br>CAAUAUAGCAACACUAAAAACUCGAUGUACUUCCGAGGAAGCGCAG<br>UGCAUAAUGCUGCGCAGUGUUGCCACAUAACCACUAUAUUAACCAU<br>UUAUCUAGCGGACGCCAAAAACUCAAUGUAUUUCUGAGGAAGCGUG<br>GUGCAUAAUGCCACGCAGCGUCUGCAUAACUUUUAUUAUUUCUUUU<br>AUUAAUCAACAAAAUUUUGUUUUUAACAUUUCAAAAAAAAAAAAAA<br>AAAAAAAAAAAUCUAGAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAAAAAAAAAA |
| 3060 (SEQ ID NO:105) | STARR$^{TM}$ gp70 | 3060 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA |

TABLE 9-continued

UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG

TABLE 9-continued

| | | |
|---|---|---|
| | | GCUCCCAGCAGGGCCUGCAGCAGGACCAGCCUGGUGAGCACCCCAC |
| | | CCGGCGUGAACAGGGUGAUCACCAGGGAGGAACUGGAGGCCCUGAC |
| | | ACCCAGCAGGACCCCCAGCAGGUCCGUGAGCAGGACUAGUCUGGUG |
| | | UCCAACCCACCCGGCGUGAACAGGGUGAUCACCAGGGAGGAAUUCG |
| | | AGGCCUUCGUGGCCCAGCAACAGAGACGGUUCGACGCCGGCGCCUA |
| | | CAUCUUCAGCAGCGACACCGGCCAGGGACACCUGCAGCAAAAGAGC |
| | | GUGAGGCAGACCGUGCUGAGCGAGGUGGUGCUGGAGAGGACCGAGC |
| | | UGGAAAUCAGCUACGCCCCCAGGCUGGACCAGGAGAAGGAGGAACU |
| | | GCUCAGGAAGAAACUGCAGCUGAACCCCACCCCAGCCAACAGGAGC |
| | | AGGUACCAGAGCAGGAAGGUGGAGAACAUGAAGGCCAUCACCGCCA |
| | | GGCGGAUCCUGCAGGGCCUGGGACACUACCUGAAGGCCGAGGGCAA |
| | | GGUGGAGUGCUACAGGACCCUGCACCCCGUGCCACUGUACAGCUCC |
| | | AGCGUGAACAGGGCCUUCUCCAGCCCCAAGGUGGCCGUGGAGGCCU |
| | | GCAACGCUAUGCUGAAGGAGAACUUCCCCACCGUGGCCAGCUACUG |
| | | CAUCAUCCCCGAGUACGACGCCUACCUGGACAUGGUGGACGGCGCC |
| | | AGCUGCUGCCUGGACACCGCCAGCUUCUGCCCCGCCAAGCUGAGGA |
| | | GCUUCCCCAAGAAACACAGCUACCUGGAGCCCACCAUCAGGAGCGC |
| | | CGUGCCCAGCGCCAUCCAGAACACCCUGCAGAACGUGCUGGCCGCU |
| | | GCCACCAAGAGGAACUGCAACGUGACCCAGAUGAGGGAGCUGCCCG |
| | | UGCUGGACAGCGCUGCCUUCAACGUGGAGUGCUUCAAGAAAUACGC |
| | | CUGCAACAACGAGUACUGGGAGACCUUCAAGGAGAACCCCAUCAGG |
| | | CUGACCGAAGAGAACGUGGUGAACUACAUCACCAAGCUGAAGGGCC |
| | | CCAAGGCCGCUGCCCUGUUCGCUAAGACCCACAACCUGAACAUGCU |
| | | GCAGGACAUCCCAAUGGACAGGUUCGUGAUGGACCUGAAGAGGGAC |
| | | GUGAAGGUGACACCCGGCACCAAGCACACCGAGGAGAGGCCCAAGG |
| | | UGCAGGUGAUCCAGGCCGCUGACCCACUGGCCACCGCCUACCUGUG |
| | | CGGCAUCCACAGGGAGCUGGUGAGGCGGCUGAACGCCGUGCUGCUG |
| | | CCCAACAUCCACACCCUGUUCGACAUGAGCGCCGAGGACUUCGACG |
| | | CCAUCAUCGCCGAGCACUUCCAGCCCGGCGACUGCGUGCUGGAGAC |
| | | CGACAUCGCCAGCUUCGACAAGAGCGAGGAUGACGCUAUGGCCCUG |
| | | ACCGCUCUGAUGAUCCUGGAGGACCUGGGCGUGGACGCCGAGCUGC |
| | | UCACCCUGAUCGAGGCUGCCUUCGGCGAGAUCAGCUCCAUCCACCU |
| | | GCCCACCAAGACCAAGUUCAAGUUCGGCGCUAUGAUGAAAAGCGGA |
| | | AUGUUCCUGACCCUGUUCGUGAACACCGUGAUCAACAUUGUGAUCG |
| | | CCAGCAGGGUGCUGCGGGAGAGGCUGACCGGCAGCCCCUGCGCUGC |
| | | CUUCAUCGGCGACGACAACAUCGUGAAGGGCGUGAAAAGCGACAAG |
| | | CUGAUGGCCGACAGGUGCGCCACCUGGCUGAACAUGGAGGUGAAGA |
| | | UCAUCGACGCCGUGGUGGGCGAGAAGGCCCCCUACUUCUGCGGCGG |
| | | AUUCAUCCUGUGCGACAGCGUGACCGGCACCGCCUGCAGGGUGGCC |
| | | GACCCCCUGAAGAGGCUGUUCAAGCUGGGCAAGCCACUGGCCGCUG |
| | | ACGAUGAGCACGACGAUGACAGGCGGAGGGCCCUGCACGAGGAAAG |
| | | CACCAGGUGGAACAGGGUGGGCAUCCUGAGCGAGCUGUGCAAGGCC |
| | | GUGGAGAGCAGGUACGAGACCGUGGGCACCAGCAUCAUCGUGAUGG |
| | | CUAUGACCACACUGGCCAGCUCCGUCAAGAGCUUCUCCUACCUGAG |
| | | GGGGGCCCCUAUAACUCUCUACGGCUAACCUGAAUGGACUACGACA |
| | | UAGUCUAGUCCGCCAAGGCCGCCACCAUGAGAGUGACAGCCCCUAG |
| | | AACCUUACUGCUUCUGCUUUGGGGAGCUGUUGCUCUGACAGAGACA |
| | | UGGGCUGGAUCUCUGAGCGAGGUGACCGGCCAGGGCCUGUGCAUCG |
| | | GCGCCGUGCCCAAGACCCACCAGGUGCUGUGCAACACCACCCAGAA |
| | | GACCAGCGACGGCAGCUACUACCUGGCCGCUCCCACCGGCACCACC |
| | | UGGGCCUGCAGCACCGGCCUGACCCCUUGCAUCAGCACCACCAUCC |
| | | UGAACCUGACCACCGACUACUGCGUGCUGGUGGAGCUGUGGCCCAG |
| | | GGUGACCUACCACAGCCCCAGCUACGCCUACCACCAGUUCGAGAGG |
| | | AGGGCCAAGUACAAGAGGGAGCCCGUGAGCCUGACCCUGGCCCUGC |
| | | UGCUGGGCGGCCUGACAAUGGGCGGCAUCGCCGCCGGCGUGGGCAC |
| | | CGGCACCACCGCCCUGGUGGCCACCCAGCAGUUCCAGCAGCUGCAG |
| | | GCCGCCAUGCACGACGACCUGAAGGAGGUGGAGAAGUCCAUCACCA |
| | | ACCUGGAGAAGUCCCUGACCAGCCUGAGCGAGGUGGUGCUGCAGAA |
| | | CAGGAGGGGCCUGGACCUGCUGUUCCUGAAGGAGGGCGGCCUGUGC |
| | | GCCGCCCUGAAGGAGGAGUGCUGCCUGUACGCCGACCACACCGGCC |
| | | UGGUGAUCGUGGGCAUUGUCGCUGGCCUGGCCGUCCUCGCCGUGGU |
| | | GGUGAUUGGAGCUGUGGUCGCAGCUGUUAUGUGCAGAAGAAAGUCA |
| | | UCCGGCGGAAAGGGAGGCUCCUACUCUCAGGCUGCUUCUGCUACAG |
| | | UGCCUAGAGCUCUUAUGUGUUUAUCUCAGCUGUAAACUCGAGUAUG |
| | | UUACGUGCAAAGGUGAUUGUCACCCCCCGAAAGACCAUAUUGUGAC |
| | | ACACCCUCAGUAUCACGCCCAAACAUUUACAGCCGCGGUGUCAAAA |
| | | ACCGCGUGGACGUGGUUAACAUCCCUGCUGGGAGGAUCAGCCGUAA |
| | | UUAUUAUAAUUGGCUUGGUGCUGGCUACUAUUGUGGCCAUGUACGU |
| | | GCUGACCAACCAGAAACAUAAUUGAAUACAGCAGCAAUUGGCAAGC |
| | | UGCUUACAUAGAACUCGCGGCGAUUGGCAUGCCGCCUUAAAAUUUU |
| | | UAUUUUAUUUUUUCUUUUCUUUUCCGAAUCGGAUUUUGUUUUUAAU |
| | | AUUUCAAAAAAAAAAAAAAAAAAAAAAUCUAGAAAAAAAAAAAAAA |
| | | AAAAAAAAAAAAAAAAAAAAAAAAAAAAAAAAAAAAAAAAAAAAAA |
| | | AAAAAAAAAAAAAAAAAAAAAAAAAAAAAAAAAAAAAAAAAAA |
| 3061 (SEQ ID NO:106) | STARR$^{TM}$ 3061 AH1A5 | AUGGGCGGCGCAUGAGAGAAGCCCAGACCAAUUACCUACCCAAA |
| | | AUGGAGAAAGUUCACGUUGACAUCGAGGAAGACAGCCCAUUCCU |
| | | CAGAGCUUUGCAGCGGAGCUUCCCGCAGUUUGAGGUAGAAGCCA |
| | | AGCAGGUCACUGAUAAUGACCAUGCUAAUGCCAGAGCGUUUUCG |
| | | CAUCUGGCUUCAAAACUGAUCGAAACGGAGGUGGACCCAUCCGA |

TABLE 9-continued

CACGAUCCUUGACAUUGGAAGUGCGCCCGCCCGCAGAAUGUAUU
CUAAGCACAAGUAUCAUUGUAUCUGUCCGAUGAGAUGUGCGGAA
GAUCCGGACAGAUUGUAUAAGUAUGCAACUAAGCUGAAGAAAAA
CUGUAAGGAAAUAACUGAUAAGGAAUUGGACAAGAAAAUGAAGG
AGCUGGCCGCCGUCAUGAGCGACCCUGACCUGGAAACUGAGACU
AUGUGCCUCCACGACGACGAGUCGUGUCGCUACGAAGGGCAAGU
CGCUGUUUACCAGGAUGUAUACGCCGUCGACGGCCCCACCAGCC
UGUACCACCAGGCCAACAAGGGCGUGAGGGUGGCCUACUGGAUC
GGCUUCGACACCACACCCUUCAUGUUCAAGAACCUGGCCGGCGC
CUACCCCAGCUACAGCACCAACUGGGCCGACGAGACCGUGCUGA
CCGCCAGGAACAUCGGCCUGUGCAGCAGCGACGUGAUGGAGAGG
AGCCGGAGAGGCAUGAGCAUCCUGAGGAAGAAAUACCUGAAGCC
CAGCAACAACGUGCUGUUCAGCGUGGGCAGCACCAUCUACCACG
AGAAGAGGGACCUGCUCAGGAGCUGGCACCUGCCCAGCGUGUUC
CACCUGAGGGGCAAGCAGAACUACACCUGCAGGUGCGAGACCAU
CGUGAGCUGCGACGGCUACGUGGUGAAGAGGAUCGCCAUCAGCC
CCGGCCUGUACGGCAAGCCCAGCGGCUACGCCGCUACAAUGCAC
AGGGAGGGCUUCCUGUGCUGCAAGGUGACCGACACCCUGAACGG
CGAGAGGGUGAGCUUCCCCGUGUGCACCUACGUGCCCGCCACCC
UGUGCGACCAGAUGACCGGCAUCCUGGCCACCGACGUGAGCGCC
GACGACGCCCAGAAGCUGCUCGUGGGCCUGAACCAGAGGAUCGU
GGUCAACGGCAGGACCCAGAGGAACACCAACACAAUGAAGAACU
ACCUGCUGCCCGUGGUGGCCCAGGCUUUCGCCAGGUGGGCCAAG
GAGUACAAGGAGGACCAGGAAGACGAGAGGCCCCUGGGCCUGAG
GGACAGGCAGCUGGUGAUGGGCUGCUGCUGGGCCUUCAGGCGGC
ACAAGAUCACCAGCAUCUACAAGAGGCCCGACACCCAGACCAUC
AUCAAGGUGAACAGCGACUUCCACAGCUUCGUGCUGCCCAGGAU
CGGCAGCAACACCCUGGAGAUCGGCCUGAGGACCCGGAUCAGGA
AGAUGCUGGAGGAACACAAGGAGCCCAGCCCACUGAUCACCGCC
GAGGACGUGCAGGAGGCCAAGUGCGCUGCCGACGAGGCCAAGGA
GGUGAGGGAGGCCGAGGAACUGAGGGCCGCCCUGCCACCCCUGG
CUGCCGACGUGGAGGAACCCACCCUGGAAGCCGACGUGGACCUG
AUGCUGCAGGAGGCCGGCGCCGGAAGCGUGGAGACACCCAGGGG
CCUGAUCAAGGUGACCAGCUACGACGGCGAGGACAAGAUCGGCA
GCUACGCCGUGCUGAGCCCACAGGCCGUGCUGAAGUCCGAGAAG
CUGAGCUGCAUCCACCCACUGGCCGAGCAGGUGAUCGUGAUCAC
CCACAGCGGCAGGAAGGGCAGGUACGCCGUGGAGCCCUACCACG
GCAAGGUGGUCGUGCCCGAGGGCCACGCCAUCCCCGUGCAGGAC
UUCCAGGCCCUGAGCGAGAGCGCCACCAUCGUGUACAACGAGAG
GGAGUUCGUGAACAGGUACCUGCACCAUAUCGCCACCCACGGCG
GAGCCCUGAACACCGACGAGGAAUACUACAAGACCGUGAAGCCC
AGCGAGCACGACGGCGAGUACCUGUACGACAUCGACAGGAAGCA
GUGCGUGAAGAAAGAGCUGGUGACCGGCCUGGGACUGACCGGCG
AGCUGGUGGACCCACCCUUCCACGAGUUCGCCUACGAGAGCCUG
AGGACCAGACCCGCCGCUCCCUACCAGGUGCCCACCAUCGGCGU
GUACGGCGUGCCCGGCAGCGGAAAGAGCGGCAUCAUCAAGAGCG
CCGUGACCAAGAAAGACCUGGUGGUCAGCGCCAAGAAAGAGAAC
UGCGCCGAGAUCAUCAGGGACGUGAAGAAGAUGAAAGGCCUGGA
CGUGAACGCGCGCACCGUGGACAGCGUGCUGCUGAACGGCUGCA
AGCACCCCGUGGAGACCCUGUACAUCGACGAGGCCUUCGCUUGC
CACGCCGGCACCCUGAGGGCCCUGAUCGCCAUCAUCAGGCCCAA
GAAAGCCGUGCUGUGCGGCGACCCCAAGCAGUGCGGCUUCUUCA
ACAUGAUGUGCCUGAAGGUGCACUUCAACCACGAGAUCUGCACC
CAGGUGUUCCACAAGAGCAUCAGCAGGCGGUGCACCAAGAGCGU
GACCAGCGUCGUGAGCACCCUGUUCUACGACAAGAAAAUGAGGA
CCACCAACCCCAAGGAGACCAAAAUCGUGAUCGACACCACAGGC
AGCACCAAGCCCAAGCAGGACGACCUGAUCCUGACCUGCUUCAG
GGGCUGGGUGAAGCAGCUGCAGAUCGACUACAAGGGCAACGAGA
UCAUGACCGCCGCUGCCAGCCAGGGCCUGACCAGGAAGGGCGUG
UACGCCGUGAGGUACAAGGUGAACGAGAACCCACUGUACGCUCC
CACCAGCGAGCACGUGAACGUGCUGCUGACCAGGACCGAGGACA
GGAUCGUGUGGAAGACCCUGGCCGGCGACCCCUGGAUCAAGACC
CUGACCGCCAAGUACCCCGGCAACUUCACCGCCACCAUCGAAGA
GUGGCAGGCCGAGCACGACGCCAUCAUGAGGCACAUCCUGGAGA
GGCCCGACCCCACCGACGUGUUCCAGAACAAGGCCAACGUGUGC
UGGGCCAAGGCCCUGGUGCCCGUGCUGAAGACCGCCGGCAUCGA
CAUGACCACAGAGCAGUGGAACACCGUGGACUACUUCGAGACCG
ACAAGGCCCACAGCGCCGAGAUCGUGCUGAACCAGCUGUGCGUG
AGGUUCUUCGGCCUGGACCUGGACAGCGGCCUGUUCAGCGCCCC
CACCGUGCCACUGAGCAUCAGGAACAACCACUGGGACAACAGCC
CCAGCCCAAACAUGUACGGCCUGAACAAGGAGGUGGUCAGGCAG
CUGAGCAGGCGGUACCCACAGCUGCCCAGGGCCGUGGCCACCGG
CAGGGUGUACGACAUGAACACCGGCACCCUGAGGAACUACGACC
CCAGGAUCAACCUGGUGCCCGUGAACAGGCGGCUGCCCCACGCC
CUGGUGCUGCACCACAACGAGCACCCACAGAGCGACUUCAGCUC
CUUCGUGAGCAAGCUGAAAGGCAGGACCGUGCUGGUCGUGGGCG
AGAAGCUGAGCGUGCCCGGCAAGAUGGUGGACUGGCUGAGCGAC
AGGCCCGAGGCCACCUUCCGGGCCAGGCUGGACCUCGGCAUCCC
CGGCGACGUGCCCAAGUACGACAUCAUCUUCGUGAACGUCAGGA
CCCCAUACAAGUACCACCAUUACCAGCAGUGCGAGGACCACGCC

TABLE 9-continued

AUCAAGCUGAGCAUGCUGACCAAGAAGGCCUGCCUGCACCUGAA
CCCCGGAGGCACCUGCGUGAGCAUCGGCUACGGCUACGCCGACA
GGGCCAGCGAGAGCAUCAUUGGCGCCAUCGCCAGGCUGUUCAAG
UUCAGCAGGGUGUGCAAACCCAAGAGCAGCCUGGAGGAAACCGA
GGUGCUGUUCGUGUUCAUCGGCUACGACCGGAAGGCCAGGACCC
ACAACCCCUACAAGCUGAGCAGCACCCUGACAAACAUCUACACC
GGCAGCAGGCUGCACGAGGCCGGCUGCGCCCCCAGCUACCACGU
GGUCAGGGGCGAUAUCGCCACCGCCACCGAGGGCGUGAUCAUCA
ACGCUGCCAACAGCAAGGGCCAGCCCGGAGGCGGAGUGUGCGGC
GCCCUGUACAAGAAGUUCCCCGAGAGCUUCGACCUGCAGCCCAU
CGAGGUGGGCAAGGCCAGGCUGGUGAAGGGCGCCGCUAAGCACA
UCAUCCACGCCGUGGGCCCCAACUUCAACAAGGUGAGCGAGGUG
GAAGGCGACAAGCAGCUGGCCGAAGCCUACGAGAGCAUCGCCAA
GAUCGUGAACGACAAUAACUACAAGAGCGUGGCCAUCCCACUGC
UCAGCACCGGCAUCUUCAGCGGCAACAAGGACAGGCUGACCCAG
AGCCUGAACCACCUGCUCACCGCCCUGGACACCACCGAUGCCGA
CGUGGCCAUCUACUGCAGGGACAAGAAGUGGGAGAUGACCCUGA
AGGAGGCCGUGGCCAGGCGGGAGGCCGUGGAAGAGAUCUGCAUC
AGCGACGACUCCAGCGUGACCGAGCCCGACGCCGAGCUGGUGAG
GGUGCACCCCAAGAGCUCCCUGGCCGGCAGGAAGGGCUACAGCA
CCAGCGACGGCAAGACCUUCAGCUACCUGGAGGGCACCAAGUUC
CACCAGGCCGCUAAGGACAUCGCCGAGAUCAACGCUAUGUGGCC
CGUGGCCACCGAGGCCAACGAGCAGGUGUGCAUGUACAUCCUGG
GCGAGAGCAUGUCCAGCAUCAGGAGCAAGUGCCCCGUGGAGGAA
AGCGAGGCCAGCACACCACCCAGCACCCUGCCCUGCCUGUGCAU
CCACGCUAUGACACCCGAGAGGGUGCAGCGGCUGAAGGCCAGCA
GGCCCGAGCAGAUCACCGUGUGCAGCUCCUUCCCACUGCCCAAG
UACAGGAUCACCGGCGUGCAGAAGAUCCAGUGCAGCCAGCCCAU
CCUGUUCAGCCCAAAGGUGCCCGCCUACAUCCACCCCAGGAAGU
ACCUGGUGGAGACCCCACCCGUGGACGAGACACCCGAGCCAAGC
GCCGAGAACCAGAGCACCGAGGGCACACCCGAGCAGCCACCCCU
GAUCACCGAGGACGAGACAAGGACCCGGACCCCAGAGCCCAUCA
UUAUCGAGGAAGAGGAAGAGGACAGCAUCAGCCUGCUGAGCGAC
GGCCCCACCCACCAGGUGCUGCAGGUGGAGGCCGACAUCCACGG
CCCACCCAGCGUGUCCAGCUCCAGCUGGAGCAUCCCACACGCCA
GCGACUUCGACGUGGACAGCCUGAGCAUCCUGGACACCCUGGAG
GGCGCCAGCGUGACCUCCGGCGCCACCAGCGCCGAGACCAACAG
CUACUUCGCCAAGAGCAUGGAGUUCCUGGCCAGGCCCGUGCCAG
CUCCCAGGACCGUGUUCAGGAACCCACCCCACCCAGCUCCCAGG
ACCAGGACCCCAAGCCUGGCUCCCAGCAGGGCCUGCAGCAGGAC
CAGCCUGGUGAGCACCCCACCCGGCGUGAACAGGGUGAUCACCA
GGGAGGAACUGGAGGCCCUGACACCCAGCAGGACCCCCAGCAGG
UCCGUGAGCAGGACUAGUCUGGUGUCCAACCCACCCGGCGUGAA
CAGGGUGAUCACCAGGGAGGAAUUCGAGGCCUUCGUGGCCCAGC
AACAGAGACGGUUCGACGCCGGCGCCUACAUCUUCAGCAGCGAC
ACCGGCCAGGGACACCUGCAGCAAAAGAGCGUGAGGCAGACCGU
GCUGAGCGAGGUGGUGCUGGAGAGGACCGAGCUGGAAAUCAGCU
ACGCCCCCAGGCUGGACCAGGAGAAGGAGGAACUGCUCAGGAAG
AAACUGCAGCUGAACCCCACCCCAGCCAACAGGAGCAGGUACCA
GAGCAGGAAGGUGGAGAACAUGAAGGCCAUCACCGCCAGGCGGA
UCCUGCAGGGCCUGGGACACUACCUGAAGGCCGAGGGCAAGGUG
GAGUGCUACAGGACCCUGCACCCCGUGCCACUGUACAGCUCCAG
CGUGAACAGGGCCUUCUCCAGCCCCAAGGUGGCCGUGGAGGCCU
GCAACGCUAUGCUGAAGGAGAACUUCCCCACCGUGGCCAGCUAC
UGCAUCAUCCCCGAGUACGACGCCUACCUGGACAUGGUGGACGG
CGCCAGCUGCUGCCUGGACACCGCCAGCUUCUGCCCCGCCAAGC
UGAGGAGCUUCCCCAAGAAACACAGCUACCUGGAGCCCACCAUC
AGGAGCGCCGUGCCCAGCGCCAUCCAGAACACCCUGCAGAACGU
GCUGGCCGCUGCCACCAAGAGGAACUGCAACGUGACCCAGAUGA
GGGAGCUGCCCGUGCUGGACAGCGCUGCCUUCAACGUGGAGUGC
UUCAAGAAAUACGCCUGCAACAACGAGUACUGGGAGACCUUCAA
GGAGAACCCCAUCAGGCUGACCGAAGAGAACGUGGUGAACUACA
UCACCAAGCUGAAGGGCCCCAAGGCCGCUGCCCUGUUCGCUAAG
ACCCACAACCUGAACAUGCUGCAGGACAUCCCAAUGGACAGGUU
CGUGAUGGACCUGAAGAGGGACGUGAAGGUGACACCCGGCACCA
AGCACACCGAGGAGAGGCCCAAGGUGCAGGUGAUCCAGGCCGCU
GACCCACUGGCCACCGCCUACCUGUGCGGCAUCCACAGGGAGCU
GGUGAGGCGGCUGAACGCCGUGCUGCUGCCCAACAUCCACACCC
UGUUCGACAUGAGCGCCGAGGACUUCGACGCCAUCAUCGCCGAG
CACUUCCAGCCCGGCGACUGCGUGCUGGAGACCGACAUCGCCAG
CUUCGACAAGAGCGAGGAUGACGCUAUGGCCCUGACCGCUCUGA
UGAUCCUGGAGGACCUGGGCGUGGACGCCGAGCUGCUCACCCUG
AUCGAGGCUGCCUUCGGCGAGAUCAGCUCCAUCCACCUGCCCAC
CAAGACCAAGUUCAAGUUCGGCGCUAUGAUGAAAAGCGGAAUGU
UCCUGACCCUGUUCGUGAACACCGUGAUCAACAUUGUGAUCGCC
AGCAGGGUGCUGCGGGAGAGGCUGACCGGCAGCCCCUGCGCUGC
CUUCAUCGGCGACGACAACAUCGUGAAGGGCGUGAAAAGCGACA
AGCUGAUGGCCGACAGGUGCGCCACCUGGCUGAACAUGGAGGUG
AAGAUCAUCGACGCCGUGGUGGGCGAGAAGGCCCCCUACUUCUG
CGGCGGAUUCAUCCUGUGCGACAGCGUGACCGGCACCGCCUGCA

TABLE 9-continued

| | | | |
|---|---|---|---|
| | | | GGGUGGCCGACCCCCUGAAGAGGCUGUUCAAGCUGGGCAAGCCA<br>CUGGCCGCUGACGAUGAGCACGACGAUGACAGGCGGAGGGCCCU<br>GCACGAGGAAAGCACCAGGUGGAACAGGGUGGGCAUCCUGAGCG<br>AGCUGUGCAAGGCCGUGGAGAGCAGGUACGAGACCGUGGGCACC<br>AGCAUCAUCGUGAUGGCUAUGACCACACUGGCCAGCUCCGUCAA<br>GAGCUUCUCCUACCUGAGGGGGGCCCCUAUAACUCUCUACGGCU<br>AACCUGAAUGGACUACGACAUAGUCUAGUCCGCCAAGGCCGCCA<br>CCAUGAGAGUGACAGCCCCUAGAACCUUACUGCUUCUGCUUUGG<br>GGAGCUGUUGCUCUGACAGAGACAUGGGCUGGAUCUUACCACAG<br>CCCCAGCUACGCCUACCACCAGUUCGAGAGGGGGGGAGGAGGCU<br>CCGGGGGAGGAGGCUCCCUGAAGAUCAGCCAGGCCGUGCACGCC<br>GCCCACGCCGAGAUCAACGAGGCCGGCCGGGAGGUGAUCGUGGG<br>CAUUGUCGCUGGCCUGGCCGUCCUCGCCGUGGUGGUGAUUGGAG<br>CUGUGGUCGCAGCUGUUAUGUGCAGAAGAAAGUCAUCCGGCGGA<br>AAGGGAGGCUCCUACUCUCAGGCUGCUUCUGCUACAGUGCCUAG<br>AGCUCUUAUGUGUUUAUCUCAGCUGUAAACUCGAGUAUGUUACG<br>UGCAAAGGUGAUUGUCACCCCCCGAAAGACCAUAUUGUGACACA<br>CCCUCAGUAUCACGCCCAAACAUUUACAGCCGCGGUGUCAAAAA<br>CCGCGUGGACGUGGUUAACAUCCCUGCUGGGAGGAUCAGCCGUA<br>AUUAUUAUAAUUGGCUUGGUGCUGGCUACUAUUGUGGCCAUGUA<br>CGUGCUGACCAACCAGAAACAUAAUUGAAUACAGCAGCAAUUGG<br>CAAGCUGCUUACAUAGAACUCGCGGCGAUUGGCAUGCCGCCUUA<br>AAAUUUUUAUUUUAUUUUUUCUUUUCUUUUCCGAAUCGGAUUUU<br>GUUUUUAAUAUUUCAAAAAAAAAAAAAAAAAAAAAAAAAUCUAG<br>AAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAA |
| 3067 (SEQ ID NO:107) | STARR™ gp70-FLAG | 3067 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC<br>AUCAGGGACGUGAAGAAGAUGAAAGGCCUGGACGUGAACGCGCGCA<br>CCGUGGACAGCGUGCUGCUGAACGGCUGCAAGCACCCCGUGGAGAC |

TABLE 9-continued

CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU

TABLE 9-continued

| | | |
|---|---|---|
| | | GCAACGCUAUGCUGAAGGAGAACUUCCCCACCGUGGCCAGCUACUG<br>CAUCAUCCCCGAGUACGACGCCUACCUGGACAUGGUGGACGGCGCC<br>AGCUGCUGCCUGGACACCGCCAGCUUCUGCCCCGCCAAGCUGAGGA<br>GCUUCCCCAAGAAACACAGCUACCUGGAGCCCACCAUCAGGAGCGC<br>CGUGCCCAGCGCCAUCCAGAACACCCUGCAGAACGUGCUGGCCGCU<br>GCCACCAAGAGGAACUGCAACGUGACCCAGAUGAGGGAGCUGCCCG<br>UGCUGGACAGCGCUGCCUUCAACGUGGAGUGCUUCAAGAAAUACGC<br>CUGCAACAACGAGUACUGGGAGACCUUCAAGGAGAACCCCAUCAGG<br>CUGACCGAAGAGAACGUGGUGAACUACAUCACCAAGCUGAAGGGCC<br>CCAAGGCCGCUGCCCUGUUCGCUAAGACCCACAACCUGAACAUGCU<br>GCAGGACAUCCCAAUGGACAGGUUCGUGAUGGACCUGAAGAGGGAC<br>GUGAAGGUGACACCCGGCACCAAGCACACCGAGGAGAGGCCCAAGG<br>UGCAGGUGAUCCAGGCCGCUGACCCACUGGCCACCGCCUACCUGUG<br>CGGCAUCCACAGGGAGCUGGUGAGGCGGCUGAACGCCGUGCUGCUG<br>CCCAACAUCCACACCCUGUUCGACAUGAGCGCCGAGGACUUCGACG<br>CCAUCAUCGCCGAGCACUUCCAGCCCGGCGACUGCGUGCUGGAGAC<br>CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCAUGAGAGUGACAGCCCCUAG<br>AACCUUACUGCUUCUGCUUUGGGGAGCUGUUGCUCUGACAGAGACA<br>UGGGCUGGAUCUCUGAGCGAGGUGACCGGCCAGGGCCUGUGCAUCG<br>GCGCCGUGCCCAAGACCCACCAGGUGCUGUGCAACACCACCCAGAA<br>GACCAGCGACGGCAGCUACUACCUGGCCGCUCCCACCGGCACCACC<br>UGGGCCUGCAGCACCGGCCUGACCCCUUGCAUCAGCACCACCAUCC<br>UGAACCUGACCACCGACUACUGCGUGCUGGUGGAGCUGUGGCCCAG<br>GGUGACCUACCACAGCCCCAGCUACGCCUACCACCAGUUCGAGAGG<br>AGGGCCAAGUACAAGAGGGAGCCCGUGAGCCUGACCCUGGCCCUGC<br>UGCUGGGCGGCCUGACAAUGGGCGGCAUCGCCGCCGGCGUGGGCAC<br>CGGCACCACCGCCCUGGUGGCCACCCAGCAGUUCCAGCAGCUGCAG<br>GCCGCCAUGCACGACGACCUGAAGGAGGUGGAGAAGUCCAUCACCA<br>ACCUGGAGAAGUCCCUGACCAGCCUGAGCGAGGUGGUGCUGCAGAA<br>CAGGAGGGGCCUGGACCUGCUGUUCCUGAAGGAGGGCGGCCUGUGC<br>GCCGCCCUGAAGGAGGAGUGCUGCCUGUACGCCGACCACACCGGCC<br>UGGUGAUCGUGGGCAUUGUCGCUGGCCUGGCCGUCCUCGCCGUGGU<br>GGUGAUUGGAGCUGUGGUCGCAGCUGUUAUGUGCAGAAGAAAGUCA<br>UCCGGCGGAAAGGGAGGCUCCUACUCUCAGGCUGCUUCUGCUACAG<br>UGCCUAGAGCUCUUAUGUGUUUAUCUCAGCUGGGCGGCGGAGGCAG<br>CGACUACAAGGACGACGAUGACAAGUAAACUCGAGUAUGUUACGUG<br>CAAAGGUGAUUGUCACCCCCCGAAAGACCAUAUUGUGACACACCCU<br>CAGUAUCACGCCCAAACAUUUACAGCCGCGGUGUCAAAAACCGCGU<br>GGACGUGGUUAACAUCCCUGCUGGGAGGAUCAGCCGUAAUUAUUAU<br>AAUUGGCUUGGUGCUGGCUACUAUUGUGGCCAUGUACGUGCUGACC<br>AACCAGAAACAUAAUUGAAUACAGCAGCAAUUGGCAAGCUGCUUAC<br>AUAGAACUCGCGGCGAUUGGCAUGCCGCCUUAAAAUUUUUAUUUUA<br>UUUUUUCUUUUCUUUUCCGAAUCGGAUUUUGUUUUUAAUAUUUCAA<br>AAAAAAAAAAAAAAAAAAAAAAAAUCUAGAAAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAA |
| 3068 (SEQ ID NO:108) | STARR™ 3068 AH1A 5- FLAG | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC |

TABLE 9-continued

AUCUACCACGAGAAGAGGGACCUGCUCAGGAGCUGGCACCUGCCCA
GCGUGUUCCACCUGAGGGGCAAGCAGAACUACACCUGCAGGUGCGA
GACCAUCGUGAGCUGCGACGGCUACGUGGUGAAGAGGAUCGCCAUC
AGCCCCGGCCUGUACGGCAAGCCCAGCGGCUACGCCGCUACAAUGC
ACAGGGAGGGCUUCCUGUGCUGCAAGGUGACCGACACCCUGAACGG
CGAGAGGGUGAGCUUCCCCGUGUGCACCUACGUGCCCGCCACCCUG
UGCGACCAGAUGACCGGCAUCCUGGCCACCGACGUGAGCGCCGACG
ACGCCCAGAAGCUGCUCGUGGGCCUGAACCAGAGGAUCGUGGUCAA
CGGCAGGACCCAGAGGAACACCAACACAAUGAAGAACUACCUGCUG
CCCGUGGUGGCCCAGGCUUUCGCCAGGUGGGCCAAGGAGUACAAGG
AGGACCAGGAAGACGAGAGGCCCCUGGGCCUGAGGGACAGGCAGCU
GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCCAGGAUCGGCAGCAACACCCUGGA
GAUCGGCCUGAGGACCCGGAUCAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG

TABLE 9-continued

GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGAGAGUGACAGCCCCUAG
AACCUUACUGCUUCUGCUUUGGGGAGCUGUUGCUCUGACAGAGACA
UGGGCUGGAUCUUACCACAGCCCCAGCUACGCCUACCACCAGUUCG
AGAGGGGGGGAGGAGGCUCCGGGGGAGGAGGCUCCCUGAAGAUCAG
CCAGGCCGUGCACGCCGCCCACGCCGAGAUCAACGAGGCCGGCCGG
GAGGUGAUCGUGGGCAUUGUCGCUGGCCUGGCCGUCCUCGCCGUGG
UGGUGAUUGGAGCUGUGGUCGCAGCUGUUAUGUGCAGAAGAAAGUC
AUCCGGCGGAAAGGGAGGCUCCUACUCUCAGGCUGCUUCUGCUACA
GUGCCUAGAGCUCUUAUGUGUUUAUCUCAGCUGGGCGGCGGAGGCA
GCGACUACAAGGACGACGAUGACAAGUAAACUCGAGUAUGUUACGU
GCAAAGGUGAUUGUCACCCCCCGAAAGACCAUAUUGUGACACACCC
UCAGUAUCACGCCCAAACAUUUACAGCCGCGGUGUCAAAAACCGCG
UGGACGUGGUUAACAUCCCUGCUGGGAGGAUCAGCCGUAAUUAUUA

TABLE 9-continued

```
UAAUUGGCUUGGUGCUGGCUACUAUUGUGGCCAUGUACGUGCUGAC
CAACCAGAAACAUAAUUGAAUACAGCAGCAAUUGGCAAGCUGCUUA
CAUAGAACUCGCGGCGAUUGGCAUGCCGCCUUAAAAUUUUUAUUUU
AUUUUUUCUUUUCUUUUCCGAAUCGGAUUUUGUUUUUAAUAUUUCA
AAAAAAAAAAAAAAAAAAAAAAAAUCUAGAAAAAAAAAAAAAAAAA
AAAAAAAAAAAAAAAAAAAAAAAAAAAAAAAAAAAAAAAAAAAAAA
AAAAAAAAAAAAAAAAAAAAAAAAAAAAAAAAAAAA
```

| | non structural protein of SINV | |
|---|---|---|
| mARM # | | |
| 2842 and 2862 (SEQ ID NO:109) | SINV nsP1-4 AA | MEKPVVNVDVDPQSPFVVQLQKSFPQFEVVAQQVTPNDHANARAFS HLASKLIELEVPTTATILDIGSAPARRMFSEHQYHCVCPMRSPEDP DRMMKYASKLAEKACKITNKNLHEKIKDLRTVLDTPDAETPSLCFH NDVTCNMRAEYSVMQDVYINAPGTIYHQAMKGVRTLYWIGFDTTQF MFSAMAGSYPAYNTNWADEKVLEARNIGLCSTKLSEGRTGKLSIMR KKELKPGSRVYFSVGSTLYPEHRASLQSWHLPSVFHLNGKQSYTCR CDTVVSCEGYVVKKITISPGITGETVGYAVTHNSEGFLLCKVTDTV KGERVSFPVCTYIPATICDQMTGIMATDISPDDAQKLLVGLNQRIV INGRTNRNTNTMQNYLLPIIAQGFSKWAKERKDDLDNEKMLGTRER KLTYGCLWAFRTKKVHSFYRPPGTQTCVKVPASFSAFPMSSVWTTS LPMSLRQKLKLALQPKKEEKLLQVSEELVMEAKAAFEDAQEEARAE KLREALPPLVADKGIEAAAEVVCEVEGLQADIGAALVETPRGHVRI IPQANDRMIGQYIVVSPNSVLKNAKLAPAHPLADQVKIITHSGRSG RYAVEPYDAKVLMPAGGAVPWPEFLALSESATLVYNEREFVNRKLY HIAMHGPAKNTEEEQYKVTKAELAETEYVFDVDKKRCVKKEEASGL VLSGELTNPPYHELALEGLKTRPAVPYKVETIGVIGTPGSGKSAII KSTVTARDLVTSGKKENCREIEADVLRLRGMQITSKTVDSVMLNGC HKAVEVLYVDEAFACHAGALLALIAIVRPRKKVVLCGDPMQCGFFN MMQLKVHFNHPEKDICTKTFYKYISRRCTQPVTAIVSTLHYDGKMK TTNPCKKNIEIDITGATKPKPGDIILTCFRGWVKQLQIDYPGHEVM TAAASQGLTRKGVYAVRQKVNENPLYAITSEHVNVLLTRTEDRLVW KTLQGDPWIKQLTNIPKGNFQATIEDWEAEHKGIIAAINSPTPRAN PFSCKTNVCWAKALEPILATAGIVLTGCQWSELFPQFADDKPHSAI YALDVICIKFFGMDLTSGLFSKQSIPLTYHPADSARPVAHWDNSPG TRKYGYDHAIAAELSRRFPVFQLAGKGTQLDLQTGRTRVISAQHNL VPVNRNLPHALVPEYKEKQPGPVEKFLNQFKHHSVLVVSEEKIEAP RKRIEWIAPIGIAGADKNYNLAFGFPPQARYDLVFINIGTKYRNHH FQQCEDHAATLKTLSRSALNCLNPGGTLVVKSYGYADRNSEDVVTA LARKFVRVSAARPDCVSSNTEMYLIFRQLDNSRTRQFTPHHLNCVI SSVYEGTRDGVGAAPSYRTKRENIADCQEEAVVNAANPLGRPGEGV CRAIYKRWPTSFTDSATETGTARMTVCLGKKVIHAVGPDFRKHPEA EALKLLQNAYHAVADLVNEHNIKSVAIPLLSTGIYAAGKDRLEVSL NCLTTALDRTDADVTIYCLDKKWKERIDAALQLKESVTELKDEDME IDDELVWIHPDSCLKGRKGFSTTKGKLYSYFEGTKFHQAAKDMAEI KVLFPNDQESNEQLCAYILGETMEAIREKCPVDHNPSSSPPKTLPC LCMYAMTPERVHRLRSNNVKEVTVCSSTPLPKHKIKNVQKVQCTKV VLFNPHTPAFVPARKYIEVPEQPTAPPAQAEEAPEVVATPSPSTAD NTSLDVTDISLDMDDSSEGSLFSSFSGSDNSITSMDSWSSGPSSLE IVDRRQVVVADVHAVQEPAPIPPPRLKKMARLAAARKEPTPPASNS SESLHLSFGGVSMSLGSIFDGETARQAAVQPLATGPTDVPMSFGSF SDGEIDELSRRVTESEPVLFGSFEPGEVNSIISSRSAVSFPLRKQR RRRRSRRTEY*LTGVGGYIFSTDTGPGHLQKKSVLQNQLTEPTLER NVLERIHAPVLDTSKEEQLKLRYQMMPTEANKSRYQSRKVENQKAI TTERLLSGLRLYNSATDQPECYKITYPKPLYSSSVPANYSDPQFAV AVCNNYLHENYPTVASYQITDEYDAYLDMVDGTVACLDTATFCPAK LRSYPKKHEYRAPNIRSAVPSAMQNTLQNVLIAATKRNCNVTQMRE LPTLDSATFNVECFRKYACNDEYWEEFARKPIRITTEFVTAYVARL KGPKAAALFAKTYNLVPLQEVPMDRFVMDMKRDVKVTPGTKHTEER PKVQVIQAAEPLATAYICGIHRELVRRLTAVLLPNIHTLFDMSAED FDAIIAEHFKQGDPVLETDIASFDKSQDDAMALTGLMILEDLGVDQ PLLDLIECAFGEISSTHLPTGTRFKFGAMMKSGMFLTLFVNTVLNV VIASRVLEERLKTSRCAAFIGDDNIIHGVVSDKEMAERCATWLNME VKIIDAVIGERPPYFCGGFILQDSVTSTACRVADPLKRLFKLGKPL PADDEQDEDRRRALLDETKAWFRVGITGTLAVAVTTRYEVDNITPV LLALRTFAQSKRAFQAIRGEIKHLYGGPK |

Example 11

This example describes analysis of the immunogenicity of influenza hemagglutinin (HA) expressed from self-replicating RNA or mRNA.

Self-replicating RNA and mRNA vaccine constructs were designed to encode the full-length hemagglutinin (HA) protein from influenza virus A/California/07/2009 (H1N1) (SEQ ID NO:113 and 114). As described above for Example 1, the mRNA vaccine construct encoding HA included a tobacco etch virus (TEV) 5' UTR and a *Xenopus* beta-globin (Xbg) 3' UTR. Both self-replicating RNA (SEQ ID NO:56; entire RNA mARM3039) and mRNA vaccine constructs (SEQ ID NO: 116; entire RNA sequence mARM3038) were encapsulated in the same lipid nanoparticle (LNP) composition that included four lipid excipients (an ionizable cationic lipid, 1,2-distearoyl-sn-glycero-3-phosphocholine (DSPC), cholesterol, and PEG2000-DMG) dispersed in HEPES buffer (pH 8.0) containing sodium chloride and the cryoprotectants sucrose and glycerol. The N:P ratio of complexing lipid and RNA was approximately 9:1. The ionizable cationic lipid had the following structure:

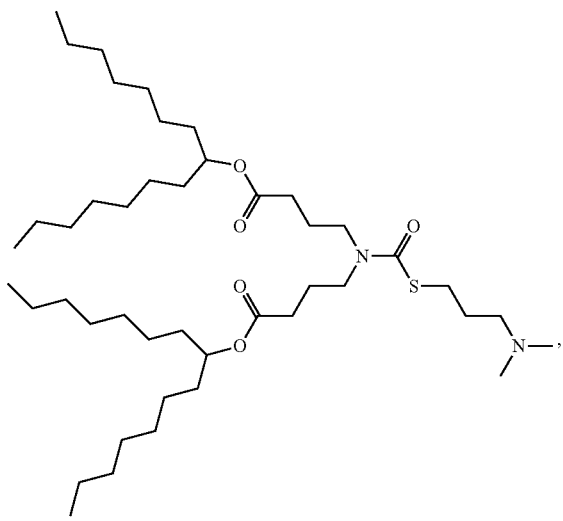 [SMILES: CCCCCCCC(CCCCCCC)OC(=O)CCCN(CCCC(=O)OC(CCCCCCC)CCCCCCC)C(=O)SCCCN(C)C]

Five female, 8-10 week old Balb/c mice were injected intramuscularly with 2 mg of mRNA or self-replicating RNA encoding HA. Mice were bled on days 14, 28, 42, and 56, followed by hemagglutination inhibition (HAI) assay using serially diluted sera. The reciprocal of the highest dilution of serum that caused inhibition of hemagglutination was considered the HAI titer, with a titer of 1/40 being protective against influenza virus infection and four-fold higher titers than baseline indicating seroconversion.

Figure 23:
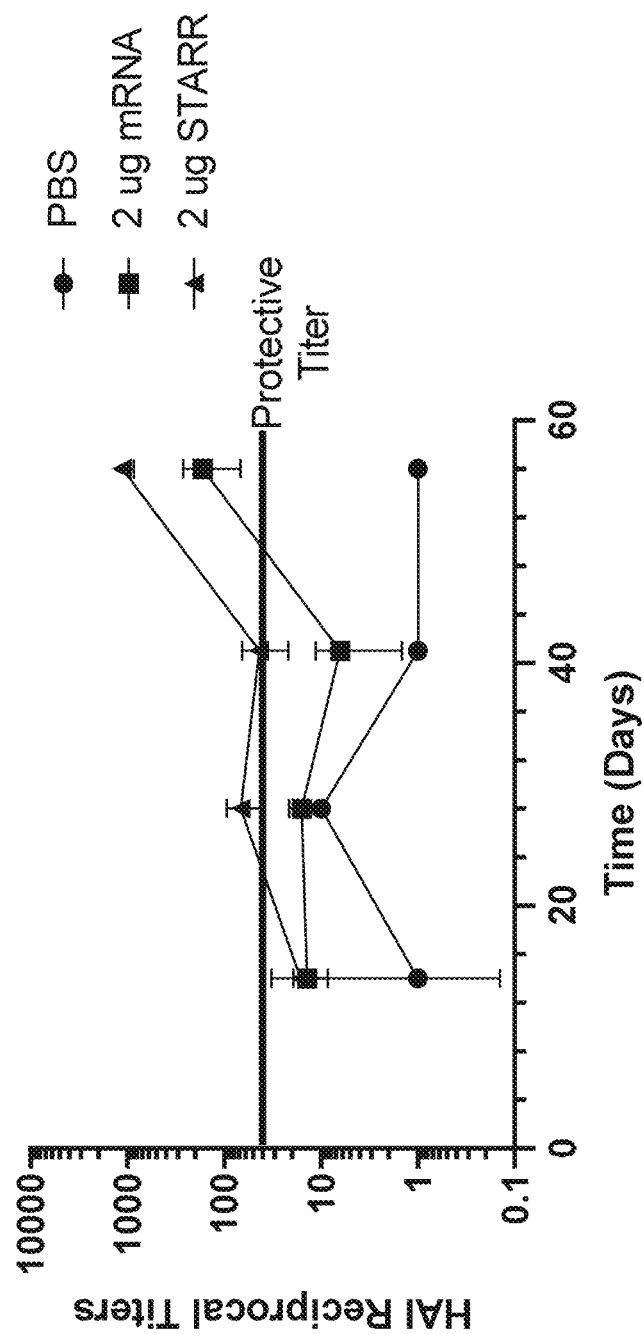
FIG. 23 shows HA titers obtained for self-replicating RNA (STARR™) and mRNA constructs encoding the hemagglutinin of influenza virus A/California/07/2009 (H1N1).

Results in FIG. 23 show that greater HAI titers were obtained with self-replicating RNA encoding HA as compared to mRNA encoding HA. HAI titers for the self-replicating RNA construct encoding HA were greater than HAI titers for the mRNA encoding HA at all time points beginning at day 28. In addition, protective HAI titers were seen for the self-replicating RNA construct encoding HA beginning at day 28 that were maintained for at least 56 days. By contrast, mRNA encoding HA showed protective HAI titers only at day 56 that were lower than HAI titers seen for the self-replicating RNA HA construct. At all other time points, HAI titers for the mRNA construct encoding HA were below the protective titer threshold, with an HAI titer that was comparable to injection with PBS control at day 28.

These results show that the self-replicating RNA construct encoding HA elicited protective HA antibody titers, with greater HAI titers as compared to the mRNA construct encoding HA.

Example 12

This example describes dsRNA production and luciferase expression for self-replicating RNA.

Several self-replicating RNA systems from different alphaviruses were tested for expression in vitro using either green fluorescent protein (GFP) or firefly luciferase (Luc) as reporter genes. Initial transfection of cells with increasing amounts of self-replicating RNA resulted in expression of reporter genes at a lower dose compared to mRNA. However, as the amount of input self-replicating RNA increased, detectable expression of the reporter gene decreased.

Self-replicating RNA produces double stranded RNA (dsRNA) as an intermediate in the amplification process. Overproduction of dsRNA can suppress translation. To evaluate the effect of dsRNA production on transgene expression, dsRNA and the expression of reporter gene luciferase were measured simultaneously. HEK293 cells were transfected with 2 µg of replicon A (SEQ ID NO:115; entire RNA sequence mARM2826) or replicon B (SEQ ID NO:100, entire RNA sequence mARM2809) self-replicating RNA, or mRNA expressing Luc (SEQ ID NO:102, entire mRNA sequence mARM1782) using a commercial RNA transfection reagent. Untransfected cells (UTC) served as a control. dsRNA production (FIG. 24A) was quantified using immunohistochemical staining for dsRNA, followed by fluorescence quantification using a fluorescence scanner 24 hours after transfection. Luciferase expression (FIG. 24B) was assayed by measuring bioluminescence in parallel.

Figure 15A:
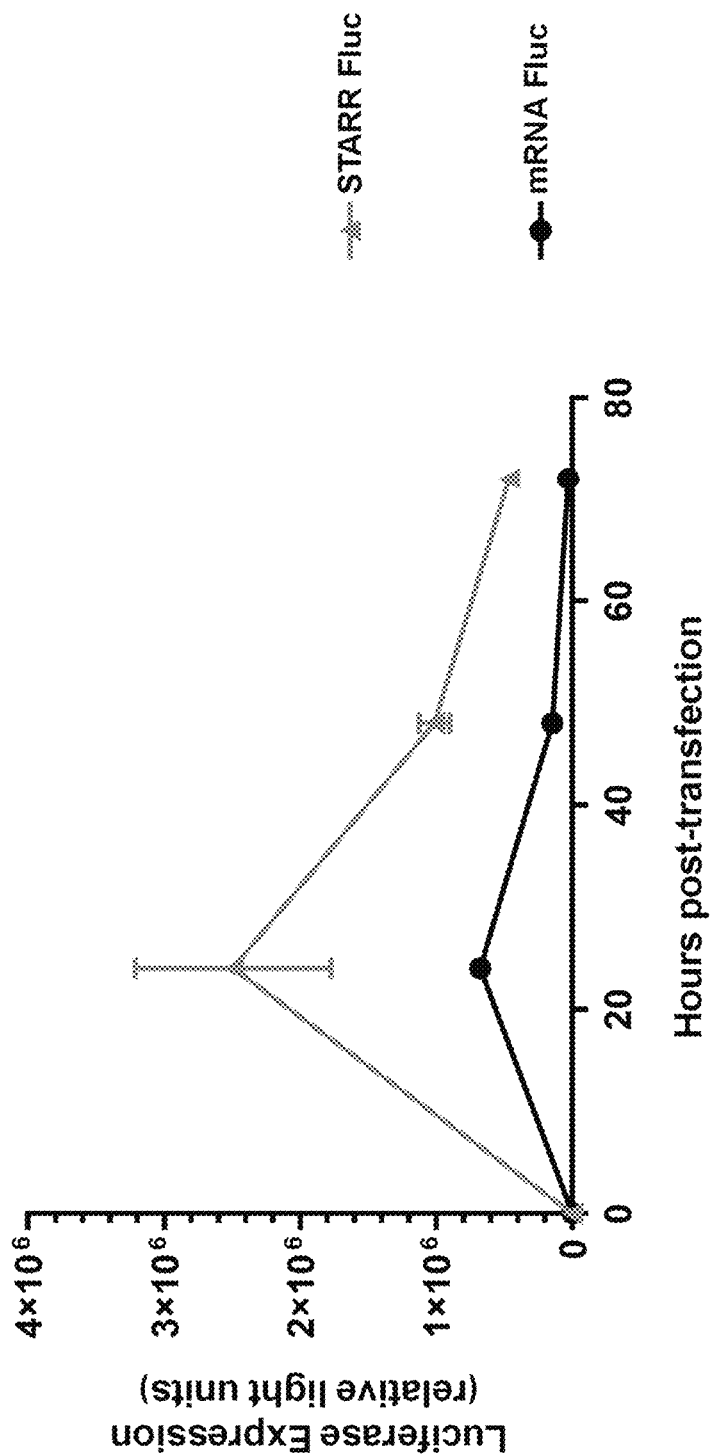
FIGS. 15A-15C show duration of luciferase reporter gene expression for self-replicating (replicon) RNA (STARR™), such as (15A) STARR™ FLuc, (15B) STARR™ FLuc IRES-E3L, and (15C) STARR™ FLuc IRES E3L (short 3' UTR) as compared to mRNA.
Figure 15B:
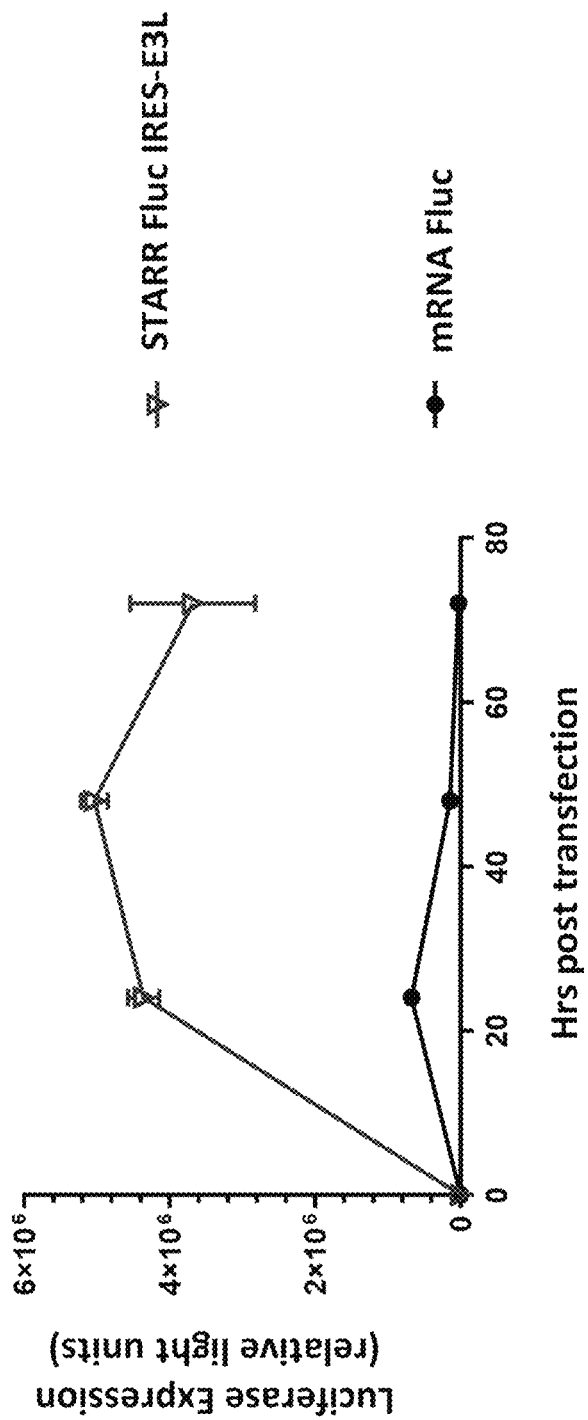
Figure 15C:
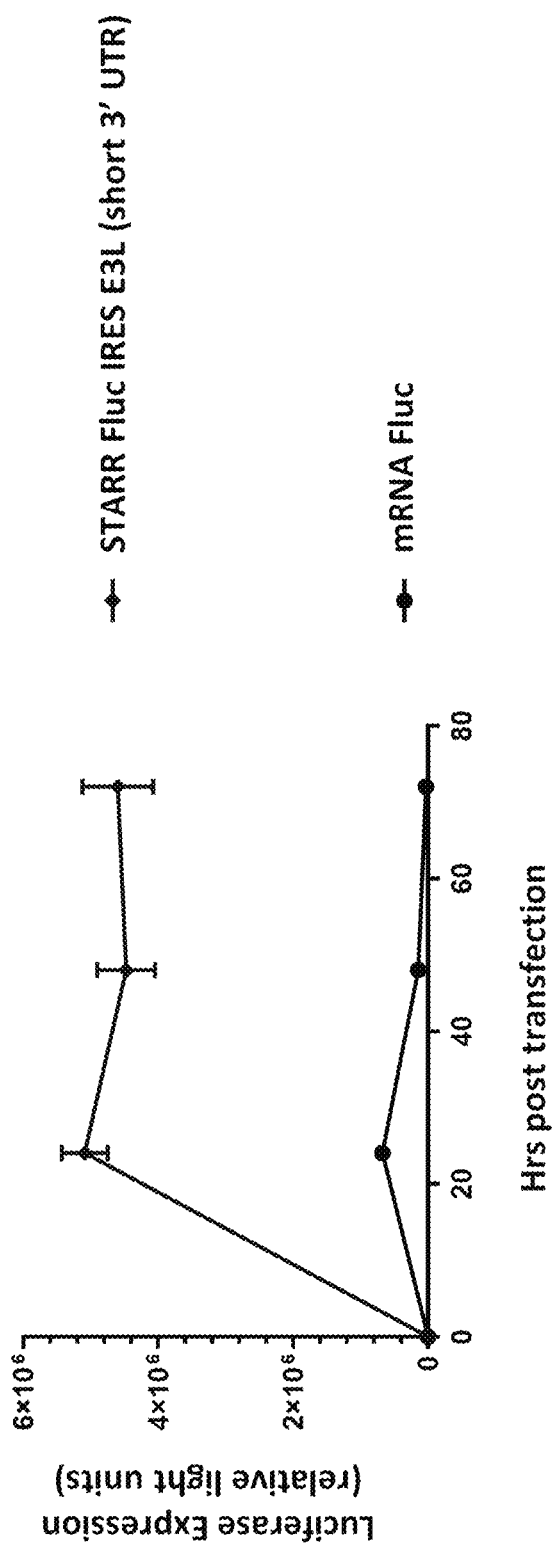
Figure 16A:
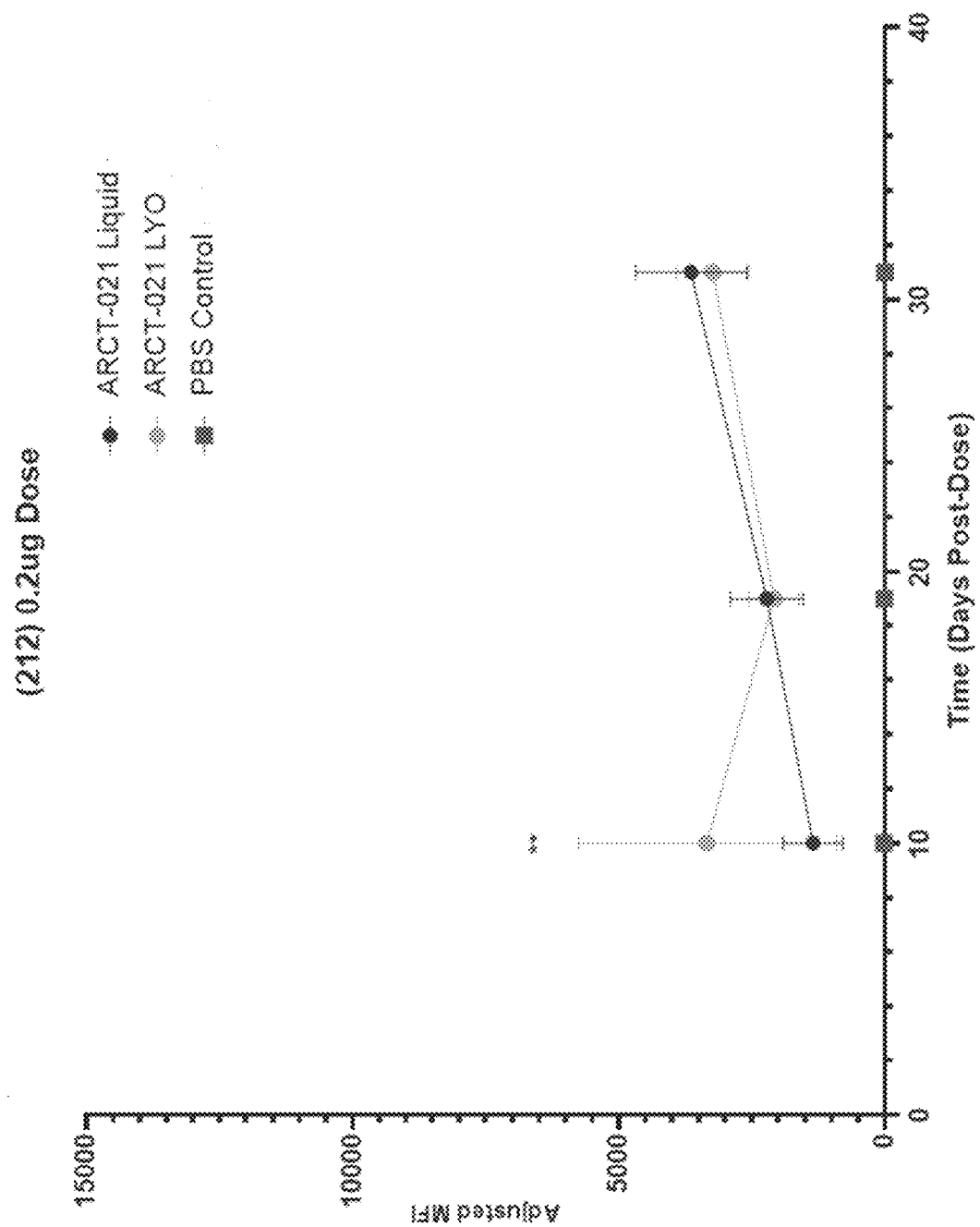
FIG. 16A-16D show results of Luminex Assay for anti-SARS-Cov-2 Spike Glycoprotein IgG in two pre-clinical studies. BALB/c mice were vaccinated with increasing RNA doses of self-replicating RNA (SEQ ID NO:125) formulated as lyophilized lipid nanoparticles (LYO-LNP) and liquid (frozen) lipid nanoparticles (Liquid-LNP). (16A) First Study 0.2 µg, (16B) First Study 2 µg, (16C) Second Study 0.2 µg, and (16D) Second Study 2 µg. Blood was collected and processed to serum at various times post-vaccination and evaluated for anti-SARS-CoV-2 spike glycoprotein IgG. Two way ANOVA, Tukey's multiple comparison post-test compared LYO-LNP to Liquid-LNP where * p<0.0332,  p<0.0021, * p<0.0002, **** p<0.0001.
Figure 16B:
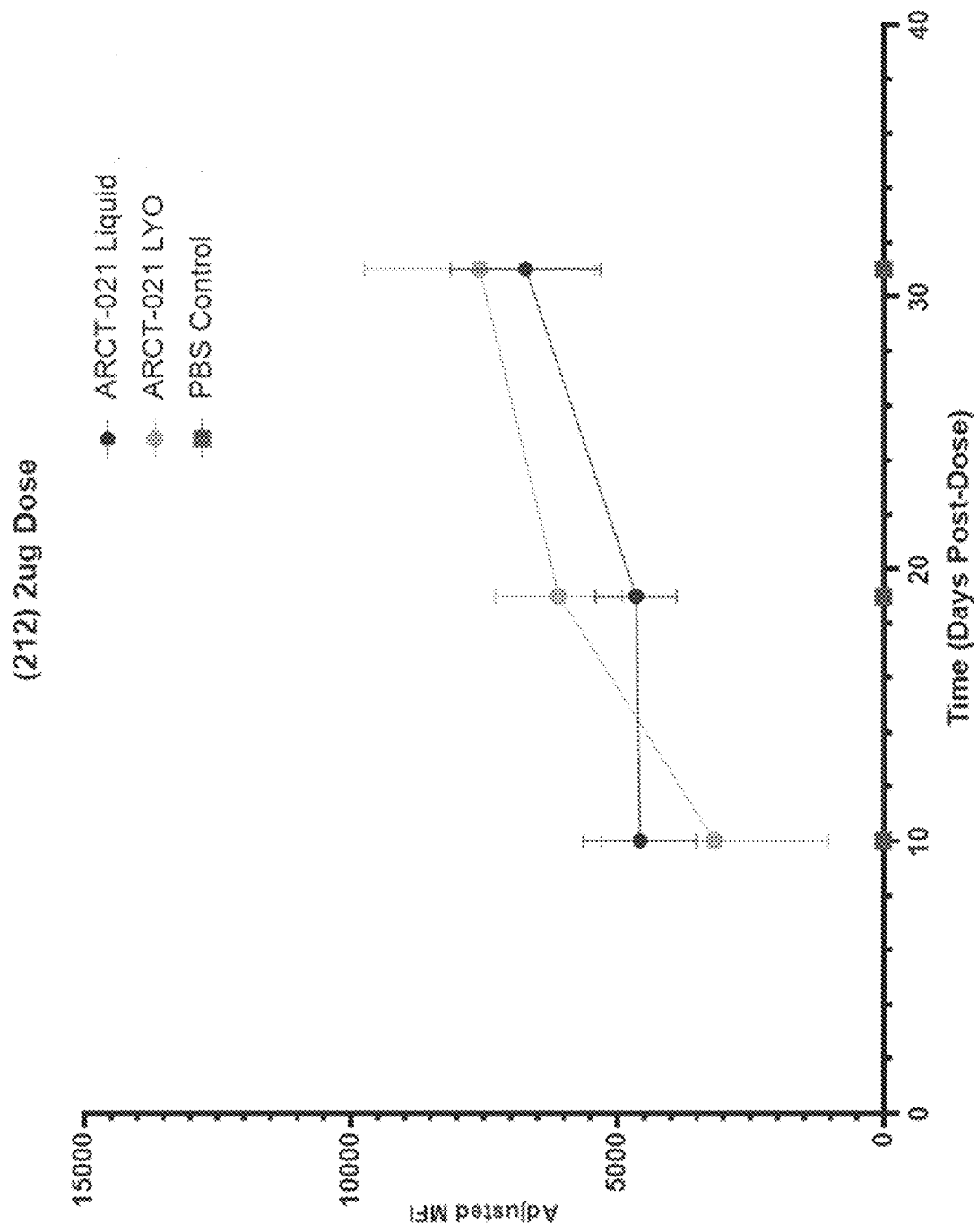
Figure 16C:
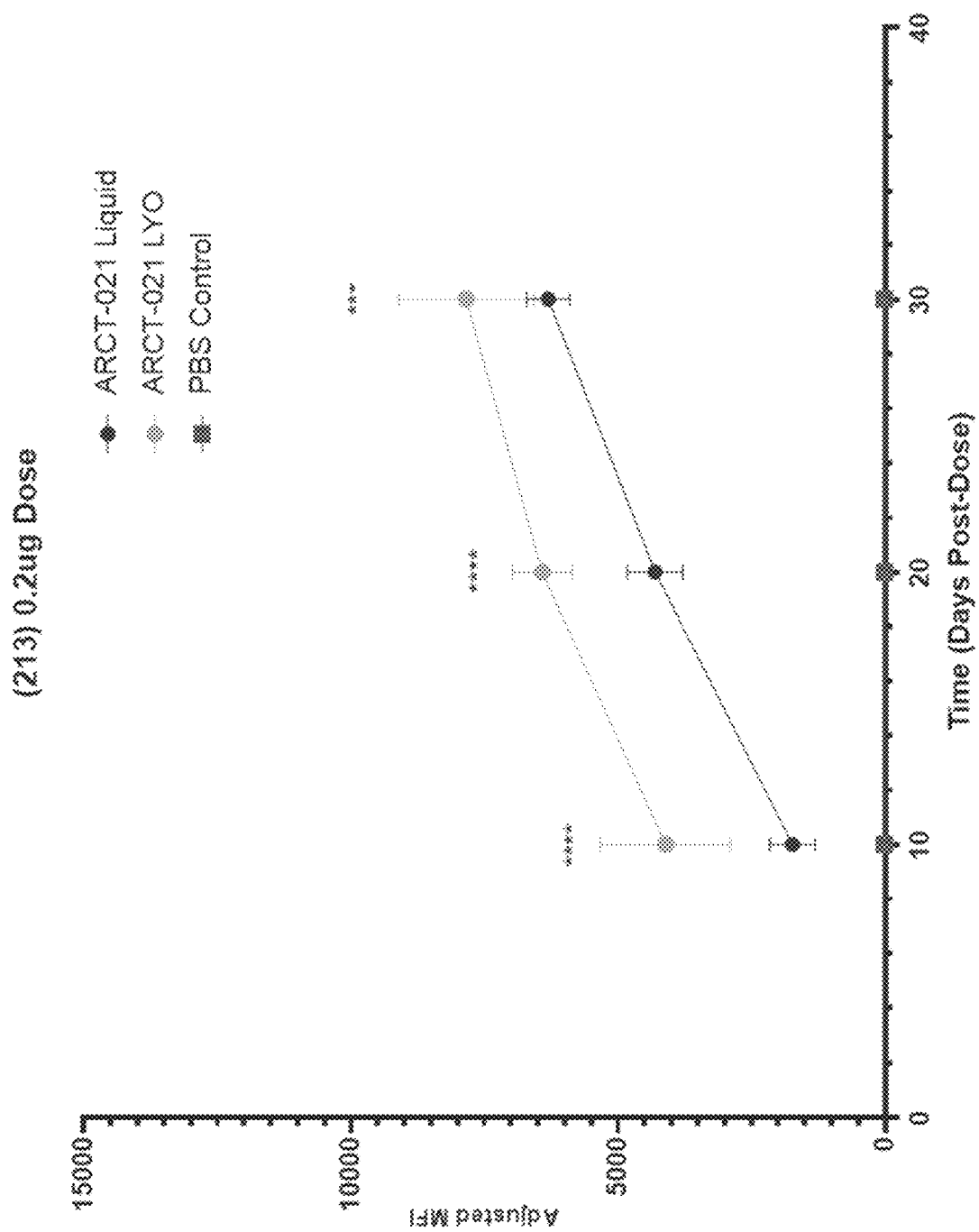
Figure 16D:
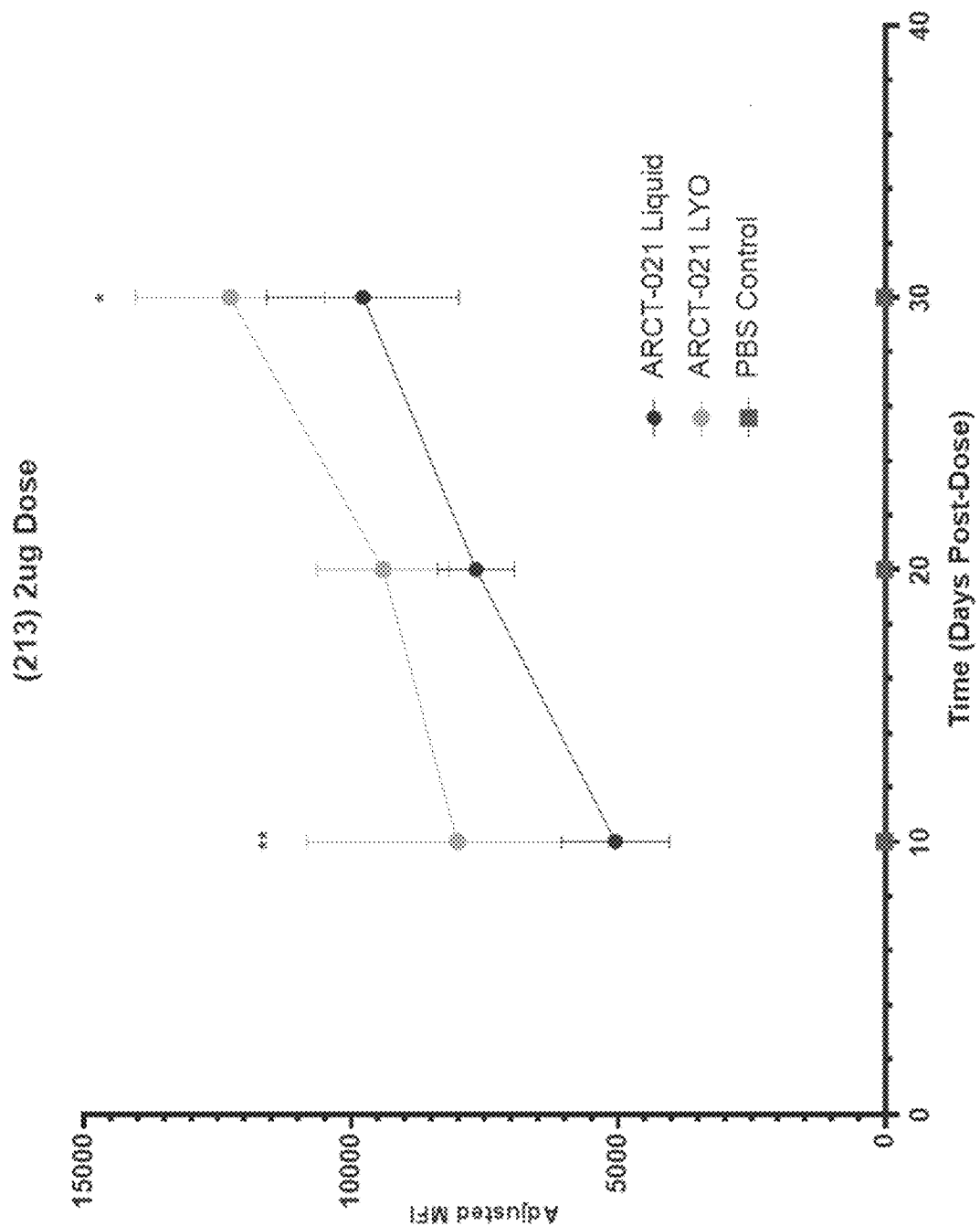
Figure 24A:
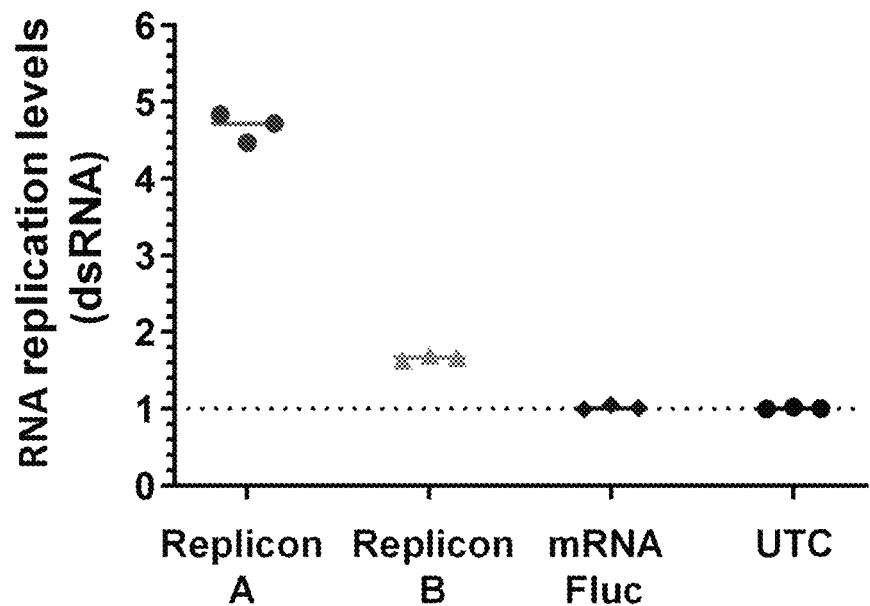
FIGS. 24A-24B show RNA replication levels (FIG. 24A) and luciferase reporter gene expression levels (FIG. 24B) for the indicated self-replicating (replicon) RNAs as compared to mRNA.
Figure 24B:
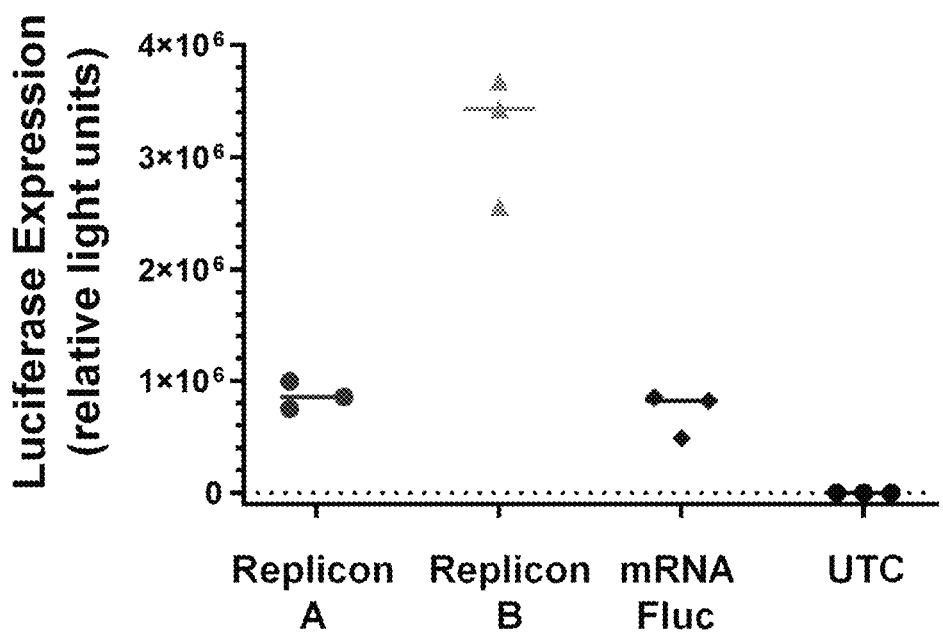

Replicon A produced a 3-fold higher level of dsRNA than replicon B 24 hrs after transfection (FIG. 24A). However, replicon B produced a 2.4-fold higher expression level of luciferase compared to replicon A. Furthermore, the level of luciferase expression from replicon A was equivalent to that observed for mRNA. Thus, even though replicon A had the ability to amplify the amount of replicon RNA and transcribed mRNA encoding luciferase, translation of the amplified mRNA was inhibited, consistent with overproduction of dsRNA inhibiting translation. Furthermore, higher levels of luciferase gene expression were seen for replicon RNA as compared to mRNA at 24, 48, and 72 hours after transfection of HEK293 cells (FIG. 15A). Self-replicating RNA with an expression cassette that included a luciferase reporter gene followed by an IRES and E3L also showed robust luciferase expression (FIGS. 15B, 15C; SEQ ID NOs: 128 and 129). Luciferase expression was also seen for a self-replicating RNA that expressed E3L from a first subgenomic promoter and a luciferase reporter gene from a second subgenomic promoter located 3' of the E3L open reading frame (not shown). Thus, not only did replicon RNA produce higher levels of luciferase gene expression compared to mRNA, but replicon RNA also showed increased duration of expression over a 72-hr period.

Example 13

This example describes immunogenicity of liquid and lyophilized self-replicating RNA formulations. Immunogenicity of self-replicating RNA (SEQ ID NO:125) formulated as a lyophilized lipid nanoparticle (LYO-LNP) was tested in BALB/c mice in two separate preclinical studies and compared with the liquid (frozen) LNP formulation (Liquid-LNP). Each study included the use of a PBS dosing group as a negative control and a Liquid dosing group (Liquid-LNP) as a positive control. Both LYO-LNP and Liquid-LNP formulations were dosed at 0.2 and 2 µg. There were n=5 animals per dose group in each study. Test formulations were administered intramuscularly (IM) and serum was collected at various timepoints (Days 10, 19, 31 for the first study and Days 10, 20, 30 for the second study) post-immunization to measure the production of anti-SARS-CoV-2 spike protein IgG using a Luminex bead fluorescent assay.

Figure 17B:
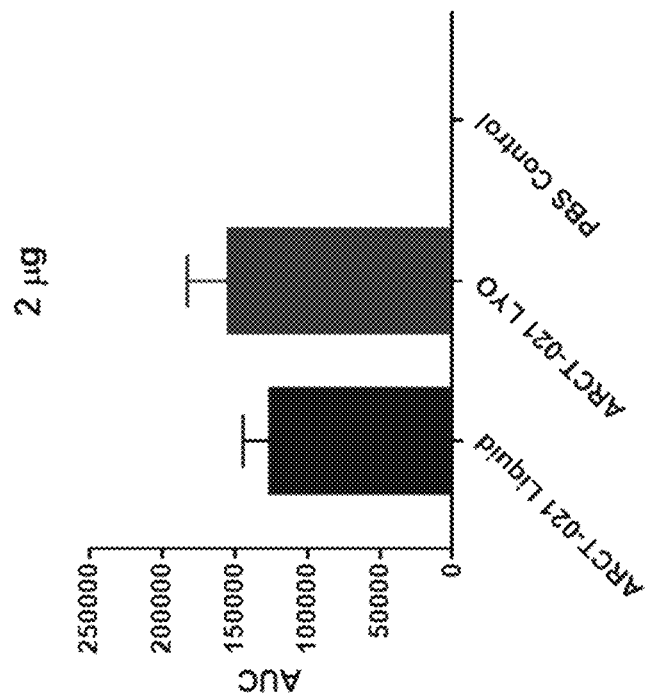
FIGS. 17A-17B show the Area Under the Curve (AUC) Analysis for anti-SARS-Cov-2 Spike Glycoprotein IgG (First and Second Study combined data). IgG assay results were combined from two studies to evaluate self-replicating RNA (SEQ ID NO:125) formulated as lyophilized lipid nanoparticles (LYO-LNP) and liquid (frozen) lipid nanoparticles (Liquid-LNP) at (17A) 0.2 µg, and (17B) 2 µg. N=10/group. First Study Day 19 and 31 results were combined with Second Study Day 20 and 30 results, respectively, and an Area Under the Curve (AUC) analysis was performed. One way ANOVA, Sidak's multiple comparison post-test compared LYO-LNP to Liquid-LNP and resulted in no statistical differences.
Figure 17A:
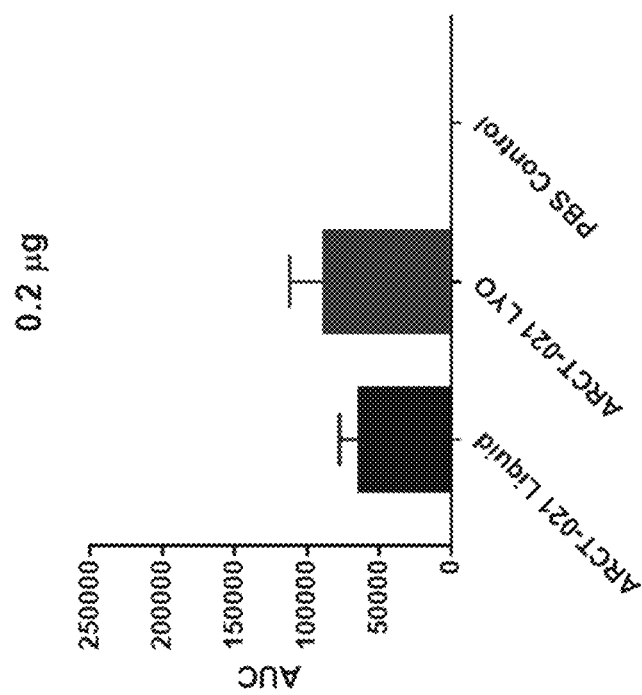

In both studies, anti-SARS-CoV-2 spike protein IgGs were detected in serum in a time- and dose-dependent manner for both Liquid-LNP and LYO-LNP formulations, whereas PBS injection did not elicit an immunogenic response (FIG. 16A-16D). There was no statistical difference in immunogenicity seen between Liquid-LNP and LYO-LNP dose groups in the first study, whereas LYO-LNP produced statistically different and greater IgG than Liquid-LNP in the second study. Without being limited by theory, under-powering (n=5/group) of these two separate studies may have contributed to the statistical differences in immunogenicity results observed in the two studies. In combining the results of both studies, no statistically significant differences were observed between Liquid-LNP and LYO-LNP formulations at the 0.2 and 2 µg dose levels (FIG. 17A, 17B). Taken together, the results of these studies demonstrate that the immunogenicity of the liquid and lyophilized formulations were comparable.

In summary, the liquid and lyophilized formulations of the self-replicating RNA vaccine (SEQ ID NO:125) showed comparable immunogenicity. The vaccine can induce effective, adaptive humoral (neutralizing antibodies) and cellular (CD8+) immune responses targeting the SARS-CoV-2 S glycoprotein. The vaccine also elicits induction of anti-spike glycoprotein antibodies (IgG) levels that are higher than a conventional mRNA vaccine and also induces production of IgG antibodies at a faster rate than a conventional mRNA vaccine. It continues to produce increasing levels of IgG up to 50 days post vaccination whereas the conventional mRNA vaccine plateaus by day 10 post vaccination. It produces an RNA dose-dependent increase in CD8+ T lymphocytes and a balanced, Th1 dominant CD4+ T helper cell immune response with no skew towards a Th2 response.

Any and all references and citations to other documents, such as patents, patent applications, patent publications, journals, books, papers, web contents, that have been made throughout this disclosure are hereby incorporated herein in their entirety for all purposes.

Although the invention has been described with reference to the above examples, it will be understood that modifications and variations are encompassed within the spirit and scope of the invention. Accordingly, the invention is limited only by the following claims.

Example 14

Lyophilization of Self-Replicating RNA-Lipid Nanoparticle Formulation Materials and Methods Generally The processes conducted in this example were conducted using lipid nanoparticle compositions that were manufactured according to well-known processes, for example, those described in U.S. application Ser. No. 16/823,212, the contents of which are incorporated by reference for the specific purpose of teaching lipid nanoparticle manufacturing processes. The lipid nanoparticle compositions and the lyophilized products were characterized for several properties. The materials and methods for these characterization processes as well as a general method of manufacturing the lipid nanoparticle compositions that were used for lyophilization experiments are provided in this example.

Lipid Nanoparticle Manufacture

Lipid nanoparticle formulations used in this example were manufactured by mixing lipids (ionizable cationic lipid (ATX-126):helper lipid:cholesterol:PEG-lipid) in ethanol with RNA dissolved in citrate buffer. The mixed material was instantaneously diluted with Phosphate Buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 10-300 (for example, 40-60) mM NaCl and 5-15% sucrose, pH 7.3. The formulation was concentrated followed by 0.2 µm filtration using PES filters. The RNA concentration in the formulation was then measured by RiboGreen fluorimetric assay, and the concentration was adjusted to a final desired concentration by diluting with HEPES buffer containing 10-100 (for example 40-60) mM NaCl, 0-15% sucrose, pH 7.2-8.5 containing glycerol. If not used immediately for further studies, the final formulation was then filtered through a 0.2 µm filter and filled into glass vials, stoppered, capped and placed at −70 t 5° C. The lipid nanoparticles formulations were characterized for their pH and osmolality. Lipid Content and RNA content were measured by high performance liquid chromatography (HPLC), and mRNA integrity by was measured by fragment analyzer.

Dynamic Light Scattering (DLS)

The average particle size (z) and polydispersity index (PD1) of lipid nanoparticle formulations used in the Examples was measured by dynamic light scattering on a Malvern Zetasizer Nano ZS (United Kingdom).

RiboGreen Assay

The encapsulation efficiency of the lipid nanoparticle formulations was characterized using the RiboGreen fluorometric assay. RiboGreen is a proprietary fluorescent dye (Molecular Probes/Invitrogen a division of Life Technologies, now part of Thermo Fisher Scientific of Eugene, Oreg., United States) that is used in the detection and quantification of nucleic acids, including both RNA and DNA. In its free form, RiboGreen exhibits little fluorescence and possesses a negligible absorbance signature. When bound to nucleic acids, the dye fluoresces with an intensity that is several orders of magnitude greater than the unbound form. The fluorescence can be then be detected by a sensor (fluorimeter) and the nucleic acid can be quantified.

Lyophilization Process

Self-Replicating RNAs (aka Replicon RNA) are typically larger than the average mRNA, and tests were designed to determine whether self-replicating RNA lipid nanoparticle formulations could be successfully lyophilized. The quality of lyophilized lipid nanoparticle formulations was assessed by analyzing the formulations post-lyophilization and comparing this to the lipid nanoparticle formulation prior to lyophilization as well as after a conventional freeze/thaw cycle (i.e., frozen at ~−70° C. then allowed to thaw at room temperature).

The analysis of the lipid nanoparticle formulations included the analysis of particle size and polydispersity (PD1) and encapsulation efficiency (% Encap). The particle size post-lyophilization was compared to the particle size pre-lyophilization and the difference can be reported as a delta (δ). The various compositions tested were screened as to whether a threshold of properties was met including minimal particle size increase (δ<10 nm), the maintenance of PD1 (<0.2), and maintenance of high encapsulation efficiency (>85%).

The lipid nanoparticle formulations were prepared as described above, with self-replicating RNA (SEQ ID NO: 125). The resulting lipid nanoparticle formulation was then processed with a buffer exchange to form a prelyophilization suspension having a concentration of 0.05 to 2.0 mg/mL self-replicating RNA, 0.01 to 0.05 M potassium sorbate, 0.01 to 0.10% w/v Poloxamer 188 (Kolliphor®), 14 to 18% w/v sucrose, 25 to 75 mM NaCl, and 15 to 25 mM pH 8.0 Tris buffer. The prelyophilization formulation was then lyophilized in a Millrock Revo Freeze Dryer (Model No.

RV85S4), using aliquots of 2.0 mL of suspension and the lyophilization cycle provided in Table 10 below. The lyophilized formulations of this example were then applied to the studies of Example 13 above as "LYO-LNP".

TABLE 10

Lyophilization Cycle for Self-Replicating RNA-Lipid Nanoparticle Formulation
Freeze drying cycle

| Step | shelf temperature (° C., ±2° C.) | step duration (h:min) | chamber vacuum (mbar) |
|---|---|---|---|
| Initial Freezing | −50 | 4:00 | atmosphere |
| Evacuation | −50 | 00:30-01:45 | from atmosph. pressure to 0.05 |
| Primary drying (ramp down) | −50 → 0 | 63:00 | 0.05 |
| Secondary drying (ramp up) | 0 → +25 | 39:30 | 0.05 |
| Backfill with N$_2$ and stoppering | 25 | 00:10-00:20 | 700 ± 50 |
| Aeration with air | 5 | 00:10-00:20 | atmosphere |

The lyophilized particles prepared following the methods described above were reconstituted in 2 mL of water and characterized using DLS and RiboGreen. The results provided in Table 11 below show that the lyophilized compositions were found to produce lyophilized lipid nanoparticle formulations with adequate size, polydispersity, and delta values (~5.3 nm) upon reconstitution.

TABLE 11

Self-Replicating RNA-Lipid Nanoparticle Characteristics Pre- and Post-LYO

| | Average Particle Size (nm) | PDI | encap (%) |
|---|---|---|---|
| Pre-LYO | 76.3 | 0.129 | 97 |
| Post-LYO | 81.6 | 0.152 | 93 |

What is claimed is:

1. A nucleic acid molecule comprising
   (a) a sequence of SEQ ID NO:124;
   (b) a sequence of SEQ ID NO:124, wherein T is substituted with U;
   (c) a sequence of SEQ ID NO:125; or
   (d) a sequence of SEQ ID NO:125, wherein T is substituted with U.

2. A composition comprising:
   (I) a nucleic acid molecule comprising:
      (A) a first polynucleotide encoding one or more viral replication proteins, wherein the first polynucleotide is codon-optimized as compared to a wild-type polynucleotide encoding the one or more viral replication proteins; and
      (B) a second polynucleotide comprising a transgene encoding an antigenic protein or a fragment thereof, wherein the antigenic protein is a coronavirus protein; and
   (II) a lipid formulation selected from a lipoplex, a liposome, a lipid nanoparticle, a polymer-based carrier, an exosome, a lamellar body, a micelle, and an emulsion, wherein the nucleic acid molecule comprises
      (a) a sequence of SEQ ID NO:124;
      (b) a sequence of SEQ ID NO:124, wherein T is substituted with U;
      (c) a sequence of SEQ ID NO:125; or
      (d) a sequence of SEQ ID NO:125, wherein T is substituted with U.

3. The composition of claim 2, wherein the lipid formulation is a lipid nanoparticle having a size of less than about 200 nm.

4. The composition of claim 2, wherein the lipid formulation comprises an ionizable cationic lipid.

5. The composition of claim 4, wherein the ionizable cationic lipid has a structure of Formula I:

$$R^5-X^6-CH_2-N(L^6-X^5-R^6)-C(O)-L^7-X^7-R^4-N(R^7)(R^8) \quad (I)$$

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

6. The composition of claim 4, wherein the ionizable cationic lipid is ATX-126:

ATX-126

7. The composition of claim 2, wherein the lipid formulation encapsulates the nucleic acid molecule or is complexed to the nucleic acid molecule.

8. The composition of claim 2, wherein the lipid formulation comprises
   (i) a helper lipid;
   (ii) a phospholipid;
   (iii) a polyethylene glycol (PEG)-lipid conjugate; or
   (iv) any combination thereof.

9. The composition of claim 8, wherein the phospholipid is selected from dioleoylphosphatidyl ethanolamine (DOPE), dimyristoylphosphatidyl choline (DMPC), distearoylphosphatidyl choline (DSPC), dimyristoylphosphatidyl glycerol (DMPG), dipalmitoyl phosphatidylcholine (DPPC), and phosphatidylcholine (PC).

10. The composition of claim 8, wherein the PEG-lipid conjugate is PEG-DMG.

11. The composition of claim 2, wherein the lipid portion of the lipid formulation comprises about 40 mol % to about 60 mol % of the ionizable cationic lipid, about 4 mol % to about 16 mol % DSPC, about 30 mol % to about 47 mol % cholesterol, and about 0.5 mol % to about 3 mol % PEG2000-DMG.

12. The composition of claim 2, wherein the composition has a total lipid:nucleic acid molecule weight ratio of about 50:1 to about 10:1.

13. The composition of claim 2, wherein the composition further comprises
  (i) a HEPES or TRIS buffer at a pH of about 7.0 to about 8.5;
  (ii) a HEPES or TRIS buffer at a concentration of about 7 mg/mL to about 15 mg/mL;
  (iii) about 2.0 mg/mL to about 4.0 mg/mL of NaCl;
  (iv) one or more cryoprotectants;
  (v) one or more cryoprotectants selected from sucrose, glycerol, or a combination of sucrose and glycerol; or
  (vi) any combination thereof.

14. The composition of claim 13, wherein the composition comprises a combination of sucrose at a concentration of about 70 mg/mL to about 110 mg/mL and glycerol at a concentration of about 50 mg/mL to about 70 mg/mL.

15. The composition of claim 2, wherein the composition is a lyophilized composition.

16. The composition of claim 15, wherein the lyophilized composition comprises one or more lyoprotectants.

17. The composition of claim 15, wherein the lyophilized composition comprises a poloxamer, potassium sorbate, sucrose, or any combination thereof.

18. The composition of claim 15, wherein the lyophilized composition comprises
  (i) about 0.01 to about 1.0% w/w of the nucleic acid molecule;
  (ii) about 1.0 to about 5.0% w/w lipids;
  (iii) about 0.5 to about 2.5% w/w of TRIS buffer;
  (iv) about 0.75 to about 2.75% w/w of NaCl;
  (v) about 85 to about 95% w/w of a sugar;
  (vi) about 0.01 to about 1.0% w/w of a poloxamer;
  (vii) about 1.0 to about 5.0% w/w of potassium sorbate; or
  (viii) any combination thereof.

19. The composition of claim 18, wherein the sugar is sucrose.

20. The composition of claim 18, wherein the poloxamer is poloxamer 188.

21. A lipid nanoparticle composition comprising
  (a) a lipid formulation comprising
    (i) about 45 mol % to about 55 mol % of an ionizable cationic lipid having the structure of ATX-126:

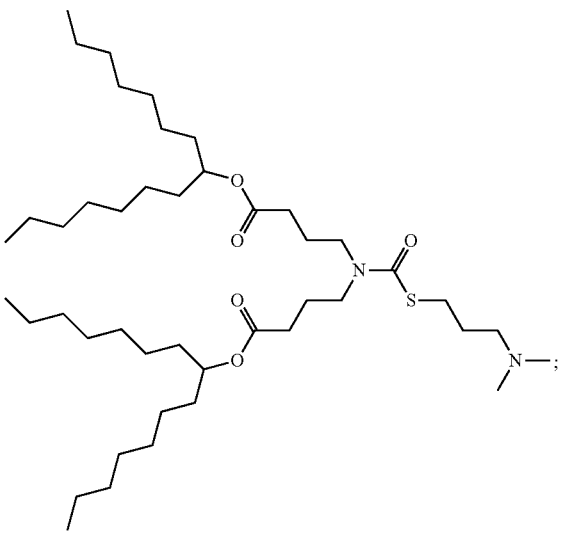

ATX-126

(ii) about 8 mol % to about 12 mol % DSPC;
    (iii) about 35 mol % to about 42 mol % cholesterol; and
    (iv) about 1.25 mol % to about 1.75 mol % PEG2000-DMG; and
  (b) a nucleic acid molecule having at least 85% sequence identity to SEQ ID NO:125;
    wherein the lipid formulation encapsulates the nucleic acid molecule and the lipid nanoparticle has a size of about 60 to about 90 nm.

22. A method of administering the composition of claim 2 to a subject in need thereof, wherein the composition is lyophilized and is reconstituted prior to administration.

23. A method of preventing or ameliorating COVID-19, comprising administering the composition of claim 2 to a subject in need thereof.

24. The method of claim 23, wherein the composition is administered one time or two times.

25. A method of administering a booster dose to a vaccinated subject, comprising administering the composition of claim 2 to a subject who was previously vaccinated against coronavirus.

26. The method of claim 23, wherein the composition is administered at a dosage of about 0.01 µg to about 1,000 µg of nucleic acid.

27. A method of inducing an immune response against a coronavirus in a subject comprising:
  administering to the subject an effective amount of a nucleic acid molecule of claim 1.

28. A method of inducing an immune response against a coronavirus in a subject comprising:
  administering to the subject an effective amount of a composition of claim 2.

* * * * *